(12) United States Patent
Sakai et al.

(10) Patent No.: US 6,939,895 B2
(45) Date of Patent: Sep. 6, 2005

(54) CALCIUM RECEPTOR-ACTIVE COMPOUNDS

(75) Inventors: Teruyuki Sakai, Gunma (JP); Atsuya Takami, Gunma (JP); Rika Nagao, Gunma (JP)

(73) Assignee: NPS Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 10/326,713

(22) Filed: Dec. 19, 2002

(65) Prior Publication Data

US 2003/0144526 A1 Jul. 31, 2003

Related U.S. Application Data

(62) Division of application No. 10/053,133, filed on Jan. 17, 2002, now Pat. No. 6,750,255, which is a continuation of application No. 09/214,552, filed as application No. PCT/JP97/02358 on Jul. 8, 1997, now Pat. No. 6,362,231.

(30) Foreign Application Priority Data

| Jul. 8, 1996 | (JP) | ............................................. 8-178315 |
|---|---|---|
| Dec. 27, 1996 | (JP) | ............................................. 8-350393 |
| Apr. 24, 1997 | (JP) | ............................................. 9-107778 |

(51) Int. Cl.$^7$ ...................... A61K 31/145; C07C 321/28
(52) U.S. Cl. ....................... 514/654; 564/305; 564/336; 564/341; 564/353; 564/354; 514/655; 548/491
(58) Field of Search .......................... 548/491; 514/415, 514/654, 655; 564/305, 336, 340, 353, 354, 341, 346

(56) References Cited

U.S. PATENT DOCUMENTS

| 2,767,168 A | 10/1956 | Cheney |
| 2,770,653 A | 11/1956 | Hanslick et al. |
| 2,868,833 A | 1/1959 | Szabo et al. |
| 2,876,236 A | 3/1959 | Szabo et al. |
| 5,981,599 A | * 11/1999 | Moe et al. .................. 514/654 |
| 6,362,231 B1 | * 3/2002 | Sakai et al. ................. 514/654 |

FOREIGN PATENT DOCUMENTS

| EP | 0 269 363 A | 6/1988 |
| GB | 982 572 A | 2/1965 |
| JP | 6-510531 A | 11/1994 |
| WO | WO 94/18959 A1 | 9/1994 |
| WO | 96/12697 A1 | 5/1996 |

OTHER PUBLICATIONS

Chemical Abstracts 122:55688 1995 Xueliang Huaxue Shiji 16 (3)132–135 1994.*
Takeno et al., "A facile route to tetrahydroisoquinoline alkaloids via sulfoxide mediated cyclization." Heterocycles, 35(1): 47–52, 1993.
Riley et al., "Synthesis and α–adrenolytic activity of chiral β–haloethylamines." J.Pharm.Sci., 65(4):544–547, 1976.
Chemical Abstract, vol. 63, 1965, Columbus, Ohio, Abstract No. 2928b, Wellcome Foundation Ltd., "Improvements in and relating to quaternary ammonium compounds and the preparation thereof." GB Patent Specification 982,572.

Chemical Abstract, vol. 60, 1964, Columbus, Ohio, Abstract No. 11246g, Robert P. Halliday et al., "Evaluation of certain hypotensive agents. V. substituted polymethylenediamines." J. Pharm. Sci., 53(1):19–23, 1964.
Chemical Abstracts, vol. 60, 1964, Columbus, Ohio, Abstract No. 1692c, Jerry E. Robinson et al., "Hypotensives. VI. Disubstituted alkylenediamines and related compounds." J.Med. Chemistry, 6(6): 805–807, 1963.
Chemical Abstracts, vol. 60, 1964, Columbus, Ohio, Abstract No. 4920f, L. Schusteritz et al., "Structure and action o piperazine and ethylenediamine derivatives." Arzneimittel–Forsch., 9:628–633, 1959.
Chemical Abstracts, vol. 53, 1959, Columbus, Ohio, Abstract No. 12303e, Joseph L. Szabo et al., "Heterocyclic diamines and salts thereof." US Patent No. 2, 876, 236.
Chemical Abstracts, vol. 53, 1959, Columbus, Ohio, Abstract No. 9251b, Joseph L. Szabo et al., "Aliphatic diamines and their salts." US Patent No. 2, 868, 833.
Chemical Abstracts, vol. 53, 1959, Columbus, Ohio, Abstract No. 8788d, Roy S. Hauslick et al., "Diaralkylenediamine Preparation." US Patent No. 2, 770, 653.
Chemical Abstracts, vol. 51, 1957, Columbus, Ohio, Abstract No. 7428i, Lee C. Cheney, "Purification of streptomycin." US Patent No .2, 767, 168.
International Search Report, International Application No. PCT/JP97/02358.
Halliday et al. Evaluation of certain hypotensive agents V: Substituted polymethylenediamines. Journal of Pharmaceutical Sciences. 53: 19–23, 1964.
Robertson et al., Hypotensives. VI. Disubstituted alkylenediamines and related compounds. Journal of Medicinal Chemistry. 6:805–807, 1963.
Schusteritz et al., Struktur und wirkung von piperazin– und athylendiamin–derivaten. Arzneimittel Forschung, 9: 628–633, 1959.
Supplementary Partial European Search Report for Application No. EP 97 92 9555 mailed Aug. 12, 2004.

* cited by examiner

*Primary Examiner*—Golam M M Shameem
(74) *Attorney, Agent, or Firm*—Foley & Lardner LLP

(57) ABSTRACT

A novel calcium receptor active compound having the formula is provided:

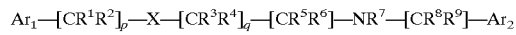

$$Ar_1-[CR^1R^2]_p-X-[CR^3R^4]_q-[CR^5R^6]-NR^7-[CR^8R^9]-Ar_2$$

wherein:
$Ar_1$ is selected from the group consisting of aryl, heteroaryl, bis(arylmethyl)amino, bis(heteroarylmethyl)amino and arylmethyl(heteroarylmethyl)amino;
X is selected from the group consisting of oxygen, sulfur, sulfinyl, sulfonyl, carbonyl and amino;
$R^1$, $R^2$, $R^3$, $R^4$, $R^5$, $R^6$, $R^7$, $R^8$ and $R^9$ are, for example, hydrogen or alkyl;
$Ar_2$ is selected from the group consisting of aryl and heteroaryl;
p is an integer of from 0 to 6, inclusive; and,
q is an integer of from 0 to 14, inclusive.

20 Claims, 94 Drawing Sheets

K-2033

K-2047

K-2034

K-2048

K-2035

K-2049

K-2040

K-2050

K-2041

K-2051

K-2045

K-2052

K-2046

K-2055

K-2056

K-2076

K-2057

K-2078

K-2058

K-2079

K-2059

K-2080

K-2061

K-2082

K-2066

K-2084

K-2075

K-2085

S1: n=1    S4: n=4    S7: n=7
S2: n=2    S5: n=5
S3: n=3    S6: n=6

S8: n=1    S11: n=4    S14: n=7
S9: n=2    S12: n=5    S15: n=9
S10: n=3    S13: n=6    S16: n=11

S17: n=1    S20: n=4    S23: n=7
S18: n=2    S21: n=5
S19: n=3    S22: n=6

S24: n=1    S27: n=6
S25: n=2    S28: n=7
S26: n=5

S29: n=1    S32: n=4    S35: n=7
S30: n=2    S33: n=5
S31: n=3    S34: n=6

S36: n=1    S39: n=4    S42: n=7
S37: n=2    S40: n=5
S38: n=3    S41: n=6

S43: n=1  S46: n=4  S49: n=7
S44: n=2  S47: n=5
S45: n=3  S48: n=6

S50: n=1  S53: n=4  S56: n=7
S51: n=2  S54: n=5
S52: n=3  S55: n=6

S57: n=1  S60: n=4  S63: n=7
S58: n=2  S61: n=5
S59: n=3  S62: n=6

S64: n=1  S67: n=4  S70: n=7
S65: n=2  S68: n=5
S66: n=3  S69: n=6

S71: n=1  S74: n=4  S77: n=7
S72: n=2  S75: n=5
S73: n=3  S76: n=6

S78: n=1  S81: n=4  S84: n=7
S79: n=2  S82: n=5
S80: n=3  S83: n=6

S85: n=2    S88: n=5
S86: n=3    S89: n=6
S87: n=4    S90: n=7

S91: n=2    S94: n=5
S92: n=3    S95: n=6
S93: n=4    S96: n=7

S97: n=1    S100: n=4    S103: n=7
S98: n=2    S101: n=5
S99: n=3    S102: n=6

S104: n=1   S107: n=4    S110: n=7
S105: n=2   S108: n=5
S106: n=3   S109: n=6

S111: n=1   S114: n=4    S117: n=7
S112: n=2   S115: n=5
S113: n=3   S116: n=6

S118: n=1   S121: n=4    S124: n=7
S119: n=2   S122: n=5
S120: n=3   S123: n=6

S125: n=1  S128: n=4  S131: n=7
S126: n=2  S129: n=5
S127: n=3  S130: n=6

S132: n=1  S135: n=4  S138: n=7
S133: n=2  S136: n=5
S134: n=3  S137: n=6

S139: n=1  S142: n=4  S145: n=7
S140: n=2  S143: n=5
S141: n=3  S144: n=6

S146: n=1  S149: n=4  S152: n=7
S147: n=2  S150: n=5
S148: n=3  S151: n=6

S153: n=1  S156: n=4  S159: n=7
S154: n=2  S157: n=5
S155: n=3  S158: n=6

S160: n=1  S163: n=4  S166: n=7
S161: n=2  S164: n=5
S162: n=3  S165: n=6

S261: n=1
S262: n=2

S263: n=4
S264: n=5

S265

S266

F-116

F-117

F-118

F-119

F-120

CALCIUM RECEPTOR-ACTIVE COMPOUNDS

CROSS-REFERENCE TO RELATED APPLICATIONS

This application is a divisional of U.S. application Ser. No. 10/053,133, filed Jan. 17, 2002 now U.S. Pat. No. 6,750,255, which is a continuation of a U.S. application Ser. No. 09/214,552, filed Jan. 6, 1999 now U.S. Pat. No. 6,362,231, which claims priority to an International Application No. PCT/JP97/02358 filed on Jul. 8, 1997, which claims priority to Japanese Application Nos. 9/107778, filed Apr. 24, 1997; 8/350393, filed Dec. 27, 1996 and 8/178315, filed Jul. 8, 1996, all which are incorporated by reference herein.

FIELD OF THE INVENTION

This invention relates to the design, development, composition and use of novel molecules able to modulate the activity of inorganic ion receptor.

BACKGROUND OF THE INVENTION

Certain cells in the body respond not only to chemical signals, but also to ions such as extracellular calcium ions ($Ca^{2+}$). Changes in the concentration of extracellular $Ca^{2+}$ (referred to herein as "[$Ca^{2+}$]") alter the functional responses of these cells. One such specialized cell is the parathyroid cell which secretes parathyroid hormone (PTH). PTH is the principal endocrine factor relating $Ca^{2+}$ homeostasis in the blood and extracellular fluids.

PTH, by acting on bone and kidney cells, increases the level of $Ca^{2+}$ in the blood. This increase in [$Ca^{2+}$] then acts as a negative feedback signal, depressing PTH secretion. The reciprocal relationship between [$Ca^{2+}$] and PTH secretion forms the essential mechanism maintaining bodily $Ca^{2+}$ homeostasis.

Extracellular $Ca^{2+}$ acts directly on parathyroid cells to regulate PTH secretion. The existence of a parathyroid cell surface protein which detects changes in [$Ca^{2-}$] has been confirmed. Brown et al., 366 Nature 574, 1993. In parathyroid cells, this protein acts as a receptor for extracellular $Ca^{2+}$ ("the calcium receptor"), and detects changes in [$Ca^{2+}$] and to initiate a functional cellular response, PTH secretion.

Extracellular $Ca^{2+}$ can exert effects on different cell functions, reviewed in Nemeth, et al., 11 Cell Calcium 319, 1990. The role of extracellular $Ca^{2+}$ in parafolicular (C cells) and parathyroid cells is discussed in Nemeth, 11 Cell Calcium 323, 1990. These cells have been shown to express similar $Ca^{2+}$ receptor. Brown et al., 366 Nature 574, 1993; Mithal et al., 9 Suppl. 1 J. Bone and Mineral Res. s282, 1994; Rogers et al., 9 Suppl. 1 J. Bone and Mineral Res. s409 1994; Garrett et al., 9 Suppl. 1 J. Bone and Mineral Res. s409, 1994. The role of extracellular $Ca^{2+}$ on bone osteoclasts is discussed by Zaidi, 10 Bioscience Reports 493, 1990. in addition keratinocytes, juxtaglomerular cells, trophoblasts, pancreatic beta cells and fat/adipose cells all respond to increases in extracellular calcium which likely reflects activation of calcium receptors of these cells.

The ability of various compounds to mimic extracellular $Ca^{2-}$ in vitro is discussed by Nemeth et al., (spermine and spermidine) in "Calcium-Binding Proteins in Health and Disease", 1987, Academic Press, Inc., pp.33–35; Brown et al., (e.g., neomycin) 128 Endocrinology 3047, 1991; Chen et al., (diltiazem and its analog, TA-3090) 5 J. Bone and Mineral Res. 581, 1990; and Zaidi et al., (verapamil) 167 Biochem. Biophys. Res. Commun. 807, 1990. Nemeth et al., PCT/US93/01642, International Publication Number WO 94/18959, Nemeth et al., PCT/US92/07175, International Publication Number WO 93/04373, Nemeth et al., PCT/US94/12117, International Publication Number WO 95/11221 and Nemeth et al., PCT/US95/13704, International Publication Number WO 96/12697 describe various compounds which can modulate the effect of an inorganic ion on a cell having an inorganic ion receptor, preferably modulate the effects of calcium on a calcium receptor.

The object of the present invention is to provide a novel inorganic ion receptor active compound having the structure different from the compounds described above.

DISCLOSURE OF THE INVENTION

The present invention features molecules which can modulate one or more activities of an inorganic ion receptor. Preferably, the molecule can mimic or block the effect of extracellular $Ca^{2+}$ on a calcium receptor. The preferred use of such molecules is to treat diseases or disorders by altering inorganic ion receptor activity, preferably calcium receptor activity.

The present invention provides a novel calcium receptor active compound of the formula:

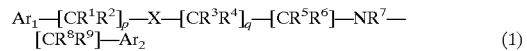

$$Ar_1—[CR^1R^2]_p—X—[CR^3R^4]_q—[CR^5R^6]—NR^7—[CR^8R^9]—Ar_2 \qquad (1)$$

wherein:

$Ar_1$ is selected from the group consisting of aryl, heteroaryl, bis(arylmethyl)amino, bis(heteroarylmethyl)amino and arylmethyl(heteroarylmethyl)amino;

X is selected from the group consisting of oxygen, sulfur, sulfinyl, sulfonyl, carbonyl and amino;

$R^1, R^2, R^3, R^4, R^5, R^6, R^8$ and $R^9$ are independently selected from the group consisting of hydrogen, alkyl, cycloalkyl, alkenyl, alkynyl, trihalomethyl, aryl, heteroaryl, heteroalicyclic, halogen, hydroxy, alkoxy, thioalkoxy, aryloxy, thioaryloxy, carbonyl, thiocarbonyl, C-carboxyl, O-carboxyl, C-amido, N-amido, O-carbamyl, N-carbamyl, O-thiocarbamyl, N-thiocarbamyl, cyano, nitro, amino and $NR^{10}R^{11}$; wherein, $R^{10}$ and $R^{11}$ are independently selected from the group consisting of hydrogen, alkyl, alkenyl, alkynyl, cycloalkyl, aryl, carbonyl, trihaloacetyl, sulfonyl, trihalomethanesulfonyl and, combined, a five- or six-member heteroalicyclic ring containing at least one nitrogen;

any two adjacent "R" groups may be combined to form five- or six-member fused cycloalkyl groups;

$R^7$ is selected from the group consisting of hydrogen, alkyl, cycloalkyl, alkenyl, alkynyl, aryl, halogen, cyano, hydroxy, alkoxy, O-carboxyl, trihaloacetyl and trihalomethanesulfonyl;

$Ar_2$ is selected from the group consisting of aryl and heteroaryl;

p is an integer of from 0 to 6, inclusive; and, q is an integer of from 0 to 14, inclusive;

or a pharmaceutically acceptable salt or hydrate of said compound.

As used herein, the term "aryl" refers to an all-carbon monocyclic or fused ring polycyclic (i.e., rings which share adjacent pairs of carbon atoms) groups in which one or more of the rings has a completely conjugated pi-electron system. Examples, without limitation, of aryl groups, are phenyl, naphthyl, anthracenyl, phenanthrenyl, fluorenyl, and indanyl. The aryl group may be substituted or unsubstituted. When substituted, the substituted group(s) is preferably one or more selected from halogen, trihalomethyl, alkyl, alkenyl, alkynyl, hydroxy, alkoxy, aryloxy, thiohydroxy, thioalkoxy, thioaryloxy, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, S-sulfonamido, N-sulfonamido, trihalomethane-sulfonamido, amino and $NR^{10}R^{11}$ wherein: $R^{10}$ and $R^{11}$ are independently selected from the group consisting of hydrogen, alkyl, cycloalkyl, aryl, carbonyl, sulfonyl, trihalomethanesulfonyl, and, combined, a five- or six-member heteroalicyclic ring which heteroalicyclic ring may be unsubstituted or substituted with one or more halogens.

A "heteroaryl" group refers to a monocyclic or fused ring (i.e., rings which share an adjacent pair of atoms) group having in the ring(s) one or more atoms selected from the group consisting of nitrogen, oxygen and sulfur and, in addition, at least one of the rings has a completely conjugated pi-electron system. Examples, without limitation, of heteroaryl groups are pyrrole, furan, dibenzofuran, carbazole, acridine, thiophene, imidazole, benzimidazole, oxazole, thiazole, phenothiazine, triazole, thiadiazole, pyrazole, benzoxazole, benzthiazole, indole, benzofuran, indazole, pyridine, pyrimidine, quinoline, isoquinoline, quinazoline, purine, phthalazine and flavone. The heteroaryl group may be substituted or unsubstituted. When substituted, the substituted group(s) is preferably one or more selected from alkyl, cycloalkyl, halogen, trihalomethyl, hydroxy, alkoxy, aryloxy, thiohydroxy, thioalkoxy, thioaryloxy, cyano, nitro, carbonyl, thiocarbonyl, sulfonamido, C-carboxy, O-carboxy, sulfinyl, sulfonyl, C-carbamyl, N-carbamyl, O-thiocarbamyl, N-thiocarbamyl, C-amido, N-amido, S-sulfonamido, N-sulfonamido, trihalomethanesulfonamido, amino and $NR^{10}R^{11}$ where $R^{10}$ and $R^{11}$ are previously defined herein.

As used herein, the term "alkyl" refers to a saturated aliphatic hydrocarbon including straight chain and branched chain groups. Preferably, the alkyl group has 1 to 20 carbon atoms. More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from cycloalkyl, aryl, heteroaryl, heteroalicyclic, hydroxy, alkoxy, aryloxy, thiohydroxy, thioalkoxy, thioaryloxy, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, sulfonamido, trihalomethane-sulfonamido, amino and $NR^{10}R^{11}$ where $R^{10}$ and $R^{11}$ are previously defined herein. More preferably, the alkyl group is a medium or lower alkyl which is optionally substituted with one or more groups independently selected from halogen, hydroxy, nitro, cyano and unsubstituted lower alkoxy, lower alkoxy substituted with one or more halogens; an unsubstituted lower alkyl; and a lower alkyl substituted with one or more halogens.

A "cycloalkyl" group refers to an all-carbon monocyclic or fused ring (i.e., rings which share an adjacent pair of carbon atoms) group wherein none of the rings has a completely conjugated pi-electron system. Examples, without limitation, of cycloalkyl groups are cyclopropane, cyclobutane, cyclopentane, cyclopentene, cyclohexane, cyclohexadiene, cycloheptane and, cycloheptatriene. A cycloalkyl group may be substituted or unsubstituted. When substituted, the substituent group(s) is preferably one or more individually selected from alkyl, aryl, heteroaryl, heteroalycyclic, hydroxy, alkoxy, aryloxy, thiohydroxy, thioalkoxy, thioaryloxy, cyano, halogen, carbonyl, thiocarbonyl, C-carboxy, O-carboxy, O-carbamyl, N-carbamyl, C-amido, N-amido, S-sulfonamido, N-sulfonamido, nitro, amino and $NR^{10}R^{11}$, where $R^{10}$ and $R^{11}$ are previously defined herein. Preferably the cycloalkyl group is selected from unsubstituted cyclopropane, unsubstituted cyclopentane, unsubstituted cyclohexane, and cyclopropane, cyclopentane and cyclohexane substituted with one or more groups independently selected from halogen, nitro, cyano, hydroxy, unsubstituted lower alkoxy, C-carboxyl wherein R" is unsubstituted lower alkyl and O-carboxyl wherein R" is unsubstituted lower alkyl.

An "alkenyl" group refers to an alkyl group, as defined herein, consisting of at least two carbon atoms and at least one carbon—carbon double bond. A "lower alkenyl" group refers to a lower alkyl group containing at least one double bond.

A "cycloalkenyl" group refers to a cycloalkyl group which contains one or more double bonds in the ring wherein the double bonds do not produce a completely conjugated pi-electron system within the ring.

An "alkynyl" group refers to an alkyl group, as defined herein, consisting of at least two carbon atoms and at least one carbon-carbon triple bond. A "lower alkynyl" group refers to a lower alkyl group containing at least one triple bond.

A "heteroalicyclic" group refers to a monocyclic or fused ring group having in the ring(s) one or more atoms selected from the group consisting of nitrogen, oxygen and sulfur. The rings may also have one or more double bonds. However, none of the rings has a completely conjugated pi-electron system. The heteroalicyclic ring may be substituted or unsubstituted. When substituted, the substituted group(s) is preferably one or more selected from alkyl, cycloalkyl, halogen, trihalomethyl, hydroxy, alkoxy, aryloxy, thiohydroxy, thioalkoxy, thioaryloxy, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, S-sulfonamido, N-sulfonamido, C-amido, N-amido, amino and $NR^{10}R^{11}$ where $R^{10}$ and $R^{11}$ are previously defined herein.

A "phenyl" group refers to a six-member ring aryl group.

A "benzyl" group refers to a phenyl-$CH_2$— group.

A "hydroxy" group refers to an —OH group.

An "alkoxy" group refers to both an —O-alkyl and an —O-cycloalkyl group, as defined herein; preferably an alkoxy group refers to a methoxy or trihalomethoxy.

A "trihalomethoxy" group refers to a $Y_3CO$— group with Y as defined herein; preferably Y is fluorine.

A "benzyloxy" refers to a benzyl-O— group.

An "aryloxy" group refers to both an —O-aryl and an —O-heteroaryl group, as defined herein. A "phenoxy" group refers to an aryloxy group in which the aryl group is a phenyl group. A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "carbonyl" or "acyl" group refers to a —C(=O)—R" group, where R" is selected from the group consisting of hydrogen, alkyl, cycloalkyl, aryl, heteroaryl (bonded through a ring carbon) and heteroalicyclic (bonded through a ring carbon), as defined herein.

An "formyl" group refers to a carbonyl group wherein R" is hydrogen.

An "acetyl" group refers to a carbonyl group wherein R" is $CH_3$.

A "thiocarbonyl" group refers to a —C(=S)—R" group, with R" as defined herein.

A "trihalomethyl" group refers to a —CY$_3$ group wherein Y is a halogen group; preferably Y is fluorine.

A "trihaloacetyl" group refers to a Y$_3$CC(=O)— group with Y as defined herein.

A "C-carboxyl" group refers to a —C(=O)O—R" groups, with R" as defined herein.

An "O-carboxyl" group refers to a R"C(=O)O— group, with R" as defined herein.

An "acetoxy" group refers to an O-carboxyl group in which R" is CH$_3$.

A "carboxylic acid" group refers to a C-carboxyl group in which R" is hydrogen.

A "halo" or "halogen" group refers to fluorine, chlorine, bromine or iodine.

A "trihalomethanesulfonyl" group refers to a Y$_3$CS(=C)$_2$— groups with Y as defined above.

A "trihalomethanesulfonamido" group refers to a Y$_3$CS(=O)$_2$NR$^{10}$— group with Y and R$^{10}$ as defined herein.

A "sulfinyl" group refers to a —S(=O)—R" group, with R" as defined herein or R" may not exist if both S-bonds are already in use internally in a particular molecule.

A "sulfonyl" group refers to a —S(=O)$_2$R" group, with R" as defined herein. or R" may not exist is both S-bonds are already in use internally in an particular molecule.

An "S-sulfonamido" group refers to a —S(=O)$_2$NR$^{10}$R$^{11}$, with R$^{10}$ and R$^{11}$ as defined herein.

An "N-sulfonamido" group refers to a R$^{10}$S(=O)$_2$NR$^{11}$— group, with R$^{10}$ and R$^{11}$ as defined herein.

An "O-carbamyl" group refers to a —OC(=O)NR$^{10}$R$^{11}$ group with R$^{10}$ and R$^{11}$ as defined herein.

An "N-carbamyl" group refers to a R$^{10}$OC(=O)NR$^{11}$— group, with R$^{10}$ and R$^{11}$ as defined herein.

An "O-thiocarbamyl" group refers to a —OC(=S)NR$^{10}$R$^{11}$ group with R$^{10}$ and R$^{11}$ as defined herein.

An "N-thiocarbamyl" group refers to a R$^{10}$OC(=S)NR$^{11}$— group, with R$^{10}$ and R$^{11}$ as defined herein.

An "amino" group refers to an —NR$^{10}$R$^{11}$ group, with R$^{10}$ and R$^{11}$ as defined herein.

A "C-amido" group refers to a —C(=O)NR$^{10}$R$^{11}$ group with R$^{10}$ and R$^{11}$ as defined herein.

An "N-amido" group refers to a R$^{10}$C(=O)NR$^{11}$— group, with R$^{10}$ and R$^{11}$ as defined herein.

A "nitro" group refers to a —NO$_2$ group.

A "methylenedioxy" group refers to a —OCH$_2$O— group in which the two oxygens are covalently bonded to adjacent carbon atoms of an aryl or heteroaryl group.

An "ethylenedioxy" group refers to a —OCH$_2$CH$_2$O— groups in which the two oxygens are covalently bonded to adjacent carbon atoms of an aryl or heteroaryl group.

Preferably, in the formula (1), R$^5$ is selected from the group consisting of hydrogen, unsubstituted lower alkyl and lower alkyl substituted with one or more halogens; R$^1$, R$^2$, R$^3$, R$^4$, R$^5$, R$^6$ and R$^7$ are hydrogen; and R$^8$ and R$^9$ are independently selected from the group consisting of hydrogen, unsubstituted alkyl, lower alkyl substituted with one or more halogens, unsubstituted alkenyl, lower alkenyl substituted with one or more halogens, unsubstituted alkynyl, alkynyl substituted with one or more halogens and, combined, unsubstituted cycloalkyl and cycloalkenyl. Also preferably, Ar$_1$ is selected from the group consisting of phenyl, naphthyl, indolyl, fluorenyl, dibenzofuranyl, carbazolyl, benzoxazole-2-yl, benzthiazole-2-yl, pyridin-4-yl, quinolin-2-yl and dibenzylamino and Ar$_2$ is selected from the group consisting of phenyl, naphthyl, quinolin-4-yl, pyridin-2-yl, pyridin-3-yl, pyridin-4-yl, pyrimidinyl, furan-2-yl, furan-3-yl, thiophen-2-yl, thiophen-3-yl, pyrrol-2-yl and pyrrol-3-yl. More preferably, Ar$_1$ is phenyl substituted with one or more groups selected from the group consisting of unsubstituted lower alkyl, halogen, trihalomethyl, unsubstituted lower alkoxy, trihalomethoxy, trihaloacetyl and nitro, and Ar$_2$ is selected from the group consisting of optionally substituted phenyl and optionally substituted naphthyl. Even more preferably, Ar$_2$ is 3-methoxyphenyl or unsubstituted naphthyl. Preferably, R$^8$ is hydrogen, R$^9$ is methyl and X is oxygen or sulfur.

In another aspect, the present invention provides a compound of the formula:

wherein:

Ar$_3$ is selected from the group consisting of aryl and heteroaryl optionally substituted with one or more groups independently selected from the group consisting of unsubstituted lower alkyl, lower alkyl substituted with one or more halogens, unsubstituted lower alkenyl, lower alkenyl substituted with one or more halogens, halogen, hydroxy, unsubstituteci lower alkoxy, lower alkoxy substituted with one or more halogens, unsubstituted lower thioalkoxy, nitro, formyl, acetoxy, acetyl, —CH$_2$OH, CH$_3$CH(OH)—, —(=O)NH$_2$, cyano, —N(lower alkyl)$_2$, phenyl, phenoxy, benzyl, benzyloxy, methylenedioxy, ethylenedioxy, α,α-dimethylbenzyl, and —OCH$_2$COOH;

Ar$_4$ is selected from the group consisting of aryl and heteroaryl optionally substituted with one or more groups independently selected from the group consisting of unsubstituted lower alkyl, lower alkyl substituted with one or more halogens, unsubstituted lower alkenyl, lower alkenyl substituted with one or more halogens, unsubstituted lower alkoxy, lower alkoxy substituted with one or more halogens, hydroxy, lower thioalkoxy, halogen; methylenedioxy, ethylenedioxy, acetoxy, —OCH$_2$COOH, —C(=O)NH$_2$, cyano, and —CH$_2$OH;

r is an integer of from 0 to 6, inclusive;

s is an integer of from 0 to 14, inclusive;

Q is selected from the group consisting of oxygen, sulfur, carbonyl and —NH—;

R$^{13}$ is hydrogen or lower alkyl; and

R$^{14}$ and R$^{15}$ are independently selected from the group consisting of hydrogen, alkyl and, combined, cycloalkyl and cycloalkenyl;

or a pharmaceutically acceptable salt or hydrate of said compound.

Preferably, in the formula (2), Ar$_3$ is selected from the groups consisting of unsubstituted phenyl, phenyl substituted with one or more groups selected from the group consisting of unsubstituted lower alkyl, lower alkyl substituted with one or more halogens, halogen, unsubstituted lower alkoxy, lower alkoxy substituted with one or more halogens, nitro, dimethylamino and unsubstituted phenyl, and optionally substituted naphthyl; and Ar$_4$ is selected from the groups consisting of unsubstituted phenyl, phenyl substituted with one or more groups selected from the group consisting of unsubstituted lower alkyl, lower alkyl substituted with one or more halogens, unsubstituted lower alkoxy, lower alkoxy substituted with one or more halogens, and halogen, and optionally substituted naphthyl.

In another aspect, the present invention provides a compound of the formula:

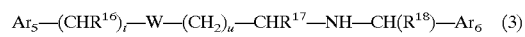

wherein:

Ar$_5$ is aryl, dicyclic or tricyclic heteroaryl, arylmethyl (arylmethyl)amino, heteroarylmethy(heteroarylmethyl)

amino or arylmethyl(heteroarylmethyl)amino optionally substituted with one or more groups independently selected from the group consisting of unsubstituted lower alkyl, unsubstituted lower alkenyl, halogen, hydroxy, unsubstituted lower alkoxy, unsubstituted lower thicalkoxy, lower alkyl substituted with one or more halogens, lower alkenyl substituted with one or more halogens, lower alkoxy substituted with one or more halogens, nitro, formyl, acetoxy, acetyl, —CH$_2$OH, CH$_3$CH(OH)—, —C(=O)NH$_2$, cyano, —N(unsubstituted lower alkyl)$_2$, phenyl, phenoxy, benzyl, benzyloxy, α,α-dimethylbenzyl, methylenedioxy, ethylenedioxy and —OCH$_2$COOH;

Ar$_6$ is aryl or dicyclic or tricyclic heteroaryl optionally substituted with one or more groups independently selected from the group consisting of unsubstituted lower alkyl, lower alkyl substituted with one or more halogens, unsubstituted lower alkenyl, lower alkenyl substituted with one or more halogens, unsubstituted lower alkoxy, lower alkoxy substituted with one or more halogens, halogen, hydroxy, unsubstituted lower thioalkoxy, lower thioalkoxy substituted with one or more halogens, benzyloxy, methylenedioxy, ethylenedioxy, acetoxy, —OCH$_2$COOH, —C(=O)NH$_2$, cyano, and —CH$_2$OH;

t is 0 or 1;

u is an integer of from 0 to 11, inclusive;

W is selected from.the group consisting of oxygen, sulfur, sulfinyl, sulfonyl, carbonyl and amino;

R$^{16}$ and R$^{17}$ are H or unsubstituted lower alkyl; and

R$^{18}$ is unsubstituted lower alkyl;

or a pharmaceutically acceptable salt or hydrate of said compound.

Preferably, in the formula (3), Ar$_5$ is phenyl, indole, benzothiazole, benzoxazole, dibenzofuran, carbazole, pyridine, fluorene, quinoline, naphthalene, chromenone, tetrahydrobenzothiazepine, dibenzylamino, benzyl (naphthylmethyl)amino, benzyl(pyridylmethyl)amino, thienylmethyl(benzyl)amino, furylmethyl(benzyl)amino or N-alkyl-pyrrolylmethyl(benzyl)amino optionally substituted with one or more groups independently selected from the group consisting of unsubstituted lower alkyl, halogen, unsubstituted lower alkoxy, lower alkyl substituted with one or more halogens, lower alkoxy substituted with one or more halogens, nitro, dimethylamino and unsubstituted phenyl; and Ar$_6$ is thiophene, furan, pyrrole, phenyl, naphthalene, pyridine, pyrazine or thiazole optionally substituted with one or more groups independently selected from the group consisting of unsubstituted lower alkyl, halogen, unsubstituted lower alkoxy, lower alkyl substituted with one or more halogens, lower alkoxy substituted with one or more halogens, hydroxy and benzyloxy optionally substituted with halogen or methyl. More preferably, Ar$_5$ is selected from the group consisting of phenyl optionally substituted with one or more groups independently selected from the group consisting of unsubstituted lower alkyl, halogen, unsubstituted lower alkoxy, lower alkyl substituted with one or more halogens and lower alkoxy substituted with one or more halogens; and Ar$_6$ is 3-methoxyphenyl or α-naphthyl, more preferably, α-naphthyl. Also preferably, Ar$_5$ is dibenzylamino, benzyl (naphthylm ethyl) amino or benzyl (pyridylmethyl)amino optionally substituted with one or more groups independently selected from the group consisting of unsubstituted lower alkyl, halogen, unsubstituted lower alkoxy, lower alkyl substituted with one or more halogens and lower alkoxy substituted with one or more halogens, and Ar$_6$ is naphthyl or methoxyphenyl. More preferably, Ar$_5$ is dibenzylamino optionally substituted with unsubstituted alkyl, and Ar$_6$ is α-naphthyl.

Preferably, the compound of the present invention represented by the formulae (1), (2) or (3) is the R enantiomer. The present invention also provides a prodrug of any of the compounds described above.

The present invention provides a method for modulating calcium receptor activity by using a compound described herein. The featured compounds preferably modulate an interaction of Ca$^{2-}$ with Ca$^{2+}$ receptors by mimicking (including potentiating) the effect of Ca$^{2+}$ on a Ca$^{2+}$ receptor (calcimimetic modulation) or blocking the effect of Ca$^{2+}$ on a Ca$^{2+}$ receptor (calcilytic modulation); preferably calcimimetic modulation.

Also provided is a method for the treatment in a patient of disorders characterized by an abnormal concentrations of one or more inorganic ions or other physiological biochemical substances, the concentration of which is regulated by an activity of one or more calcium receptors. In particular, treatment using the compounds disclosed hereof is contemplated for disorders characterized by abnormal extracellular Ca$^{2+}$ concentration ([Ca$^{2+}$]) or abnormal intracellular Ca$^{2+}$ concentration ([Ca$^{2+}$]$_i$) in one or more cells including for example, but without limitation, parathyroid cells, bone osteoclasts, juxtaglomerular kidney cells, proximal tubule kidney cells, keratinocytes, parafollicular thyroid cells and placental trophoblasts.

An "abnormal" state is characterized by a level of a property that is statistically different from the level of that property observed in patients not suffering from a particular disorder. Thus, for example, the term "abnormal" as it relates to inorganic ion concentrations refers to a concentration of the ion in question which would be recognized by members of the medical community as being outside the normal range of such ion concentration in healthy patients.

As used herein, the terms "treat", "treating" and "treatment" refer to a method of alleviating, abrogating, and/or having a prophylactic effect with regard to, a disease or disorder and/or one or more, preferably all, its attendant symptoms.

In another aspect, the present invention provides a method for the treatment or prevention of primary and secondary hyperparathyroidism, renalosteodystrophy, hypercalcemia malignancy, osteoporosis, Paget's disease and hypertension comprising administering a therapeutically effective amount of a compound of this invention to a patient.

The term "administering" as used herein refers to a method for introducing a compound of this invention in vitro or in vivo. Thus, for example, the importance of inorganic ion receptor activity can be studied and associated diseases and disorders prevented or treated by the compounds and methods set forth herein. Cells existing outside the organism can be maintained or grown in cell culture dishes. In this context, the ability of a particular compound to affect an inorganic ion receptor activity can be determined; i.e., the IC50 or EC50, preferably the EC50, of a compound, defined below, before the use of the compounds in complex multicellular living organisms such as a human is attempted. For cells outside the organism, multiple methods exist, and are well-known to those skilled in the arts, to administer compounds including, but not limited to, cell micro-injection, transformation and numerous carrier techniques.

For cells harbored within a multicellular living organism, myriad methods also exist, and are likewise well-known to those skilled in the art, to administer compounds including, but not limited to, oral, parenteral, dermal, injection and aerosol applications.

The present invention features a method for the modulation of one or more activities of an inorganic ion receptor using the compounds disclosed herein. Preferably, the inorganic ion receptor is a $Ca^{2+}$ receptor. The compounds of this invention can either mimic (including potentiation) or block the effect of extracellular $Ca^{2+}$ on a calcium receptor. The preferred use of such compounds is to treat selected disorders by modulating the inorganic ion receptor activity. In particular the compounds of this invention can be used to treat the indicated disorders by modulating $Ca^{2+}$ receptor activity.

Extracellular $Ca^{2+}$ is under tight homeostatic control and controls various processes such as blood clotting, nerve and muscle excitability, and proper bone formation. Calcium receptor proteins enable certain specialized cells to respond to changes in extracellular $Ca^{2+}$ concentration. For example, extracellular $Ca^{2+}$ inhibits the secretion of parathyroid hormone from parathyroid cells, inhibits bone resorption by osteoclasts, and stimulates secretion of calcitonin from C-cells.

Compounds modulating inorganic ion receptor activity can be used to treat diseases or disorders by affecting one or more activities of an inorganic ion receptor resulting in a beneficial effect to the patient. For example, osteoporosis is an age related disorder characterized by loss of bone mass and increased risk of bone fracture. Compounds blocking osteoclastic bone resorption either directly (e.g., a osteoclast ionmimetic compound) or indirectly by increasing endogenous calcitonin levels (e.g., a C-cell ionmimetic), and/or by decreasing parathyroid hormone levels (e.g., a parathyroid cell ionmimetic). can retard bone loss and, thus, result in beneficial effects to patients suffering from osteoporosis.

In addition, it is known that intermittent low dosing with PTH results in an anabolic effect on bone mass and appropriate bone remodeling. Thus, compounds and dosing regiments evoking transient increases in parathyroid hormone (e.g., intermittent dosing with a parathyroid cell ionlytic) can increase bone mass in patients suffering from osteoporosis.

Additionally, diseases or disorders characterized by a defect in one or more inorganic ion receptor activities may be treated by the present invention. For example, certain forms of primary hyperparathyroidism are characterized by abnormally high levels of parathyroid hormone and decreased parathyroid gland responsiveness to circulating calcium. Calcium receptor modulating agents can be used to modulate parathyroid cell responsiveness to calcium.

Preferably, the compound modulates calcium receptor activity and is used in the treatment of diseases or disorders which can be affected by modulating one or more activities of a calcium receptor. Preferably, the disease or disorder is characterized by abnormal bone and mineral homeostasis, more preferably calcium homeostasis.

Abnormal calcium homeostasis is characterized by one or more of the following activities: (1) an abnormal increase or decrease in serum calcium; (2) an abnormal increase or decrease in urinary excretion of calcium; (3) an abnormal increase or decrease in bone calcium levels, for example, as assessed by bone mineral density measurements; (4) an abnormal absorption of dietary calcium; and (5) an abnormal increase or decrease in the production and/or release of circulating messengers or hormones which affect calcium homeostasis such as parathyroid hormone and calcitonin. The abnormal increase or decrease in these different aspects of calcium homeostasis is relative to that occurring in the general population and is generally associated with a disease or disorder.

More generally, a molecule which modulates the activity of an inorganic ion receptor is useful in the treatment of diseases characterized by abnormal inorganic ion homeostasis. Preferably, the molecule modulates one or more effects of an inorganic ion receptor. Inorganic ion receptor modulating agents include ionmimetics, ionlytics, calcimimetics, and calcilytics.

Ionmimetics are molecules which mimic the effects of increasing ion concentration at an inorganic ion receptor. Preferably, the molecule affects one or more calcium receptor activities. Calcimimetics are ionmimetics which affect one or more calcium receptor activities and preferably binds to a calcium receptor.

Ionlytics are molecules which reduce or block one or more activities caused by an inorganic ion on an inorganic ion receptor. Preferably, the molecule inhibits one or more calcium receptor activities. Calcilytics are ionlytics which inhibit one or more calcium receptor activities evoked by extracellular calcium and preferably bind to a calcium receptor.

Inorganic ion receptor modulating agents can be formulated as pharmacological agents or compositions to facilitate administration in a patient. Pharmacological agents or compositions are agents or compositions in a form suitable for administration into a mammal, preferably a human. considerations concerning forms suitable for administration are known in the art and include toxic effects, solubility, route of administration, and maintaining activity.

Other aspects of the present invention feature methods for using the agents described herein for treating diseases or disorders by modulating inorganic ion receptor activity. Patients in need of such treatments can be identified by standard medical techniques, such as routine blood analysis. For example, by detecting a deficiency of protein whose production or secretion is affected by changes in inorganic ion concentrations, or by detecting abnormal levels of inorganic ions or hormones which effect inorganic ion homeostasis.

Therapeutic methods involve administering to the patient a therapeutically effective amount of an inorganic ion receptor modulating agent. In preferred embodiments these methods are used to treat a disease or disorder characterized by abnormal inorganic ion homeostasis, more preferably a disease or disorder characterized by abnormal calcium homeostasis. Diseases and disorders characterized by abnormal calcium homeostasis include hyperparathyroidism, osteoporosis, renalosteodystrophy and other bone and mineral-related disorders, and the like (as described, e.g., in standard medical text books, such as "Harrison's Principles of Internal Medicine"). Such diseases and disorders are treated using calcium receptor modulating agents which mimic or block one or more of the effects of $Ca^{2+}$ and, thereby, directly or indirectly affect the levels of proteins or other molecules in the body of the patient.

By "therapeutically effective amount" is meant an amount of an agent which relieves to some extent one or more symptoms of the disease or disorder in the patient; or returns to normal either partially or completely one or more physiological or biochemical parameters associated with or causative of the disease or disorder.

In a preferred embodiment, the patient has a disease or disorder characterized by an abnormal level of one or more calcium receptor regulated components and the molecule is active on a calcium receptor of a cell selected from the group consisting of parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

More preferably, the cell is a parathyroid cell and the molecule reduces the level of parathyroid hormone in the serum of the patient, even more preferably the level is reduced to a degree sufficient to cause a decrease in plasma $Ca^{2+}$, most preferably the parathyroid hormone level is reduced to that present in a normal individual.

Thus, the present invention features agents and methods useful in the treatment of diseases and disorders by modulating inorganic ion receptor activity. For example, the molecules of the present invention can be used to target calcium receptors on different cell types that detect and respond to changes to external calcium. For example, molecules mimicking external calcium may be used to selectively depress secretion of parathyroid hormone from parathyroid cells, or depress bone resorption by osteoclasts, or stimulate secretion of calcitonin from C-cells. Such molecules can be used to treat diseases or disorders characterized by abnormal calcium homeostasis such as hyperparathyroidism, renalosteodystrophy and osteoporosis.

Other features and advantages of the invention will be apparent from the following description of the preferred embodiments thereof and from the claims.

PREFERRED EMBODIMENTS OF THE INVENTION

Figure 1:
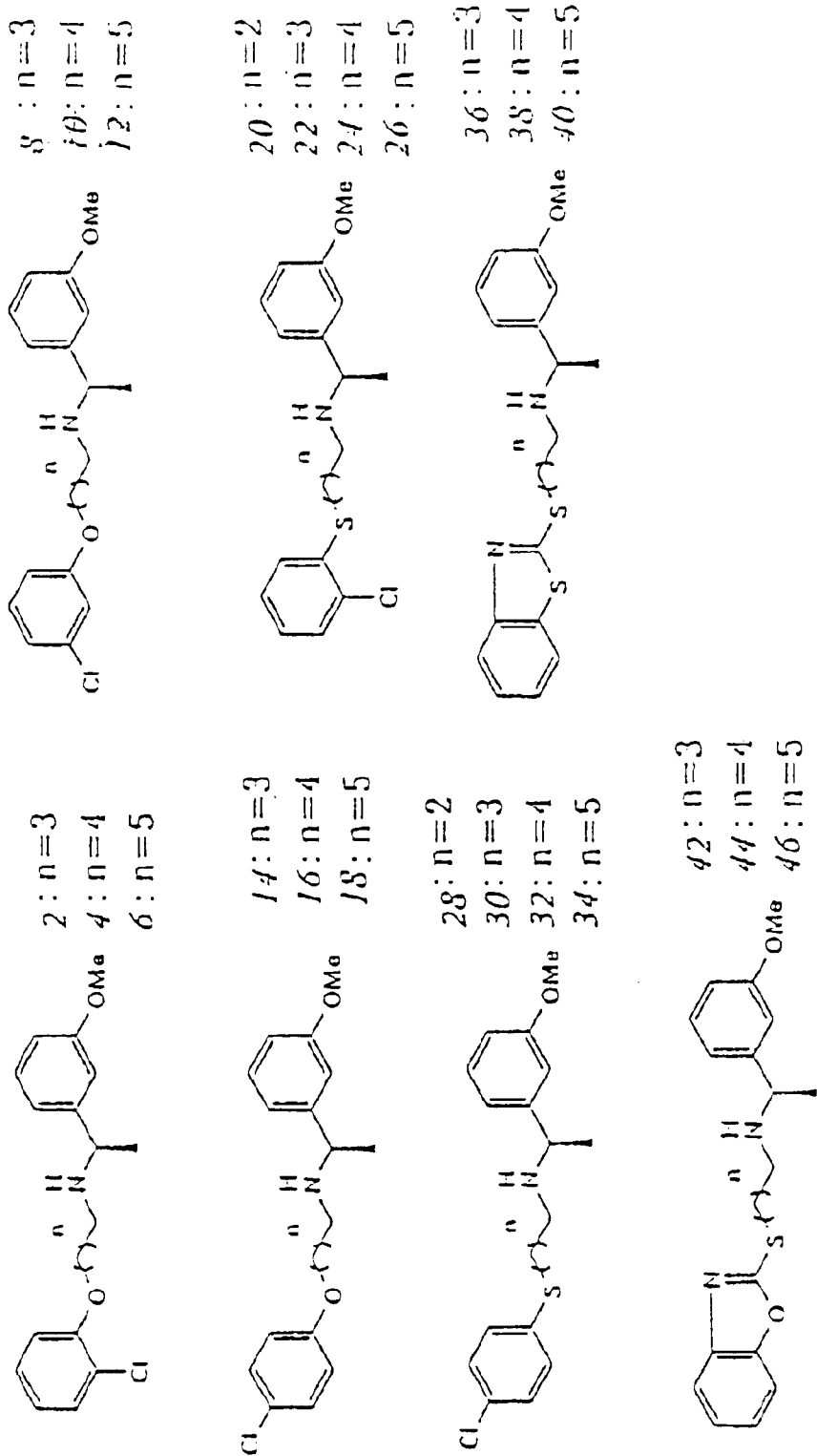
FIG. 1 shows the structures of the compounds of the present invention synthesized in Examples 1 to 23.

The present invention describes inorganic ion receptor modulating agents able to mimic or block an effect of an inorganic ion at an inorganic ion receptor. The preferred use of inorganic ion receptor modulating agents is to treat a disease or disorder by modulating inorganic ion receptor activity. Preferably, the molecules are used to treat diseases or disorders characterized by abnormal ion homeostasis, more preferably abnormal calcium homeostasis. Other uses of inorganic ion receptor modulating agents, such as diagnostics uses, are known in the art. Nemeth et al., PCT/US93/01642, International Publication Number WO 94/18959.

I. Calcium Receptors

Calcium receptors and nucleic acid encoding calcium receptors are described by Nemeth et al., PCT/US93/01642, International Publication Number WO 94/18959. Calcium receptors are present on different cell types such as parathyroid cell, bone osteoclast, juxtaglomerular kidney cell, proximal tubule kidney cell, distal tubule kidney cell, central nervous system cell, peripheral nervous system cell, cell of the thick ascending limb of Henle's loop and/or collecting duct, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, and GI tract cell. The calcium receptor on these cell types may be different. It is also possible that a cell can have more than one type of calcium receptor.

Comparison of calcium receptor activities and amino acid sequences from different cells indicate that distinct calcium receptor types exist. For example, calcium receptors can respond to a variety of di- and trivalent cations. The parathyroid calcium receptor responds to calcium and $Gd^{3+}$, while osteoclasts respond to divalent cations such as calcium but does not respond to $Gd^{3+}$. Thus, the parathyroid calcium receptor is pharmacologically distinct from calcium receptor on the osteoclast.

On the other hand, the nucleic acid sequences encoding calcium receptors present in parathyroid cells and C-cells indicate that these receptors have a very similar amino acid structure. Nevertheless, calcimimetic compounds exhibit differential pharmacology and regulate different activities at parathyroid cells and C-cells. Thus, pharmacological properties of calcium receptors may vary significantly depending upon the cell type or organ in which they are expressed even though the calcium receptors may have similar structures.

Calcium receptors, in general, have a low affinity for extracellular $Ca^{2+}$ (apparent $K_d$ generally greater than about 0.5 mM). Calcium receptors may include a free or bound effector mechanism as defined by Cooper, Bloom and Roth, "The Biochemical Basis of Neuropharmacology", Ch. 4, and are thus distinct from intracellular calcium receptors, e.g., calmodulin and the troponins.

Calcium receptors respond to changes in extracellular calcium levels. The exact changes depend on the particular receptor and cell line containing the receptor. For example, the in vitro effect of calcium on the calcium receptor in a parathyroid cell include the following:

1. An increase in internal calcium. The increase is due to the influx of external calcium and/or mobilization of internal calcium. Characteristics of the increase in internal calcium include the following:
   (a) A rapid (time to peak <5 seconds) and transient increase in $[Ca^{2+}]_i$, that is refractory to inhibition by 1 mM $La^{3+}$ or 1 mM $Gd^{3+}$ and is abolished by pretreatment with ionomycin (in the absence of extracellular $Ca^{2+}$);
   (b) The increase is not inhibited by dihydropyridines;
   (c) The transient increase is abolished by pretreatment for 10 minutes with 10 mM sodium fluoride;
   (d) The transient increase is diminished by pretreatment with an activator of protein kinase C (PKC), such as phorbol myristate acetate (PMA), mezerein or (−)-indolactam V. The overall effect of the protein kinase C activator is to shift the concentration-response curve to calcium to the right without affecting the maximal response; and
   (e) Treatment with pertussis toxin (100 ng/ml for >4 hours) does not affect the increase.
2. A rapid (<30 seconds) increase in the formation of inositol-1,4,5-triphosphate or diacylglycerol. Treatment with pertussis toxin (100 ng/ml for >4 hours) does not affect this increase;
3. The inhibition of dopamine- and isoproterenol-stimulated cyclic AMP formation. This effect is blocked by pretreatment with pertussis toxin (100 ng/ml for >4 hours); and
4. The inhibition of PTH secretion. Treatment with pertussis toxin (100 ng/ml for >4 hours) does not affect the inhibition in PTH secretion.

Using techniques known in the art, the effect of calcium on other calcium receptors in different cells can be readily determined. Such effects may be similar in regard to the increase in internal calcium observed in parathyroid cells. However, the effect is expected to differ in other aspects, such as causing or inhibiting the release of a hormone other than parathyroid hormone.

II. Inorganic Ion Receptor Modulating Agents

Inorganic ion receptor modulating agents either evokes one or more inorganic ion receptor activities, or blocks one or more inorganic ion receptor activities caused by an extracellular inorganic ion. Calcium receptor modulating agents can mimic or block an effect of extracellular $Ca^{2+}$ on a calcium receptor. Preferred calcium receptor modulating agents are calcimimetics and calcilytics.

Inorganic ion receptor modulating agents can be identified by screening molecules which are modeled after a molecule shown to have a particular activity (i.e., a lead molecule). Nemeth et al., PCT/US93/01642, International Publication Number WO 94/18959.

Preferred inorganic ion receptor modulation agents described by the present invention have considerably low $EC_{50}$ values.

The $EC_{50}$ is the concentration of the molecule which evokes a half-maximal effect. The $IC_{50}$ is the concentration of molecule which causes a half-maximal blocking effect. The $EC_{50}$ or $IC_{50}$ can be determined by assaying one or more of the activities of an inorganic ion at an inorganic ion receptor. Preferably, such assays are specific to a particular calcium receptor. For example, assays which measure hormones whose production or secretion is modulated by a particular inorganic ion receptor are preferred.

Increases in $[Ca^{2+}]_i$ can be detected using standard techniques such as by using fluorimetric indicators or by measuring an increase in $Cl^-$ current in a Xenopus oocyte injected with nucleic acid coding for a calcium receptor. Nemeth et al., PCT/US93/01642, International Publication Number WO 94/18959. For example, poly(A)$^+$ mRNA can be obtained from cells expressing a calcium receptor, such as a parathyroid cell, bone osteoclast, juxtaglomerular kidney cell, proximal tubule kidney cell, distal tubule kidney cell, cell of the thick ascending limb of Henle's loop and/or collecting duct, keratinocyte in the epidermis, parafollicular cell in the thyroid (C-cell), intestinal cell, central nervous system cell, peripheral nervous system cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell, and GI tract cell. Preferably, the nucleic acid is from a parathyroid cell, C-cell, or osteoclast. More preferably, the nucleic acid encodes a calcium receptor and is present on a plasmid or vector.

Preferably, the molecule is either a calcimimetic or calcilytic having an $EC_{50}$ or $IC_{50}$ at a calcium receptor of less than or equal to 5 mM, and even more preferably less than or equal to 1 mM, 100 nmolar, 10 nmolar, or 1 nmolar. Such lower $EC_{50}$'s or $IC_{50}$'s are advantageous since they allow lower concentrations of molecules to be used in vivo or in vitro for therapy or diagnosis. The discovery of molecules with such low $EC_{50}$'s and $IC_{50}$'s enables the design and synthesis of additional molecules having similar potency and effectiveness.

In preferred embodiments the calcium receptor modulating agent is a calcimimetic which inhibits parathyroid hormone secretion from a parathyroid cell in vitro and decreases PTH secretion in vivo; stimulates calcitonin secretion from a C-cell in vitro and elevates calcitonin levels in vivo; or blocks osteoclastic bone resorption in vitro and inhibits bone resorption in vivo.

In another preferred embodiment the calcium receptor modulating agent is a calcilytic which evokes the secretion of parathyroid hormone from parathyroid cells in vitro and elevates the level of parathyroid hormone in vivo.

Preferably, the agent selectively targets inorganic ion receptor activity, more preferably calcium receptor activity, in a particular cell. By "selectively" is meant that the molecule exerts a greater effect on inorganic ion receptor activity in one cell type than at another cell type for a given concentration of agent. Preferably, the differential effect is 10-fold or greater. Preferably, the concentration refers to blood plasma concentration and the measured effect is the production of extracellular messengers such as plasma calcitonin, parathyroid hormone or plasma calcium. For example, in a preferred embodiment, the agent selectively targets PTH secretion over calcitonin secretion.

In another preferred embodiment, the molecule has an $EC_{50}$ or $IC_{50}$ less than or equal to 1 mM at one or more, but not all cells chosen from the group consisting of parathyroid cell, bone osteoclast, juxtaglomerular kidney cell, proximal tubule kidney cell, distal tubule kidney cell, cell of the thick ascending limb of Henle's loop and/or collecting duct, central nervous system cell, peripheral nervous system cell, keratinocyte in the epidermis, parafollicular cell in the thyroid (C-cell), intestinal cell, trophoblast in the placenta, platelet, vascular smooth muscle cell, cardiac atrial cell, gastrin-secreting cell, glucagon-secreting cell, kidney mesangial cell, mammary cell, beta cell, fat/adipose cell, immune cell and GI tract cell.

Preferably, inorganic ion receptor modulating agents mimic or block all of the effects of extracellular ion in a cell having an inorganic ion receptor. For example, calcium receptor modulating agents preferably mimic or block all of the effects of extracellular ion in a cell having a calcium receptor. Calcimimetics need not possess all the biological activities of extracellular $Ca^{2+}$, but, rather, at least one such activity is mimicked. Similarly, calcilytics need not reduce or prevent all of the activities caused by extracellular calcium. Additionally, different calcimimetics and different calcilytics do not need to bind to the same site on the calcium receptor as does extracellular $Ca^{2+}$ to exert their effects.

A. Calcimimetics

The ability of molecules to mimic or block the activity of $Ca^{2+}$ at calcium receptors can be determined using procedures known in the art and described by Nemeth et al., PCT/US93/01642, International Publication Number WO 94/18959. For example, calcimimetics possess one or more and preferably all of the following activities when tested on parathyroid cells in vitro:

1. The molecule causes a rapid (time to peak <5 seconds) and transient increase in $[Ca^{2+}]_i$ that is refractory to inhibition by 1 mM $La^{3+}$ or 1 mM $Gd^{3+}$. The increase in $[Ca^{2+}]_i$ persists in the absence of extracellular $Ca^{2+}$ but is abolished by pretreatment with ionomycin (in the absence of extracellular $Ca^{2+}$);
2. The molecule potentiates increases in $[Ca^{2+}]_i$ elicited by submaximal concentrations of extracellular $Ca^{2+}$;
3. The increase in $[Ca^{2+}]_i$ elicited by extracellular $Ca^{2+}$ is not inhibited by dihydropyridines;
4. The transient increase in $[Ca^{2+}]_i$ caused by the molecule is abolished by pretreatment for 10 minutes with 10 mM sodium fluoride;
5. The transient increase in $[Ca^{2+}]_i$ caused by the molecule is diminished by pretreatment with an activator of protein kinase C (PKC), such as phorbol myristate acetate (PMA), mezerein or (−)-indolactam V. The overall effect of the protein kinase C activator is to shift the concentration-response curve of the molecule to the right without affecting the maximal response;
6. The molecule causes a rapid (<30 seconds) increase in the formation of inositol-1,4,5-triphosphate and/or diacylglycerol;

7. The molecule inhibits dopamine- or isoproterenol-stimulated cyclic AMP formation;
8. The molecule inhibits PTH secretion;
9. Pretreatment with pertussis toxin (100 ng/ml for >4 hours) blocks the inhibitory effect of the molecule on cyclic AMP formation but does not effect increases in $[Ca^{2+}]_i$, inositol-1,4,5-triphosphate, or diacylglycerol, nor decreases in PTH secretion;
10. The molecule elicits increases in Cl⁻ current in Xenopus oocytes injected with poly (A)⁺-enriched mRNA from bovine or human parathyroid cells, but is without effect in Xenopus oocytes injected with water, or rat brain or liver mRNA; and
11. Similarly, using a cloned calcium receptor from a parathyroid cell, the molecule will elicit a response in Xenopus oocytes injected with the specific cDNA or mRNA encoding the receptor.

Different calcium activities can be measured using available techniques. Nemeth et al., PCT/US93/01642, International Publication Number WO 94/18959. Parallel definitions of molecules mimicking $Ca^{2+}$ activity on other calcium responsive cell, preferably at a calcium receptor, are evident from the examples provided herein and Nemeth et al., PCT/US93/01642, International Publication Number WO 94/18959.

Preferably, the agent as measured by the bioassays described herein, or by Nemeth et al., PCT/US93/01642, International Publication Number WO 94/18959, has one or more, more preferably all of the following activities: evokes a transient increase in internal calcium, having a duration of less that 30 seconds (preferably by mobilizing internal calcium); evokes a rapid increase in $[Ca^{2+}]_i$, occurring within thirty seconds; evokes a sustained increase(greater than thirty seconds) in $[Ca^{2+}]_i$ (preferably by causing an influx of external calcium); evokes an increase in inositol-1,4,5-triphosphate or diacylglycerol levels, preferably within less than 60 seconds; and inhibits dopamine- or isoproterenol-stimulated cyclic AMP formation.

The transient increase in $[Ca^{2+}]_i$ is preferably abolished by pretreatment of the cell for ten minutes with 10 mM sodium fluoride, or the transient increase is diminished by brief pretreatment (not more than ten minutes) of the cell with an activator of protein kinase C, preferably, phorbol myristate acetate (PMA), mezerein or (−)-indolactam V.

B. Calcilytics

The ability of a molecule to block the activity of external calcium can be determined using standard techniques. Nemeth et al., PCT/US93/01642, International Publication Number WO 94/18959. For example, molecules which block the effect of external calcium, when used in reference to a parathyroid cell, possess one or more, and preferably all of the following characteristics when tested on parathyroid cells in vitro:
1. The molecule blocks, either partially or completely, the ability of increased concentrations of extracellular $Ca^{2+}$ to:
   (a) increase $[Ca^{2+}]_i$
   (b) mobilize intracellular $Ca^{2+}$,
   (c) increase the formation of inositol-1,4,5-triphosphate,
   (d) decrease dopamine- or isoproterenol-stimulated cyclic AMP formation, and
   (e) inhibit PTH secretion;
2. The molecule blocks increases in Cl⁻ current in Xenopus oocytes. injected with poly (A)⁺ mRNA from bovine or human parathyroid cells elicited by extracellular $Ca^{2+}$ or calcimimetic compounds, but not in Xenopus oocytes injected with water or liver mRNA;
3. Similarly, using a cloned calcium receptor from a parathyroid cell, the molecule will block a response in Xenopus oocytes injected with the specific cDNA, mRNA or cRNA encoding the calcium receptor, elicited by extracellular $Ca^{2+}$ or a calcimimetic compound.

Parallel definitions of molecules blocking $Ca^{2+}$ activity on a calcium responsive cell, preferably at a calcium receptor, are evident from the examples provided herein and Nemeth et al., PCT/US93/01642, International Publication Number WO 94/18959.

III. Treatment of Diseases or Disorders

A preferred use of the compounds described by the present invention is in the treatment or prevention of different diseases or disorders by modulating inorganic ion receptor activity. The inorganic ion receptor modulating agents of the present invention can exert an affect on a inorganic ion receptor causing one or more cellular effects ultimately producing a therapeutic effect.

Different diseases and disorders can be treated by the present invention by targeting cells having an inorganic ion receptor, such as a calcium receptor. For example, primary hyperparathyroidism (HPT) is characterized by hypercalcemia and elevated levels of circulating PTH. A defect associated with the major type of HPT is a diminished sensitivity of parathyroid cells to negative feedback regulation by extracellular $Ca^{2+}$. Thus, in tissue from patients with primary HPT, the "set-point" for extracellular $Ca^{2+}$ is shifted to the right so that higher than normal concentrations of extracellular $Ca^{2+}$ are required to depress PTH secretion. Moreover, in primary HPT, even high concentrations of extracellular $Ca^{2+}$ often depress PTH secretion only partially. In secondary (uremic) HPT, a similar increase in the set-point for extracellular $Ca^{2+}$ is observed even though the degree to which $Ca^{2+}$ suppresses PTH secretion is normal. The changes in PTH secretion are paralleled by changes in $[Ca^{2+}]_i$: the set-point for extracellular $Ca^{2+}$-induced increases in $[Ca^{2+}]_i$ is shifted to the right and the magnitude of such increases is reduced.

Molecules that mimic the action of extracellular $Ca^{2+}$ are beneficial in the long-term management of both primary and secondary HPT. Such molecules provide the added impetus required to suppress PTH secretion which the hypercalcemic condition alone cannot achieve and, thereby, help to relieve the hypercalcemic condition. Molecules with greater efficacy than extracellular $Ca^{2+}$ may overcome the apparent nonsuppressible component of PTH secretion which is particularly troublesome in adeiomatous tissue. Alternatively or additionally, such molecules can depress synthesis of PTH, as prolonged hypercalcemia has been shown to depress the levels of preproPTH mRNA in bovine and human adenomatbus parathyroid tissue. Prolonged hypercalcemia also depresses parathyroid cell proliferation in vitro, so calcimimetics can also be effective in limiting the parathyroid cell hyperplasia characteristic of secondary HPT.

Cells other than parathyroid cells can respond directly to physiological changes in the concentration of extracellular $Ca^{2+}$. For example, calcitonin secretion from parafollicular cells in the thyroid (C-cells) is regulated by changes in the concentration of extracellular $Ca^{2+}$.

Isolated osteoclasts respond to increases in the concentration of extracellular $Ca^{2+}$ with corresponding increases in $[Ca^{2+}]_i$ that arise partly from the mobilization of intracellular $Ca^{2+}$. Increases in $[Ca^{2+}]_i$ in osteoclasts are associated with the inhibition of bone resorption. Release of alkaline phosphatase from bone-forming osteoblasts is directly stimulated by calcium.

Renin secretion from juxtaglomerular cells in the kidney, like PTH secretion, is depressed by increased concentrations of extracellular $Ca^{2+}$. Extracellular $Ca^{2+}$ causes the mobilization of intracellular $Ca^{2+}$ in these cells. Other kidney cells respond to calcium as follows: elevated $Ca^{2+}$ inhibits formation of $1,25(OH)_2$-vitamin D by proximal tubular cells, stimulates production of calcium-binding protein in distal tubular cells, and inhibits tubular reabsorption of $Ca^{2+}$ and $Mg^{2+}$ and the action of vasopressin on the medullary thick ascending limb of Henle's loop (MTAL), reduces vasopressin action in the cortical collecting duct cells, and affects vascular smooth muscle cells in blood vessels of the renal glomerulus.

Calcium also promotes the differentiation of intestinal goblet cells, mammary cells, and skin cells; inhibits atrial natriuretic peptide secretion from cardiac atria; reduces cAMP accumulation in platelets; alters gastrin and glucagon secretion; acts on vascular smooth muscle cells to modify cell secretion of vasoactive factors; and affects cells of the central nervous system and peripheral nervous system.

Thus, there are sufficient indications to suggest that $Ca^{2+}$, in addition to its ubiquitous role as an intracellular signal, also functions as an extracellular signal to regulate the responses of certain specialized cells. Molecules of this invention can be used in the treatment of diseases or disorders associated with disrupted $Ca^{2+}$ responses in these cells.

Specific diseases and disorders which might be treated or prevented, based upon the affected cells, also include those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney such as syndrome of inappropriate ADH secretion (SIAH), cirrhosis, heart failure, and nephrosis; hypertension; preventing and/or decreasing renal toxicity from cationic antibiotics (e.g., aminoglycoside antibiotics); gut motility disorders such as diarrhea, and spastic colon; GI ulcer diseases; GI absorption diseases such as sarcoidosis; and autoimmune diseases and organ transplant rejection.

While inorganic ion receptor modulating agents of the present invention will typically be used in therapy for human patients, they may be used to treat similar or identical diseases or disorders in other warm-blooded animal species such as other primates, farm animals such as swine, cattle, and poultry; and sports animals and pets such as horses, dogs and cats.

IV. Administration

A compound of the present invention, or its pharmaceutically acceptable salt, hydrate or prodrug, can be administered to a human patient per se, or in pharmaceutical compositions where it is mixed with suitable carriers or excipient(s). Techniques for formulation and administration of drugs may be found in "Remington's Pharmaceutical Sciences," Mack Publishing Co., Easton, Pa., latest edition. Administration of ionmimetics and ionlytics is discussed by Nemeth, et al., PCT/US93/01642, International Publication No. WO 94/18959.

A "pharmaceutical composition" refers to a mixture of one or more of the compounds described herein, or pharmaceutically acceptable salts, hydrates or prodrugs thereof, with other chemical components, such as physiologically acceptable carriers and excipients. The purpose of a pharmacological composition is to facilitate administration of a compound to an organism.

A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxylic acid once inside the cell where water solubility is beneficial.

As used herein, an "ester" is a carboxyl group, as defined herein, wherein R" is any of the listed groups other than hydrogen.

As used herein, a "physiologically acceptable carrier" refers to a carrier or diluent that does not cause significant irritation to an organism and does not abrogate the biological activity and properties of the administered compound.

An "excipient" refers to an inert substance added to a pharmacological composition to further facilitate administration of a compound. Examples, without limitation, of excipients include calcium carbonate, calcium phosphate, various sugars and types of starch, cellulose derivatives, gelatin, vegetable oils and polyethylene glycols.

Suitable forms, in part, depend upon the use or the route of entry, for example oral, transdermal, or by injection. Such forms should allow the agent to reach a target cell whether the target cell is present in a multicellular host or in culture. For example, pharmacological agents or compositions injected into the blood stream should be soluble in the concentrations used. Other factors are known in the art, and include considerations such as toxicity and forms which prevent the agent or composition from exerting its effect.

Agents can also be formulated as pharmaceutically acceptable salts (e.g., acid addition salts) and complexes thereof. The preparation of such salts can facilitate the pharmacological use by altering the physical characteristics of the agent without preventing it from exerting its physiological effect. Examples of useful alterations in physical properties include lowering the melting point to facilitate transmucosal administration and increasing the solubility to facilitate administering higher concentrations of the drug.

For systemic administration, oral administration is preferred. Alternatively, injection may be used, e.g., intramuscular, intravenous, intraperitoneal, and subcutaneous. For injection, the molecules of the invention are formulated in liquid solutions, preferably in physiologically compatible buffers such as Hank's solution or Ringer's solution. In addition, the molecules may be formulated in solid form and redissolved or suspended immediately prior to use. Lyophilized forms can also be produced.

Systemic administration can also be by transmucosal or transdermal means, or the molecules can be administered orally. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration may be through nasal sprays, for example, or using suppositories. For oral administration, the molecules are formulated into conventional oral administration dosage forms such as capsules, tablets, and tonics.

For topical administration, the molecules of the invention are formulated into ointments, salves, gels, or creams, as is generally known in the art.

Generally, a therapeutically effective amount is between about 1 nmole and 3 mmole of the molecule, preferably 0.1 nmole and 1 mmole depending on its $EC_{50}$ or $IC_{50}$ and on the age and size of the patient, and the disease or disorder associated with the patient. Generally it is an amount between about 0.1 and 50 mg/kg, preferably 0.01 and 20 mg/kg, animal to be treated.

EXAMPLES

Examples of the synthesis of the compounds of the present invention are described below. However, it is to be understood that the present invention is not restricted by the exemplified compounds.

Figure 2:
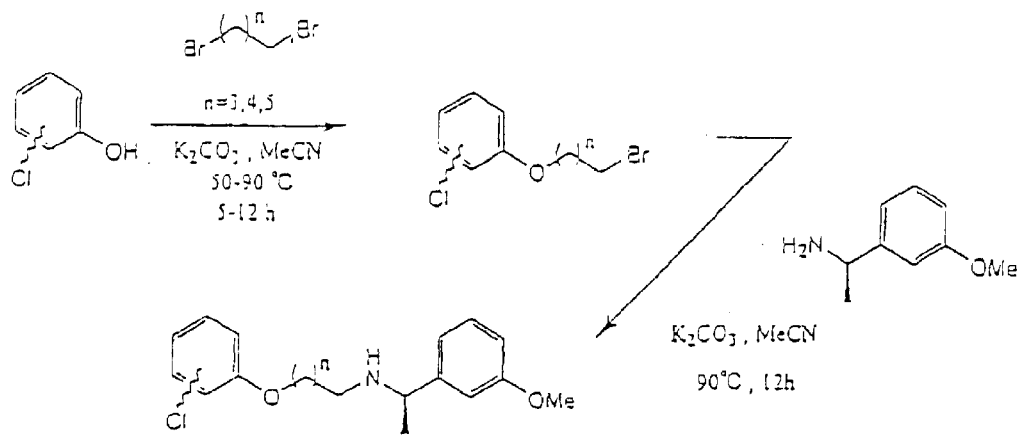
FIG. 2 shows the scheme of the synthesis of the compound of the present invention of the formula (1) wherein X is O.
Figure 3:
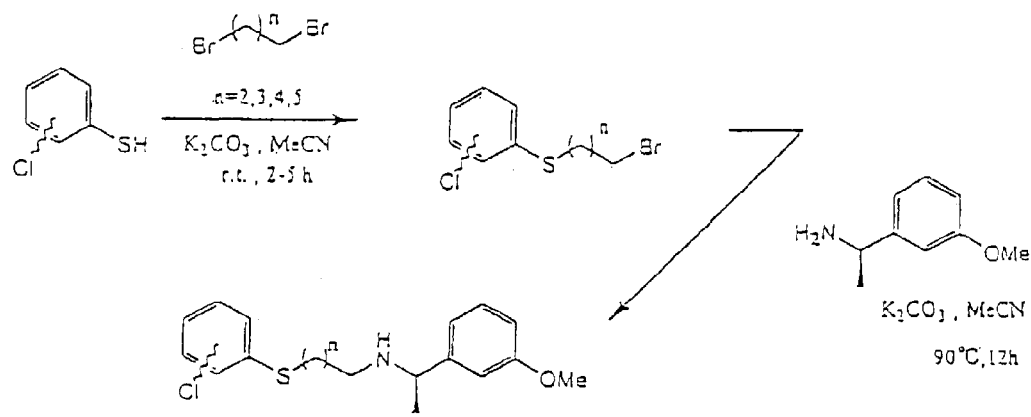
FIG. 3 shows the scheme of the synthesis of the compound of the present invention of the formula (1) wherein X is S.
Figure 4:
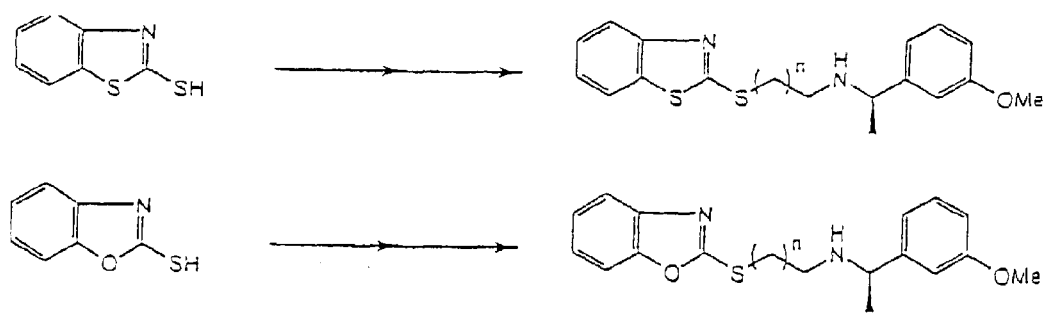
FIG. 4 shows the scheme of the synthesis of the compound of the present invention of the formula (1) wherein $Ar_1$ is benzothiazole or benzoxazole or benzoxazole.

In Examples 1 to 23, compounds represented by FIG. 1 were synthesized. The compounds of the present invention represented by the formula (1) wherein X is O were synthesized in accordance with the scheme of FIG. 2 with the use of 2-, 3- or 4-chlorophenol as the starting material. The compounds of the present invention represented by the formula (1) wherein X is S were synthesized in accordance with the scheme of FIG. 3 with the use of 2- or 4-chlorothiophenol as the starting material. However, methylene chloride was used as the solvent in some cases. The compounds of the present invention represented by the formula (1) wherein $Ar_1$ is benzthiazole or benzoxazole were synthesized in accordance with the scheme of FIG. 4.

Figure 5:
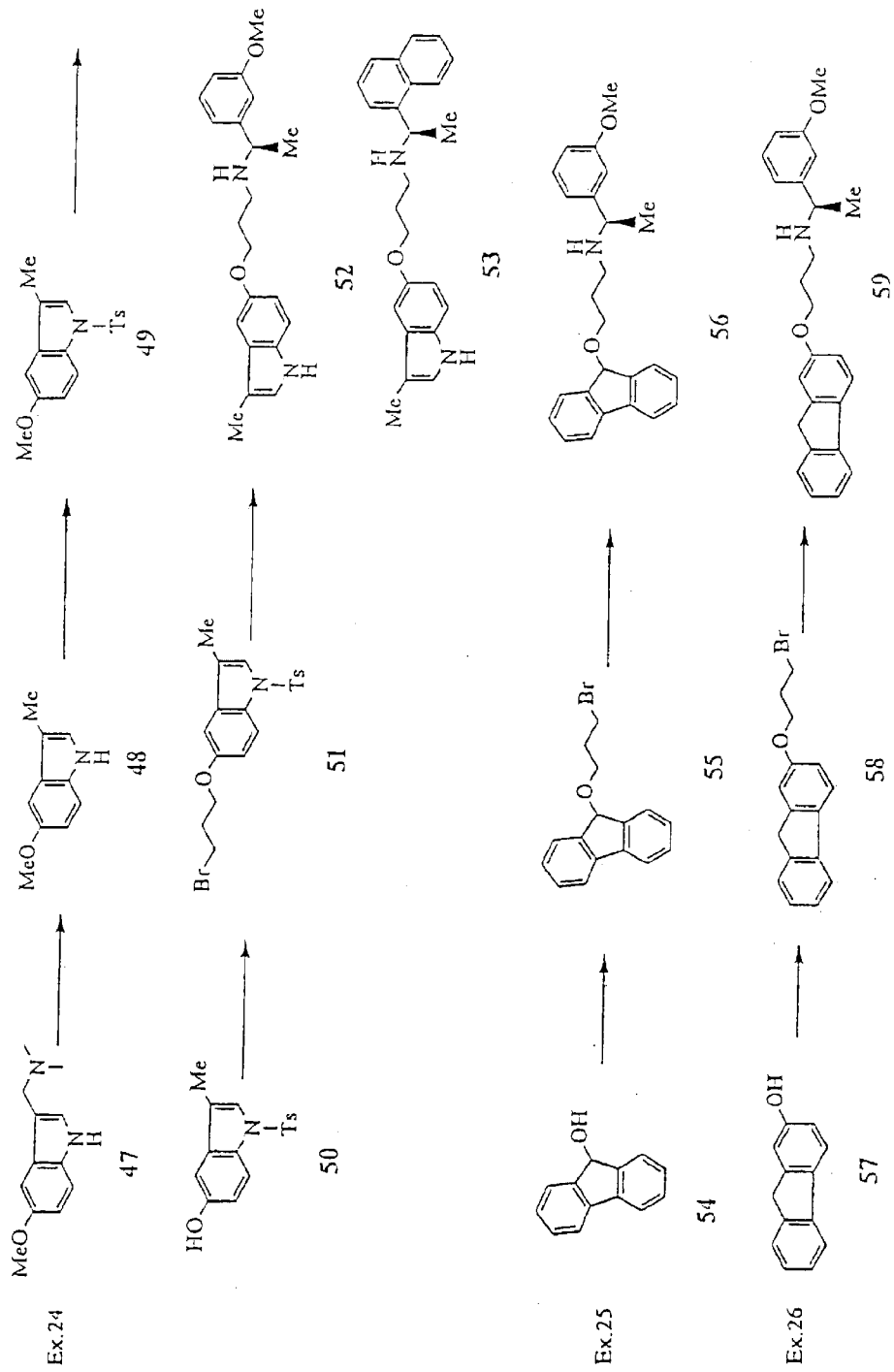
FIG. 5 shows the structures of the compounds of the present invention synthesized in Examples 24 to 26 and the scheme of the synthesis thereof.
Figure 6:
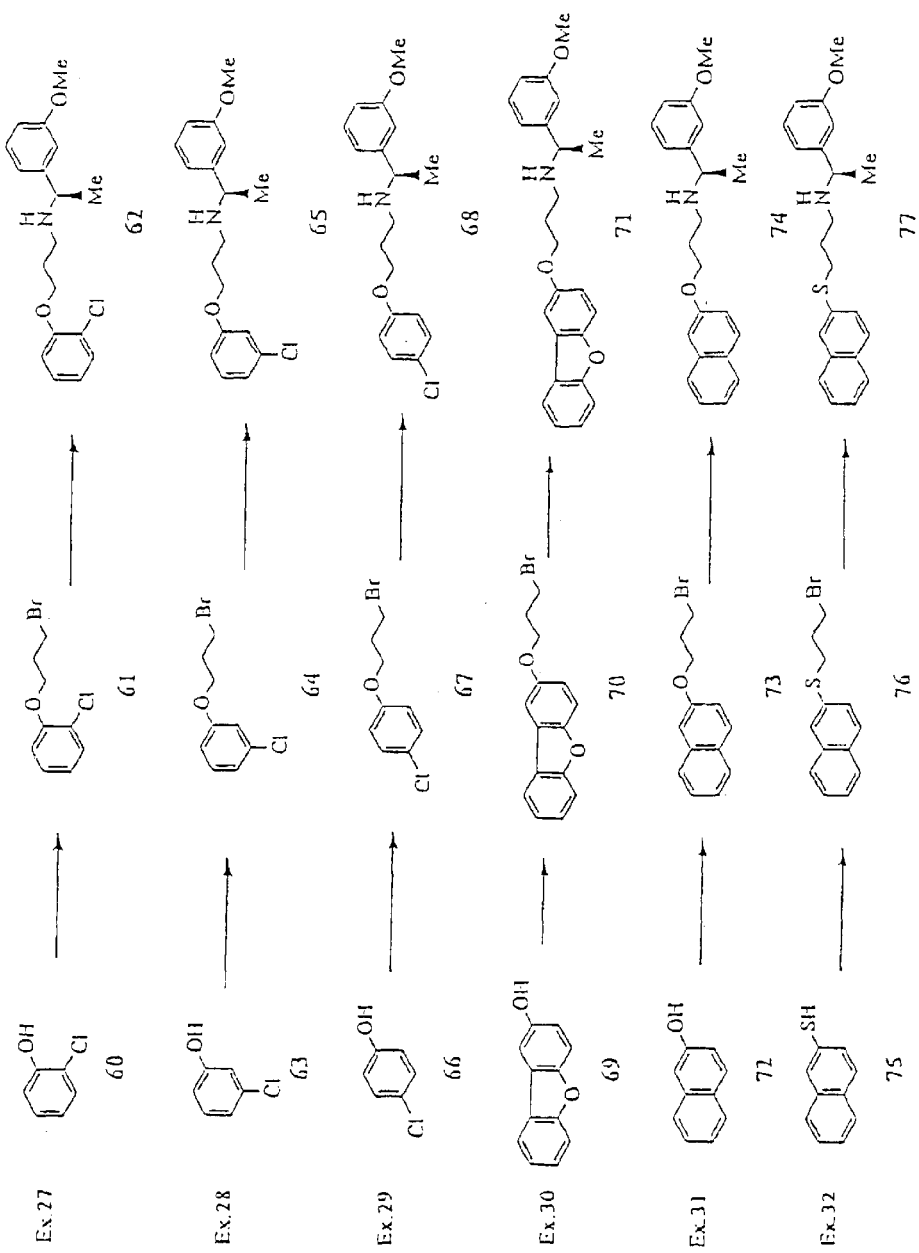
FIG. 6 shows the structures of the compounds of the present invention synthesized in Examples 27 to 32 and the scheme of the synthesis thereof.
Figure 7:
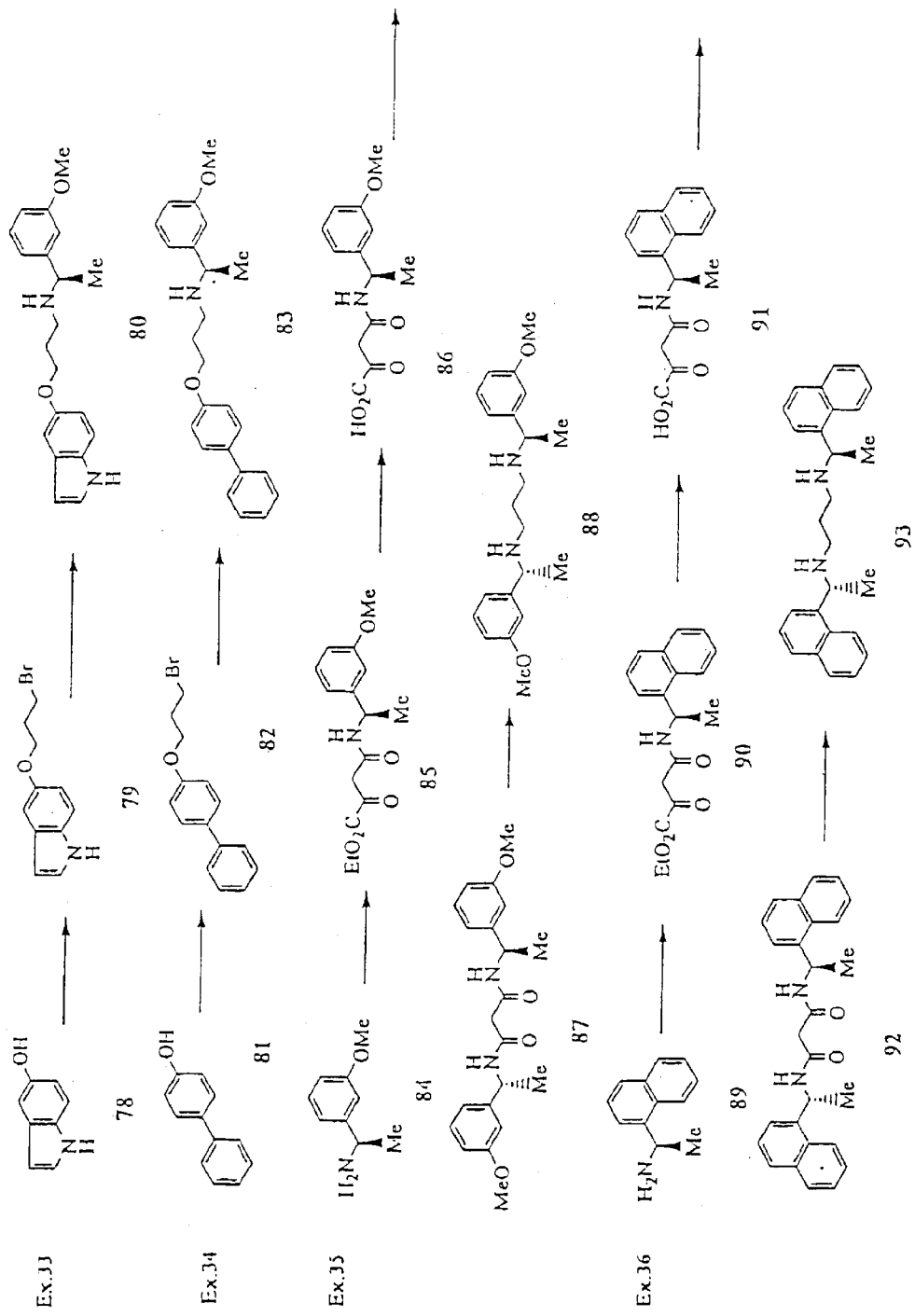
FIG. 7 shows the structures of the compounds of the present invention synthesized in Examples 33 to 36 and the scheme of the synthesis thereof.
Figure 8:
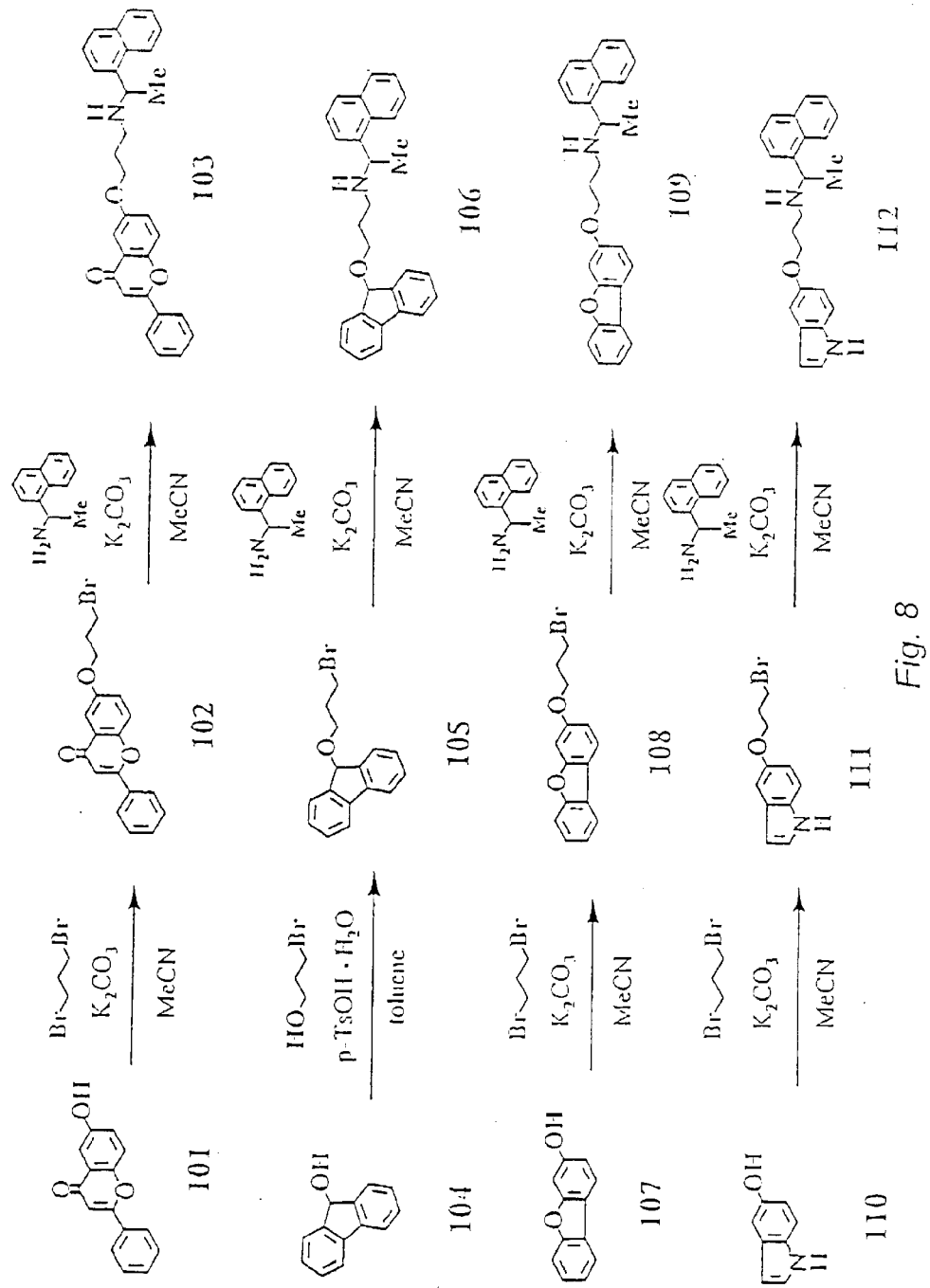
FIG. 8 shows the structures of the compounds of the present invention synthesized in Examples 37 to 40 and the scheme of the synthesis thereof.
Figure 9:
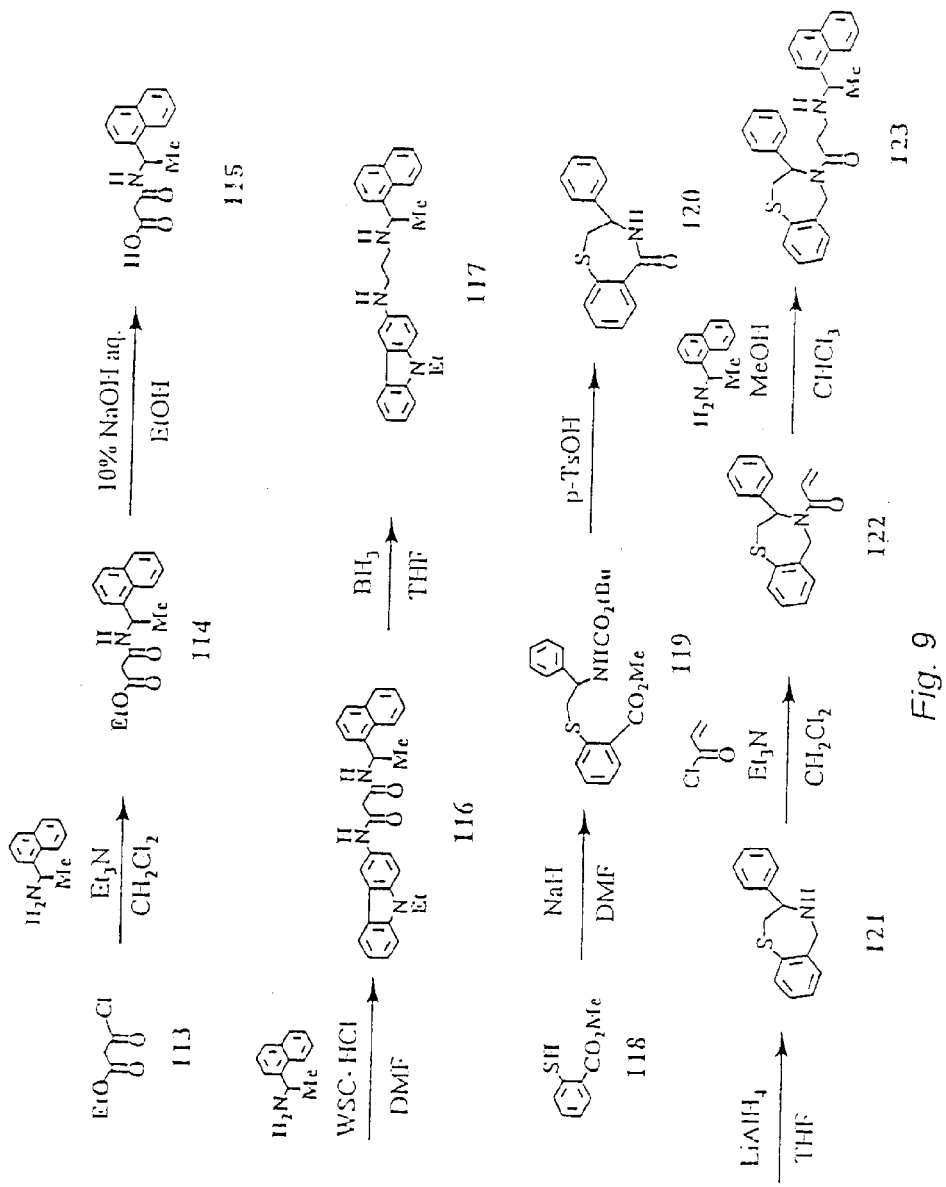
FIG. 9 shows the structures of the compounds of the present invention synthesized in Examples 41 and 42 and the scheme of the synthesis thereof.
Figure 10:
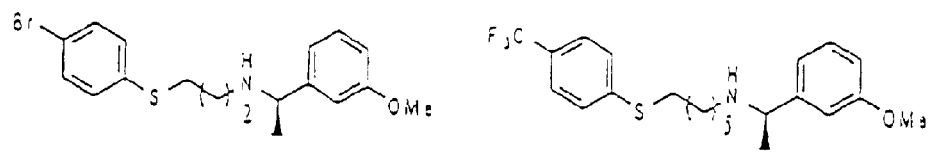
FIG. 10 shows the structures of the compounds of the present invention synthesized in Examples 43 to 56.
Figure 10:
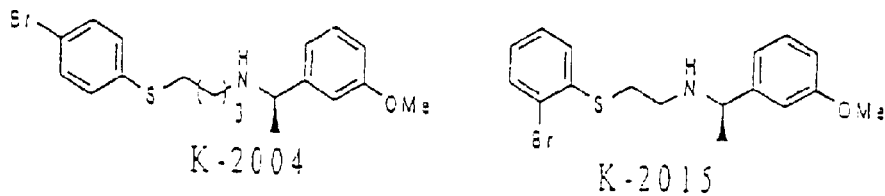
Figure 10:
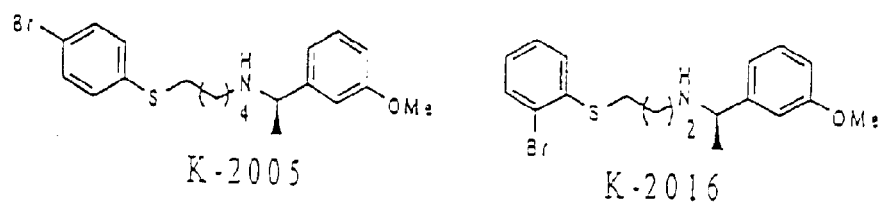
Figure 10:
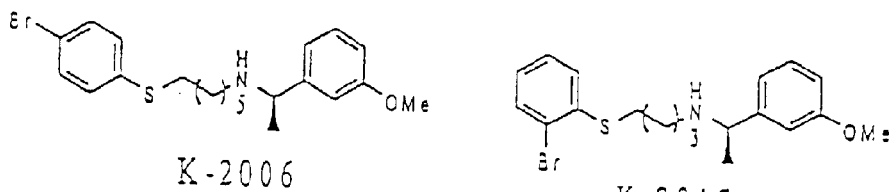
Figure 10:
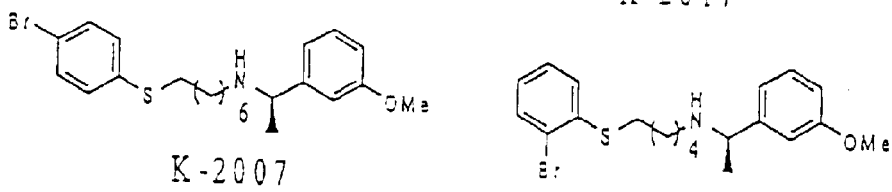
Figure 10:
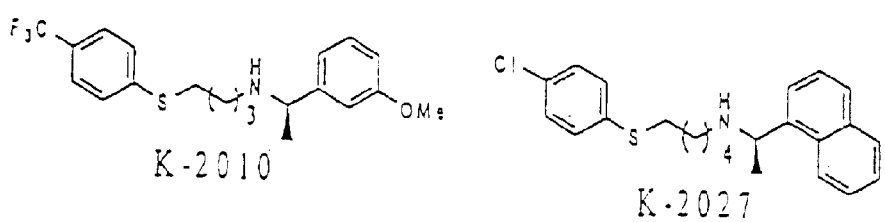
Figure 10:
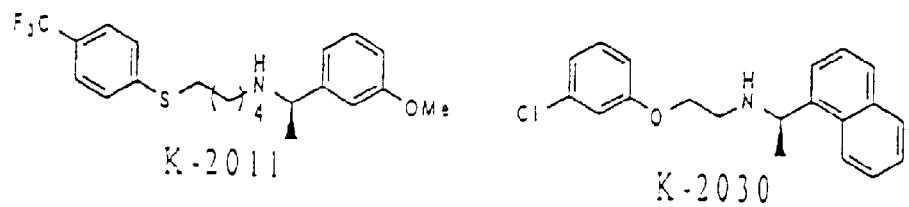
Figure 11:
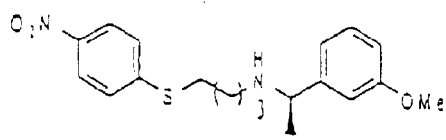
FIG. 11 shows the structures of the compounds of the present invention synthesized in Examples 57 to 70.
Figure 11:
Figure 11:
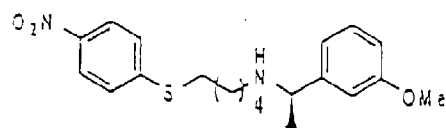
Figure 11:
Figure 11:
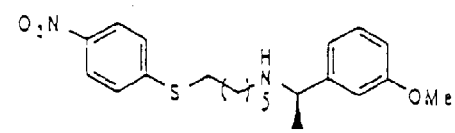
Figure 11:
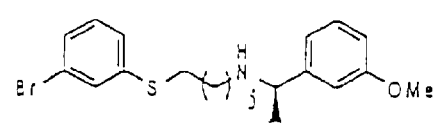
Figure 11:
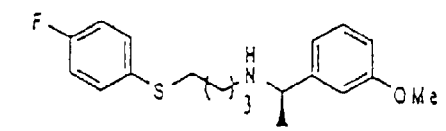
Figure 11:
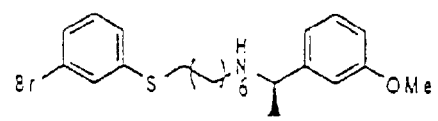
Figure 11:
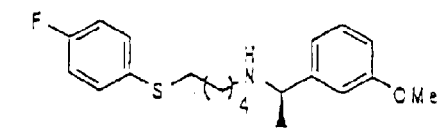
Figure 11:
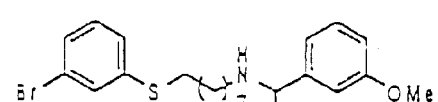
Figure 11:
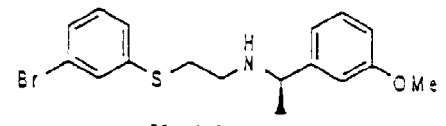
Figure 11:
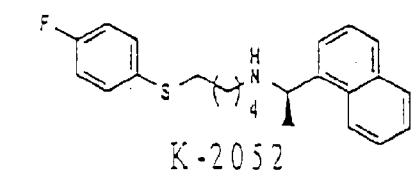
Figure 11:
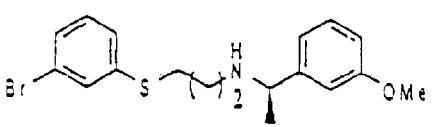
Figure 11:
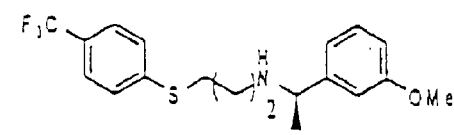
Figure 12:
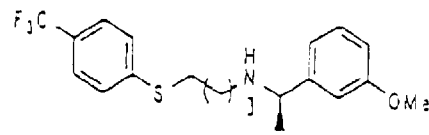
FIG. 12 shows the structures of the compounds of the present invention synthesized in Examples 71 to 84.
Figure 12:
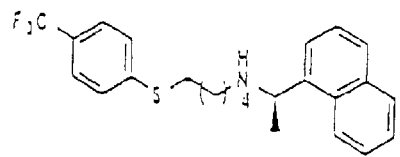
Figure 12:
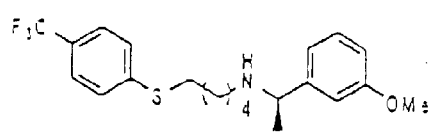
Figure 12:
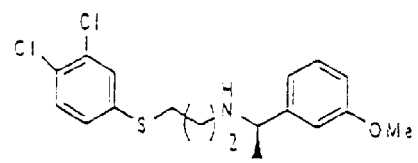
Figure 12:
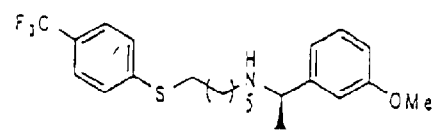
Figure 12:
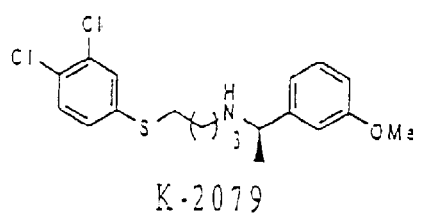
Figure 12:
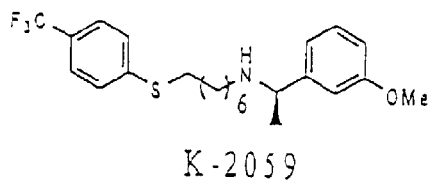
Figure 12:
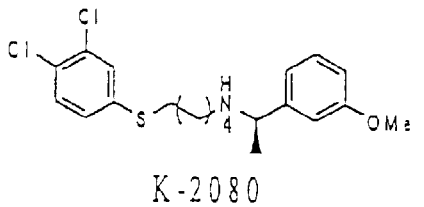
Figure 12:
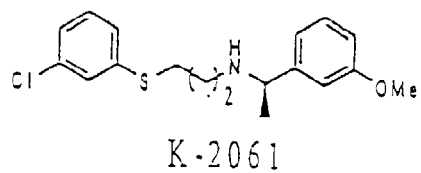
Figure 12:
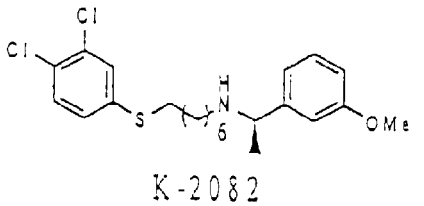
Figure 12:
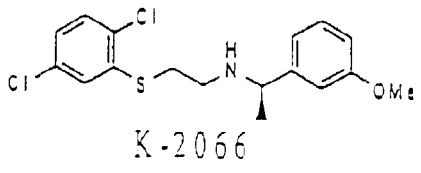
Figure 12:
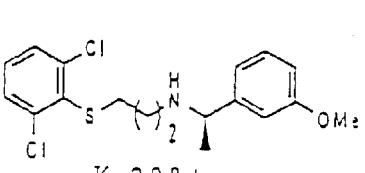
Figure 12:
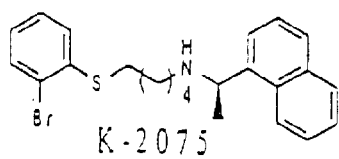
Figure 12:
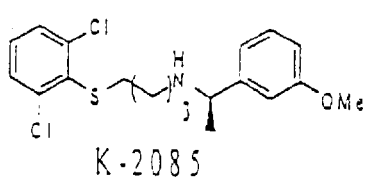
Figure 13:
FIG. 13 shows the structures of the compounds of the present invention synthesized in Examples 85 and 86.
Figure 14:
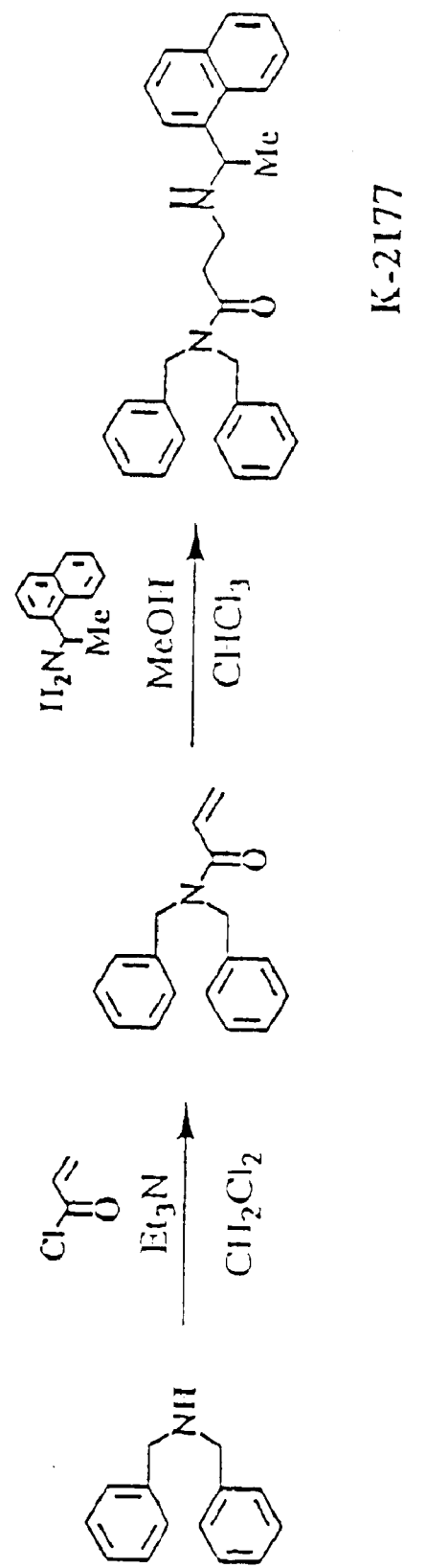
FIG. 14 shows the structure of the compound of the present invention synthesized in Example 88 and the scheme of the synthesis thereof.
Figure 15:
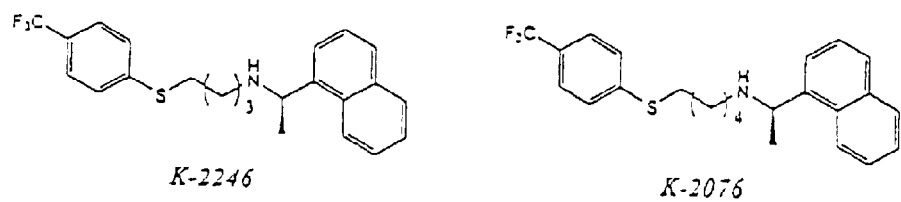
FIG. 15 shows the structures of the compounds of the present invention synthesized in Examples 89 and 90.
Figure 16:
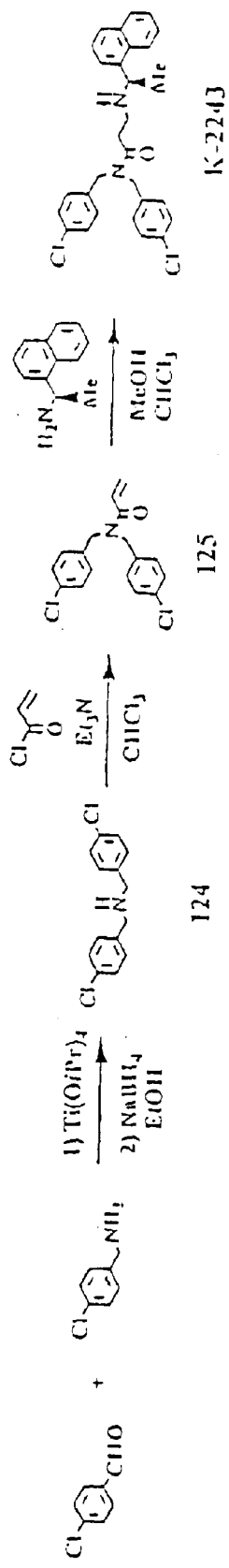
FIG. 16 shows the structure of the compound of the present invention synthesized in Examples 91 to 93 and the scheme of the synthesis thereof.
Figure 16:
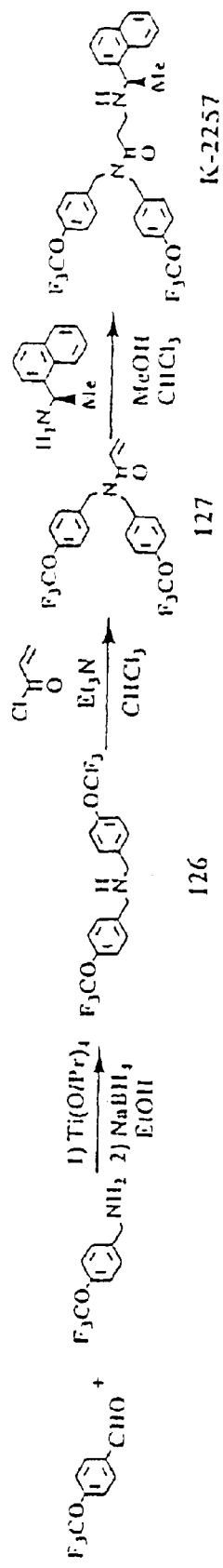
Figure 16:
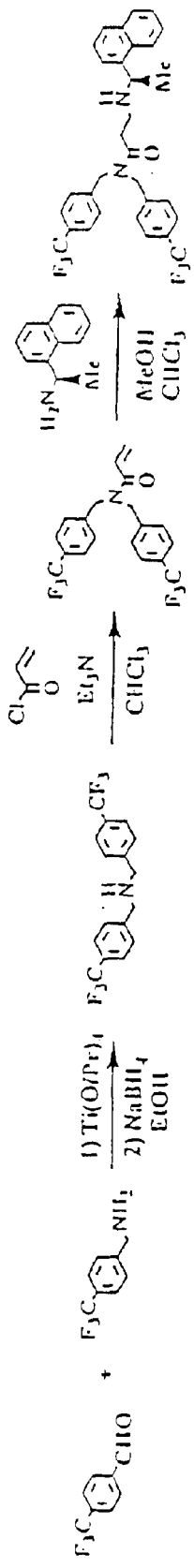
Figure 17:
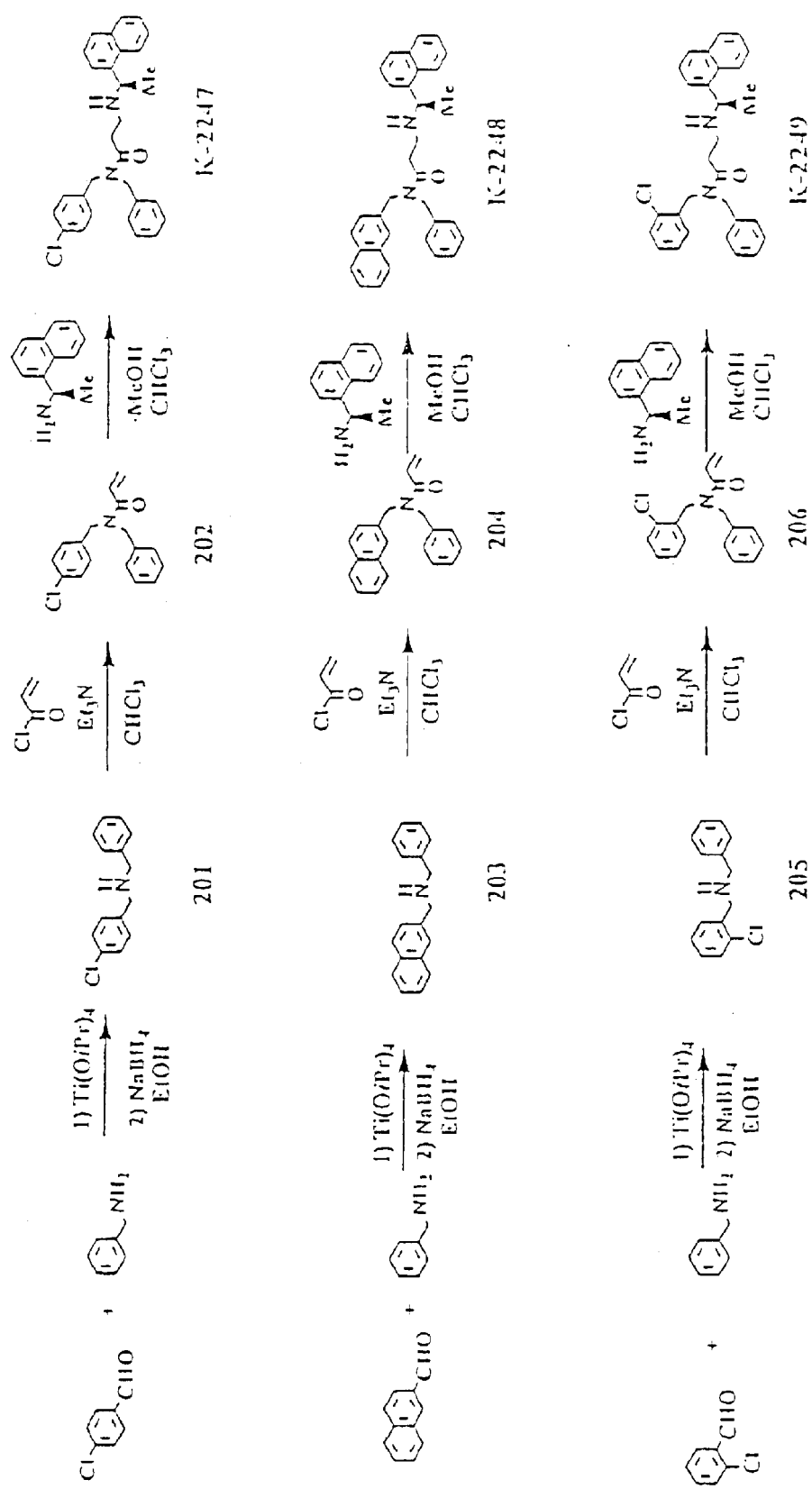
FIG. 17 shows the structures of the compounds of the present invention synthesized in Examples 94 to 96 and the scheme of the synthesis thereof.
Figure 18:
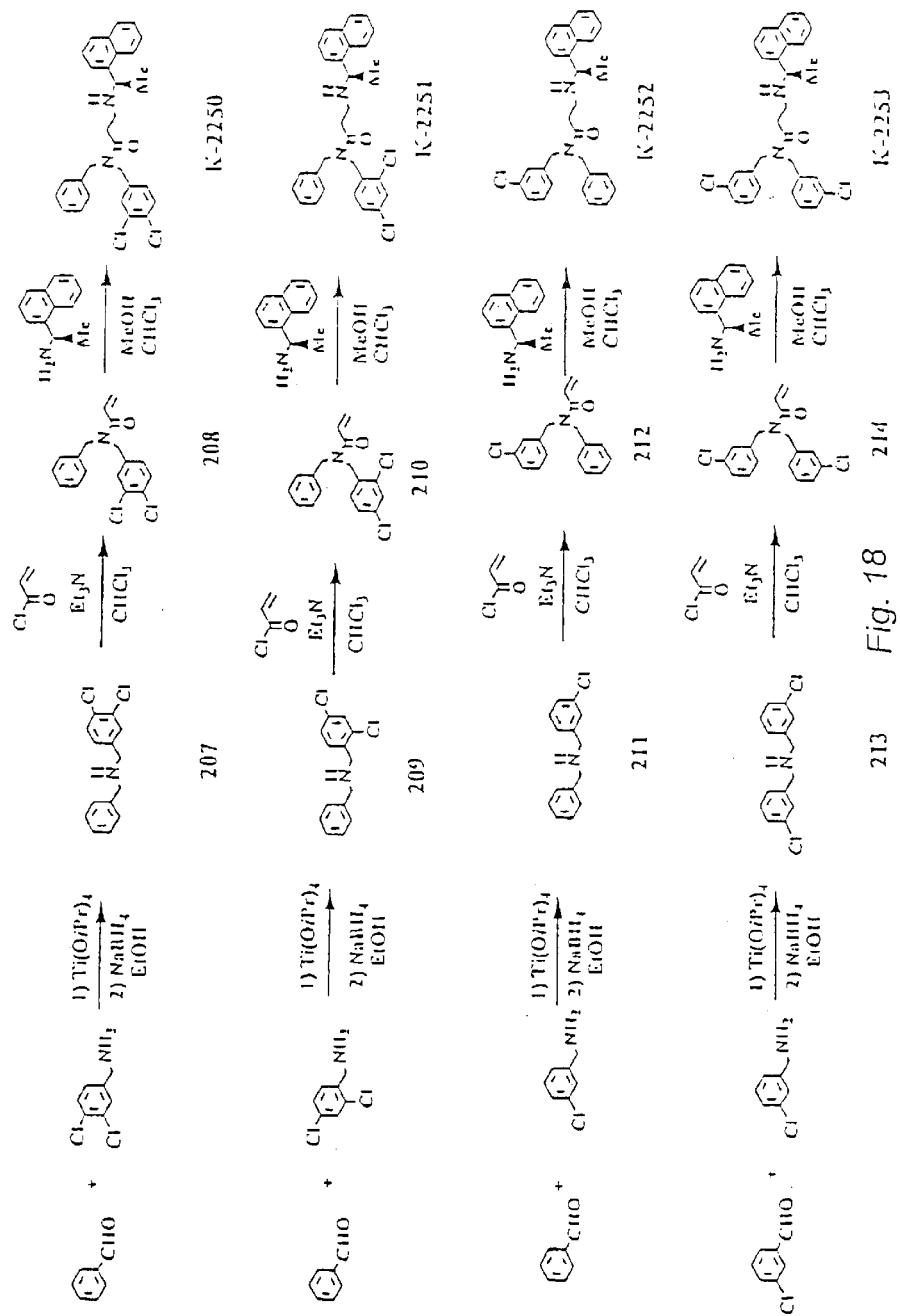
FIG. 18 shows the structures of the compounds of the present invention synthesized in Examples 97 to 100 and the scheme of the synthesis thereof.
Figure 19:
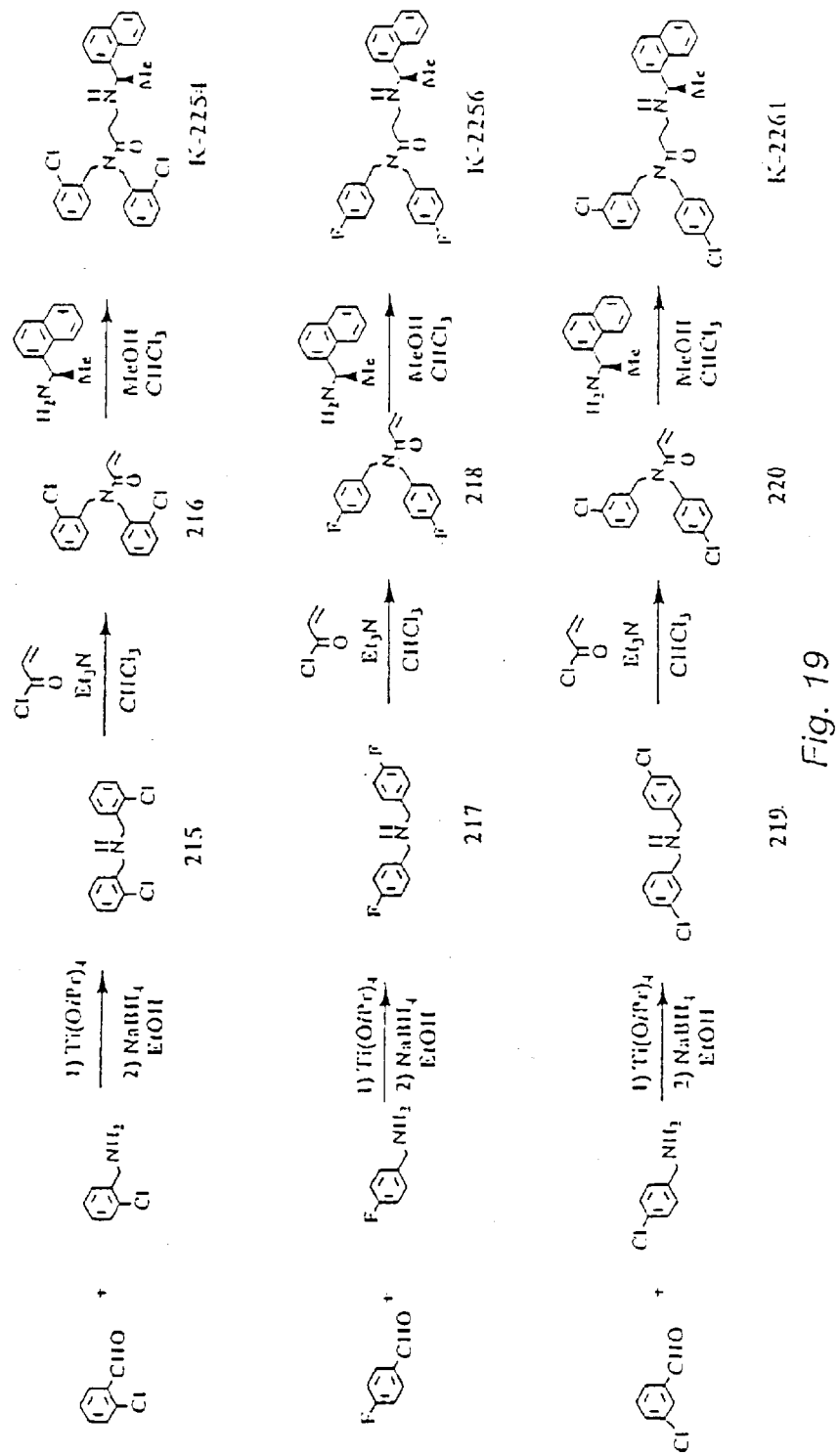
FIG. 19 shows the structures of the compounds of the present invention synthesized in Examples 101 to 103 and the scheme of the synthesis thereof.
Figure 20:
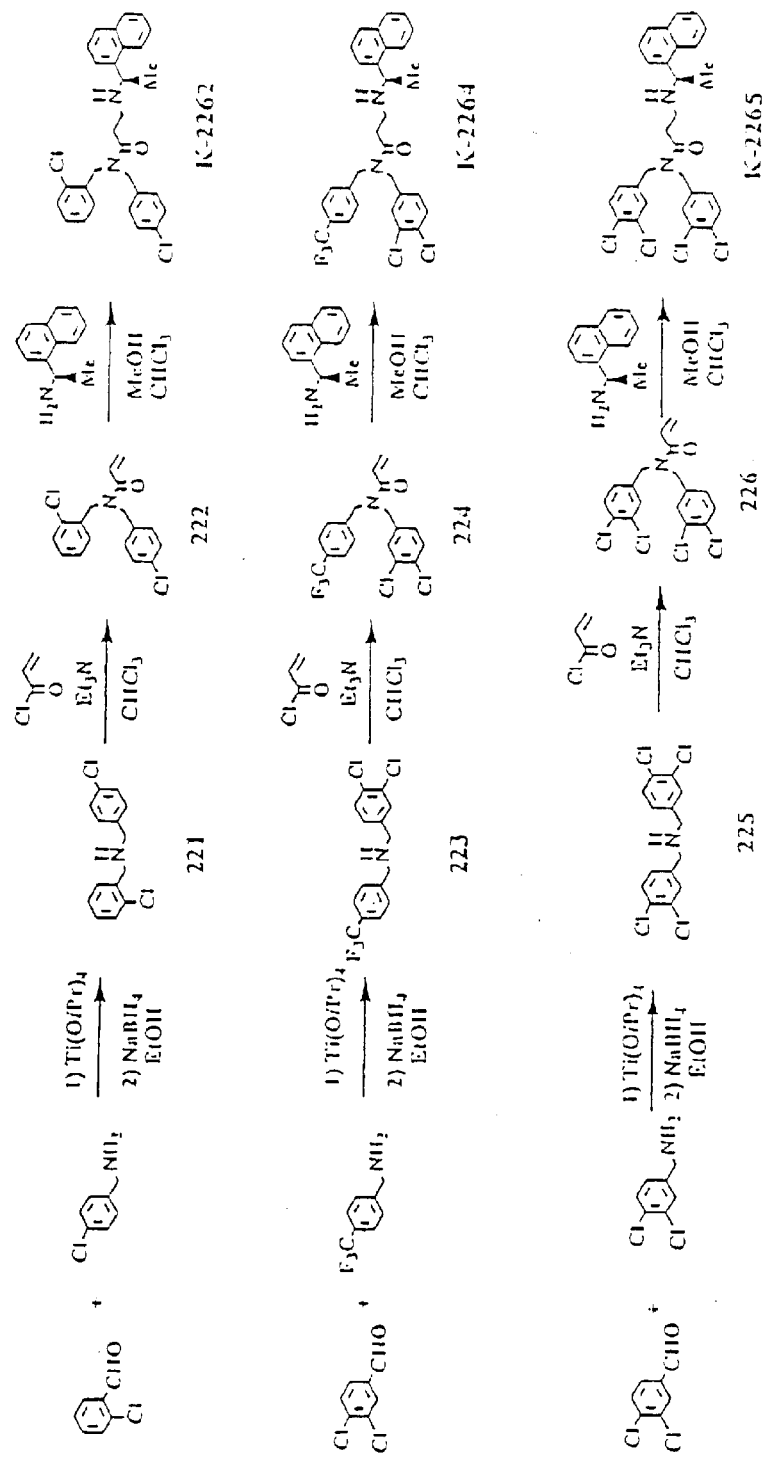
FIG. 20 shows the structures of the compounds of the present invention synthesized in Examples 104 to 106 and the scheme of the synthesis thereof.
Figure 21:
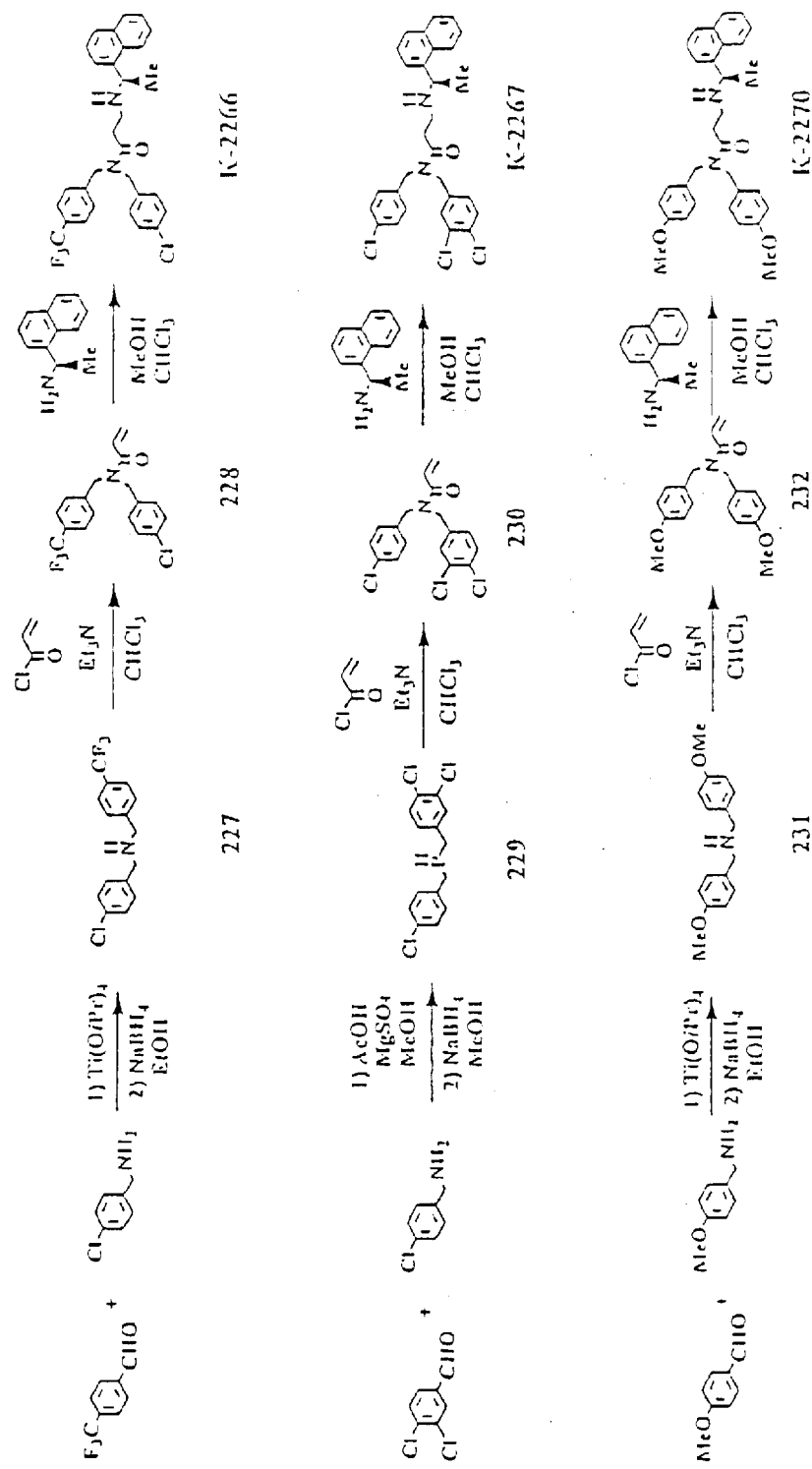
FIG. 21 shows the structures of the compounds of the present invention synthesized in Examples 107 to 109 and the scheme of the synthesis thereof.
Figure 22:
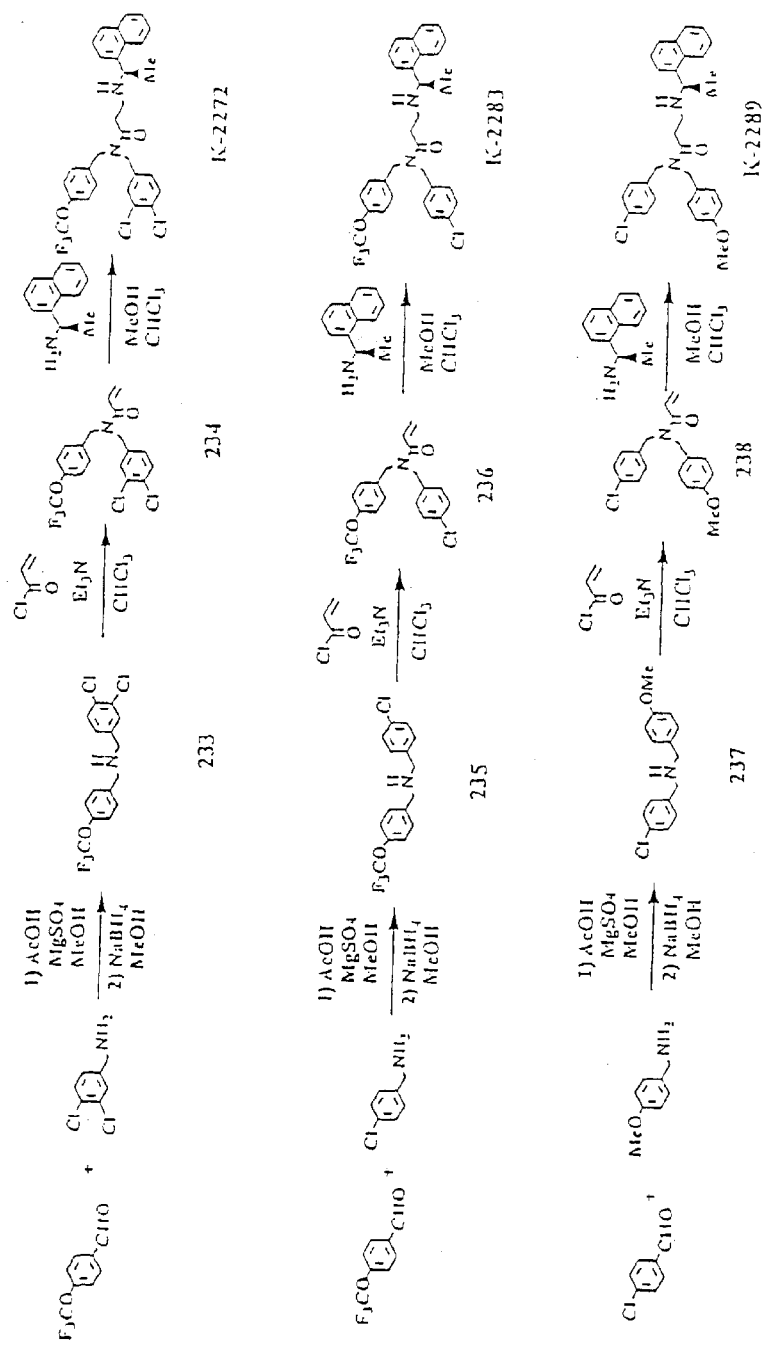
FIG. 22 shows the structures of the compounds of the present invention synthesized in Examples 110 to 112 and the scheme of the synthesis thereof.
Figure 23:
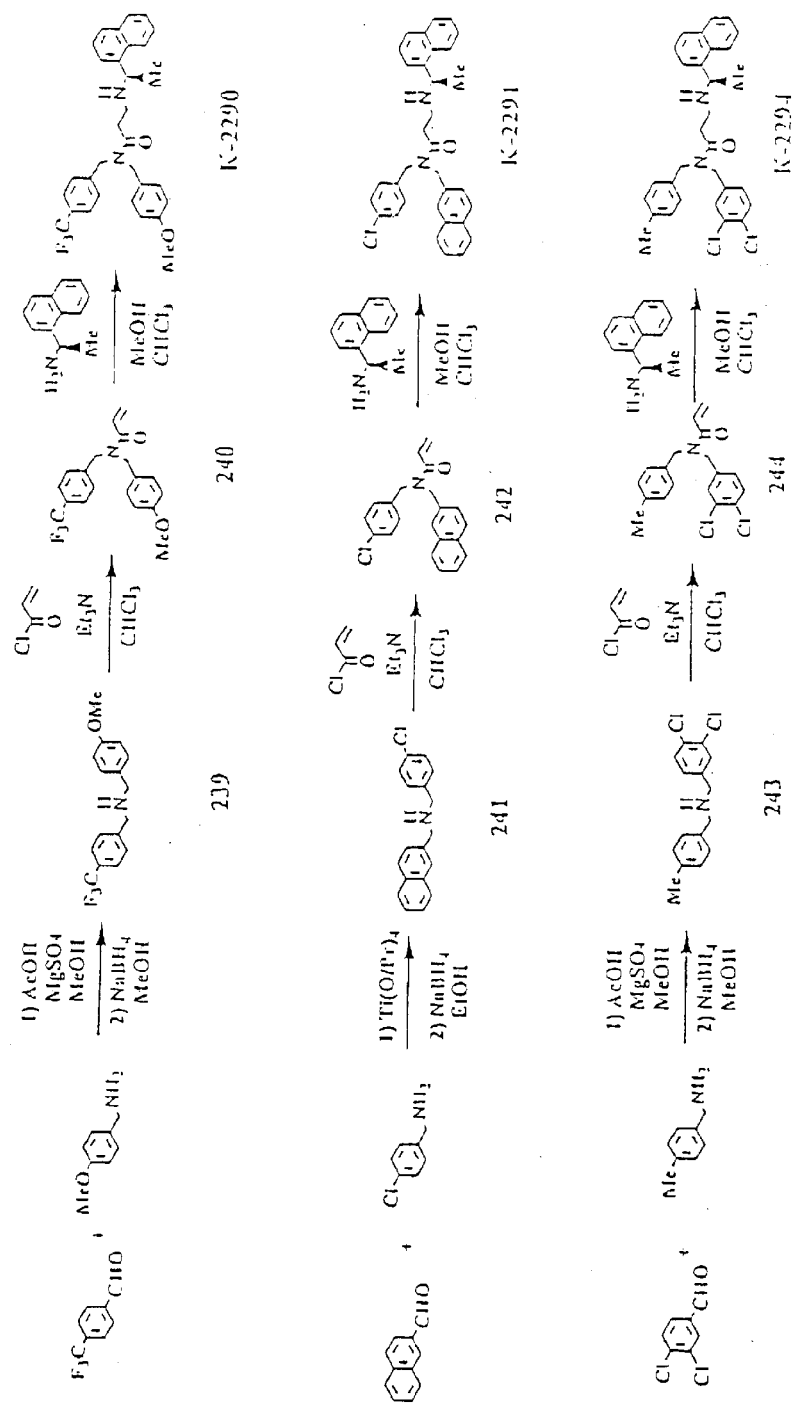
FIG. 23 shows the structures of the compounds of the present invention synthesized in Examples 113 to 115 and the scheme of the synthesis thereof.
Figure 24:
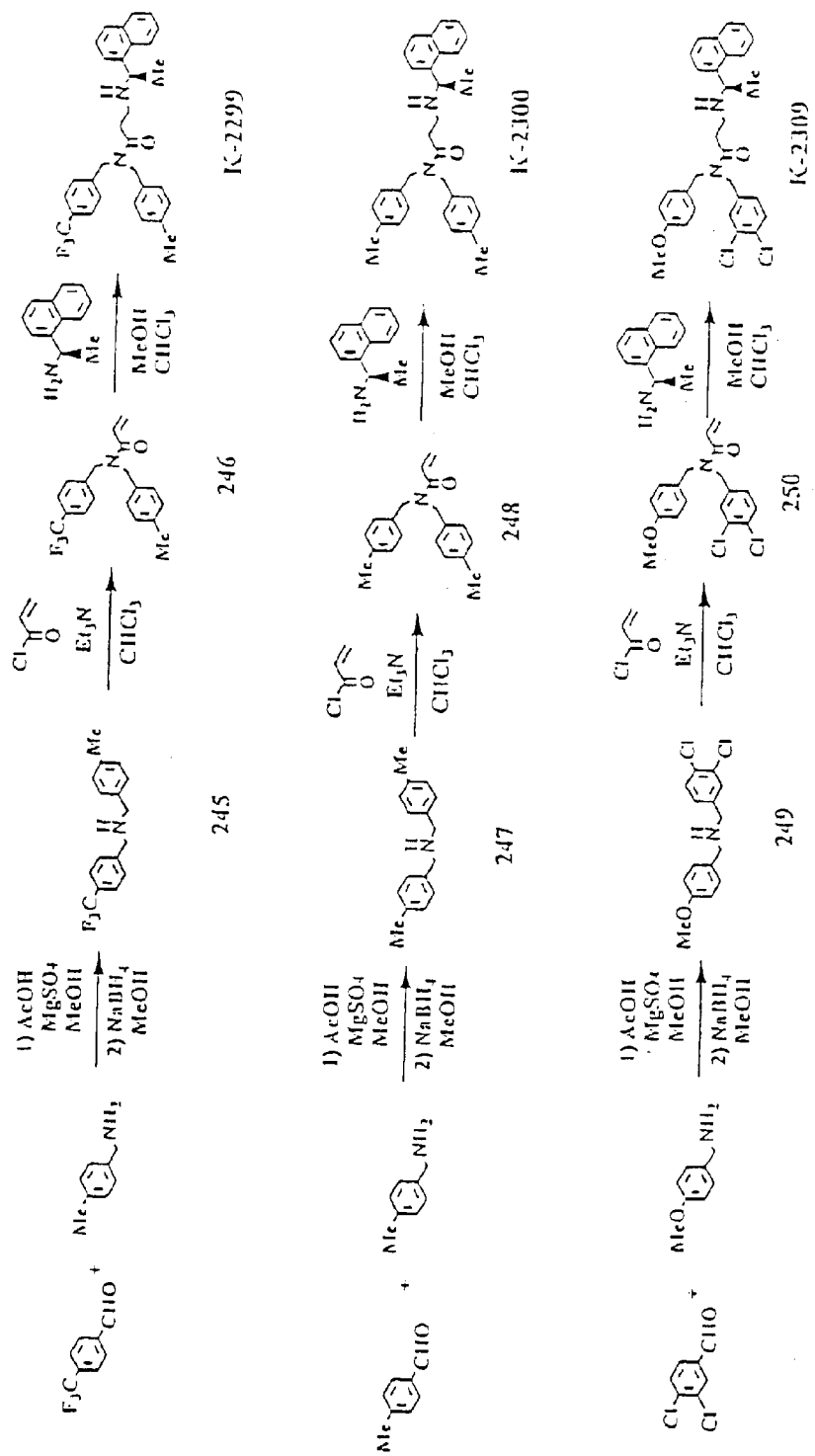
FIG. 24 shows the structures of the compounds of the present invention synthesized in Examples 116 to 118 and the scheme of the synthesis thereof.
Figure 25:
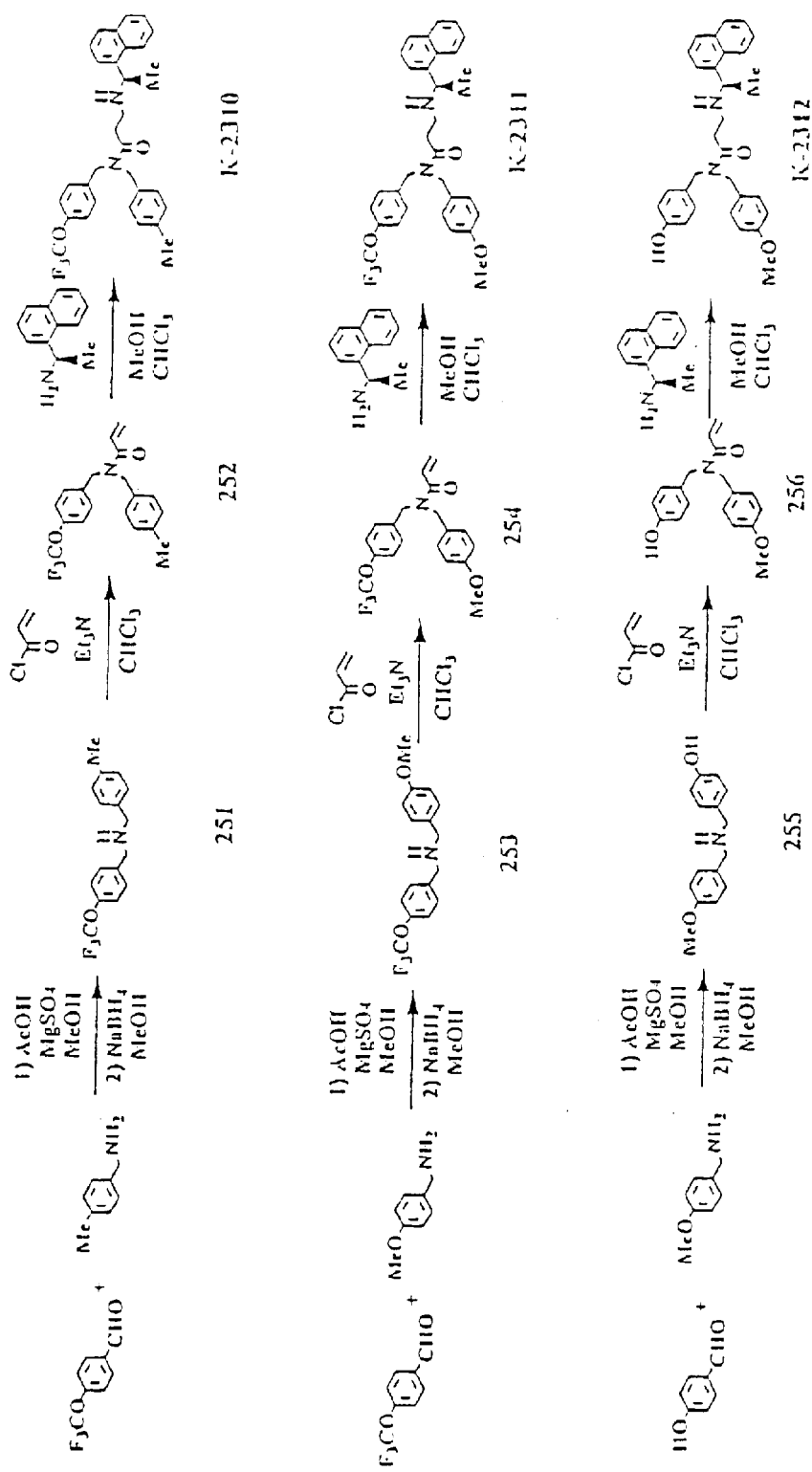
FIG. 25 shows the structures of the compounds of the present invention synthesized in Examples 119 to 121 and the scheme of the synthesis thereof.
Figure 26:
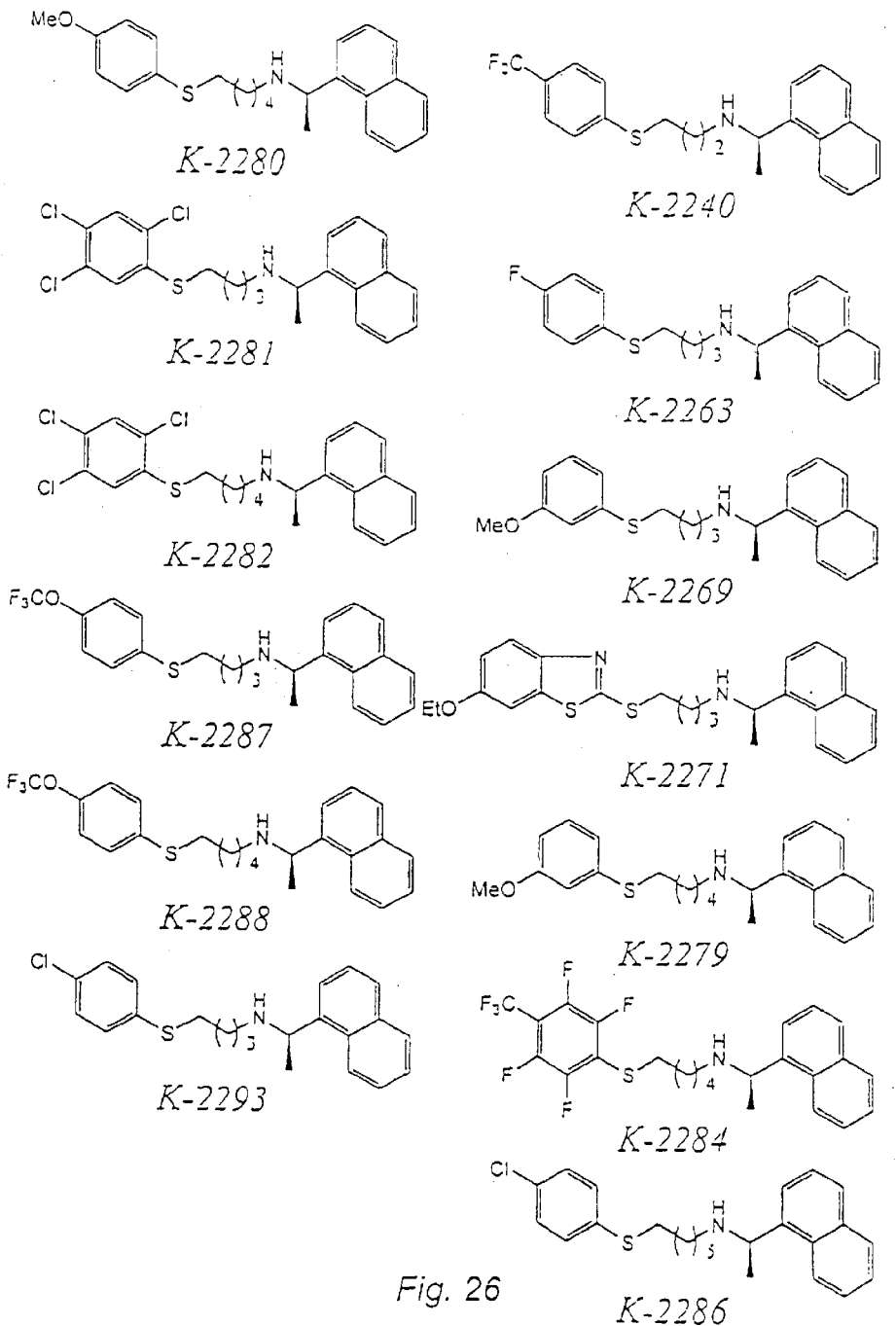
FIG. 26 shows the structures of the compounds of the present invention synthesized in Examples 122 to 134.
Figure 27:
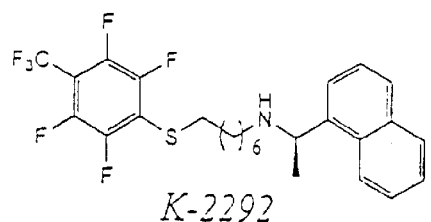
FIG. 27 shows the structures of the compounds of the present invention synthesized in Examples 135 to 147.
Figure 27:
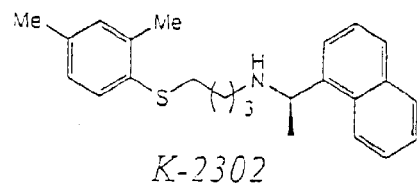
Figure 27:
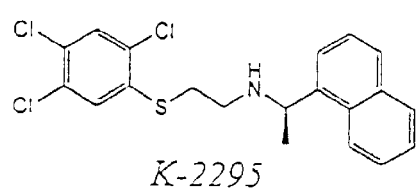
Figure 27:
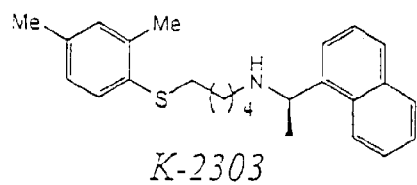
Figure 27:
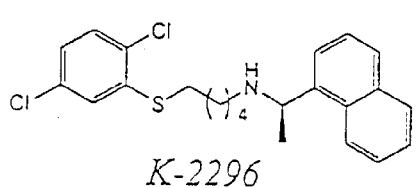
Figure 27:
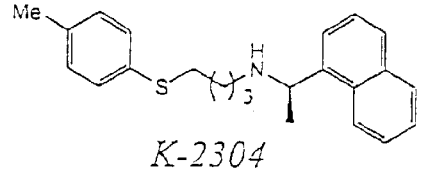
Figure 27:
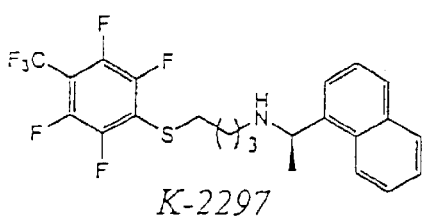
Figure 27:
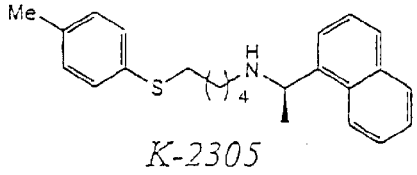
Figure 27:
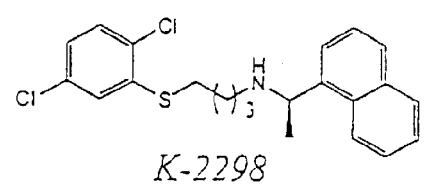
Figure 27:
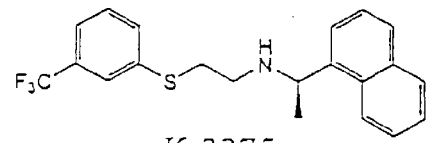
Figure 27:
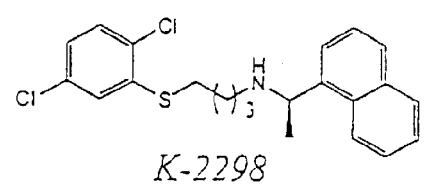
Figure 27:
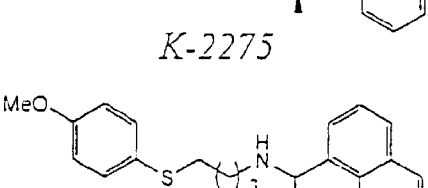
Figure 27:
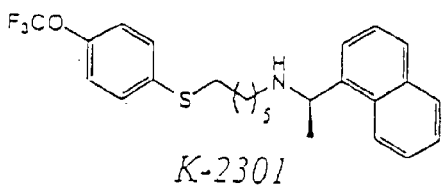
Figure 27:
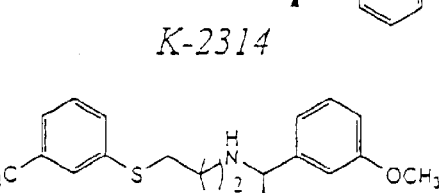
Figure 28:
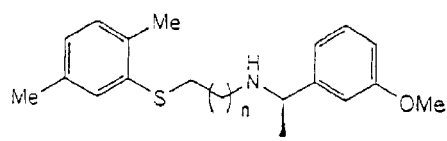
FIG. 28 shows the structures of the compounds of the present invention synthesized in Examples 148 to 189.
Figure 28:
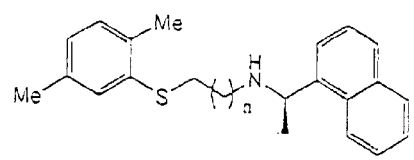
Figure 28:
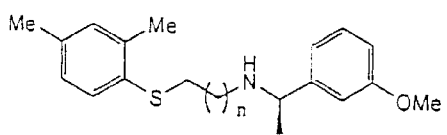
Figure 28:
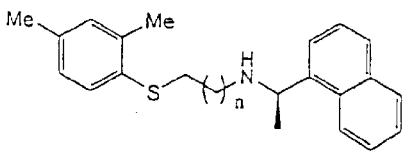
Figure 28:
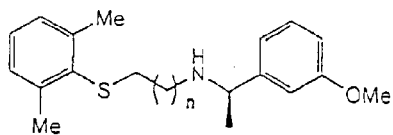
Figure 28:
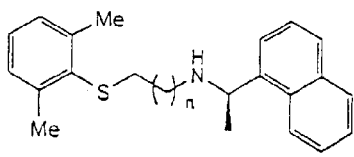
Figure 29:
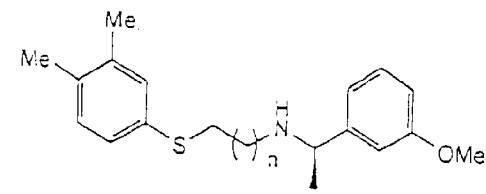
FIG. 29 shows the structures of the compounds of the present invention synthesized in Examples 190 to 231.
Figure 29:
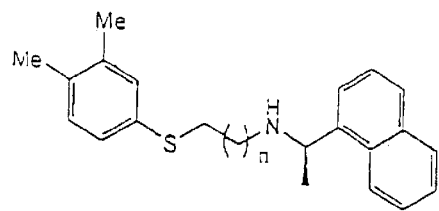
Figure 29:
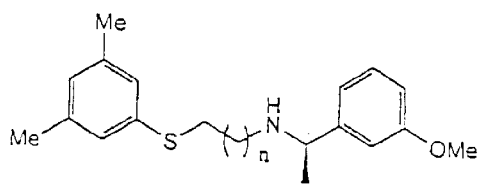
Figure 29:
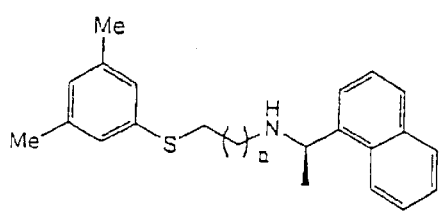
Figure 29:
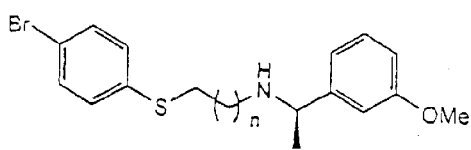
Figure 29:
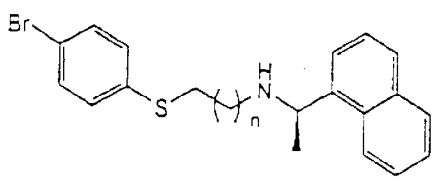
Figure 30:
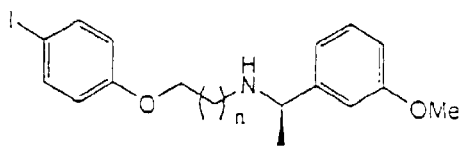
FIG. 30 shows the structures of the compounds of the present invention synthesized in Examples 232 to 271.
Figure 30:
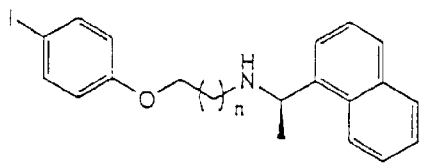
Figure 30:
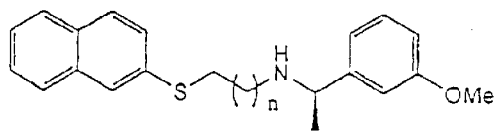
Figure 30:
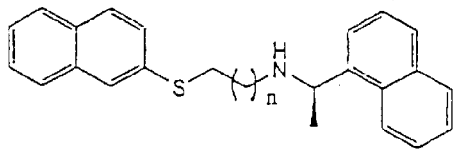
Figure 30:
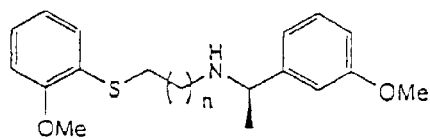
Figure 30:
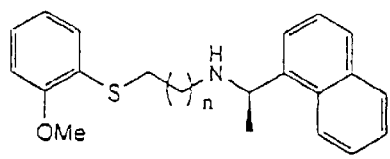
Figure 31:
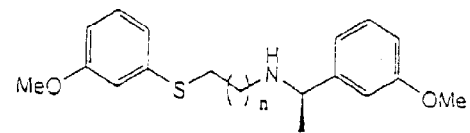
FIG. 31 shows the structures of the compounds of the present invention synthesized in Examples 272 to 313.
Figure 31:
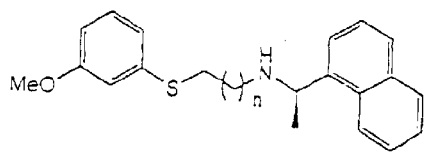
Figure 31:
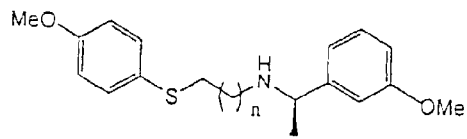
Figure 31:
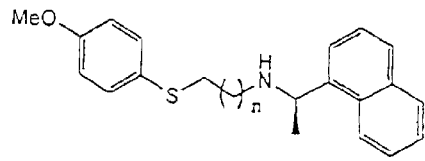
Figure 31:
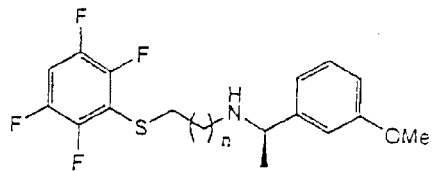
Figure 31:
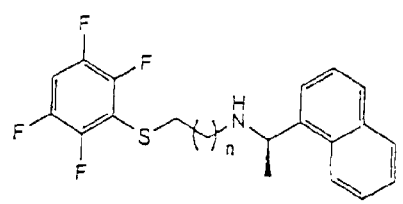
Figure 32:
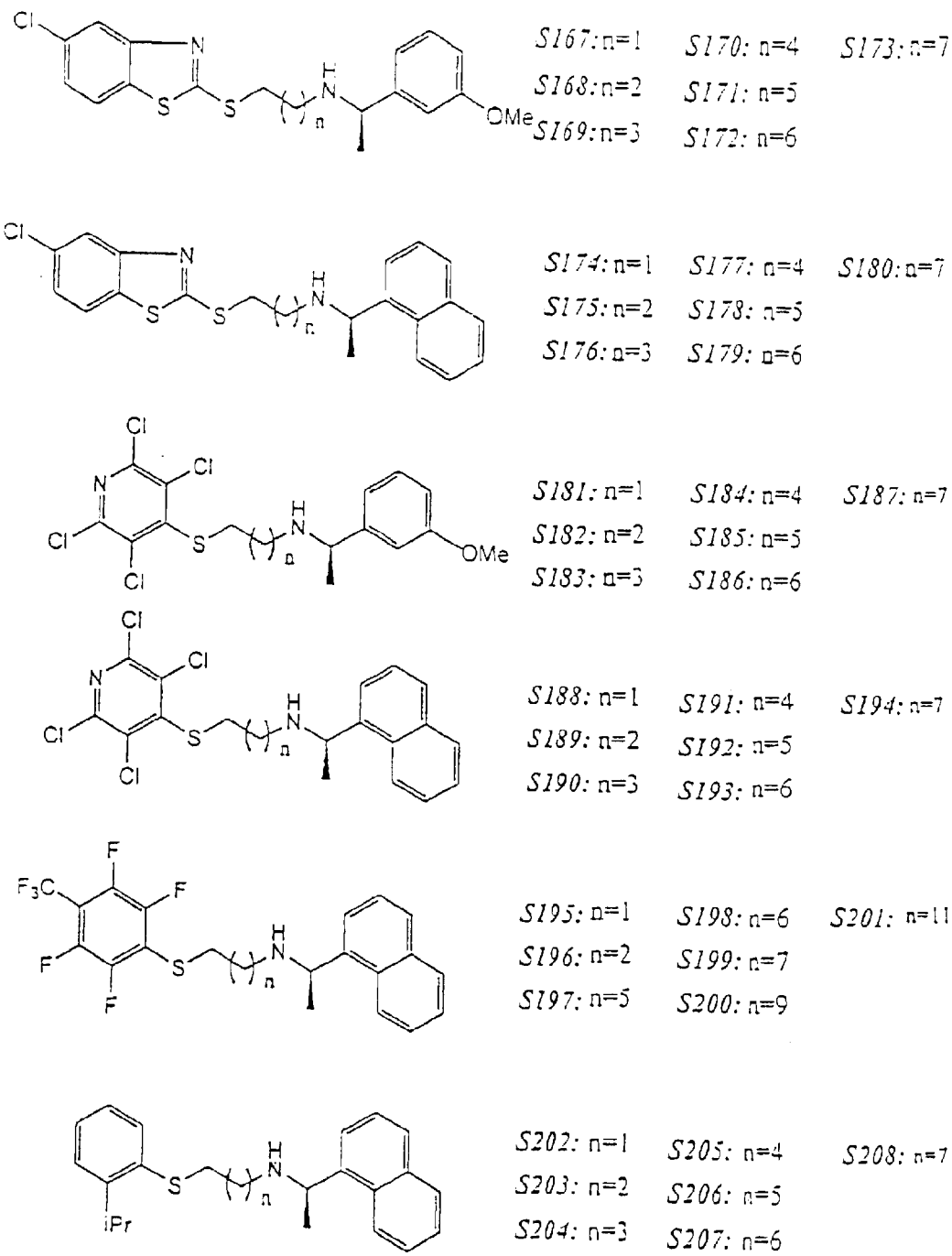
FIG. 32 shows the structures of the compounds of the present invention synthesized in Examples 314 to 355.
Figure 33:
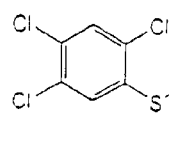
FIG. 33 shows the structures of the compounds of the present invention synthesized in Examples 356 to 387.
Figure 33:
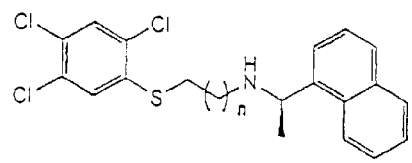
Figure 33:
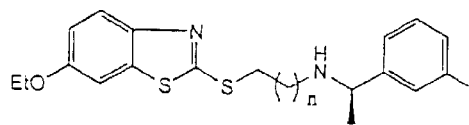
Figure 33:
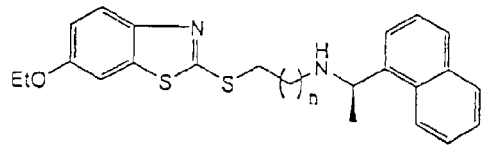
Figure 33:
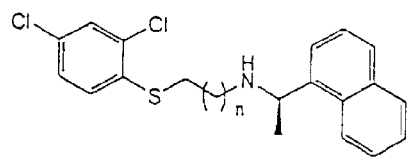
Figure 33:
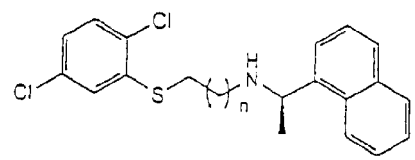
Figure 34:
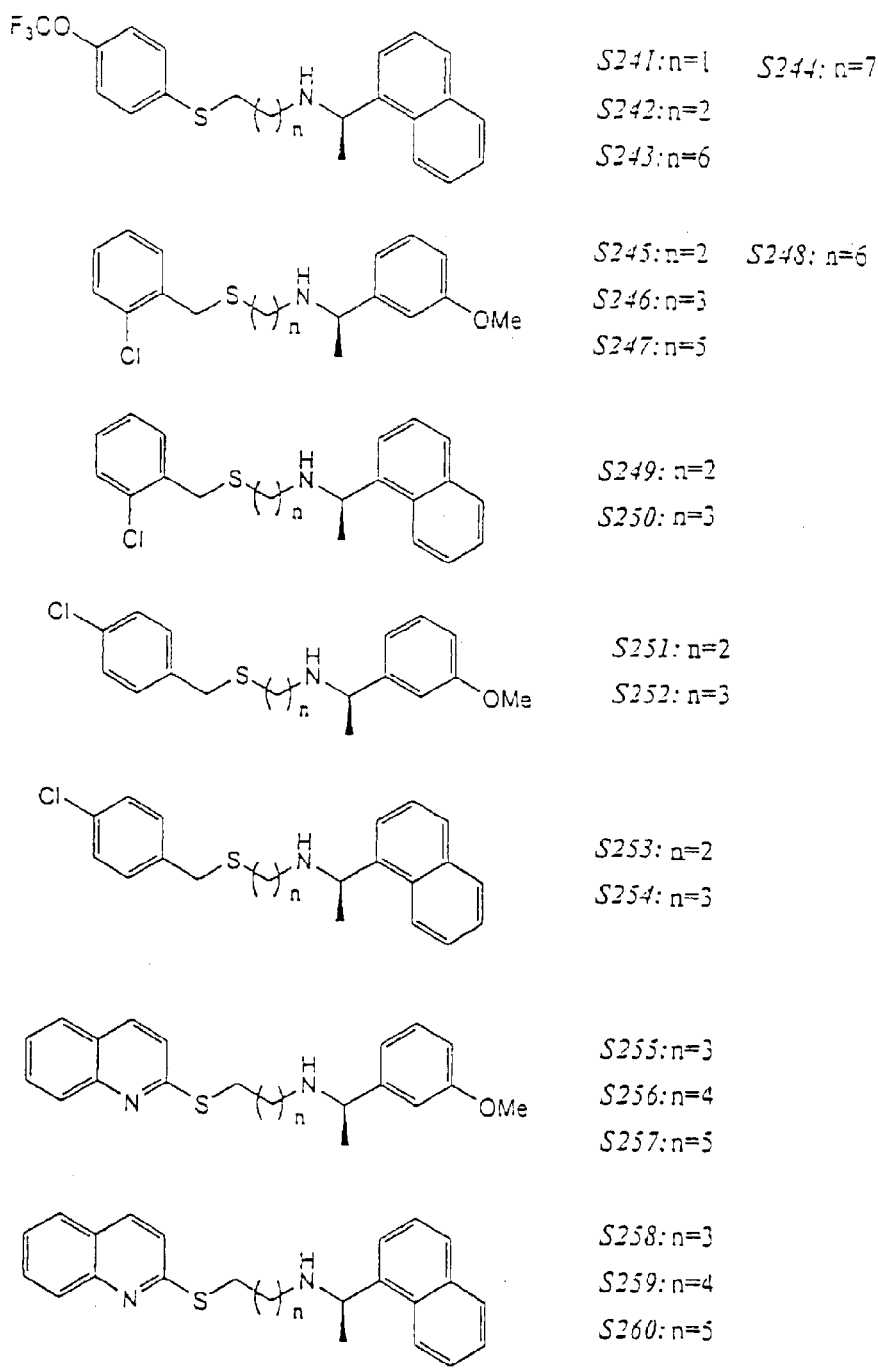
FIG. 34 shows the structures of the compounds of the present invention synthesized in Examples 388 to 407.
Figure 35:
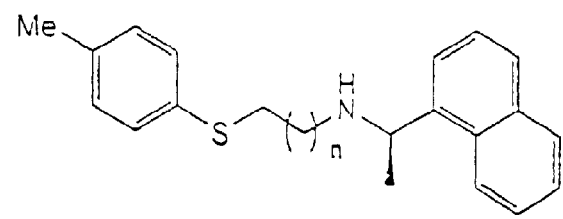
FIG. 35 shows the structures of the compounds of the present invention synthesized in Examples 408 to 413.
Figure 35:
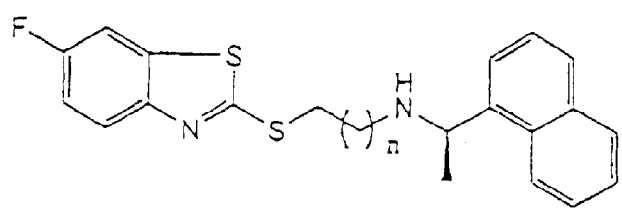
Figure 35:
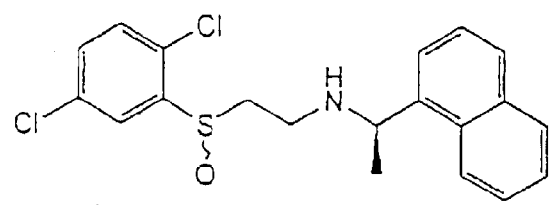
Figure 35:
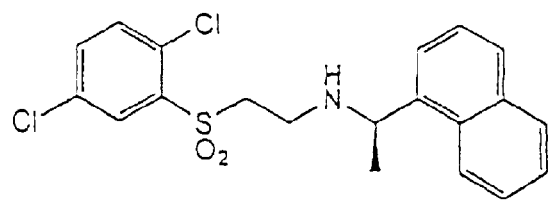
Figure 36:
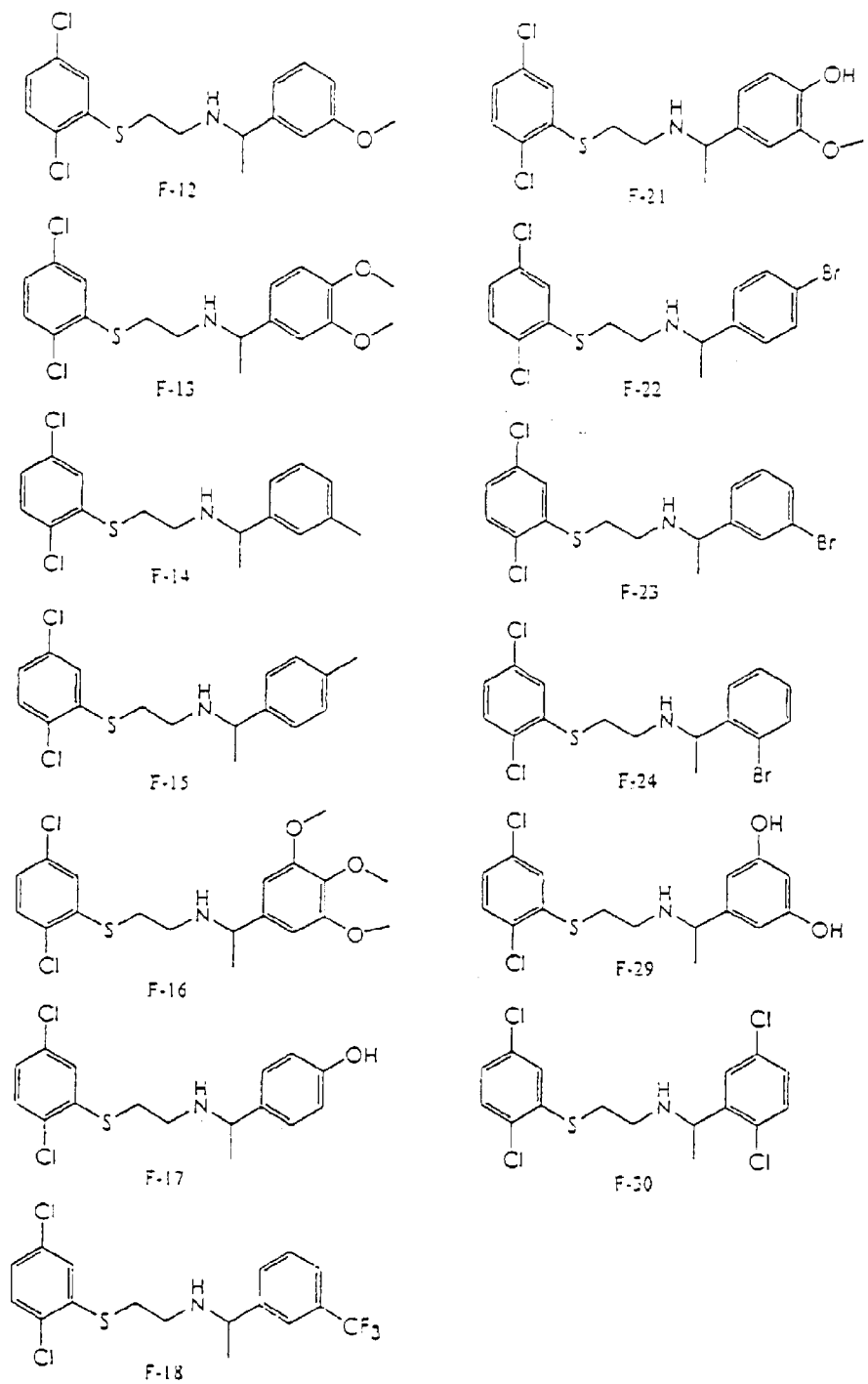
FIG. 36 shows the structures of the compounds of the present invention synthesized in Examples 416 to 428.
Figure 37:
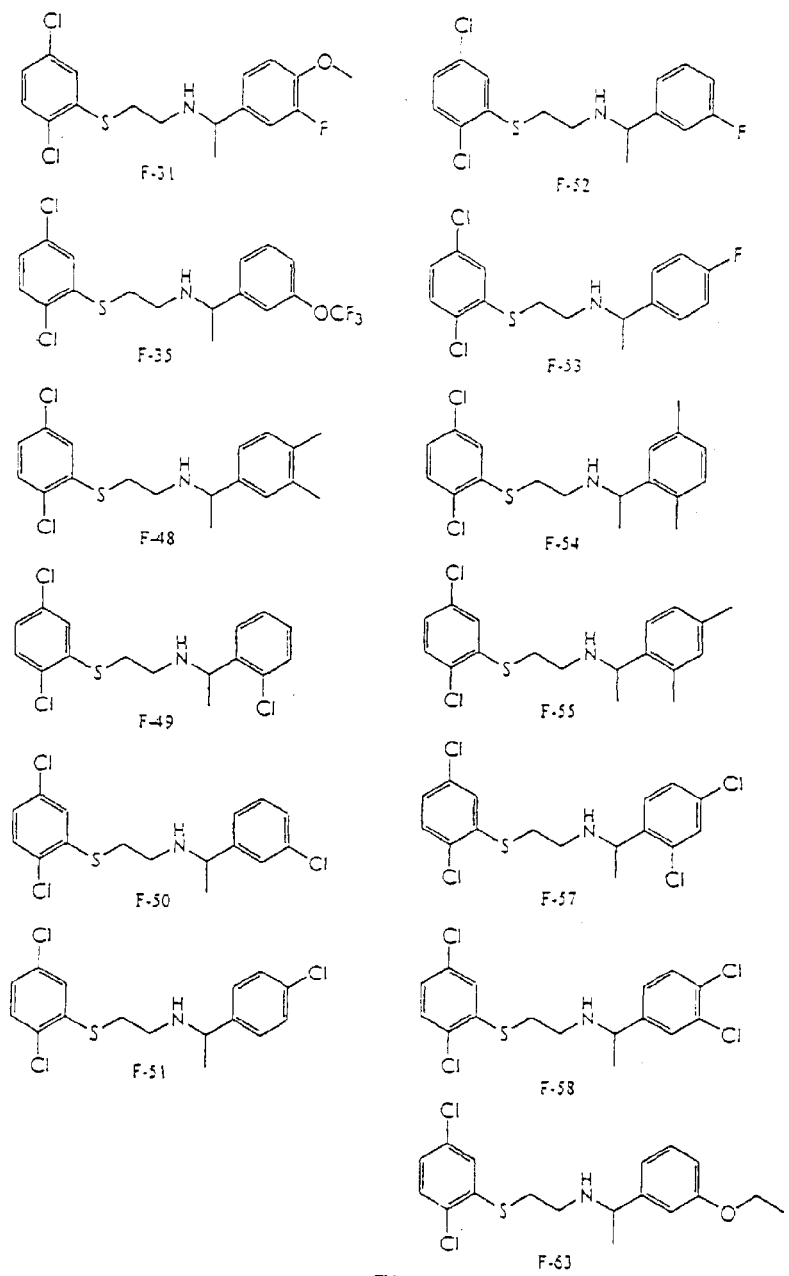
FIG. 37 shows the structures of the compounds of the present invention synthesized in Examples 429 to 441.
Figure 38:
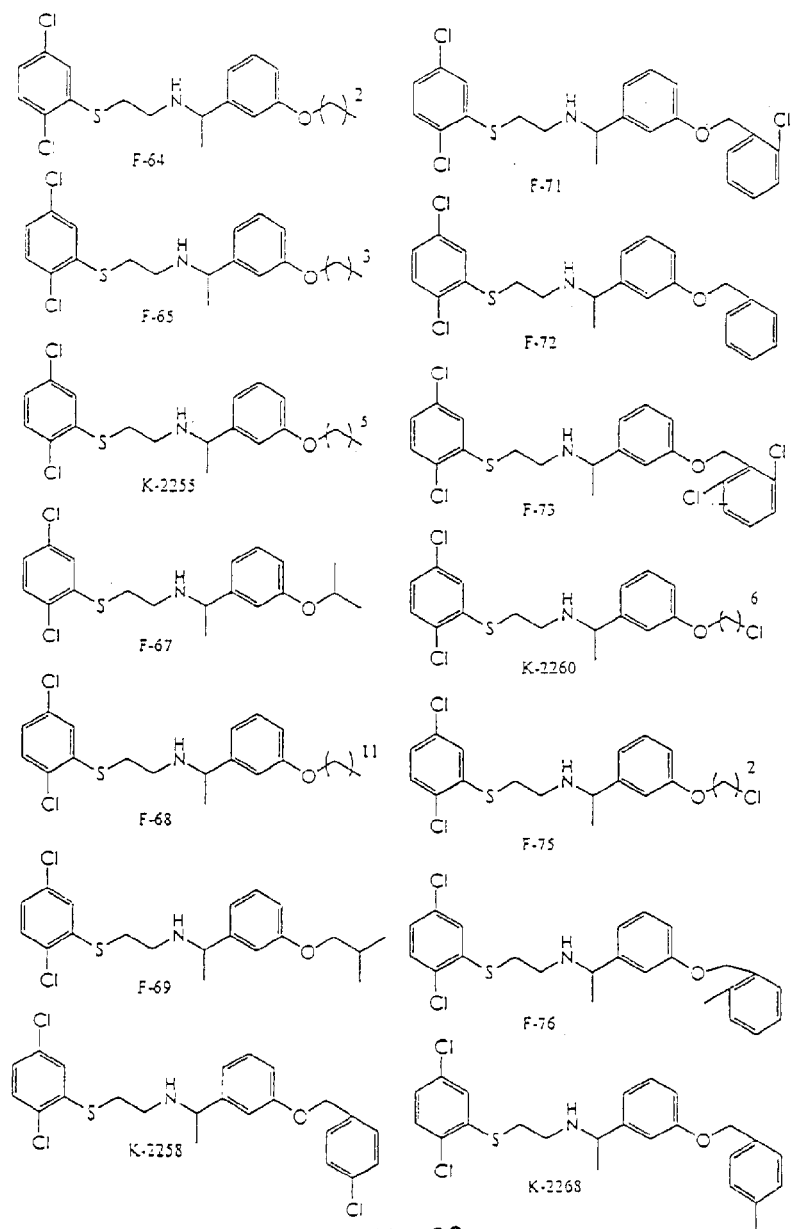
FIG. 38 shows the structures of the compounds of the present invention synthesized in Examples 442 to 455.
Figure 39:
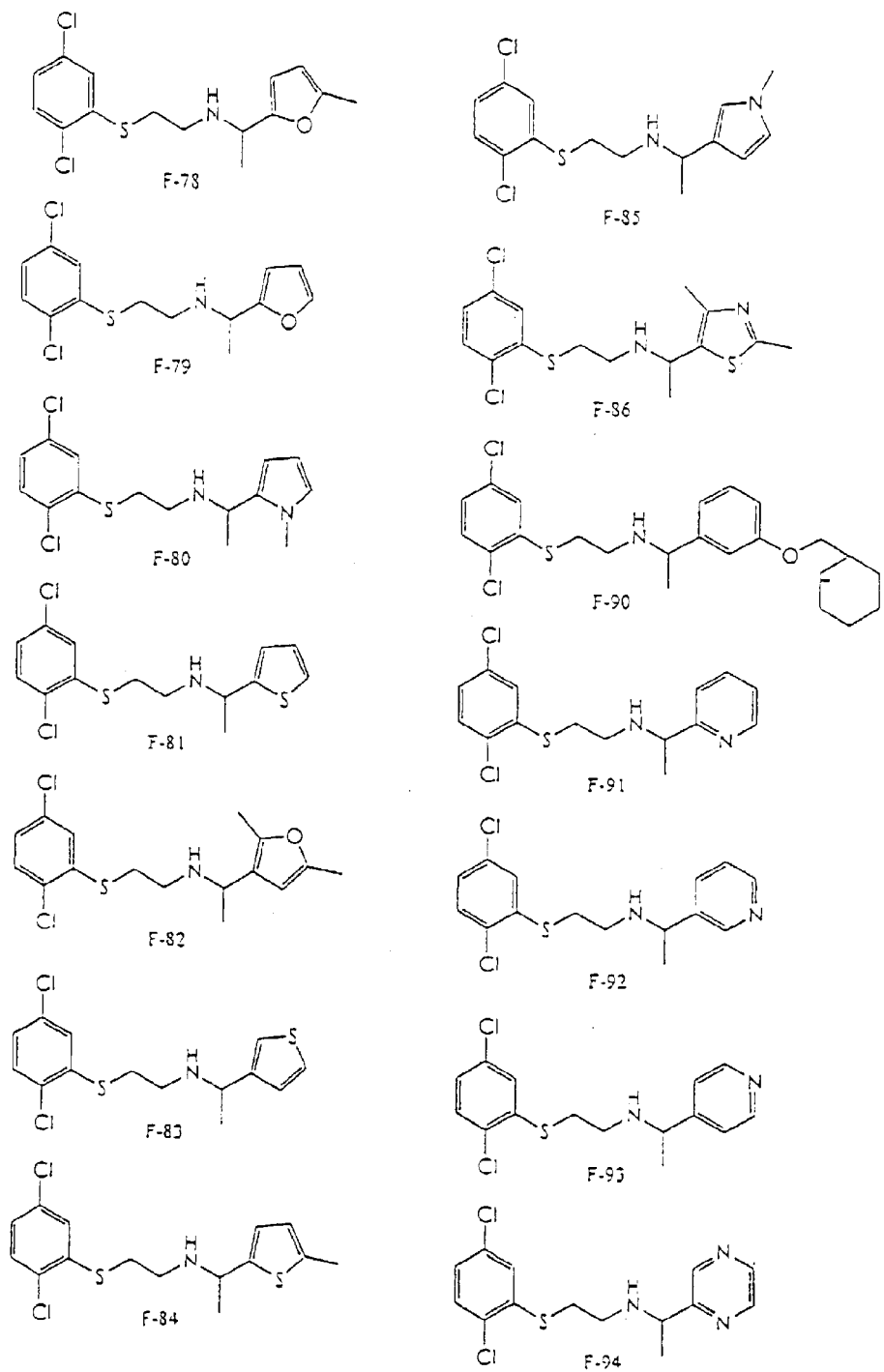
FIG. 39 shows the structures of the compounds of the present invention synthesized in Examples 456 to 469.
Figure 40:
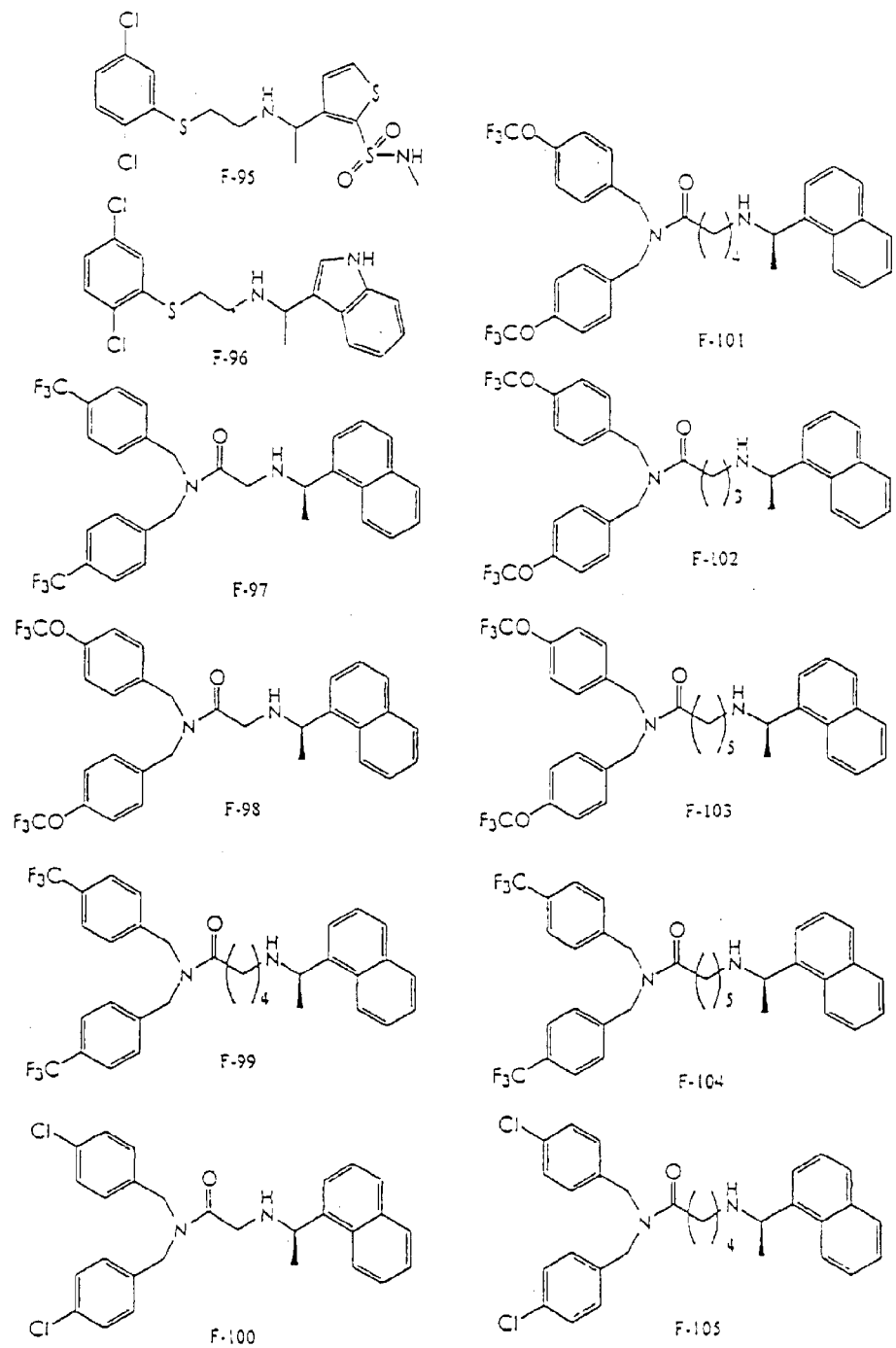
FIG. 40 shows the structures of the compounds of the present invention synthesized in Examples 470 to 480.
Figure 41:
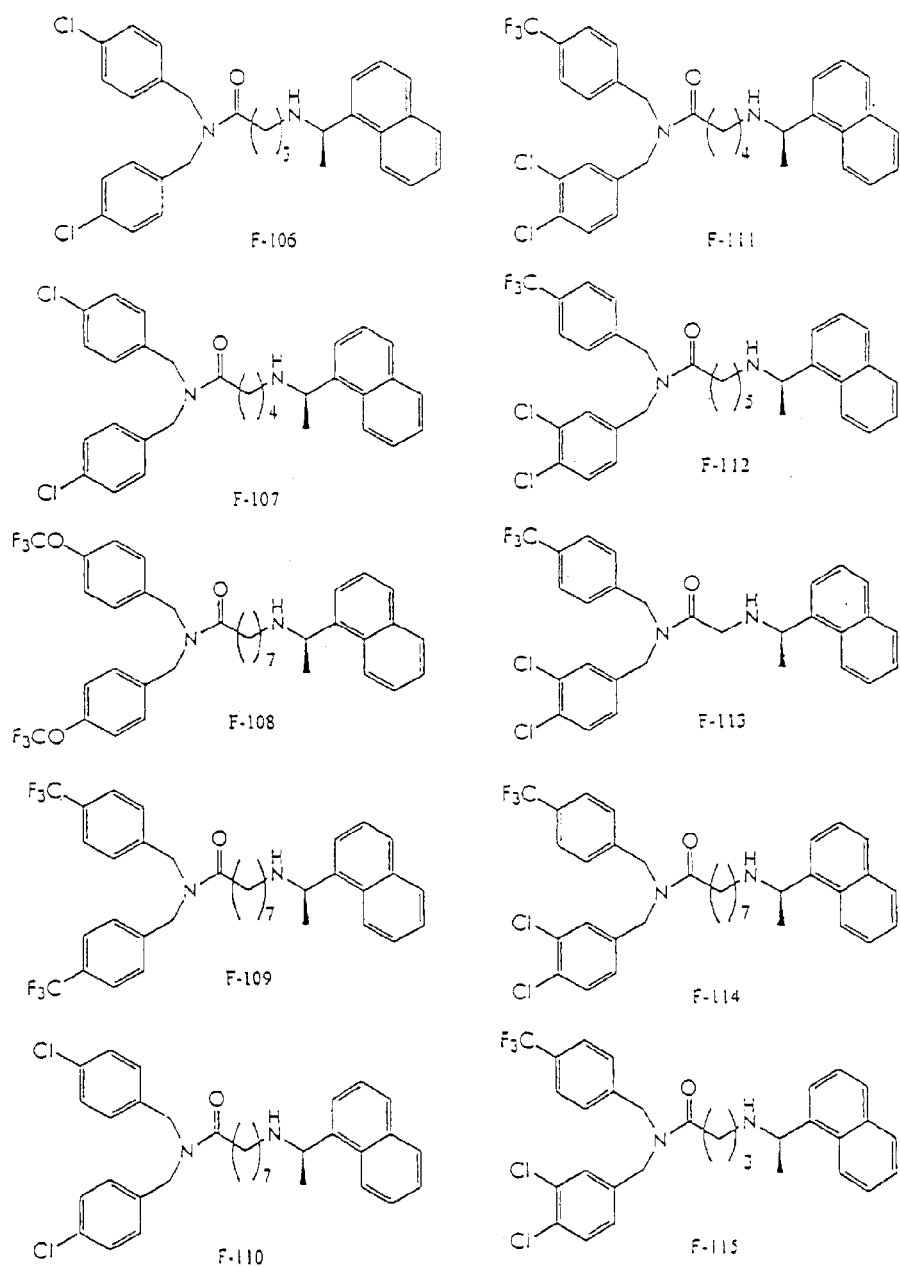
FIG. 41 shows the structures of the compounds of the present invention synthesized in Examples 481 to 490.
Figure 42:
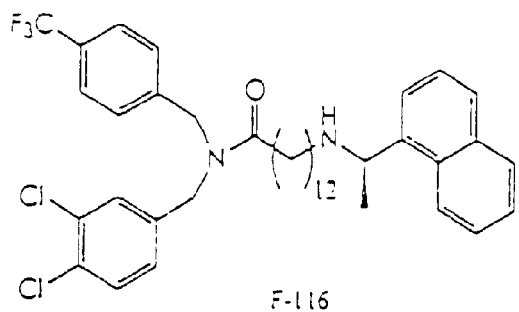
FIG. 42 shows the structures of the compounds of the present invention synthesized in Examples 491 to 495.
Figure 42:
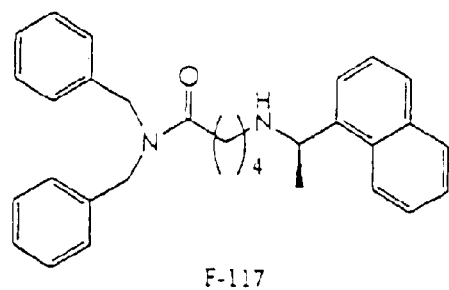
Figure 42:
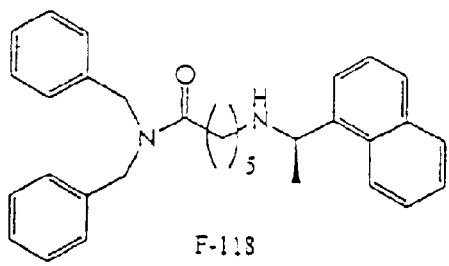
Figure 42:
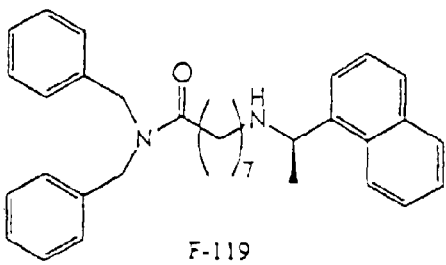
Figure 42:
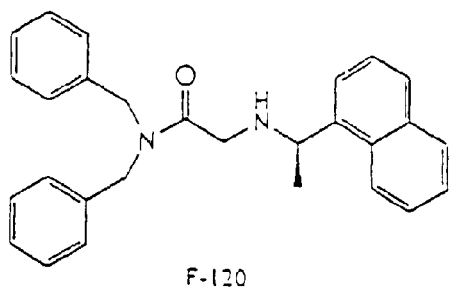
Figure 43:
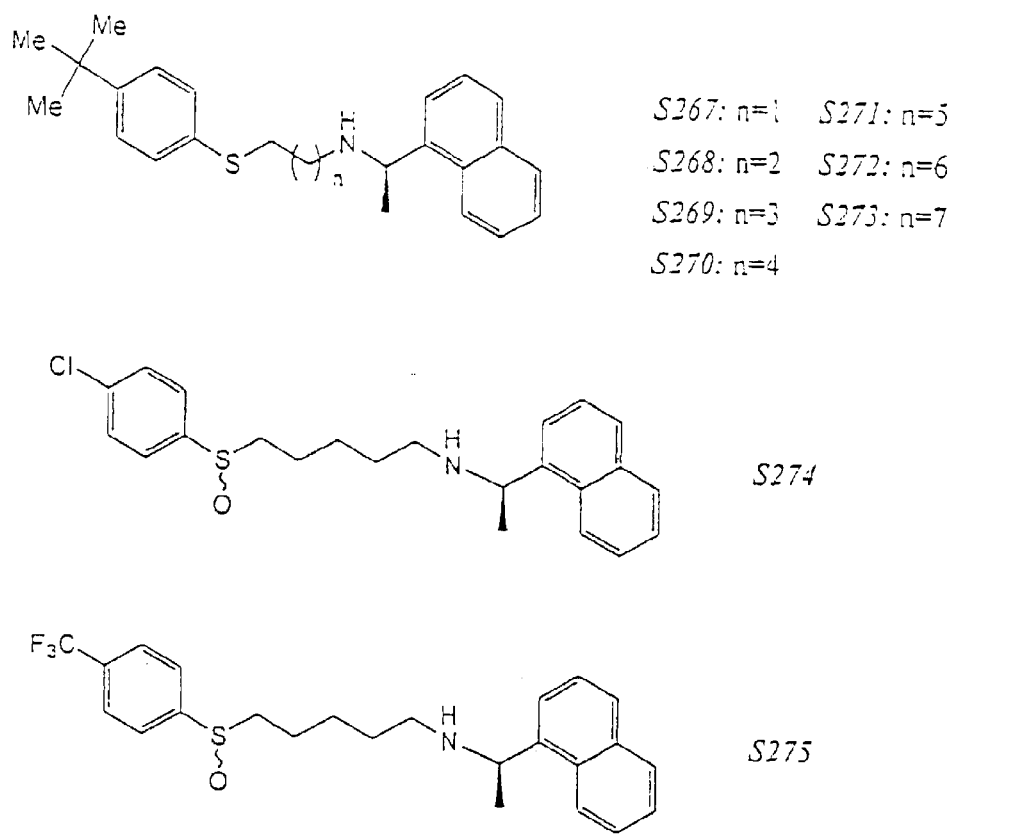
FIG. 43 shows the structures of the compounds of the present invention synthesized in Examples 496 to 504.
Figure 44:
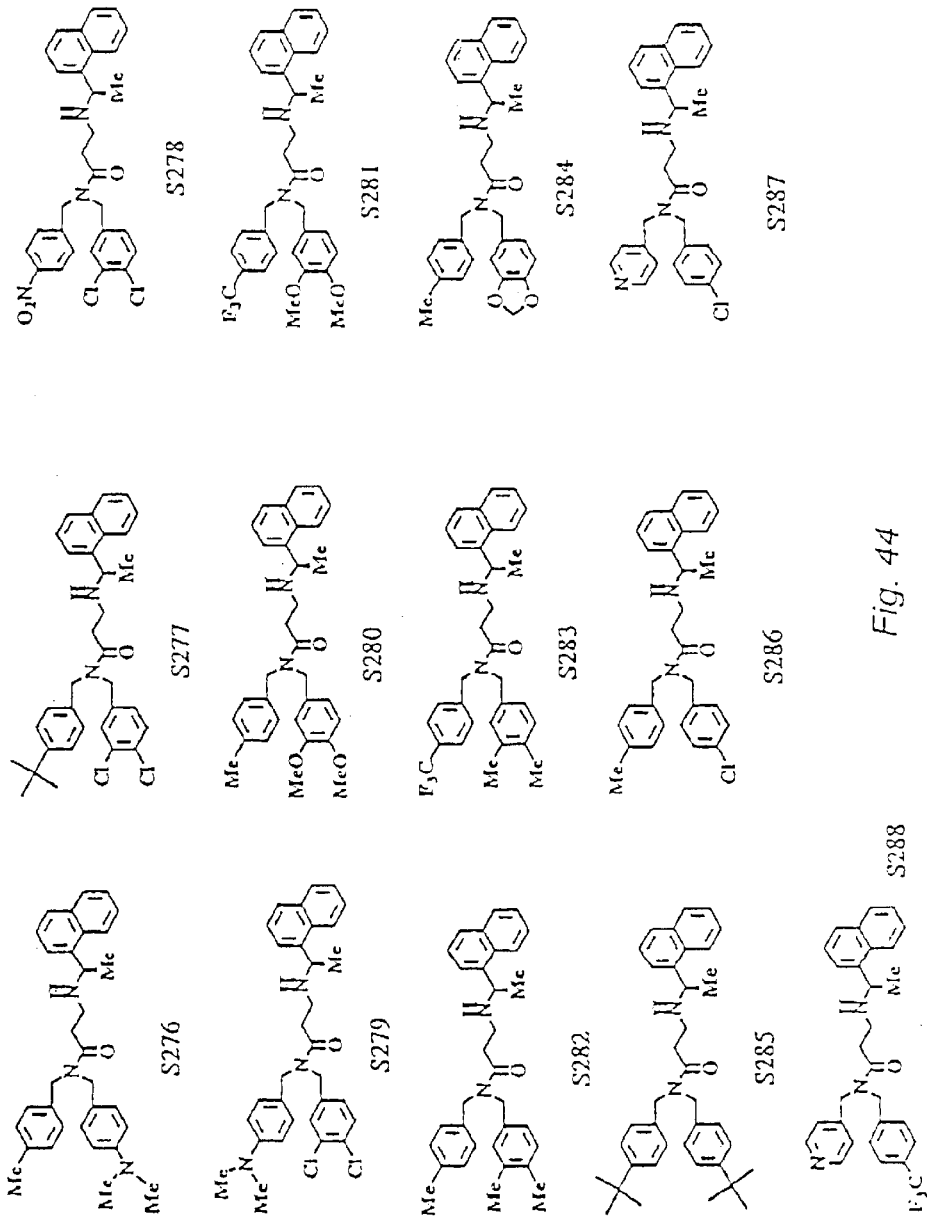
FIG. 44 shows the structures of the compounds of the present invention synthesized in Examples 505 to 517.
Figure 45:
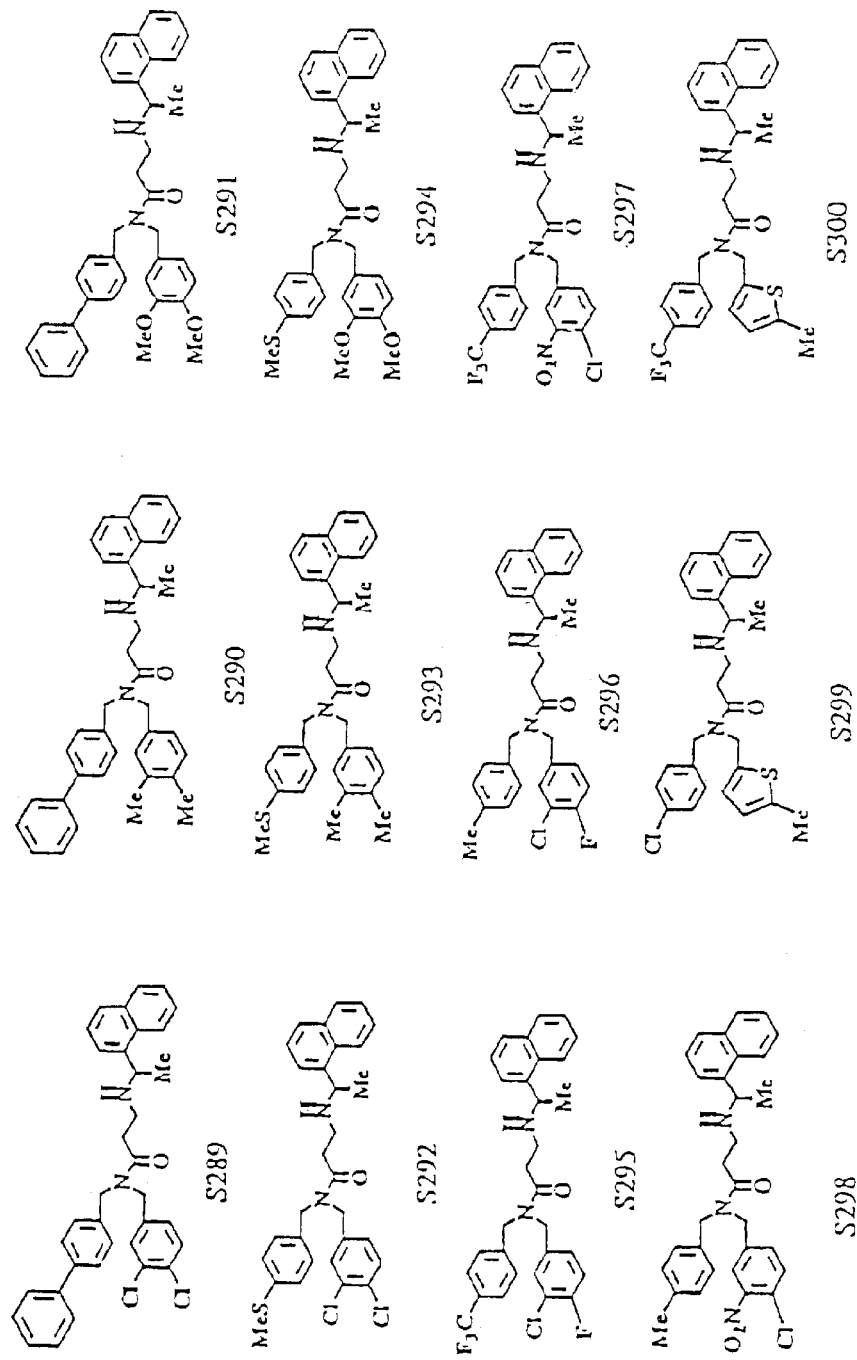
FIG. 45 shows the structures of the compounds of the present invention synthesized in Examples 518 to 529.
Figure 46:
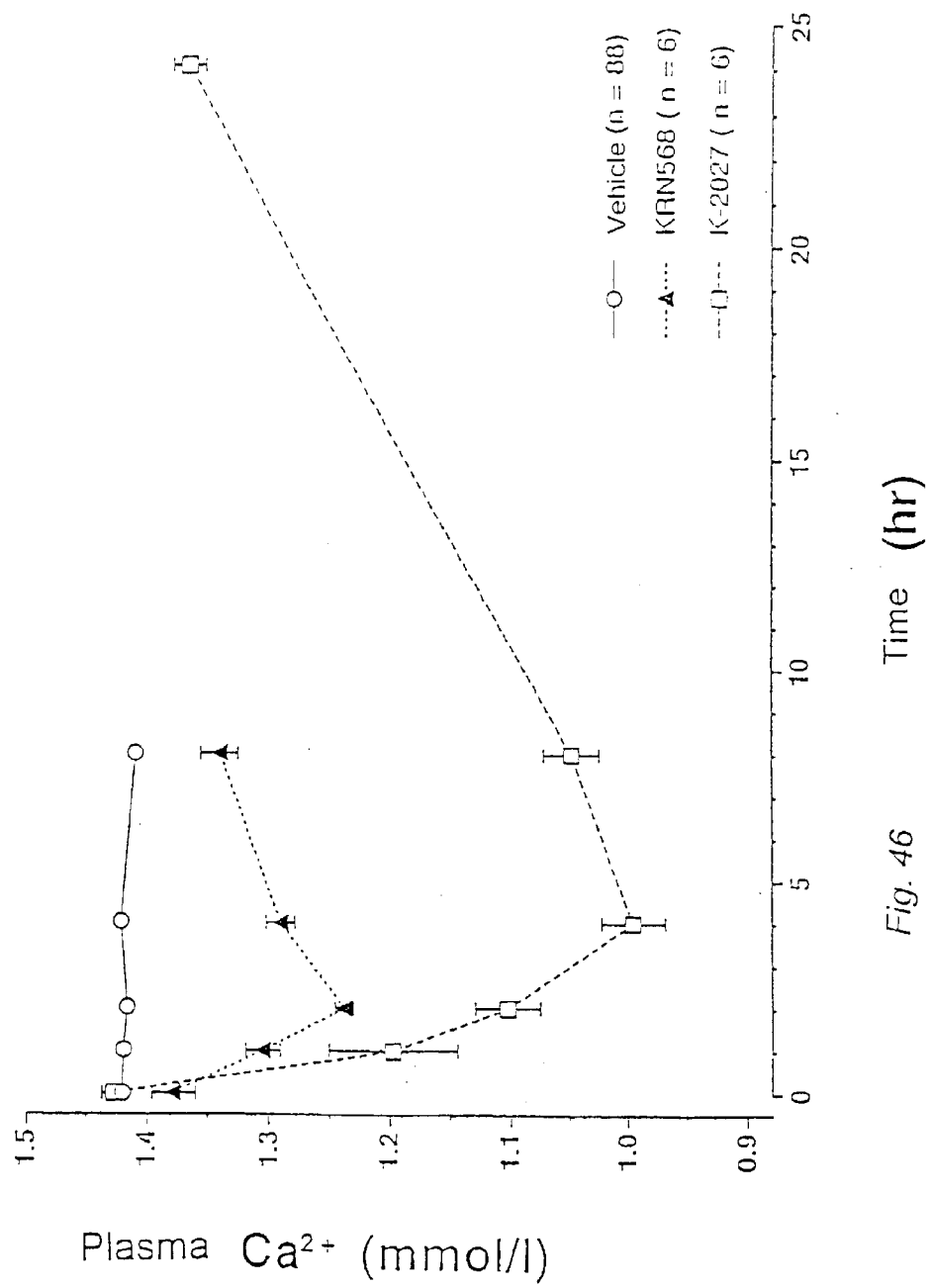
FIG. 46 shows changes in the plasma $Ca^{2+}$ level of the rats to which the compound of the present invention K-2027 was administered.
Figure 47:
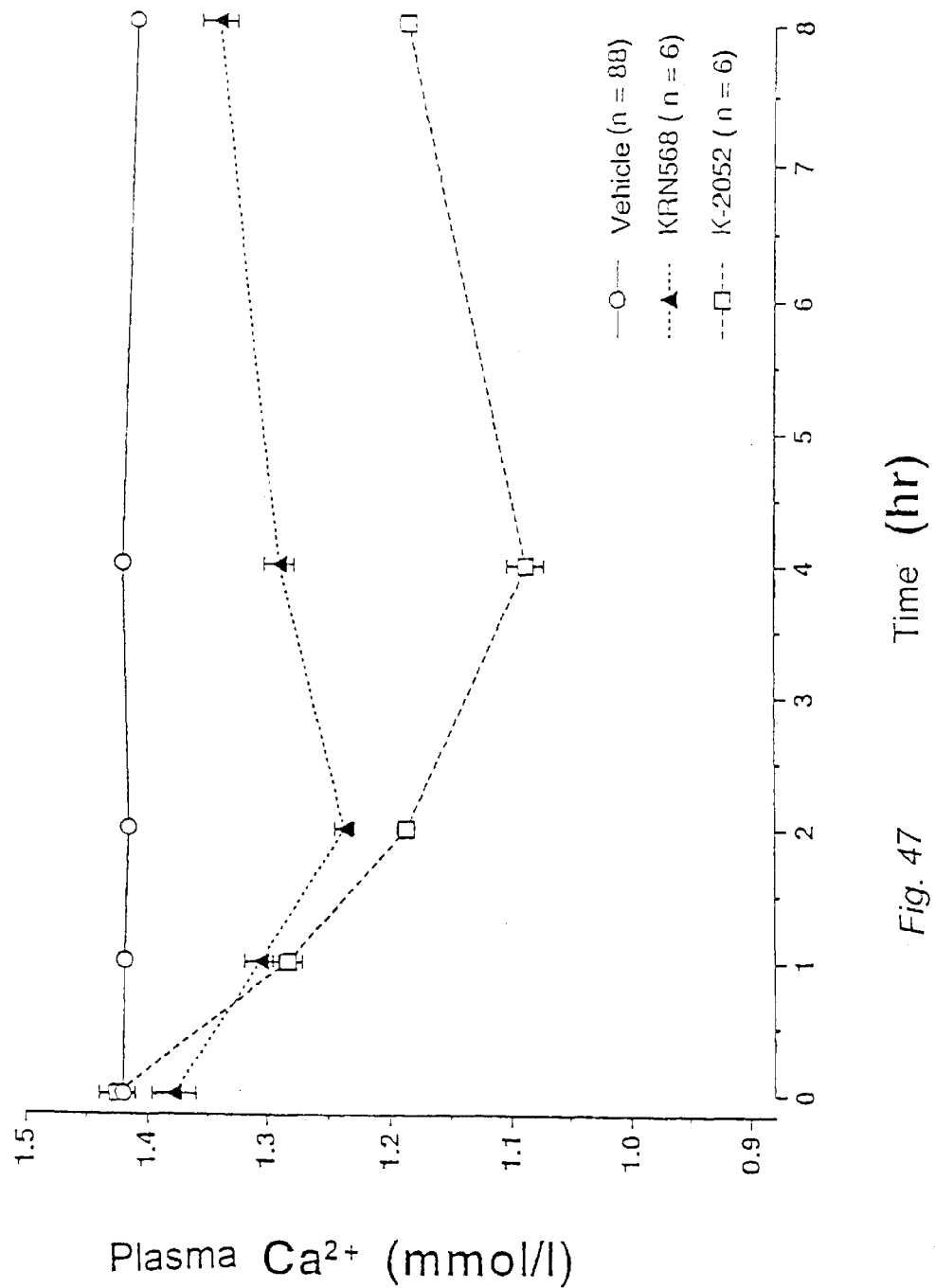
FIG. 47 shows changes in the plasma $Ca^{2+}$ level of the rats to which the compound of the present invention K-2052 was administered.
Figure 48:
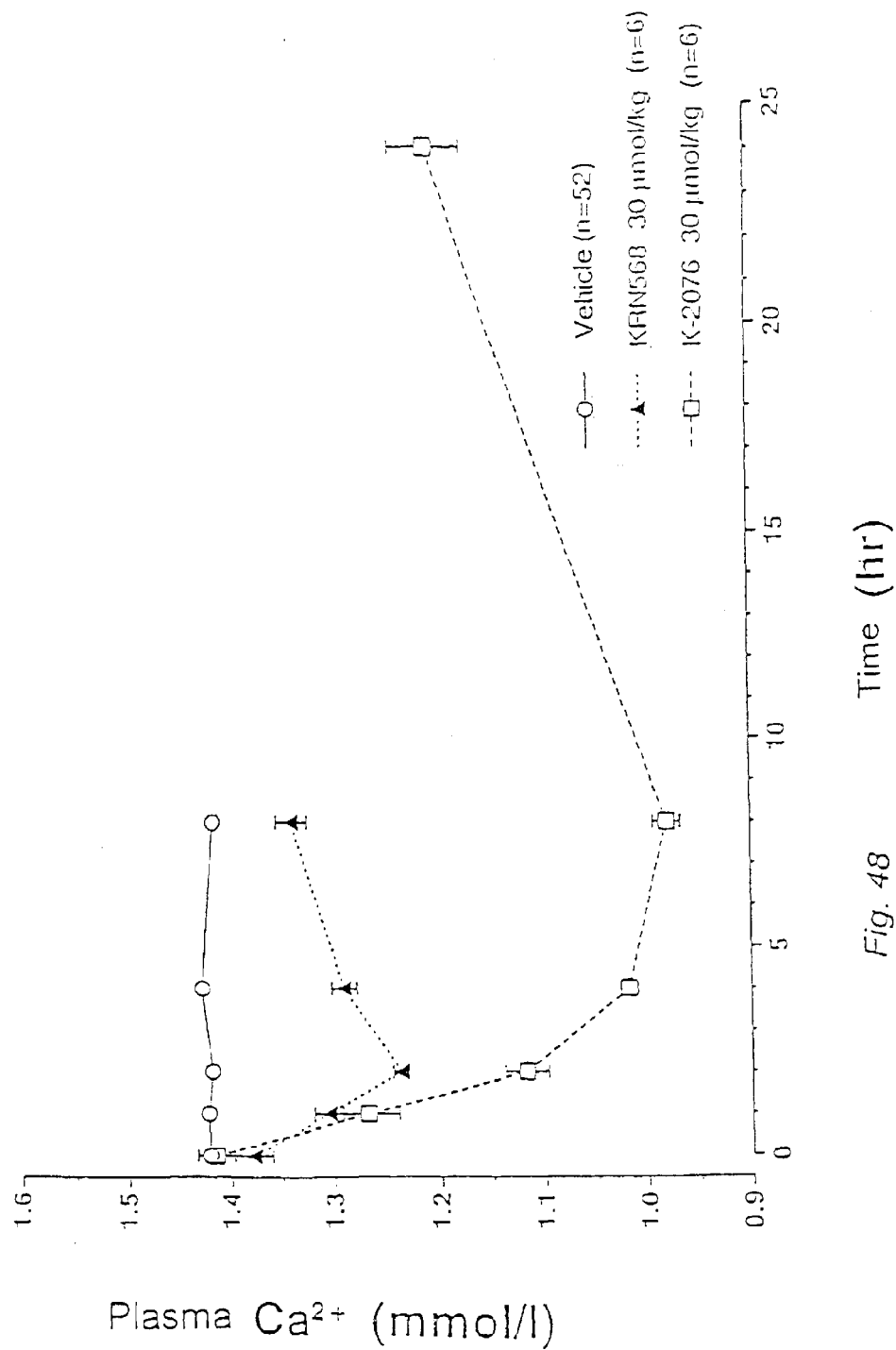
FIG. 48 shows changes in the plasma $Ca^{2+}$ level of the rats to which the compound of the present invention K-2076 was administered.
Figure 49:
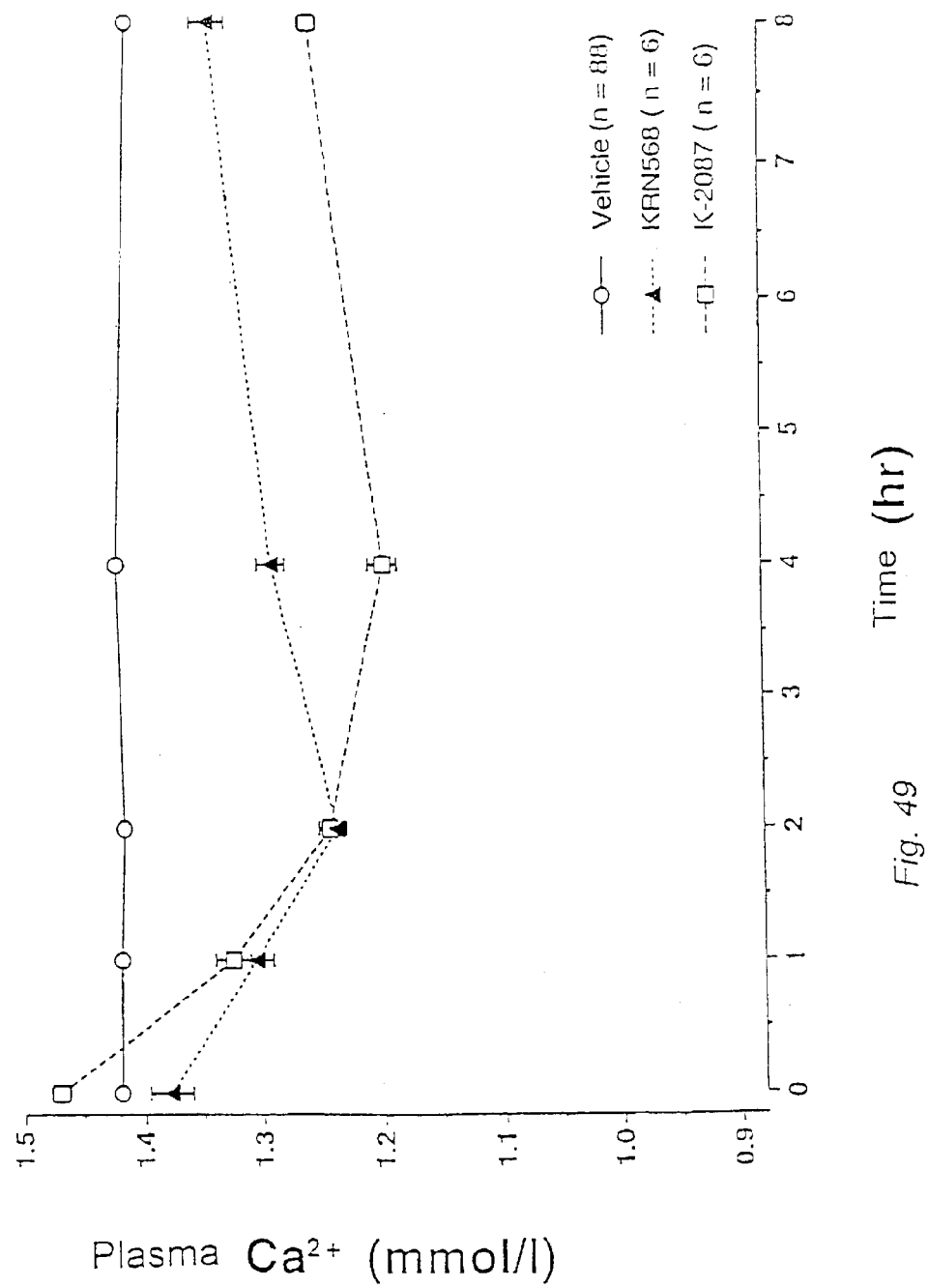
FIG. 49 shows changes in the plasma $Ca^{2-}$ level of the rats to which the compound of the present invention K-2087 was administered.
Figure 50:
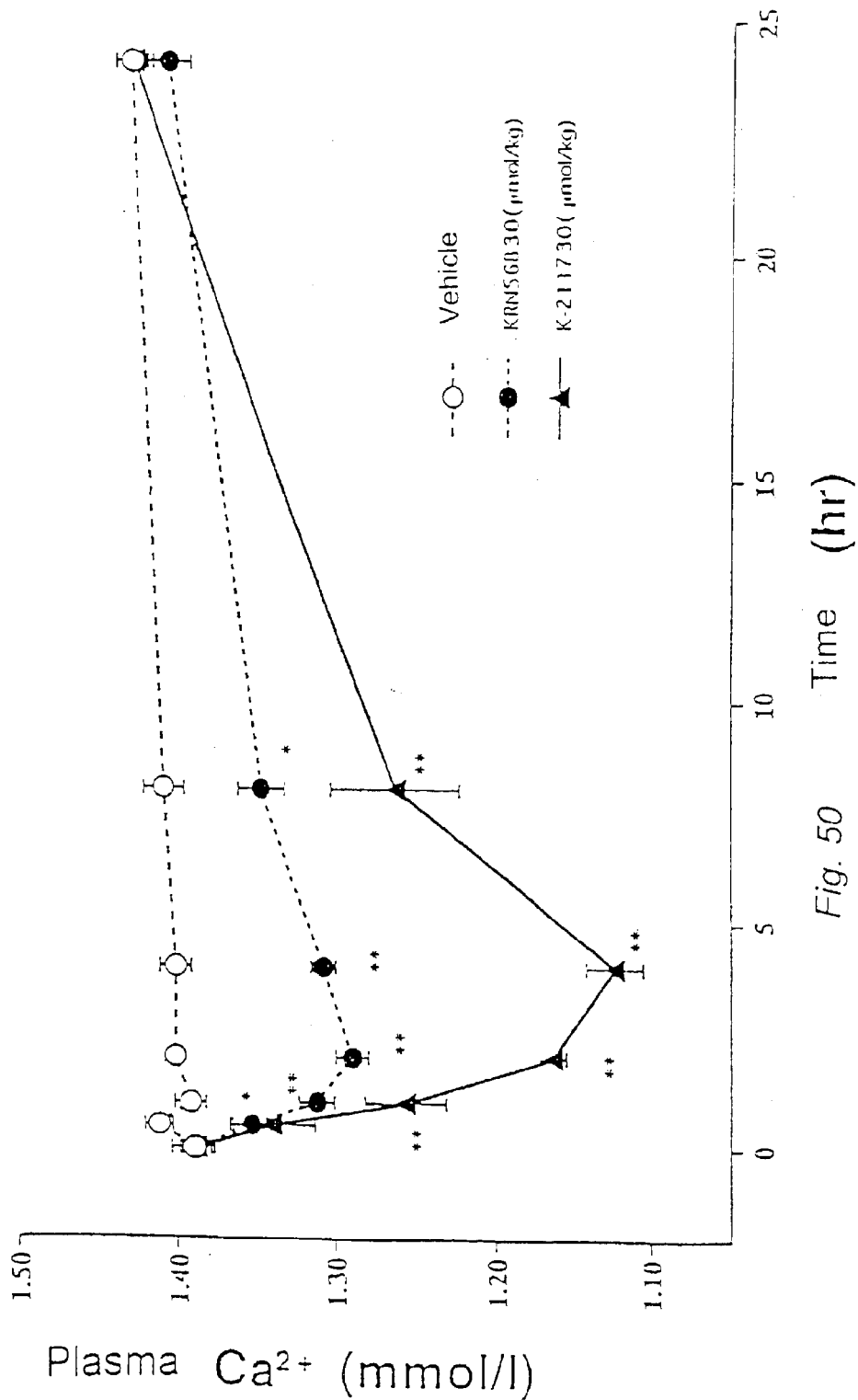
FIG. 50 shows changes in the plasma $Ca^{2+}$ level of the rats to which the compound of the present invention K-2117 was administered.
Figure 51:
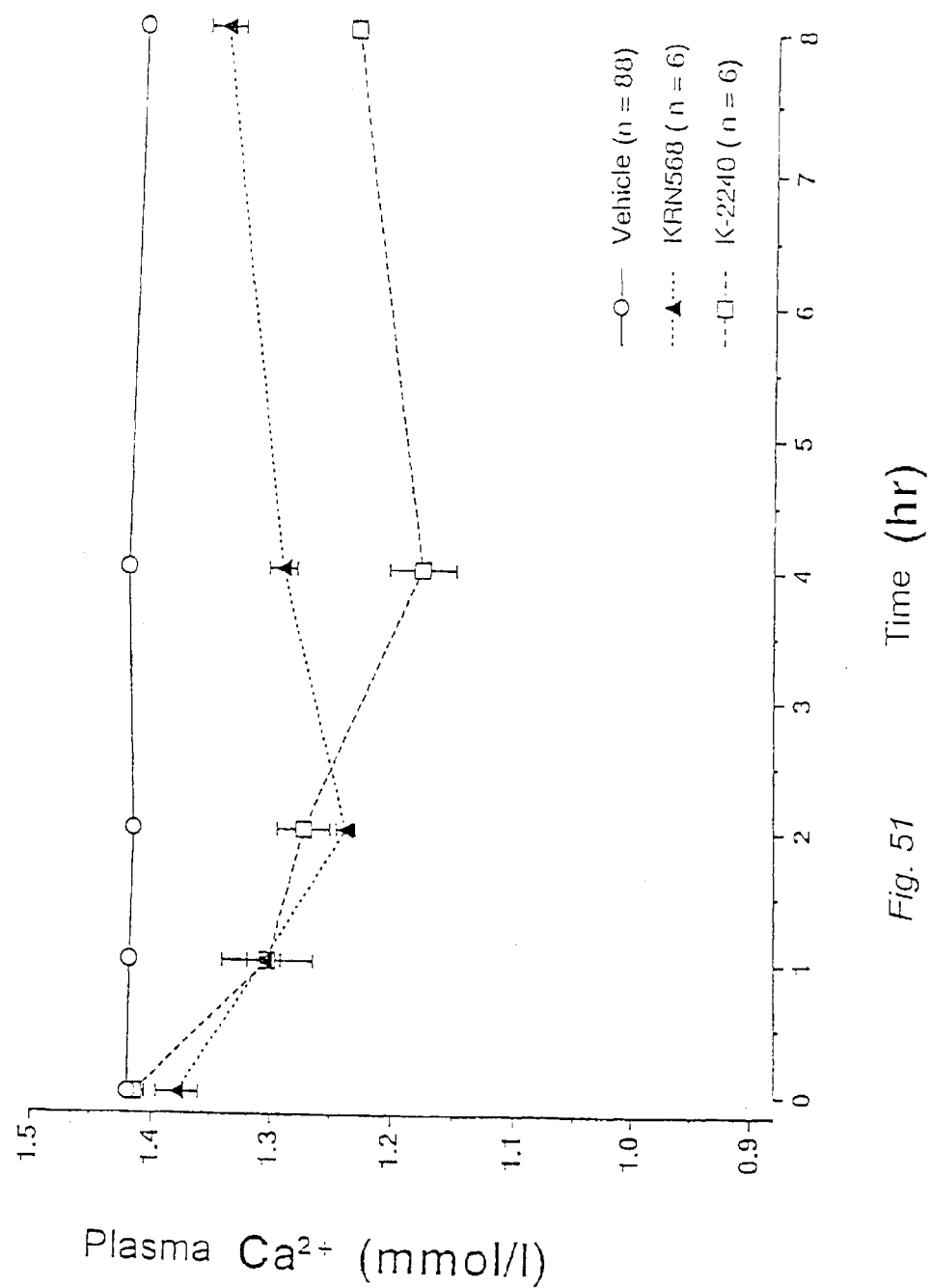
FIG. 51 shows changes in the plasma $Ca^{2+}$ level of the rats to which the compound of the present invention K-2240 was administered.
Figure 52:
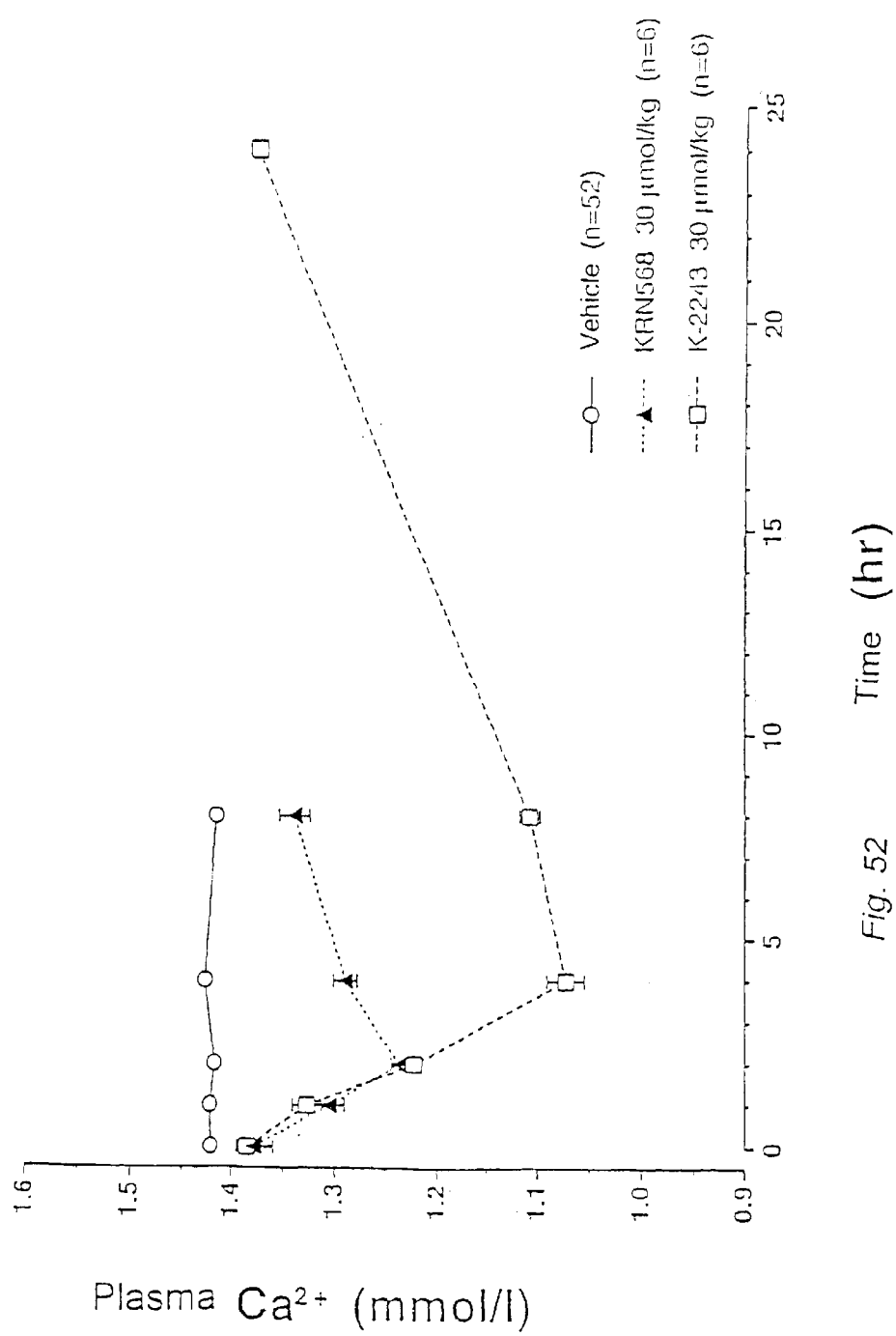
FIG. 52 shows changes in the plasma $Ca^{2+}$ level of the rats to which the compound of the present invention K-2243 was administered.
Figure 53:
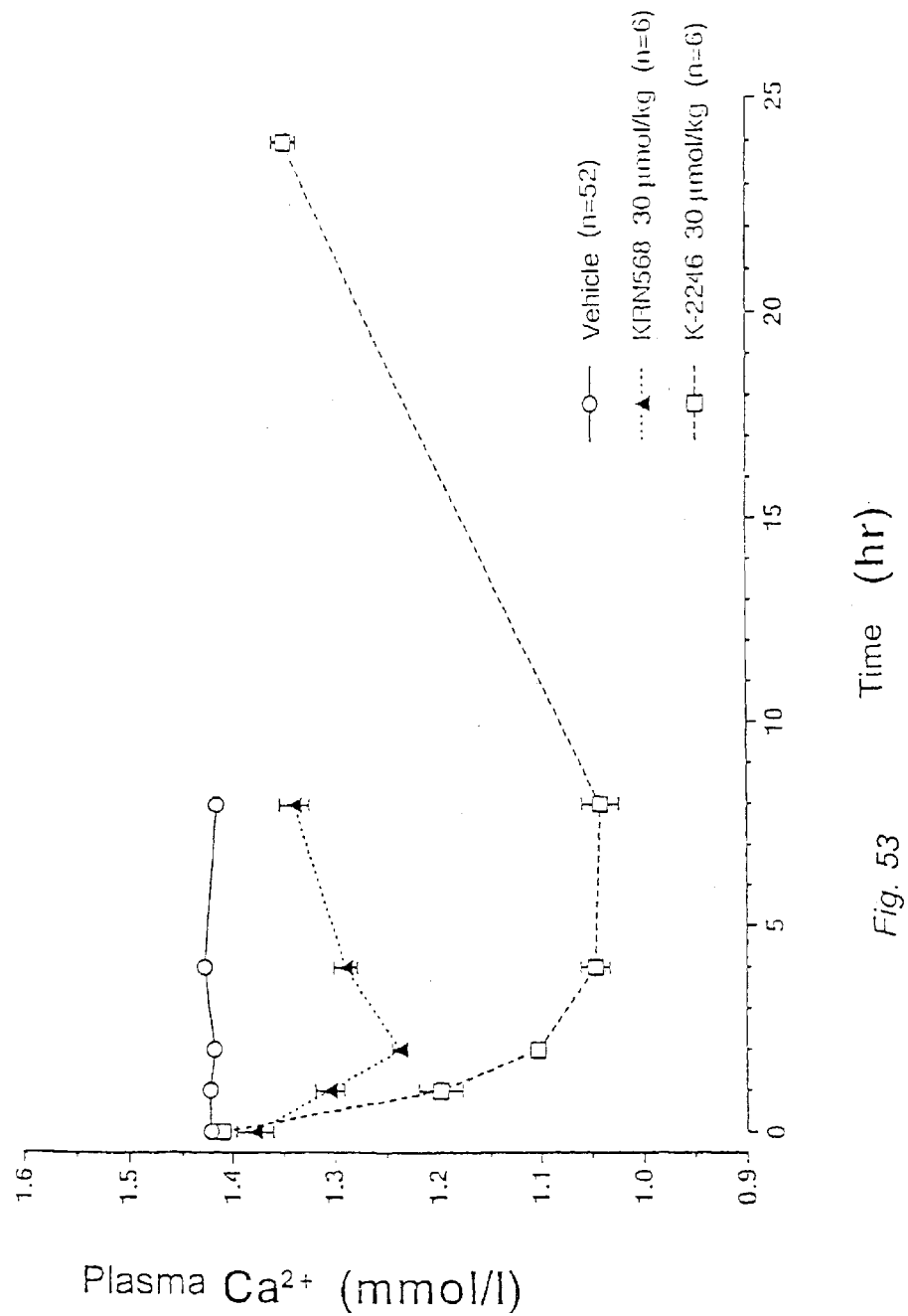
FIG. 53 shows changes in the plasma $Ca^{2+}$ level of the rats to which the compound of the present invention K-2246 was administered.
Figure 54:
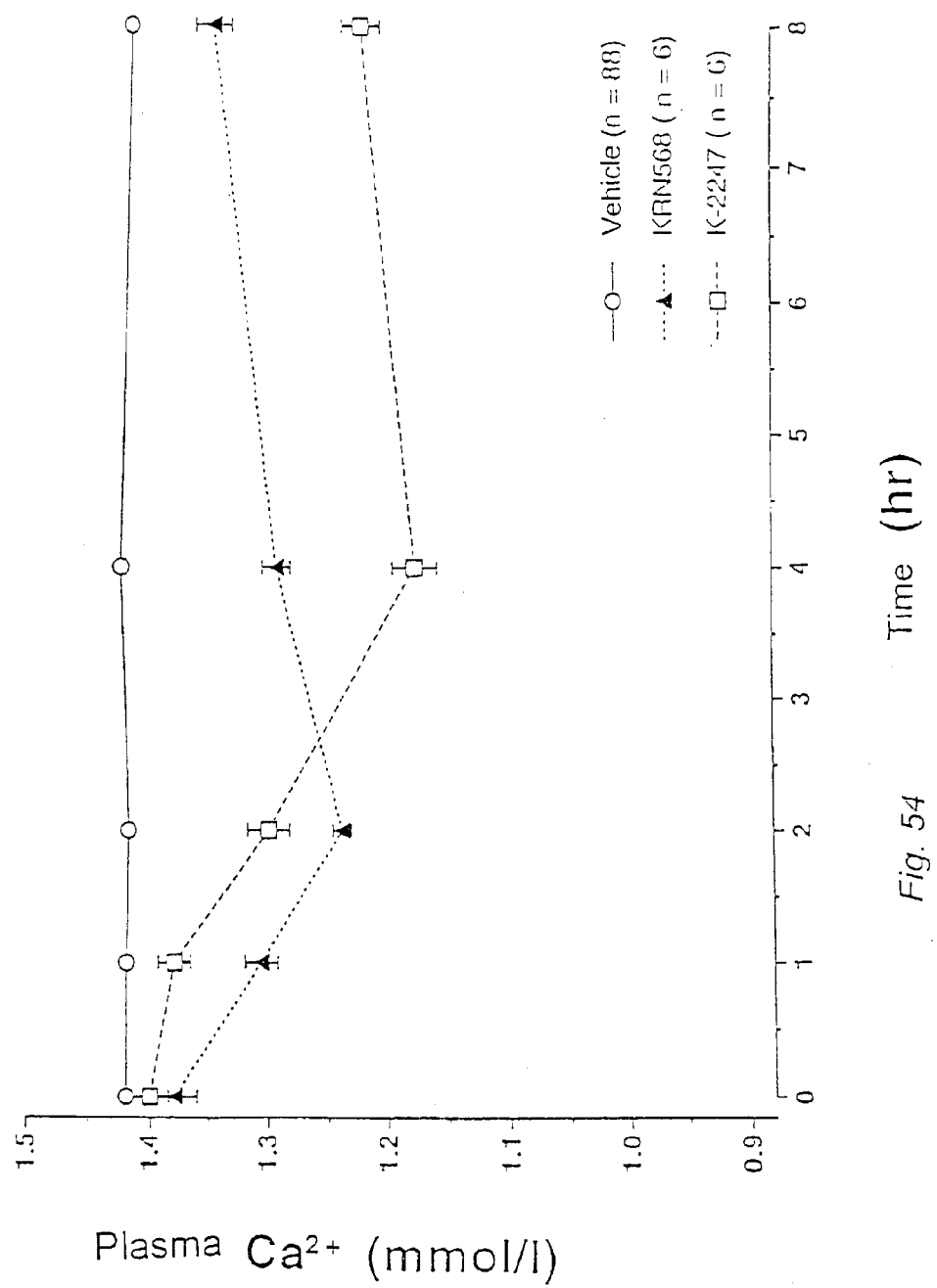
FIG. 54 shows changes in the plasma $Ca^{2+}$ level of the rats to which the compound of the present invention K-2247 was administered.
Figure 55:
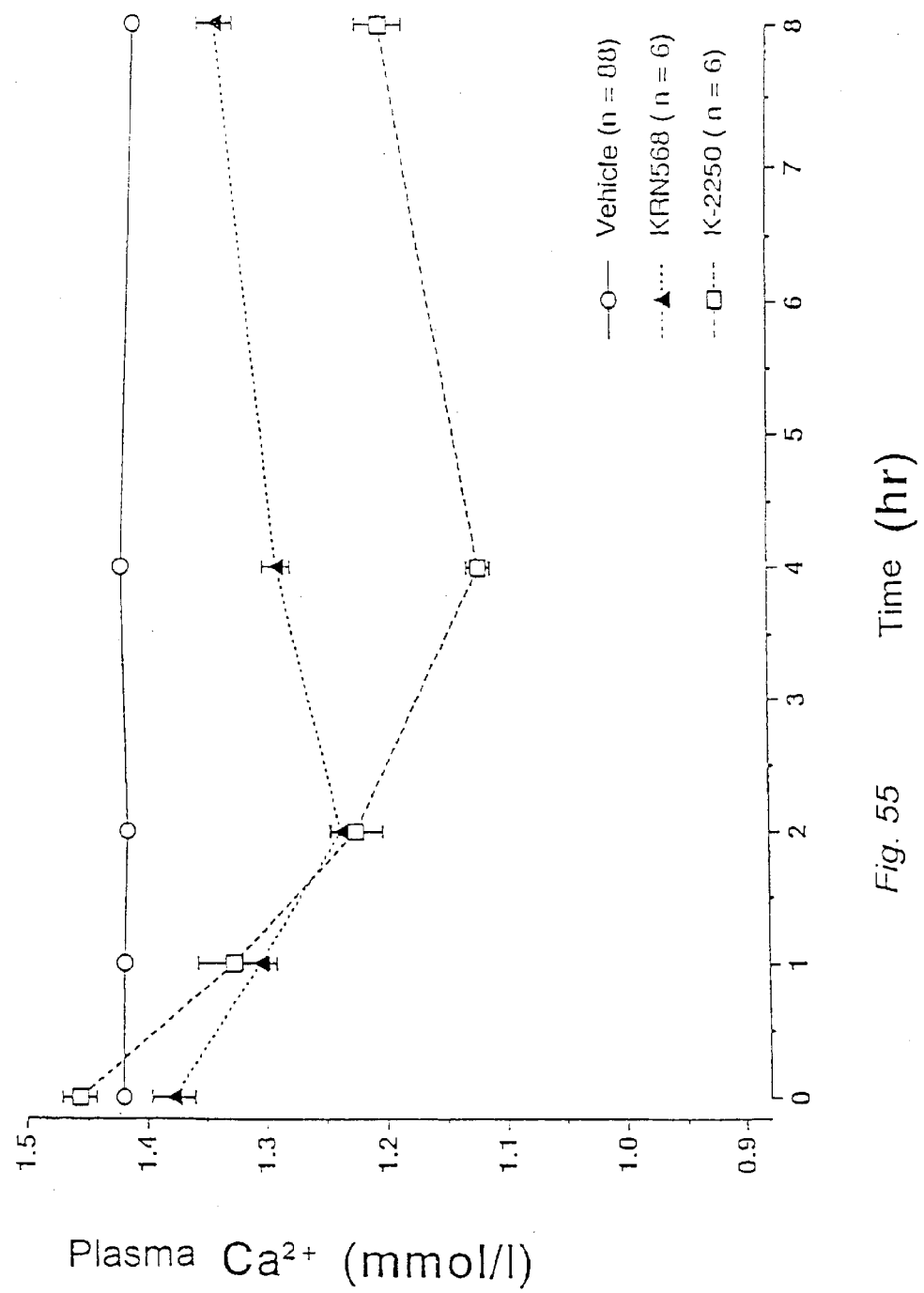
FIG. 55 shows changes in the plasma $Ca^{2+}$ level of the rats to which the compound of the present invention K-2250 was administered.
Figure 56:
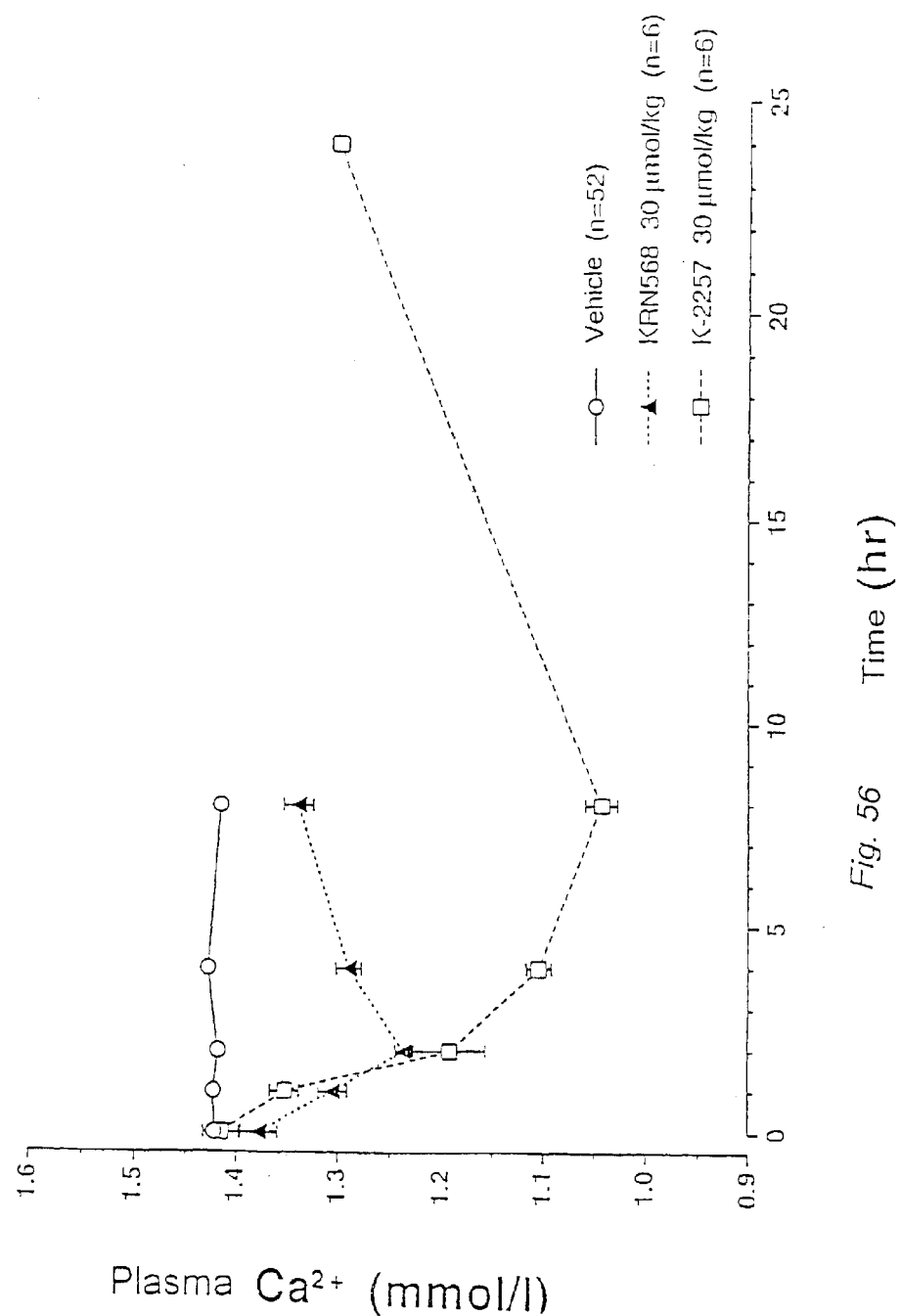
FIG. 56 shows changes in the plasma $Ca^{2+}$ level of the rats to which the compound of the present invention K-2257 was administered.
Figure 57:
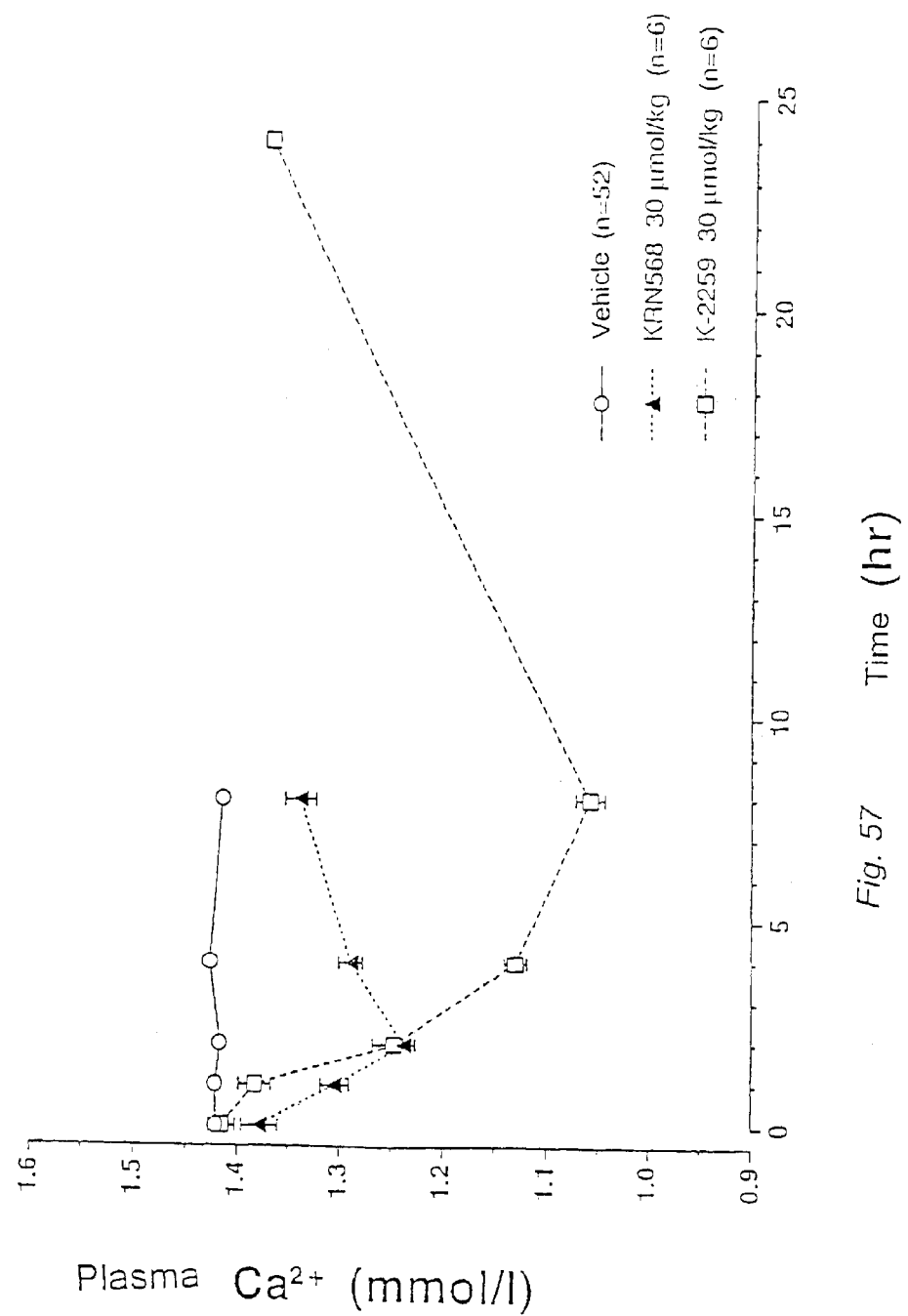
FIG. 57 shows changes in the plasma $Ca^{2+}$ level of the rats to which the compound of the present invention K-2259 was administered.
Figure 58:
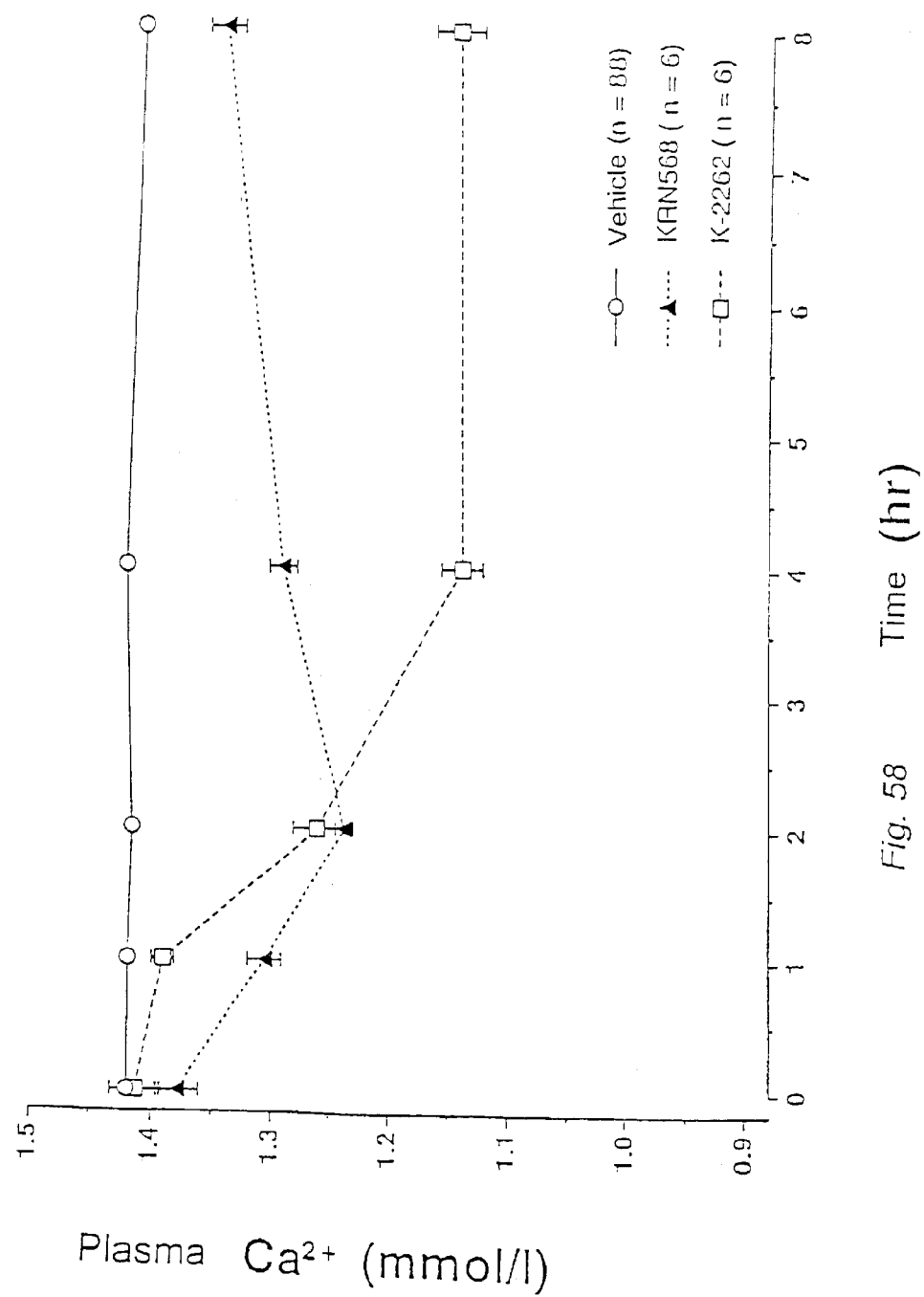
FIG. 58 shows changes in the plasma $Ca^{2+}$ level of the rats to which the compound of the present invention K-2262 was administered.
Figure 59:
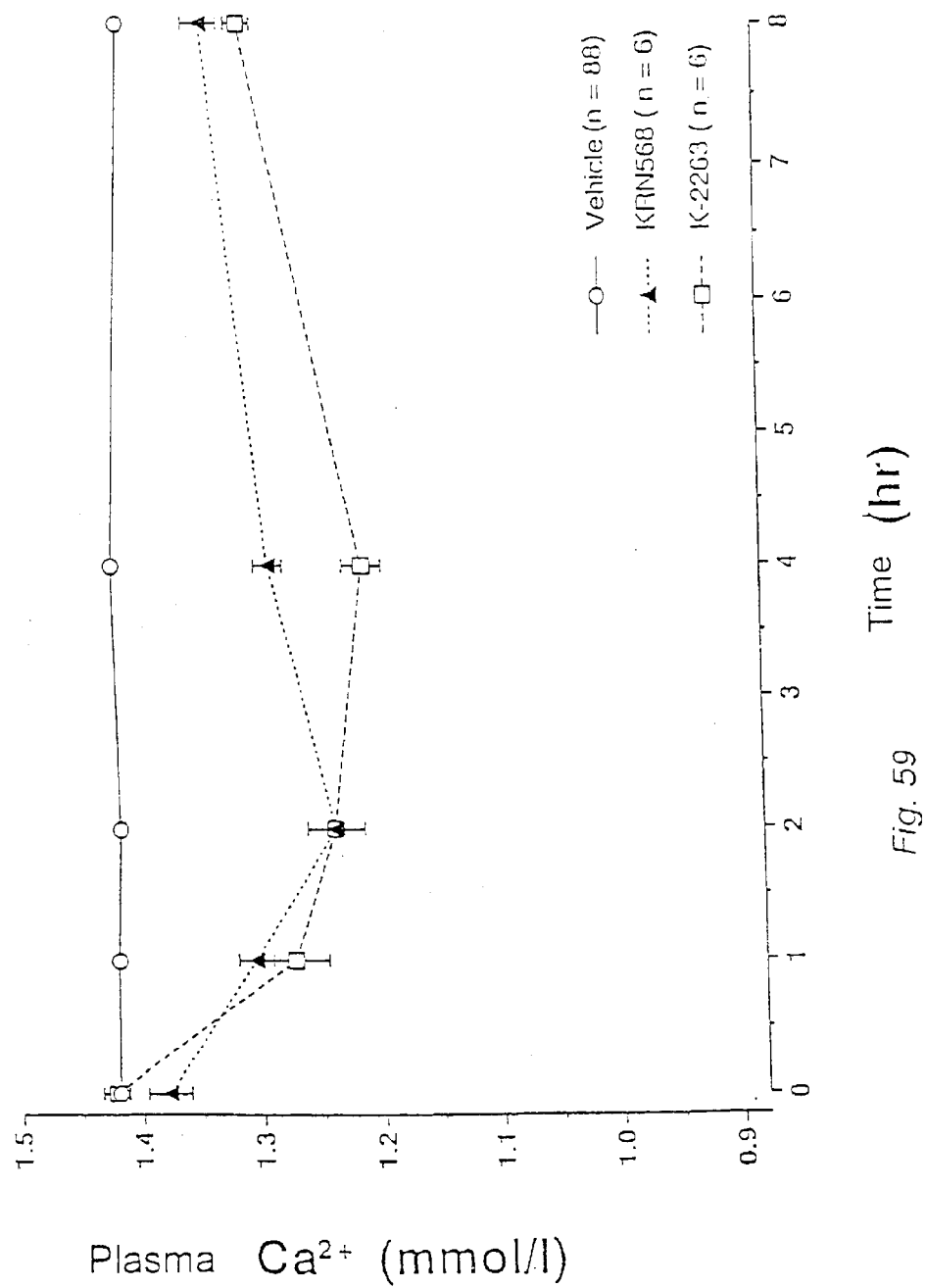
FIG. 59 shows changes in the plasma $Ca^{2+}$ level of the rats to which the compound of the present invention K-2263 was administered.
Figure 60:
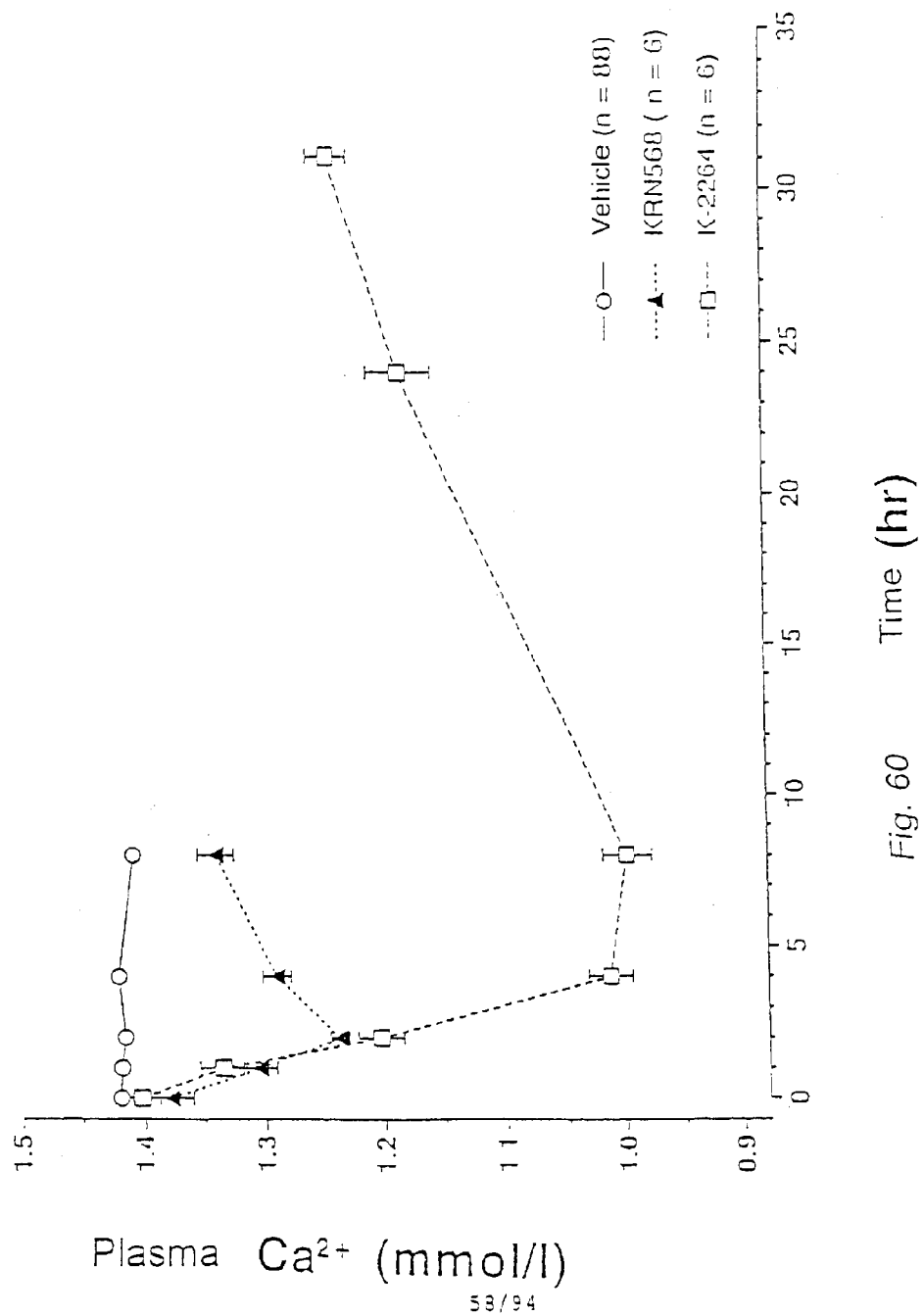
FIG. 60 shows changes in the plasma $Ca^{2+}$ level of the rats to which the compound of the present invention K-2264 was administered.
Figure 61:
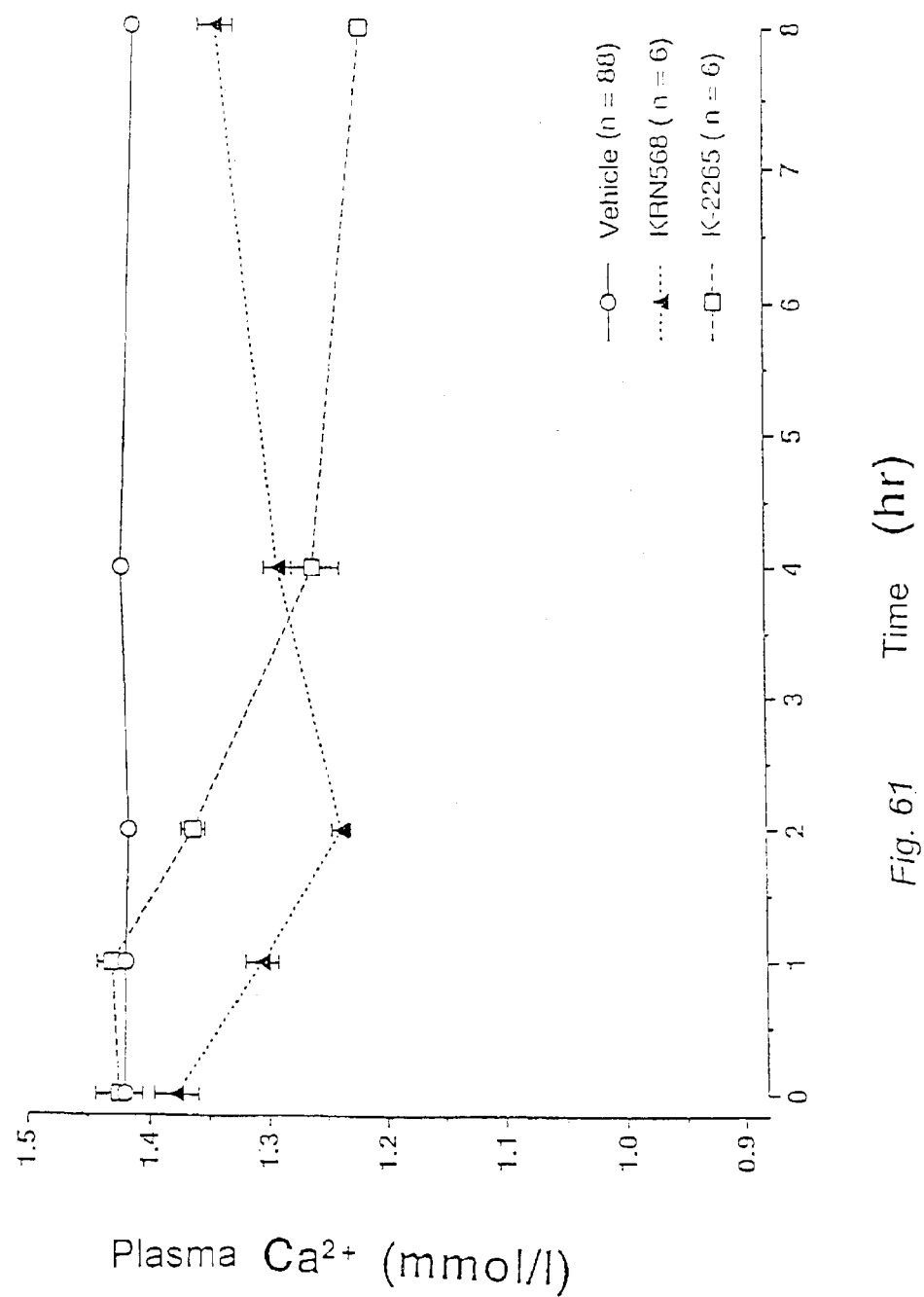
FIG. 61 shows changes in the plasma $Ca^{2+}$ level of the rats to which the compound of the present invention K-2265 was administered.
Figure 62:
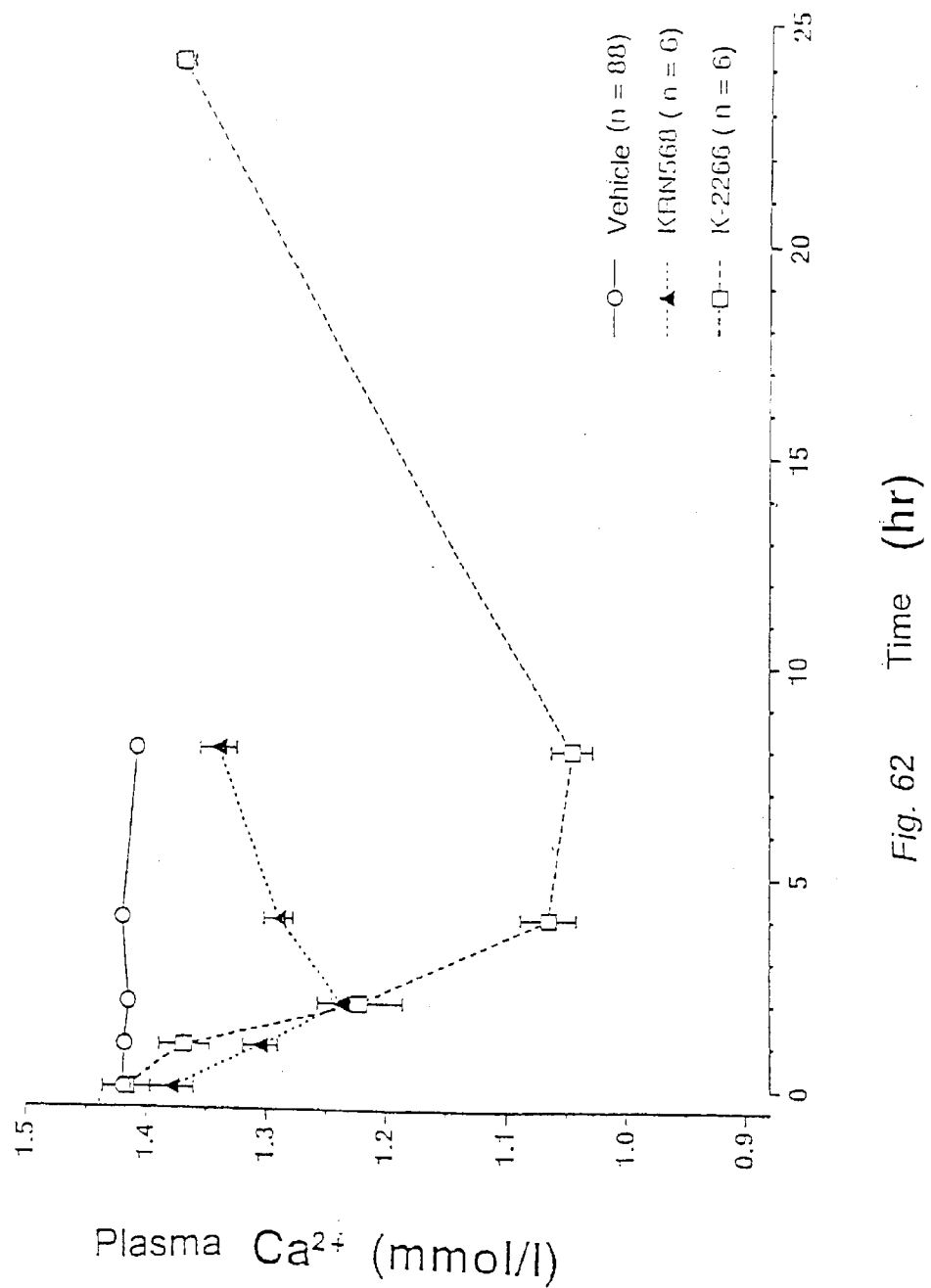
FIG. 62 shows changes in the plasma $Ca^{2+}$ level of the rats to which the compound of the present invention K-2266 was administered.
Figure 63:
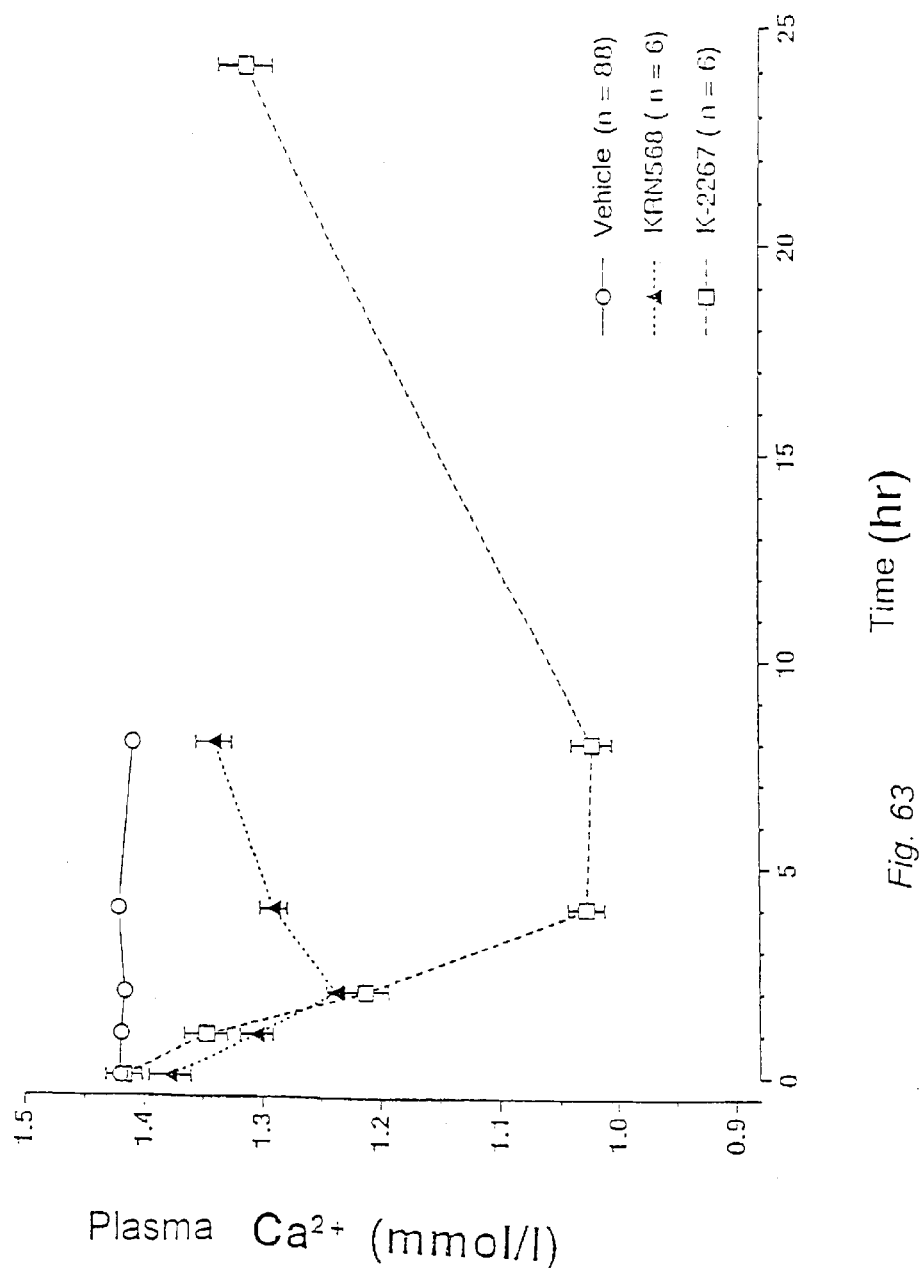
FIG. 63 shows changes in the plasma $Ca^{2+}$ level of the rats to which the compound of the present invention K-2267 was administered.
Figure 64:
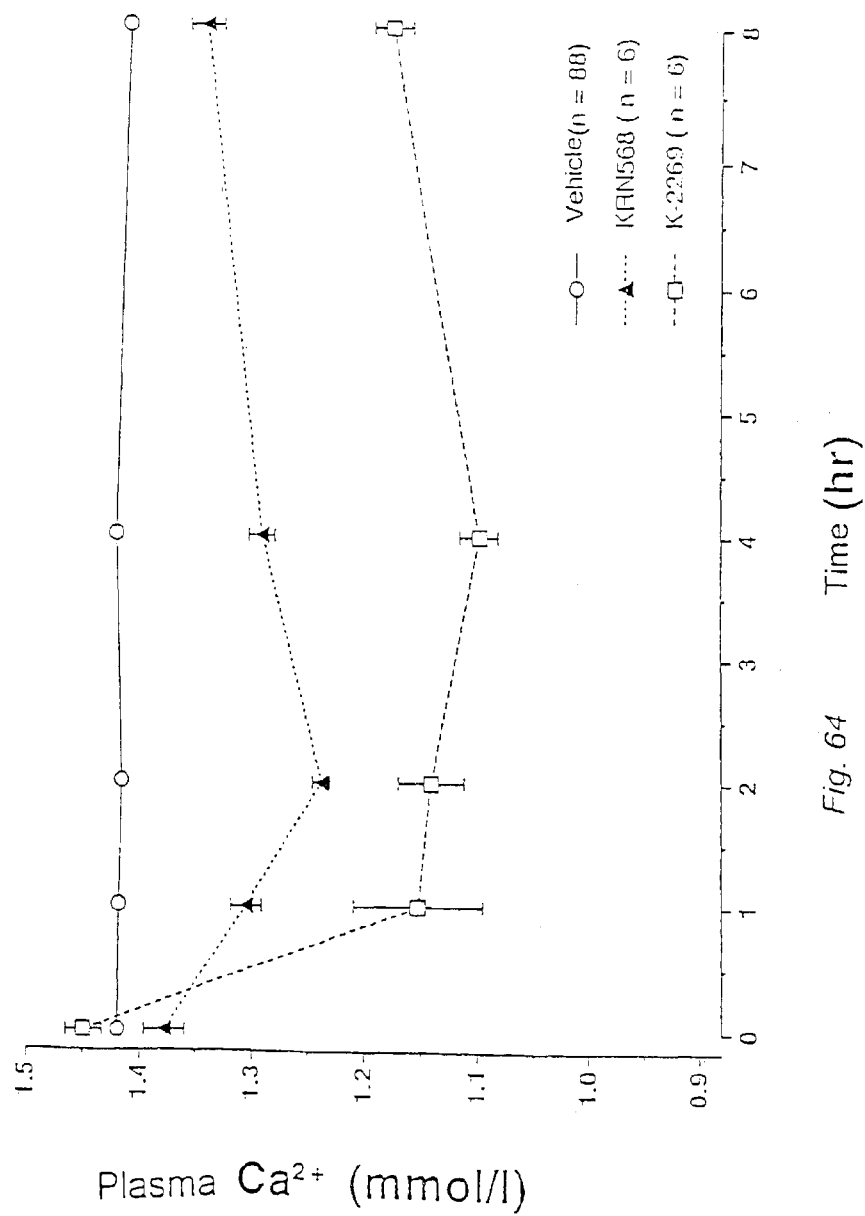
FIG. 64 shows changes in the plasma $Ca^{2+}$ level of the rats to which the compound of the present invention K-2269 was administered.
Figure 65:
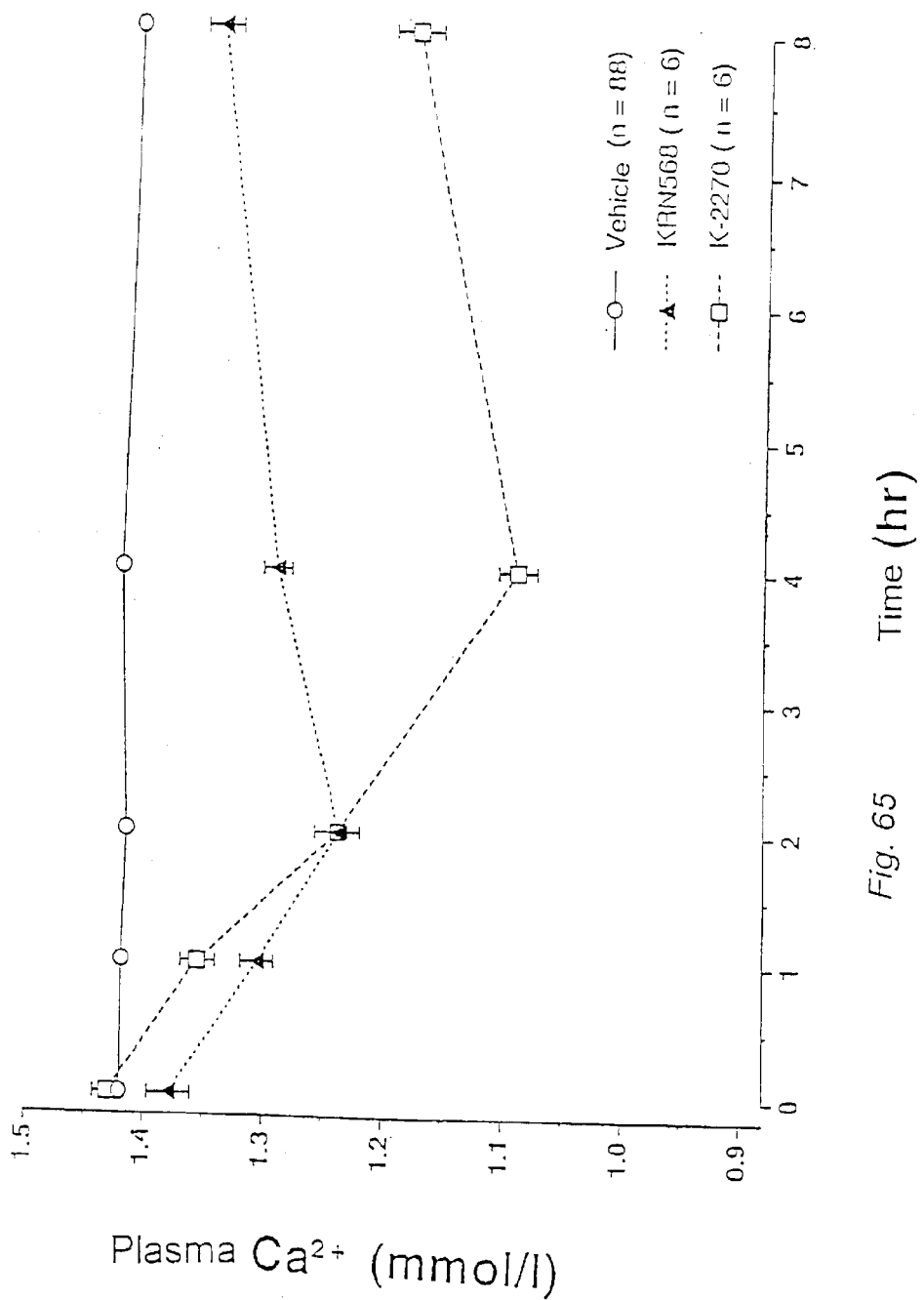
FIG. 65 shows changes in the plasma $Ca^{2+}$ level of the rats to which the compound of the present invention K-2270 was administered.
Figure 66:
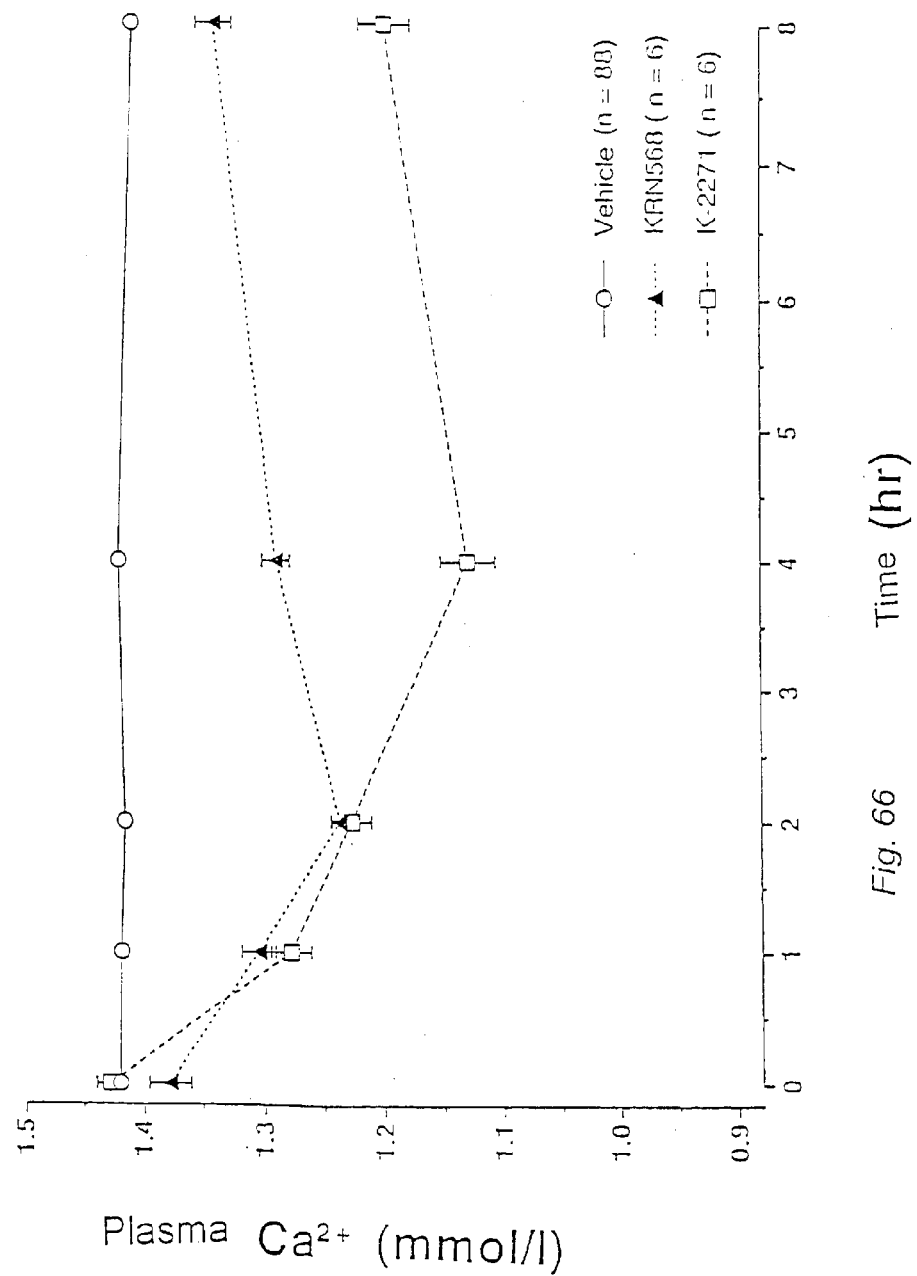
FIG. 66 shows changes in the plasma $Ca^{2+}$ level of the rats to which the compound of the present invention K-2271 was administered.
Figure 67:
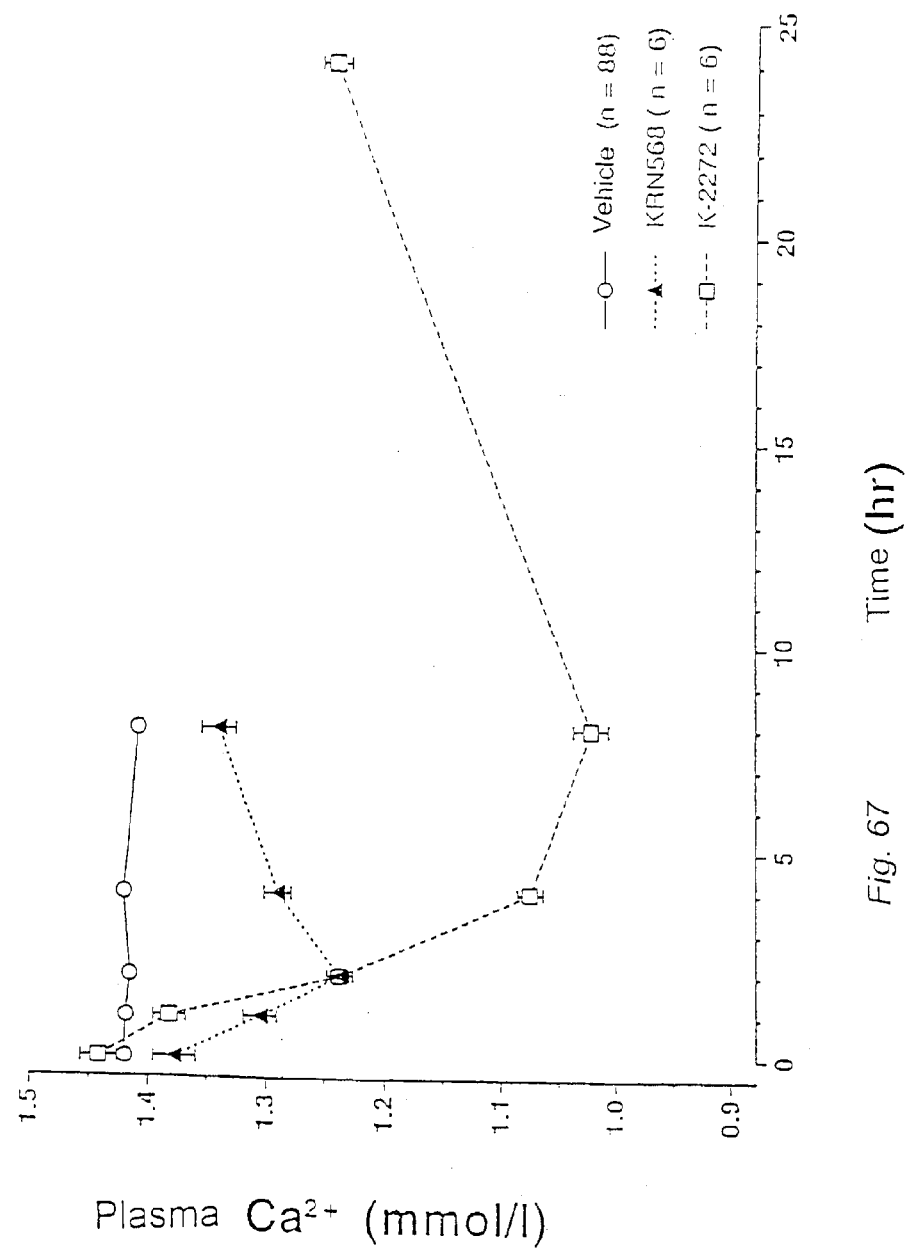
FIG. 67 shows changes in the plasma $Ca^{2+}$ level of the rats to which the compound of the present invention K-2272 was administered.
Figure 68:
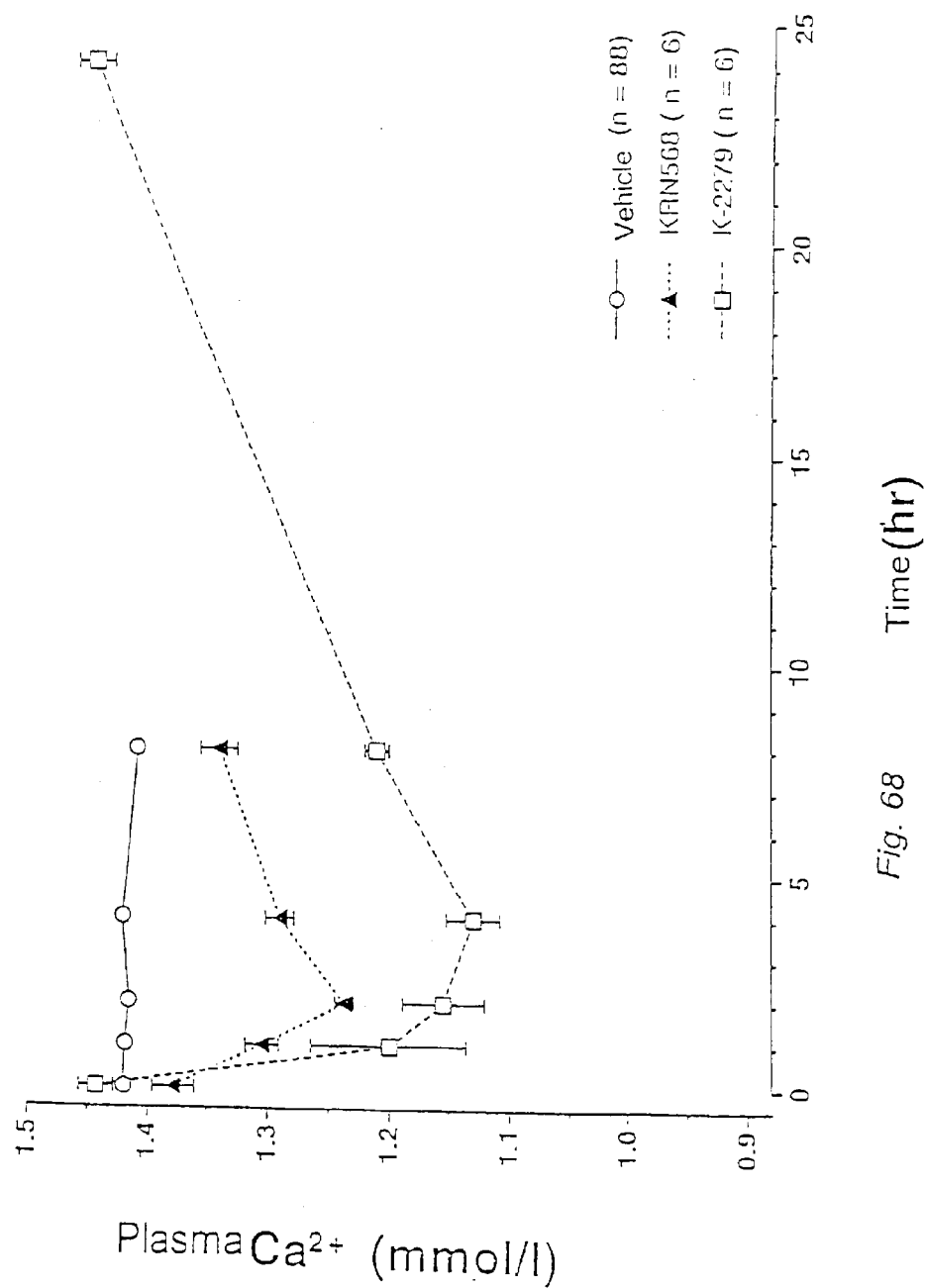
FIG. 68 shows changes in the plasma $Ca^{2+}$ level of the rats to which the compound of the present invention K-2279 was administered.
Figure 69:
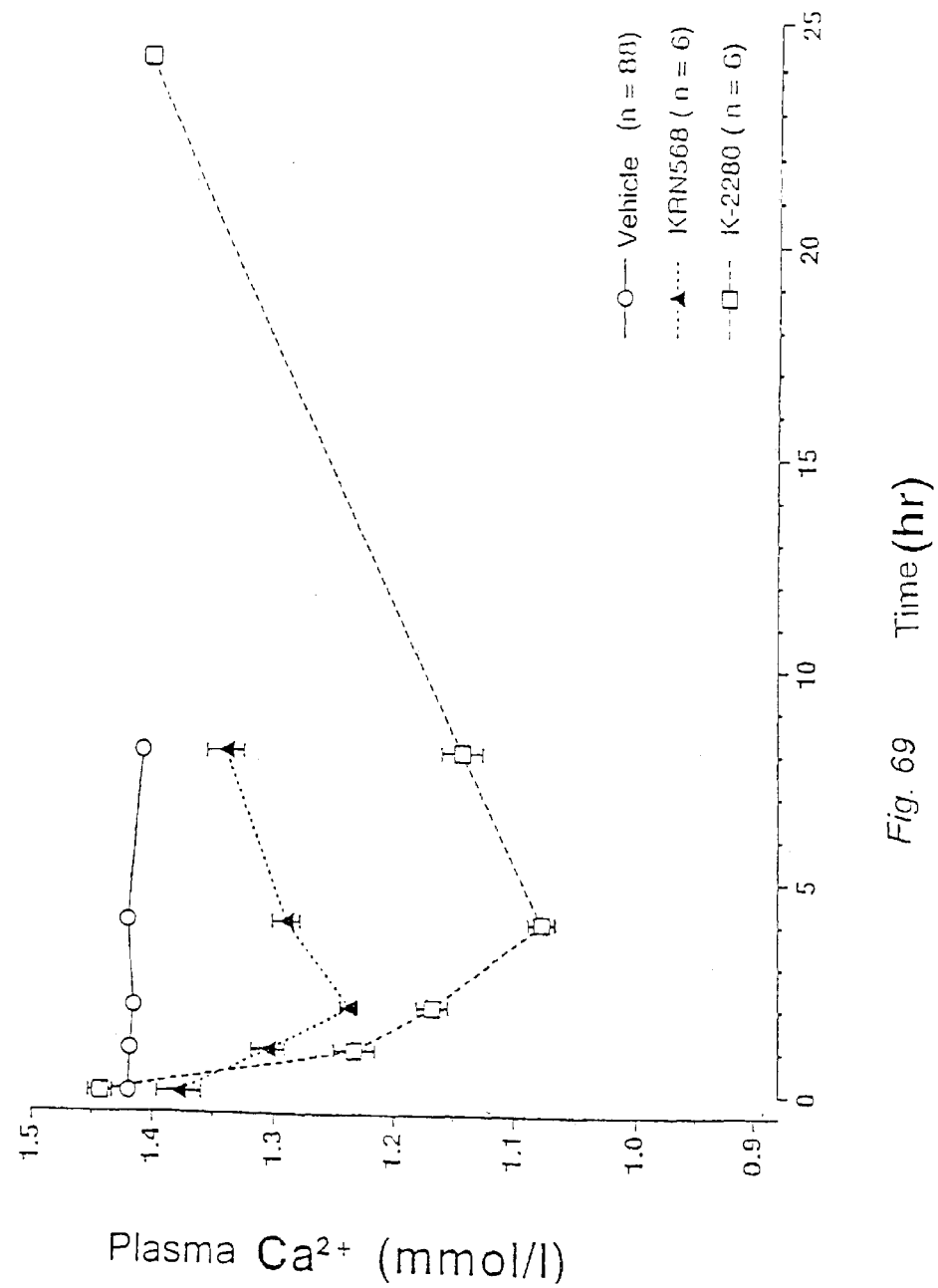
FIG. 69 shows changes in the plasma $Ca^{2+}$ level of the rats to which the compound of the present invention K-2280 was administered.
Figure 70:
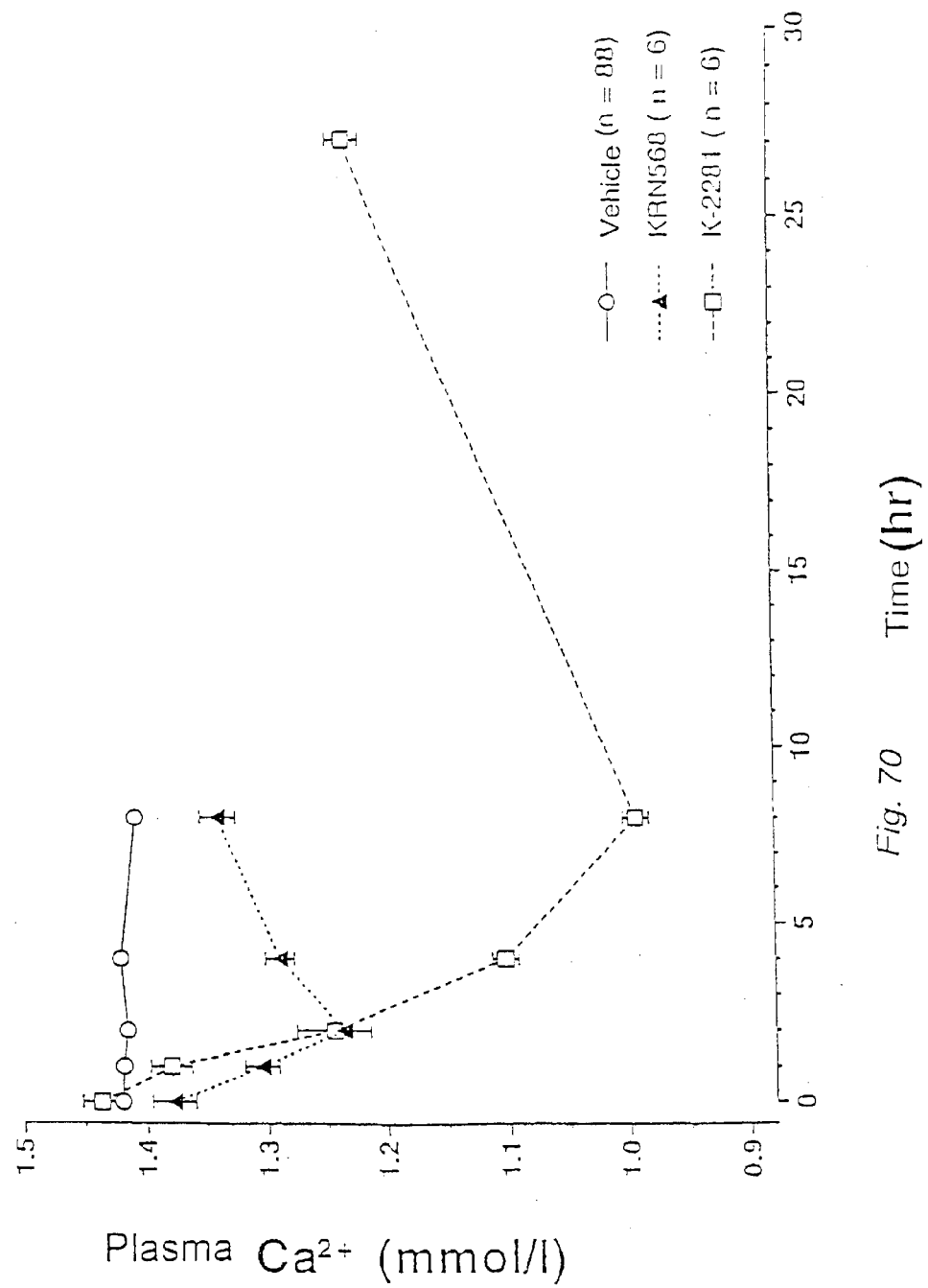
FIG. 70 shows changes in the plasma $Ca^{2+}$ level of the rats to which the compound of the present invention K-2281 was administered.
Figure 71:
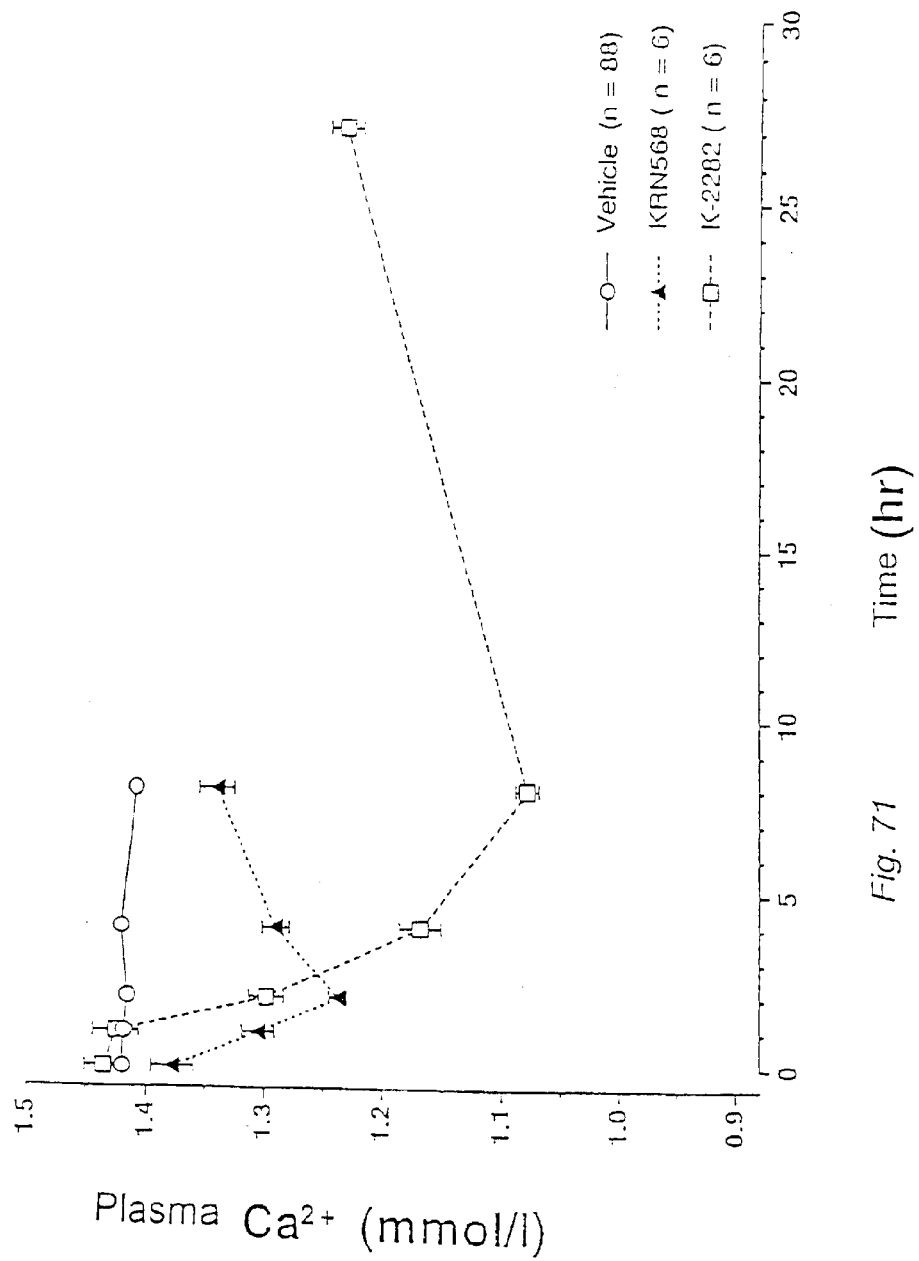
FIG. 71 shows changes in the plasma $Ca^{2+}$ level of the rats to which the compound of the present invention K-2282 was administered.
Figure 72:
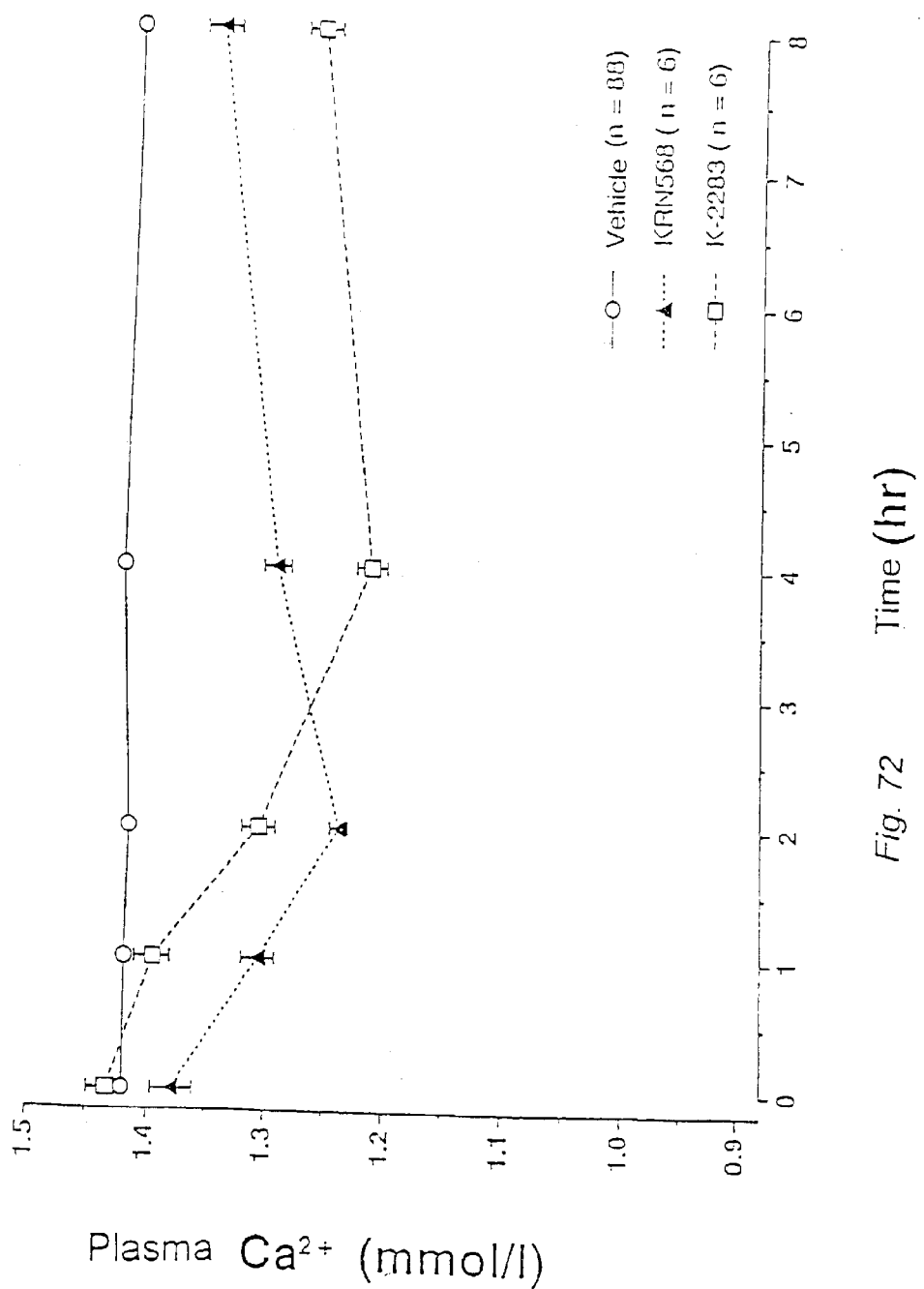
FIG. 72 shows changes in the plasma $Ca^{2+}$ level of the rats to which the compound of the present invention K-2283 was administered.
Figure 73:
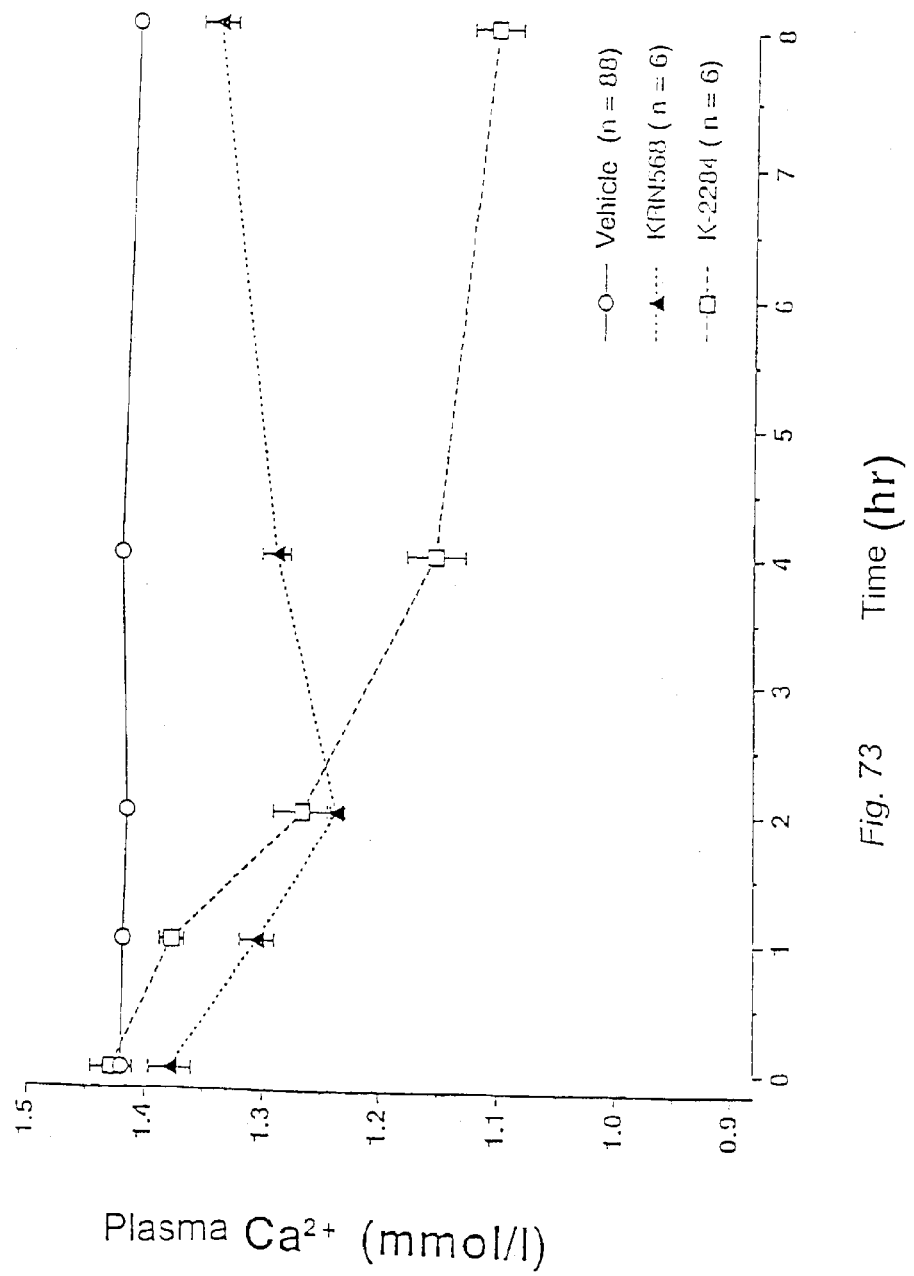
FIG. 73 shows changes in the plasma $Ca^{2+}$ level of the rats to which the compound of the present invention K-2284 was administered.
Figure 74:
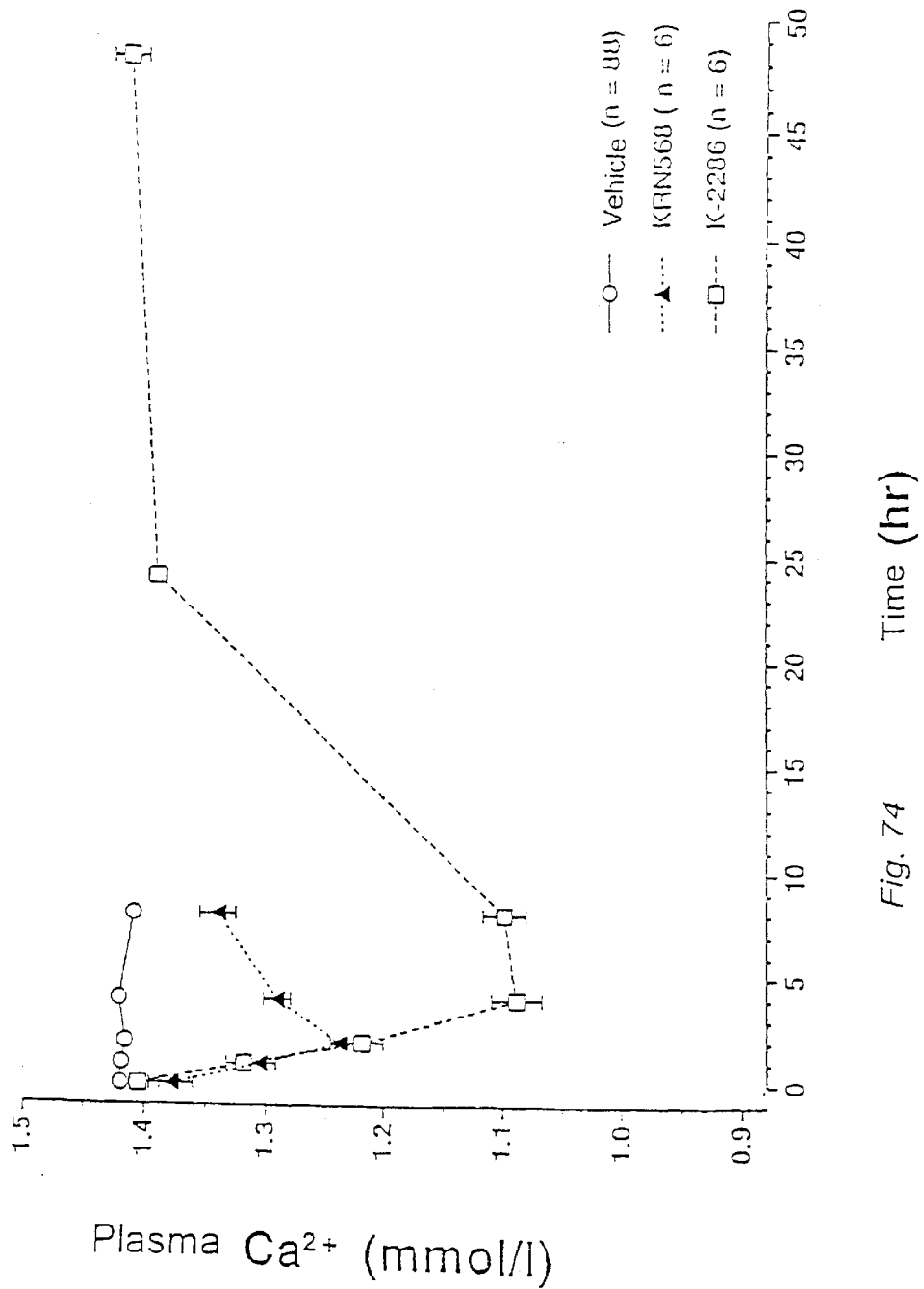
FIG. 74 shows changes in the plasma $Ca^{2+}$ level of the rats to which the compound of the present invention K-2286 was administered.
Figure 75:
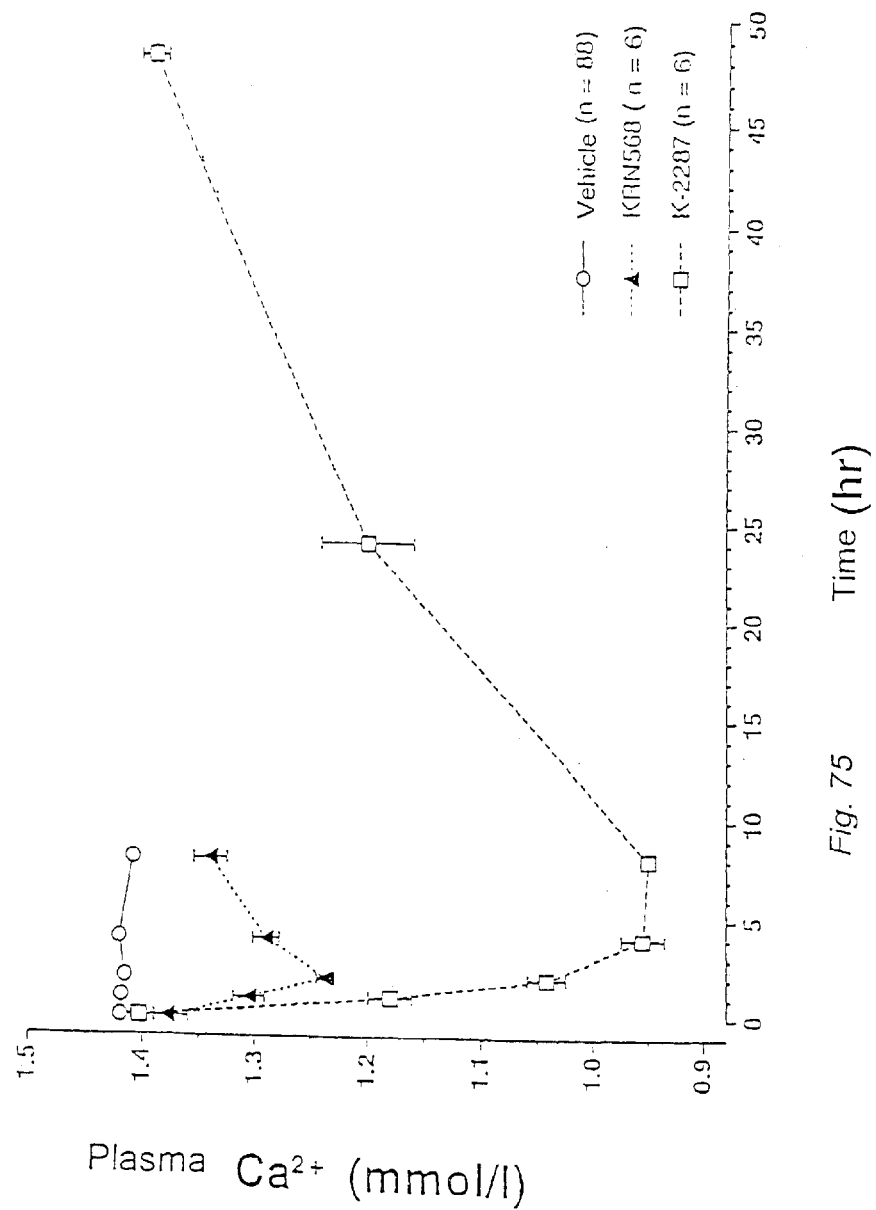
FIG. 75 shows changes in the plasma $Ca^{2+}$ level of the rats to which the compound of the present invention K-2287 was administered.
Figure 76:
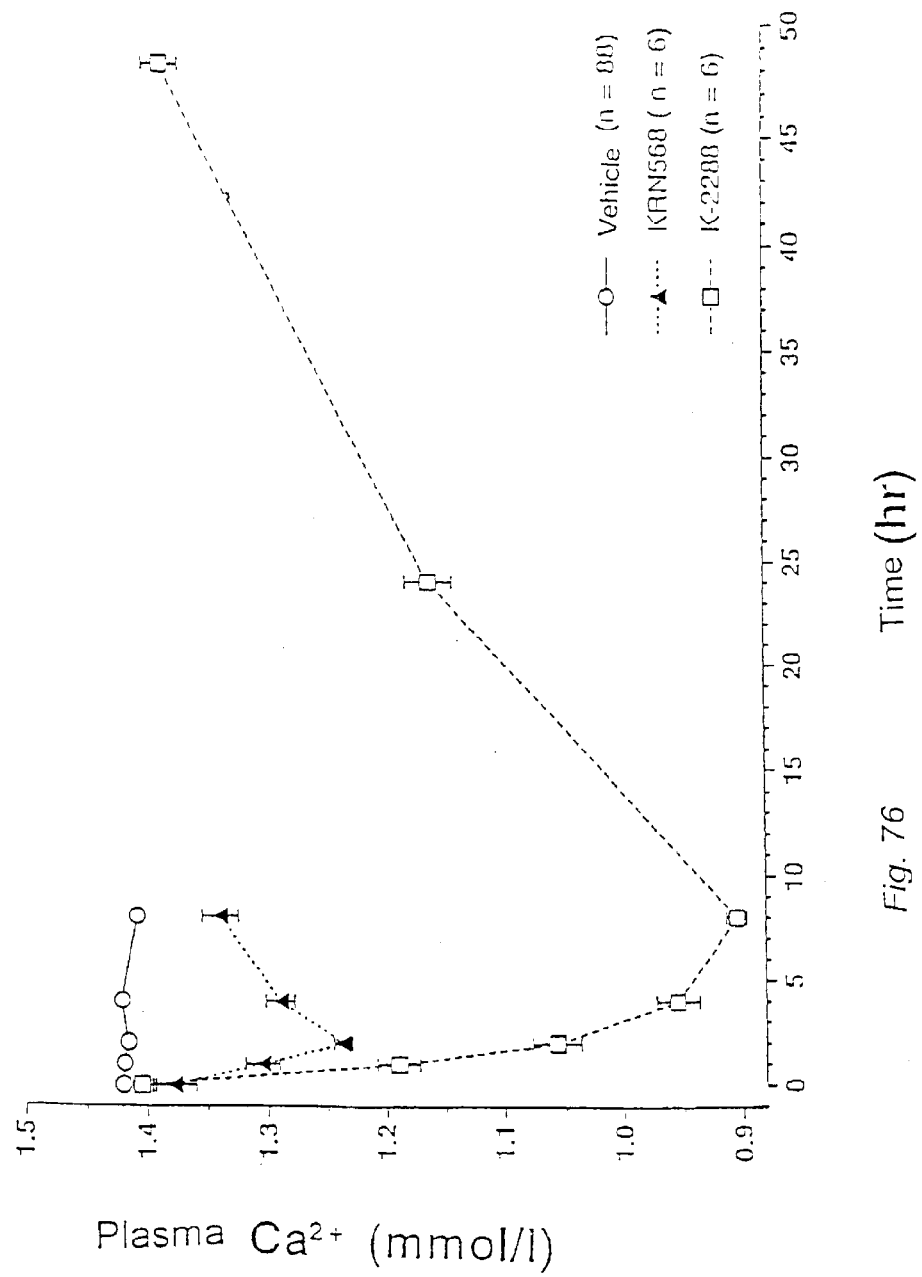
FIG. 76 shows changes in the plasma $Ca^{2+}$ level of the rats to which the compound of the present invention K-2288 was administered.
Figure 77:
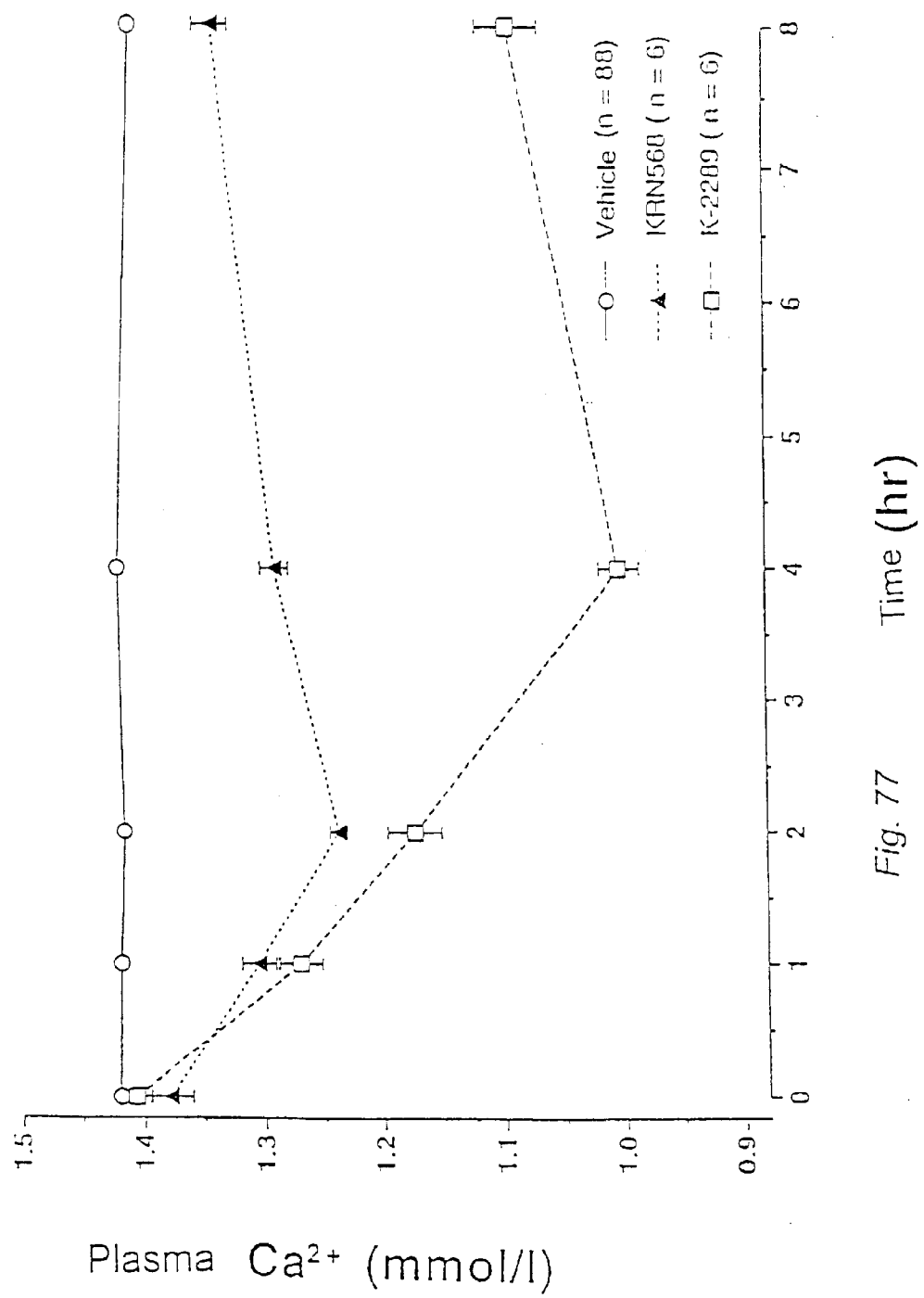
FIG. 77 shows changes in the plasma $Ca^{2+}$ level of the rats to which the compound of the present invention K-2289 was administered.
Figure 78:
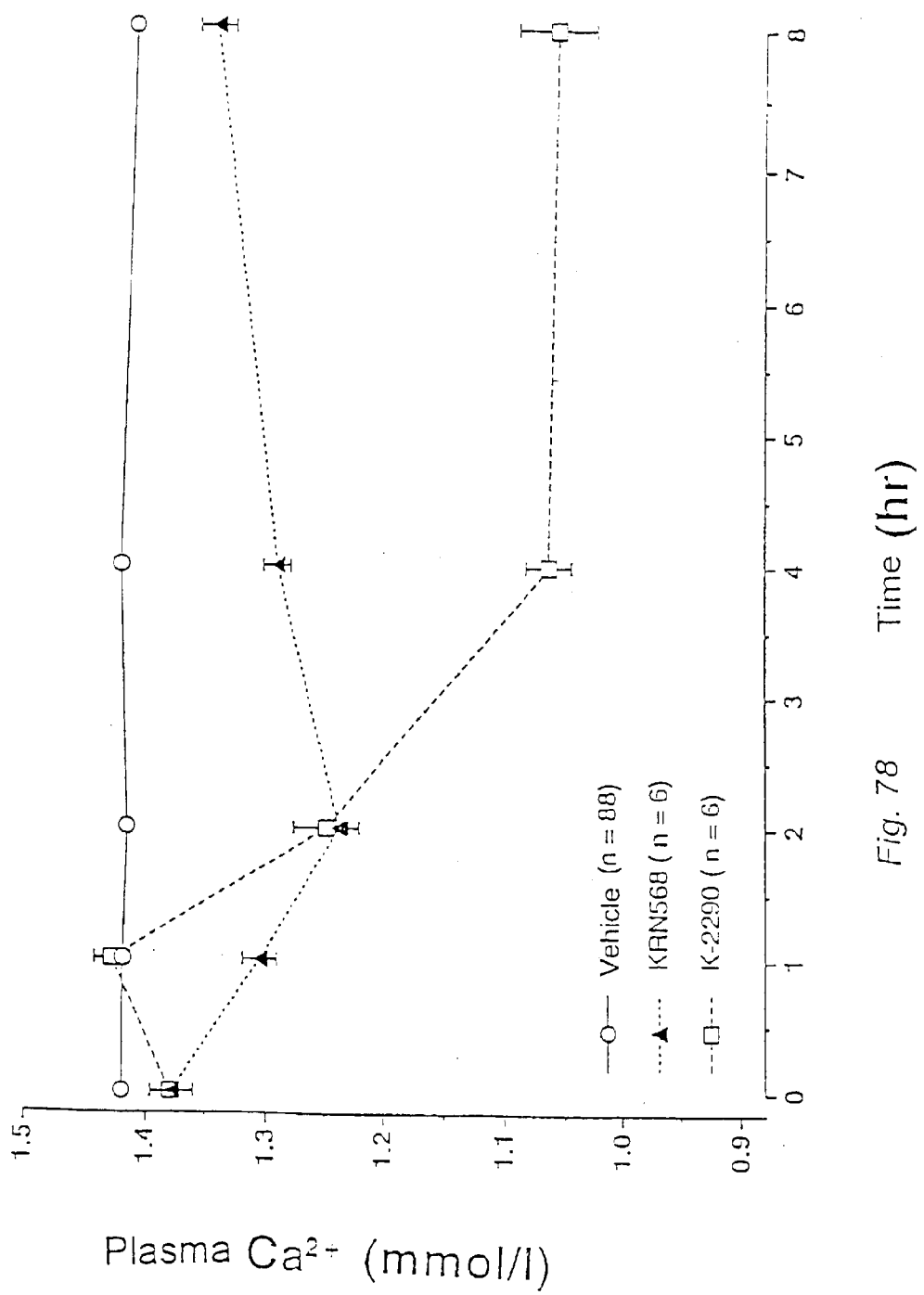
FIG. 78 shows changes in the plasma $Ca^{2+}$ level of the rats to which the compound of the present invention K-2290 was administered.
Figure 79:
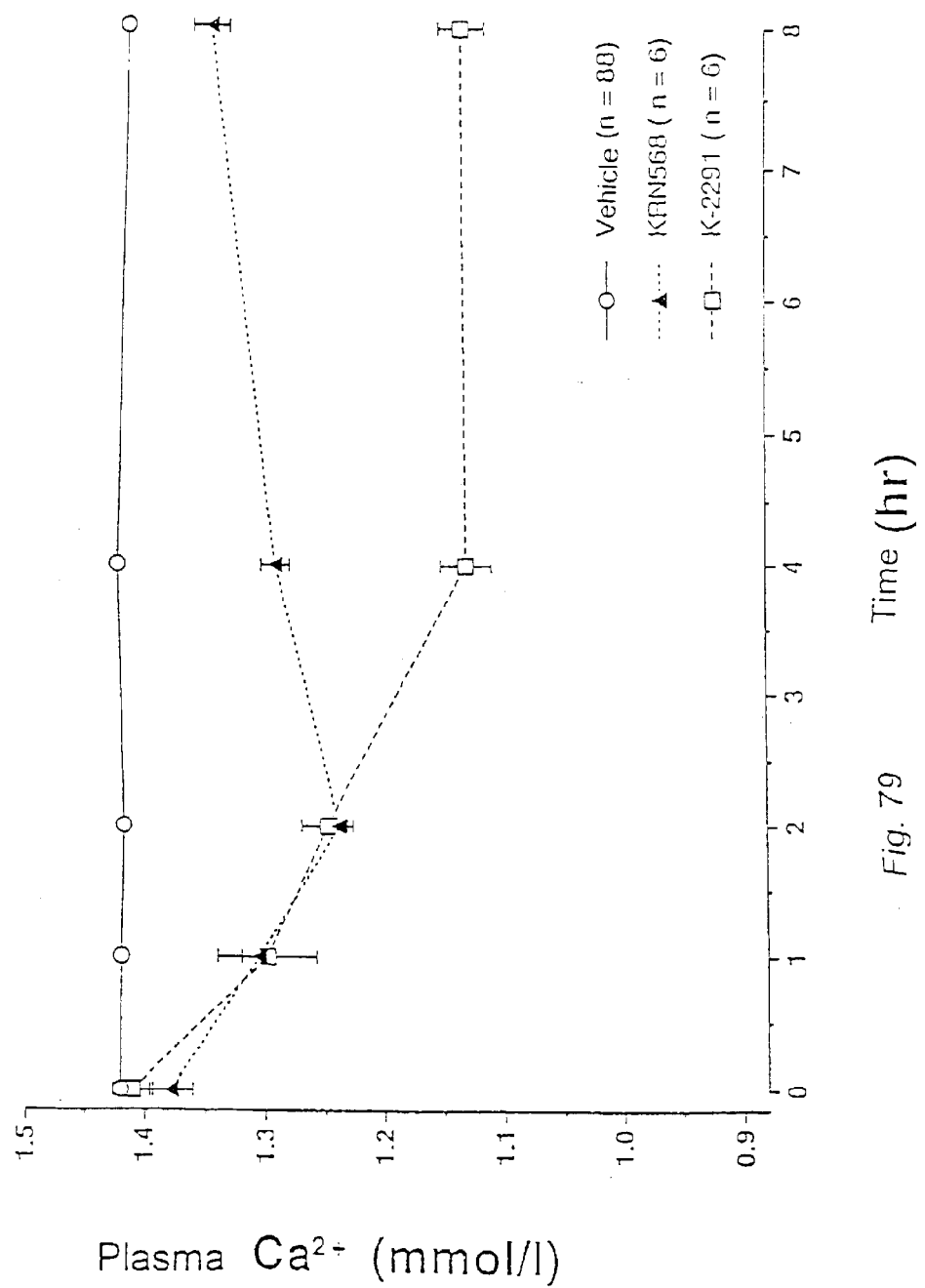
FIG. 79 shows changes in the plasma $Ca^{2+}$ level of the rats to which the compound of the present invention K-2291 was administered.
Figure 80:
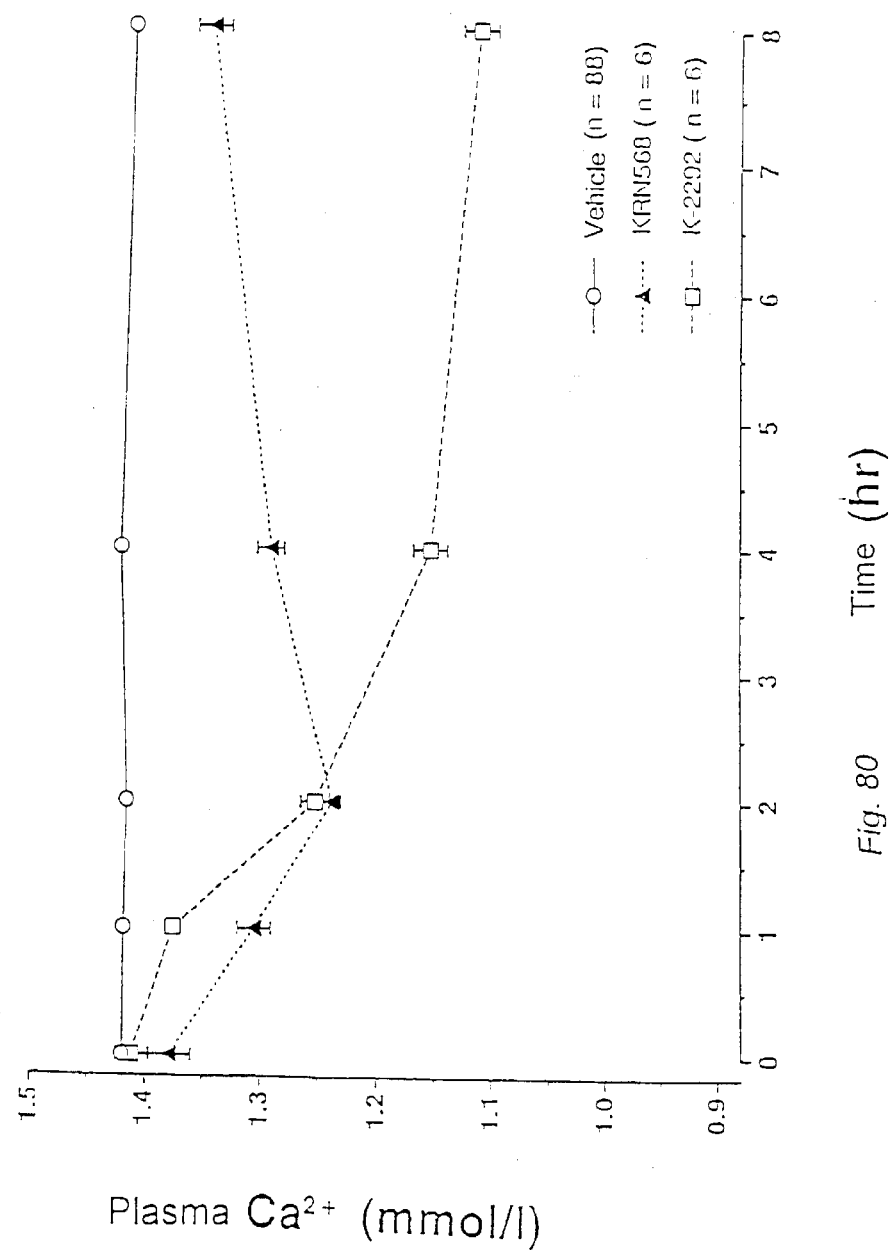
FIG. 80 shows changes in the plasma $Ca^{2+}$ level of the rats to which the compound of the present invention K-2292 was administered.
Figure 81:
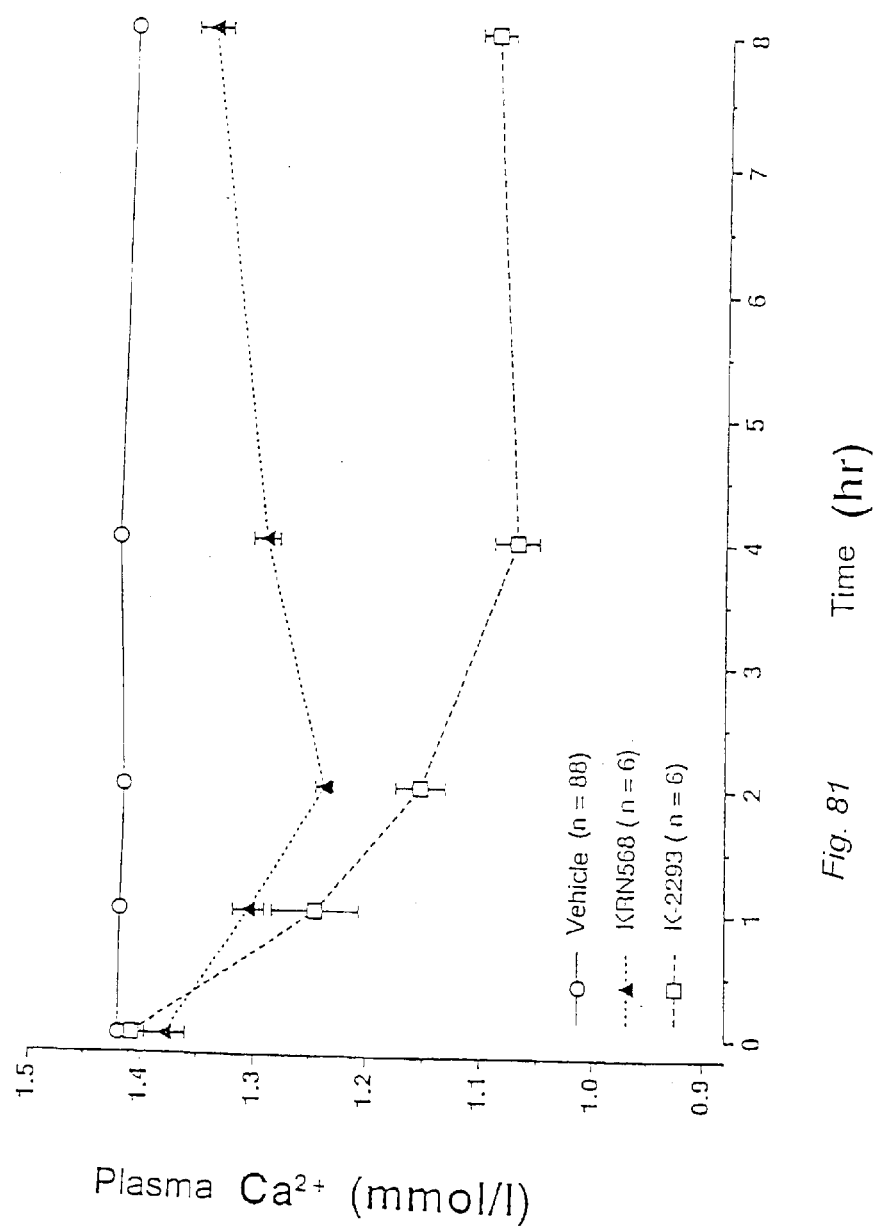
FIG. 81 shows changes in the plasma $Ca^{2+}$ level of the rats to which the compound of the present invention K-2293 was administered.
Figure 82:
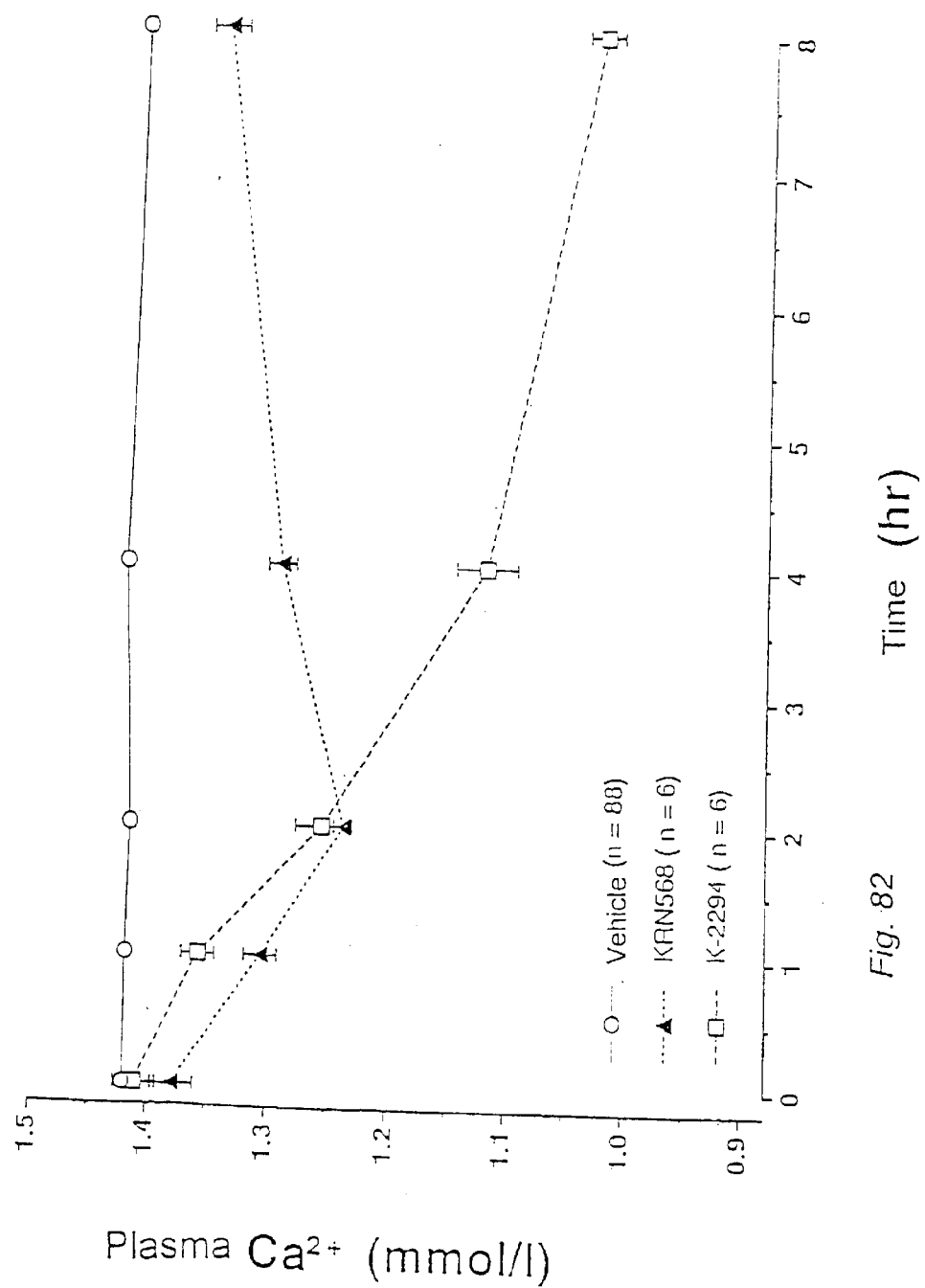
FIG. 82 shows changes in the plasma $Ca^{2+}$ level of the rats to which the compound of the present invention K-2294 was administered.
Figure 83:
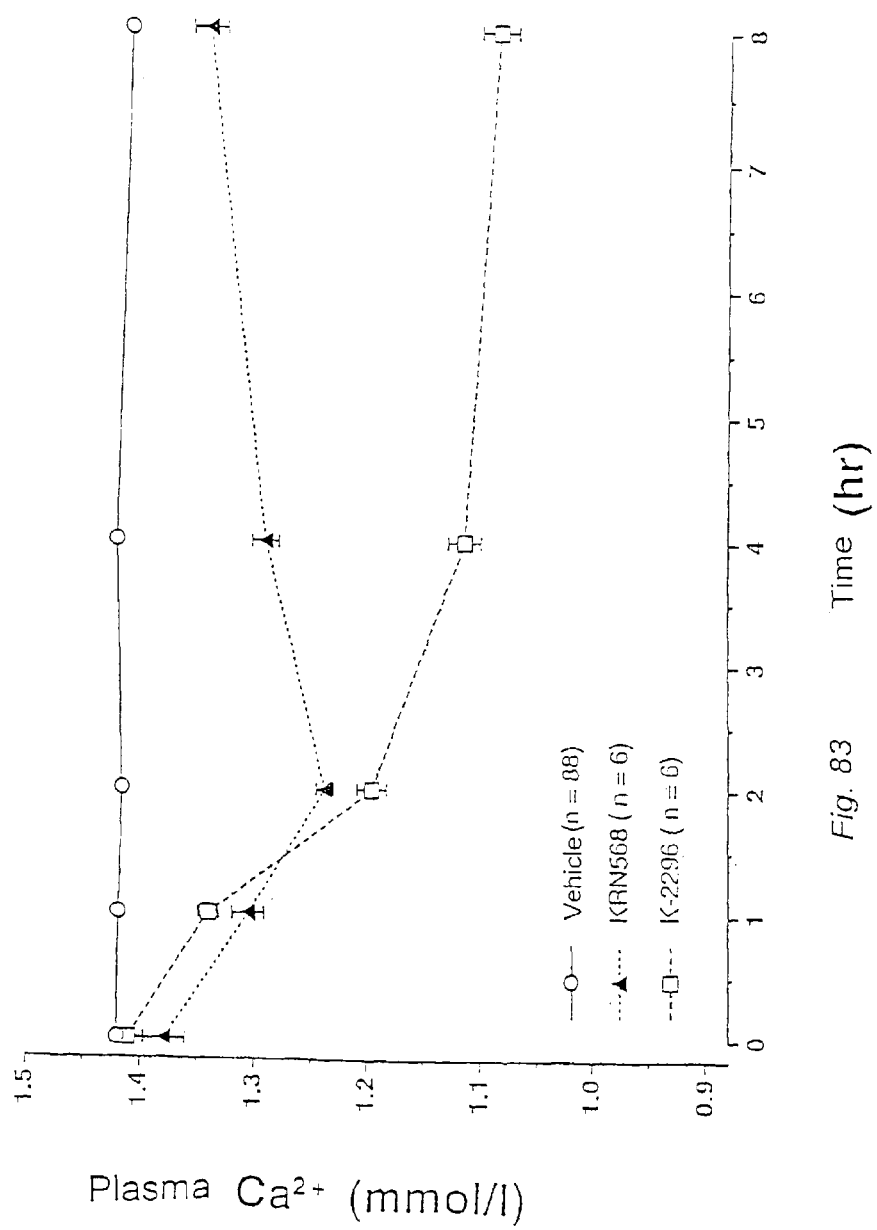
FIG. 83 shows changes in the plasma $Ca^{2+}$ level of the rats to which the compound of the present invention K-2296 was administered.
Figure 84:
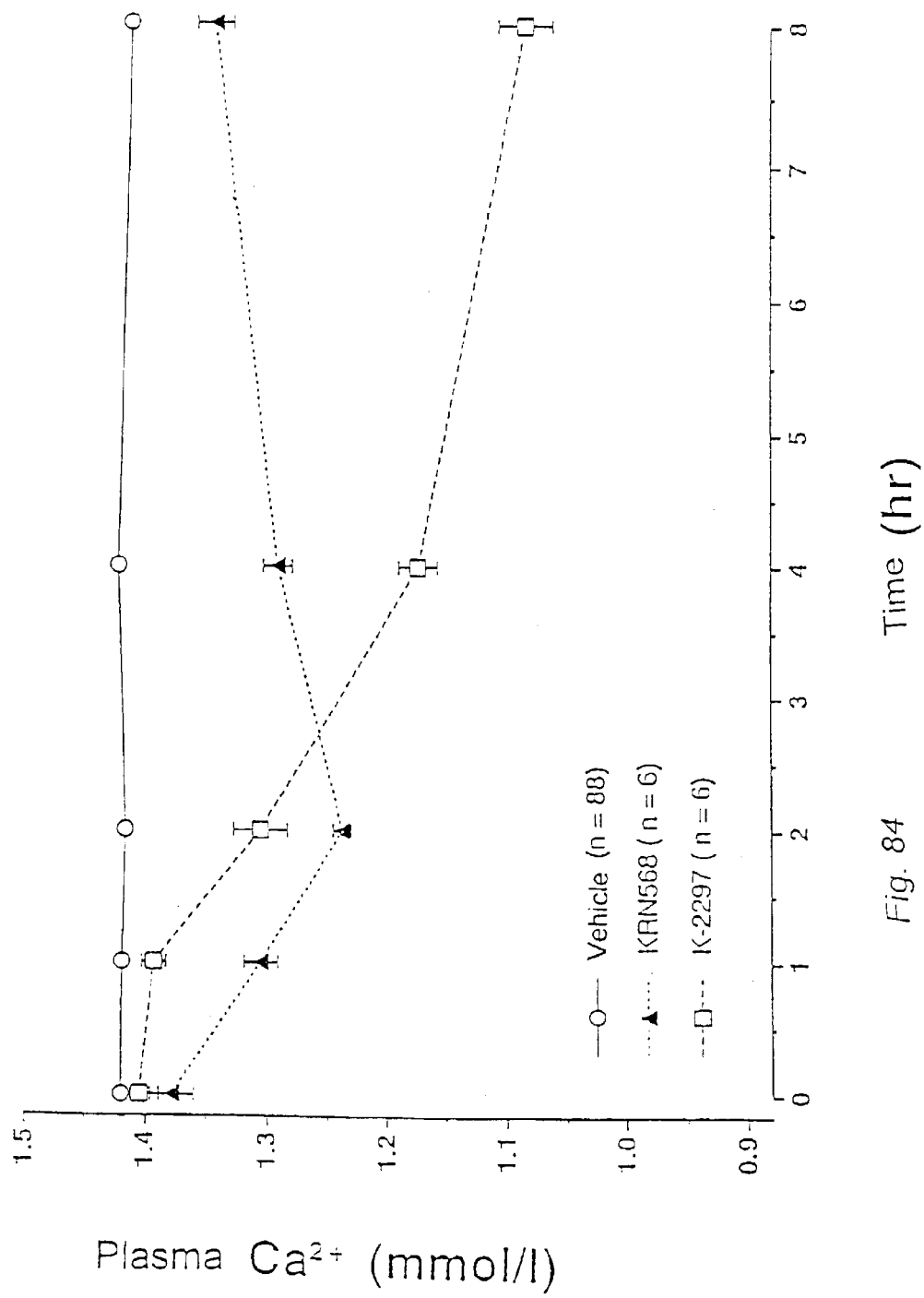
FIG. 84 shows changes in the plasma $Ca^{2+}$ level of the rats to which the compound of the present invention K-2297 was administered.
Figure 85:
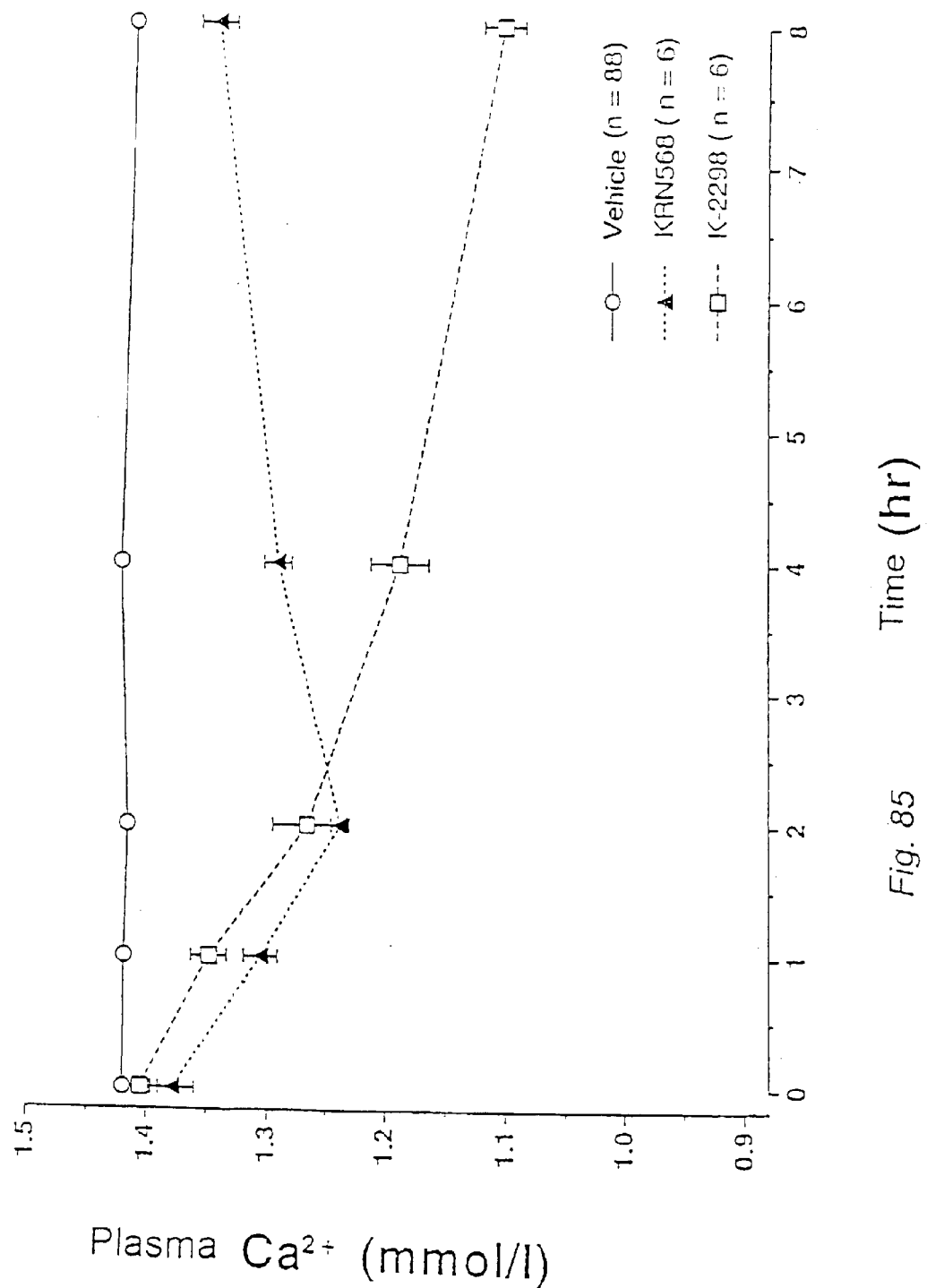
FIG. 85 shows changes in the plasma $Ca^{2+}$ level of the rats to which the compound of the present invention K-2298 was administered.
Figure 86:
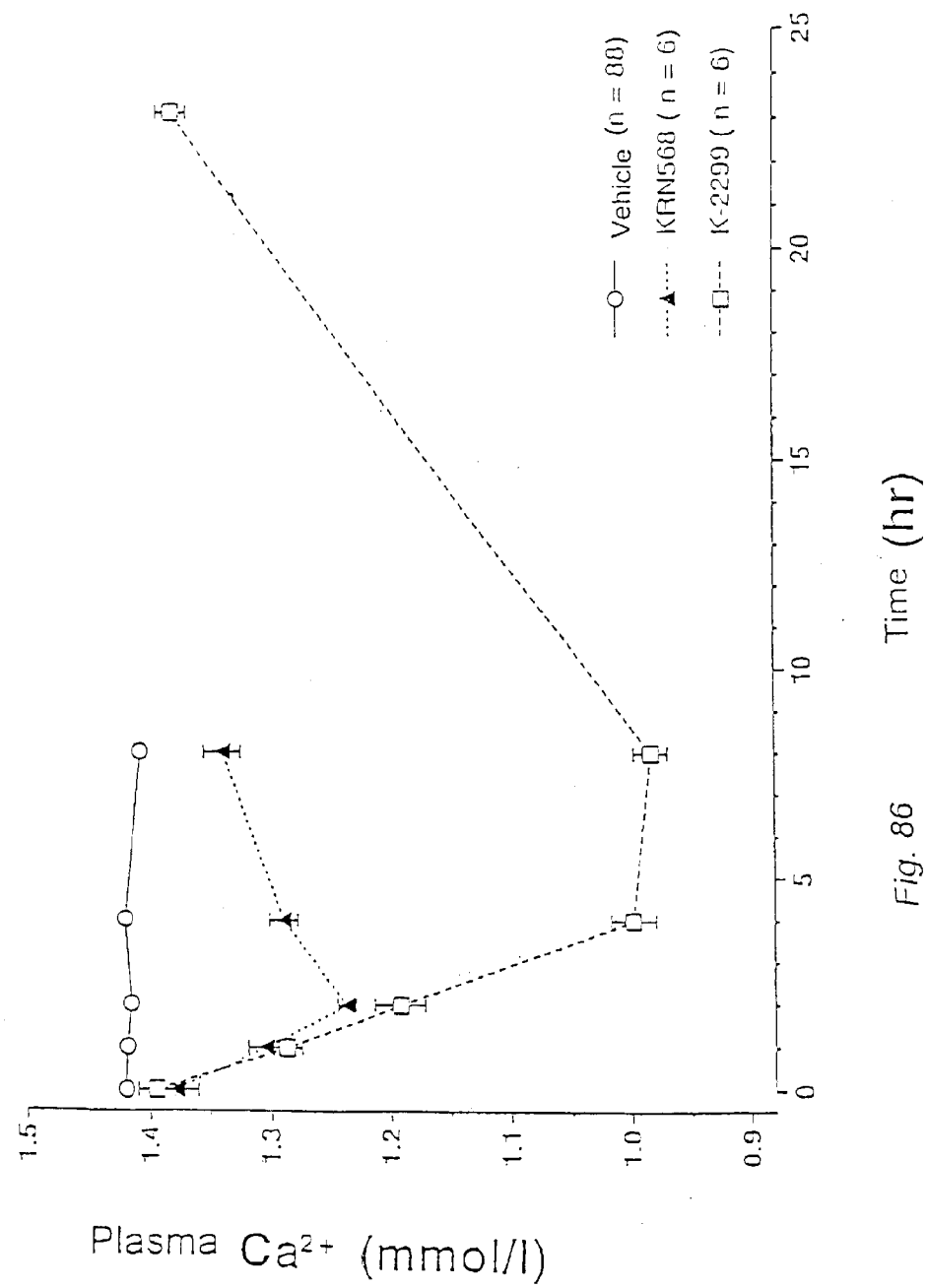
FIG. 86 shows changes in the plasma $Ca^{2+}$ level of the rats to which the compound of the present invention K-2299 was administered.
Figure 87:
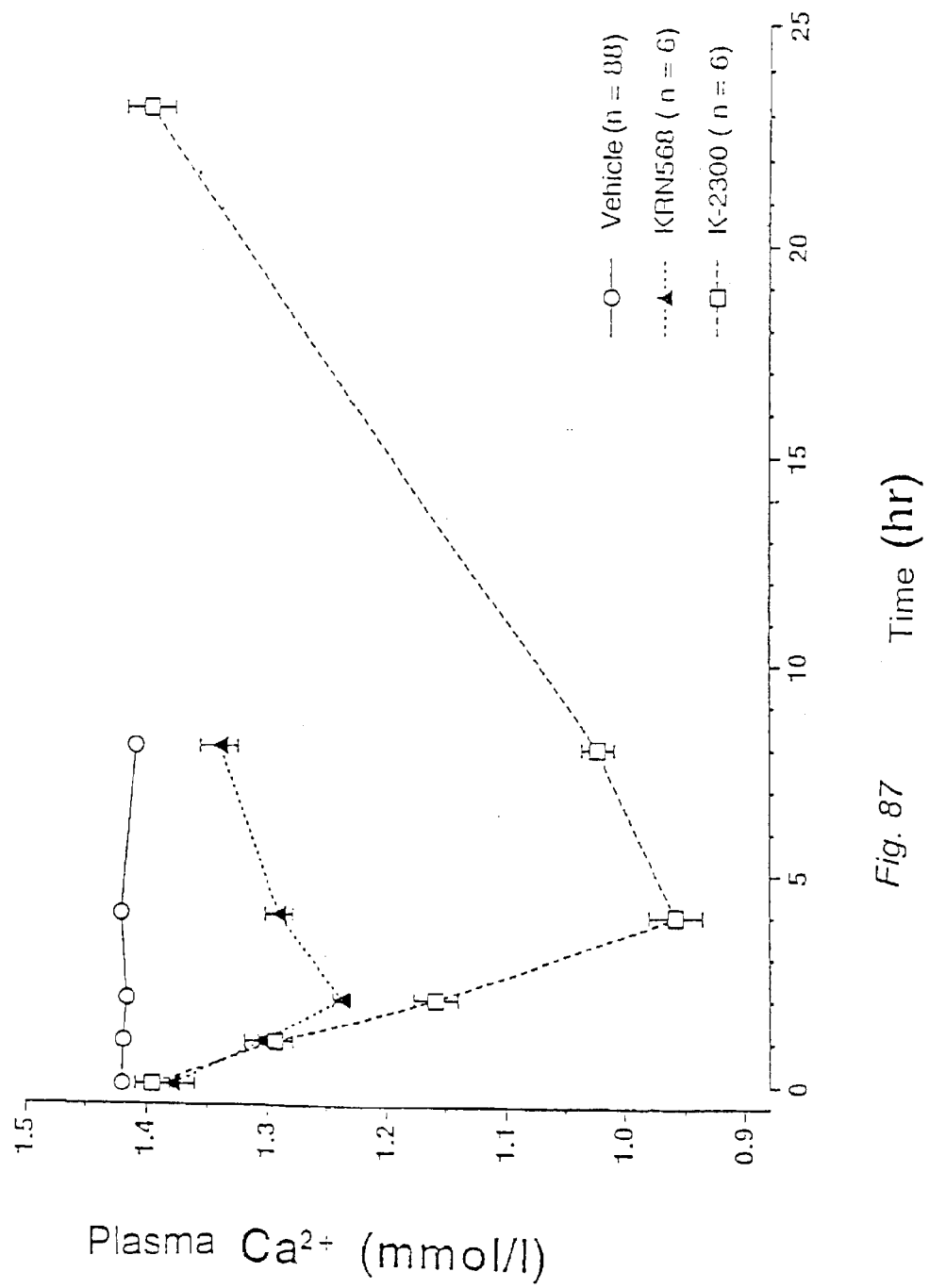
FIG. 87 shows changes in the plasma $Ca^{2+}$ level of the rats to which the compound of the present invention K-2300 was administered.
Figure 88:
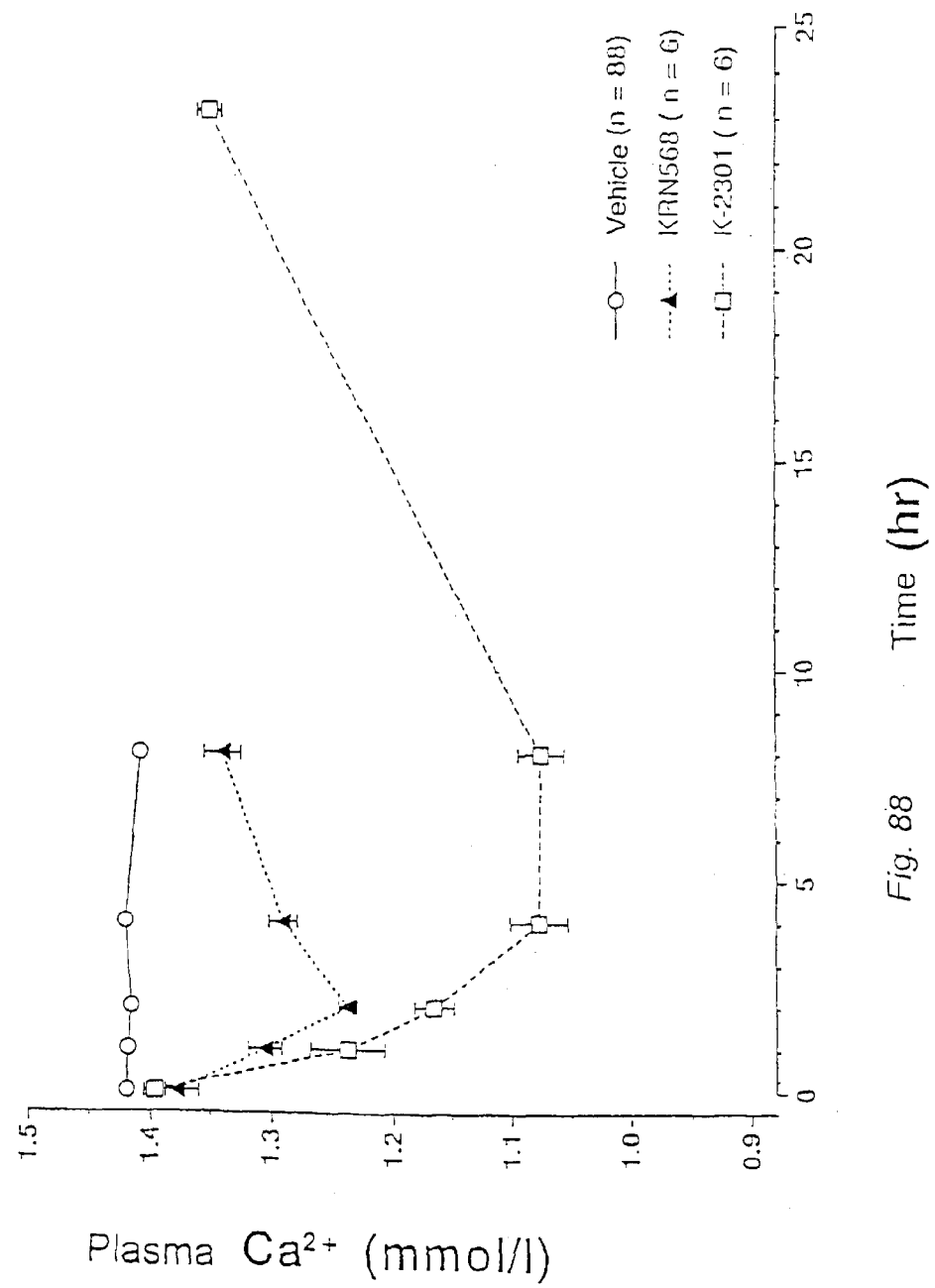
FIG. 88 shows changes in the plasma $Ca^{2+}$ level of the rats to which the compound of the present invention K-2301 was administered.
Figure 89:
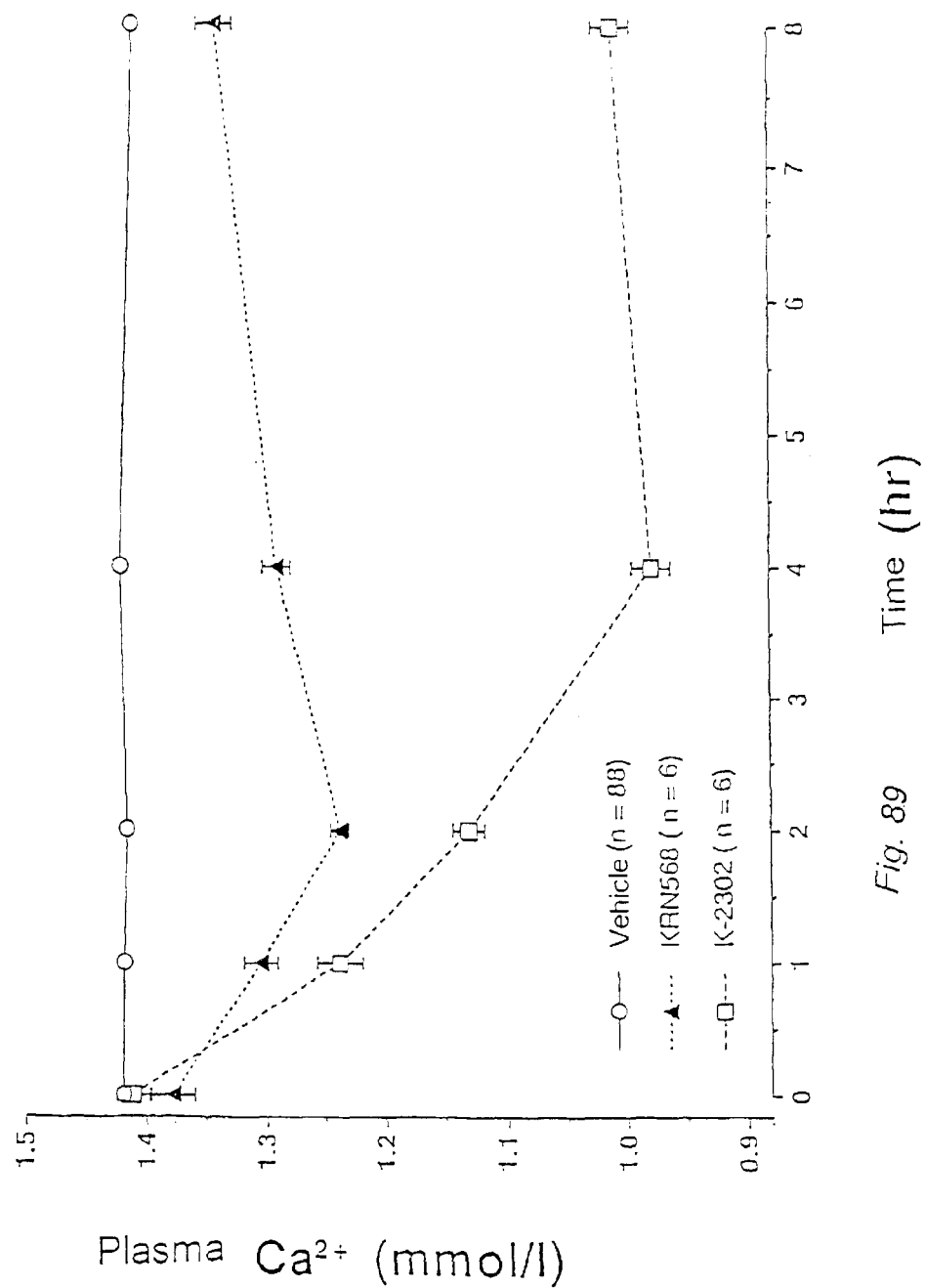
FIG. 89 shows changes in the plasma $Ca^{2+}$ level of the rats to which the compound of the present invention K-2302 was administered.
Figure 90:
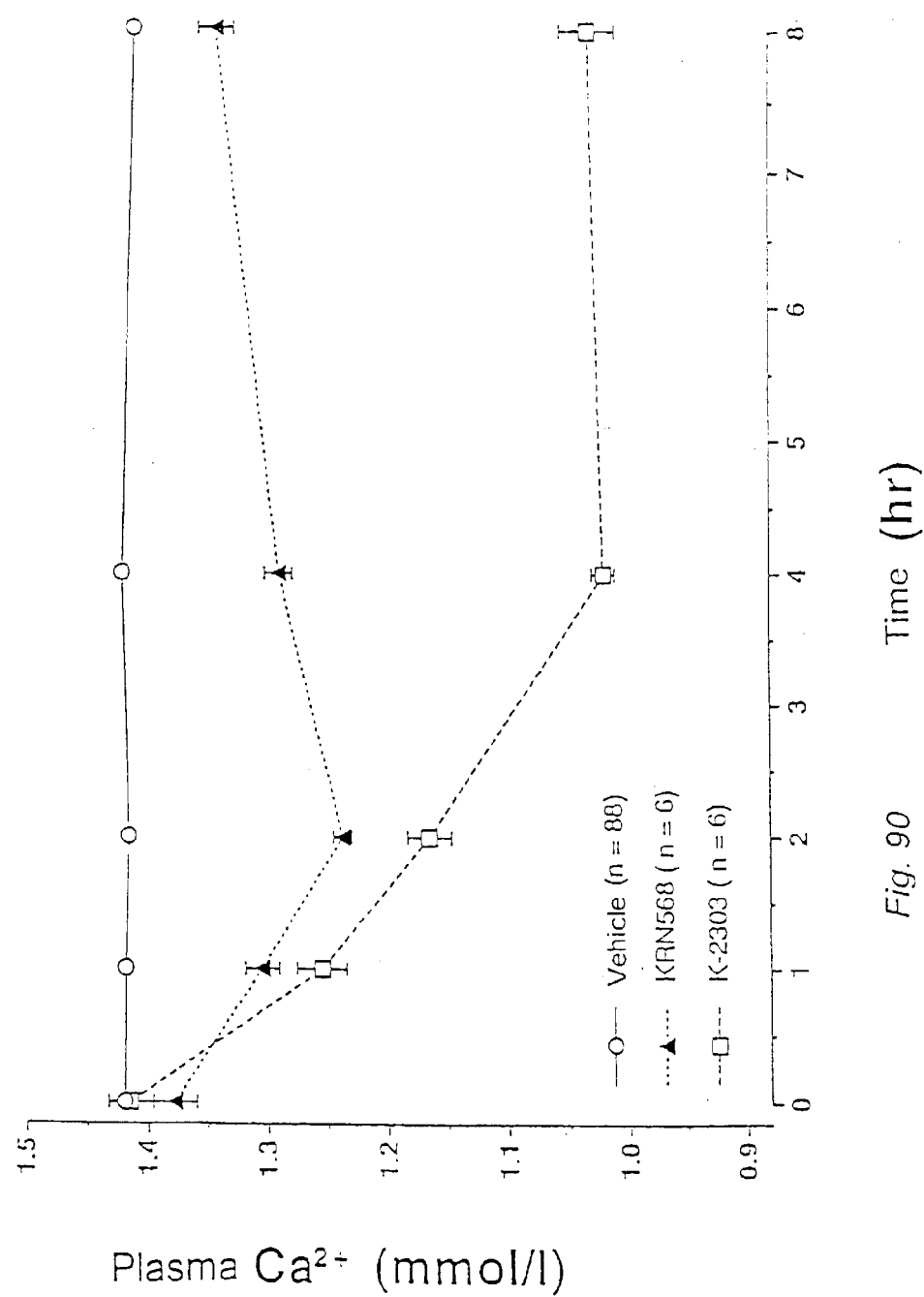
FIG. 90 shows changes in the plasma $Ca^{2+}$ level of the rats to which the compound of the present invention K-2303 was administered.
Figure 91:
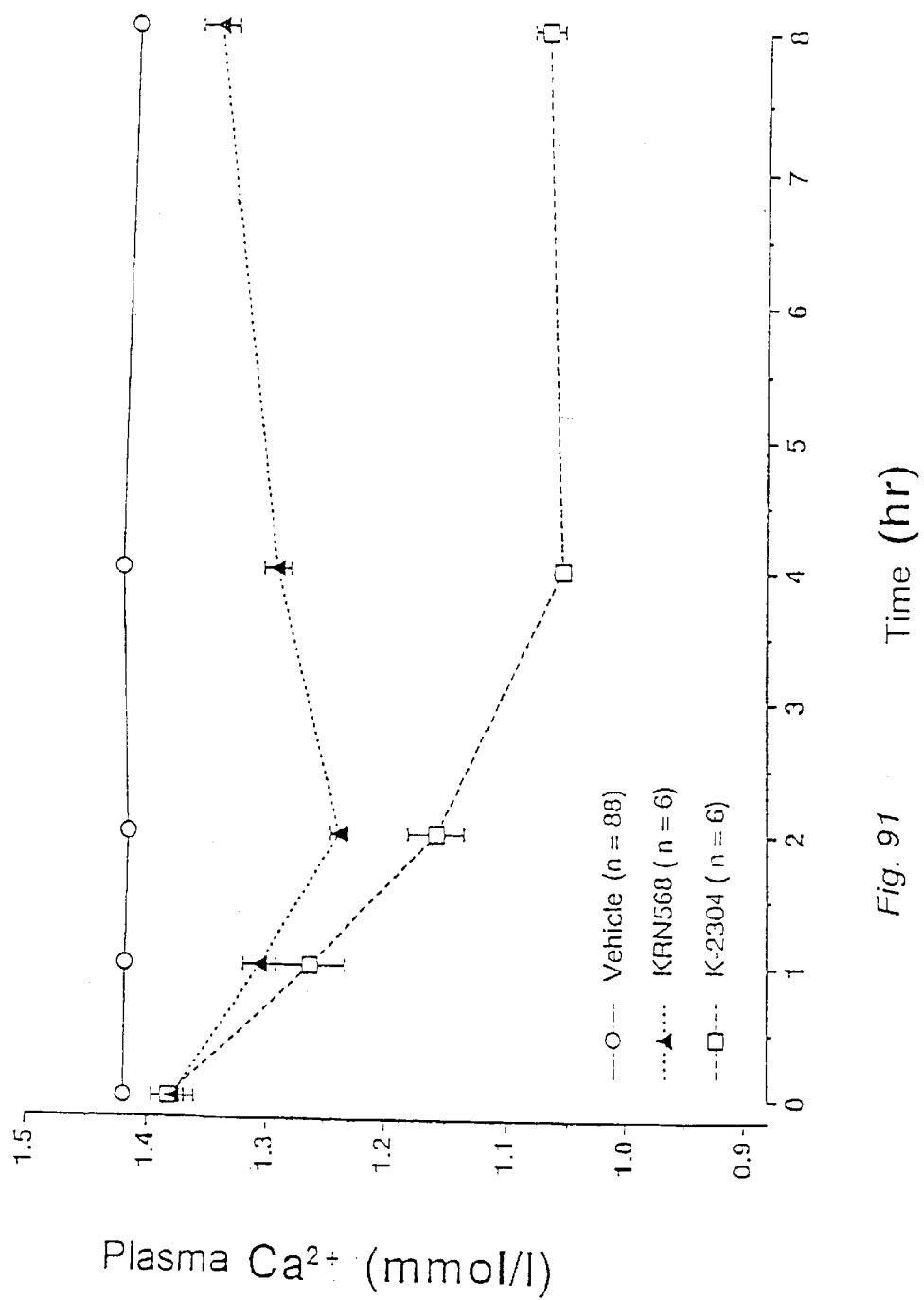
FIG. 91 shows changes in the plasma $Ca^{2+}$ level of the rats to which the compound of the present invention K-2304 was administered.
Figure 92:
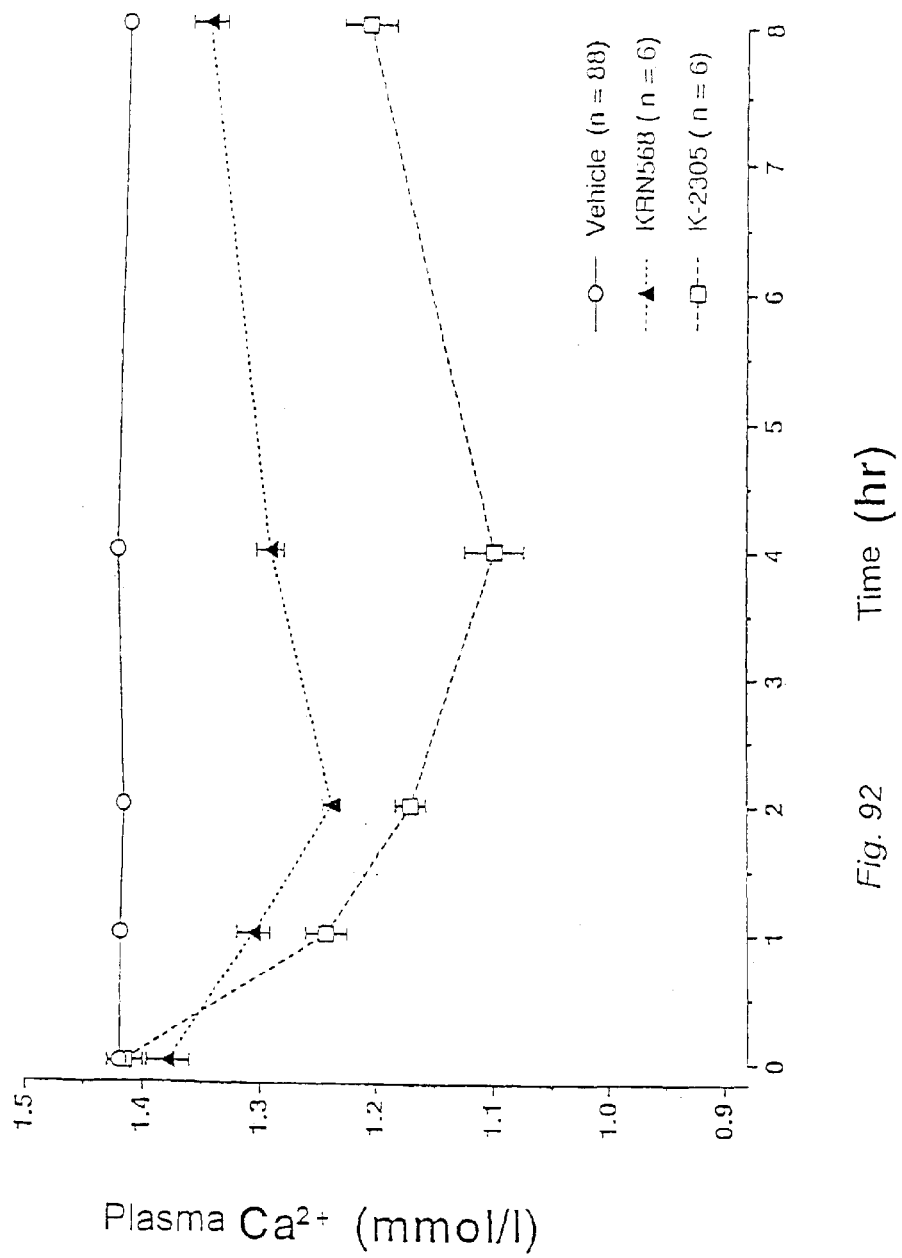
FIG. 92 shows changes in the plasma $Ca^{2+}$ level of the rats to which the compound of the present invention K-2305 was administered.
Figure 93:
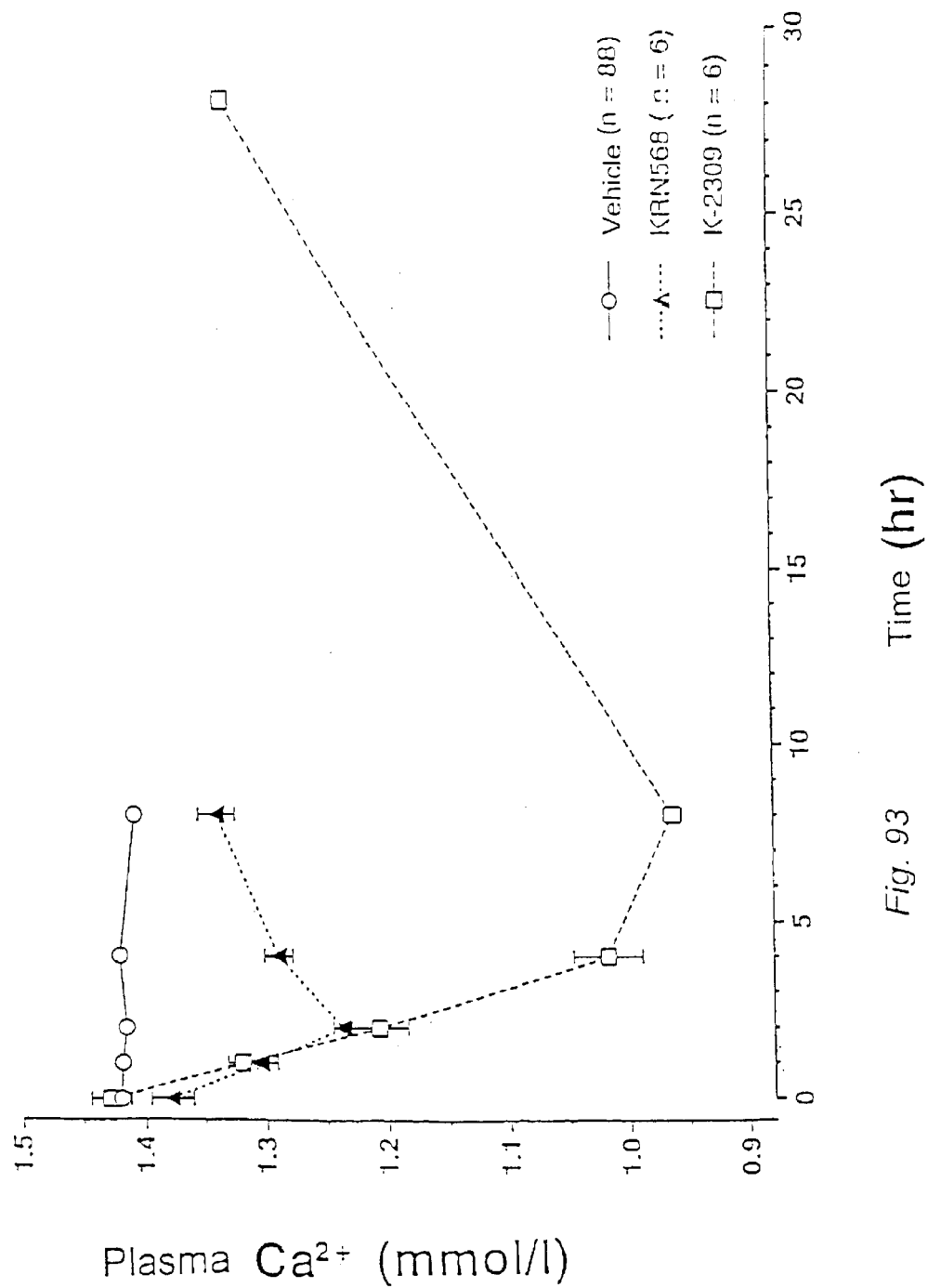
FIG. 93 shows changes in the plasma $Ca^{2+}$ level of the rats to which the compound of the present invention K-2309 was administered.
Figure 94:
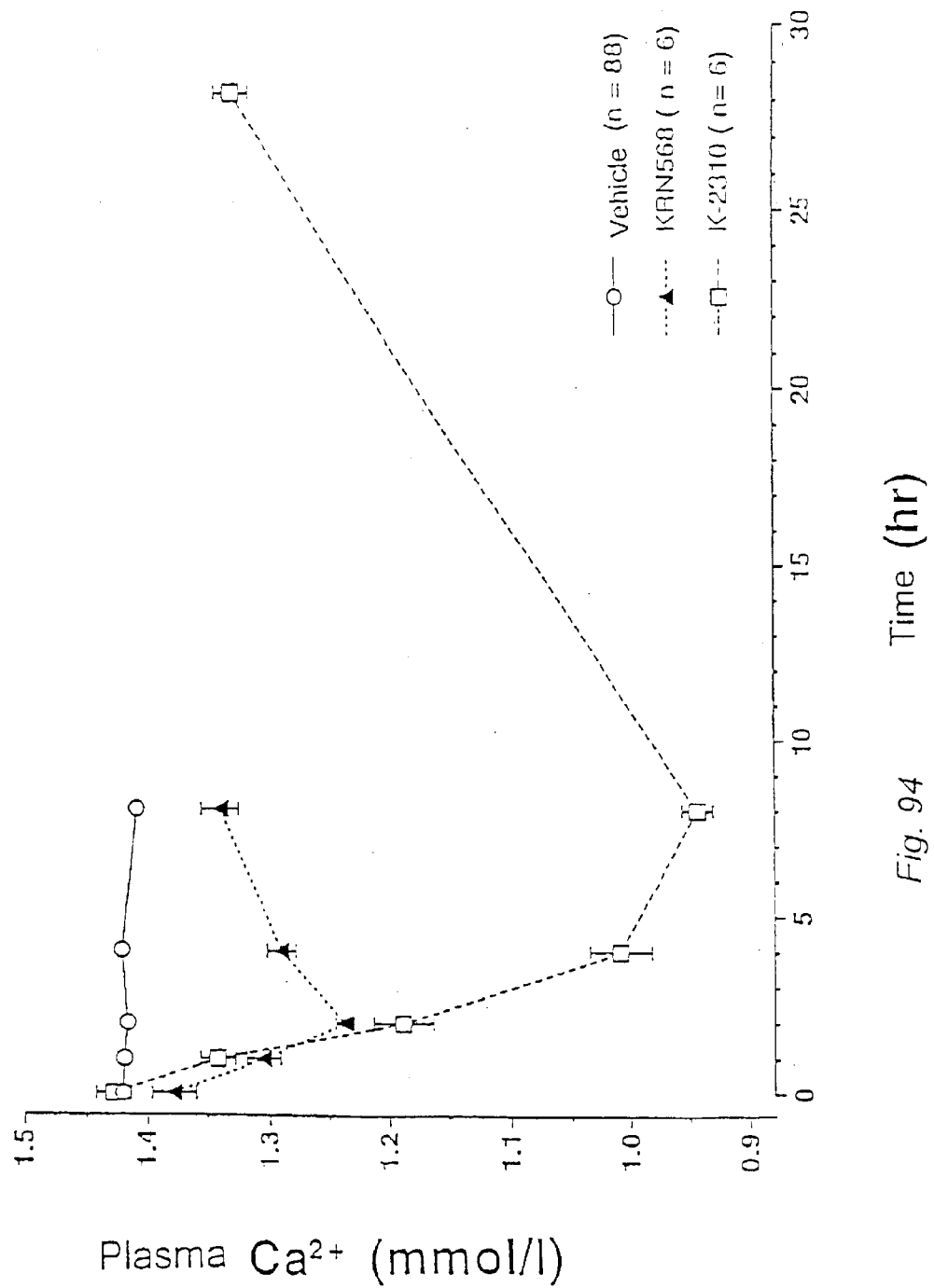
FIG. 94 shows changes in the plasma $Ca^{2+}$ level of the rats to which the compound of the present invention K-2310 was administered.
Figure 95:
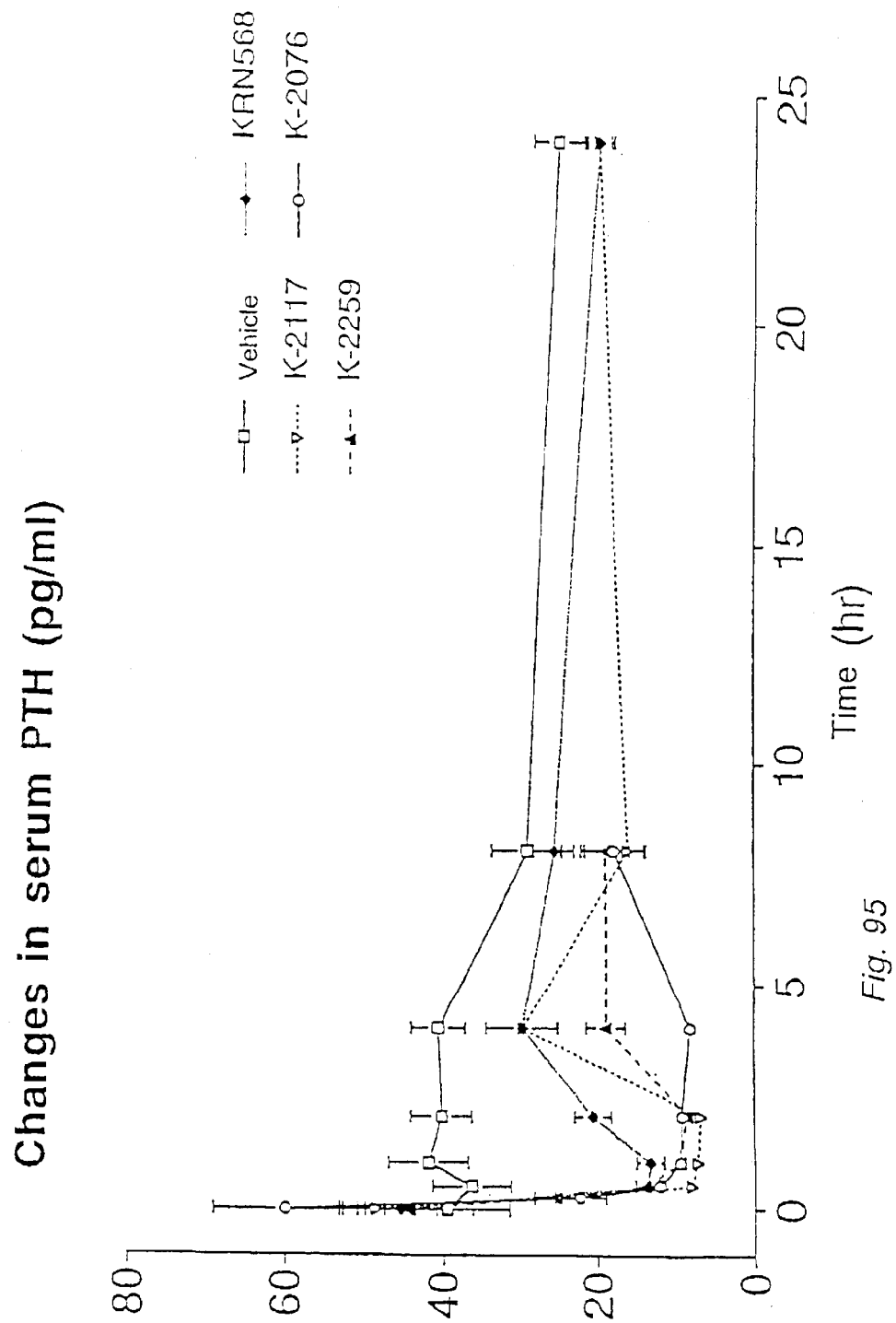
FIG. 95 shows changes in the serum PTH level of the rats to which the compound of the present invention K-2076, K-2117 or K-2259 was administered.
Figure 96:
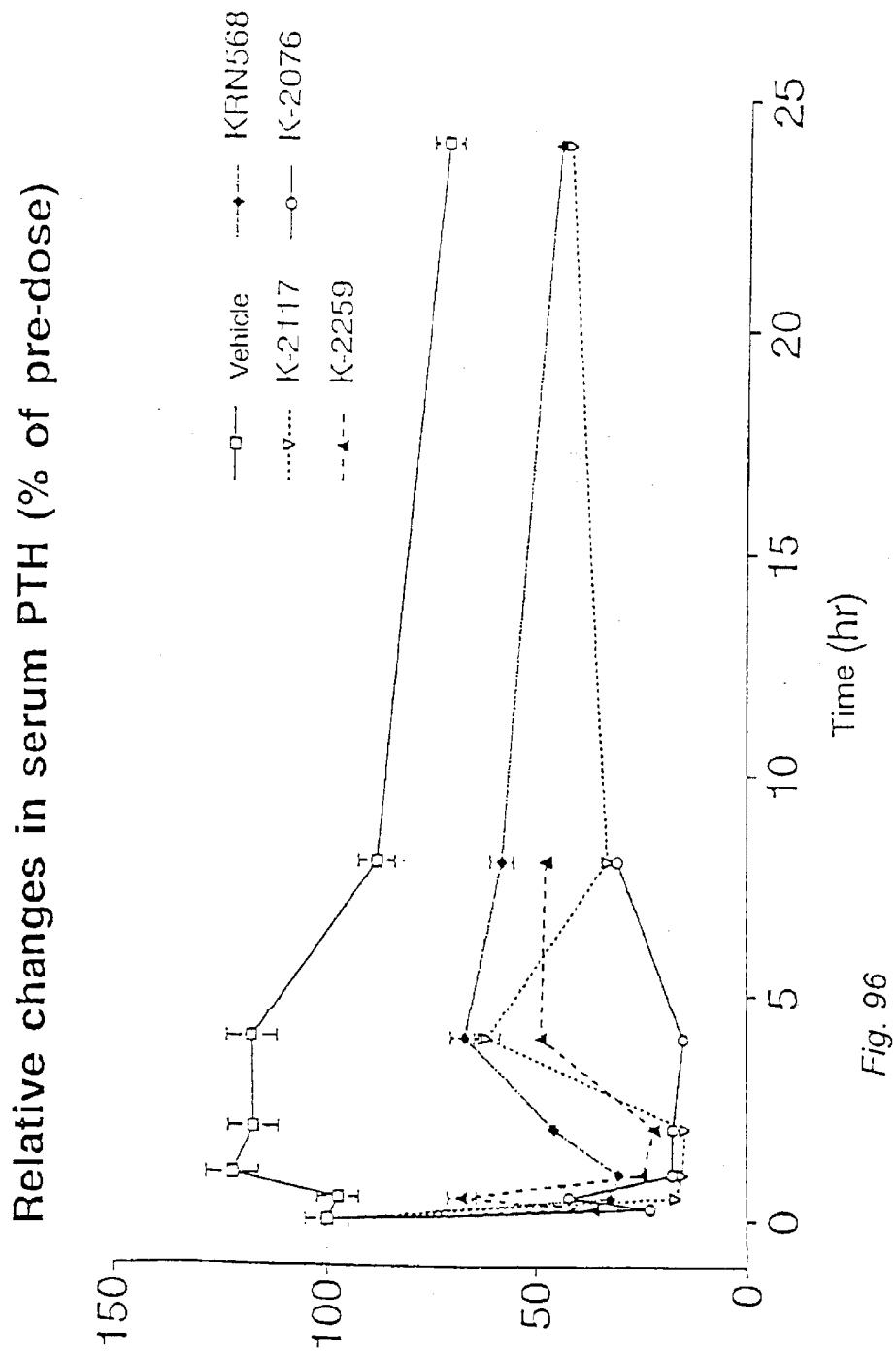
FIG. 96 shows relative changes in the serum PTH level of the rats to which the compound of the present invention K-2076, K-2117 or K-2259 was administered to the pre-administration level.

In Examples 24 to 36, the compounds of the present invention were synthesized in accordance with the schemes shown in FIGS. 5 to 7.

Example 1

Synthesis of Compound 2

500 mg (3.88 mmol) of 2-chlorophenol was dissolved in 10 ml of acetonitrile. After adding thereto 582 mg (4.28 mmol) of potassium carbonate and 1,4-dibromobutane at room temperature, the mixture was reacted while heating to 80° C. under reflux for 3 hours. After the completion of the reaction, the reaction mixture was allowed to stand at room temperature and water was added thereto followed by separating extraction with ethyl acetate. The organic layer thus obtained was washed with a saturated aqueous solution of sodium chloride and dried over sodium sulfate. Then the organic layer was concentrated under reduced pressure and the residue thus obtained was purified by silica gel column chromatography (50 g; hexane/acetone=12:1) to thereby give 994 mg (3.88 mmol) of the compound 1 as a colorless and transparent syrup at a yield of 100%.

Next, 994 mg (3.88 mmol) of the compound 1 obtained above was dissolved in 18 ml of acetonitrile. After adding thereto 652 mg (4.7 mmol) of potassium carbonate and 1.1 g (7.28 mmol) of (R)-3-methoxy-a-methylbenzylamine at room temperature, the mixture was stirred while heating to 90° C. under reflux for 12 hours. After the completion of the reaction, the reaction mixture was allowed to stand at room temperature and water was added thereto. Then it was subjected to separating extraction with ethyl acetate and washed with a saturated aqueous solution of sodium chloride. The organic layer thus obtained was dried over sodium sulfate and concentrated under reduced pressure. The residue thus obtained was purified by silica gel column chromatography (100 g; chloroform/methanol=50:1) to thereby give 643 mg (1.93 mmol) of the compound 2 as a pale yellow and transparent syrup at a yield of 50.2%.

MS m/z: 333. 1H-NMR d: 1.34(3H, d, J=6.7 Hz), 1.60–1.73 (1H, m), 1.78–1.90 (1H, m), 2.48–2.62 (2H, m), 3.75 (3H, q, J=6.7 Hz), 3.81 (3H, s), 3.98 (2H, t, J=6.7 Hz), 6.77 (1H, dd, J=7.4 Hz, J=2.0 Hz), 6.89–6.90 (4H, m), 7.16–7.26(2H, m), 7.34 (1H, dd, J=9.0 Hz, J=2.6 Hz).

Example 2

Synthesis of Compound 4

The two steps described above were repeated but substituting the 1,4-dibromobutane with 1,5-dibromopentane to thereby give the desired compound 4.

MS m/z: 347. 1H-NMR d: 1.35 (3H, d, J=6.5 Hz), 1.48–1.57 (4H, m), 1.79–1.84 (2H, m), 2.44–2.55 (2H, m), 3.74 (1H, q, J=6.5 Hz), 3.81 (3H, s), 4.00 (2H, t, J=6.5 Hz), 6.77–6.79 (1H, m), 6.85–6.89 (4H, m), 7.16–7.26 (2H, m)

Example 3

Synthesis of Compound 6

The two steps described above were repeated but substituting the 1,4-dibromobutane with 1,6-dibromohexane to thereby give the desired compound 6.

MS m/z: 361. 1H-NMR d: 1.35 (3H, d, J=7.0 Hz), 1.34–1.39 (2H, m), 1.45–1.54 (4H, m), 1.78–1.84 (2H, m), 2.41–2.54 (2H, m), 3.73 (1H, q, J=7.0 Hz), 3.81 (3H, s), 4.00 (2H, t, J=6.5 Hz), 6.77–6.78 (1H, m), 6.85–6.90 (4H, m), 7.17–7.26 (2H, m), 7.34 (1H, dd, J=8.0 Hz, J=1.0 Hz).

Example 4

Synthesis of Compound 8

548 mg (4.25 mmol) of 3-chlorophenol was dissolved in 10 ml of acetonitrile. After adding thereto 652 mg (4.72 mmol) of potassium carbonate and 0.56 ml (4.69 mmol) of 1,4-dibromobutane at room temperature, the mixture was reacted while heating to 80° C. under reflux for 3 hours. After the completion of the reaction, the reaction mixture was allowed to stand at room temperature and water was added thereto followed by separating extraction with ethyl acetate. The organic layer thus obtained was washed with a saturated aqueous solution of sodium chloride and dried over sodium sulfate. Then the organic layer was concentrated under reduced pressure and the residue thus obtained was purified by silica gel column chromatography (50 g; hexane/acetone=12:1) to thereby give 846 mg (3.31 mmol) of the compound 7 as a colorless and transparent syrup at a yield of 88.3%.

Next, 846 mg (3.31 mmol) of the compound 7 obtained above was dissolved in 18 ml of acetonitrile. After adding thereto 523 mg (3.78 mmol) of potassium carbonate and 550 mg (3.64 mmol) of (R)-3-methoxy-a-methylbenzylamine at room temperature, the mixture was stirred while heating to 90° C. under reflux for 12 hours. After the completion of the reaction, the reaction mixture was allowed to stand at room temperature and water was added thereto. Then it was subjected to separating extraction with ethyl acetate and washed with a saturated aqueous solution of sodium chloride. The organic layer thus obtained was dried over sodium sulfate and concentrated under reduced pressure. The residue thus obtained was purified by silica gel column chromatography (100 g; chloroform/methanol=50:1) to thereby give 481 mg (1.46 mmol) of the compound 8 as a pale yellow and transparent syrup at a yield of 45.0%.

MS m/z :333. 1H-NMR d: 1.35 (3H, d, J=6.5 Hz), 1.57–1.67 (2H, m), 1.73–1.83 (2H, m), 2.46–2.60 (2H, m), 3.74 (1H, q), 3.81 (3H, s), 3.90 (2H, t, J=6.5 Hz), 6.74 (1H, dd, J=8.0 Hz, J=2.5 Hz), 6.85–6.86 (1H, m), 7.5–7.18 (1H, dd, J=2.7 Hz), 7.22–7.26 (1H, m).

Example 5

Synthesis of Compound 10

The two steps described above were repeated but substituting the 1,4-dibromobutane with 1,5-dibromopentane to thereby give the desired compound 10.

MS m/z: 347. 1H-NMR d: 1.35 (3H, d, J=6.0 Hz), 1.43–1.56 (4H, m), 1.72–1.77 (2H, m), 2.43–2.56 (2H, m), 3.73 (1H, q, J=6.5 Hz), 3.81 (3H, s), 3.90 (2H, t J=7.0 Hz), 6.76 (1H, dd, J=2.0 Hz, J=8.5 Hz), 6.70–6.79 (1H, m), 6.86–6.91(4H, m), 7.17 (1H, dd, J=3.0 Hz), 7.22–7.26 (1H, m).

Example 6

Synthesis of Compound 12

The two steps described above were repeated but substituting the 1,4-dibromobutane with 1,6-dibromohexane to thereby give the desired compound 12.

MS m/z: 361. 1H-NMR d: 1.35 (3H, d, J=6.5 Hz), 1.33–1.53 (6H, m), 1.72–1.77 (2H, m), 3.73 (1H, m), 3.81 (3H, s), 3.90 (2H, t, J=6.5 Hz), 6.74–6.79 (2H, m), 6.86–6.91 (4H, m), 7.17 (1H, dd, J=8.3 Hz), 7.22–7.26 (1H, m).

Example 7

Synthesis of Compound 14

362 mg (2.82 mmol) of 4-chlorophenol was dissolved in 5 ml of acetonitrile. After adding thereto 429 mg (3.10 mmol) of potassium carbonate and 0.36 ml (3.01 mmol) of dibromobutane at room temperature, the mixture was reacted while heating to 80° C. under reflux for 3 hours. After the completion of the reaction, the reaction mixture was allowed to stand at room temperature and water was added thereto followed by separating extraction with ethyl acetate. The organic layer thus obtained was washed with a saturated aqueous solution of sodium chloride and dried over sodium sulfate. Then the organic layer was concentrated under reduced pressure and the residue thus obtained was purified by silica gel column chromatography (50 g; hexane/acetone=12:1) to thereby give 414 mg (1.62 mmol) of the compound 13 as a colorless and transparent syrup at a yield of 69.4%.

Next, 846 mg (3.31 mmol) of the compound 13 obtained above was dissolved in 18 ml of acetonitrile. After adding thereto 523 mg (3.78 mmol) of potassium carbonate and 550 mg (3.64 mmol) of (R)-3-methoxy-a-methylbenzylamine at room temperature, the mixture was stirred while heating to 90° C. under reflux for 12 hours. After the completion of the reaction, the reaction mixture was allowed to stand at room temperature and water was added thereto. Then it was subjected to separating extraction with ethyl acetate and washed with a saturated aqueous solution of sodium chloride. The organic layer thus obtained was dried over sodium sulfate and concentrated under reduced pressure. The residue thus obtained was purified by silica gel column chromatography (100 g; chloroform/methanol=50:1) to thereby give 481 mg (1.46 mmol) of the compound 14 as a pale yellow and transparent syrup at a yield of 45.0%.

MS m/z: 333. 1 H-NMR d: 1.35 (3H, d, J=6.5 Hz), 1.56–1.67 (2H, m), 1.73–1.83 (2H, m), 2.46–2.60 (2H, m), 3.72–3.76 (1H, q, J=6.5 Hz), 3.81 (3H, s), 3.89 (2H, t, J=7.0 Hz), 6.77–6.79 (3H, m), 6.88–6.90 (2H, m), 7.19–7.26 (3H, m).

Example 8

Synthesis of Compound 16

The two steps described above were repeated but substituting the 1,4-dibromobutane with 1,5-dibromopentane to thereby give the desired compound 16.

MS m/z: 347. 1 H-NMR d: 1.34 (3H, d, J=6.5 Hz), 1.43–1.56 (4H, m), 1.71–1.77 (2H, m), 2.42–2.55 (2H, m), 3.72 (2H, q, J=6.5 Hz), 3.80 (3H, s), 3.89 (2H, t, J=6.5 Hz), 6.76–6.80 (3H, m), 6.87–6.89 (2H, m), 7.19–7.26 (3H, m).

Example 9

Synthesis of Compound 18

The two steps described above were repeated but substituting the 1,4-dibromobutane with 1,6-dibromohexane to thereby give the desired compound 18. MS m/z: 361. 1H-NMR d: 1.35 (3H, d, J=7.0 Hz), 1.32–1.53 (6H, m), 1.71–1.77 (2H, m), 2.41–2.58 (2H, m) 3.73 (1H, m), 3.81 (3H, s), 3.89 )2H, t, J=7.0 Hz), 6.77–6.81 (3H, m), 6.88–6.89 (3H, m), 7.19–7.26 (3H, m).

Example 10

Synthesis of Compound 20

330 mg (2.28 mmol) of 2-chlorothiophenol was dissolved in 6.5 ml of methylene chloride. After adding thereto 0.35 ml (2.51 mmol) of triethylamine and 0.23 ml (2.26 mmol) of 1,3-dibromopropane at room temperature, the mixture was reacted while heating to 45° C. under reflux for 6 hours. After the completion of the reaction, 0.30 ml (2.15 mmol) of triethylamine was dropped again into the reaction at room temperature. Then 350 mg (2.31 mmol) of (R)-3-methoxy-a-methylbenzylamine was added thereto and the resulting mixture was stirred while heating to 90° C. under reflux for 12 hours. After the completion of the reaction, the reaction mixture was allowed to stand at room temperature and water was added thereto. Then it was subjected to separating extraction with ethyl acetate and washed with a saturated aqueous solution of sodium chloride. The organic layer thus obtained was dried over sodium sulfate and concentrated under reduced pressure. The residue thus obtained was purified by silica gel column chromatography (50 g; chloroform/methanol=65:1) to thereby give 102 mg (0.304 mmol) of the compound 20 as a pale yellow and transparent syrup at an overall yield of the two steps of 13.2%.

MS m/z: 335. 1H-NMR d: 1.35(3H, d, J=6.7 Hz), 1.79–1.86 (2H, m), 2.55–2.69 (2H, m), 2.91–3.03 (2H, m), 3.74 (1H, q, J=6.7 Hz), 3.81 (3H, s), 6.78 (1H, dd, J=2.5 Hz, J=8.0 Hz), 6.88–6.90 (2H, m), 7.07–7.11 (1H, m), 7.18–7.26 (3H, m), 7.34 (1H, dd, J=8.0 Hz, J=1.2 Hz).

Example 11

Synthesis of Compound 22

The two steps described above were repeated but substituting the 1,3-dibromopropane with 1,4-dibromopentane to thereby give the desired compound 22.

MS m/z: 349. 1H-NMR d: 1.33 (3H, d, J=6.5 Hz), 1.58–1.72 (4H, m), 2.43–2.56 (2H, m), 2.90 (2H, t, J=7.5 Hz), 3.72 (1H, q, J=6.5 Hz), 3.80 (3H, s), 6.76–6.78 (1H, m), 6.87–6.88 (2H, m), 7.07–7.10 (1H, m), 7.18–7.26 (3H, m), 7.35 (1H, dd, J=8.0 Hz).

Example 12

Synthesis of Compound 24

The two steps described above were repeated but substituting the 1,3-dibromopropane with 1,5-dibromopentane to thereby give the desired compound 24.

MS m/z: 363. 1H-NMR d: 1.34 (3H, d, J=7.0 Hz), 1.42–1.55 (4H, m), 1.64–1.72 (2H, m), 2.40–2.53 (2H, m), 2.90 (2H, t, J=7.5 Hz), 3.72 (1H, q, J=7.0 Hz), 3.81 (3H, s),6.77–6.79 (1H, m), 6.87–6.91 (2H, m), 7.07–7.10 (1H, m), 7.18–7.26 (3H, m), 7.35 (1H, d, J=8.0 Hz).

Example 13

Synthesis of Compound 26

The two steps described above were repeated but substituting the 1,3-dibromopropane with 1,6-dibromohexane to thereby give the desired compound 26.

MS m/z: 377. 1H-NMR d: 1.34 (3H, d, J=6.5 Hz), 1.41–1.50 (4H, m), 1.64–1.70 (2H, m), 2.90 (2H, t, J=7.5 Hz), 3.72 (1H, q, J=6.5 Hz), 3.81 (3H, s), 6.77–6.79 (1H, m), 6.88–6.89 (2H, m), 7.06–7.11 (1H, m), 7.19–7.26 (3H, m), 7.35 (1H, d, J=8.0 Hz).

Example 14

Synthesis of Compound 28

540 mg (3.77 mmol) of 4-chlorothiophenol was dissolved in 10 ml of methylene chloride. After adding thereto 1.60 ml (11.5 mmol) of triethylamine and 0.63.ml (4.10 mmol) of 1,3-dibromopropane at room temperature, the mixture was reacted while heating to 45° C. under reflux for 3 hours. After the completion of the reaction, the methylene chloride was once removed under reduced pressure and the residue was dissolved in 9 ml of acetonitrile. Next, 500 mg (3.62 mmol) of potassium carbonate was added thereto at room temperature and 350 mg (2.31 mmol) of (R)-3-methoxy-a-methylbenzylamine was dropped thereinto. Then the resulting mixture was stirred while heating to 90° C. under reflux for 12 hours. After the completion of the reaction, the reaction mixture was allowed to stand at room temperature and water was added thereto. Then it was subjected to separating extraction with ethyl acetate and washed with a saturated aqueous solution of sodium chloride. The organic layer thus obtained was dried over sodium sulfate and concentrated under reduced pressure. The residue thus obtained was purified by silica gel column chromatography (75 g; chloroform/methanol=65:1) to thereby give 397 mg (1.13 mmol) of the compound 23 as a pale yellow and transparent syrup at an overall yield of the two steps of 33.1%.

MS m/z: 335. 1H-NMR d: 1.33 (3H, d, J=7.0 Hz), 1.72–1.78 (2H, m), 2.50–2.55 (1H, m), 2.56–2.64 (1H, m), 2.86–2.97 (2H, m), 3.71 (1H, q, J=7.0 Hz), 3.81 (3H, s), 6.77–6.79 (1H, m), 6.85–6.89 (2H, m), 7.22–7.25 (4H, m).

Example 15

Synthesis of Compound 30

The two steps described above were repeated but substituting the 1,3-dibromopropane with 1,4-dibromobutane to thereby give the desired compound 30.

MS m/z: 363. 1H-NMR d: 1.35 (3H, d, J=6.7 Hz), 1.39–1.49 (2H, m), 1.60 (2H, tt, J=7.5 Hz), 2.39–2.44 (1H, m), 2.86 (2H, t, J=7.3 Hz), 3.72 (1H, q, J=6.7 Hz), 3.81 (3H, s), 6.77–6.79 (1H, m), 6.87–6.88 (2H, m), 7.20–7.26 (5H, m).

Example 16

Synthesis of Compound 32

The two steps described above were repeated but substituting the 1,3-dibromopropane with 1,5-dibromopentane to thereby give the desired compound 32.

MS m/z: 377. 1H-NMR d: 1.35 (3H, d, J=6.7 Hz), 1.27–1.48 (4H, m), 1.60 (2H, tt, J=7.5 Hz), 2.39–2.44 (1H, m), 2.46–2.51 (1H, m), 2.85 (2H, t, J=7.3 Hz), 3.72 (1H, q, J=6.7 Hz), 3.81 (3H, s), 6.76–6.79 (1H, m), 6.87–6.89 (2H, m), 7.21–7.26 (5H, m).

Example 17

Synthesis of Compound 34

The two steps described above were repeated but substituting the 1,3-dibromopropane with 1,6-dibromohexane to thereby give the desired compound 34.

MS m/z: 349. 1H-NMR d: 1.34 (3H, d, J=6.5 Hz), 1.52–1.67 (6H, m), 2.40–2.45 (1H, m), 2.48–2.53 (1H, m), 2.86 (2H, t, J=7.0 Hz), 3.71 (1H, q, J=6.5 Hz), 3.80 (3H, s), 6.76–6.79 (1H, m), 6.86–6.88 (2H, m)

Example 18

Synthesis of Compound 36

440 mg (2.63 mmol) of 2-mercaptobenzothiazole was dissolved in 9 ml of methylene chloride. After adding thereto 1.1 ml (7.89 mmol) of triethylamine and 0.35 ml (2.93 mmol) of 1,4-dibromobutane at room temperature, the mixture was reacted at the same temperature for 12 hours. After the completion of the reaction, the methylene chloride was once removed under reduced pressure and the residue was dissolved in 8 ml of acetonitrile. Next, 800 mg (5.79 mmol) of potassium carbonate was added thereto at room temperature and 320 mg (2.12 mmol) of (R)-3-methoxy-a-methylbenzylamine was dropped thereinto. Then the resulting mixture was stirred while heating to 90° C. under reflux for 12 hours. After the completion of the reaction, the reaction mixture was allowed to stand at room temperature and water was added thereto. Then it was subjected to separating extraction with ethyl acetate and washed with a saturated aqueous solution of sodium chloride. The organic layer thus obtained was dried over sodium sulfate and concentrated under reduced pressure. The residue thus obtained was purified by silica gel column chromatography (70 g; chloroform/methanol=50:1) to thereby give 267 mg (0.72 mmol) of the compound 36 as a pale yellow and transparent syrup at an overall yield of the two steps of 27.1%.

MS m/z: 372. 1H-NMR d: 1.34 (3H, d, J=6.5 Hz), 1.61–1.68 (2H, m), 1.82–1.88 (2H, m), 2.46–2.60 (2H, m), 3.32( 2H, t, J=7.5 Hz), 3.73 (1H, q, J=6.5 Hz), 3.80 (3H, s),6.76–6.78 (1H, m), 6.87–6.89 (2H, m), 7.21–7.30 (2H, m), 7.38–7.42 (1H, m), 7.74 (1H, d, J=8.0 Hz), 7.84 (1H, d, J=8.0 Hz).

Example 19

Synthesis of Compound 38

409 mg (2.45 mmol) of 2-mercaptobenzothiazole was dissolved in 4 ml of acetonitrile. After adding thereto 690 mg (4.99 mmol) of potassium carbonate and 0.32 ml (2.68 mmol) of 1,5-dibromopentane at room temperature, the mixture was stirred at the same temperature for 1 hour. After the completion of the reaction, 420 mg (3.04 mmol) of potassium carbonate was added thereto again and 260 mg (1.72 mmol) of (R)-3-methoxy-a-methylbenzylamine was dropped thereinto. Then the resulting mixture was stirred while heating to 90° C. under reflux for 12 hours. After the completion of the reaction, the reaction mixture was allowed to stand at room temperature and water was added thereto. Then it was subjected to separating extraction with ethyl acetate and washed with a saturated aqueous solution of sodium chloride. The organic layer thus obtained was dried over sodium sulfate and concentrated under reduced pressure. The residue thus obtained was purified by silica gel column chromatography (50 g; chloroform/methanol=50:1) to thereby give 215 mg (0.57 mmol) of the compound 38 as a pale yellow and transparent syrup at an overall yield of the two steps of 45.0%.

MS m/z: 386. 1H-NMR d: 1.33 (3H, d, J=6.5 Hz), 1.44–1.56 (4H, m), 1.78–1.84 (2H, m), 2.42–2.51 (2H, m), 3.32 (2H, t, J=7.3 Hz), 3.71 (1H, q, J=6.5 Hz), 3.81 (3H, s), 6.76–6.78 (1H, m), 6.86–6.88 (2H, m), 7.22 (1H, dd, J=8.0 Hz), 7.26–7.30 (1H, m), 7,39–7.42 (1H, m), 7.74 (1H, d, J=7.5 Hz), 7.85 (1H, d, J=8.5 Hz).

Example 20

Synthesis of Compound 40

The two steps described above were repeated but substituting the 1,5-dibromopentane with 1,6-dibromohexane to thereby give the desired compound 40.

MS m/z: 400. 1H-NMR d: 1.34 (3H, d, J=6.5 Hz), 1.43–1.50 (6H, m), 1.80 (2H, tt, J=7.5 Hz), 2.40–2.52 (2H, m), 3.32 (2H, t, J=7.8 Hz), 3.72 (1H, q, J=6.5 Hz), 3.81 (3H, s), 6.76–6.78 (1H, m), 6.87–6.89 (2H, m), 7.22–7.30 (2H, m), 7.40 (1H, dd, J=7.5 Hz), 7.74 (1H, d, J=7.5 Hz), 7.85 (1H, d, J=8.0 Hz).

Example 21

Synthesis of Compound 42

467 mg (3.09 mmol) of 2-mercaptobenzothiazole was dissolved in 7 ml of acetonitrile. After adding thereto 527 mg (3.81 mmol) of potassium carbonate and 0.41 ml (3.43 mmol) of 1,4-dibromobutane at room temperature, the mixture was stirred at the same temperature for 12 hours. After the completion of the reaction, 4.4 ml of acetonitrile and 420 mg (3.04 mmol) of potassium carbonate were added thereto again and 320 mg (2.12 mmol) of (R)-3-methoxy-a-methylbenzylamine was dropped thereinto. Then the resulting mixture was stirred while heating to 90° C. under reflux for 12 hours. After the completion of the reaction, the reaction mixture was allowed to stand at room temperature and water was added thereto. Then it was subjected to separating extraction with ethyl acetate and washed with a saturated aqueous solution of sodium chloride. The organic layer thus obtained was dried over sodium sulfate. Then the organic layer was concentrated under reduced pressure and the residue thus obtained was purified by silica gel column chromatography (50 g; chloroform/methanol=60:1) to thereby give 147 mg (0.41 mmol) of the compound 42 as a pale yellow and transparent syrup at an overall yield of the two steps of 13.4%.

MS m/z: 356. 1H-NMR d: 1.35 (3H, d, J=6.7), 1.61–1.68 (2H, m), 1.81–1.89 (2H, m), 2.46–2.59 (2H, m), 3.28 (2H, t, J=7.5 Hz), 3.73 (1H, q, J=6.7 Hz), 3.80 (3H, s), 6.76–6.78 (1H, m), 6.88–6.89 (2H, m), 7.21–7.28 (3H, m), 7.42 (1H, d, J=8.0 Hz), 7.58 (1H, d, J=8.0 Hz).

Example 22

Synthesis of Compound 44

The two steps described above were repeated but substituting the 1,4-dibromobutane with 1,5-dibromopentane to thereby give the desired compound 44.

MS m/z: 370. 1H-NMR d: 1.33 (3H, d, J=6.8 Hz), 1.46–1.56 (4H, m), 1.81 (2H, m), 2.41–2.53 (2H, m), 3.29 (2H, t, J=7.3 Hz), 3.72 (1H, q, J=6.8 Hz), 3.81 (3H, s), 6.76–6.78 (1H, m), 6.86–6.89 (2H, m), 7.20–7.29 (1H, d, J=8.0 Hz), 7.42 (1H, d, J=8.0 Hz), 7.59 (1H, d, J=7.5 Hz).

Example 23

Synthesis of Compound 46

The two steps described above were repeated but substituting the 1,4-dibromobutane with 1,6-dibromohexane to thereby give the desired compound 46.

MS m/z: 384. 1H-NMR d: 1.34 (3H, d, J=6.5 Hz), 1.32–1.62 (6H, m), 1.81 (2H, qq, J=7.5 Hz), 2.40–2.52 (2H, m), 3.29 (2H, t, J=7.5 Hz), 3.72 (1 H, q, J=6.5 Hz), 3.81 (3H, s), 6.76–6.79 (1H, m), 6.87–6.89 (2H, m), 7.21–7.29 (3H, m), 7.43 (1H, d, J=8.0 Hz), 7.59 (1H, d, J=8.0 Hz).

Example 24

Synthesis of Compounds 52 and 53

To a solution of 25 g (122.4 mmol) of 5-methoxygramine 47 in 500 ml of ethanol was added 21.5 g (568.3 mmol, 4.6 moleq.) of sodium tetrahydroborate and the mixture was stirred under heating for 5.5 hours. After the completion of the reaction, ammonium chloride was added to the reaction mixture. Then the mixture was stirred at room temperature, poured into water and extracted with ethyl acetate. The ethyl acetate layer was washed with water and a saturated aqueous solution of sodium chloride and dried over sodium sulfate. After distilling off the solvent under reduced pressure, the obtained crystals were purified by column chromatography (silica gel, chloroform-ethyl acetate) to thereby give 17.31 g (87.8%) of colorless prism crystals 48.

To a solution of 17.3 g of the compound 48 (107.5 mmol) in 500 ml of absolute tetrahydrofuran was added 20 g (500 mmol, 4.6 moleq.) of 52.9% sodium hydride and the mixture was stirred at room temperature for 1.5 hours. Then 30 g (d=1.333, 157.4 mmol, 1.5 moleq.) of tosyl chloride was added thereto and the resulting mixture was stirred at room temperature for 6 hours. After the completion of the reaction, the reaction mixture was poured into water under ice-cooling and extracted with ethyl acetate. The ethyl acetate layer was washed with water and a saturated aqueous solution of sodium chloride and dried over sodium sulfate. After distilling off the solvent under reduced pressure, the obtained crystals were purified by column chromatography (silica gel, chloroform-ethyl acetate) to thereby give 36.8 g (82.8%) of colorless prism crystals 49.

17 ml (d=2.698, 183.1 mmol) of boron tribromide was dropped into a solution of 28.43 g (90.25 mmol) of the compound 49 in 800 ml of methylene chloride at an internal temperature of 0 to 5° C. The mixture was stirred at room temperature for 4 hours. After the completion of the reaction, the reaction mixture was poured into water under ice-cooling and extracted with methylene chloride. The methylene chloride layer was washed with water and a saturated aqueous solution of sodium chloride and dried over sodium sulfate. After distilling off the solvent under reduced pressure, the obtained crystals were purified by column chromatography (silica gel: 400 g, chloroform-methanol=1000:1) to thereby give 16.46 g (60.6%) of colorless prism crystals 50.

To a solution of 16.46 g (54.7 mmol) of the compound 50 in 300 ml of acetonitrile were added 11.2 ml (d=1.333, 109.5 mmol, 2.0 moleq.) of 1,3-dibromopropane and 22 g (1 59.2 mmol, 2.9 moleq.) of potassium carbonate and the resulting mixture was stirred under heating at an external temperature of 60° C. for 2.5 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained crystals were purified by column chromatography (silica gel, n-hexane-acetone) to thereby give 18.34 g (79.7%) of colorless prism crystals 51.

To a solution of 200 mg (0.48 mmol) of the compound 51 in 3 ml of acetonitrile were added 142.52 mg (0.95 mmol, 2.0 moleq.) of (R)-3-methoxy-a-methylbenzylamine and 131.3 mg.(0.95 mmol, 2.0 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained yellowish brown residue was dissolved in 3 ml of ethanol and 1 ml of a 35% aqueous solution of potassium hydroxide was added thereto. Then the mixture was stirred under heating at an external temperature of 80° C. for 2 hours. After the completion of the reaction, the reaction mixture was concentrated, poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 122.6 mg (93.8%) of a colorless oil 52.

MS m/z: 338(M$^+$). $^1$H-NMR d: 1.36 (3H, d, J=6.7 Hz, CH$_3$), 1.97 (2H, dt, J=6.7, 12.8 Hz, CH$_2$), 2.30 (3H, s, CH$_3$), 2.67 (1H, dt, J=6.7, 11.6 Hz, CH$_2$), 2.74 (1H, dt, J=6.7, 13.4 Hz, CH$_2$), 3.77 (1H, q, J=6.7 Hz, CH), 3.78 (3H, s, OCH$_3$), 4.07 (2H, m, CH$_2$), 6.78 (1H, dd, J=1.8, 7.9 Hz, C$_6$—H), 6.82 (1H, dd, J=1.8, 7.9 Hz, C$_6$'—H), 6.90 (2H, d, J=1.8 Hz, C$_2$—H), 6.91 (1H, d, J=7.9 Hz, C$_4$—H), 6.94 (1H, s, C$_2$'—H), 6.99 (1H, d, J=1.8 Hz, C$_4$'—H), 7.21 (1H, d, J=7.9 Hz, C$_7$'—H), 7.23 (1H, t, J=7.9 Hz, C$_5$—H), 7.81 (1H, s, NH).

To a solution of 200 mg (0.48 mmol) of the compound 51 in 3 ml of acetonitrile were added 162.7 mg (0.95 mmol, 2.0 moleq.) of (R)-1-(1-naphthyl)ethylamine and 131.3 mg (0.95 mmol, 2.0 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained yellowish brown residue was dissolved in 1 ml of ethanol and 1 ml of a 35% aqueous solution of potassium hydroxide was added thereto. Then the mixture was stirred under heating at an external temperature of 80° C. for 2 hours. After the completion of the reaction, the reaction mixture was concentrated, poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 122.6 mg (93.8%) of a colorless oil 53.

MS m/z: 358 (M$^+$). $^1$H-NMR d: 1.53 (3H, d, J=6.7 Hz, CH$_3$), 2.03 (2H, dt, J=6.7, 12.8 Hz, CH$_2$), 2.30 (3H, s, CH$_3$), 2.83 (2H, dt, J=6.7, 12.8 Hz, CH$_2$), 4.12 (2H, dt, J=3.1, 9.2 Hz, CH$_2$), 4.68 (1H, q, J=6.7 Hz, CH), 6.83 (1H, dd, J=1.8, 9.2 Hz, C$_2$—H), 6.94 (1H, s, C$_2$'—H), 7.01 (1H, d, J=1.8 Hz, C$_4$'—H), 7.21 (1H, d, J=7.9 Hz, C$_4$—H), 7.48 (1H, t, J=7.9 Hz, C$_3$—H), 7.49 (1H, t, J=7.9 Hz, C$_6$—H), 7.50 (1H, t, J = 7.9 Hz, C$_7$—H), 7.68 (1H, d, J=7.9 Hz, C$_5$—H), 7.75 (1H, d, J=7.9 Hz, C$_8$—H), 7.82 (1H, s, NH), 7.88 (1H, dd, J=1.8, 7.9 Hz, C$_6$'—H), 8.21 (1H, d, J=7.9 Hz, C$_7$'—H).

Example 25

Synthesis of Compound 56

To a solution of 500 mg (2.74 mmol) of 9-hydroxyfluorene 54 in 5 ml of toluene were added 0.273 ml (d=1.537, 3.02 mmol, 1.1 moleq.) of 3-bromo-1-propanol and 5.1 mg (0.027 mmol, 0.01 moleq.) of p-toluenesulfonic acid and the resulting mixture was stirred at room temperature for 1 hour. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, n-hexane-ethyl acetate) to thereby give 723.4 mg (87.0%) of a colorless oil 55.

To a solution of 200 mg (0.66 mmol) of the compound 55 in 3 ml of acetonitrile were added 148.5 mg (0.99 mmol, 1.5 moleq.) of (R)-3-methoxy-a-methylbenzylamine and 136.8 mg (0.99 mmol, 1.5 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 216.6 mg (88.0%) of a colorless oil 56.

MS m/z: 373 (M$^+$). $^1$H-NMR d: 1.30 (3H, d, J=6.7 Hz, CH$_3$), 1.67 (2H, dt, J=6.7, 13.4 Hz, CH$_2$), 2.49 (1H, dt, J=6.7, 14.0 Hz, CH$_2$), 2.56 (1H, dt, J=6.7, 11.6 Hz, CH$_2$), 3.21 (2H, t, J=6.7 Hz, CH$_2$), 3.69 (1H, q, J=6.7 Hz, CH), 3.78 (3H, s, OCH$_3$), 5.59 (1H, s, CH), 6.76 (1H, dd, J=1.8, 7.9 Hz, C$_6$—H), 6.85 (1H, d, J=1.8 Hz, C$_2$—H ), 6.87 (1H, d, J=7.9 Hz, C$_4$—H ), 7.21 (1H, t, J=7.9 Hz C$_5$—H), 7.28 (2H, t, J=7.9 Hz, C$_3$', C$_6$'—H), 7.37 (2H, t, J =7.9 Hz, C$_2$', C$_7$'H), 7.53 (1H, d, J 7.9 Hz, C$_4$'—H), 7.55 (1H, d, J=7.9 Hz, C$_5$'—H), 7.65 (2H, d, J=7.9 Hz, C$_1$', C$_6$'—H), 7.81 (1H, s, NH).

Example 26

Synthesis of Compound 59

To a solution of 200 mg (1.1 mmol) of 2-hydroxyfluorene 57 in 3 ml of acetonitrile were added 0.22 ml (d=1.333, 2.2 mmol, 2.0 moleq.) of 1,3-dibromopropane and 182.0 mg (1.32 mmol, 1.2 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained crystals were purified by column chromatography (silica gel, n-hexane-ethyl acetate) to thereby give 202.4 mg (73.3%) of a colorless prism crystals 58.

$^1$H-NMR d: 2.35 (2H, dt, J=6.1, 12.2 Hz, $CH_2$), 3.64 (2H, t, J=6.1 Hz, $CH_2$), 3.86 (2H, s, $C_9$—$H_2$), 4.17 (2H, t, J=6.1 Hz, $CH_2$), 6.93 (1H, dd, J=1.8, 7.3 Hz, $C_2$—H), 7.11 (1H, d, J=1.8 Hz, $C_4$—H), 7.23 (1H, t, J=7.3 Hz, $C_6$—H), 7.34 (1H, t, J=7.3 Hz, $C_7$—H), 7.50 (1H, d, J=7.3 Hz, $C_1$—H), 7.67 (1H, d, J=6.7 Hz, $C_8$—H), 7.69 (1H, t, J=6.7 Hz, $C_5$—H).

To a solution of 100 mg (0.33 mmol) of the compound 58 in 3 ml of acetonitrile were added 49.5 mg (0.33 mmol, 1.0 moleq.) of (R)-3-methoxy-a-methylbenzylamine and 54.7 mg (0.40 mmol, 1.2 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 216.6 mg (88.0%) of a colorless oil 59.

MS m/z: 373 ($M^+$). $^1$H-NMR d: 1.36 (3H, d, J=6.7 Hz, $CH_3$), 1.96 (2H, m, $CH_2$), 2.65 (1H, dt, J=6.7, 11.6 Hz, $CH_2$), 2.73 (1H, dt, J=6.7, 12.2 Hz, $CH_2$), 3.77 (1H, q, J=6.7 Hz, $CH$), 3.78 (3H, s, $OCH_3$), 3.85 (2H, s, $CH_2$), 4.07 (2H, q, J=5.5 Hz, $C_9$—$H_2$), 6.77 (1H, dd, J=1.8, 7.3 Hz, $C_6$—H), 6.89 (1H, d, J=1.2 Hz, $C_2$—H)6.90 (1H, d, J=7.3 Hz, $C_4$—H), 6.90 (1H, d, J=7.3 Hz, $C_2$'—H), 7.06 (1H, s, $C_4$'—H), 7.22 (1H, t, J=7.3 Hz, $C_5$—H), 7.22 (1H, t, J=7.3 Hz, $C_6$'—H), 7.33 (1H, t, J=7.3 Hz, $C_7$'—H), 7.49 (1H, d, J=7.3 Hz, $C_1$'—H), 7.65 (1H, d, J=7.3 Hz, $C_8$'—H), 7.68 (1H, d, J=7.3 Hz, $C_5$'—H).

Example 27

Synthesis of Compound 62

To a solution of 500 mg (3.89 mmol) of o-chlorophenol 60 in 3 ml of acetonitrile were added 0.39 ml (d=1.989, 3.89 mmol, 1.0 moleq.) of 1,3-dibromopropane and 591.2 mg (4.28 mmol, 1.1 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 824.0 mg (84.9%) of a colorless oil 61.

To a solution of 200 mg (0.66 mmol) of the compound 61 in 3 ml of acetonitrile were added 148.5 mg (0.99 mmol, 1.5 moleq.) of (R)-3-methoxy-a-methylbenzylamine and 136.8 mg (0.99 mmol, 1.5 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 222.6 mg (87.1%) of a colorless oil 62.

MS m/z: 319 ($M^+$). $^1$H-NMR d: 1.37 (3H, d, J=6.7 Hz, $CH_3$), 1.99 (2H, dt, J=6.7, 12.2 Hz, $CH_2$), 2.67 (1H, dt, J=6.7, 13.4 Hz, $CH_2$), 2.75 (1H, dt, J=6.7, 11.6 Hz, $CH_2$), 3.75–3.79 (1H, m, $CH$), 3.78 (3H, s, $OCH_3$), 4.09 (2H, dt, J=1.8, 6.1 Hz, $CH_2$), 6.77 (1H, dd, J=1.8, 7.3 Hz, $C_6$—H), 6.89 (1H, t, J=7.9 Hz, $C_4$—H), 6.90 (1H, d, J=1.8 Hz, $C_2$—H), 6.90 (1H, d, J=7.9 Hz, $C_4$—H), 6.90 (1H, d, J=7.9 Hz, $C_3$'—H), 7.20 (1H, dt, J=1.8, 7.3 Hz, $C_5$'—H), 7.22 (1H, t, J=7.9 Hz, $C_5$—H), 7.4 (1H, dd, J=1.8, 7.9 Hz, $C_6$'—H).

Example 28

Synthesis of Compound 65

To a solution of 500 mg (3.89 mmol) of m-chlorophenol 63 in 3 ml of acetonitrile were added 0.39 ml (d=1.989, 3.89 mmol, 1.0 moleq.) of 1,3-dibromopropane and 591.2 mg (4.28 mmol, 1.1 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 884.2 mg (91.1%) of a colorless oil 64.

To a solution of 200 mg (0.66 mmol) of the compound 64 in 3 ml of acetonitrile were added 148.5 mg (0.99 mmol, 1.5 moleq.) of (R)-3-methoxy-a-methylbenzylamine and 136.8 mg (0.99 mmol, 1.5 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 229.3 mg (89.7%) of a colorless oil 65.

MS m/z: 319 ($M^+$). $^1$H-NMR d: 1.35 (3H, d, J=6.7 Hz, $CH_3$), 1.88–1.96 (2H, m, $CH_2$), 2.61 (1H, dt, J=6.7, 11.6 Hz, $CH_2$), 2.70 (1H, dt, J=6.7, 11.6 Hz, $CH_2$), 3.75 (1H, q, J=6.7 Hz, $CH$), 3.80 (3H, s, $OCH_3$), 3.96–4.04 (2H, m, $CH_2$), 6.75 (1H, d, J=7.9 Hz, $C_6$—H), 6.78 (1H, d, J=7.9 Hz, $C_6$—H), 6.88 (1H, s), 6.88–6.92 (3H, m), 7.17 (1H, t, J=7.9 Hz, $C_5$'—H), 7.23 (1H, t, J=7.9 Hz, $C_5$—H).

Example 29

Synthesis of Compound 68

To a solution of 500 mg (3.89 mmol) of p-chlorophenol 66 in 3 ml of acetonitrile were added 0.39 ml (d=1.989, 3.89 mmol, 1.0 moleq.) of 1,3-dibromopropane and 591.2 mg (4.28 mmol, 1.1 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 876.5 mg (90.3%) of a colorless oil 67.

To a solution of 200 mg (0.66 mmol) of the compound 67 in 3 ml of acetonitrile were added 148.5 mg (0.99 mmol, 1.5 moleq.) of (R)-3-methoxy-a-methylbenzylamine and 136.8 mg (0.99 mmol, 1.5 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 293.1 mg (87.2%) of a colorless oil 68.

MS m/z: 319 (M$^+$). $^1$H-NMR (90 MHz) d: 1.35 (3H, d, J=6.4 Hz, C$\underline{H_3}$), 1.91 (2H , dt, J=6.4, 12.7 Hz, C$\underline{H_2}$), 2.67 (2H, dt, J=2.4, 6.4 Hz, C$\underline{H_2}$), 3.75 (1H, q, J=6.4 Hz, C$\underline{H}$), 3.79 (3H, s, OC$\underline{H_3}$), 3.98 (2H, t, J=6.4 Hz, C$\underline{H_2}$), 6.70–6.91 (5H, m), 7.14 (3$\underline{H}$, m).

Example 30

Synthesis of Compound 71

To a solution of 500 mg (2.71 mmol) of 3-hydroxybenzofuran 69 in 5 ml of acetonitrile were added 0.55 ml (d=1.989, 5.43 mmol, 2.0 moleq.) of 1,3-dibromopropane and 750.1 mg (5.43 mmol, 2.0 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 804.3 mg (77.0%) of colorless prism crystals 70.

To a solution of 800 mg (2.62 mmol) of the compound 70 in 5 ml of acetonitrile were added 590.2 mg (3.93 mmol, 1.5 moleq.) of (R)-3-methoxy-a-methylbenzylamine and 543.7 mg (3.93 mmol, 1.5 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 880.8 mg (89.5%) of a colorless oil 71.

MS m/z: 375 (M$^+$). $^1$H-NMR d: 1.38 (3H, d, J=6.7 Hz, C$\underline{H_3}$), 2.01 (2H, m, C$\underline{H_2}$2.70 (1H, dt, J=6.7, 14.0 Hz, C$\underline{H_2}$), 2.77 (1H, dt, J=6.7, 13.4 Hz, C$\underline{H_2}$), 3.80 (1H, q, J=6.7 Hz, C$\underline{H}$), 3.80 (3H, s, OC$\underline{H_3}$), 4.10–4.17 (2H, m, C$\underline{H_2}$), 6.79 (1H, dd, J=1.8, 7.3 Hz, C$_6$—H), 6.91 (1H, d, J=1.8 Hz, C$_2$—H), 6.92 (1H, d, J=7.3 Hz, C$_4$—H), 7.02 (1H, dd, J=2.5, 8.6 Hz, C$_3$'—H), 7.24 (1H, t, J=7.3 Hz, C$_5$—H), 7.33 (1H, t, J=7.3 Hz, C$_6$'—H), 7.41 (1H, d, J=2.5 Hz, C$_1$'—H), 7.45 (1H, dt, J=1.2, 7.3 Hz, C$_7$'—H), 7.46 (1H, d, J=7.3 Hz, C$_5$'—H), 7.55 (1H, d, J=8.6 Hz, C$_4$'—H), 7.91 (1H, d, J=7.3 Hz, C$_8$'—H).

Example 31

Synthesis of Compound 74

To a solution of 300.0 mg (2.16 mmol) of 2-naphthol 72 in 3 ml of absolute tetrahydrofuran were added 300 ml (d=1.537, 2.16 mmol, 1.0 moleq.) of 3-bromo-1-propanol and 622.7 mg (2.37 mmol, 1.1 moleq.) of triphenylphosphine. Then a solution of 0.41 ml (d=1.106, 2.37 mmol, 1.1 moleq.) of DEAD in 3 ml of absolute tetrahydrofuran was added thereto and the resulting mixture was stirred at room temperature for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 551.8 mg (100%) of a colorless oil 73.

To a solution of 200 mg (0.75 mmol) of the compound 73 in 5 ml of acetonitrile were added 169.8 mg (1.13 mmol, 1.5 moleq.) of (R)-3-methoxy-a-methylbenzylamine and 156.5 mg (1.13 mmol, 1.5 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 230.8 mg (91.3%) of a colorless oil 74.

MS m/z: 335(M$^+$). $^1$H-NMR d: 1.41 (3H, d, J=6.7 Hz, C$\underline{H_3}$), 2.13 (2H, dt, J=6.7, 12.8 Hz, C$\underline{H_2}$), 2.73 (1H, dt, J=6.7, 11.6 Hz, C$\underline{H_2}$), 2.85 (1H, dt, J=6.7, 11.6 Hz, C$\underline{H_2}$), 3.79 (3H, s, OC$\underline{H_3}$), 3.83 (1H, q, J=6.7 Hz, C$\underline{H}$), 4.23 (2$\underline{H}$, dt, J=1.2, 6.1 Hz, C$\underline{H_2}$), 6.80 (1H, dd, J=2.4, 7.9 Hz, C$_6$—H), 6.83 (1H, d, J=7.3 Hz, C$_2$'—H), 6.92 (1H, d, J=2.4 Hz, C$_2$—H), 6.93 (1H, d, J=7.9 Hz, C$_4$—H), 7.24 (1H, t, J=7.9 Hz, C$_5$—H), 7.39 (1H, t, J=7.9 Hz, C$_6$'—H), 7.45 (1H, d, J=7.9 Hz, C$_4$'—H), 7.48 (1H, dd, J=1.2, 7.9 Hz, C$_3$'—H), 7.52 (1H, dt, J=1.2, 7.9 Hz, C$_7$'—H), 7.83 (1H, d, J=7.9 Hz, C$_5$'—H), 8.22 (1H, d, J=7.9 Hz, C$_8$'—H).

Example 32

Synthesis of Compound 77

To a solution of 300 mg (1.87 mmol) of 2-naphthalenethiol 75 in 5 ml of methylene chloride were added 0.23 ml (d=1.989, 2.25 mmol, 1.2 moleq.) of 1,3-dibromopropane and 0.31 mg (d=0.726, 2.25 mmol, 1.2 moleq.) of triethylamine and the resulting mixture was stirred under heating at an external temperature of 40° C. for 4 hours. After the completion of the reaction, the reaction mixture was poured into water and extracted with ethyl acetate. The ethyl acetate layer was washed with a 5% aqueous solution of hydrochloric acid, water and a saturated aqueous solution of sodium chloride and dried over sodium sulfate. After distilling off the solvent under reduced pressure, the obtained residue was purified by column chromatography (silica gel, ethyl acetate-n-hexane) to thereby give 241.3 mg (45.9%) of a colorless oil 76.

To a solution of 241 mg (0.86 mmol) of the compound 76 in 5 ml of acetonitrile were added 193.0 mg (1.29 mmol, 1.5 moleq.) of (R)-3-methoxy-a-methylbenzylamine and 177.8 mg (1.29 mmol, 1.5 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 209.8 mg (69.7%) of a colorless oil 77.

MS m/z: 351(M$^+$). $^1$H-NMR d: 1.38 (3H, d, J=6.7 Hz, C$\underline{H_3}$), 2.01 (2H, dt, J=6.7 Hz, C$\underline{H_2}$), 2.73 (2H, dt, J=6.7, 25.0 Hz, C$\underline{H_2}$), 3.80 (1H, q, J=6.7 Hz, C$\underline{H}$), 3.80 (3H, s, OC$\underline{H_3}$), 4.13 (2$\underline{H}$, m, C$\underline{H_2}$), 6.79 (1H, dd, J=1.8, 7.3 Hz, C$_6$—$\underline{H}$), 6.91 (1H, d, J=1.2 Hz, C$_2$—$\underline{H}$), 6.92 (1H, d, J=7.3 Hz, C$_4$—$\underline{H}$), 7.02 (1H, dd, J=2.5, 7.3 Hz, C$_3$'—$\underline{H}$), 7.24 (1H, t, J=7.3 Hz, C$_5$—$\underline{H}$), 7.33 (1H, t, J=7.3 Hz, C$_6$'—$\underline{H}$), 7.41 (1H, d, J=2.5 Hz, C$_1$'—$\underline{H}$), 7.45 (1H, dt, J=1.2, 7.3 Hz, C$_7$'—$\underline{H}$), 7.46 (1H, d, J=7.3 Hz, C$_4$'—$\underline{H}$), 7.55 (1H, d, J=7.3 Hz, C$_5$'—$\underline{H}$), 7.91 (1H, d, J=7.3 Hz, C$_8$'—$\underline{H}$).

Example 33

Synthesis of Compound 80

To a solution of 500 mg (3.76 mmol) of 5-hydroxyindole 78 in 5 ml of acetonitrile were added 833.9 mg (d=1.989, 4.13 mmol, 1.1 moleq.) of 1,3-dibromopropane and 570.9 mg (4.13 mmol, 1.1 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 586 mg (61.4%) of a colorless oil 79.

$^1$H-NMR d: 2.33 (2H, dt, J=6.1, 12.2 Hz, C$\underline{H_2}$), 3.63 (2H, t, J=6.1 Hz, C$\underline{H_2}$), 4.13 (2H, t, J=6.1 Hz, C$\underline{H_2}$), 6.47 (1H, t, J=2.4 Hz, C$_3$—$\underline{H}$), 6.85 (1H, dd, J=2.4, 8.5 Hz, C$_6$—H), 7.12 (1H, d, J=2.4 Hz, C$_4$—H), 7.17 (1H, t, J=2.4 Hz, C$_2$—H), 7.26 (1H,d, J=8.5 Hz, C$_7$—H), 8.03 (1H, s, N$\underline{H}$).

To a solution of 200 mg (0.79 mmol) of the compound 79 in 3 ml of acetonitrile were added 118.1 g (0.79 mmol, 1.5 moleq.) of (R)-3-methoxy-a-methylbenzylamine and 130.6 mg (0.94 mmol, 1.2 moleq.) of potassium carbonate and the resulting mixture was stirred under heating at an external temperature of 40° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 265.1 mg (82.8%) of a colorless oil 80.

MS m/z: 324(M$^+$). $^1$H-NMR d: 1.38 (3H, d, J=6.7 Hz, C$\underline{H_3}$), 2.01 (2H, dt, J=6.7, 12.8 Hz, C$\underline{H_2}$), 2.67 (1H, dt, J=6.7, 11.6 Hz, C$\underline{H_2}$), 2.74 (1H, dt, J=6.7, 13.4 Hz, C$\underline{H_2}$), 3.78 (1H, q, J=6.7 Hz, C$\underline{H}$), 3.81 (3H, s, OC$\underline{H_3}$), 4.02–4.09 (2H, m, C$\underline{H_2}$), 6.47 (1H, t, J=3.1 Hz, C$_3$'—H), 6.78 (1H, dd, J=3.1, 7.9 Hz, C$_6$—H), 6.83 (1H, dd, J=2.4, 8.5 Hz, C$_6$'—H), 6.90 (1H, d, J=3.1 Hz, C$_2$—H), 6.91 (1H, d, J=7.9 Hz, C$_4$—H), 7.09 (1H, d, J=2.4 Hz, C$_4$'—H), 7.18 (1H, t, J=3.1 Hz, C$_2$'—H), 7.23 (1H, t, J=7.9 Hz, C$_5$—H), 7.27 (1H, d, J=8.5 Hz, C$_7$'—H), 8.07 (1H, s, N$\underline{H}$).

Example 34

Synthesis of Compound 83

To a solution of 400 mg (2.35 mmol) of 4-phenylphenol 81 in 5 ml of acetonitrile were added 0.48 ml (d=1.989, 4.7 mmol, 2.0 moleq.) of 1,3-dibromoprbpane and 389.7 mg (2.82 mmol, 1.2 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 564.9 mg (82.5%) of colorless prism crystals 82.

To a solution of 300 mg (1.03 mmol) of the compound 82 in 4 ml of acetonitrile were added 309.3 mg (2.06 mmol, 2.0 moleq.) of (R)-3-methoxy-a-methylbenzylamine and 284.9 mg (2.06 mmol, 2.0 moleq.) of potassium carbonate and the resulting mixture was stirred under heating at an external temperature of 60° C. for 4 hours. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, ethyl acetate-n-hexane) to thereby give 311.9 mg (83.8%) of colorless prism crystals 83.

MS m/z: 361(M$^+$). $^1$H-NMR d: 1.36 (3H, d, J=6.7 Hz, C$\underline{H_3}$), 1.93–2.01 (2H, m, C$\underline{H_2}$), 2.65 (1H, dt, J=6.7, 11.6 Hz, C$\underline{H_2}$), 2.73 (1H, dt, J=6.7, 11.6 Hz, C$\underline{H_2}$), 3.77 (1H, q, J=6.7 Hz, C$\underline{H}$), 3.80 (3H, s, OCH$_3$), 4.02–4.10 (2H, m, C$\underline{H_2}$), 6.79 (1H,dd, J=1.8, 7.3 Hz, C$_6$—H), 6.90 (1H, d, J=1.8 Hz, C$_2$—H), 6.91 (1H, d, J=7.3 Hz, C$_4$—H), 6.95 (2H, dt, J=2.4, 9.2 Hz, C$_3$'—H), 7.24 (1H, t, J=7.3 Hz, C$_5$—H), 7.30 (1H, t, J=7.3 Hz, C$_4$"—H), 7.42 (2H, t, J=7.3 Hz, C$_3$",$_5$"—H), 7.51 (2H, dt, J=2.4, 9.2 Hz, C$_2$",$_6$"—H), 7.55 (2H, dd, J=1.2, 7.3 Hz, C$_2$',$_6$'—H).

Example 35

Synthesis of Compound 88

To a solution of 600 mg (4.0 mmol) of (R)-3-methoxy-a-methylbenzylamine 84 in 5 ml of methylene chloride were added 662.4 mg (d=1.176, 4.4 mmol, 1.1 moleq.) of ethylmalonyl chloride and 0.66 ml (d=0.726, 4.8 mmol, 1.2 moleq.) of triethylamine and the resulting mixture was stirred at room temperature for 2 hours. After the completion of the reaction, the reaction mixture was poured into water and extracted with methylene chloride. The methylene chloride layer was washed with a 5% aqueous solution of hydrochloric acid, water and a saturated aqueous solution of sodium chloride and dried over sodium sulfate. After distilling off the solvent under reduced pressure, the obtained crystals were purified by column chromatography (silica gel, n-hexane-ethyl acetate) to thereby give 790.0 mg (98.4%) of colorless prism crystals 85.

$^1$H-NMR d: 1.21 (3H, t, J=6.7 Hz, CH$_2$C$\underline{H}_3$), 1.42 (3H, d, J=6.7 Hz, CH$_3$), 3.23 (2H, d, J=4.3 Hz, C$\underline{H}_2$), 3.73 (3H, s, OCH$_3$), 4.12 (2H, q, J=6.7 Hz, C$\underline{H}_2$CH$_3$), 5.04 (1H, dt, J=6.7, 14.0 Hz, C$\underline{H}$), 6.72 (1H, dd, J=1.8, 7.9 Hz, C$_6$—H), 6.79 (1H, d, J=1.8 Hz, C$_2$—H), 6.83 (1H, d, J=7.9 Hz, C$_4$—H), 7.18 (1H, t, J=7.9 Hz, C$_5$—H), 7.36 (1H, s, N$\underline{H}$).

To a solution of 897.6 mg (3.39 mmol) of the compound 85 in 5 ml of ethanol was added 2 ml of a 10% aqueous solution of sodium hydroxide and the resulting mixture was stirred under heating at an external temperature of 80° C. for 1 hour. After the completion of the reaction, the reaction mixture was concentrated and acidified with a 5% aqueous solution of hydrochloric acid. Then the reaction mixture was poured into water and extracted with ethyl acetate. The ethyl acetate layer was washed with a 5% aqueous solution of hydrochloric acid, water and a saturated aqueous solution of sodium chloride and dried over sodium sulfate. After distilling off the solvent under reduced pressure, the obtained crystals were was purified by column chromatography (silica gel, n-hexane-ethyl acetate) to thereby give 790.0 mg (98.4%) of colorless prism crystals 86.

$^1$H-NMR d: 1.47 (3H, d, J=6.7 Hz, CH$_3$), 3.27 (2H, d, J=9.2 Hz, C$\underline{H}_2$), 3.77 (3H, s, OCH$_3$), 5.05 (1H, dt, J=6.7, 14.0 Hz, C$\underline{H}$), 6.78 (1H, dd, J=2.4, 7.9 Hz, C$_6$—H), 6.83 (1H, d, J=2.4 Hz, C$_2$—H), 6.86 (1H, d, J=7.9 Hz, C$_4$—H), 7.23 (1H, t, J=7.9 Hz, C$_5$—H ), 7.47 (1H, d, J=7.9 Hz, N$\underline{H}$).

To a solution of 400 mg (1.68 mmol) of the compound 86 in 5 ml of dimethylformamide were added 278.5 mg (1.86 mmol, 1.1 moleq.) of (R)-3-methoxy-a-methylbenzylamine and 389.5 mg (2.02 mmol, 1.2 moleq.) of WSCxHCl and the resulting mixture was stirred at room temperature for 1 hour. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained crystals were purified by column chromatography (silica gel, n-hexane-ethyl acetate) to thereby give 615.4 mg (98.5%) of colorless prism crystals 87.

MS m/z: 370 (M$^+$). $^1$H-NMR d: 1.42 (6H, d, J=6.7 Hz, CH$_3$), 3.15 (2H, s, C$\underline{H}_2$), 3.75 (6H, s, OCH$_3$), 5.04 (2H, dt, J=7.9, 14.7 Hz, C$\underline{H}$), 6.77 (2H, dd, J=2.4, 7.9 Hz, C$_{6,6'}$—H), 6.80 (2H, d, J=2.4 Hz, C$_{2,2'}$—H), 6.83 (2H, d, J=7.9 Hz, C$_{4,4'}$—H), 7.20 (2H, t, J=7.9 Hz, C$_{5,5'}$—H), 7.47 (2H, s, N$\underline{H}$).

To a solution of 100 mg (0.270 mmol) of the compound 87 in 5 ml of absolute tetrahydrofuran was added 0.59 ml (0.59 mmol, 1.2 moleq.) of a 1 mol solution of boron trihydride in tetrahydrofuran. The resulting mixture was heated to room temperature and then stirred for 3 hours. After the completion of the reaction, the reaction mixture was poured into water, acidified with a 5% aqueous solution of hydrochloric acid and then extracted with ethyl acetate. The hydrochloric acid layer was made alkaline by adding a 5% aqueous solution of sodium hydroxide and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, n-hexane-ethyl acetate) to thereby give 76.3 mg (82.6%) of a colorless oil 88.

MS m/z: 342(M$^+$). $^1$H-NMR d: 1.43 (6H, d, J=6.7Hz, CH$_3$), 1.62 (2H, dt, J=6.7, 13.4 Hz, C$\underline{H}_2$), 2.46 (2H, dt, J=6.7, 13.4 Hz, C$\underline{H}_2$), 2.54 (2H, dt, J=6.7, 11.6 Hz, C$\underline{H}_2$), 3.70 (2H, q, J=6.7 Hz, C$\underline{H}$), 3.80 (6H, s, OC$\underline{H}_3$), 6.77 (2H, dd, J=2.4, 7.3 Hz, C$_{6,6'}$—H), 6.86 (2H, d, J=2.4 Hz, C$_{2,2'}$—H), 6.87 (2H, d, J=7.3 Hz, C$_{4,4'}$—H), 7.23 (2H, t, J=7.3 Hz, C$_{5,5'}$—H).

Example 36

Synthesis of Compound 93

To a solution of 600 mg (3.5 mmol) of (R)-1-(1-naphthyl)ethylamine 89 in 5 ml of methylene chloride were added 580.3 mg (d=1.176, 3.85 mmol, 1.1 moleq.) of ethylmalonyl chloride and 0.59 ml (d=0.726, 4.2 mmol, 1.2 moleq.) of triethylamine and the resulting mixture was stirred at room temperature for 2 hours. After the completion of the reaction, the reaction mixture was poured into water and extracted with methylene chloride. The methylene chloride layer was washed with a 5% aqueous solution of hydrochloric acid, water and a saturated aqueous solution of sodium chloride and dried over sodium sulfate. After distilling off the solvent, the obtained crystals were purified by column chromatography (silica gel, n-hexane-ethyl acetate) to thereby give 662.9 mg (66.5%) of colorless prism crystals 90.

$^1$H-NMR d: 1.16 (3H, t, J=7.3 Hz, CH$_2$C$\underline{H}_3$), 1.60 (3H, d, J=7.3 Hz, CH$_3$), 3.24 (2H, dd, J=17.7, 26.3 Hz, C$\underline{H}_2$), 4.07 (2H, q, J=7.3 Hz, C$\underline{H}_2$OH$_3$), 5.89 (1H, dt, J=7.3, 14.6 Hz, C$\underline{H}$), 7.35 (1H, d, J=7.9 Hz, N$\underline{H}$), 7.38 (1H, t, J=7.9 Hz, C$_3$—H), 7.44 (1H, t, J=12.2 Hz, C$_6$—H), 7.45 (1H, d, J=7.9 Hz, C$_2$—H), 7.46 (1H, t, J=12.2 Hz, C$_7$—H), 7.72 (1H, d, J=7.9 Hz, C$_4$—H), 7.79 (1H, d, J=7.9 Hz, C$_5$—H), 8.03 (1H, d, J=7.9 Hz, C$_8$—H).

To a solution of 662.5 mg (2.32 mmol) of the compound 90 in 5 ml of ethanol was added 2 ml of a 10% aqueous solution of sodium hydroxide. The resulting mixture was stirred under heating at an external temperature of 80° C. for 1 hour. After the completion of the reaction, the reaction mixture was concentrated, acidified with a 5% aqueous solution of hydrochloric acid. The reaction mixture was poured into water and extracted with ethyl acetate. The ethyl acetate layer was washed with a 5% aqueous solution of hydrochloric acid, water and a saturated aqueous solution of sodium chloride and dried over sodium sulfate. After distilling off the solvent under reduced pressure, the obtained crystals were purified by column chromatography (silica gel, n-hexane-ethyl acetate) to thereby give 596.0 mg (99.8%) of colorless prism crystals 91.

$^1$H-NMR d: 1.66 (3H, d, J=6.7 Hz, CH$_3$), 3.20 (2H, dd, J=18.3, 29.9 Hz, C$\underline{H}_2$), 5.91 (1H, dt, J=6.7, 14.7 Hz, C$\underline{H}$), 6.99 (1H, d, J=7.3 Hz, N$\underline{H}$), 7.43 (1H, t, J=7.9 Hz, C$_3$—H), 7.48 (1H, t, J=7.9 Hz, C$_6$—H), 7.49 (1H, d, J=7.9 Hz, C$_2$—H), 7.53 (1H, dt, J=1.2, 7.9 Hz, C$_7$—H), 7.77 (1H, d, J=7.9 Hz, C$_4$—H), 7.83 (1H, d, J=7.9 Hz, C$_5$—H), 8.00 (1H, d, J=7.9 Hz, C$_8$—H).

To a solution of 400 mg (1.56 mmol) of the compound 91 in 5 ml of dimethylformamide were added 293.2 mg (1.71 mmol, 1.1 moleq.) of (R)-1-(1-naphthyl)ethylamine and 359.2 mg (1.87 mmol, 1.2 moleq.) of WSCxHCl and the resulting mixture was stirred at room temperature for 1 hour. After the completion of the reaction, the reaction mixture was poured into water and extracted with ethyl acetate. The ethyl acetate layer was washed with water and a saturated aqueous solution of sodium chloride and dried over sodium sulfate. After distilling off the solvent under reduced pressure, the obtained crystals were purified by column chromatography (silica gel, n-hexane-ethyl acetate) to thereby give 615.1 mg (96.4%) of colorless prism crystals 92.

To a solution of 100 mg (0.24 mmol) of the compound 92 in 5 ml of absolute tetrahydrofuran was added 0.54 ml (0.54 mmol, 2.2 moleq.) of a 1 mol solution of boron trihydride in tetrahydrofuran. The resulting mixture was heated to room temperature and then stirred for 3 hours. After the completion of the reaction, the reaction mixture was poured into water, acidified with a 5% aqueous solution of hydrochloric acid and then extracted with ethyl acetate. The hydrochloric acid layer was made alkaline by adding a 5% aqueous solution of sodium hydroxide and extracted with ethyl acetate. The ethyl acetate layer was washed with water and a saturated aqueous solution of sodium chloride and dried over sodium sulfate. After distilling off the solvent under reduced pressure, the obtained residue was purified by column chromatography (silica gel, n-hexane-ethyl acetate) to thereby give 82.0 mg (88.0%) of a colorless oil 93.

MS m/z: 382(M$^+$). $^1$H-NMR d: 1.47 (6H, d, J=6.7 Hz, CH$_3$), 1.72 (2H, dt, J=6.7, 13.4 Hz, CH$_2$), 2.62 (2H, dt, J=6.7, 13.4 Hz, CH$_2$), 2.68 (2H, dt, J=6.7, 11.6 Hz, CH$_2$), 4.60 (2H, q, J=6.7, CH), 7.45 (2H, t, J=7.9 Hz, C$_{3,3'}$—H), 7.48 (2H, dt, J=1.8, 7.9 Hz, C$_{6,6'}$—H), 7.50 (2H, t, J=7.9 Hz, C$_{7,7'}$—H), 7.60 (2H, d, J=7.9 Hz, C$_{2,2'}$—H), 7.74 (2H, d, J=7.9 Hz, C$_{4,4'}$H), 7.87 (2H, dd, J=1.8, 7.9 Hz, C$_{5,5'}$—H), 8.16 (2H, d, J=7.9 Hz, C$_{8,8'}$—H).

Example 37

Synthesis of Compound 103

Compound 102:

To a solution of 6-hydroxyflavone 101 (300 mg, 1.26 mmol) in acetonitrile (5 ml) were added 1,3-dibromopropane (0.26 ml, d=1.989, 2.52 mmol, 2.0 mol eq.) and potassium carbonate (208.8 mg, 1.51 mmol, 1.2 mol eq.) and the resulting mixture was stirred under heating at an outer temperature of 60° C. for 4 hours.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The residue thus obtained was purified by column chromatography [silica gel, ethyl acetate/n-hexane] to thereby give 361.8 mg (80.0%) of the compound 102 as colorless prisms.

MS m/z: 375(M$^+$). $^1$H-NMR δ: 2.34–2.39(2H, m, CH$_2$), 3.62(2H, t, J=6.7 Hz, CH$_2$), 4.22(2H, t, J=6.7 Hz, CH$_2$), 6.82(1H, s, Ar—H), 7.29(1H, dd, J=3.1, 9.2 Hz, Ar—H), 7.51 (4H, m, Ar—H), 7.61(1H, d, J=3.1 Hz, Ar—H), 7.92 (1H, dd, J=1.8, 7.9 Hz, Ar—H), 7.19(1H, dd, J=3.1, 9.2 Hz, Ar—H), 7.44–7.53(7H, m, Ar—H), 7.57(1H, d, J=3.1 Hz, Ar—H), 7.68(1H, d, J=7.3 Hz, Ar—H), 7.74(1H, d, J=7.9 Hz, Ar—H), 7.86(1H, d, J=7.9 Hz, Ar—H), 7.91–7.93(2H, m, Ar—H), 8.19(1H, d, J=8.5 Hz, Ar—H).

Compound 103:

To a solution of the above compound 102 (125.8 mg, 0.38 mmol, 1.2 mol eq.) in acetonitrile (3 ml) were added (R)-(+)-(1-naphthyl)ethylamine (50 mg, 0.29 mmol) and potassium carbonate (60.5 mg, 0.44 mmol, 1.5 mol eq.) and the resulting mixture was stirred under heating at an outer temperature of 40° C. for 6 hours.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The residue thus obtained was purified by column chromatography [silica gel, ethyl acetate/n-hexane] to thereby give 67.1 mg (89.5%) of the compound 103 as a colorless oil.

MS m/z: 449(M$^+$). $^1$H-NMR δ: 1.55(3H, d, J=6.7 Hz, CH$_3$), 2.04(2H, t, J=6.1 Hz, CH$_2$), 2.07(1H, s, NH), 2.82(2H, m, CH$_2$), 4.15(1H, t, J=6.1 Hz, CH$_2$), 4.71 (1H, q, J=6.7 Hz, CH), 6.82(1H, s, Ar—H), 7.19(1H, dd, J=3.1, 9.2 Hz, Ar—H), 7.44–7.53(7H, m, Ar—H), 7.57(1H, d, J=3.1 Hz, Ar—H), 7.68(1H, d, J,=7.3 Hz, Ar—H), 7.74(1H, d, J=7.9 Hz, Ar—H), 7.86(1H, d, J=7.9 Hz, Ar—H), 7.91–7.93(2H, m, Ar—H), 8.19(1H, d, J=8.5 Hz, Ar—H).

Example 38

Synthesis of Compound 106

Compound 105:

To a solution of 9-hydroxyfluorene 104 (500 mg, 2.74 mmol) in toluene (5 ml) were added 3-bromo-1-propanol (0.273 ml, d=1.537, 3.02 mmol, 1.1 mol eq.) and p-toluenesulfonic acid hydrate (5.1 mg, 0.027 mmol, 0.01 mol eq.) and the resulting mixture was stirred at room temperature for 1 hour.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The residue thus obtained was purified by column chromatography [silica gel, n-hexane/ethyl acetate] to thereby give the compound 105 (723.4 mg, 87.0%) as a colorless oil.

Compound 106:

To a solution of the above compound 105 (106.2 mg, 0.35 mmol, 1.2 mol eq.) in acetonitrile (3 ml) were added (R)-(+)-(1-naphthyl)ethylamine (50 mg, 0.29 mmol) and potassium carbonate (48.4 mg, 0.35 mmol, 1.2 mol eq.) and the resulting mixture was stirred under heating at an outer temperature of 60° C. for 6 hours.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The residue thus obtained was purified by column chromatography [silica gel, ethyl acetate/n-hexane] to thereby give 33.7 mg (76.1%) of the compound 106 as a colorless oil.

MS m/z: 393(M$^+$). $^1$H-NMR δ: 1.47(3H, d, J=6.1 Hz, CH$_3$), 1.70–1.76(2H, m, CH$_2$), 2.60–2.71(2H, m, CH$_2$), 3.26(2H, t, J=6.1 Hz, CH$_2$), 4.61(1H, q, J=6.7 Hz, CH), 5.59(1H, s, CH), 7.26(1H, t, J=7.3 Hz, Ar—H), 7.28(1H, t, J=7.3 Hz, Ar—H), 7.37(1H, d, J=7.3 Hz, Ar—H), 7.38(1H, t, J=7.3 Hz, Ar—H), 7.46(1H, t, J=7.3 Hz, Ar—H), 7.48(1H, t, J=7.3 Hz, Ar—H), 7.49(1H, t, J=7.9 Hz, Ar—H), 7.53(1H, d, J=7.3 Hz, Ar—H), 7.54(1H, d, J=7.3 Hz, Ar—H), 7.63 (1H, d, J=6.7 Hz, Ar—H), 7.66(2H, d, J=7.9 Hz, Ar—H), 7.75(1H, d, J=8.5 Hz, Ar—H), 7.88(1H, d, J=7.9 Hz, Ar—H), 8.20(1H, d, J=8.5 Hz, Ar—H).

Example 39

Synthesis of Compound 109

Compound 108:

To a solution of 2-hydroxybenzofuran 107 (500 mg, 2.71 mmol) in acetonitrile (5 ml) were added 1,3-dibromopropane (0.55 ml, d=1.989, 5.43 mmol, 2.0 mol eq.) and potassium carbonate (750.1 mg, 5.43 mmol, 2.0 mol eq.) and the resulting mixture was stirred at an outer temperature of 60° C. for 4 hours.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The residue thus obtained was purified by column chromatography [silica gel, ethyl acetate/n-hexane] to thereby give 804.3 mg (77.0%) of the compound 108 as colorless prisms.

Compound 109:

To a solution of the above compound 108 (106.9 mg, 0.35 mmol, 1.2 mol eq.) in acetonitrile (3 ml) were added (R)-(+)-1-(1-naphthyl)ethylamine (50 mg, 0.29 mmol) and potassium carbonate (60.5 mg, 0.44 mmol, 1.5 mol eq.) and the resulting mixture was stirred under heating at an outer temperature of 60° C. for 6 hours.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The residue thus obtained was purified by column chromatography [silica gel, ethyl acetate/n-hexane] to thereby give 67.2 mg (58.3%) of the compound 109 as a colorless oil.

MS m/z: 395($M^+$). $^1$H-NMR δ: 1.53(3H, d, J=6.7 Hz, C$H_3$), 2.02–2.07 (2H, m, C$H_2$), 2.78–2.89(2H, m, C$H_2$), 4.13–4.16(2H, m, C$H_2$), 4.69(1H, q, J=6.7 Hz, CH), 7.00 (1H, dd, J=2.4, 8.6 Hz, Ar—H), 7.33(1H, t, J=7.3 Hz, Ar—H), 7.38(1H, d, J=2.4 Hz, Ar—H), 7.44–7.51(6H, m, Ar—H), 7.67(1H, d, J=7.3 Hz, Ar—H), 7.75(1H, d, J=7.9 Hz, Ar—H), 7.87(1H, dd, J=2.4, 9.7H, Ar—H), 7.89(1H, d, J=7.9 Hz, Ar—H), 8.22(1H, d, J=8.6 Hz, Ar—H).

Example 40

Synthesis of Compound 112

Compound 111:

To a solution of 5-hydroxyindole 110 (500 mg, 3.76 mmol) in acetonitrile (5 ml) were added 1,3-dibromopropane (833.9 mg, d=1.989, 4.13 mmol, 1.1 mol eq.) and potassium carbonate (570.9 mg, 4.13 mmol, 1.1 mol eq.) and the resulting mixture was stirred under heating at an outer temperature of 60° C. for 4 hours.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The residue thus obtained was purified by column chromatography [silica gel, ethyl acetate/n-hexane] to thereby give 586 mg (61.4%) of the compound 111 as a colorless oil.

$^1$H-NMR δ: 1.70(3H, d, J=6.7 Hz, C$H_2$), 3.63(2H, t, J=6.7 Hz, C$H_2$), 4.13J=6.7 Hz, C$H_2$), 6.47(1H, t, J=2.4 Hz, Ar—H), 6.85(1H, dd, J=2.4, 9.2 Hz, Ar—H), 7.12(1H, d, J=2.4 Hz, Ar—H), 7.17(1H, t, J=2.4 Hz, Ar—H), 7.26(1H, d, J=8.5 Hz, Ar—H), 8.03(1H, s, NH).

Compound 112:

To a solution of the above compound 111 (65.3 mg, 0.26 mmol, 1.5 mol eq.) in acetonitrile (3 ml) were added (R)-(+)-1-(1-naphthyl)ethylamine (29.3 mg, 0.17 mmol) and potassium carbonate (35.5 mg, 0.26 mmol, 1.5 mol eq.) and the resulting mixture was stirred under heating at an outer temperature of 60° C. for 6 hours.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The residue thus obtained was purified by column chromatography [silica gel, ethyl acetate/n-hexane] to thereby give 36.5 mg (62.0%) of the compound 112 as a colorless oil.

MS m/z: 344($M^+$). $^1$H-NMR δ: 1.52(3H, d, J=6.1 Hz, C$H_3$), 1.99–2.04(2H, m C$H_2$), 2.76–2.86(2H, m, C$H_2$), 4.05–4.12(2H, m, C$H_2$), 4.67(1H, q, J=6.1 Hz, CH), 6.47 (1H, s, Ar—H), 6.83(1H, dd, J=2.4, 8.6 Hz, Ar—H), 7.09 (1H, d, J=2.4 Hz, Ar—H), 7.17(1H, t, J=2.4 Hz, Ar—H), 7.26(1H, d, J=9.2 Hz, Ar—H), 7.44–7.50(3H, m, Ar—H), 7.67(1H, d, J=7.3 Hz, Ar—H), 7.74(1H, d, J=8.5 Hz, Ar—H), 7.87(1H, dd, J=2.4, 6.7 Hz, Ar—H), 8.10(1H, s, NH), 8.20(1H, d, J=7.9 Hz, Ar—H).

Example 41

Synthesis of Compound 117

Compound 114:

To a solution of (R)-(+)-1-(1-naphthyl)ethylamine (600 mg, 3.5 mmol) in dichloromethane (5 ml) were added ethylmalonyl chloride 113 (580.3 mg, 3.85 mmol, 1.1 mol eq.) and triethylamine (0.59 ml, d=0.726, 3.85 mmol, 1.1 mol eq.) and the resulting mixture was stirred at room temperature for 2 hours.

After the completion of the reaction, the reaction mixture was poured into water and extracted with dichloromethane. The dichloromethane layer was washed successively with a 5% aqueous solution of hydrochloric acid, water and a saturated aqueous solution of sodium chloride. After drying over sodium sulfate, the solvent was distilled off under reduced pressure. The crystals thus obtained were purified by column chromatography [silica gel, ethyl acetate/n-hexane] to thereby give 662.9 mg (66.5%) of the compound 114 as colorless prisms.

$^1$H-NMR δ: 1.16(3H, t, J=7.3 Hz, C$H_2$C$H_3$), 1.60(3H, d, J=7.3 Hz, C$H_3$), 3.24(2H, dd, J=17.7, 26.3 Hz, C$H_2$), 4.07 (2H, q, J=7.3 Hz, C$H_2$C$H_3$), 5.89(1H, dt, J=7.3, 14.6 Hz, CH), 7.35(1H, d, J=7.9 Hz, NH), 7.38(1H, t, J=7.9 Hz), Ar—H, 7.44(1H, t, J=12.2 Hz, Ar—H), 7.46(1H, t, J=12.2 Hz, Ar—H), 7.72(1H, d, J=7.9 Hz, Ar—H), 7.79(1H, d, J=7.9 Hz, Ar—H), 8.03(1H, d, J=7.9 Hz, Ar—H).

Compound 115:

To a solution of the above compound 114 (662.5 mg, 2.32 mmol) in ethanol (5 ml) was added a 10% aqueous solution of sodium hydroxide (1 ml) and the resulting mixture was stirred under heating at an outer temperature of 80° C. for 1 hour.

After the completion of the reaction, the reaction mixture was concentrated, acidified with a 5% aqueous solution of hydrochloric acid, poured into water and extracted with ethyl acetate. The ethyl acetate layer was washed successively with a 5% aqueous solution of hydrochloric acid, water and a saturated aqueous solution of sodium chloride. After drying over sodium sulfate, the solvent was distilled off under reduced pressure. The crystals thus obtained were purified by column chromatography [silica gel, ethyl acetate/n-hexane] to thereby give 659.5 mg of the compound 115 as colorless prisms.

$^1$H-NMR δ: 1.66(3H, d, J=6.7 Hz, C$H_3$), 3.20(2H, dd, J=18.3, 29.9 Hz, C$H_2$), 5.91(1H, dt, J=6.7, 14.7 Hz, CH), 6.99(1H, d, J=7.3 Hz, NH), 7.43(1H, t, J=7.9 Hz, Ar—H), 7.48(1H, d, J=7.9 Hz, Ar—H), 7.53(1H, dt, J=1.2, 6.7 Hz, Ar—H), 7.77(1H, d, J=8.5 Hz, Ar—H), 7.83(1H, d, J=7.9 Hz, Ar—H), 8.00(1H, d, J=8.5 Hz, Ar—H).

Compound 116:

To a solution of the above compound 115 (50 mg, 0.19 mmol) in N,N-dimethylformamide (3 ml) were added (R)-(+)-1-(1-naphthyl)ethylamine (45.0 mg, 0.21 mmol, 1.1 mol eq.) and WSC HCl (44.9 mg, 0.23 mmol, 1.2 mol eq.) and the resulting mixture was stirred at room temperature for 1 hour.

After the completion of the reaction, the reaction mixture was poured into water and extracted with ethyl acetate. The ethyl acetate layer was washed with water and a saturated aqueous solution of sodium chloride. After drying over sodium sulfate, the solvent was distilled off under reduced pressure. The crystals thus obtained were purified by column chromatography [silica gel, ethyl acetate/n-hexane] to thereby give 61.6 mg (70.5%) of the compound 116 as colorless prisms.

$^1$H-NMR δ: 1.43(3H, d, J=6.7 Hz, CH$_2$CH$_3$), 1.72(3H, d, J=6.7 Hz, CH$_3$), 3.38(2H, d, J=2.5 Hz, CH$_2$), 4.36(2H, q, J=6.7 Hz, CH$_2$CH$_3$), 5.32–6.01(1 H, m, CH), 6.88(1H, d, J=9.2 Hz, Ar—H), 7.21(1H, t, J=6.7 Hz, Ar—H), 7.33(1H, d, J=8.6 Hz, Ar—H), 7.40(1H, d, J=7.9 Hz, Ar—H), 7.44–7.56(5H, m, Ar—H), 7.80(1H, d, J=7.9 Hz, Ar—H), 7.88(1H, d, J=9.2 Hz, Ar—H), 8.06(1H, d, J=7.9 Hz, Ar—H), 8.11(1H, d, J=8.5 Hz, Ar—H), 8.29(1H, d, J=1.8 Hz, Ar—H).

Compound 117:

To a solution of the above compound 116 (50 mg, 0.11 mol) in tetrahydrofuran (3 ml) was added a 1 M solution of borane-tetrahydrofuran (0.24 ml, 0.24 mmol, 2.2 mol eq.) under ice-cooling. Then the temperature was elevated to room temperature and the mixture was stirred for 6 hours.

After the completion of the reaction, water was poured into the reaction mixture. Then the mixture was acidified with a 5% aqueous solution of hydrochloric acid and extracted with ethyl acetate. The layer of the 5% aqueous solution of hydrochloric acid was made alkaline by adding a 5% aqueous solution of sodium hydroxide and then extracted with ethyl acetate. After washing with water and a saturated aqueous solution of sodium chloride and drying over sodium sulfate, the solvent was distilled off under reduced pressure. The crystals thus obtained were purified by column chromatography [silica gel, ethyl acetate/n-hexane] to thereby give 18.0 mg (88.0%) of the compound 117 as a colorless oil.

MS m/z: 421(M$^+$). $^1$H-NMR δ: 1.38(3H, d, J=7.3 Hz, CH$_2$CH$_3$), 1.56(3H, d J=6.7 Hz, CH$_3$), 1.90(2H, m, CH$_2$), 2.75(1H, m, CH$_2$), 2.81(2H, m, CH$_2$), 3.29(2H, t, J=6.7 Hz, CH$_2$), 4.29(2H, q, J=7.3 Hz, CH$_2$CH$_3$), 4.79(1H, q, J=6.1 Hz, CH), 6.81(1H, dd, J=1.8, 8.6 Hz, Ar—H), 7.13(1H, t, J=7.3 Hz, Ar—H), 7.20(1H, d, J=8.6 Hz, Ar—H), 7.27(1H, d, J=1.8 Hz, Ar—H), 7.32(1H, d, J=7.9 Hz, Ar—H), 7.39 (1H, t, J=7.3 Hz, Ar—H), 7.46(3H, m, Ar—H), 7.65(1H, d, J=10.4 Hz, Ar—H), 7.75(1H, d, J=8.6 Hz, Ar—H), 7.86(1H, dd, J=2.4, 6.7 Hz, Ar—H), 7.98(1H, d, J=7.3 Hz, Ar—H), 8.16(1H, d, J=8.6 Hz, Ar—H).

Example 42

Synthesis of Compound 123

Compound 119:

2-Methoxycarbonylthiophenol 118 (9.7 g) was dissolved in N,N-dimethylformamide (200 ml) and sodium hydride (60%) (2.7 g) was added thereto at 0° C. When foaming was ceased, (±)-2-tert-butoxycarbonylamino-1-methanesulfonyloxy-2-phenylethane (20.0 g) was added thereto and the resulting mixture was stirred at room temperature for 12 hours.

After the completion of the reaction, ammonium chloride was added thereto in excess and the reaction. mixture was extracted with ethyl acetate. The extract was washed with a saturated aqueous solution of sodium chloride and dried over sodium sulfate. After distilling off the solvent under reduced pressure, the crystals thus obtained were purified by column chromatography [silica gel, ethyl acetate/n-hexane] to thereby give 16.0 g of the compound 119.

Compound 120:

The above compound 119 (1.9 g) was dissolved in diphenyl ether and p-toluenesulfonic acid hydrate (100 mg) was added thereto. The resulting mixture was heated at 250 to 260° C. for 40 minutes.

After cooling by allowing to stand, it was purified by column chromatography and eluted with ethyl acetate/n-hexane to thereby give 700 mg of the compound 120.

Compound 121:

The above compound 120 (150 g) was dissolved in tetrahydrofuran and lithium aluminum hydride (310 mg) was added thereto. The resulting mixture was then heated under reflux for 5 hours.

After the completion of the reaction, sodium sulfate decahydrate was added in excess thereto and the mixture was filtered through celite. The filtrate was concentrated and thus 330 mg of the compound 121 was obtained.

Compound 122:

The above compound 121 (3.0 g) and triethylamine (1.5 g) were dissolved in tetrahydrofuran and acryloyl chloride (1.2 g) was added thereto under ice-cooling. After stirring the mixture at room temperature for 30 minutes, a saturated aqueous solution of sodium hydrogen carbonate was added thereto followed by extraction with chloroform. The extract was washed with a saturated aqueous solution of sodium chloride and dried over sodium sulfate. After distilling off the solvent under reduced pressure, the obtained residue was purified by column chromatography [silica gel, ethyl acetate/n-hexane] to thereby give 1.5 g of the compound 122.

Compound 123:

The above compound 122 (150 mg, 0.51 mmol) and (R)-(+)-1-(1-naphthyl)ethylamine (104.5 mg, 0.61 mmol, 1.2 mol eq.) were dissolved in chloroform/methanol (3 ml) and then allowed to stand at room temperature for 1 week.

After the completion of the reaction, the solvent was distilled off under reduced pressure. The oil thus obtained was purified by column chromatography [silica gel, chloroform/methanol] to thereby give 167.4 mg (70.7%) of the compound 123 as a colorless oil.

MS m/z: 466(M$^+$). $^1$H-NMR δ: 1.46(3H, q, J=6.7 Hz, CH$_3$), 2.33–2.36(1H, m, CH$_2$), 2.79–2.93(3H, m, CH$_2$), 3.25–3.38(1H, m, CH$_2$), 3.57–3.65(1 H, m, CH$_2$), 4.41–4.45 (1H, m, CH$_2$), 4.56–4.65(2H, m, CH$_2$), 6.30–6.34(1H, m, CH), 7.07–7.17(3H, m, Ar—H), 7.27–7.51(9H, m, Ar—H), 7.63(1H, t, J=4.9 Hz, Ar—H), 7.73(1H, t, J=8.5 Hz, Ar—H), 7.84–7.87(1H, m, Ar—H), 8.11–8.19(1H, m, Ar—H).

Example 43

Synthesis of K-2003

4-Bromophenol (520 mg, 3.01 mmol) was dissolved in acetonitrile (11 ml) and then potassium carbonate (1.243 g, 8.99 mmol) and 1,3-dibromopropane (0.37 ml, 3.64 mmol) were successively added thereto at room temperature. The resulting mixture was stirred under heat-reflux at 95° C. for 4 hours. After confirming the completion of the reaction by TLC, potassium carbonate (800 mg, 5.79 mmol) and (R)-(+)-3-methoxy-α-methylbenzylamine (450 mg, 2.98 mmol) were added at room temperature to the reaction system and the resulting mixture was stirred at 95° C. for additional 18 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=100:1) to thereby give 364 mg (1.00 mmol) of the compound K-2003 as a pale yellow syrup at a yield of 33%.

500 MHz NMR 7.22(1H, dd, J=8.3 Hz, J=8.3 Hz), 7.34 (2H, dd, J=8.3 Hz, J=8.3 Hz), 6.87–6.88(1H, m), 6.87(1H, s), 6.76–6.78(1H, m), 6.74(2H, dd, J=8.3 Hz, J=2.0 Hz), 3.93–4.00(2H, m), 3.79(3H, s), 3.74(1H, q, J=6.5 Hz), 2.58–2.71(2H, m), 1.88–1.95(2H, m), 1.53(1H, m), 1.34(3H, d, J=6.5 Hz), m/z=363, 365.

Example 44

Synthesis of K-2004

4-Bromophenol (570 mg, 3.29 mmol) was dissolved in acetonitrile (11 ml) and then potassium carbonate (1.08 g, 7.81 mmol) and 1,4-dibromobutane (0.44 ml, 3.68 mmol) were successively added thereto at room temperature. The resulting mixture was stirred under heat-reflux at 95° C. for 4 hours. After confirming the completion of the reaction by TLC, potassium carbonate (455 mg, 3.29 mmol) and (R)-(+)-3-methoxy-α-methylbenzylamine (400 mg, 2.64 mmol) were added at room temperature to the reaction system and the resulting mixture was stirred at 95° C. for additional 18 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=100:1) to thereby give 422 mg (1.11 mmol) of the compound K-2004 as a pale yellow syrup at a yield of 43%.

500 MHz NMR 7.34(2H, d, J=9.0 Hz), 7.23(1H, dd, J=8.3 Hz, J=8.3 Hz), 6.77–6.88(3H, m), 6.73(2H, d, J=6.5 Hz), 3.86(2H, t, J=6.5 Hz), 3.80(3H, s), 3.72(1H, q, J=7.0 Hz), 2.46–2.59(2H, m), 1.73–1.83(2H, m), 1.56–1.67(2H, m),1.51(1H, s), 1.34(3H, d, J=7.0 Hz), m/z=377, 379.

Example 45

Synthesis of K-2005

4-Bromophenol (710 mg, 4.10 mmol) was dissolved in acetonitrile (11 ml) and then potassium carbonate (710 mg, 5.14 mmol) and 1,5-dibromopentane (0.44 ml, 4.55 mmol) were successively added thereto at room temperature. The resulting mixture was stirred under heat-reflux at 95° C. for 4 hours. After confirming the completion of the reaction by TLC, potassium carbonate (455 mg, 3.29 mmol) and (R)-(+)-3-methoxy-α-methylbenzylamine (370 mg, 2.45 mmol) were added at room temperature to the reaction system and the resulting mixture was stirred at 95° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=100:1) to thereby give 295 mg (0.75 mmol) of the compound K-2005 as a pale yellow syrup at a yield of 31%.

500 MHz NMR 7.34(2H, d, J=7.0 Hz), 7.23(1H, dd, J=8.5 Hz, J=8.5 Hz), 6.87–6.89(2H, m), 6.77(1H, dd, J=8.5 Hz, J=1.5 Hz), 6.74(2H, d, J=8.5 Hz), 3.88(2H, t, J=6.3 Hz), 3.80(3H, m), 3.72(1H, q, J=6.5 Hz), 2.36–2.55(4H, m), 1.55–1.77(2H, m), 1.43–1.57(2H, m), 1.34(3H, d, J=6.5 Hz), m/z=391, 393.

Example 46

Synthesis of K-2006

4-Bromophenol (500 mg, 2.89 mmol) was dissolved in acetonitrile (10 ml) and then potassium carbonate (540 mg, 3.90 mmol) and 1,6-dibromohexane (0.49 ml, 3.18 mmol) were successively added thereto at room temperature. The resulting mixture was stirred under heat-reflux at 95° C. for 4 hours. After confirming the completion of the reaction by TLC, potassium carbonate (400 mg, 2.89 mmol) and (R)-(+)-3-methoxy-α-methylbenzylamine (270 mg, 1.79 mmol) were added at room temperature to the reaction system and the resulting mixture was stirred at 95° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=100:1) to thereby give 364 mg (0.896 mmol) of the compound K-2006 as a pale yellow syrup at a yield of 50%.

500 MHz NMR 7.34(2H, d, J=8.0 Hz), 7.23(1H, dd, J=8.0 Hz, J=8.0 Hz), 6.88–6.89(1H, m), 6.88(1H, s), 6.78(1H, dd, J=8.0 Hz, J=3.0 Hz), 6.75(2H, d, J=8.0 Hz), 3.88(2H, t, J=6.3 Hz), 3.81(3H, s), 3.73(1H, q, J=7.0 Hz), 2.41–2.53 (2H, m), 1.71–1.77(2H, m), 1.35–1.52(7H, m), 1.34(3H, d, J=7.0 Hz), m/z=405, 407.

Example 47

Synthesis of K-2007

4-Bromophenol (490 mg, 2.83 mm ol) was dissolved in acetonitrile (10 ml) and then potassium carbonate (495 mg, 3.58 mmol) and 1,7-dibromoheptane (0.53 ml, 3.10 mmol) were successively added thereto at room temperature. The resulting mixture was stirred under heat-reflux at 95° C. for 4 hours. After confirming the completion of the reaction by TLC, potassium carbonate (400 mg, 2.89 mmol) and (R)-(+)-3-methoxy-α-methylbenzylamine (300 mg, 1.98 mmol) were added at room temperature to the reaction system and the resulting mixture was stirred at 95° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=100:1) to thereby give 150 mg (0.36 mmol) of the compound K-2007 as a pale yellow syrup at a yield of 18%.

500 MHz NMR 7.34(2H, d, J=8.5 Hz), 7.24(1H, dd, J=7.8 Hz, J=7.8 Hz), 6.90–6.93(2H, m), 6.79(1H, dd, J=7.8 Hz, J=1.8 Hz), 6.75(2H, d, J=8.5 Hz), 3.88(2H, t, J=6.3 Hz), 3.82(3H, s), 3.79–3.80(1H, m), 2.43–2.54(2H, m), 1.70–1.84(2H, m), 1.20–1.56(9H, m), 1.41(3H, d, J=6.5 Hz), m/z=419, 421.

Example 48

Synthesis of K-2010

3-Trifluoromethylthiophenol (615 mg, 3.45 mmol) was dissolved in acetonitrile (12 ml) and then potassium carbonate (467 mg, 3.38 mmol) and 1,4-dibromobutane (0.46 ml, 3.85 mmol) were successively added thereto at room temperature. The resulting mixture was stirred at the same temperature for 5 hours. After confirming the completion of the reaction by TLC, potassium carbonate (210 mg, 1.52 mmol) and (R)-(+)-3-methoxy-α-methylbenzylamine (360 mg, 2.38 mmol) were added at room temperature to the reaction system and the resulting mixture was stirred at 95° C. for additional 18 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 180 mg (0.47 mmol) of the compound K-2010 as a pale yellow syrup at a yield of 20%.

500 MHz NMR 7.51(1H, s), 7.35–7.44(3H, m), 7.23(1H, dd, J=8.0 HZ, J=8.0 Hz), 6.86–6.88(2H, m), 6.76–6.78(1H, m), 3.80(3H, s), 3.71(1H, q, J=6.5 Hz), 2.93(2H, t, J=7.5 Hz), 2.50–2.55(1H, m), 2.42–2.47(1H, m), 1.55–1.71(4H, m), 1.45(1H, s), 1.33(3H, d, J=6.5 Hz), m/z=383.

Example 49

Synthesis of K-2011

3-Trifluoromethylthiophenol (600 mg, 3.37 mmol) was dissolved in acetonitrile (12 ml) and then potassium carbonate (540 mg, 3.96 mmol) and 1,5-dibrornopentane (0.50 ml, 3.67 mmol) were successively added thereto at room temperature. The resulting mixture was stirred at the same temperature for 5 hours. After confirming the completion of the reaction by TLC, potassium carbonate (240 mg, 1.74 mmol) and (R)-(+)-3-methoxy-α-methylbenzylamine (300 mg, 1.98 mmol) were added at room temperature to the reaction system and the resulting mixture was stirred at 95° C. for additional 18 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 220 mg (0.55 mmol) of the compound K-2011 as a pale yellow syrup at a yield of 28%.

500 MHz NMR 7.51(1H, s), 7.45–7.44(1H, m), 7.35–7.40 (2H, m), 7.23(1H, dd, J=8.0 Hz, J=8.0 Hz), 6.86–6.88(2H, m), 6.76–6.79(1H, m), 3.81(3H, s), 3.71 (1H, q, J=6.5 Hz), 2.93(2H, t, J=7.3 Hz), 2.47–2.52(1H, m), 2.40–2.45(1H, m), 1.61–1.67(2H, m), 1.41–1.52(5H, m), 1.34(3H, d, J=6.5 Hz), m/z=397.

Example 50

Synthesis of K-2012

3-Trifluoromethylthiophenol (515 mg, 2.89 mmol) was dissolved in acetonitrile (10 ml) and then potassium carbonate (440 mg, 3.18 mmol) and 1,6-dibromohexane (0.45 ml, 2.93 mmol) were successively added thereto at room temperature. The resulting mixture was stirred at the same temperature for 5 hours. After confirming the completion of the reaction by TLC, potassium carbonate (270 mg, 1.95 mmol) and (R)-(+)-3-methoxy-α-methylbenzylamine (260 mg, 1.72 mmol) were added at room temperature to the reaction system and the resulting mixture was stirred at 95° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 272 mg (0.66 mmol) of the compound K-2012 as a pale yellow syrup at a yield of 38%.

500 MHz NMR 7.51(1H, s), 7.43–7.45(1H, m), 7.35–7.40 (2H, m), 7.23(1H, dd, J=7.5 Hz, J=7.5 Hz), 6.87–6.89(2H, m), 6.76–6.79(1H, m), 3.81(3H, s), 3.71 (1H, q, J=6.5 Hz), 2.93(2H, t, J=7.5 Hz), 2.46–2.51(1H, m), 2.40–2.44(1H, m), 1.61–1.67(2H, m), 1.38–1.50(7H, m), 1.34(3H, d, J=6.5 Hz), m/z=411.

Example 51

Synthesis of K-2015

2-Bromobenzenethiol (445 mg, 2.35 mmol) was dissolved in acetonitrile (10 ml) and then potassium carbonate (420 mg, 3.04 mmol) and 1-bromo-2-chloroethane (0.22 ml, 2.64 mmol) were successively added thereto at room temperature. The resulting mixture was stirred at the same temperature for 4 hours. After confirming the completion of the reaction by TLC, potassium carbonate (315 mg, 2.28 mmol) and (R)-(+)-3-methoxy-α-methylbenzylamine (250 mg, 1.65 mmol) were added at room temperature to the reaction system and the resulting mixture was stirred at 95° C. for additional 120 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 207 mg (0.57 mmol) of the compound K-2015 as a pale yellow syrup at a yield of 34%.

500 MHz NMR 7.53(1H, d, J=8.0 Hz), 7.18–7.26(4H, m), 6.87–6.88(2H, m), 6.78–6.81(1H, m), 3.81(3H, s), 3.04(2H, t, J=7.0 Hz), 3.76(1H, q, J=6.5 Hz), 2.67–2.81(2H, m), 1.73(1H, s), 1.35(3H, d, J=6.5 Hz), m/z=365, 367.

Example 52

Synthesis of K-2016

2-Bromobenzenethiol (517 mg, 2.73 mmol) was dissolved in acetonitrile (10 ml) and then potassium carbonate (475 mg, 3.44 mmol) and 1,3-dibromopropane (0.31 ml, 3.05 mmol) were successively added thereto at room temperature. The resulting mixture was stirred at the same temperature for 4 hours. After confirming the completion of the reaction by TLC, potassium carbonate (352 mg, 2.76 mmol) and (R)-(+)-3-methoxy-α-methylbenzylamine (250 mg, 1.65 mmol) were added at room temperature to the reaction system and the resulting mixture was stirred at 100° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 249 mg (0.66 mmol) of the compound K-2016 as a pale yellow syrup at a yield of 40%.

500 MHz NMR 7.52(1H, d, J=7.5 Hz), 7.22–7.26(3H, m), 7.00(1H, ddd, J=7.5 Hz, J=7.5 Hz, J=2.0 Hz), 6.88(1H, d, J=7.5 Hz), 6.87(1H, s), 6.77(1H, dd, J=7.5 Hz, J=2.0 Hz), 3.81(3H, s), 3.73(1H, q, J=7.0 Hz), 2.90–3.02(2H, m), 2.55–2.69(2H, m), 1.80–1.86(2H, m), 1.46(1H, s), 1.34(3H, d, J=7.0 Hz), m/z=379, 3.81.

Example 53

Synthesis of K-2017

2-Bromobenzenethiol (505 mg, 2.67 mmol) was dissolved in acetonitrile (10 ml) and then potassium carbonate (445 mg, 3.22 mmol) and 1,4-dibromobutane (0.35 ml, 2.93 mmol) were successively added thereto at room temperature. The resulting mixture was stirred at the same temperature for 4 hours. After confirming the completion of the reaction by TLC, potassium carbonate (330 mg, 2.39 mmol) and (R)-(+)-3-methoxy-α-methylbenzylamine (250 mg, 1.65 mmol) were added at room temperature to the reaction system and the resulting mixture was stirred at 95° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 311 mg (0.79 mmol) of the compound K-2017 as a pale yellow syrup at a yield of 48%.

500 MHz NMR 7.52(1H, d, J=8.0 Hz), 7.19–7.25(3H, m), 7.00(1H, ddd, J=8.0 Hz, 8.0 Hz, J=2.0 Hz), 6.87–6.88(2H, m), 6.78(1H, dd, J=2.0 Hz, J=8.0 Hz), 3.80(3H, s), 3.72(1H, q, J=6.5 Hz), 2.90(2H, t, J=7.5 Hz), 2.43–2.56(2H, m), 1.68–1.73(2H, m), 1.68–1.73(2H, m), 1.58–1.67(2H, m), 1.47(1H, s), 1.34(3H, d, J=6.5 Hz), m/z=393, 395.

Example 54

Synthesis of K-2018

2-Bromobenzenethiol (445 mg, 2.35 mmol) was dissolved in acetonitrile (10 ml) and then potassium carbonate (407 mg, 2.95 mmol) and 1,5-dibromopentene (0.31 ml, 2.60 mmol) were successively added thereto at room temperature. The resulting mixture was stirred at the same temperature for 4 hours. After confirming the completion of the reaction by TLC, potassium carbonate (330 mg, 2.39 mmol) and (R)-(+)-3-methoxy-α-methylbenzylamine (220 mg, 1.46 mmol) were added at room temperature to the reaction system and the resulting mixture was stirred at 95° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 307 mg (0.75 mmol) of the compound K-2018 as a pale yellow syrup at a yield of 52%.

500 MHz NMR 7.52(1H, d, J=6.5 Hz), 7.18–7.25(3H, m), 6.99(1H, dd, J=7.5 Hz, J=7.5 Hz), 6.87–6.89(2H, m), 6.78 (1H, dd, J=7.5 Hz, J=2.0 Hz), 3.81(3H, s), 3.72(1H, q, J=6.5 Hz), 2.90(2H, q, J=7.5 Hz), 2.41–2.51(2H, m), 1.65–1.69 (2H, m), 1.44–1.53(5H, m), 1.34(3H, d, J=6.5 Hz), m/z=409.

Example 55

Synthesis of K-2027 (N-{5-[(4-chlorophenyl)thio] pentyl}-N-[(1R)-1-(1-naphthyl)ethyl]amine)

4-Chlorobenzenethiol (550 mg, 3.80 mmol) was dissolved in acetonitrile (6.0 ml) and then potassium carbonate (520 mg, 3.76 mmol) and 1,5-dibromopentane (0.52 ml, 3.82 mmol) were successively added thereto at room temperature. The resulting mixture was stirred at the same temperature for 1 hour. After confirming the completion of the reaction by TLC, potassium carbonate (241 mg, 1.74 mmol) and (R)-(+)-1-(1-naphthyl)ethylamine (0.31 ml, 1.92 mmol) were added at room temperature to the reaction system and the resulting mixture was stirred at 95° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic esidue was purified by silica gel column chromatography (chloroform:methanol=150:1) to thereby give 288 mg (0.75 mmol) of the compound K-2027 as a pale yellow syrup at a yield of 40%.

500 MHz NMR 8.17(1H, d, J=8.0 Hz), 7.87(1H, d, J=7.5 Hz), 7.74(1H, d, J=9.0 Hz), 7.63(1H, d, J=9.0 Hz), 7.63(1H, d, J=7.5 Hz), 7.45–7.52(3H, m), 7.19–7.23(4H, m), 4.61(1H, q, J=6.5 Hz), 2.85(2H, t, J=7.2 Hz), 2.50–2.61(2H, m), 1.41–1.63(7H, m), 1.48(3H, d, J=6.5 Hz), m/z=383.

Example 56

Synthesis of K-2030

3-Chlorophenol (420 mg, 3.27 mmol) was dissolved in acetonitrile (9.0 ml) and then potassium carbonate (1.19 g, 8.61 mmol) and 1-bromo-2-chloroethane (0.41 ml, 4.93 mmol) were successively added thereto at room temperature. The resulting mixture was stirred at 70° C. for 24 hours. After confirming the completion of the reaction by TLC, potassium carbonate (1.70 g, 12.3 mmol) and (R)-(+)-1-(1-naphthyl)ethylamine (0.45 ml, 2.79 mmol) were added at room temperature to the reaction system and the resulting mixture was stirred at 100° C. for additional 120 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 321 mg (0.99 mmol) of the compound K-2030 as a pale yellow syrup at a yield of 35%.

500 MHz NMR 8.21(1H, d, J=8.5 Hz), 7.87(1H, d, J=7.5 Hz), 7.75(1H, d, J=8.0 Hz), 7.69(1H, d, J=8.0 Hz), 7.46–7.53(3H, m), 7.18(1H, dd, J=8.0 Hz), 6.89–3.93(2H, m), 6.76–6.78(1H, dd, J=1.5 Hz, J=8.0 Hz), 4.71(1H, q, J=6.5 Hz), 4.04(2H, t, J=5.3 Hz), 2.90–3.00(2H, m), 1.78 (1H, s), 1.53(3H, d, J=6.5 Hz), m/z=325.

Example 57

Synthesis of K-2033

4-Nitrobenzenethiol (470 mg, 3.03 mmol) was dissolved in acetonitrile (7.0 ml) and then potassium carbonate (450 mg, 3.26 mmol) and 1,4-dibromobutane (0.36 ml, 3.01 mmol) were successively added thereto at room temperature. The resulting mixture was stirred at the same temperature for 3 hours. After confirming the completion of the reaction by TLC, potassium carbonate (250 mg, 1.81 mmol) and (R)-(+)-3-methoxy-α-methylbenzylamine (250 mg, 1.65 mmol) were added at room temperature to the reaction system and the resulting mixture was stirred at 100° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 206 mg (0.57 mmol) of the compound K-2033 as a yellow syrup at a yield of 35%.

500 MHz NMR 8.11(2H, d, J=9.0 Hz), 7.29(2H, d, J=9.0 Hz), 7.24(1H, dd, J=8.0 Hz, J=8.0 Hz), 6.88(1H, d, J=8.0 Hz), 6.87(1H, s), 6.79(1H, dd, J=8.0 Hz, J=2.5 Hz), 3.81(3H, s), 3.72(1H, q, J=6.5 Hz), 2.99(2H, t, J=7.5 Hz), 2.44–2.60 (2H, m), 1.71–1.76(2H, m), 1.60–1.66(3H, m), 1.35(3H, d, J=6.5 Hz), m/z=360.

Example 58

Synthesis of K-2034

4-Nitrobenzenethiol (520 mg, 3.35 mmol) was dissolved in acetonitrile (7.0 ml) and then potassium carbonate (492 mg, 3.56 mmol) and 1,5-dibromopentane (0.46 ml, 3.38 mmol) were successively added thereto at room temperature. The resulting mixture was stirred at the same temperature for 3 hours. After confirming the completion of the reaction by TLC, potassium carbonate (300 mg, 2.17 mmol) and (R)-(+)-3-methoxy-α-methylbenzylamine (300 mg, 1.98 mmol) were added at room temperature to the reaction system and the resulting mixture was stirred at 100° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 102 mg (0.27 mmol) of the compound K-2034 as a yellow syrup at a yield of 14%.

500 MHz NMR 8.11(2H, d, J=9.5 Hz), 7.28(2H, d, J=9.5 Hz), 7.24(1H, dd, J=7.8 Hz, J=7.8 Hz), 6.87–6.89(2H, m), 6.77–6.79(1H, m), 3.81(3H, s), 3.72(1H, q, J=6.5 Hz), 2.99(2H, q, J=7.5 Hz), 2.49–2.52(1H, m), 2.41–2.45(1H, m), 1.67–1.72(2H, m), 1.45–1.53(5H, m), 1.35(3H, d, J=6.5 Hz), m/z=374.

Example 59

Synthesis of K-2035

4-Nitrobenzenethiol (460 mg, 2.96 mmol) was dissolved in acetonitrile (7.0 ml) and then potassium carbonate (432 mg, 3.13 mmol) and 1,6-dibromohexane (0.46 ml, 2.99 mmol) were successively added thereto at room temperature. The resulting mixture was stirred at the same temperature for 3 hours. After confirming the completion of the reaction by TLC, potassium carbonate (120 mg, 0.86 mmol) and (R)-(+)-3-methoxy-α-methylbenzylamine (230 mg, 1.52 mmol) were added at room temperature to the reaction system and the resulting mixture was stirred at 100° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 133 mg (0.342 mmol) of the compound K-2035 as a yellow syrup at a yield of 23 %.

500 MHz NMR 8.12(2H, d, J=9.0 Hz), 7.29(2H, d, J=9.0 Hz), 7.24(1H, dd, J=8.0 Hz), 6.88(1H, d, J=8.0 Hz), 6.88 (1H, s), 6.77–6.79(1H, m), 3.81(3H, s), 3.73(1H, q, J=6.5 Hz), 2.99(2H, t, J=7.5 Hz), 2.40–2.53(2H, m), 1.67–1.73 (2H, m), 1.41–1.50(5H, m), 1.25–1.36(2H, m), 1.35(3H, d, J=6.5 Hz), m/z=388.

Example 60

Synthesis of K-2040

4-Fluorobenzenethiol (520 mg, 4.06 mmol) was dissolved in acetonitrile (10.0 ml) and then potassium carbonate (864 mg, 6.26 mmol) and 1,4-dibromobutane (0.49 ml, 4.12 mmol) were successively added thereto at room temperature. The resulting mixture was stirred at the same temperature for 10 hours. After confirming the completion of the reaction by TLC, potassium carbonate (320 mg, 2.32 mmol)

and (R)-(+)-3-methoxy-α-methylbenzylamine (310 mg, 2.05 mmol) were added at room temperature to the reaction system and the resulting mixture was stirred at 100° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 170 mg (0.51 mmol) of the compound K-2040 as a pale yellow syrup at a yield of 25%.

500 MHz NMR 7.28–7.32(2H, m), 7.23(1H, dd, J=8.3 Hz, J=8.3 Hz), 6.95–6.70(2H, m), 6.86–6.87(2H, m), 6.76–6.79(1H, m), 3.80(3H, s), 3.71(1H, q, J=6.5 Hz), 2.83(2H, dd, J=7.0 Hz, J=7.0 Hz), 2.47–2.52(1H, m), 2.39–2.44(1H, m), 1.52–1.64(5H, m), 1.33(3H, d, J=6.5 Hz), m/z=333.

Example 61

Synthesis of K-2041

4-Fluorobenzenethiol (590 mg, 4.61 mmol) was dissolved in acetonitrile (10.0 ml) and then potassium carbonate (340 mg, 2.46 mmol) and 1,5-dibromopentane (0.63 ml, 4.62 mmol) were successively added thereto at room temperature. The resulting mixture was stirred at the same temperature for 3 hours. After confirming the completion of the reaction by TLC, potassium carbonate (340 mg, 2.46 mmol) and (R)-(+)-3-methoxy-α-methylbenzylamine (350 mg, 2.31 mmol) were added at room temperature to the reaction system and the resulting mixture was stirred at 100° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 245 mg (0.71 mmol) of the compound K-2041 as a pale yellow syrup at a yield of 31%.

500 MHz NMR 7.29–7.32(2H, m), 7.23(1H, dd, J=8.0 Hz, J=8.0 Hz), 6.96–6.99(2H, m), 6.86–6.88(2H, m), 6.77–6.79(1H, m), 3.81(3H, s), 3.71(1H, q, J=7.0 Hz), 2.83(2H, t, J=7.2 Hz), 2.45–2.50(1 H, m), 2.38–2.43(1H, m), 1.54–1.60(2H, m), 1.38–1.48(3H, m), 1.34(3H, d, J=7.0 Hz), m/z=347.

Example 62

Synthesis of K-2045

3-Bromobenzenethiol (650 mg, 3.44 mmol) was dissolved in acetonitrile (10.0 ml) and then potassium carbonate (524 mg, 3.79 mmol) and 1-bromo-2-chloroethane (0.29 ml, 3.48 mmol) were successively added thereto at room temperature. The resulting mixture was stirred at the same temperature for 3 hours. After confirming the completion of the reaction by TLC, potassium carbonate (280 mg, 2.02 mmol) and (R)-(+)-3-methoxy-α-methylbenzylamine (420 mg, 2.78 mmol) were added at room temperature to the reaction system and the resulting mixture was stirred at 100° C. for additional 120 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=185:1) to thereby give 395 mg (1.23 mmol) of the compound K-2045 as a pale yellow syrup at a yield of 44%.

500 MHz NMR 7.43(1H, s), 7.28(1H, d, J=8.0 Hz), 7.22(1H, dd, J=8.0 Hz, J=8.0 Hz), 7.18(1H, d, J=8.0 Hz), 7.19(1H, dd, J=7.5 Hz, J=7.5 Hz), 6.87(1H, d, J=7.5 Hz), 6.86(1H, s), 6.77(1H, dd, J=7.5 Hz, J=1.5 Hz), 3.80(3H, s), 3.74(1H, q, J=6.5 Hz), 3.02(2H, t, J=6.5 Hz), 2.66–2.77(2H, m), 1.68(1H, s), 1.34(3H, d, J=6.5 Hz), m/z=365, 367.

Example 63

Synthesis of K-2046

3-Bromobenzenethiol (580 mg, 3.06 mmol) was dissolved in acetonitrile (9.0 ml) and then potassium carbonate (432 mg, 3.13 mmol) and 1,3-dibromopropane (0.31 ml, 3.05 mmol) were successively added thereto at room temperature. The resulting mixture was stirred at the same temperature for 5 hours. After confirming the completion of the reaction by TLC, potassium carbonate (280 mg, 2.02 mmol) and (R)-(+)-3-methoxy-α-methylbenzylamine (230 mg, 1.52 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 213 mg (0.56 mmol) of the compound K-2046 as a pale yellow syrup at a yield of 37%.

500 MHz NMR, 7.40–7.41(1H, m), 7.18–7.28(3H, m), 7.11(1H, dd, J=8.0 Hz, J=8.0 Hz), 6.86–6.88(2H, m), 6.76–6.79(1H, m), 3.80(3H, s), 3.72(1H, q, J=7.0 Hz), 2.88(2H, m), 2.49–2.54(1H, m), 2.41–2.46(1H, m), 1.54–1.69(2H, m), 1.34(3H, d, J=7.0 Hz), m/z=379, 381.

Example 64

Synthesis of K-2047

3-Bromobenzenethiol (470 mg, 2.49 mmol) was dissolved in acetonitrile (10.0 ml) and then potassium carbonate (347 mg, 2.51 mmol) and 1,4-dibromobutane (0.30 ml, 2.51 mmol) were successively added thereto at room temperature. The resulting mixture was stirred at the same temperature for 5 hours. After confirming the completion of the reaction by TLC, potassium carbonate (320 mg, 2.32 mmol) and (R)-(+)-3-methoxy-α-methylbenzylamine (200 mg, 1.32 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 185 mg (0.47 mmol) of the compound K-2047 as a pale yellow syrup at a yield of 36%.

500 MHz NMR 7.19–7.28(3H, m), 7.02–7.13(2H, m), 6.86–6.88(2H, m), 6.76–6.79(1H, m), 3.81(3H, s), 3.77(1H, q, J=6.5 Hz), 1.76–1.79(2H, m), 2.89–3.01(2H, m), 2.60–2.65(1H, m), 2.51–2.56(1H, m), 2.31–2.42(2H, m), 1.52(1H, s), 1.33(3H, d, J=6.5 Hz), m/z=393, 395.

Example 65

Synthesis of K-2048

3-Bromobenzenethiol (530 mg, 2.80 mmol) was dissolved in acetonitrile (10.0 ml) and then potassium carbonate (395 mg, 2.86 mmol) and 1,5-dibromopentane (0.38 ml, 2.78 mmol) were successively added thereto at room temperature. The resulting mixture was stirred at the same temperature for 2 hours. After confirming the completion of the reaction by TLC, potassium carbonate (213 mg, 1.54 mmol) and (R)-(+)-3-methoxy-α-methylbenzylamine (200 mg, 1.32 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 226 mg (0.55 mmol) of the compound K-2048 as a pale yellow syrup at a yield of 42%.

500 MHz NMR 7.41(1H, s), 7.18–7.28(3H, m), 7.11(1H, dd, J=7.5 Hz, J=7.5 Hz), 6.88(1H, d, J=7.5 Hz), 6.87(1H, s), 6.78(1H, dd, J=7.5 Hz, J=2.5 Hz), 3.81(3H, s), 3.72(1H, q, J=6.5 Hz), 2.89(2H, q, J=7.2 Hz), 2.47–2.51(1H, m), 2.40–2.43(1H, m), 1.62(2H, m), 1.40–1.50(5H, m), 1.234 (3H, d, J=6.5 Hz).

Example 66

Synthesis of K-2049

3-Bromobenzenethiol (600 mg, 3.17 mmol) was dissolved in acetonitrile (10.0 ml) and then potassium carbonate (500 mg, 3.62 mmol) and 1,6-dibromohexane (0.50 ml, 3.25 mmol) were successively added thereto at room temperature. The resulting mixture was stirred at the same temperature for 2 hours. After confirming the completion of the reaction by TLC, potassium carbonate (205 mg, 1.48 mmol) and (R)-(+)-3-methoxy-α-methylbenzylamine (250 mg, 1.66 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 267 mg (0.63 mmol) of the compound K-2049 as a pale yellow syrup at a yield of 38%.

500 MHz NMR 7.41(1H, dd, J=1.8 Hz, J=1.8 Hz), 7.19–7.27(3H, m), 7.11(1H, dd, J=8.0 Hz, J=8.0 Hz), 6.87–6.89(2H, m), 6.77(1H, dd, J=8.0 Hz, J=2.5 Hz), 3.81 (3H, s), 3.72(1H, t, J=6.5 Hz), 2.88(2H, t, J=7.8 Hz), 2.39–2.51(2H, m), 1.50–1.65(2H, m), 1.25–1.49(7H, m), 1.34(3H, d, J=6.5 Hz).

Example 67

Synthesis of K-2050

3-Bromobenzenethiol (525 mg, 2.78 mmol) was dissolved in acetonitrile (10.0 ml) and then potassium carbonate (325 mg, 2.36 mmol) and 1,7-dibromoheptane (0.47 ml, 2.75 mmol) were successively added thereto at room temperature. The resulting mixture was stirred at the same temperature for 1 hour. After confirming the completion of the reaction by TLC, potassium carbonate (182 mg, 1.32 mmol) and (R)-(+)-3-methoxy-α-methylbenzylamine (210 mg, 1.39 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 260 mg (0.60 mmol) of the compound K-2050 as a pale yellow syrup at a yield of 43%.

500 MHz NMR 7.41(1H, dd, J=2.0 Hz, J=2.0 Hz), 7.23–7.27(2H, m), 7.18–7.21 (1H, m), 7.11(1H, dd, J=8.0 Hz, J=8.0 Hz), 6.90–6.93(2H, m), 6.80(1H, dd, J=8.0 Hz, J=2.5 Hz), 3.82(3H, s), 3.77–3.80(1H, m), 2.88(2H, t, J=7.5 Hz), 2.42–2.54(2H, m), 1.58–1.64(2H, m), 1.50–1.55(1H, m), 1.35–1.45(4H, m), 1.42(3H, d, J=7.5 Hz), 1.21–1.29(4H, m), m/z=4.35, 437.

Example 68

Synthesis of K-2051

3-Bromobenzenethiol (610 mg, 3.22 mmol) was dissolved in acetonitrile (10.0 ml) and then potassium carbonate (490 mg, 3.55 mmol) and 1,8-dibromooctane (0.59 ml, 3.20 mmol) were successively added thereto at room temperature. The resulting mixture was stirred at the same temperature for 1 hour. After confirming the completion of the reaction by TLC, potassium carbonate (218 mg, 1.58 mmol) and (R)-(+)-3-methoxy-α-methylbenzylamine (250 mg, 1.66 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 170 mg (0.33 mmol) of the compound K-2051 as a pale yellow syrup at a yield of 24%.

500 Hz NMR 7.41–7.42(1H, m), 7.19–7.27(3H, m), 7.11 (1H, dd, J=7.8 Hz, J=7.8 Hz), 6.90–6.92(2H, m), 6.79(1H, dd, J=7.5 Hz, J=2.0 Hz), 3.82(3H, s), 3.76–3.82(1H, m), 2.89(2H, t, J=7.8 Hz), 2.42–2.53(2H, m), 1.59–1.65(2H, m), 1.49(1H, m), 1.41(3H, d, J=6.5 Hz), 1.36–1.43(4H, m), 1.22–1.28(6H, m), m/z=449, 451.

Example 69

Synthesis of K-2052 (N-{5-[(4-fuluorophenyl)thio]pentyl}-N-[(1R)-1-(1-naphthyl)ethyl]amine)

4-Fluorobenzenethiol (460 mg, 3.60 mmol) was dissolved in acetonitrile (10.0 ml) and then potassium carbonate (500 mg, 3.62 mmol) and 1,5-dibromopentane (0.50 ml, 3.67 mmol) were successively added thereto at room temperature. The resulting mixture was stirred at the same temperature for 1 hour. After confirming the completion of the reaction by TLC, potassium carbonate (210 mg, 1.52 mmol) and (R)-(+)-1-(1-naphthyl)ethylamine (300 mg, 1.86 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 210 mg (0.57 mmol) of the compound K-2052 as a pale yellow syrup at a yield of 31%.

500 MHz NMR 8.17(1H, d, J=8.0 Hz), 7.87(1H, d, J=8.5 Hz), 7.74(1H, d, J=8.0 Hz), 7.62(1H, d, J=8.0 Hz), 7.41–7.50(5H, m), 7.29(2H, d, J=8.5 Hz), 4.61(1H, q, J=6.5 Hz), 2.82(2H, t, J=7.5 Hz), 2.56–2.57(2H, m), 2.37–2.43 (2H, m), 1.40–1.59(5H, m), 1.46(3H, d, J=6.5 Hz), m/z=367.

Example 70

Synthesis of K-2055

4-Trifluoromethylbenzenethiol (408 mg, 2.29 mmol) was dissolved in acetonitrile (10.0 ml) and then potassium carbonate (330 mg, 2.39 mmol) and 1,3-dibromopropane (0.23 ml, 2.28 mmol) were successively added thereto at room temperature. The resulting mixture was stirred at the same temperature for 1 hour. After confirming the completion of the reaction by TLC, potassium carbonate (172 mg, 1.25 mmol) and (R)-(+)-3-methoxy-α-methylbenzylamine (210 mg, 1.39 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 122 mg (0.33 mmol) of the compound K-2055 as a pale yellow syrup at a yield of 24%.

500 MHz NMR 7.44–7.50(2H, m), 7.32(1H, d, J=8.5 Hz), 7.23(1H, dd, J=8.5 Hz, J=8.5 Hz), 7.17–7.20(1H, m), 6.85–6.88(2H, m), 6.77–6.79(1H, m), 3.80(3H, s), 3.70–3.74(1H, m), 1.77–1.83(2H, m), 1.34(3H, d, J=6.5 Hz), 1.25–1.26(1H, m), m/z=369.

Example 71

Synthesis of K-2056

4-Trifluoromethylbenzenethiol (487 mg, 2.74 mmol) was dissolved in acetonitrile (10.0 ml) and then potassium carbonate (374 mg, 2.71 mmol) and 1,4-dibromobutane (0.33 ml, 2.77 mmol) were successively added thereto at room temperature. The resulting mixture was stirred at the same temperature for 1 hour. After confirming the completion of the reaction by TLC, potassium carbonate (172 mg, 1.25 mmol) and (R)-(+)-3-methoxy-α-methylbenzyiamine (250 mg, 1.65 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 152 mg (0.40 mmol) of the compound K-2056 as a pale yellow syrup at a yield of 24%.

500 MHz NMR 7.49(2H, d, J=8.5 Hz), 7.32(2H, d, J=8.0 Hz), 7.23(1H, dd, J=8.0 Hz, J=8.0 Hz), 6.86–6.88(2H, m), 6.76–6.79(1H, m), 3.80(1H, s), 3.71(1H, q, J=6.5 Hz), 2.92–2.95(2H, t, J=7.5 Hz), 1.55–1.73(4H, m), 1.47(1H, s),1.33(3H, d, J=6.5 Hz), 2.50–2.55(1H, m), 2.42–2.47(1H, m), m/z=383.

Example 72

Synthesis of K-2057

4-Trifluoromethylbenzenethiol (560 mg, 3.15 mmol) was dissolved in acetonitrile (10.0 ml) and then potassium carbonate (440 mg, 3.19 mmol) and 1,5-dibromopentane (0.43 ml, 3.16 mmol) were successively added thereto at room temperature. The resulting mixture was stirred at the same temperature for 1 hour. After confirming the completion of the reaction by TLC, potassium carbonate (240 mg, 1.74 mmol) and (R)-(+)-3-methoxy-α-methylbenzylamine (290 mg, 1.92 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 129 mg (0.32 mmol) of the compound K-2057 as a pale yellow syrup at a yield of 17%.

500 MHz NMR 7.49(2H, d, J=8.5 Hz), 7.31(2H, d, J=8.0 Hz), 7.23(1H, dd, J=8.0 Hz, J=8.0 Hz), 6.86–6.89(2H, m), 6.76–6.79(1H, m), 3.81(3H, s), 3.71(1H, q, J=6.8 Hz), 2.94(2H, t, J=7.3 Hz), 2.40–2.51(2H, m), 1.63–1.68(2H, m), 1.42–1.51(5H, m), 14.34(3H, d, J=6.8 Hz), m/z=397.

Example 73

Synthesis of K-2058

4-Trifluoromethylbenzenethiol (500 mg, 2.81 mmol) was dissolved in acetonitrile (10.0 ml) and then potassium carbonate (420 mg, 3.64 mmol) and 1,6-dibromohexane (0.43 ml, 2.79 mmol) were successively added thereto at room temperature. The resulting mixture was stirred at the same temperature for 1 hour. After confirming the completion of the reaction by TLC, potassium carbonate (150 mg, 1.09 mmol) and (R)-(+)-3-methoxy-α-methylbenzylamine (260 mg, 1.72 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 155 mg (0.38 mmol) of the compound K-2058 as a pale yellow syrup at a yield of 22%.

500 MHz NMR 7.49(2H, d, J=8.5 Hz), 7.32(2H, d, J=7.0 Hz), 7.23(1H, dd, J=8.0 Hz, J=8.0 Hz), 6.87–6.89(2H, m), 6.76–6.79(1H, m), 3.81(3H, s), 3.72(1H, q, J=6.5 Hz), 2.94(2H, t, J=7.5 Hz), 2.39–2.52(2H, m), 1.63–1.69(2H, m), 1.39–1.50(5H, m), 1.29–1.34(2H, m), 1.34(3H, d, J=6.5 Hz), m/z=411.

Example 74

Synthesis of K-2059

4-Trifluoromethylbenzenethiol (500 mg, 2.81 mmol) was dissolved in acetonitrile (10.0 ml) and then potassium carbonate (420 mg, 3.64 mmol) and 1,7-dibromoheptane (0.48 ml, 2.81 mmol) were successively added thereto at room temperature. The resulting mixture was stirred at the same temperature for 1 hour. After confirming the completion of the reaction by TLC, potassium carbonate (150 mg, 1.09 mmol) and (R)-(+)-3-methoxy-α-methylbenzylamine (260 mg, 1.72 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 204 mg (0.48 mmol) of the compound K-2059 as a pale yellow syrup at a yield of 28%.

500 MHz NMR 7.49(2H, d, J=8.5 Hz), 7.32(2H, d, J=6.5 Hz), 7.23(1H, dd, J=6.0 Hz, J=6.0 Hz), 6.87–6.89(2H, m), 6.76–6.79(1H, m), 3.81(3H, s), 3.73(1H, q, J=6.0 Hz), 2.94(2H, t, J=6.5 Hz), 2.39–2.51(2H, m), 1.62–1.68(2H, m), 1.34–1.48(9H, m), 1.35(3H, d, J=6.0 Hz), m/z=425.

Example 75

Synthesis of K-2061

3-Chlorobenzenethiol (460 mg, 3.18 mmol) was dissolved in acetonitrile (10.0 ml) and then potassium carbonate (440 mg, 3.19 mmol) and 1,3-dibromopropane (0.32 ml, 3.15 mmol) were successively added thereto at room temperature. The resulting mixture was stirred at the same temperature for 2 hours. After confirming the completion of the reaction by TLC, potassium carbonate (210 mg, 1.52 mmol) and (R)-(+)-3-methoxy-α-methylbenzylamine (300 mg, 1.99 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 272 mg (0.81 mmol) of the compound K-2061 as a pale yellow syrup at a yield of 41%.

500 MHz NMR 7.11–7.27(5H, m), 6.86–6.88(2H, m), 6.77–6.79(1 H, m), 3.81(3H, s), 3.70(1H, q, J=6.5 Hz), 2.89–3.01(2H, m), 2.60–2.65(1H, m), 2.51–2.56(1H, m), 1.75–1.81(2H, m), 1.47(1H, s), 1.33(3H, d, J=6.5 Hz), m/z=335.

Example 76

Synthesis of K-2066

2,5-Dichlorobenzenethiol (575 mg, 3.21 mmol) was dissolved in acetonitrile (11.0 ml) and then potassium carbonate (440 mg, 3.19 mmol) and 1-bromo-2-chloroethane (0.26 ml, 3.12 mmol) were successively added thereto at room temperature. The resulting mixture was stirred at the same temperature for 1 hour. After confirming the completion of the reaction by TLC, potassium carbonate (225 mg, 1.63 mmol) and (R)-(+)-3-methoxy-α-methylbenzylamine (340 mg, 2.25 mmol) were added at room temperature to the reaction system and the resulting mixture was stirred at 100° C. for additional 100 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 182 mg (0.51 mmol) of the compound K-2066 as a pale yellow syrup at a yield of 23%.

500 MHz NMR 7.21–7.30(3H, m), 7.19(1H, d, J=2.5 Hz), 6.88–6.89(2H, m), 6.77(1H, dd, J=8.5 Hz, J=2.5 Hz), 3.81 (3H, s), 3.76(1H, q, J=6.5 HZ), 3.04(2H, t, J=7.0 Hz), 2.72–2.83(2H, m), 1.66(1H, s), 1.36(3H, d, J=6.5 Hz), m/z=355, 357.

Example 77

Synthesis of K-2075

2-Bromobenzenethiol (702 mg, 3.71 mmol) was dissolved in acetonitrile (14.0 ml) and then potassium carbonate (525 mg, 3.80 mmol) and 1,5-dibromopentane (0.50 ml, 3.67 mmol) were successively added thereto at room temperature. The resulting mixture was stirred at the same temperature for 1 hour. After confirming the completion of the reaction by TLC, potassium carbonate (247 mg, 1.79 mmol) and (R)-(+)-1-(1-naphthyl)ethylamine (0.30 ml, 1.86 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=200:1) to thereby give 144 mg (0.34 mmol) of the compound K-2075 as a pale yellow syrup at a yield of 18%.

500 MHz NMR 8.18(1H, d, J=8.5 Hz), 7.87(1H, d, J=8.5 Hz), 7.64(1H, d, J=8.5 Hz), 7.74(1H, d, J=8.5 Hz), 7.45–7.53(4H, m), 7.13–7.25(2H, m), 6.99(1H, ddd, J=1.5 Hz, J=6.0 Hz, J=6.0 Hz), 4.62(1H, q, J=7.0 Hz), 2.89(2H, t, J=7.5 Hz), 2.52–2.63(2H, m), 1.66–1.71(2H, m), 1.45–1.59 (5H, m), 1.49(3H, d, J=7.0 Hz), m/z=427.

Example 78

Synthesis of K-2076(N-[(1R)-1-(1-naphthyl)ethyl]-N-(5-{[4-(trifluoromethyl)phenyl]thio}pentyl)amine)

4-Trifluoromethylbenzenethiol (510 mg, 2.861 mmol) was dissolved in acetonitrile (12.0 ml) and then potassium carbonate (400 mg, 2.89 mmol) and 1,5-dibromopentane (0.39 ml, 2.86 mmol) were successively added thereto at room temperature. The resulting mixture was stirred at the same temperature for 1 hour. After confirming the completion of the reaction by TLC, potassium carbonate (200 mg, 1.45 mmol) and (R)-(+)-1-(1-naphthyl)ethylamine (0.28 ml, 1.73 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=180:1) to thereby give 53 mg (0.13 mmol) of the compound K-2076 as a pale yellow syrup at a yield of 7%.

500 MHz NMR 8.18(1H, d, J=8.5 Hz), 7.87(1H, d, J=7.0 Hz), 7.74(1H, d, J=6.5 Hz), 7.63(1H, d, J=6.5 Hz), 7.45–7.52(5H, m), 7.30(2H, d, J=8.0 Hz), 4.62(1H, q, J=6.5 Hz), 2.93(2H, t, J=6.5 Hz), 2.93(2H, t, J=7.0 Hz), 2.51–2.63 (2H, m), 1.63–1.69(2H, m), 1.44–1.56(5H, m), 1.49(3H, d, J=6.5 Hz), m/z=417.

Example 79

Synthesis of K-2078

3,4-Dichlorobenzenethiol (469 mg, 2.62 mmol) was dissolved in acetonitrile (10.0 ml) and then potassium carbonate (400 mg, 2.89 mmol) and 1,3-dibromopropane (0.27 ml, 2.67 mmol) were successively added thereto at room temperature. The resulting mixture was stirred at the same temperature for 1 hour. After confirming the completion of the reaction by TLC, potassium carbonate (180 mg, 1.30 mmol) and (R)-(+)-3-methoxy-α-methylbenzylamine (240 mg, 1.59 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 143 mg (0.39 mmol) of the compound K-2078 as a pale yellow syrup at a yield of 25%.

500 MHz NMR 7.36(1H, d, J=1.5 Hz), 7.31(1H, d, J=8.5 Hz), 7.24(1H, dd, J=6.5 Hz, J=6.5 Hz), 7.10(1H, dd, J=8.5 Hz, J=1.5 Hz), 6.85–6.88(2H, m), 6.77–6.79(1H, m), 3.81 (3H, s), 3.71(1H, q, J=6.5 Hz), 2.88–3.00(2H, m), 2.50–2.64 (2H, m), 1.71–1.81(2H, m), 1.52(1 H, s), 1.33(3H, d, J=6.5 Hz), m/z=369, 371.

Example 80

Synthesis of K-2079

3,4-Dichlorobenzenethiol (556 mg, 3.11 mmol) was dissolved in acetonitrile (12.0 ml) and then potassium carbonate (412 mg, 2.99 mmol) and 1,4-dibromobutane (0.37 ml, 3.10 mmol) were successively added thereto at room temperature. The resulting mixture was stirred at the same temperature for 1 hour. After confirming the completion of the reaction by TLC, potassium carbonate (242 mg, 1.75 mmol) and (R)-(+)-3-methoxy-α-methylbenzylamine (280 mg, 1.85 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 156 mg (0.41 mmol) of the compound K-2079 as a pale yellow syrup at a yield of 22%.

500 MHz NMR 7.34(1H, d, J=2.5 Hz), 7.31(1H, d, J=8.5 Hz), 7.23(1H, dd, J=7.5 Hz, J=7.5 Hz), 7.10(1H, dd, J=8.5 Hz, J=2.5 Hz), 6.87(1H, d, J=7.5 Hz), 6.86(1H, s), 6.76–6.79 (1H, m), 3.80(3H, s), 3.71(1H, q, J=7.0 Hz), 2.87(2H, t, J=7.0 Hz), 2.41–2.54(2H, m), 1.53–1.68(4H, m), 1.46(1H, s), 1.33(3H, d, J=7.0 Hz), m/z=383, 385.

Example 81

Synthesis of K-2080

3,4-Dichlorobenzenethiol (515 mg, 2.88 mmol) was dissolved in acetonitrile (11.0 ml) and then potassium carbonate (410 mg, 2.97 mmol) and 1,5-dibromopentane (0.39 ml, 2.86 mmol) were successively added thereto at room temperature. The resulting mixture was stirred at the same temperature for 1 hour. After confirming the completion of the reaction by TLC, potassium carbonate (230 mg, 1.66 mmol) and (R)-(+)-3-methoxy-α-methylbenzylamine (260 mg, 1.72 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 250 mg (0.63 mmol) of the compound K-2080 as a pale yellow syrup at a yield of 37%.

500 MHz NMR 7.34(1H, d, J=2.5 Hz), 7.31(1H, d, J=8.5 Hz), 7.22–7.25(1H, m), 7.09(1H, dd, J=2.5 Hz, J=8.5 Hz), 6.88(1H, d, J=8.5 Hz), 6.87(1H, s), 6.78dd, J=8.5 Hz, J=2.5 Hz), 3.81(3H, s), 3.72(1H, q, J=6.5 Hz), 2.87(2H, t, J=8.0 Hz), 2.39–2.52(2H, m), 1.59–1.64(2H, m), 1.38–1.51(5H, m), 1.34(3H, d, J=6.5 Hz), m/z=395, 397.

Example 82

Synthesis of K-2082

3,4-Dichlorobenzenethiol (720 mg, 4.02 mmol) was dissolved in acetonitrile (15.0 ml) and then potassium carbonate (550 mg, 3.98 mmol) and 1,7-dibromoheptane (0.64 ml, 3.75 mmol) were successively added thereto at room temperature. The resulting mixture was stirred at the same temperature for 1 hour. After confirming the completion of the reaction by TLC, potassium carbonate (230 mg, 1.66 mmol) and (R)-(+)-3-methoxy-α-methylbenzylamine (360 mg, 2.38 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The. organic layer thus obtained was dried over anhydrous sodium sulfate and concentrated under reduced pressure. The organic residue was purified by silica gel column chromatography (chloroform:methanol=150:1) to thereby give 253 mg (0.59 mmol) of the compound K-2082 as a pale yellow syrup at a yield of 25%.

500 MHz NMR 7.35(1H, d, J=2.5 Hz), 7.31(1H, d, J=8.0 Hz), 7.22–7.25(1H, m), 7.10(1H, dd, J=8.5 Hz, J=2.5 Hz), 6.88–6.90(1H, m), 6.90(1H, s), 6.78(1H, dd, J=2.5 Hz, J=8.5 Hz), 3.81(3H, s), 3.75(1H, q, J=6.5 Hz), 2.87(2H, t, J=7.3 Hz), 2.40–2.52(2H, m), 1.58–1.64(2H, m), 1.48(1H, s), 1.34–1.64(2H, m), 1.37(3H, d, J=6.5 Hz), 1.24–1.33(4H, m), m/z=425, 427.

Example 83

Synthesis of K-2084

2,6-Dichlorobenzenethiol (540 mg, 3.02 mmol) was dissolved in acetonitrile ( 11.0 ml) and then potassium carbonate (420 mg, 3.04 mmol) and 1,3-dibromopropane (0.31 ml, 3.05 mmol) were successively added thereto at room temperature. The resulting mixture was stirred at the same temperature for 1 hour. After confirming the completion of the reaction by TLC, potassium carbonate (234 mg, 1.69 mmol) and (R)-(+)-3-methoxy-α-methylbenzylamine (230 mg, 1.52 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 182 mg (0.49 mmol) of the compound K-2084 as a pale yellow syrup at a yield of 32%.

500 MHz NMR 7.6(2H, d, J=8.0 Hz), 7.22(1H, dd, J=8.0 Hz, J=8.0 Hz), 7.16(1H, dd, J=8.0 Hz, J=8.0 Hz), 6.86(1H, d, J=8.0 Hz), 6.85(1H, s), 6.76–6.78(1H, m), 3.81(3H, s), 3.70(1H, q, J=6.0 Hz), 2.89–2.98(2H, m), 2.52–2.64(2H, m), 1.65–1.71(2H, m), 1.46(1H, s), 1.32(3H, d, J=6.0 Hz), m/z=369, 371.

Example 84

Synthesis of K-2085

2,6-Dichlorobenzenethiol (500 mg, 2.79 mmol) was dissolved in acetonitrile (10.0 ml) and then potassium carbonate (400 mg, 2.90 mmol) and 1,4-dibromobutane (0.33 ml, 2.76 mmol) were successively added thereto at room temperature. The resulting mixture was stirred at the same temperature for 1 hour. After confirming the completion of the reaction by TLC, potassium carbonate (230 mg, 1.65 mmol) and (R)-(+)-3-methoxy-α-methylbenzylamine (250 mg, 1.65 mmol) were added at room temperature to the reaction system and the resulting mixture was stirred at 100° C. for additional 24 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 293 mg (0.76 mmol) of the compound K-2085 as a pale yellow syrup at a yield of 46%.

500 MHz NMR 7.36(2H, d, J=7.5 Hz), 7.23(1H, dd, J=7.5 Hz, J=7.5 Hz), 7.16(1H, dd, J=8.0 Hz, J=8.0 Hz), 6.85–6.87(1 H, m), 6.86(1H, s), 6.76–6.78(1H, m), 3.81(3H, s), 3.70(1H, q, J=6.5 Hz), 2.89(2H, t, J=7.0 Hz), 2.38–2.51 (2H, m, 1.51–1.63(4H, m), 1.49(1H, s), 1.32(3H, d, J=6.5 Hz).

Example 85

Synthesis of K-2087(N-[(1R)-1-(1-naphthyl)ethyl]-N-(4-{[3-(trifluoromethyl)phenyl]thio}butyl)amine)

3-Trifluoromethylbenzenethiol (670 mg, 3.76 mmol) was dissolved in acetonitrile (14.0 ml) and then potassium carbonate (516 mg, 3.73 mmol) and 1,4-dibromobutane (0.45 ml, 3.77 mmol) were successively added thereto at room temperature. The resulting mixture was stirred under ice-cooling for 2 hours. After confirming the completion of the reaction by TLC, potassium carbonate (300 mg, 2.17 mmol)

and (R)-(+)-1-(1-naphthyl)ethylamine (0.30 ml, 1.86 mmol) were added at room temperature to the reaction system and the resulting mixture was stirred at 100° C. for additional 12 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=150:1) to thereby give 298 mg (0.74 mmol) of the compound K-2087 as a pale yellow syrup at a yield of 40%.

500 MHz NMR 8.18(1H, d, J=8.0 Hz), 7.86–7.88(1H, m), 7.74(1H, d, J=8.0 Hz), 7.63(1H, d, J=7.5 Hz), 7.45–7.52(4H, m), 7.41–7.43(1H, m), 7.33–7.39(2H, m), 4.62(1H, q, J=6.5 Hz), 2.92(2H, d, J=7.0 Hz), 2.60–2.65(1H, m), 2.52–2.57 (1H, m), 1.63–1.72(4H, m), 4.54(1H, s), 1.48(3H, d, J=6.5 Hz), m/z=403.

Example 86

Synthesis of K-2117((R)-N-[1-(1'-naphthyl)ethyl]-2-(2',5'-dichlorophenylthio)ethylamine)

2,5-Dichlorobenzenethiol (5.10 g, 28.5 mmol) was dissolved in acetonitrile (30 ml) and then potassium carbonate (4.20 g, 30.4 mmol) and 1-bromo-2-chloroethane (2.45 ml, 29.4 mmol) were successively added thereto at room temperature. The resulting mixture was stirred under ice-cooling for 2 hours. After confirming the completion of the reaction by TLC, potassium carbonate (4.0 g, 28.9 mmol) and (R)-(+)-1-(1-naphthyl)ethylamine (3.70 ml, 22.9 mmol) were added at room temperature to the reaction system and the resulting mixture was stirred at 100° C. for additional 120 hours.

After the completion of the reaction, the reaction mixture was cooled by allowing to stand at room temperature. After pouring water thereinto, the mixture was subjected to separatory extraction with chloroform and washed with a saturated aqueous solution of sodium chloride. The organic layer thus obtained was dried over anhydrous sodium sulfate and concentrated under reduced pressure. The organic residue was purified by silica gel column chromatography (chloroform:methanol=200:1) to thereby give 5.70 g (15.2 mmol) of the compound K-2117 as a pale yellow syrup at a yield of 66%.

500 MHz NMR 8.17(1H, d, J=8.5 Hz), 7.85–7.87(1H, m), 7.73(1H, d, J=8.0 Hz), 7.65(1H, d, J=7.5 Hz), 7.44–7.52(4H, m), 7.26(1H, d, J=8.5 Hz), 7.20(1H, d, J=2.5 Hz), 7.05(1H, dd, J=2.5 Hz, J=8.5 Hz), 4.65(1H, q, J=6.5 Hz), 3.09(2H, m), 2.82–2.91(2H, m), 1.68(1H, s), 1.51(3H, d, J=6.5 Hz), m/z=375, 377.

Example 87

Synthesis of K-2117 Hydrochloride

The compound K-2117(7.01 g, 18.6 mmol) was dissolved in a 30% hydrochloric acid-methanol solution (HCl-MeOH) (40 ml) and stirred at room temperature for 5 minutes.

After the completion of the reaction, the reaction system was concentrated in situ under reduced pressure to thereby completely remove the hydrochloric acid-methanol solution. The residue was filtered through a Kiriyama funnel and the resulting crystals were washed with hexane. Thus 5.87 g (14.2 mmol) of K-2117 hydrochloride was obtained in the form of white crystals at a yield of 76%.

m/z=375, 377. $^1$H-NMR (400 MHz) 10.97 (1H, bs), 10.30 (1H, bs), 8.18 (1H, d, J=7.32 Hz), 7.88–7.97 (3H, m), 7.53–7.66 (3H, m), 7.31 (1H, d, J=2.4 Hz), 7.14 (1H, d, J=8.56 Hz), 7.01 (1H, dd, J=1.36 Hz, J=8.56 Hz), 5.23–5.27 (1H, m), 3.55–3.61 (2H, m), 2.95–3.10 (2H, m), 2.04 (3H, d, J=6.60 Hz).

Example 88

Synthesis of K-2177

Dibenzylamine (1.0 g, 0.51 mmol) and triethylamine (0.85 ml, 0.61 mmol, 1.2 mol eq.) were dissolved in chloroform and acryloyl chloride (0.505 g, 0.56 mmol, 1.1 mol eq.) was added under-ice cooling thereto. The resulting mixture was stirred at room temperature for 30 minutes.

After the completion of the reaction, the reaction mixture was poured into water and extracted with chloroform. The chloroform layer was washed with water and a saturated aqueous solution of sodium chloride. After drying over sodium sulfate, the solvent was distilled off under reduced pressure. The crystals thus obtained were purified by column chromatography (silica gel, chloroform-methanol) to thereby give colorless prisms (1.085 g, 85.0%).

The compound thus obtained (50 mg, 0.20 mmol) and (R)-(+)-1-(1-naphthyl)ethylamine (41.0 mg, 0.24 mmol, 1.2 mol eq.) were dissolved in chloroform-methanol (2 ml) and allowed to stand at room temperature for 1 week.

After the completion of the reaction, the solvent was distilled off under reduced pressure. The oil thus obtained was purified by column chromatography (silica gel, chloroform-methanol) to thereby give 50.9 mg of K-2177 as a colorless oil at a yield of 60.5%.

MS m/z: 422(M$^+$). $^1$H-NMR δ: 1.53(3H, d, J=6.7 Hz, C$\underline{H}_3$), 2.60–2.70(2H, m, C$\underline{H}_2$), 2.86–2.96(2H, m, C$\underline{H}_2$), 4.42(2H, s, C$\underline{H}_2$), 4.62(2H, s, C$\underline{H}_2$), 4.69(1H, q, J=6.7 Hz, C$\underline{H}$), 7.13(2H, d, J=7.3 Hz, Ar—$\underline{H}$), 7.21(2H, d, J=6.7 Hz, Ar—$\underline{H}$), 7.27–7.36(6H, m, Ar—$\underline{H}$), 7.45–7.50(3H, m, Ar—$\underline{H}$), 7.70(1H, d, J=6.7 Hz, Ar—$\underline{H}$), 7.74(1H, d, J=7.9 Hz, Ar—$\underline{H}$), 7.86(1H, dd, J=1.8, 6.7 Hz, Ar—$\underline{H}$), 8.16(1H, d, J=7.9 Hz, Ar—$\underline{H}$).

Example 89

Synthesis of K-2246(N-[(1R)-1-(1-naphthyl)ethyl]-N-(4-{[4-(trifluoromethyl) phenyl]thio}butyl) amine)

960 mg (5.39 mmol) of 4-trifluoromethylthiophenol was dissolved in 8 ml of acetonitrile. Subsequently, 802 mg (5.80 mmol) of potassium carbonate and 0.65 ml (5.44 mmol) of 1,4-dibromobutane were added thereto at room temperature and the obtained mixture was stirred at the same temperature for 30 minutes. After confirming the completion of the reaction by TLC, 5 ml of acetonitrile, 693 mg (5.01 mmol) of potassium carbonate and 0.49 ml (2.96 mmol) of (R)-(+)-1-(1-naphthyl)ethylamine were added thereto at room temperature and the obtained mixture was stirred at 85° C. for 12 hours.

After the completion of the reaction, the mixture was cooled by allowing to stand at room temperature and water was poured thereinto. Next, it was subjected to separating extraction with chloroform and a saturated aqueous solution of sodium chloride and the organic layer thus obtained was dried over sodium sulfate. Further, the organic layer was concentrated under reduced pressure and the obtained residue was purified by silica gel column chromatography (80 g, chloroform/methanol=200/1) to thereby give 210 mg (0.52 mmol, 17.6%) of K-2246 as a pale yellow transparent syrup.

Subsequently, the K-2246 thus obtained was dissolved in a 10% solution of hydrochloric acid in methanol, stirred for 5 minutes and then concentrated as such under reduced pressure. The crystals thus formed were washed with diethyl ether to thereby give 104 mg (0.24 mmol, 8.1%) of K-2246 hydrochloride as white crystals.

$^1$H-NMR (400 MHz) 10.6 (1H, bs), 10.1 (1H, bs), 8.24 (1H, d, J=7.08 Hz), 7.99(1H, d, J=8.52 Hz), 7.90–7.96 (2H, m), 7.55–7.67 (3H, m), 7.39–7.41 (2H, m), 7.17–7.19 (2H, m), 5.17–5.24 (1H, m), 2.73–2.84 (4H, m), 2.11–2.18 (2H, m), 2.06 (3H, d, J=6.60 Hz), 1.57–1.62 (4H, m), m/z=403.

Example 90

Synthesis of K-2076

1.040 g (5.83 mmol) of 4-trifluoromethylthiophenol was dissolved in 10 ml of acetonitrile. Subsequently, 1.024 g (7.40 mmol) of potassium carbonate and 0.80 ml (5.87 mmol) of 1,5-dibromopentane were added thereto at room temperature and the obtained mixture was stirred at the same temperature for 1 hour. After confirming the completion of the reaction by TLC, 8 ml of acetonitrile, 853 mg (6.17 mmol) of potassium carbonate and 0.60 ml. (3.63 mmol) of (R)-(+)-1-(1-naphthyl)ethylamine were added thereto at room temperature and the obtained mixture was stirred at 85° C. for 12 hours.

After the completion of the reaction, the mixture was cooled by allowing to stand at room temperature and water was poured thereinto. Next, it was subjected to separating extraction with chloroform and a saturated aqueous solution of sodium chloride and the organic layer thus obtained was dried over sodium sulfate. Further, the organic layer was concentrated under reduced pressure and the obtained residue was purified by silica gel column chromatography (100 g, chloroform/methanol=200/1) to thereby give 240 mg (0.57 mmol, 17.7%) of K-2076 as a pale yellow transparent syrup.

Subsequently, the K-2076 thus obtained was dissolved in a 10% solution of hydrochloric acid in methanol, stirred for 5 minutes and then concentrated as such under reduced pressure. The crystals thus formed were washed with diethyl ether to thereby give 115 mg (0.25 mmol, 6.9%) of K-2076 hydrochloride as white crystals.

$^1$H-NMR (400 MHz) 10.55 (1H, bs), 10.01 (1H, bs), 8.24 (1H, d, J=7.08 Hz), 7.89–7.99 (3H, m), 7.52–7.66 (3H, m), 7.44 (2H, d, J=8.32 Hz), 7.23 (2H, d, J=8.32 Hz), 5.19 (1H, bs), 2.82 (2H, t, J=7.08 Hz), 2.74 (2H, bs), 2.04 (3H, d, J=6.36 Hz), 1.96–2.04 (2H, m), 1.50–1.57 (2H, m), 1.30–1.38 (2H, m), m/z=417.

Example 91

Synthesis of K-2243 (N1,N1-di(4-chlorobenzyl)-3{[(1R)-1-(1-naphthyl)ethyl]amino}propanamide)

To 500 mg (3.56 mmol) of p-chlorobenzaldehyde and 503.6 mg (3.56 mmol, 1.0 mol eq.) of p-chlorobenzylamine was added 1.26 ml (4.27 mmol, 1.2 mol eq.) of titanium tetraisopropoxide and the obtained mixture was stirred at room temperature for 4 hours. After the completion of the reaction, the reaction mixture was dissolved in methanol and 538.7 mg (14.24 mmol, 4.0 mel eq.) of sodium boron hydride was added thereto. The obtained mixture was stirred at room temperature for 12 hours.

After the completion of the reaction, the solvent was distilled off under reduced pressure. Ethyl acetate and water were poured into the residue, and filtered through celite. The residue was washed with ethyl acetate and then the washing liquor was combined with the filtrate and extracted with ethyl acetate. The ethyl acetate layer was washed with water and a saturated aqueous solution of sodium chloride and dried over sodium sulfate. After distilling off the solvent under reduced pressure, the obtained oil was purified by column chromatography (silica gel, chloroform) to thereby give 819 mg (86.6%) of the compound 124 as a colorless oil.

MS m/z:266. $^1$H-NMR δ:3.74 (4H, d, J=2.7, C$\underline{H}_2$×2), 7.24–7.30 (8H, m, Ar—H).

500 mg (1.88 mmol) of the above-mentioned compound 124 and 0.31 ml (2.26 mmol, 1.2 mol eq.) of triethylamine were dissolved in chloroform and 187.1 mg (2.07 mmol, 1.1 mol eq.) of acryloyl chloride was added thereto under ice-cooling. The obtained mixture was then stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent under reduced pressure, the obtained oil was purified by column chromatography (silica gel, chloroform) to thereby give 570.3 mg (94.4%) of the compound 125 as a colorless oil.

MS m/z:320. $^1$H-NMR 67:4.47 (2H, s, C$\underline{H}_2$), 4.59(2H, s, C$\underline{H}_2$), 5.77 (1H, dd, J=2.7, 9.8 Hz, CH=C$\underline{H}_2$), 6.52 (1H, d, J=2.7 Hz, C$\underline{H}$=CH$_2$), 6.54(1H, d, J=9.8 Hz, CH=C$\underline{H}_2$), 7.08 (2H, d, J=8.1 Hz, Ar—H), 7.18 (2H, d, J=8.1 Hz, Ar—H), 7.29 (2H, d, J=8.1 Hz, Ar—H), 7.33 (2H, d, J=8.1 Hz, Ar—H).

100 mg (0.31 mmol) of the above-mentioned compound 125 and 64.2 mg (0.38 mmol, 1.2 mol eq.) of (R)-(+)-(1-naphthyl)ethylamine were dissolved in chloroform/methanol (4:1) and allowed to stand at room temperature for 1 week. After the completion of the reaction, the solvent was distilled off under reduced pressure and the oil thus obtained was purified by column chromatography (silica gel, chloroform) to thereby give 106.6 mg (69.5%) of K-2243 as a colorless oil.

MS m/z:491. $^1$H-NMR δ:1.51 (3H, d, J=6.6Hz, CH$_3$), 2.60 (2H, t, J=6.1 Hz, C$\underline{H}_2$), 2.84–2.96 (2H, m, C$\underline{H}_2$), 4.35 (2H, s, C$\underline{H}_2$), 4.53(2H, s, C$\underline{H}_2$), 4.66 (1H, q, J=6.6 Hz, C$\underline{H}$), 7.03 (2H, d, J=8.3 Hz, Ar—H), 7.12 (2H, d, J=8.3 Hz, Ar—H), 7.27(2H, d, J=8.3 Hz, Ar—H), 7.30 (2H, d, J=8.3 Hz, Ar—H), 7.47 (1H, t, J=5.1 Hz, Ar H), 7.48 (1H, t, J=5.1 Hz, Ar—H), 7.49 (1H, t, J=5.1 Hz, Ar—H), 7.67 (1H, d, J=5.1 Hz, Ar—H), 7.74 (1H, d, J=5.1 Hz, Ar—H), 7.87 (1H, d, J=7.5 Hz, Ar—H), 7.16(1H, d, J=7.5 Hz, Ar—H).

Example 92

Synthesis of K-2257 (N1,N1-di[4-(trifluoromethoxy)benzyl]-3-{[(1R)-1-(1-naphthyl)ethyl]amino}propanamide)

To 500 mg (2.62 mmol) of p-(trifluoromethoxy) benzylamine and 497.3 mg (2.62 mmol, 1.0 mol eq.) of p-(trifluoromethoxy)-benzaldehyde was added 0.926 ml (3.14 mmol, 1.2 mol eq.) of titanium tetraisopropoxide and the obtained mixture was stirred at room temperature for 4 hours. After the completion of the reaction, the reaction mixture was dissolved in methanol and 396.5 mg (10.48 mmol, 4.0 mol eq.) of sodium boron hydride was added thereto. The obtained mixture was stirred at room temperature for 12 hours. After the completion of the reaction, the solvent was distilled off under reduced pressure. Ethyl acetate and water were poured into the residue and filtered through celite. The residue was washed with ethyl acetate and then the washing liquor was combined with the filtrate and extracted with ethyl acetate. The ethyl acetate layer was washed with water and a saturated aqueous solution of sodium chloride and dried over sodium sulfate. After distilling off the solvent under reduced pressure, the obtained oil was purified by column chromatography (silica gel, chloroform) to thereby give 835.2 mg (87.5%) of the compound 126 as a colorless oil.

MS m/z:365. $^1$H-NMR δ:3.80 (4H, s, C$\underline{H}_2$×2), 7.17 (4H, d, J=8.1 Hz, Ar—H), 7.36 (4H, d, J=8.1 $\overline{Hz}$, Ar—H).

500 mg (1.37 mmol) of the above-mentioned compound 126 and 0.23 ml (1.64 mmol,1.2 mol eq.) of triethylamine were dissolved in chloroform and 136.3 mg (1.51 mmol, 1.1 mol eq.) of acryloyl chloride was added thereto under ice-cooling. The obtained mixture was then stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent under reduced pressure, the obtained oil was purified by column chromatography (silica gel, chloroform) to thereby give 519.3 mg (90.5%) of the compound 127 as a colorless oil.

MS m/z:419. $^1$H-NMR 5:4.53 (2H, S, C$\underline{H}_2$), 4.64 (2H, s, C$\underline{H}_2$), 5.79 (1H, dd, J=2.7, 9.5 Hz, CH=C$\overline{H}_2$), 6.53 (1H, d, J=$\overline{2.7}$ Hz, C$\underline{H}$=CH$_2$), 6.56 (1H, d, J=9.5 $\overline{Hz}$, CH=C$\underline{H}_2$), 7.15–7.31 (8H, m, Ar—H).

450 mg (1.07 mmol) of the above-mentioned compound 127 and 220.7 mg (1.29 mmol, 1.2 mol eq.) of (R)-(+)-(1-naphthyl)ethylamine were dissolved in chloroform/methanol (4: 1) and allowed to stand at room temperature for 1 week. After the completion of the reaction, the solvent was distilled off under reduced pressure and the oil thus obtained was purified by column chromatography (silica gel, chloroform) to thereby give 363 mg (57.3%) of K-2257 as a colorless oil.

MS m/z:590. $^1$H-NMR δ:1.50 (3H, d, J=6.6 Hz, CH$_3$), 2.60 (2H, t, J=5.9 Hz, CH$_2$), 2.84–2.97 (2H, m, CH$_2$), $\overline{4.41}$ (2H, s, CH$_2$), 4.57 (2H, s,$\overline{C}$H$_2$), 6.65 (1H, q, J=6.6 $\overline{Hz}$, C$\underline{H}$) 7.12–7.2$\overline{9}$ (8H, m, Ar—H), $\overline{7.}$44–7.51(3H, m, Ar—H), 7.66 (1H, d, J=6.8 Hz, Ar—H), 7.73 (1H, d, J=8.3 Hz, Ar—H), 7.86 (1H, dd, J=2.4, 7.1 Hz, Ar—H), 8.17 (1H, d, J=7.1 Hz, Ar—H).

Example 93

Synthesis of K-2259 (N1,N1-di[4-(trifluoromethyl) benzyl]-3-{[(l R)-1-(1-naphthyl)ethyl] amino}propanamide)

To 500 mg (2.85 mmol) of p-(trifluoromethyl) benzylamine and 497.1 mg (2.85 mmol, 1.0 mol eq.) of p-(trifluoromethyl)- benzaldehyde was added 1.01 ml (3.43 mmol, 1.2 mol eq.) of titanium tetraisopropoxide and the obtained mixture was stirred at room temperature for 4 hours. After the completion of the reaction, the reaction mixture was dissolved in methanol and 431.3 mg (11.4 mmol, 4.0 mol eq.) of sodium boron hydride was added thereto. The obtained mixture was stirred at room temperature for 12 hours. After the completion of the reaction, the solvent was distilled off under reduced pressure. Ethyl acetate and water were poured into the residue and filtered through celite. The residue was washed with ethyl acetate and then the washing liquor was combined with the filtrate and extracted with ethyl acetate. The ethyl acetate layer was washed with water and a saturated aqueous solution of sodium chloride and dried over sodium sulfate. After distilling off the solvent under reduced pressure, the obtained oil was purified by column chromatography (silica gel, chloroform) to thereby give 458.7 mg (48.3%) of the compound 128 as a colorless oil.

MS m/z:333. $^1$H-NMR δ:3.86 (4H, s, C$\underline{H}_2$×2), 7.47 (4H, d, J=8.1 Hz, Ar—H), 7.59 (4H, d, J=8.1 $\overline{Hz}$, Ar—H).

450 mg (1.35 mmol) of the above-mentioned compound 128 and 0.23 ml (1.62 mmol, 1.2 mol eq.) of triethylamine were dissolved in chloroform and 134.4 mg (1.48 mmol, 1.1 mol eq.) of acryloyl chloride was added thereto under ice-cooling. The obtained mixture was then stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent under reduced pressure, the obtained oil was purified by column chromatography (silica gel, chloroform) to thereby give 519.3 mg (99.3%) of the compound 129 as a colorless oil.

MS m/z:387. $^1$H-NMR δ:4.59 (2H, s, C$\underline{H}_2$), 4.70(2H, s, C$\underline{H}_2$), 5.80 (1H, dd, J=3.7, 8.8 Hz, CH=C$\overline{H}_2$), 6.54 (1H, d, J=$\overline{3.7}$ Hz, C$\underline{H}$=CH$_2$), 6.56(1H, d, J=8.8 $\overline{Hz}$, CH=C$\underline{H}_2$), 7.23–7.64 (8H, m, Ar—H).

800 mg (2.06 mmol) of the above-mentioned compound 129 and 424.0 mg (2.48 mmol, 1.2 mol eq.) of (R)-(+)-(1-naphthyl)ethylamine were dissolved in chloroform/methanol (4:1) and allowed to stand at room temperature for 1 week. After the completion of the reaction, the solvent was distilled off under reduced pressure and the oil thus obtained was purified by column chromatography (silica gel, chloroform) to thereby give 580.7 mg (50.3%) of K-2259 as a colorless oil.

MS m/z:558. $^1$H-NMR δ:1.51 (3H, d, J=6.6 Hz, CH$_3$), 2.60 (2H, t, J=6.1 Hz, CH$_2$), 2.85–2.98 (2H, m, CH$_2$), $\overline{4.47}$ (2H, s, CH$_2$), 4.64(2H, s,$\overline{C}$H$_2$), 4.65 (1H, q, J=6.6 Hz, C$\underline{H}$), 7.23 (2$\overline{H,}$ d, J=8.3 Hz, Ar$\overline{—H}$), 7.31 (2H, d, J=8.3 Hz, Ar—H), 7.44–7.51(3H, m, Ar—H), 7.55 (2H, d, J=8.3 Hz, Ar—H), 7.59 (2H, d, J=8.3 Hz, Ar—H), 7.66 (1H, d, J=8.1 Hz, Ar—H), 7.74 (1H, d, J=8.1 Hz, Ar—H), 7.87 (1H, dd, J=2.4, 8.1 Hz, Ar—H), 8.18 (1H, dd, J=2.4, 8.1 Hz, Ar—H).

Example 94

Synthesis of K-2247 (N1-benzyl-N1-(4-chlorobenzyl)-3-{[(1R)-1-(1-naphthyl)ethyl] amino}propanamide)

To 4-chlorobenzaldehyde (500 mg, 3.56 mmol) and benzylamine (381.2 mg, 3.56 mmol, 1.0 mol eq.) was added titanium tetraisopropoxide (1.26 ml, 4.27 mmol, 1.2 mol eq.) and the mixture was stirred at room temperature for 4 hours. After the completion of the reaction, the reaction mixture was dissolved in ethanol and sodium boron hydride (538.7 mg, 14.24 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 201 (572.6 mg, 69.5%). MS m/z:231.

The dibenzylamine compound 201 (300 mg, 1.29 mmol) and triethylamine (0.22 ml, 1.55 mmol, 1.2 mol eq.) were dissolved in chloroform and acryloyl chloride (128.9 mg, 1.42 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 202 (372.1 mg, 100.0%). MS m/z: 285.

The conjugated ketone compound 202 (100.3 mg, 0.35 mmol, 1.2 mol eq.) and (R)-(+)-1-(1-naphthyl)ethylamine (50 mg, 0.29 mmol) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2247 (64.5 mg, 40.2%).

MS m/z: 456, $^1$H-NMR δ: 1.53 (3H, d, J=6.7 Hz, $CH_3$), 2.60–2.67(2H, m, $CH_2$), 2.86–2.95 (2H, m, $CH_2$), 4.39 ($\overline{2H}$, d, J=18.3 Hz, $CH_2$), $\overline{4.58}$(2H, d, J=13.4 Hz, $C\overline{H_2}$), 4.69 (1H, q, J=6.7 Hz, $C\underline{H}$), 7.04 (1H, d, J=8.5 Hz, Ar—$\overline{H}$), 7.12 (1H, d, J=6.7 Hz, Ar—H), 7.15 (1H, d, J=8.5 Hz, Ar—H), 7.20 (1H, d, J=6.7 Hz, Ar—H), 7.28–7.36 (5H, m, Ar—H), 7.46–7.51 (3H, m, Ar—H), 7.69 (1H, d, J=7.3 Hz, Ar—H), 7.75 (1H, d, J=7.9 Hz, Ar—H), 7.87 (1H, dd, J=1.8, 7.9 Hz, Ar—H), 8.17 (1H, d, J=7.9 Hz, Ar—H).

Example 95

Synthesis of K-2248

To 2-naphthaldehyde (500 mg, 3.20 mmol) and benzylamine (343.1 mg, 3.20 mmol, 1.0 mol eq.) was added titanium tetraisopropoxide (1.13 ml, 3.84 mmol, 1.2 mol eq.) and the mixture was stirred at room temperature for 4 hours. After the completion of the reaction, the reaction mixture was dissolved in ethanol and sodium boron hydride (484.2 mg, 12.8 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 203 (769.1 mg, 97.1%). MS m/z: 247.

The dibenzylamine compound 203 (500 mg, 2.02 mmol) and triethylamine (0.34 ml, 2.43 mmol, 1.2 mol eq.) were dissolved in chloroform and acryloyl chloride (201.3 mg, 2.22 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 204 (579.7 mg, 95.0%). MS m/z: 301.

The conjugated ketone compound 204 (105.8 mg, 0.35 mmo, 1.2 mol eq.) and (R)-(+)-1-(1-naphthyl)ethylamine (50 mg, 0.29 mmol) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2248 (69.8 mg, 42.0%).

MS m/z: 472, $^1$H-NMR δ: 1.52 (3H, dd, J=6.7, 8.5 Hz, $CH_3$), 2.66–2.69 (2H, m, $CH_2$), 2.89–3.00 (2H, m, $CH_2$), 4.51 (2H, d, J=65.3 Hz, $CH_2$), 4.67 (1H, q, J=36.7 Hz, $C\overline{H}$), 4.75 (2H, d, J=48.2 Hz, $\overline{CH_2}$), 7.16 (1H, d, J=7.3 Hz, Ar—H), 7.22–7.39 (5H, m, Ar—H), 7.43–7.52 (5H, m, Ar—H), 7.58 (1H, d, J=25.6 Hz, Ar—H), 7.68–7.88 (6H, m, Ar—H), 8.17 (1H, dd, J=7.9, 21.4 Hz, Ar—H).

Example 96

Synthesis of K-2249

To 2-chlorobenzaldehyde (500 mg, 3.56 mmol) and benzylamine (381.2 mg, 3.56 mmol, 1.0 mol eq.) was added titanium tetraisopropoxide (1.26 ml, 4.17 mmol, 1.2 mol eq.) and the mixture was stirred at room temperature for 4 hours. After the completion of the reaction, the reaction mixture was dissolved in ethanol and sodium boron hydride (538.7 mg, 14.24 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 205 (427.7 mg, 51.9%). MS m/z: 231.

The dibenzylamine compound 205 (300 mg, 1.29 mmol) and triethylamine (0.22 ml, 1.55 mmol, 1.2 mol eq.) were dissolved in chloroform and acryloyl chloride (128.9 mg, 1.42 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 206 (358.8 mg, 96.8%). MS m/z: 285.

The conjugated ketone compound 206 (100.3 mg, 0.35 mmol, 1.2 mol eq.) and (R)-(+)-1-(1-naphthyl)ethylamine (50 mg, 0.29 mmol) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2249 (67.8 mg, 50.8%).

MS m/z: 456, $^1$H-NMR δ: 1.53 (3H, dd, J=6.7–4.3 Hz, CH$_3$), 2.51–2.74 (2H, m, CH$_2$), 2.85–2.98 (2H, m, CH$_2$), 4.50 (2H, d, J=9.8 Hz, CH$_2$), 4.64 (1H, s, CH$_2$), 4.66–4.70 (1H, m, CH), 4.78 (1H, s, CH$_2$), 7.15(1H, d, J=7.9 Hz, Ar—H), 7.19–7.39(8H, m, Ar—H), 7.45–7.51 (3H, m, Ar—H), 7.70 (1H, t, J=7.9 Hz, Ar—H), 7.74(1H, dd, J=3.7, 7.9 Hz, Ar—H), 7.87 (1H, d, J=7.3 Hz, Ar—H), 8.17 (1H, t, J=7.3 Hz, Ar—H).

Example 97

Synthesis of K-2250 (N1-benzyl-N1-(3,4-dichloro-benzyl)-3-{[(1R)-1-(1-naphthyl)ethyl]amino}propanamide)

To benzaldehyde (300 mg, 2.83 mmol) and 3,4-dichlorobenzylamine (497.7 mg, 2.83 mmol, 1.0 mol eq.) was added titanium tetraisopropoxide (1.00 ml, 3.39 mmol, 1.2 mol eq.) and the mixture was stirred at room temperature for 4 hours. After the completion of the reaction, the reaction mixture was dissolved in ethanol and sodium boron hydride (428.2 mg, 11.32 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 207 (568 mg, 75.5%). MS m/z: 266.

The dibenzylamine compound 207 (300 mg, 1.13 mmol) and triethylamine (0.189 ml, 1.35 mmol, 1.2 mol eq.) were dissolved in chloroform and acryloyl chloride (112.3 mg, 1.24 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 208 (358.3 mg, 99.3%). MS m/z: 320.

The conjugated ketone compound 208 (100 mg, 0.31 mmol) and (R)-(+)-1-(1-naphthyl)ethylamine (64.2 mg, 0.38 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2250 (96.5 mg, 62.9%).

MS m/z: 491, $^1$H-NMR δ: 1.51 (3H, d, J=6.6 Hz, CH$_3$), 2.49–2.68(2H, m, CH$_2$), 2.82–2.96 (2H, m, CH$_2$), 4.38 (2H, d, J=32.4 Hz, CH$_2$), 4.54 (1H, s, CH$_2$), (1H, d, J=42.5 Hz, CH$_2$), 4.66 (1H, q, J=6.6 Hz, CH), 7.11(1H, d, J=6.6 Hz, Ar—H), 7.19 (1H, d, J=6.8 Hz, Ar—H), 7.21–7.41 (6H, m, Ar—H), 7.43–7.51 (3H, m, Ar—H), 7.67 (1H, dd, J=2.0, 7.1 Hz, Ar—H), 7.74 (1H, d, J=8.3Hz, Ar—H), 7.86 (1H, dd, J=2.2, 8.1 Hz, Ar—H), 8.16 (1H, d, J=7.3 Hz, Ar—H).

Example 98

Synthesis of K-2251

To benzaldehyde (300 mg, 2.83 mmol) and 2,4-dichlorobenzylamine (497.7 mg, 2.83 mmol, 1.0 mol eq.) was added titanium tetraisopropoxide (1.00 ml, 3.39 mmol, 1.2 mol eq.) and the mixture was stirred at room temperature for 4 hours. After the completion of the reaction, the reaction mixture was dissolved in ethanol and sodium boron hydride (428.2 mg, 11.32 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 209 (469 mg, 62.4%). MS m/z: 266.

The dibenzylamine compound 209 (300 mg, 1.13 mmol) and triethylamine (0.189 ml, 1.35 mmol, 1.2 mol eq.) were dissolved in chloroform and acryloyl chloride (112.3 mg, 1.24 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 210 (311.6 mg, 86.3%). MS m/z: 320.

The conjugated ketone compound 210 (1 00 mg, 0.31 mmol) and (R)-(+)-1-(1-naphthyl)ethylamine (64.2 mg, 0.38 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2251 (126.7 mg, 82.6%).

MS m/z: 491, $^1$H-NMR δ: 1.51 (3H, dd, J=2.5, 6.6 Hz, CH$_3$), 2.51–2.53 (1H, m, CH$_2$), 2.64–2.68 (1H, m, CH$_2$), 2.84–2.96(2H, m, CH$_2$), 4.46 (2H, d, J=13.4 Hz, CH$_2$), 4.60 (1H, s, CH$_2$), 4.65–4.68(1H, m, CH), 4.69 (1H, s, CH$_2$), 7.13 (1H, d, J=7.3 Hz, Ar—H), 7.17–7.39 (7H, m, Ar—H), 7.44–7.50 (3H, m, Ar—H), 7.67 (1H, t, J=7.3 Hz, Ar—H), 7.73 (1H, dd, J=3.7, 7.9 Hz, Ar—H), 7.86 (1H, d, J=7.3 Hz, Ar—H), 8.16 (1H, d, J=7.9 Hz, Ar—H).

Example 99

Synthesis of K-2252

To benzaldehyde (500 mg, 4.71 mmol) and 3-chlorobenzylamine (667.2 mg, 4.71 mmol, 1.0 mol eq.) was added titanium tetraisopropoxide (1.67 ml, 5.65 mmol, 1.2 mol eq.) and the mixture was stirred at room temperature for 4 hours. After the completion of the reaction, the reaction mixture was dissolved in ethanol and sodium boron hydride (712.7 mg, 18.84 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over.sodium sulfate and the solvent was distilled off under reduced pressure. The oil thus obtained was purified by column chromatography [silica gel, chloroform] to thereby give a colorless oil 211 (930.5 mg, 85.2%). MS m/z: 231.

The dibenzylamine compound 211 (500 mg, 2.16 mmol) and triethylamine (0.36 ml, 2.59 mmol, 1.2 mol eq.) were dissolved in chloroform and acryloyl chloride (214.8 mg, 2.37 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 212 (308.5 mg, 50.0%). MS m/z: 285.

The conjugated ketone compound 212 (100 mg, 0.35 mmol) and (R)-(+)-1-(1-naphthyl)ethylamine (71.8 mg, 0.42 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2252 (85.0 mg, 53.2%).

MS m/z: 456, $^1$H-NMR δ: 1.50 (3H, d, J=6.6 Hz, $CH_3$), 2.61(2H, dt, J=6.1, 21.0 Hz, $CH_2$), 2.82–2.96 (2H, m, $C\overline{H}_2$), 4.40 (2H, d, J=19.3 Hz, $CH_2$), $\overline{4.60}$ (2H, d, J=13.7 Hz, $C\overline{H}_2$), 4.66 (1H, q, J=6.6 Hz, $C\underline{H}$), 7.13 (2H, d, J=7.1 Hz, Ar—$\overline{H}$), 7.20–7.37 (7H, m, Ar—H), 7.43–7.51 (3H, m, Ar—H), 7.68 (1H, d, J=8.1 Hz, Ar—H), 7.73 (1H, d, J=8.1 Hz, Ar—H), 7.86 (1H, dd, J=2.2, 7.3 Hz, Ar—H), 8.17 (1H, d, J=7.6 Hz, Ar—H).

Example 100

Synthesis of K-2253

To 3-chlorobenzaldehyde (500 mg, 3.56 mmol) and 3-chlorobenzylamine (503.7 mg, 3.56 mmol, 1.0 mol eq.) was added titanium tetraisopropoxide (1.26 ml, 4.27 mmol, 1.2 mol eq.) and the mixture was stirred at room temperature for 4 hours. After the completion of the reaction, the reaction mixture was dissolved in ethanol and sodium boron hydride (538.7 mg, 14.24 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 213 (756.5 mg, 80.3%). MS m/z: 266.

The dibenzylamine compound 213 (500 mg, 1.88 mmol) and triethylamine (0.31 ml, 2.26 mmol, 1.2 mol eq.) were dissolved in chloroform and acryloyl chloride (187.1 g, 2.07 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 214 (595.3 mg, 98.8%). MS m/z: 320.

The conjugated ketone compound 214 (100 mg, 0.31 mmol) and (R)-(+)-1-(1-naphthyl)ethylamine (64.2 mg, 0.38 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2253 (96.5 mg, 62.9%).

MS m/z: 491, $^1$H-NMR δ: 1.51 (3H, d, J=6.1 Hz, $CH_3$), 2.58(2H, t, J=6.1 Hz, $CH_2$), 2.85–2.97 (2H, m, $CH_2$), $\overline{4.38}$ (2H, s, $CH_2$), 4.57 (2H, d, $\overline{J}$=3.1 Hz, $CH_2$), 4.65 (1$\overline{H, q}$, J=6.1 Hz, $C\underline{H}$), $\overline{6.99}$ (1H, d, J=5.5 Hz, Ar—$\overline{H}$), 7.08(1H, d, J=6.1 Hz, Ar—H), 7.11 (1H, s, Ar—H), 7.20 (1H, s, Ar—H), 7.23–7.27 (4H, m, Ar—H), 7.44–7.49 (3H, m, Ar—H), 7.67 (1H, d, J=7.3 Hz, Ar—H), 7.72 (1H, d, J=7.9 Hz, Ar—H), 7.85 (1H, d, J=7.9 Hz, Ar—H), 8.18 (1H, d, J=7.9 Hz, Ar—H).

Example 101

Synthesis of K-2254

To 2-chlorobenzaldehyde (500 mg, 3.56 mmol) and 2-chlorobenzylamine (503.6 mg, 3.56 mmol, 1.0 mol eq.) was added titanium tetraisopropoxide (1.25 ml, 4.27 mmol, 1.2 mol eq.) and the mixture was stirred at room temperature for 4 hours. After the completion of the reaction, the reaction mixture was dissolved in ethanol and sodium boron hydride (538.7 mg, 14.2 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 215 (632.6 mg, 66.9%). MS m/z: 266.

The dibenzylamine compound 215 (400 mg, 1.50 mmol) and triethylamine (0.25 ml, 1.80 mmol, 1.2 mol eq.) were dissolved in chloroform and acryloyl chloride (149.7 g, 1.65 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 216 (391.7 mg, 81.2%). MS m/z: 320.

The conjugated ketone compound 216 (100 mg, 0.31 mmol) and (R)-(+)-1-(1-naphthyl)ethylamine (64.2 mg, 0.38 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2254 (72.7 mg, 47.4%).

MS m/z: 491, $^1$H-NMR δ: 1.49 (3H, d, J=6.6 Hz, $CH_3$), 2.53–2.60 (2H, m, $CH_2$), 2.83–2.93 (2H, m, $CH_2$), 4.57 (2H, s, $CH_2$), 4.64 (1H, q, J=6.6 Hz, $CH_2$), 4.77(2H, s, $CH_2$), 7.13–7.38 (8H, m, Ar—H), 7.44–7.51 (3H, m, Ar—H), 7.66 (1H, d, J=6.6 Hz, Ar—H), 7.72 (1H, d, J=8.1 Hz, Ar—H), 7.85 (1H, dd, J=2.4, 7.1 Hz, Ar—H), 8.14 (1H, dd, J=2.2, 7.1 Hz, Ar—H).

Example 102

Synthesis of K-2256

To 4-fluorobenzaldehyde (483.2 mg, 3.90 mmol) and 4-fluorobenzylamine (500 mg, 3.90 mmol, 1.0 mol eq.) was added titanium tetraisopropoxide (1.38 ml, 4.68 mmol, 1.2 mol eq.) and the mixture was stirred at room temperature for 4 hours. After the completion of the reaction, the reaction mixture was dissolved in ethanol and sodium boron hydride (590.1 mg, 15.6 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 217 (783.2 mg, 84.0%). MS m/z: 233.

The dibenzylamine compound 217 (500 mg, 2.15 mmol) and triethylamine (0.36 ml, 2.58 mmol, 1.2 mol eq.) were dissolved in chloroform and acryloyl chloride (213.6 g, 2.36 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 218 (572.6 mg, 86.8%). MS m/z: 287.

The conjugated ketone compound 218 (800 mg, 1.63 mmol) and (R)-(+)-1-(1-naphthyl)ethylamine (33.7 mg, 1.95 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2256 (375.1 mg, 48.2%).

MS m/z: 458, $^1$H-NMR δ: 1.50 (3H, d, J=6.6 Hz, $CH_3$), 2.60(2H, t, J=6.1 Hz, $CH_2$), 2.84–2.96 (2H, m, $CH_2$), 4.36 (2H, s, $CH_2$), 4.54 (2H, s, $CH_2$), 4.66 (1H, q, J=6.6 Hz, $CH$), 6.95–7.09 (6H, m, Ar—H), 7.16 (1H, d, J=8.8 Hz, Ar—H), 7.17 (1H, d, J=8.8 Hz, Ar—H ), 7.43–7.51 (3H, m, Ar—H), 7.67 (1H, d, J=6.6 Hz, Ar—H), 7.73 (1H, d, J=8.3 Hz, Ar—H), 7.87 (1H, dd, J=2.4, 7.0 Hz, Ar—H), 8.17 (1H, dd, J=2.0, 7.3 Hz, Ar—H).

Example 103

Synthesis of K-2261

To 3-chlorobenzaldehyde (992.7 mg, 7.06 mmol) and 4-chlorobenzylamine (1 g, 7.06 mmol, 1.0 mol eq.) was added titanium tetraisopropoxide (2.5 ml, 8.47 mmol, 1.2 mol eq.) and the mixture was stirred at room temperature for 4 hours. After the completion of the reaction, the reaction mixture was dissolved in ethanol and sodium boron hydride (1.0683 g, 28.4 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 219 (1.5847 g, 84.4%). MS m/z: 266.

The dibenzylamine compound 219 (1.3 g, 4.89 mmol) and triethylamine (0.82 ml, 5.86 mmol, 1.2 mol eq.) were dissolved in chloroform and acryloyl chloride (486.6 mg, 5.38 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 220 (1.2967 g, 82.7%). MS m/z: 320.

The conjugated ketone compound 220 (1 g, 3.13 mmol) and (R)-(+)-1-(1-naphthyl)ethylamine (642.2 mg, 3.75 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2261 (624.8 mg, 40.7%).

MS m/z: 491, $^1$H-NMR δ: 1.50 (3H, d, J=6.6 Hz, $CH_3$), 2.54–2.63 (2H, m, $CH_2$), 2.82–2.96 (2H, m, $CH_2$), 4.36 (2H, d, J=4.4 Hz, $CH_2$), 4.55 (2H, d, J=2.9 Hz, $CH_2$), 4.65 (1H, q, J=6.6 Hz, $CH$), 7.04 (2H, d, J=8.6 Hz, Ar—H), 7.13 (2H, d, J=8.6 Hz, Ar—H), 7.18–7.31 (4H, m, Ar—H), 7.44–7.51 (3H, m, Ar—H), 7.67 (1H, d, J=7.3 Hz, Ar—H), 7.73 (1H, d, J=8.1 Hz, Ar—H), 7.85 (1H, dd, J=2.2 Hz, J=7.3 Hz, Ar—H), 8.16 (1H, d, J=7.6 Hz, Ar—H).

Example 104

Synthesis of K-2262 (N1-(2-chlorobenzyl)-N1-(4-chlorobenzyl)-3-{[(1R)-1-(1-naphthyl)ethyl]amino}propanamide)

To 2-chlorobenzaldehyde (992.7 mg, 7.06 mmol) and 4-chlorobenzylamine (1 g, 7.06 mmol, 1.0 mol eq.) was added titanium tetraisoprbpoxide (2.5 ml, 8.47 mmol, 1.2 mol eq.) and the mixture was stirred at room temperature for 4 hours. After the completion of the reaction, the reaction mixture was dissolved in ethanol and sodium boron hydride (1.0683 g, 28.4 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 221 (673.6 mg, 40%). MS m/z: 266.

The dibenzylamine compound 221 (600 mg, 2.26 mmol) and triethylamine (0.38 ml, 2.71 mmol, 1.2 mol eq.) were dissolved in chloroform and acryloyl chloride (224.6 mg, 2.48 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 222 (684.2 mg, 94.8%). MS m/z: 320.

The conjugated ketone compound 222 (500 mg, 1.56 mmol) and (R)-(+)-1-(1-naphthyl)ethylamine (321.1 mg, 1.88 mmol,1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2262 (552.4 mg, 72.0%).

MS m/z: 491, $^1$H-NMR δ: 1.56 (3H, d, J=6.6 Hz, $CH_3$), 2.51–2.72 (2H, m, $CH_2$), 2.83–2.98 (2H, m, $CH_2$), 4.43 (1H, s, $CH_2$), 4.48 (1H, s, $CH_2$), 4.56 (1H, d, J=4.5 Hz, $CH_2$), 4.68–4.72 (1H, m, CH), 4.73 (1H, d, J=5.6 Hz, $CH_2$), 7.05 (1H, d, J=8.3 Hz, Ar—H), 7.15 (1H, d, J=8.3 Hz, Ar—H), 7.20–7.39 (6H, m, Ar—H), 7.45–7.52(3H, m, Ar—H), 7.68 (1H, d, J=6.3 Hz, Ar—H), 7.75 (1H, d, J=8.3 Hz, Ar—H), 7.87(1H, d, J=7.1 Hz, Ar—H), 8.14 (1H, d, J=6.6 Hz, Ar—H).

Example 105

Synthesis of K-2264 (N1-(3,4-dichlorobenzyl)-N1-[(4-trifluoromethyl) benzyl]-3-{[(1R)-1-(1-naphthyl)ethyl]-amino}propanamide)

To 3,4-dichlcrobenzaldehyde (1 g, 5.71 mmol) and 4-trifluoromethylbenzylamine (1 g, 5.71 mmol, 1.0 mol eq.) was added titanium tetraisopropoxide (2.02 ml, 6.86 mmol, 1.2 mol eq.) and the mixture was stirred at room temperature for 4 hours. After the completion of the reaction, the reaction mixture was dissolved in ethanol and sodium boron hydride (864.6 mg, 22.86 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 223 (1.668 g, 87.4%).

MS m/z: 334, $^1$H-NMR d: 3.75 (2H, s, $CH_2$), 3.84(2H, s, $CH_2$), 7.17 (1H, dd, J=2.2, 8.3 Hz, Ar—H), 7.39 (2H, d, 8.3 Hz, Ar—H), 7.45 (1H, d, J=8.3 Hz, Ar—H), 7.46 (1H, d, J=2.2 Hz, Ar—H), 7.59 (2H, d, J=8.3 Hz, Ar—H).

The dibenzylamine compound 223 (800 mg, 2.39 mmol) and triethylamine (0.4 ml, 2.87 mmol, 1.2 mol eq.) were dissolved in chloroform and acryloyl chloride (238.4 mg, 2.63 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 224 (930 mg, 100.0%).

MS m/z: 388, $^1$H-NMR d: 4.54 (2H, d, J=42.0 Hz, $CH_2$), 4.64 (2H, d, J=39.0 Hz, $CH_2$), 5.79–5.82 (1H, m, CH=$CH_2$), 6.53–6.60 (2H, m, CH=$CH_2$), 7.23–7.45 (5H, m, Ar—H), 7.58 (1H, d, J=7.8 Hz, Ar—H), 7.63 (1H, d, J=7.8 Hz, Ar—H).

The conjugated ketone compound 224 (800 mg, 2.06 mmol) and (R)-(+)-1-(1-naphthyl)ethylamine (387.7 mg, 2.26 mmol, 1.1 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2264 (807.4 mg, 70.1%).

MS m/z: 559, $^1$H-NMR d: 1.51 (3H, d, J=6.6 Hz, $CH_3$), 2.59(2H, t, J=6.1 Hz, $CH_2$), 2.85–2.98 (2H, m, $CH_2$), 4.41 (2H, d, J=42.0 Hz, $CH_2$), 4.58 (2H, d, J=38.1 Hz, $CH_2$), 4.66 (1H, q, J=6.6 Hz, CH), 7.19 (1H, d, J=2.0 Hz, Ar—H), 7.22 (1H, d, J=8.3 Hz, Ar—H), 7.30 (2H, d, J=8.3 Hz, Ar—H), 7.44–7.52 (3H, m, Ar—H), 7.55 (1H, d, J=8.3 Hz, Ar—H), 7.59 (1H, d, J=8.3 Hz, Ar—H), 7.66 (1H, d, J=7.1 Hz, Ar—H), 7.74 (1H, d, J=8.3 Hz, Ar—H), 7.86 (1 H, dd, J=2.9, 6.6 Hz, Ar—H), 8.17 (1H, d, J=8.3 Hz, Ar—H).

Example 106

Synthesis of K-2265 (N1,N1-di(3,4-dichlorobenzyl)-3{[(1R)-1-(1-naphthyl)ethyl]amino}propanamide)

To 3,4-dichlorobenzaldehyde (500 mg, 2.86 mmol) and 3,4-dichlorobenzylamine (0.382 ml, 2.86 mmol) was added titanium tetraisopropoxide (1.51 ml, 5.14 mmol, 1.8 mol eq.) and the mixture was stirred at room temperature for 28 hours. After the completion of the reaction, the reaction mixture was dissolved in ethanol and sodium boron hydride (443 mg, 11.44 mmol, 4.0 mol eq.) was added thereto. Then the obtained mixture was stirred at room temperature for 20 hours. After the completion of the reaction, the solvent was distilled off under reduced pressure. To the obtained residue were added chloroform and water and the mixture was filtered through celite. The residue was washed with chloroform and the washing liquor was combined with the filtrate and extracted with chloroform. The chloroform layer was washed with water and a saturated aqueous solution of sodium chloride and dried over sodium sulfate and the solvent was distilled off under reduced pressure. The oil thus obtained was purified by column chromatography [silica gel, hexane:ethyl acetate (9:1-4:1)] to thereby give a colorless oil 225 (71.2.2 mg, 74.3%).

MS m/z: 335, $^1$H-NMR d: 3.74 (4H, d, J=2.7, $CH_2 \times 2$), 7.17 (2H, dd, J=2.0, 8.3 Hz, Ar—H), 7.39 (2H, d, J=8.3 Hz, Ar—H), 7.44 (2H, d, J=2.0 Hz, Ar—H).

The dibenzylamine compound 225 (315 mg, 0.94 mmol) and triethylamine (0.16 ml, 1.13 mmol, 1.2 mol eq.) were dissolved in chloroform and acryloyl chloride (94 mg, 1.04 mmol, 1.1 mol eq.) dissolved in chloroform was added thereto under ice-cooling. The reaction mixture was stirred at room temperature for 1 hour. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 226 (347.1 mg, 94.9%).

MS m/z: 389, $^1$H-NMR d: 4.47 (2H, s, $CH_2$), 4.58 (2H, s, $CH_2$), 5.58 (1H, dd, J=5.9, 6.6 Hz, CH=$CH_2$), 6.52 (1H, d, J=5.9 Hz, CH=$CH_2$), 6.52 (1H, d, J=6.6 Hz CH=$CH_2$), 6.99 (1H, d, J=7.6 Hz, Ar—H), 7.08 (1H, d, J=7.6 Hz, Ar—H), 7.23 (1H, s, Ar—H), 7.32 (1H, s, Ar—H), 7.39 (1H, d, J=7.8 Hz, Ar—H), 7.44 (1H, d, J=7.3 Hz, Ar—H).

The conjugated ketone compound 226 (280 mg, 0.72 mmol) and (R)-(+)-1-(1-naphthyl)ethylamine (148 mg, 0.864 mmol, 1.2 mol eq.) were dissolved in chloroform/methanol (4:1) and allowed to stand at room temperature for 8 days. After the completion of the reaction, the solvent was distilled off under reduced pressure and the oil thus obtained was purified by column chromatography [silica gel, chloroform] to thereby give a colorless oil K-2265 (314.1 mg, 77.9%). Subsequently, the obtained K-2265 (201.7 mg, 0.36 mmol) was dissolved in a 10% solution of hydrochloric acid/methanol and stirred for 10 minutes. Then it was concentrated as such under reduced pressure. The crystals thus formed were recrystallized from ethanol/water to thereby give K-2265 hydrochloride (188.2 mg, 87.6%) as colorless crystals.

MS m/z: 560, $^1$H-NMR d: 1.56 (3H, d, J=6.6 Hz, $CH_3$), 2.55–2.63 (2H, m, $CH_2$), 2.86–2.99 (2H, m, $CH_2$), 4.35 (2H, s, $CH_2$), 4.51 (2H, s, $CH_2$), 4.71 (1H, q, J=6.6 Hz, CH), 6.94 (1H, dd, J=2.2, 8.3 Hz, Ar—H), 7.04(1H, dd, J=2.2, 8.1 Hz, Ar—H), 7.18 (1H, d, J=2.0 Hz, Ar—H), 7.27 (1H, d, J=2.0 Hz, Ar—H), 7.37 (1H, d, J=8.1 Hz, Ar—H), 7.40 (1H, d, J=8.3 Hz, Ar—H), 7.45–7.52 (3H, m, Ar—H), 7.68 (1H, d, J=6.6 Hz, Ar—H), 7.75 (1H, d, J=8.1 Hz, Ar—H), 7.87 (1H, dd, J=2.2, 7.3 Hz, Ar—H), 8.15 (1H, d, J=7.3 Hz, Ar—H).

Example 107

Synthesis of K-2266 (N1-(4-chlorobenzyl)-N1-[(4-trifluoromethyl)benzyl]-3-{[(1R)-1-(1-naphthyl)ethyl]amino}propanamide)

To 4-(trifluoromethyl)benzaldehyde (1 g, 5.74 mmol) and 4-chlorobenzylamine (813.2 mg, 5.74 mmol, 1.0 mol eq.) was added titanium tetraisopropoxide (2.03 ml, 6.89 mmol, 1.2 mol eq.) and the mixture was stirred at room temperature for 4 hours. After the completion of the reaction, the reaction mixture was dissolved in ethanol and sodium boron hydride (868.6 mg, 22.96 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 227 (1.6267 g, 94.5%).

MS m/z: 299, $^1$H-NMR d: 3.77 (2H, s, $CH_2$), 3.84 (2H, s, $CH_2$), 7.27 (2H, d, J=9.0 Hz, Ar—H), 7.30 (2H, d, J=9.0 Hz, Ar—H), 7.46 (2H, d, J=8.1 Hz, Ar—H), 7.58 (2H, d, J=8.1 Hz, Ar—H).

The dibenzylamine compound 227 (800 mg, 2.67 mmol) and triethylamine (0.45 ml, 3.20 mmol, 1.2 mol eq.) were dissolved in chloroform and acryloyl chloride (265.7 mg, 2.94 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 228 (938.5 mg, 99.3%).

MS m/z: 353, $^1$H-NMR d: 4.53 (2H, d, J=26.8 Hz, $CH_2$), 4.65 (2H, d, J=24.4 Hz, $CH_2$), 5.79 (1H, dd, J=2.4, 9.8 Hz, CH=$CH_2$), 6.50 (1H, dd, J=2.4, 16.6 Hz, CH=$CH_2$), 6.59 (1H, dd, J=9.8, 16.6 Hz, CH=$CH_2$), 7.10 (1H, d, J=8.3 Hz, Ar—H), 7.19 (1H, d, J=8.3 Hz, Ar—H), 7.27 (1H, d, J=8.3 Hz, Ar—H), 7.29 (1H, d, J=8.3 Hz, Ar—H), 7.34 (1H, d, J=7.8 Hz, Ar—H), 7.36 (1H, d, J=6.5 Hz, Ar—H), 7.57 (1H, d, J=7.8 Hz, Ar—H), 7.62 (1H, d, J=7.8 Hz, Ar—H).

The conjugated ketone compound 228 (800 mg, 2.26 mmol) and (R)-(+)-1-(1-naphthyl)ethylamine (425.4 mg, 2.48 mmol, 1.1 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2266 (981.5 mg, 82.8%).

MS m/z: 524, $^1$H-NMR d: 1.52 (3H, d, J=6.6 Hz, $CH_3$), 2.57–2.64 (2H, m, $CH_2$), 2.84–2.97 (2H, m, $CH_2$), 4.41 (2H, d, J=23.9 Hz, $CH_2$), 4.59 (2H, d, J=24.9 Hz, $CH_2$), 4.67 (1H, q, J=6.6 Hz, CH), 7.04 (1H, d, J=8.3 Hz, Ar—H), 7.13 (1H, d, J=8.3 Hz, Ar—H), 7.21 (1H, d, J=8.3 Hz, Ar—H), 7.26–7.31 (3H, m, Ar—H), 7.44–7.51 (3H, m, Ar—H), 7.55 (1H, d, J=8.1 Hz, Ar—H), 7.59 (1H, d, J=8.1 Hz, Ar—H), 7.67 (1H, dd, J=3.0, 6.6 Hz, Ar—H), 7.74 (1H, d, J=8.1 Hz, Ar—H); 7.87 (1H dd, J=2.0, 8.1 Hz, Ar—H), 8.17 (1H, d, J=8.1 Hz, Ar—H).

Example 108

Synthesis of K-2267 (N1-(4-chlorobenzyl)-N1-(3,4-dichlorobenzyl)-3-{[(1R)-1 (1-naphthyl)ethyl]amino}propanamide)

4-Chlorobenzylamine (1 g, 7.06 mmol) and 3,4-dichlorobenzaldehyde (1.36 g, 7.77 mmol, 1.1 mol eq.) were dissolved in methanol and MgSO₄ (1.02 g, 8.47 mmol, 1.2 mol eq.) and AcOH (10 drops) were added thereto. Then the obtained mixture was stirred at room temperature for 2 hours. After the completion of the reaction, sodium boron hydride (334.0 mg, 8.83 mmol, 1.25 mol eq.) was added under ice-cooling to the reaction mixture. Then the obtained mixture was stirred at room temperature for 12 hours. After the completion of the reaction, the solvent was distilled off under reduced pressure. The obtained residue was extracted with ethyl acetate. The ethyl acetate layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, chloroform] to thereby give a colorless oil 229 (1.6777 g, 79.2%).

MS m/z: 279, ¹H-NMR d: 3.72 (2H, s, C$\underline{H}_2$), 3.73 (2H, s, C$\underline{H}_2$), 7.15 (1H, dd, J=2.0, 8.1 Hz, Ar—$\overline{H}$), 7.24 (2H, d, J=8.8 Hz, Ar—H), 7.29 (2H, d, J=8.8 Hz, Ar—H), 7.38 (1H, d, J=8.1 Hz, Ar—H), 7.43 (1H, d, J=2.0 Hz, Ar—H).

The dibenzylamine compound 229 (800 mg, 2.66 mmol) and triethylamine (0.45 ml, 3.19 mmol, 1.2 mol eq.) were dissolved in chloroform and acryloyl chloride (265 mg, 2.93 mmol, 1.1 mol eq.) dissolved in chloroform was added thereto under ice-cooling. The reaction mixture was stirred at room temperature for 30 minutes. After the completion of.the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 230 (768.9 mg, 81.4%).

MS m/z: 333, ¹H-NMR d: 4.47 (2H, d, J=13.4 Hz, C$\underline{H}_2$), 4.57 (2H, d, J=13.9 Hz, C$\underline{H}_2$), 5.79 (1H, dd, J=3.2, 9.0 $\overline{Hz}$, CH=C$\underline{H}_2$), 6.50 (1H, dd, $\overline{J}$=3.2, 16.6 Hz, C$\underline{H}$=CH₂), 6.57 (1H, d$\overline{d}$, J=9.0, 16.6 Hz, CH=CH₂), 7.08–7.46 (7H, m, Ar—H).

The conjugated ketone compound 230 (600 mg, 1.69 mmol) and (R)-(+)-1-(1-naphthyl)ethylamine (347.2 mg, 2.03 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2267 (721.3 mg, 81.1%).

MS m/z: 504, ¹H-NMR d: 1.51 (3H, d, J=6.6 Hz, CH₃), 2.55–2.62 (2H, m, C$\underline{H}_2$), 2.84–2.97 (2H, m, C$\underline{H}_2$), 4.35 ($\overline{2H}$, d, J=18.3 Hz, C$\underline{H}_2$), 4.52 (2H, d, J=12.9 Hz, C$\underline{H}_2$), 4.66 (1H, q, J=6.6 Hz, C$\underline{H}$), 7.04 (2H, d, J=8.3 Hz, Ar—$\overline{H}$), 7.13 (1H, d, J=8.3 Hz, Ar—H), 7.27–7.29 (1H, m, Ar-H), 7.31 (1H, d, J=8.3 Hz, Ar—H), 7.36 (1H, d, J=8.1 Hz, Ar—H), 7.39 (1 H, d, J=8.1 Hz, Ar—H), 7.45–7.50 (3H, m, Ar—H), 7.66 (1H, d, J=7.1 Hz, Ar—H), 7.74 (1H, d, J=8.3 Hz, Ar—H), 7.87 (1H, dd, J=2.2, 8.3 Hz, Ar—H), 8.17 (1H, d, J=7.1 Hz, Ar—H).

Example 109

Synthesis of K-2270 (N1,N1-di(4-methoxybenzyl)-3-{[(1R)-1-(1-naphthyl)ethyl]amino}propanamide)

To 4-anisaldehyde (0.447 ml, 3.67 mmol) and 4-methoxybenzylamine (0.479 ml, 3.67 mmol, 1.0 mol eq.) was added titanium tetraisopropoxide (1.30 ml, 4.40 mmol, 1.2 mol eq.) and the mixture was stirred at room temperature for 10 hours. After the completion of the reaction, the reaction mixture was dissolved in ethanol and sodium boron hydride (555 mg, 14.68 mmol, 4.0 mol eq.) was added thereto. Then the obtained mixture was stirred at room temperature for 12 hours. After the completion of the reaction, the solvent was distilled off under reduced pressure. To the obtained residue were added ethyl acetate and water and the mixture was filtered through celite. The residue was washed with ethyl acetate and the washing liquor was combined with the fiitrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 231 (762.7 mg, 80.9%).

MS m/z: 257, ¹H-NMR d: 3.73 (4H, s, C$\underline{H}_2$), 3.80 (6H, s, OCH₃), 6.86 (4H, d, J=8.5 Hz, Ar—H), 7.25 (4H, d, J=8.5 Hz,$\overline{Ar}$—H).

The dibenzylamine compound 231 (500 mg, 1.95 mmol) and triethylamine (0.33 ml, 2.33 mmol, 1.2 mol eq.) were dissolved in chloroform and acryloyl chloride (195 mg, 2.15 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 232 (602.8 mg, 99.4%).

MS m/z: 311, ¹H-NMR d: 3.80 (3H, s, OCH₃), 3.81 (3H, s, OCH₃), 4.43 (2H, s, C$\underline{H}_2$), 4.56 (2H, s, C$\underline{H}_2$), 5.73 (1H, dd, J=2.2,$\overline{10}$.2 Hz, CH=C$\overline{H}_2$), 6.48 (1H, d$\overline{d}$, J=2.2, 16.6 Hz, C$\underline{H}$=CH₂), 6.62 (1H, d$\overline{d}$, J=10.2, 16.6 Hz, CH=CH₂), 6.85 (2H, d, J=8.5 Hz, Ar—H), 6.88 (3H, d, J=8.5 Hz,$\overline{Ar}$—H), 7.08 (2H, d, J=8.5 Hz, Ar—H), 7.19 (1H, d, J=8.5 Hz, Ar—H).

The conjugated ketone compound 232 (450 mg, 1.45 mmol) and (R)-(+)-1-(1-naphthyl)ethylamine (297 mg, 1.74 mmol, 1.2 mol eq.) were dissolved in chloroform/methanol (4:1) and allowed to stand at room temperature for 2 weeks. After the completion of the reaction, the solvent was distilled off under reduced pressure and the oil thus obtained was purified by column chromatography [silica gel, chloroform] to thereby give a colorless oil K-2270 (366.9 mg, 52.5%). Subsequently, the obtained K-2270 (244.5 mg, 0.51 mmol) was dissolved in a 10% solution of hydrochloric acid/methanol and stirred for 10 minutes. Then it was concentrated as such under reduced pressure. The crystals thus formed were recrystallized from ethanol/water to thereby give K-2270 hydrochloride (150.7 mg, 57.3%) as colorless crystals.

MS m/z: 482, ¹H-NMR d: 1.58 (3H, d, J=6.6 Hz, CH₃), 2.63–2.75 (2H, m, C$\underline{H}_2$), 2.86–2.98 (2H, m, C$\underline{H}_2$), 3.79 ($\overline{3H}$, s, OCH₃), 3.80 (3H, s,$\overline{OCH}_3$), 4.32 (2H, s, C$\underline{H}_2$), 4.48 (1H, d, J=1$\overline{4.5}$ Hz, C$\underline{H}_2$), 4.55 (1$\overline{H}$, d, J=14.5 Hz, C$\underline{H}_2$), 4.75 (1H, q, J=6.6 Hz, C$\underline{H}$), 6.83 (2H, d, J=8.8 Hz, Ar—$\overline{H}$), 6.86 (2H, d, J=8.6 Hz, Ar—H), 7.03 (2H, d, J=8.5 Hz, Ar—H), 7.14 (2H, d, J=8.5 Hz, Ar—H), 7.46–7.53 (3H, m, Ar—H), 7.74 (1H, d, J=7.8 Hz, Ar—H), 7.76 (1H, d, J=8.8 Hz, Ar—H), 7.88 (1H, d, J=7.6 Hz, Ar—H), 8.15 (1H, d, J=8.1 Hz, Ar—H).

Example 110

Synthesis of K-2272 (N1-(3,4-dichlorobenzyl)-N1-[4-(trifluoromethoxy) benzyl)-3-{[(1R)-1-(1-naphthyl) ethyl]-amino}propanamide)

3,4-Dichlorobenzylamine (0.379 ml, 2.84 mmol) and 4-(trifluoromethoxy)benzaldehyde (503.6 mg, 3.56 mmol, 1.0 mol eq.) were dissolved in methanol and MgSO$_4$ (410.2 mg, 3.41 mmol, 1.2 mol eq.) and AcOH (3 drops) were added thereto. Then the obtained mixture was stirred at room temperature for 30 minutes. After the completion of the reaction, sodium boron hydride (134 mg, 3.55 mmol, 1.25 mol eq.) was added to the reaction mixture. Then the obtained mixture was stirred at room temperature for 10 minutes. After the completion of the reaction, the solvent was distilled off under reduced pressure. The obtained residue was extracted with chloroform. The chloroform layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography (silica gel, hexane : ethyl acetate (9:1-4:1)] to thereby give a colorless oil 233 (777.3 mg, 78.2%).

MS m/z: 350, $^1$H-NMR d: 3.76 (2H, s, C$\underline{H}_2$), 3.79 (2H, s, C$\underline{H}_2$), 7.18 (1H, dd, J=2.0, 8.5 Hz, Ar—$\underline{H}$), 7.18 (2H, d, J=8.5 Hz, Ar—H), 7.36 (2H, d, J=8.5 Hz, Ar—H), 7.39 (1H, d, J=8.5 Hz, Ar—H), 7.46 (1H, d, J=2.0 Hz, Ar—H).

The dibenzylamine compound 233 (500 mg, 1.43 mmol) and triethylamine (0.238 ml, 1.71 mmol, 1.2 mol eq.) were dissolved in chloroform and acryloyl chloride (142 mg, 1.57 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 234 (454.6 mg, 78.7%).

MS m/z: 404, $^1$H-NMR d: 4.50 (2H, d, J=19.0 Hz, C$\underline{H}_2$), 4.61 (2H, d, J=21.7 Hz, C$\underline{H}_2$), 5.80 (1H, dd, J=1.7, 9.5 Hz, CH=C$\underline{H}_2$), 6.53 (1H, d, J=1.7, 16.6 Hz, C$\underline{H}$=CH$_2$), 6.58 (1H, d, J=9.5, 16.6 Hz, CH=CH$_2$), 7.16-7.22 (5H, m, Ar—H), 7.32 (1H, s, Ar—H), 7.41 (1H, d, J=8.3 Hz, Ar—H).

The conjugated ketone compound 234 (350 mg, 0.87 mmol) and (R)-(+)-1-(1-naphthyl)ethylamine (178 mg, 1.04 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2272 (360.7 mg, 72.4%). Subsequently, the obtained K-2272 (250 mg, 0.435 mmol) was dissolved in a 10% solution of hydrochloric acid/methanol and stirred for 10 minutes. Then it was concentrated as such under reduced pressure. The crystals thus formed were recrystallized from ethanol/water to thereby give K-2270 hydrochloride (230.2 mg, 86.5%) as colorless crystals.

MS m/z: 575, $^1$H-NMR d: 1.60 (3H, d, J=6.6 Hz, CH$_3$), 2.60-2.76 (2H, m, CH$_2$), 2.88-3.02 (2H, m, CH$_2$), 4.37 (2H, d, J=22.7 Hz, C$\underline{H}_2$), 4.51 (1H, d, J=2.4 Hz, C$\underline{H}_2$), 4.57 (1H, d, J=6.1 Hz, C$\underline{H}_2$), 4.72-4.82 (1H, m, C$\underline{H}$), 7.13 (1H, d, J=8.8 Hz, Ar—H), 7.15 (1H, d, J=7.3 Hz, Ar—H), 7.17 (1H, d, J=6.8 Hz, Ar—H), 7.19 (1H, d, J=8.8 Hz, Ar—H), 7.22 (1H, d, J=8.8 Hz, Ar—H), 7.28 (1H, d, J=2.0 Hz, Ar—H), 7.37 (1H, d, J=8.3 Hz, Ar—H), 7.38 (1H, dd, J=8.3, 9.3 Hz, Ar—H), 7.47-7.55 (3H, m, Ar—H), 7.72 (1H, d, J=7.1 Hz, Ar—H), 7.77 (1H, d, J=8.1 Hz, Ar—H), 7.88 (1H, dd, J=2.0, 7.8 Hz, Ar—H), 8.14 (1H, d, J=7.8 Hz, Ar—H).

Example 111

Synthesis of K-2283 (N1-(4-chlorobenzyl)-N1-[4-(triflucromethoxy)benzyl)-3-{[(1R)-1-(1-naphthyl) ethyl]-amino}propanamide)

4-(Trifluoromethoxy)benzaldehyde (0.555 ml, 3.88 mmol, 1.1 mol eq.) and 4-chlorobenzylamine (0.430 ml, 3.53 mmol) were dissolved in methanol and MgSO$_4$ (509:89 mg, 4.24 mmol, 1.2 mol eq.) and AcOH (3 drops) were added thereto. Then the obtained mixture was stirred at room temperature for 10 minutes. After the completion of the reaction, sodium boron hydride (167 mg, 4.41 mmol, 1.25 mol eq.) was added to the reaction mixture. Then the obtained mixture was stirred at room temperature for 10 minutes. After the completion of the reaction, the solvent was distilled off under reduced pressure. The obtained residue was extracted with chloroform. The chloroform layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, hexane: ethyl acetate (9:1-4:1)] to thereby give a colorless oil 235 (1.092 g, 98.1%).

MS m/z: 315, $^1$H-NMR d: 3.77 (2H, s, C$\underline{H}_2$), 3.79 (2H, s, C$\underline{H}_2$), 7.18 (2H, d, J=7.8 Hz, Ar—H), 7.29 (4$\underline{H}$, d, J=2.2 Hz, Ar—H), 7.37 (2H, d, J=8.9 Hz, Ar—H).

The dibenzylamine compound 235 (500 mg, 1.58 mmol) and triethylamine (0.265 ml, 1.90 mmol, 1.2 mol eq.) were dissolved in chloroform and acryloyl chloride (158 mg, 1.74 mmol, 1.1 mol eq.) dissolved in chloroform was added thereto under ice-cooling. The reaction mixture was stirred at room temperature for 40 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 236 (521.3 mg, 89.3%).

MS m/z: 369, $^1$H-NMR d: 4.50 (2H, d, J=4.9 Hz, C$\underline{H}_2$), 4.61 (2H, d, J=8.1 Hz, C$\underline{H}_2$), 5.78 (1H, dd, J=2.7, 9.5 Hz, CH=C$\underline{H}_2$), 6.50 (1H, dd, J=2.7, 16.6 Hz, C$\underline{H}$=CH$_2$), 6.57 (1H, dd, J=9.5, 16.6 Hz, CH=CH$_2$), 7.09 (1H, d, J=8.3 Hz, Ar—H), 7.15-7.21 (4H, m, Ar—H), 7.27 (1H, d, J=8.1 Hz, Ar—H), 7.28 (1H, d, J=8.1 Hz, Ar—H), 7.33 (1H, d, J=8.1 Hz, Ar—H).

The conjugated ketone compound 236 (400 mg, 1.08 mmol) and (R)-(+)-1-(1-naphthyl)ethylamine (222 mg, 1.30 mmol, 1.2 mol eq.) were dissolved in chloroform/methanol (4:1) and allowed to stand at room temperature for 8 days. After the completion of the reaction, the solvent was distilled off under reduced pressure and the oil thus obtained was purified by column chromatography [silica gel, chloroform] to thereby give a colorless oil K-2283 (452.0 mg, 77.4%). Subsequently, the obtained K-2283 (248.9 mg, 0.46 mmol) was dissolved in a 10% solution of hydrochloric acid/methanol and stirred for 15 minutes. Then it was concentrated as such under reduced pressure. The crystals thus formed were washed with diethyl ether to thereby give K-2283 hydrochloride (235.0 mg, 88.5%) as colorless crystals.

MS m/z: 540, $^1$H-NMR d: 1.60 (3H, d, J=6.3 Hz, CH$_3$), 2.62-2.74 (2H, m, CH$_2$), 2.87-2.99 (2H, m, CH$_2$), 4.38 (2H, d, J=4.9 Hz, C$\underline{H}_2$), 4.55 (2H, t, J=8.3 Hz, C$\underline{H}_2$), 4.75-4.80 (1H, m, C$\underline{H}$), 7.04 (1H, d, J=8.5 Hz, Ar—H), 7.12 (2H, d, J=8.5 Hz, Ar—H), 7.14 (1H, d, J=8.5 Hz, Ar—H), 7.22 (1H, d, J=8.5 Hz, Ar—H), 7.27 (2H, d, J=8.5 Hz, Ar—H), 7.30 (1H, d, J=8.5 Hz, Ar—H), 7.45–7.53 (3H, m, Ar—H), 7.72 (1H, d, J=7.1 Hz, Ar—H), 7.77 (1H, d, J=8.1 Hz, Ar—H), 7.88 (1H, dd, J=2.0, 7.3 Hz, Ar—H), 8.14 (1H, d, J=7.8 Hz, Ar—H).

Example 112

Synthesis of K-2289 (N1-(4-chlorobenzyl)-N1-(4-methoxybenzyl)-3-{[(1R)-1-(1-naphthyl)ethyl]amino}propanamide)

4-Chlorobenzaldehyde (564 mg, 4.01 mmol, 1.1 mol eq.) and 4-methoxybenzylamine (476 mg, 3.64 mmol) were dissolved in methanol and $MgSO_4$ (525.8 mg, 4.37 mmol, 3.64 mol eq.) and AcOH (5 drops) were added thereto. Then the obtained mixture was stirred at room temperature for 40 minutes. After the completion of the reaction, sodium boron hydride (172 mg, 4.55 mmol, 1.25 mol eq.) was added to the reaction mixture. Then the obtained mixture was stirred at room temperature for 15 minutes. After the completion of the reaction, the solvent was distilled off under reduced pressure. The obtained residue was extracted with chloroform. The chloroform layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, hexane: ethyl acetate (9:1-4:1)] to thereby give a colorless oil 237 (711.8 mg, 74.8%).

MS m/z: 261, $^1$H-NMR d: 3.72 (2H, s, $CH_2$), 3.75 (2H, s, $CH_2$) 3.80 (3H, s, $OCH_3$), 6.86 (2H, d, J=8.5 Hz, Ar—H), 7.24 (2H, d, J=8.5 Hz, Ar—H), 7.28 (4H, d, J=2.2 Hz, Ar—H).

The dibenzylamine compound 237 (501.4 mg, 1.92 mmol) and triethylamine (0.32 ml, 2.30 mmol, 1.2 mol eq.) were dissolved in chloroform and acryloyl chloride (191 mg, 2.11 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 238 (557.2 mg, 91.9%).

MS m/z: 315, $^1$H-NMR d: 3.80 (3H, d, J=5.4 Hz, $OCH_3$), 4.44 (2H, d, J=8.5 Hz, $CH_2$), 4.57 (2H, d, J=4.1 Hz, $CH_2$), 5.75 (1H, dd, J=1.7, 10.3 Hz, CH=$CH_2$), 6.48 (1H, dd, J=1.7, 16.6 Hz, CH=$CH_2$), 6.64 (1H, dd, J=10.3, 16.6 Hz, CH=$CH_2$), 6.85 (1H, d, J=8.3 Hz, Ar—H), 6.88 (1H, d, J=8.5 Hz, Ar—H), 7.07 (1H, d, J=8.3 Hz, Ar—H), 7.08 (1H, d, J=6.3 Hz, Ar—H), 7.17 (1H, d, J=8.8 Hz, Ar—H), 7.19 (1H, d, J=8.3 Hz, Ar—H), 7.28 (1H, d, J=8.5 Hz, Ar—H), 7.32 (2H, d, J=7.8 Hz, Ar—H).

The conjugated ketone compound 238 (414 mg, 1.31 rnmol) and (R)-(+)-1-(1-naphthyl)ethylamine (270.mg, 1.57 mmol, 1.2 mol eq.) were dissolved in chloroform/methanol (4:1) and allowed to stand at room temperature for 12 days. After the completion of the reaction, the solvent was distilled off under reduced pressure and the oil thus obtained was purified by column chromatography [silica gel, chloroform] to thereby give a colorless oil K-2289 (441.8 mg, 69.3%). Subsequently, the obtained K-2289 (269.4 mg, 0.55 mmol) was dissolved in a 10% solution of hydrochloric acid/methanol and stirred for 10 minutes. Then it was concentrated as such under reduced pressure. The crystals thus formed were recrystallized from ethanol/water to thereby give K-2289 hydrochloride (270.1 mg, 93.2%) as colorless crystals.

MS m/z: 486, $^1$H-NMR d: 1.56 (3H, d, J=6.6 Hz, $CH_3$), 2.57–2.70 (2H, m, $CH_2$), 2.84–2.95 (2H, m, $CH_2$), 3.80 (3H, d, J=2.2 Hz, $OCH_3$), 4.33 (2H, d, J=5.4 Hz, $CH_2$), 4.52 (2H, t, J=6.6 Hz, $CH_2$), 4.70–4.74 (1H, m, CH), 6.83 (1H, d, J=9.0 Hz, Ar—H), 6.85 (1H, d, J=9.0 Hz, Ar—H), 7.02 (1H, d, J=8.5 Hz, Ar—H), 7.03 (1H, d, J=8.5 Hz, Ar—H), 7.12 (1H, d, J=8.5 Hz, Ar—H), 7.13 (1H, d, J=8.3 Hz, Ar—H), 7.27 (1H, d, J=8.5 Hz, Ar—H), 7.29 (1H, d, J=8.5 Hz, Ar—H), 7.46–7.52 (3H, m, Ar—H), 7.71 (1H, dd, J=3.4, 6.8 Hz, Ar—H), 7.75 (1H, d, J=8.3 Hz, Ar—H), 7.87 (1H, d, J=7.6 Hz, Ar—H), 8.15 (1H, d, J=7.6 Hz, Ar—H).

Example 113

Synthesis of K-2290 (N1-(4-methoxybenzyl)-N1-[4-(trifluoromethyl) benzyl)-3-{[(1R)-1-(1-naphthyl)ethyl]amino}propanamide)

4-(Trifluoromethyl)benzaldehyde (1.269 g, 7.29 mmol) and 4-methoxybenzylamine (1 g, 7.29 mmol, 1.0 mol eq.) were dissolved in methanol and $MgSO_4$ (1.0530 g, 8.75 mmol, 1.2 mol eq.) and AcOH (10 drops) were added thereto. Then the obtained mixture was stirred at room temperature for 2 hours. After the completion of the reaction, the reaction mixture was dissolved in methanol and sodium boron hydride (344.7 mg, 9.11 mmol, 1.25 mol eq.) was added thereto. Then the obtained mixture was stirred at room temperature for 12 hours. After the completion of the reaction, the solvent was distilled off under reduced pressure. The obtained residue was extracted with ethyl acetate. The ethyl acetate layer was washed with a saturated aqueous solution of sodium hydrogencarbonate, water and a saturated aqueous solution of sodium chloride and dried over sodium suifate and the solvent was distilled off under reduced pressure. The oil thus obtained was purified by column chromatography [silica gel, chloroform] to thereby give a colorless oil 239 (1.40 g, 65.0%).

MS m/z: 295, $^1$H-NMR d: 3.73 (2H, s, $CH_2$), 3.80 (3H, s, $OCH_3$), 3.83 (2H, s, $CH_2$), 6.87 (2H, d, J=8.5 Hz, Ar—H), 7.24 (2H, d, J=8.5 Hz, Ar—H), 7.45 (2H, d, J=3.5 Hz, Ar—H), 7.57 (1H, d, J=8.5 Hz, Ar—H), 7.59 (1H, d, J=8.5 Hz, Ar—H).

The dibenzylamine compound 239 (1.30 g, 4.40 mmol) and triethylamine (0.74 ml, 5.28 mmol, 1.2 mol eq.) were dissolved in chloroform and acryloyl chloride (438.3 mg, 4.84 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 240 (974.7 mg, 63.5%).

MS m/z: 349, $^1$H-NMR d: 3.80 (3H, d, J=4.9 Hz, $OCH_3$), 4.53 (2H, d, J=52.0 Hz, $CH_2$), 4.61 (2H, d, J=45.1 Hz, $CH_2$), 5.77 (1H, dd, J=2.0, 10.5 Hz, CH=$CH_2$), 6.49 (1H, dd, J=2.0, 16.6 Hz, CH=$CH_2$), 6.65 (1H, dd, J=10.5, 16.6 Hz, CH=$CH_2$), 6.85 (1H, d, J=8.3 Hz, Ar—H), 6.89 (1 H, d, J=8.5 Hz, Ar—H), 7.07 (1H, d, J=8.3 Hz, Ar—H), 7.17 (1H, d, J=8.1 Hz, Ar—H), 7.27 (1H, d, J=6.8 Hz, Ar—H), 7.35 (1H, d, J=7.8 Hz, Ar—H), 7.56 (1H, d, J=8.1 Hz, Ar—H), 7.61 (1H, d, J=7.3 Hz, Ar—H).

The conjugated ketone compound 240 (874.7 mg, 2.50 mmol) and (R)-(+)-1-(1-naphthyl)ethylamine (513.9 mg, 3.00 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2290 (1.005 g, 77.2%).

MS m/z: 520, $^1$H-NMR d: 1.51 (3H, dd, J=3.0, 6.6 Hz, $CH_3$), 2.55 (1H, t, J=6.1 Hz, $CH_2$), 2.67 (1H, t, J=6.1 Hz, $CH_2$), 2.82–2.98 (2H, m, $CH_2$), 3.79 (3H, d, J=4.6 Hz, $OCH_3$), 4.39 (2H, d, J=28.3 Hz, $CH_2$), 4.57 (2H, d, J=30.0 Hz, $CH_2$), 4.64–4.70 (1H, m, $CH$), 6.83 (1H, d, J=8.8 Hz, Ar—H), 6.86 (1H, d, J=8.8 Hz, Ar—H), 7.03 (1H, d, J=8.8 Hz, Ar—H), 7.12 (1H, d, J=8.6 Hz, Ar—H), 7.21 (1H, d, J=8.1 Hz, Ar—H), 7.30 (1H, d, J=8.3 Hz, Ar—H), 7.43–7.51 (3H, m, Ar—H), 7.54 (1H, d, J=8.3 Hz, Ar—H), 7.57 (1H, d, J=8.1 Hz, Ar—H), 7.68 (1H, t, J=7.6 Hz, Ar—H), 7.73 (1H, dd, J=3.7, 8.1 Hz, Ar—H), 7.86 (1H, dd, J=2.4, 7.3 Hz, Ar—H), 8.17 (1H, d, J=7.6 Hz, Ar—H).

Example 114

Synthesis of K-2291 (N1-(4-chlorobenzyl)-N1-(2-naphthylmethyl)-3-{[(1R)-1-(1-naphthyl)ethyl]amino}propanamide)

To 2-naphthaldehyde (500 mg, 3.20 mmol) and 4-chlorobenzylamine (0.389 ml, 3.20 mmol, 1.0 mol eq.) was added titanium isopropoxide (1.70 ml, 5.76 mmol, 1.8 mol eq.) and the obtained mixture was stirred at room temperature for 4 hours. After the completion of the reaction, the reaction mixture was dissolved in ethanol and sodium boron hydride (485 mg, 12.82 mmol, 4.0 mol eq.) was added thereto. Then the obtained mixture was stirred. at room temperature for 29 hours. After the completion of the reaction, the solvent was distilled off under reduced pressure. To the obtained residue were added ethyl acetate and water and the mixture was filtered through celite. The residue was washed with ethyl acetate and the washing liquor was combined with the filtrate and extracted with ethyl acetate. The ethyl acetate layer was washed with water and a saturated aqueous solution of sodium chloride and dried over sodium sulfate and the solvent was distilled off under reduced pressure. The oil thus obtained was purified by column chromatography [silica gel, chloroform] to thereby give a colorless oil 241 (767.4 mg, 85.2%).

MS m/z: 281, $^1$H-NMR d: 3.80 (2H, s, $CH_2$), 3.95 (2H, s, $CH_2$), 7.26 (2H, d, J=12.0 Hz, Ar—H), 7.31 (2H, d, J=12.0 Hz, Ar—H), 7.42–7.49 (3H, m, Ar—H), 7.75 (1H, s, Ar—H), 7.81 (1H, d, J=8.1 Hz, Ar—H), 7.82 (1H, d, J=8.5 Hz, Ar—H), 7.83 (1H, d, J=8.1 Hz, Ar—H).

The dibenzylamine compound 241 (506.7 mg, 1.80 mmol) and triethylamine (0.301 ml, 2.16 mmol, 1.2 mol eq.) were dissolved in chloroform and acryloyl chloride (179 mg, 1.98 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 242 (652.4 mg, 100%).

MS m/z: 335, $^1$H-NMR d: 4.58 (2H, d, J=65.9 Hz, $CH_2$), 4.74 (2H, d, J=52.0 Hz, $CH_2$), 5.76 (1H, dd, J=2.0, 10.2 Hz, CH=$CH_2$), 6.53 (1H, dd, J=2.0, 16.6 Hz, $CH$=$CH_2$), 6.54 (1H, dd, J=10.2, 16.6 Hz, CH=$CH_2$), 7.10 (1H, d, J=8.1 Hz, Ar—H), 7.21–7.35 (4H, m, Ar—H), 7.47–7.62 (3H, m, Ar—H), 7.79–7.86 (3H, m, Ar—H).

The conjugated ketone compound 242 (500 mg, 1.49 mmol) and (R)-(+)-1-(1-naphthyl)ethylamine (307 mg, 1.79 mmol, 1.2 mol eq.) were dissolved in chloroform/methanol (4:1) and allowed to stand at room temperature for 13 days. After the completion of the reaction, the solvent was distilled off under reduced pressure and the oil thus obtained was purified by column chromatography [silica gel, chloroform] to thereby give a colorless oil K-2291 (521.1 g, 69.0%). Subsequently, the obtained K-2291 (394.1 mg, 0.78 mmol) was dissolved in a 10 solution of hydrochloric acid/methanol and stirred for 15 minutes. Then it was concentrated as such under reduced pressure. The crystals thus formed were recrystallized from ethanol/water to thereby give K-2291 hydrochloride (358.7 mg, 85.1%) as colorless crystals.

MS m/z: 506, $^1$H-NMR d: 1.56 (3H, d, J=6.8 Hz, $CH_3$), 2.61–2.76 (2H, m, $CH_2$), 2.88–3.01 (2H, m, $CH_2$), 4.38 (1H, s, $CH_2$), 4.55 (1H, s, $CH_2$), 4.62 (1H, d, J=3.7 Hz, $CH_2$), 4.75 (1H, d, J=6.8 Hz, $CH_2$), 4.70–4.76 (1H, m, $CH$), 7.05 (1H, d, J=8.5 Hz, Ar—H), 7.16 (1H, d, J=8.3 Hz, Ar—H), 7.28 (1H, d, J=8.5 Hz, Ar—H), 7.3 (1H, d, J=8.5 Hz, Ar—H), 7.44–7.58 (6H, m, Ar—H), 7.69–7.89 (7H, m, Ar—H), 8.10–8.17 (1H, m, Ar—H).

Example 115

Synthesis of K-2294 (N1-(3,4-dichlorobenzyl)-N1-(4-methylbenzyl)-3{[(1R)-1-(1-naphthyl)ethyl]amino}propanamide)

3,4-Dichlorobenzaldehyde (1.555 g, 8.25 mmol) and 4-methylbenzylamine (1 g, 8.25 mmol, 1.0 mol eq.) were dissolved in methanol and $MgSO_4$ (1.1920 g, 9.90 mmol, 1.2 mol eq.) and AcOH (10 drops) were added thereto. Then the obtained mixture was stirred at room temperature for 2 hours. After the completion of the reaction, the reaction mixture was dissolved in methanol and sodium boron hydride (390.2 mg, 10.30 mmol, 1.25 mol eq.) was added thereto. Then the obtained mixture was stirred at room temperature for 12 hours. After the completion of the reaction, the solvent was distilled off under reduced pressure. The obtained residue was extracted with ethyl acetate. The ethyl acetate layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, chloroform] to thereby give a colorless oil 243 (1.5942 g, 69.2%).

MS m/z: 280, $^1$H-NMR d: 2.34 (3H, s, $CH_3$), 3.73 (4H, s, $CH_3$×2), 7.14 (2H, d, J=8.1 Hz, Ar—H), 7.16 (1H, dd, J=2.0, 8.1 Hz, Ar—H), 7.19 (2H, d, J=8.1 Hz, Ar—H), 7.37 (1H, d, J=8.1 Hz, Ar—H), 7.43 (1H, d, J=2.0 Hz, Ar—H).

The dibenzylamine compound 243 (1.4942 g, 5.35 mmol) and triethylamine (0.89 ml, 6.42 mmol, 1.2 mol eq.) were dissolved in chloroform and acryloyl chloride (532.6 mg, 5.88 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 244 (1.6587 g, 92.9%).

MS m/z: 334, $^1$H-NMR d: 2.34 (3H, d, J=6.3 Hz, $CH_3$), 4.46 (2H, d, J=13.4 Hz, $CH_2$), 4.58 (2H, d, J=16.1 Hz, $C\underline{H}_2$), 5.76 (1H, dd, J=2.0, 10.2 Hz, CH=$C\underline{H}_2$), 6.48 (1H, dd, J=2.0, 16.8 Hz, $C\underline{H}$=$CH_2$), 6.63 (1H, dd, J=10.2, 16.8 Hz, CH=$CH_2$), 7.04 (2H, d, J=7.8 Hz, Ar—H), 7.09 (1H, d, J=8.3 Hz, Ar—H), 7.17 (2H, d, J=7.8 Hz, Ar—H), 7.31 (1H, s, Ar—H), 7.37 (1H, d, J=8.3 Hz, Ar—H).

The conjugated ketone compound 244 (1.5587 g, 4.67 mmol) and (R)-(+)-1-(1-naphthyl)ethylamine (959.6 mg, 5.60 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2294 (2.1115 g, 89.3%).

MS m/z: 505, $^1$H-NMR d: 1.50 (3H, d, J=6.6 Hz, $CH_3$), 2.34 (3H, d, J=6.6 Hz, $CH_3$), 2.52 (1H, dt, J=3.4, 9.3 Hz, $CH_2$), 2.63 (1H, t, J=6.3 Hz $CH_2$), 2.74–2.96 (2H, m, $CH_2$), 4.35 (2H, d, J=22.0 Hz, $CH_2$), 4.53 (2H, d, J=13.7 Hz, $C\underline{H}_2$), 4.62–4.68 (1H, m, $C\underline{H}$), 6.99 (1H, d, J=7.8 Hz, Ar—H), 7.04 (1H, dd, J=2.0, 8.1 Hz, Ar—H), 7.09 (1H, d, J=8.3 Hz, Ar—H), 7.12 (1H, d, J=8.1 Hz, Ar—H), 7.14 (1H, d, J=8.1 Hz, Ar—H), 7.26 (1H, d, J=2.0 Hz, Ar—H), 7.34 (1H, d, J=8.3 Hz, Ar—H), 7.43–7.52 (3H, m, Ar—H), 7.68 (1H, d, J=7.1 Hz, Ar—H), 7.72 (1H, d, J=8.1 Hz, Ar—H), 7.85 (1H, d, J=7.1 Hz, Ar—H), 8.17 (1H, d, J=7.1 Hz, Ar—H).

Example 116

Synthesis of K-2299 (N1-(4-methylbenzyl)-N1-[4-(trifluoromethyl)benzyl]-3-{[(1R)-1-(1-naphthyl)ethyl]amino}propanamide)

4-(Trifluoromethyl)benzaldehyde (1.4369 9, 8.25 mmol) and 4-methylbenzylamine (1 g, 8.25 mmol, 1.0 mol eq.) were dissolved in methanol and $MgSO_4$ (1.1920 g, 9.90 mmol, 1.2 mol eq.) and AcOH (10 drops) were added thereto. Then the obtained mixture was stirred at room temperature for 2 hours. After the completion of the reaction, the reaction mixture was dissolved in methanol and sodium boron hydride (390.2 mg, 10.30 mmol, 1.25 mol eq.) was added thereto. Then the obtained mixture was stirred at room temperature for 12 hours. After the completion of the reaction, the solvent was distilled off under reduced pressure. The obtained residue was extracted with ethyl acetate. The ethyl acetate layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, chloroform] to thereby give a colorless oil 245 (1.6877 g, 73.2%).

MS m/z: 279, $^1$H-NMR d: 2.34 (3H, s, $CH_3$) 3.76 (2H, s, $CH_2$), 3.85 (2H, s, $CH_2$), 7.14 (2H, d, J=7.8 Hz, Ar—H), 7.21 (2H, d, J=8.1 Hz, Ar—H), 7.46 (2H, d, J=8.1 Hz, Ar—H), 7.57 (2H, d, J=8.3 Hz, Ar—H).

The dibenzylamine compound 245 (1.5877 g, 5.68 mmol) and triethylamine (0.95 ml, 6.82 mmol, 1.2 mol eq.) were dissolved in chloroform and acryloyl chloride (565.96 mg, 6.25 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried-over sodium sulfate. After distilling off the solvent, the oil thus obtained was purified by column chromatography [silica gel, chloroform] to thereby give a colorless oil 246 (1.5568 g, 82.0%).

MS m/z: 333, $^1$H-NMR d: 2.34 (3H, d, J=6.8 Hz, $CH_3$), 4.52 (2H, d, J=26.8 Hz, $CH_2$), 4.65 (2H, d, J=22.4 Hz, $C\underline{H}_2$), 5.76 (1H, dd, J=1.7, 10.2 Hz, CH=$CH_2$), 6.49 (1H, dd, J=1.7, 16.8 Hz, $C\underline{H}$=$CH_2$), 6.64 (1H, dd, J=10.2, 16.8 Hz, CH=$CH_2$), 7.05 (2H, d, J=7.8 Hz, Ar—H), 7.17 (2H, d, J=7.8 Hz, Ar—H), 7.35 (2H, d, J=8.1 Hz, Ar—H), 7.56 (2H, d, J=8.1 Hz, Ar—H).

The conjugated ketone compound 246 (1.4568 g, 4.36 mmol) and (R)-(+)-1-(1-naphthyl)ethylamine (896.8 mg, 5.24 mmol, 1.2 mol eq.) were dissolved in chloroform/methanol (4:1) and allowed to stand at room temperature for 1 week. After the completion of the reaction, the solvent was distilled off under reduced pressure and the oil thus obtained was purified by column chromatography [silica gel, chloroform] to thereby give a colorless oil K-2299 (884.4 mg, 40.1%).

MS m/z: 504, $^1$H-NMR d: 1.51 (3H, d, J=6.6 Hz, $CH_3$), 2.33 (3H, d, J=6.3 Hz, $CH_3$), 2.53 (1H, dt, J=6.1, 19.3 Hz, $CH_2$), 2.66 (1H, t, J=6.1 Hz, $CH_2$), 2.77–2.97 (2H, m, $CH_2$), 4.40 (2H, d, J=19.8 Hz, $CH_2$), 4.59 (2H, d, J=24.9 Hz, $C\underline{H}_2$), 4.65–4.69 (1H, m, $C\underline{H}$), 7.00 (1H, d, J=7.8 Hz, Ar—H), 7.08 (1H, d, J=8.3 Hz, Ar—H), 7.12 (1H, d, J=7.8 Hz, Ar—H), 7.14 (1H, d, J=7.8 Hz, Ar—H), 7.20 (1H, d, J=8.1 Hz, Ar—H), 7.30 (1H, d, J=8.1 Hz, Ar—H), 7.43–7.51 (3H, m, Ar—H), 7.53 (1H, d, J=8.3 Hz, Ar—H), 7.57 (1H, d, J=8.1 Hz, Ar—H), 7.68 (1H, d, J=6.8 Hz, Ar—H), 7.73 (1H, dd, J=3.2, 8.1 Hz, Ar—H), 7.86 (1H, dd, J=2.2, 7.6 Hz, Ar—H), 8.17 (1H, d, J=7.6 Hz, Ar—H).

Example 117

Synthesis of K-2300 (N1,N1-di(4-methylbenzyl)-3-{[(1R)-1-(1-naphthyl)ethyl]amino}propanamide)

4-Tolualdehyde (500 mg, 3.56 mmol) and 4-methylbenzylamine (503.6 mg, 3.56 mmol, 1.0 mol eq.) were dissolved in methanol and $MgSO_4$ (514.2 mg, 4.27 mmol, 1.2 mol eq.) and AcOH (3 drops) were added thereto. Then the obtained mixture was stirred at room temperature for 50 minutes. After the completion of the reaction, sodium boron hydride (168.3 mg, 4.45 mmol, 1.25 mol eq.) was added to the reaction mixture. Then the obtained mixture was stirred at room temperature for 15 minutes. After the completion of the reaction, the solvent was distilled off under reduced pressure. The obtained residue was extracted with chloroform. The chloroform layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, hexane: ethyl acetate (9:1–4:1)] to thereby give a colorless oil 247 (819.4 mg, 88.2%).

MS m/z: 225, $^1$H-NMR d: 2.33 (6H, s, $CH_3$×2), 3.75 (4H, s, $CH_2$×2), 7.13 (4H, d, J=7.8 Hz, Ar—H), 7.22 (4H, d, J=7.8 Hz, Ar—H).

The dibenzylamine compound 247 (500 mg, 2.22 mmol) and triethylamine (0.372 ml, 2.67 mmol, 1.2 mol eq.) were dissolved in chloroform and acryloyl chloride (221 mg, 2.44 mmol, 1.1 mol eq.) dissolved in chloroform was added thereto under ice-cooling. The reaction mixture was stirred at room temperature for 30 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 248 (534.5 mg, 86.3%).

MS m/z: 279, $^1$H-NMR d: 2.34 (3H, s, CH$_3$), 2.35 (3H, s, CH$_3$), 4.45 (2H, s, CH$_2$), 4.60 (2H, s, CH$_2$), 5.71 (1H, dd, J=2.2, 10.2 Hz, CH=CH$_2$), 6.47 (1H, dd, J×2.2, 16.6 Hz, CH=CH$_2$), 6.60 (1H, dd, J=10.2, 16.6 Hz, CH=CH$_2$), 7.05 (2H, d, J=7.8 Hz, Ar—H), 7.13–7.17 (6H, m, Ar—H).

The conjugated ketone compound 248 (400 mg, 1.43 mmol) and (R)-(+)-1-(1-naphthyl)ethylamine (295 mg, 1.72 mmol, 1.2 mol eq.) were dissolved in chloroform/methanol (4:1) and allowed to stand at room temperature for 2 weeks. After the completion of the reaction, the solvent was distilled off under reduced pressure and the oil thus obtained was purified by column chromatography [silica gel, chloroform] to thereby give a colorless oil K-2300 (372.5 mg, 57.9%). Subsequently, the obtained K-2300 (253.6 mg, 0.56 mmol) was dissolved in a 10% solution of hydrochloric acid/methanol and stirred for 15 minutes. Then it was concentrated as such under reduced pressure. The crystals thus formed were recrystallized from ethanol/water to thereby give K-2300 hydrochloride (113.7 mg, 41.4%) as colorless crystals.

MS m/z: 450, $^1$H-NMR d: 1.57 (3H, d, J=6.6 Hz, CH$_3$), 2.34 (3H, s, CH$_3$), 2.34 (3H, s, CH$_3$), 2.60–2.71 (2H, m, CH$_2$), 4.35 (2H, s, CH$_2$), 2.85–2.97 (2H, m, CH$_2$), 4.52 (1H, d, J=14.6 Hz, CH$_2$), 4.59 (1H, d, J=14.6 Hz, CH$_2$), 4.74 (1H, q, J=6.6 Hz, CH), 7.00 (2H, d, J=8.1 Hz, Ar—H), 7.11 (4H, d, J=1.2 Hz, Ar—H), 7.14 (2H, d, J=7.8 Hz, Ar—H), 7.45–7.52 (3H, m, Ar—H), 7.74 (1H, d, J=7.8 Hz, Ar—H), 7.75 (1H, d, J=8.8 Hz, Ar—H), 7.87 (1H, dd, J=2.2, 7.8 Hz, Ar—H), 8.14 (1H, d, J=7.8 Hz, Ar—H).

Example 118

Synthesis of K-2309 (N1-(3,4-dichlorobenzyl)-N1-(4-methoxybenzyl)-3-{[(1R)-1-(1-naphthyl)ethyl]amino}propanamide)

3,4-Dichlorobenzaldehyde (702 mg, 4.01 mmol, 1.1 mol eq.) and 4-methoxybenzyiamine (0.476 ml, 3.64 mmol) were dissolved in methanol and MgSO$_4$ (525.8 mg, 4.37 mmol, 1.2 mol eq.) and AcOH (5 drops) were added thereto. Then the obtained mixture was stirred at room temperature for 30 minutes. After the completion of the reaction, sodium boron hydride (172 mg, 4.55 mmol, 1.25 mol eq.) was added to the reaction mixture. Then the obtained mixture was stirred at room temperature for 20 minutes. After the completion of the reaction, the solvent was distilled off under reduced pressure. The obtained residue was extracted with chloroform. The chloroform layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, hexane:ethyl acetate (9:1–4:1)] to thereby give a colorless oil 249 (827.0 mg, 76.8%).

MS m/z: 296, $^1$H-NMR d: 3.72 (2H, s, CH$_2$), 3.74 (2H, s, CH$_2$), 3.80 (3H, s, OCH$_3$), 6.87 (2H, d, J=8.8 Hz, Ar—H), 7.18 (1H, dd, J=2.0, 8.3 Hz, Ar—H), 7.24 (2H, d, J=8.3 Hz, Ar—H), 7.38 (1H, d, J=8.1 Hz, Ar—H), 7.45 (1H, d, J=2.0 Hz, Ar—H).

The dibenzylamine compound 249 (711.2 mg, 2.41 mmol) and triethylamine (0.402 ml, 2.89 mmol, 1.2 mol eq.) were dissolved in chloroform and acryloyl chloride (240 mg, 2.65 mmol, 1.1 mol eq.) dissolved in chloroform was added thereto under ice-cooling. The reaction mixture was stirred at room temperature for 45 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 250 (837.2 mg, 99.3%).

MS m/z: 350, $^1$H-NMR d: 3.81 (3H, s, OCH$_3$), 4.50 (2H, d, J=44.2 Hz, CH$_2$), 4.54 (2H, d, J=49.3 Hz, CH$_2$), 5.78 (1H, dd, J=1.7, 10.2 Hz, CH=CH$_2$), 6.59 (1H, dd, J=1.7, 16.6 Hz, CH=CH$_2$), 6.65 (1H, dd, J=10.2, 16.6 Hz, CH=CH$_2$), 6.89 (2H, d, J=8.5 Hz, Ar—H), 7.07 (2H, d, J=8.5 Hz, Ar—H), 7.09 (1H, d, J=8.3 Hz, Ar—H), 7.30 (1H, s, Ar—H), 7.38 (1H, d, J=8.3 Hz, Ar—H).

The conjugated ketone compound 250 (692.4 mg, 1.98 mmol) and (R)-(+)-1-(1-naphthyl)ethylamine (407 mg, 2.37 mmol, 1.2 mol eq.) were dissolved in chloroform/methanol (4:1) and allowed to stand at room temperature for 2 weeks. After the completion of the reaction, the solvent was distilled off under reduced pressure and the oil thus obtained was purified by column chromatography [silica gel, chloroform] to thereby give a colorless oil K-2309 (835.9 mg, 81.0%). Subsequently, the obtained K-2309 (630.1 mg, 1.21 mmol) was dissolved in a 10% solution of hydrochloric acid/methanol and stirred for 15 minutes. Then it was concentrated as such under reduced pressure. The crystals thus formed were recrystallized from ethanol/water to thereby give K-2309 hydrochloride (566.8 mg, 84.0%) as colorless crystals.

MS m/z: 521, $^1$H-NMR d: 1.55 (3H, d, J=6.3 Hz, CH$_3$), 2.55–2.70 (2H, m, CH$_2$), 2.86–2.97 (2H, m, CH$_2$), 3.80 (3H, d, J=3.4 Hz, OCH$_3$), 4.33 (2H, d, J=12.7 Hz, CH$_2$), 4.51 (2H, d, J=8.8 Hz, CH$_2$), 4.68–4.73 (1H, m, CH), 6.85 (2H, d, J=8.8 Hz, Ar—H), 7.02 (2H, d, J=8.5 Hz, Ar—H), 7.11 (1H, d, J=8.5 Hz, Ar—H), 7.26 (1H, s, Ar—H), 7.35 (1H, d, J=8.3 Hz, Ar—H), 7.45–7.52 (3H, m, Ar—H), 7.70 (1H, t, J=6.8 Hz, Ar—H), 7.75 (1H, d, J=8.3 Hz, Ar—H), 7.87 (1H, dd, J=2.2, 7.8 Hz, Ar—H), 8.16 (1H, d, J=7.8 Hz, Ar—H).

Example 119

Synthesis of K-2310 (N1-(4-methylbenzyl)-N1-[4-(trifluoromethoxy)benzyl]-3-{[(1R)-1-(1-naphthyl)ethyl]amino}propanamide)

4-(Trifluoromethoxy)benzaldehyde (0.648 ml, 4.54 mmol, 1.1 mol eq.) and 4-methylbenzylamine (0.525 ml, 4.13 mmol) were dissolved in methanol and MgSO$_4$ (596.6 mg, 4.96 mmol, 1.2 mol eq.) and AcOH (5 drops) were added thereto. Then the obtained mixture was stirred at room temperature for 40 minutes. After the completion of the reaction, sodium boron hydride (195 mg, 5.16 mmol, 1.25 mol eq.) was added to the reaction mixture. Then the obtained mixture was stirred at room temperature for 20 minutes. After the completion of the reaction, the solvent was distilled off under reduced. pressure. The obtained residue was extracted with chloroform. The chloroform layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, hexane: ethyl acetate (9:1–4:1)] to thereby give a colorless oil 251 (979.1 mg, 80.4%).

MS m/z: 295, $^1$H-NMR d: 2.34 (3H, s, $CH_3$), 3.76 (2H, s, $CH_2$), 3.79 (2H. s, $CH_2$), 7.14 (2H, d, J=8.1 Hz, Ar—H), 7.16 (2H, d, J=8.5 Hz, Ar—H), 7.22 (2H, d, J=8.1 Hz, Ar—H), 7.36 (2H, d, J=8.5 Hz, Ar—H).

The dibenzylamine compound 251 (846.8 mg, 2.87 mmol) and triethylamine (0.480 ml, 3.44 mmol, 1.2 mol eq.) were dissolved in chloroform and acryloyl chloride (286 mg, 3.16 mmol, 1.1 mol eq.) dissolved in chloroform was added thereto under ice-cooling. The reaction mixture was stirred at room temperature for 45 minutes. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 252 (844.5 mg, 84.3%).

MS m/z: 349, $^1$H-NMR d: 2.34 (3H, d, J=6.8 Hz, $CH_3$), 4.55 (2H, d, J=49.0 Hz, $CH_2$), 4.56 (2H, d, J=50.2 Hz, $CH_2$), 5.75 (1H, dd, J=2.2, 10.0 Hz, CH=$CH_2$), 6.49 (1H, dd, J=2.2, 16.8 Hz, CH=$CH_2$), 6.62 (1H, dd, J=10.0, 16.8 Hz, CH=$CH_2$), 7.04 (2H, d, J=7.8 Hz, Ar—H), 7.13–7.21 (4H, m, Ar—H), 7.28 (2H, d, J=8.5 Hz, Ar—H).

The conjugated ketone compound 252 (685.1 mg, 1.96 mmol) and (R)-(+)-1-(1-naphthyl)ethylamine (403 mg, 2.36 mmol, 1.2 mol eq.) were dissolved in chloroform/methanol (4:1) and allowed to stand at room temperature for 12 days. After the completion of the reaction, the solvent was distilled off under reduced pressure and the oil thus obtained was purified by column chromatography [silica gel, chloroform] to thereby give a colorless oil K-2310(777.8 mg, 76.3%). Subsequently, the obtained K-2310 (539.0 mg, 1.04 mmol) was dissolved in a 10% solution of hydrochloric acid/methanol and stirred for 15 minutes. Then it was concentrated as such under reduced pressure. The crystals thus formed were recrystallized from ethanol/water to thereby give K-2310 hydrochloride (493.0 mg, 85.1%) as colorless crystals.

MS m/z: 520, $^1$H-NMR d: 1.52 (3H, d, J=6.6 Hz, $CH_3$), 2.34 (3H, d, J=5.4 Hz, $CH_3$), 2.62 (2H, dt, J=5.9, 21.7 Hz, $CH_2$), 2.84–2.96 (2H, m, $CH_2$), 4.38 (2H, s, $CH_2$), 4.56 (2H, d, J=8.6 Hz, $CH_2$), 4.67 (1H, d, J=6.6 Hz, CH), 7.00 (2H, d, J=8.1 Hz, Ar—H), 7.07–7.18 (4H, m, Ar—H), 7.22 (2H, d, J=8.6 Hz, Ar—H), 7.44–7.51 (3H, m, Ar—H), 7.68 (1H, d, J=6.6 Hz, Ar—H), 7.73 (1H, d, J=8.1 Hz, Ar—H), 7.86 (1H, dd, J=2.2, 8.1 Hz, Ar—H), 8.16 (1H, d, J=8.5 Hz, Ar—H).

Example 120

Synthesis of K-2311

4-(Trifluoromethoxy)benzaldehyde (0.573 ml, 4.01 mmol, 1.1 mol eq.) and 4-methoxybenzylamine (0.476 ml, 3.64 mmol) were dissolved in methanol and $MgSO_4$ (525.8 mg, 4.37 mmol, 1.2 mol eq.) and AcOH (5 drops) were added thereto. Then the obtained mixture was stirred at room temperature for 30 minutes. After the completion of the reaction, sodium boron hydride (172 mg, 4.55 mmol, 1.25 mol eq.) was added to the reaction mixture. Then the obtained mixture was stirred at room temperature for 30 minutes. After the completion of the reaction, the solvent was distilled off under reduced pressure. The obtained residue was extracted with chloroform. The chloroform layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, hexane:ethyl acetate (9:1–4:1)] to thereby give a colorless oil 253 (944.0 mg, 83.4%).

MS m/z: 311, $^1$H-NMR d: 3.74 (2H, s, $CH_2$), 3.79 (2H, s, $CH_2$), 3.80 (3H, s, $OCH_3$), 6.87 (2H, d, J=8.5 Hz, Ar—H), 7.17 (2H, d, J=8.3 Hz, Ar—H), 7.25 (2H, d, J=8.3 Hz, Ar—H), 7.37 (2H, d, J=8.5 Hz, Ar—H).

The dibenzylamine compound 253 (766.5 mg, 2.46 mmol) and triethylamine (0.411 ml, 2.95 mmol, 1.2 mol eq.) were dissolved in chloroform and acryloyl chloride (245 mg, 2.71 mmol, 1.1 mol eq.) dissolved in chloroform was added thereto under ice-cooling. The reaction mixture was stirred at room temperature for 45 minutes. After the completion of the reaction, the reaction mixture was poured into water and extracted with chloroform. The chloroform layer was washed with water and a saturated aqueous solution of sodium chloride and dired over sodium sulfate. After distilling off the solvent, the oil thus obtained was purified by column chromatography [silica gel, chloroform] to thereby give a colorless oil 254 (749.0 mg, 83.4%). MS m/z:365, $^1$H-NMR δ:3.80 (3H, s, $OCH_3$), 4.48 (2H, d, J=13.4 Hz, $CH_2$), 4.60 (2H, d, J=12.4 Hz, $CH_2$), 5.76 (1H, dd, J=2.0, 10.2 Hz, CH=$CH_2$), 6.49 (1H, dd, J=8.5 Hz, Ar—H), 6.88 (1H, d, J=8.5 Hz, Ar—H), 7.07 (1H, d, J=8.3 Hz, Ar—H), 7.16 (1H, d, J=8.8 Hz, Ar—H), 7.18 (3H, d, J=7.6 Hz, Ar—H), 7.27 (1H, d, J=9.5 Hz, Ar—H).

The conjugated ketone compound 254 (612.8 mg, 1.68 mmol) and (R)-(+)-1-(1-naphthyl)ethylamine (345 mg, 2.01 mmol, 1.2 mol eq.) were dissolved in chloroform/methanol (4:1) and allowed to stand at room temperature for 12 days. After the completion of the reaction, the solvent was distilled off under reduced pressure and the oil thus obtained was purified by column chromatography [silica gel, chloroform] to thereby give a colorless oil K-2311 (668.3 mg 74.2%).

MS m/z: 536, $^1$H-NMR d: 1:53 (3H, d, J=6.6Hz, $CH_3$), 2.55–2.73 (2H, m, $CH_2$), 2.84–2.96 (2H, m, $CH_2$), 3.79 (3H, d, J=3.2 Hz, $OCH_3$), 4.36 (2H, d, J=10.0 Hz, $CH_2$), 4.54 (2H, d, J=12.9 Hz, $CH_2$), 4.70 (1H, q, J=6.6 Hz, CH), 6.82 (1H, d, J=8.8 Hz, Ar—H), 6.85 (1H, d, J=8.8 Hz, Ar—H), 7.02 (1H, d, J=8.5 Hz, Ar—H), 7.12 (1H, d, J=8.8 Hz, Ar—H), 7.13–7.18 (3H, m, Ar—H), 7.22 (1H, d, J=8.5 Hz, Ar—H), 7.45–7.51 (3H, m, Ar—H), 7.70 (1H, t, J=6.6 Hz, Ar—H), 7.74 (1H, d, J=8.3 Hz, Ar—H), 7.86 (1H, d, J=8.1 Hz, Ar—H), 8.16 (1H, d, J=8.1 Hz, Ar—H).

Example 121

Synthesis of K-2312

4-Hydroxybenzaldehyde (490 mg, 4.01 mmol, 1.1 mol eq.) and 4-methoxybenzylamine (0.476 ml, 3.64 mmol) were dissolved in methanol and $MgSO_4$ (525.8 mg, 4.37 mmol, 1.2 mol eq.) and AcOH (5 drops) were added thereto. Then the obtained mixture was stirred at room temperature for 45 minutes. After the completion of the reaction, sodium boron hydride (172 mg, 4.55 mmol, 1.25 mol eq.) was added to the reaction mixture. Then the obtained mixture was stirred at room temperature for 10 minutes. After the completion of the reaction, the solvent was distilled off under reduced pressure. The obtained residue was extracted with chloroform. The chloroform layer was washed with a saturated aqueous solution of sodium hydrogencarbonate, water and a saturated aqueous solution of sodium chloride and dried over sodium sulfate and the solvent was distilled off under reduced pressure. The oil thus obtained was purified by column chromatography [silica gel, chloroform/methanol] to thereby give a colorless oil 255 (858.9 mg, 97.1%).

MS m/z: 243, $^1$H-NMR δ: 3.69 (2H, s, C$\underline{H}_2$), 3.77 (2H, s, C$\underline{H}_2$), 3.79 (3H, s, OC$\underline{H}_3$), 6.64 (2H, d, J=8.5 Hz, Ar—H), 6.86 (2H, d, J=8.8 Hz, Ar—H), 7.09 (2H, d, J=8.5 Hz, Ar—H), 7.26 (2H, d, J=8.5 Hz, Ar—H).

The dibenzylamine compound 255 (521.4 mg, 2.15 mmol) and triethylamine (0.359 ml, 2.57 mmol, 1.2 mol eq.) were dissolved in chloroform and acryloyl chloride (214 mg, 2.36 mmol, 1.1 mol eq.) dissolved in chloroform was added thereto under ice-cooling. The reaction mixture was stirred at room temperature for 1 hour. After the completion of the reaction, the reaction mixture was poured into water and extracted with chloroform. The chloroform layer was washed with water and a saturated aqueous solution of sodium chloride and dried over sodium sulfate. After distilling off the solvent, the oil thus obtained was purified by column chromatography [silica gel, chloroform] to thereby give a colorless oil 256 (375.5 mg, 58.8%).

MS m/z: 297, $^1$H-NMR δ: 3.80 (3H, d, J=6.8 Hz, OC$\underline{H}_3$), 4.44 (2H, d, J=16.1 Hz, C$\underline{H}_2$), 4.56 (2H, d, J=9.0 Hz, C$\underline{H}_2$), 5.76 (1H, dd, J=2.2, 10.2 Hz, CH=C$\underline{H}_2$), 6.48 (1H, ddd, J=2.2, 7.1, 16.6 Hz, C$\underline{H}$=CH$_2$), 6.64 (1H, ddd, J=3.2, 10.2, 16.6 Hz, CH=C$\underline{H}_2$), 6.79 (1H, d, J=8.5 Hz, Ar—H), 6.83 (1H, d, J=8.5 Hz, Ar—H), 6.85 (1H, d, J=8.5 Hz, Ar—H), 6.89 (1H, d, J=8.5 Hz, Ar—H), 6.98 (1H, d, J=8.3 Hz, Ar—H), 7.08 (1H, d, J=6.8 Hz, Ar—H), 710 (1H, d, J=6.8 Hz, Ar—H), 7.19 (1H, d, J=8.5 Hz, Ar—H).

The conjugated ketone compound 256 (260.2 mg, 0.88 mmol) and (R)-(+)-1-(1-naphthyl)ethylamine (180 mg, 1.05 mmol, 1.2 mol eq.) were dissolved in chloroform/methanol (4:1) and allowed to stand at room temperature for 13 days. After the completion of the reaction, the solvent was distilled off under reduced pressure and the oil thus obtained was purified by column chromatography [silica gel, chloroform/methanol] to thereby give a colorless oil K-2312 (177.4 mg, 43.3%).

MS m/z: 468, $^1$H-NMR δ: 1.61 (3H, d, J=6.8 Hz, C$\underline{H}_3$), 2.63–2.71 (1H, m, C$\underline{H}_2$), 2.81–2.88 (2H, m, C$\underline{H}_2$), 2.95 (1H, d, J=5.4 Hz, C$\underline{H}_2$), 3.78 (3H, d, J=5.4 Hz, OC$\underline{H}_3$), 4.22 (2H, d, J=18.3 Hz, C$\underline{H}_2$), 4.27 (2H, d, J=30.5 Hz, C$\underline{H}_2$), 4.81–4.86 (1H, m, C$\underline{H}$), 6.72 (1H, d, J=8.5 Hz, Ar—H), 6.74 (1H, d, J=8.5 Hz, Ar—H), 6.82 (1H, d, J=8.8 Hz, Ar—H), 6.83 (1H, d, J=8.5 Hz, Ar—H), 6.85 (1H, d, J=8.5 Hz, Ar—H), 6.98 (1H, d, J=8.8 Hz, Ar—H), 7.02 (1H, d, J=8.5 Hz, Ar—H), 7.10 (1H, d, J=8.5 Hz, Ar—H), 7.45–7.54 (3H, m, Ar—H), 7.77 (2H, d, J=7.6 Hz, Ar—H), 7.88 (1H, d, J=8.1 Hz, Ar—H), 8.11 (1H, d, J=8.1 Hz, Ar—H).

Example 122

Synthesis of K-2280 (N-[5-[(4-methoxyphenyl)thio]pentyl-N-[(1R)-1-(1-naphthyl) ethyl]amine)

4-Methoxythiophenol (753 mg, 5.37 mmol) was dissolved in acetonitrile (10 ml). To the obtained solution were successively added at room temperature potassium carbonate (754 mg, 5.46 mmol) and 1,5-dibromopentane (0.73 ml, 5.35 mmol) and the reaction mixture was stirred at room temperature for 3 hours. After confirming the completion of the reaction by TLC, potassium carbonate (931 mg, 6.75 mmol) and (R)-(+)-1-(1-naphthyl)ethylamine (0.52 ml, 3.22 mmol) were added at the same temperature to the reaction system. Further, the reaction mixture was stirred at 85° C. for 12 hours. After the completion of the reaction, the mixture was cooled by allowing to stand at room temperature and water was added thereto. Next, the reaction mixture was subjected to separatory extraction with chloroform and a saturated aqueous solution of sodium chloride and washed. The organic layer thus obtained was dried over anhydrous sodium sulfate and concentrated under reduced pressure. The organic residue was purified by silica gel column chromatography (chloroform:methanol=200:1) to thereby give a pale yellow, syrupy compound K-2280 as a free compound. Subsequently, 5 ml of 10% hydrochloric acid/methanol was poured into the K-2280 obtained above and allowed to stand for 3 minutes followed by concentration. The pale yellow crystals thus obtained were subjected to Kiriyama's filtration and the precipitate was washed with diethyl ether. Thus 210 mg (0.55 mmol, yield: 20.6%) of K-2280 hydrochloride was obtained as white crystals.

400 MHz-NMR 10.49 (1H, bs), 9.98 (1H, bs), 8.24 (1H, d, J=7.32 Hz), 7.98 (1H, d, J=8.56 Hz), 7.94 (1H, dd, J=8.04 Hz, J=1.48 Hz), 7.90 (1H, d, J=8.28 Hz), 7.52–7.68 (3H, m), 7.19–7.23 (2H, m), 6.73–6.77 (2H, m), 5.14–5.24 (1H, m), 3.73 (3H, s), 2.67–2.75 (2H, m), 2.65 (2H, t, J=7.20 Hz), 2.02 (3H, d, J=6.84 Hz), 1.91–1.99 (2H, m), 1.38–1.46 (2H, m), 1.21–1.35 (2H, m), m/z=379.

Example 123

Synthesis of K-2281 (N-[(1R)-1-(1-naphthyl)ethyl]-N-{4-[(2,4,5-trichlorophenyl)thio]butyl}amine)

2,4,5-Trichlorothiophenol (770 mg, 3.61 mmol) was dissolved in acetonitrile (10 ml). To the obtained solution were successively added at room temperature potassium carbonate (560 mg, 4.05 mmol) and 1,4-dibromobutane (0.43 ml, 3.60 mmol) and the reaction mixture was stirred at room temperature for 3 hours. After confirming the completion of the reaction by TLC, potassium carbonate (545 mg, 3.94 mmol) and (R)-(+)-1-(1-naphthyl)ethylamine (0.41 ml, 3.94 mmol) were added at the same temperature to the reaction system. Further, the reaction mixture was stirred at 85° C. for 12 hours. After the completion of the reaction, the mixture was cooled by allowing to stand at room temperature and water was added thereto. Next, the reaction mixture was subjected to separatory extraction with chloroform and a saturated aqueous solution of sodium chloride and washed. The organic layer thus obtained was dried over anhydrous sodium sulfate and concentrated under reduced pressure. The organic residue was purified by silica gel column chromatography (chloroform:methanol=200:1) to thereby give a pale yellow, syrupy compound K-2281 as a free compound. Subsequently, 10 ml of 10% hydrochloric acid/methanol was poured into the K-2281 obtained above and allowed to stand for 5 minutes followed by concentration. The pale yellow crystals thus obtained were subjected to Kiriyama's filtration and the precipitate was washed with diethyl ether. Thus 280 mg (0.59 mmol, yield: 15.0%) of K-2281 hydrochloride was obtained as white crystals.

400 MHz-NMR 10.64 (1H, bs), 10.07 (1H, bs), 8.26 (1H, dd, J=7.3 Hz, J=0.7 Hz), 8.01 (1H, d=8.3 Hz), 7.90–7.95 (2H, m), 7.52–7.68 (3H, m), 7.36 (1H, s), 7.11 (1H, s), 5.20–5.26 (1H, m), 2.76 (2H, t, J=7.0 Hz), 2.76–2.82 (2H, m), 2.87 (3H, d, J=6.8 Hz), 1.53–1.63 (2H, m), m/z=437, 439.

Example 124

Synthesis of K-2282 (N-[(1R)-1-(1-naphthyl)ethyl]-N-{5-[(2,4,5-trichlorophenyl)thio]pentyl}amine)

2,4,5-Trichlorothiophenol (1.53 g, 7.15 mmol) was dissolved in acetonitrile (15 ml). To the obtained solution were successively added at room temperature potassium carbonate (1.083 g, 7.84 mmol) and 1,5-dibromopentane (0.98 ml, 7.19 mmol) and the reaction mixture was stirred at room temperature for 2.5 hours. After confirming the completion of the reaction by TLC, potassium carbonate (1.00 g, 7.25 mmol) and (R)-(+)-1-(1-naphthyl)ethylamine (0.69 ml, 4.27 mmol) were added at the same temperature to the reaction system. Further, the reaction mixture was stirred at 85° C. for 12 hours. After the completion of the reaction, the mixture was cooled by allowing to stand at room temperature arid water was added thereto. Next, the reaction mixture was subjected to separatory extraction with chloroform and a saturated aqueous solution of sodium chloride and washed. The organic layer thus obtained was dried over anhydrous sodium sulfate and concentrated under reduced pressure. The organic residue was purified by silica gel column chromatography (chloroform:methanol=200:1) to thereby give a pale yellow, syrupy compound K-2282 as a free compound. Subsequently, 15 ml of 10% hydrochloric acid/methanol was poured into the K-2282 obtained above and allowed to stand for 5 minutes followed by concentration. The pale yellow crystals thus obtained were subjected to Kiriyama's filtration and the precipitate was washed with diethyl ether. Thus 283 mg (0.58 mmol, yield: 13.5%) of K-2282 hydrochloride was obtained as white crystals.

400 MHz-NMR 10.55 (1H, bs), 10.03 (1H, bs), 8.25 (1H, d, J=7.3 Hz), 8.00 (1H, d, J=8.5 Hz), 7.90–7.95 (2H, m), 7.54–7.68 (3H, m), 7.37 (1H, s), 7.16 (1H, s), 5.17–5.26 (1H, m), 2.73–2.82 (4H, m), 1.97–2.05 (2H, m), 2.05 (3H, d, J=6.6 Hz), 1.52–1.60 (2H, m), 1.31–1.45 (2H, m), m/z= 451, 453.

Example 125

Synthesis of K-2287 (N-[(1R)-1-(1-naphthyl)ethyl]-N-(4-{[4-(trifluoromethoxy)phenyl]thio}butyl)amine)

4-Trifluoromethoxythiophenol (908 mg, 4.68 mmol) was dissolved in acetonitrile (10 ml). To the obtained solution were successively added at room temperature potassium carbonate (679 mg, 4.91 mmol) and 1,4-dibromobutane (0.568 ml, 4.69 mmol) and the reaction mixture was stirred at room temperature for 5 hours. After confirming the completion of the reaction by TLC, potassium carbonate (710 mg, 5.14 mmol) and (R)-(+)-1-(1-naphthyl)ethylamine (0.53 ml, 3.28 mmol) were added at the same temperature to the reaction system. Further, the reaction mixture was stirred at 90° C. for 1 2 hours. After the completion of the reaction, the mixture was cooled by allowing to stand at room temperature and water was added thereto. Next, the reaction mixture was subjected to separatory extraction with chloroform and a saturated aqueous solution of sodium chloride and washed. The organic layer thus obtained was dried over anhydrous sodium sulfate and concentrated under reduced pressure. The organic residue was purified by silica gel column chromatography (chloroform:methanol=200:1) to thereby give a pale yellow, syrupy compound K-2287 as a free compound. Subsequently, 10 ml of 10% hydrochloric acid/methanol was poured into the K-2287 obtained above and allowed to stand for 5 minutes followed by concentration. The pale yellow crystals thus obtained were subjected to Kiriyama's filtration and the precipitate was washed with hexane. Thus 245 mg (0.54 mmol, yield: 16.5%) of K-2287 hydrochloride was obtained as white crystals.

400 MHz-NMR 10.58 (1H, bs), 10.07 (1H, bs), 8.25 (1H, d, J=6.8 Hz), 8.00 (1H, d, J=8.5 Hz), 7.90–7.96 (2H, m), 7.52–7.67 (3H, m), 7.15–7.19 (3H, m), 7.02–7.04 (2H, m), 5.19–5.24 (1H, m), 2.73–2.76 (4H, m), 2.06–2.17 (2H, m), 2.06 (3H, d, J=6.8 Hz), 1.41–1.59 (2H, m), m/z=419.

Example 126

Synthesis of K-2288 (N-[(1R)-1-(1-naphthyl)ethyl]-N-(5-{[4-(trifluoromethoxy)phenyl]thio}pentyl)amine)

4-Trifluoromethoxythiophenol (995 mg, 5.12 mmol) was dissolved in acetonitrile (10 ml). To the obtained solution were successively added at room temperature potassium carbonate (715 mg, 5.17 mmol) and 1,5-dibromopentane (0.70 ml, 5.14 mmol) and the reaction mixture was stirred at room temperature for 5 hours. After confirming the completion of the reaction by TLC, potassium carbonate (770 mg, 5.57 mmol) and (R)-(+)-1-(1-naphthyl)ethylamine (0.58 ml, 3.59 mmol) were added at the same temperature to the reaction system. Further, the reaction mixture was stirred at 85° C. for 12 hours. After the completion of the reaction, the mixture was cooled by allowing to stand at room temperature and water was added thereto. Next, the reaction mixture was subjected to separatory extraction with chloroform and a saturated aqueous solution of sodium chloride and washed. The organic layer thus obtained was dried over anhydrous sodium sulfate and concentrated under reduced pressure. The organic residue was purified by silica gel column chromatography (chloroform:methanol=200:1) to thereby give a pale yellow, syrupy compound K-2288 as a free compound. Subsequently, 10 ml of 10% hydrochloric acid/methanol was poured into the K-2288 obtained above and allowed to stand for 5 minutes followed by concentration. The pale yellow crystals thus obtained were subjected to Kiriyama's filtration and the precipitate was washed with hexane. Thus 313 mg (0.67 mmol, yield: 18.7%) of K-2288 hydrochloride was obtained as white crystals.

400 MHz-NMR 10.53 (1H, m), 10.03 (1H, bs), 8.24–8.26 (1H, m), 7.99 (1H, d, J=8.3 Hz), 7.52–7.67 (3H, m), 7.19–7.23 (2H, m), 7.04–7.07.(2H, m), 5.15–5.25 (1H, m), 2.76 (2H, t, J=7.2 Hz), 2.69–2.78 (2H, m), 2.03 (3H, d, J=6.8 Hz), 1.92–2.04 (2H, m), 1.49 (2H, tt, J=7.4 Hz, J=7.4 Hz), 1.27–1.38 (2H, m), m/z=433.

Example 127

Synthesis of K-2293 (N-{4-[(4-chlorophenyl)thio]butyl}-N-[(1R)-1-(1-naphthyl)ethyl]amine)

4-Chlorothiophenol (782 mg, 5.41 mmol) was dissolved in acetonitrile (10 ml). To the obtained solution were successively added at room temperature potassium carbonate (850 mg, 6.15 mmol) and 1,4-dibromobutane (0.65 ml, 5.44 mmol) and the reaction mixture was stirred at room temperature for 5 hours. After confirming the completion of the reaction by TLC, potassium carbonate (775 mg, 5.61 mmol) and (R)-(+)-1-(1-naphthyl)ethylamine (0.62 ml, 3.84 mmol) were added at the same temperature to the reaction system. Further, the reaction mixture was stirred at 85° C. for 24 hours. After the completion of the reaction, the mixture was cooled by allowing to stand at room temperature and water was added thereto. Next, the reaction mixture was subjected to separatory extraction with chloroform and a saturated aqueous solution of sodium chloride and washed. The organic layer thus obtained was dried over anhydrous sodium sulfate and concentrated under reduced pressure. The organic residue was purified by silica gel column chromatography (chloroform:methanol=200:1) to thereby give a pale yellow, syrupy compound K-2293 as a free compound. Subsequently, 10 ml of 10% hydrochloric acid/methanol was poured into the K-2293 obtained above and allowed to stand for 5 minutes followed by concentration. The pale yellow crystals thus obtained were subjected to Kiriyama's filtration and the precipitate was washed with diethyl ether. Thus 420 mg (1.03 mmol, yield: 26.9%) of K-2293 hydrochloride was obtained as white crystals.

400 MHz-NMR 10.58 (1H, bs), 10.05 (1H, bs), 8.25 (1H, d, J=6.8 Hz), 7.99 (1H, d, J=8.3 Hz), 7.94 (1H, dd, J=8.0 Hz, J=1.2 Hz), 7.91 (1H, d, J=8.04 Hz), 7.52–7.67 (3H, m), 7.12–7.16 (2H, m), 7.06–7.10 (2H, m), 5.16–5.25 (1H, m), 2.70–2.74 (4H, m), 2.06–2.15 (2H, m), 2.05 (3H, d, J=6.6 Hz), 1.40–1.57 (2H, m), m/z=369.

Example 128

Synthesis of K-2240 (N-[(1R)-1-(1-naphthyl)ethyl]-N-(3-{[4-(trifluoromethyl)phenyl]thio}propyl)amine)

K-2240 hydrochloride was obtained as white crystals by the same method as the one employed for the synthesis of K-2293 but replacing the 4-chlorothiophenol and 1,4-dibromobutane respectively by 4-trifluoromethylthiophenol and 1,3-dibromopropane. m/z=339.

Example 129

Synthesis of K-2263 (N-{4-[(4-fluorophenyl)thio]butyl}-N-[(1R)-1-(1-naphthyl)ethyl]amine)

K-2263 hydrochloride was obtained as white crystals by the same method as the one employed for the synthesis of K-2293 but replacing the 4-chlorothiophenol by 4-fluorothiophenol.

400 MHz-NMR 10.57 (1H, bs), 10.04 (1H, bs), 8.24 (1H, d, J=7.3 Hz), 7.99 (1H, d, J=8.52 Hz), 7.90–7.96 (2H, m), 7.52–7.67 (3H, m), 7.15–7.20 (2H, m), 6.86–6.92 (2H, m), 5.19–5.22 (1H, m), 2.67–2.77 (2H, m), 2.69 (2H, t, J=7.1 Hz), 2.05–2.15 (2H, m), 2.05 (3H, d, J=6.8 Hz), 1.36–1.54 (2H, m), m/z=353.

Example 130

Synthesis of K-2269 (N-{4-[(3-methoxyphenyl)thio]butyl}-N-[(1R)-1-(1-naphthyl)ethyl]amine)

K-2269 hydrochloride was obtained as white crystals by the same method as the one employed for the synthesis of K-2.293 but replacing the 4-chlorothiophenol by 3-methoxythiophenol.

400 MHz-NMR 10.58 (1H, bs), 10.06 (1H, bs), 8.24–8.26 (1H, m), 7.99 (1H, d, J=8.3 Hz), 7.88–7.94 (3H, m), 7.53–7.67 (3H, m), 7.08 (1H, dd, J=8.3 Hz, J=8.3 Hz), 6.71–6.74 (2H, m), 6.64 (1H, ddd, J=8.3 Hz, J=2.4 Hz, J=1.0 Hz), 5.15–5.25 (1H, m), 2.70–2.79 (2H, m), 2.75 (2H, t, J=7.2 Hz), 2.07–2.16 (2H, m), 2.05 (3H, d, J=6.8 Hz), 1.43–1.60 (2H, m), m/z=365.

Example 131

Synthesis of K-2271 (N-{[4-(5-ethoxy-1,3-benzothiazol-2-yl)thio]butyl-N-[(1R)-1-(1-naphthyl)ethyl]amine)

K-2271 hydrochloride was obtained as white crystals by the same method as the one employed for the synthesis of K-2293 but replacing the 4-chlorothiophenol by 6-ethoxy-2-mercaptobenzothiazole.

400 MHz-NMR 10.56 (1H, bs), 10.04 (1H, bs), 8.29 (1H, d, J=7.0 Hz), 8.02 (1H, d, J=8.5 Hz), 7.87–7.92 (2H, m), 7.52–7.70 (4H, m), 7.13 (1H, d, J=2.2 Hz), 6.96 (1H, dd, J=8.8 Hz, J=2.2 Hz), 5.20–5.28 (1H, m), 4.02 (2H, dd, J=13.9 Hz, J=7.1 Hz), 3.27 (2H, dd, J=7.1Hz, J=7.1 Hz), 2.20–2.60 (4H, m), 2.12–2.23 (2H, m), 2.06 (3H, d, J=6.6 Hz), 1.76–1.87 (2H, m), 1.42 (3H, t, J=6.8 Hz), m/z=436.

Example 132

Synthesis of K-2279 (N-{[5-(3-methoxyphenyl)thio]pentyl}N-[(1R)-1-(1-naphthyl)ethyl]amine)

K-2279 hydrochloride was obtained as white crystals by the same method as the one employed for the synthesis of K-2293 but replacing the 4-chlorothiophenol and 1,4-dibromobutane respectively by 3-methoxythiophenol and 1,5-dibromopentane.

400 MHz-NMR 10.51 (1H, bs), 9.99 (1H, bs), 8.24 (1H, d, J=7.1 Hz), 7.89–7.99 (3H, m), 7.54–7.67 (3H, m), 7.10 (1H, dd, J=7.9 Hz, J=7.9 Hz), 6.75–6.79 (2H, m), 6.61–6.65 (1H, ddd, J=8.0Hz, J=2.4 Hz, J=0.7 Hz), 5.14–5.24 (1H, m), 3.72 (3H, s), 2.68–2.79 (4H, m), 2.03 (3H, d, J=6.8 Hz), 1.93–1.99 (2H, m), 1.47–1.54 (2H, m), 1.24–1.38 (2H, m), m/z=379.

Example 133

Synthesis of K-2284 (N-[(1R)-1-(1-naphthyl)ethyl]-N-(5-{[2,3,5,6-tetrafluoro-4-(trifluoromethyl)phenyl]thio}pentyl)amine)

K-2284 hydrochloride was obtained as white crystals by the same method as the one employed for the:synthesis of K-2293 but replacing the 4-chlorothiophenol and 1,4-dibromobutane respectively by 2,3,5,6-tetrafluoro-4-trifluoromethylthiophenol and 1,5-dibromopentane.

400 MHz-NMR 10.54 (1H, bs), 10.43 (1H, bs), 8.24 (1H, d, J=6.6 Hz), 7.99 (1H, d, J=8.3 Hz), 7.90–7.96 (2H, m), 7.55–7.67 (3H, m), 5.15–5.25 (1H, bs), 2.91 (2H, t, J=7.2 Hz), 2.70–2.80 (2H, m), 2.04 (3H, d, J=6.6 Hz), 1.93–2.02 (2H, m), 1.48 (2H, tt, J=7.4 Hz, J=7.4 Hz), 1.26–1.41 (2H, m), m/z=489.

Example 134

Synthesis of K-2286 (N-{6-[(4-chiorophenyl)thio]hexyl}N-[(1R)-1-(1-naphthyl)ethyl]amine)

K-2286 hydrochloride was obtained as white crystals by the same method as the one employed for the synthesis of K-2293 but replacing the 1,4-dibromobutane by 1,6-dibromohexane, m/z=397.

Example 135

Synthesis of K-2292 (N-[(1R)-1-(1-naphthyl)ethyl]-N-(7-{[2,3,5,6-tetrafluoro-4-(trifluoromethyl)phenyl]thio}heptyl)amine)

K-2292 hydrochloride was obtained as white crystals by the same method as the one employed for the synthesis of K-2293 but replacing the 4-chlorothiophenol and 1,4-dibromobutane respectively by 2,3,5,6-tetrafluoro-4-trifluorometylthiophenol and 1,7-dibromopentane.

400 MHz-NMR 10.48 (1H, bs), 9.98 (1H, bs), 8.26 (1H, d, J=6.8 Hz), 8.00 (1H, d, J=8.3 Hz), 7.94 (1H, d, J=7.3 Hz), 7.91 (1H, d, J=8.0 Hz), 7.54–7.68 (3H, m), 5.21 (1H, bs), 2.92 (2H, t, J=7.3 Hz), 2.74 (2H, bs), 2.05 (3H, d, J=5.1 Hz),

Example 136

Synthesis of K-2295

K-2295 hydrochloride was obtained as white crystals by the same method as the one employed for the synthesis of K-2293 but replacing the 4-chlorothiophenol and 1,4-dibromobutane respectively by 2,4,5-trichlorothiophenol and 1-bromo-2-chloroethane.

400 MHz-NMR 10.94 (1H, bs), 10.31 (1H, bs), 8.17 (1H, d, J=6.6 Hz), 7.88–7.96 (3H, m), 7.55–7.65 (3H, m), 7.42 (1 H, s), 7.29 (1H, s), 5.20–5.28 (1H, m), 3.47–3.59 (2H, m), 2.92–3.07 (2H, m), 2.03 (3H, d, J=6.6 Hz), m/z=409.

Example 137

Synthesis of K-2296 (N-{[5-(2,5-dichlorophenyl)thio]pentyl}N-[(1R)-1-(1-naphthyl)ethyl]amine)

K-2296 hydrochloride was obtained as white crystals by the same method as the one employed for the synthesis of K-2293 but replacing the 4-chlorothiophenol and 1,4-dibromobutane respectively by 2,5-dichlorothiophenol and 1,5-dibromopentane.

400 MHz-NMR 10.63 (1H, bs), 10.08 (1H, bs), 8.26 (1H, d, J=6.8 Hz), 8.01 (1H, d, =8.5 Hz), 7.90–7.94 (2H, m), 7.52–7.68 (3H, m), 7.18 (1H, d, J=8.3 Hz), 6.98–7.02 (2H, m), 5.18–5.28 (1H, m), 2.75–2.84 (2H, m), 2.77 (2H, t, J=7.2 Hz), 2.12–2.20 (2H, m), 2.07 (3H, d, J=6.6 Hz), 1.56–1.67 (4H, m), m/z=417.

Example 138

Synthesis of K-2297 (N-[(1R)-1-(1-naphthyl)ethyl]-N-(4-{[2,3,5,6-tetrafluoro-4-(trifluoromethyl)phenyl]thio}butyl)amine)

K-2297 hydrochloride was obtained as white crystals by the same method as the one employed for the synthesis of K-2293 but replacing the 4-chlorothiophenol by 2,3,5,6-tetrafluoro-4-trifluoromethylthiophenol.

400 MHz-NMR 10.59 (1H, bs), 10.08 (1H, b), 8.23 (1H, d, J=6.6 Hz), 8.00 (1H,d, (1H, m), 2.89 (2H, t, J=7.3 Hz), 2.70–2.82 (2H, m), 2.04–2.13 (2H, m), 2.05 (3H, d, J=6.6 Hz), 1.47–1.60 (2H, m), m/z=475.

Example 139

Synthesis of K-2298 (N-{4-[(2,5-dichlorophenyl)thio]butyl}N-[(1R)-1-(1-naphthyl)ethyl]amine)

K-2298 hydrochloride was obtained as white crystals by the same method as the one employed for the synthesis of K-2293 but replacing the 4-chlorothiophenol by 2,5-dichlorothiophenol.

400 MHz-NMR 10.64 (1H, bs), 10.09 (1H, bs), 8.26 (1H, d, J=6.6 Hz), 8.01 (1H, d, J=8.3 Hz), 7.89–7.94 (2H, m), 7.52–7.68 (3H, m), 7.18 (1H, d, J=8.3 Hz), 7.01 (1H, dd, J=6.6 Hz, J=2.4 Hz), 5.18–5.28 (1H, m), 2.73–2.85 (2H, m), 2.76 (2H, t, J=7.2 Hz), 2.16 (2H, tt, J=7.2 Hz, J=7.2 Hz), 2.07 (3H, d, J=6.8 Hz), 1.52–1.68 (2H, m), m/z=403.

Example 140

Synthesis of K-2301 (N-[(1R)-1-((1-naphthyl)ethyl]-N-(6-{[4-(trifluoromethoxy)phenyl]thio}hexyl)amine)

K-2301 hydrochloride was obtained as white crystals by the same method as the one employed for the synthesis of K-2293 but replacing the- 4-chlorothiophenol and 1,4-dibromobutane respectively by 4-trifluoromethoxythiophenol and 1,6-dibromohexane.

400 MHz-NMR 10.53 (1H, bs), 10.00 (1H, bs), 8.27 (1H, d, J=7.3 Hz), 8.00 (1H, d, J=8.3 Hz), 7.89–7.95 (2H, m), 7.52–7.68 (3H, m), 7.21–7.24 (2H, m), 7.05–7.08 (2H, m), 5.21 (1H, bs), 2.70–2.78 (2H, m), 2.76 (2H, t, J=7.3 Hz), 2.06 (3H, d, J=6.6 Hz), 1.92–2.02 (2H, m), 1.46–1.54 (2H, m), 1.17–1.35 (4H, m), m/z=447.

Example 141

Synthesis of K-2302 (N-{4-[(2,4-dimethylphenyl)thio]butyl}-N-[(1R)-1-(1-naphthyl)ethyl]amine)

K-2302 hydrochloride was obtained as white crystals by the same method as the one employed for the synthesis of K-2293 but replacing the 4-chlorothiophenol by 2,4-dimethylthiophenol.

400 MHz-NMR 10.60 (1H, bs), 10.05 (1H, bs), 8.25 (1H, d, J=7.3 Hz), 7.99 (1H, d, J=8.6 Hz), 7.93 (1H, d, J=7.84 Hz), 7.89 (1H, d, J=8.3 Hz), 7.51–7.66 (3H, m), 7.00 (1H, d, J=7.8 Hz), 6.90 (1H, s), 6.83 (1H, d, J=7.8 Hz), 5.15–5.24 (1H, m), 2.70–2.78 (2H, m), 2.66 (2H, t, J=7.2 Hz), 2.22 (6H, s), 2.07–2.13 (2H, m), 2.05 (3H, d, J=6.8 Hz), 1.40–1.55 (2H, m), m/z=363.

Example 142

Synthesis of K-2303 (N-{5-[(2,4-dimethylphenyl)thio]pentyl}N-[(1R)-1-((1-naphthyl)ethyl]amine)

K-2303 hydrochloride was obtained as white crystals by the same method as the one employed for the synthesis of K-2293 but replacing the 4-chlorothiophenol and 1,4-dibromobutane respectively by 2,4-dimethylthiophenol and 1,5-dibromohexane.

400 MHz-NMR 10.51 (1H, bs), 10.00 (1H, bs), 8.25 (1H, d, J=7.1 Hz), 7.98 (1H, d, J=8.3 Hz), 7.94 (1H, dd, J=7.8 Hz, J=1.2 Hz), 7.90 (1H, d, J=8.3 Hz), 7.53–7.67 (3H, m), 7.05 (1H, d, J=7.8 Hz), 6.90 (1 H, s), 6.85 (1H, d, J=7.8 Hz), 5.14–5.23 (1H, m), 2.67–2.78 (2H, m), 2.67 (2H, t, J=7.3 Hz), 2.24 (3H, s), 2.21 (3H, s), 2.02 (3H, d, J=6.6 Hz), 1.92–2.01 (2H, m), 1.43–1.51 (2H, m), 1.27–1.34 (2H, m), m/z=377.

Example 143

Synthesis of K-2304 (N-{4-[(4-methylphenyl)thio]butyl}-N-[(1R)-1-(1-naphthyl)ethyl]amine)

K-2304 hydrochloride was obtained as white crystals by the same method as the one employed for the synthesis of K-2293 but replacing. the 4-chlorothiophenol by 4-methylthiophenol.

400 MHz-NMR 10.55 (1H, bs), 10.03 (1H, bs), 8.25 (1H, d, J=7.1 Hz), 7.99 (1H, d, J=8.5 Hz), 7.93–7.95 (1H, m), 7.89 (1H, d, J=8.0 Hz), 7.06–7.86 (5H, m), 6.96–6.99 (2H, m), 5.18–5.22 (1H, m), 2.68–2.77 (2H, m), 2.69 (2H, t, J=7.2 Hz), 2.25 (3H, s), 2.04–2.14 (2H, m), 2.04 (3H, d, J=6.6 Hz), 1.37–1.55 (2H, m), m/z=349.

Example 144

Synthesis of K-2305 (N-{5-[(4-methylphenyl)thio]pentyl}-N-[(1R)-1-((1-naphthyl)ethyl]amine)

K-2305 hydrochloride was obtained as white crystals by the same method as the one employed for the synthesis of K-2293 but replacing the 4-chlorothiophenol and 1,4-dibromobutane respectively by 4-methylthiophenol and 1,5-dibromopentane.

400 MHz-NMR 10.50 (1H, bs), 9.99 (1H, bs), 8.25 (1H, d, J=7.1 Hz), 7.98 (1H, d, J=8.3 Hz), 7.94 (1H, dd, J=7.8 Hz, J=1.2 Hz), 7.89 (1H, d, J=8.3 Hz), 7.52–7.66 (3H, m), 7.11–7.13 (2H, m), 6.98–7.00 (2H, m), 5.18 (1H, bs), 2.68–2.73 (2H, m), 2.71 (2H, t, J=7.2 Hz), 2.24 (3H, s), 2.02 (3H, d, J=6.6 Hz), 1.91–1.99 (2H, m), 1.42–1.50 (2H, m), 1.26–1.34 (2H, m), m/z=363.

Example 145

Synthesis of K-2275

K-2305 hydrochloride was obtained as white crystals by the same method as the one employed for the synthesis of K-2293 but replacing the 4-chlorothiophenol and 1,4-dibromobutane respectively by 3-trifluoromethylthiophenol and 1-bromo-2-chloroethane.

400 MHz-NMR 10.88 (1H, bs), 10.25 (1H, bs), 8.16 (1H, d, J=6.6 Hz), 7.87–7.95 (3H, m), 7.52–7.65 (3H, m), 7.40 (1H, bs), 7.31–7.34 (2H, m), 7.21–7.26 (1H, m), 5.18–5.28 (1H, m), 3.53 (2H, t, J=7.7 Hz), 2.91–3.06 (2H, m), 2.01 (3H, d, J=6.84 Hz), m/z=375.

Example 146

Synthesis of K-2314

K-2314 hydrochloride was obtained as white crystals by the same method as the one employed for the synthesis of K-2293 but replacing the 4-chlorothiophenol by 4-methoxythiophenol.

400 MHz-NMR 10.55 (1H, bs), 10.03 (1H, bs), 8.25 (1H, d, J=7.4 Hz), 7.99 (1H, d, J=8.5 Hz), 7.89–7.95 (2H, m), 7.52–7.68 (3H, m), 7.15–7.18 (2H, m), 6.71–6.75 (2H, m), 5.18–5.22 (1H, m), 3.74 (3H, s), 2.67–2.76 (2H, m), 2.64 (2H, t, J=7.1 Hz), 2.03–2.15 (2H, m), 2.05 (2H, d, J=6.8 Hz), 1.32–1.50 (2H, m), m/z=365.

Example 147

Synthesis of K-2008

K-2008 hydrochloride was obtained as white crystals by the same method as the one employed for the synthesis of K-2293 but replacing the 4-chlorothiophenol, 1,4-dibromobutane and (R)-(+)-1-(1-naphthyl)ethylamine respectively by 3-trifluoromethylthiophenol, 1-bromo-2-chloroethane and (R)-(+)-3-methoxy-α-methylbenzylamine. m/z=355.

Example 148

Synthesis of S-1

2,5-Dimethylthiophenol (580 mg, 4.20 mmol) was dissolved in acetonitrile (6 ml). To the obtained solution were successively added at room temperature potassium carbonate (785 mg, 5.68 mmol) and 1-bromo-2-chloroethane (0.35 ml, 4.21 mmol) and the reaction mixture was stirred at room temperature for 2.5 hours. After confirming the completion of the reaction by TLC, potassium carbonate (730 mg, 5.28 mmol) and (R)-(+)-3-methoxy-α-benzylmethylamine (500 mg, 3.30 mmol) were added at the same temperature to the reaction system. Further, the reaction mixture was stirred at 90° C. for 24 hours. After the completion of the reaction, the mixture was cooled by allowing to stand at room temperature and water was added thereto. Next, the reaction mixture was subjected to separatory extraction with chloroform and a saturated aqueous solution of sodium chloride and washed. The organic layer thus obtained was dried over anhydrous sodium sulfate and concentrated under reduced pressure. The organic residue was purified by silica gel column chromatography (chloroform:methanol=200:1) to thereby give a pale yellow, syrupy compound S-1 (332 mg, 1.05 mmol, yield: 31.8%).

500 MHz-$^1$H-NMR 7.30 (1H, d, J=8.0 Hz), 7.21 (1H, dd, J=8.0 Hz, J=8.0 Hz), 7.06 (1H, s), 6.86–6.90 (3H, m), 6.75–6.78 (1H, m), 3.80 (3H, s), 3.74 (1H, q, J=6.5 Hz), 2.95–3.03 (2H, m), 2.68–2.77 (2H, m), 2.32 (3H, s), 2.27 (3H, s), 1.34 (3H, d, J=6.5 Hz), m/z=315.

Example 149

Synthesis of S-2

S-2 was synthesized by almost the same method as the one employed for the synthesis of S-1 but replacing the 1-bromo-2-chloroethane by 1,3-dibromopropane.

500 MHz-$^1$H-NMR 7.22 (1H, dd, J=8.0 Hz, J=8.0 Hz), 7.06 (1H, s), 7.02 (1H, d, J=7.5 Hz), 6.86–6.88 (3H, m), 6.76–6.78 (1H, m), 3.80 (3H, s), 3.72 (1H, q, J=6.5 Hz), 2.85–2.96 (2H, m), 2.53–2.66 (2H, m), 2.29 (3H, s), 2.28 (3H, s), 1.74–1.82 (2H, m), 1.33 (3H, d, J=6.5 Hz), m/z=329.

Example 150

Synthesis of S-3

S-3 was synthesized by almost the same method as the one employed for the synthesis of S-1 but replacing the 1-bromo-2-chloroethane by 1,4-dibromobutane.

500 MHz-$^1$H-NMR 7.22 (1H, dd, J=8.3 Hz, J=8.3 Hz), 7.04 (1H, s), 7.03 (1H, d, J=8.0 Hz), 6.85–6.89 (3H, m), 6.75–6.78 (1H, m), 3.80 (3H, s), 3.71 (1H, q, J=6.8 Hz), 2.85 (2H, t, J=7.3 Hz), 2.42–2.55 (2H, m), 2.30 (3H, s), 2.29 (3H, s), 1.56–1.70 (4H, m), 1.33 (3H, d, J=6.8 Hz), m/z=343.

Example 151

Synthesis of S-4

S-4 was synthesized by almost the same method as the one employed for the synthesis of S-1 but replacing the 1-bromo-2-chloroethane by 1,5-dibromopentane.

500 MHz-$^1$H-NMR 7.23 (1H, dd, J=8.3 Hz, J=8.3 Hz), 7.05 (1H, s), 7.03 (1H, d, J=7.5 Hz), 6.87–6.88 (3H, m), 6.76–6.78 (1H, m), 3.81 (3H, s), 3.72 (1H, q, J=6.5 Hz), 2.85 (1H, t, J=7.5 Hz), 2.40–2.51 (2H, m), 2.31 (3H, s), 2.30 (3H, s), 1.61–1.67 (2H, m), 1.42–1.51 (4H, m), 1.34 (3H, d, J=6.5 Hz), m/z=357.

Example 152

Synthesis of S-5

S-5 was synthesized by almost the same method as the one employed for the synthesis of S-1 but replacing the 1-bromo-2-chloroethane by 1,6-dibromohexane.

500 MHz-$^1$H-NMR 7.23 (1H, dd, J=8.0 Hz, J=8.0 Hz), 7.05 (1H, s), 7.03 (1H, d, J=8.0 Hz), 6.86–6.89 (3H, m), 6.76–6.78 (3H, m), 3.81 (3H, s), 3.72 (1H, q, J=7.0 Hz), 2.85 (2H, t, J=7.3 Hz), 2.39–2.52 (2H, m), 2.31 (3H, s), 2.30 (3H, s), 1.61–1.67 (2H, m), 1.39–1.50 (4H, m), 1.34 (3H, d, J=7.0 Hz), 1.29–1.34 (2H, m), m/z=371.

Example 153

Synthesis of S-6

S-6 was synthesized by almost the same method as the one employed for the synthesis of S-1 but replacing the 1-bromo-2-chloroethane by 1,7-dibromoheptane.

500 MHz-$^1$H-NMR 7.22 (1H, dd, J=8.0 Hz, J=8.0 Hz), 7.05 (1H, s), 7.03 (1H, d, J=7.5 Hz), 6.80–6.86 (3H, m), 6.75–6.78 (1H, m), 3.81 (3H, s), 3.72 (1H, q, J=6.8 Hz), 2.85 (2H, t, J=7.5 Hz), 2.38–2.51 (2H, m), 2.31 (3H, s), 2.29 (3H, s), 1.60–1.66 (2H, m), 1.37–1.48 (4H, m), 1.34 (3H, d, J=6.8 Hz), 1.27–1.30 (4H, m), m/z=385.

Example 154

Synthesis of S-7

S-7 was synthesized by almost the same method as the one employed for the synthesis of S-1 but replacing the 1-bromo-2-chloroethane by 1,8-dibromooctane.

500 MHz-$^1$H-NMR 7.23 (1H, dd, J=8.3 Hz, J=8.3 Hz), 7.06 (1H, s), 7.03 (1H, d, J=8.0 Hz), 6.87–6.89 (3H, m), 6.75–6.78 (1H, m), 3.81 (3H, s), 3.72 (1H, q, J=6.5 Hz), 2.86 (2H, t, J=7.5 Hz), 2.39–2.51 (2H, m), 2.31 (3H, s), 2.30 (3H, s), 1.61–1.67 (2H, m), 1.38–1.47 (4H, m), 1.34 (3H, d, J=6.5 Hz),1.23–1.31 (6H, m), m/z=399.

Example 155

Synthesis of S-8

S-8 was synthesized by almost the same method as the one employed for the synthesis of S-1 but replacing the (R)-(+)-3-methoxy-α-benzylmethylamine by (R)-(+)-1-(1-naphthyl)ethylamine.

500 MHz-$^1$H-NMR 8.16 (1H, d, J=8.8 Hz), 7.83–7.87 (1H, m), 7.74 (1H, d, J=8.0 Hz), 7.64 (1H, d, J=7.1 Hz), 7.42–7.51 (3H, m), 7.05 (1H, s), 7.03 (1H, d, J=8.0 Hz), 6.88 (1H, d, J=7.8 Hz), 4.63 (1 H, q, J=6.6 Hz), 3.05 (2H, t, J=6.6 Hz), 2.77–2.87 (2H, m), 2.32 (3H, s), 2.24 (3H, s), 1.49 (3H, d, J=6.6 Hz), m/z=335.

Example 156

Synthesis of S-9

S-9 was synthesized by almost the same method as the one employed for the synthesis of S-1 but replacing the 1-bromo-2-chloroethane and (R)-(+)-3-methoxy-α-benzylmethylamine respectively by 1,3-dibromopropane and (R)-(+)-1-(1-naphthyl)ethylamine.

500 MHz-$^1$H-NMR 8.18 (1H, d, J=8.3 Hz), 7.83–7.88 (1H, m), 7.74 (1H, d, J=8.3 Hz), 7.64 (1H, d, J=6.8 Hz), 7.44–7.52 (3H, m), 7.25 (1H, s), 7.06 (1H, s), 7.02 (1H, d, J=7.7 Hz), 6.87 (1H, d, J=7.7 Hz), 4.62 (1H, q, J=6.6 Hz), 2.87–3.00 (2H, m), 2.64–2.77 (2H, m), 2.28 (3H, s), 2.27 (3H, s), 1.81–1.88 (2H, m), 1.49 (3H, d, J=6.6 Hz), m/z=349.

Example 157

Synthesis of S-10

S-10 was synthesized by almost the same method as the one employed for the synthesis of S-1 but replacing the 1-bromo-2-chloroethane and (R)-(+)-3-methoxy-α-benzylmethylamine respectively by 1,4-dibromobutane and (R)-(+)-1-(1-naphthyl)ethylamine.

500 MHz-$^1$H-NMR 8.17 (1H, d, J=8.3 Hz), 7.85–7.88 (1H, m), 7.74 (1H, d, J=8.0 Hz), 7.66 (1H, d, J=6.8 Hz), 7.03 (1H, s), 7.01 (1H, d, J=7.8 Hz), 6.86–6.89 (1H, m), 4.64 (1H, q, J=6.2 Hz), 2.85 (2H, t J=6.8 Hz), 2.55–2.65 (2H, m), 2.30 (3H, s), 2.28 (3H, s),1.65–1.70 (4H, m), 1.50 (3H, d, J=6.2 Hz), m/z=363.

Example 158

Synthesis of S-11

S-11 was synthesized by almost the same method as the one employed for the synthesis of S-1 but replacing the 1-bromo-2-chloroethane and (R)-(+)-3-methoxy-α-benzylmethylamine respectively by 1,5-dibromopentane and (R)-(+)-1-(1-naphthyl)ethylamine.

500 MHz-$^1$H-NMR 8.45 (1H, d, J=8.0 Hz), 8.17 (1H, d, J=8.3 Hz), 7.85–7.88 (1H, m), 7.74 (2H, d, J=8.3 Hz), 7.64 (1H, d, J=7.1 Hz), 7.42–7.52 (3H, m), 7.01–7.04 (2H, m), 6.87 (1H, q, J=7.6 Hz), 4.62 (1H, q, J=6.5 Hz), 2.85 (2H, t, J=7.3 Hz), 2.51–2.63 (2H, m), 3.00 (3H, s),2.29 (3H, s), 1.61–1.68 (2H, m), 1.44–1.57 (4H, m), 1.49 (3H, d, J=6.5 Hz), m/z=377.

Example 159

Synthesis of S-12

S-12 was synthesized by almost the same method as the one employed for the synthesis of S-1 but replacing the 1-bromo-2-chloroethane and (R)-(+)-3-methoxy-α-benzylmethylamine respectively by 1,6-dibromohexane and (R)-(+)-1-(1-naphthyl)ethylamine.

500 MHz-$^1$H-NMR 8.17 (1H, d, J=8.3 Hz), 7.73 (1H, d, J=8.0 Hz), 7.64 (1H, d, J=7.1 Hz), 7.40–7.52 (3H, m), 6.06–6.98 (2H, m), 6.87 (1H, d, J=7.6 Hz), 4.62 (1H, q, J=6.6 Hz), 2.84 (2H, t, J=7.3 Hz), 2.49–2.63 (2H, m), 2.30 (3H, s), 2.29 (3H, s), 1.59–1.67 (2H, m), 1.46–1.55 (2H, m), 1.49 (3H, d, J=6.6 Hz), 1.27–1.46 (4H, m), m/z=391.

Example 160

Synthesis of S-13

S-13 was synthesized by almost the same method as the one employed for the synthesis of S-1 but replacing the 1-bromo-2-chloroethane and (R)-(+)-3-methoxy-α-benzylmethylamine respectively by 1,7-dibromoheptane and (R)-(+)-1-(1-naphthyl)ethylamine.

500 MHz-$^1$H-NMR 8.17 (1H, d, J=8.3 Hz), 7.85–7.88 (1H, m), 7.74 (1H, d, J=8.3 Hz), 7.68 (1H, d, J=7.1 Hz), 7.41–7.53 (3H, m), 7.04 (1H, s), 7.02 (1H, d, J=7.6 Hz), 6.87 (1H, d, J=7.6 Hz), 4.66 (1H, q, J=6.5 Hz), 2.84 (2H, t, J=7.3 Hz), 2.30 (3H, s), 2.29 (3H, s), 1.58–1.66 (2H, m), 1.53 (3H, d, J=6.5 Hz), 1.34–1.44 (2H, m), 1.26–1.30 (4H, m), m/z= 405.

Example 161

Synthesis of S-14

S-14 was synthesized by almost the same method as the one employed for the synthesis of S-1 but replacing the 1-bromo-2-chloroethane and (R)-(+)-3-methoxy-α-benzylmethylamine respectively by 1,8-dibromooctane and (R)-(+)-1-(1-naphthyl)ethylamine. m/z =419.

Example 162

Synthesis of S-15

S-15 was synthesized by almost the same method as the one employed for the synthesis of S-1 but replacing the 1-bromo-2-chloroethane and (R)-(+)-3-methoxy-α-benzylmethylamine respectively by 1,10-dibromodecane and (R)-(+)-1-(1-naphthyl)ethylamine.

400 MHz-$^1$H-NMR 8.18 (1H, d, J=8.6 Hz), 7.83–7.88 (1H, m), 7.73 (1H, d, J=8.3 Hz), 7.65 (1H, d, J=6.8 Hz), 7.40–7.52 (3H, m), 7.06 (1H, s), 7.03 (1H, d, J=7.6 Hz), 6.87 (1H, d, J=7.6 Hz), 4.63 (1H, q, J=6.5 Hz), 2.86 (2H, t, J=7.3 Hz), 2.50–2.62 (2H, m), 2.31 (3H, s), 2.30 (3H, s), 1.60–1.70 (2H, m), 1.49 (3H, d, J=6.5 Hz), 1.20–1.50 (14H, m), m/z=447.

Example 163

Synthesis of S-16

S-16 was synthesized by almost the same method as the one employed for the synthesis of S-1 but replacing the 1-bromo-2-chloroethane and (R)-(+)-3-methoxy-α-benzylmethylamine respectively by 1,12-dibromododecane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.0 Hz), 7.65 (1H, d, J=7.1 Hz), 7.46–7.53 (3H, m), 7.06 (1H, s), 7.03 (1H, d J=7.8 Hz), 6.87 (1H, d, J=7.8 Hz), 4.63 (1H, q, J=6.6 Hz), 2.87 (2H, t, J=7.4 Hz), 2.50–2.63 (2H, m), 2.31.(3H, s), 2.30 (3H, s), 1.61–1.69 (2H, m), 1.15–1.55 (18H, m), 1.50 (3H, d, J=6.6 Hz), m/z=475.

Example 164

Synthesis of S-17

S-17 was synthesized by almost the same method as the one employed for the synthesis of S-1 but replacing the 2,5-dimethylthiophenol by 2,4-dimethylthiophenol.

400 MHz-$^1$H-NMR 7.21 (1H, dd, J=8.0 Hz, J=8.0 Hz), 7.14 (1H, d, J=8.0 Hz), 6.98 (1H, s), 6.90–6.92 (1H, m), 6.85–6.88 (2H, m), 6.75–6.81 (1H, m), 3.80 (3H, s), 3.72 (1H, q, J=6.6 Hz), 2.93–2.97 (2H, m), 2.62–2.74 (2H, m), 2.34 (3H, s), 2.27 (3H, s), 1.33 (3H, d, J=6.6 Hz), m/z=315.

Example 165

Synthesis of S-18

S-18 was synthesized by almost the same method as the one employed for the synthesis of S-1 but replacing the 2,5-dimethylthiophenol and 1-bromo-2-chloroethane respectively by 2,4-dimethylthiophenol and 1,3-dibromopropane.

400 MHz-$^1$H-NMR 7.22 (1H, dd, J=8.1 Hz, J=8.1 Hz), 7.16 (1H, d, J=7.8 Hz), 6.98 (1H, s), 6.92–6.95 (1H, m), 6.86–6.88 (2H, m), 6.75–6.79 (1H, m), 3.80 (3H, s), 3.71 (1H, q, J=6.6 Hz), 2.80–2.93 (2H, m), 2.51–2.65 (2H, m), 2.32 (3H, s), 2.28 (3H, s), 1.70–1.81 (2H, m), 1.32 (3H, d, J=6.6 Hz), m/z=329.

Example 166

Synthesis of S-19

S-19 was synthesized by almost the same method as the one employed for the synthesis of S-1 but replacing the 2,5-dimethylthiophenol and 1-bromo-2-chloroethane respectively by 2,4-dimethylthiophenol and 1,4-dibromobutane.

400 MHz-$^1$H-NMR 7.23 (1H, dd, J=8.3 Hz, J=8.3 Hz), 7.16 (1H, d, J=7.8 Hz), 6.98 (1H, slike), 6.93–6.95 (1H, m), 6.86–6.88 (2H, m), 6.75–6.79 (1H, m), 3.80 (3H, s), 3.71 (1H, q, J=6.6 Hz), 2.81 (2H, t, J=6.9 Hz), 2.40–2.54 (2H, m), 2.33 (3H, s), 2.28 (3H, s), 1.53–1.66 (4H, m), 1.33 (3H, d, J=6.6 Hz), m/z=343.

Example 167

Synthesis of S-20

S-20 was synthesized by almost the same method as the one employed for the synthesis of S-1 but replacing the 2,5-dimethylthiophenol and 1-bromo-2-chloroethane respectively by 2,4-dimethylthiophenol and 1,5-dibromopentane.

400 MHz-$^1$H-NMR 7.23 (1H, dd, J=8.0 Hz, J=8.0 Hz), 7.16 (1H, d, J=7.8 Hz), 6.98 (1H, s), 6.95 (1H, d, J=8.0 Hz), 6.66–6.89 (2H, m)., 6.70–6.79 (1H, m), 3.81 (3H, s), 3.71 (1H, q, J=6.6 Hz), 2.81 (2H, t, J=7.3 Hz), 2.38–2.52 (2H, m), 2.33 (3H, s), 2.28 (3H, s), 1.56–1.64 (2H, m), 1.35–1.50 (4H, m), 1.34 (3H, d, J=6.6 Hz), m/z=357.

Example 168

Synthesis of S-21

S-21 was synthesized by almost the same method as the one employed for the synthesis of S-1 but replacing the 2,5-dimethylthiophenol and 1-bromo-2-chloroethane respectively by 2,4-dimethylthiophenol and 1,6-dibromohexane.

400 MHz-$^1$H-NMR 7.23 (1H, dd, J=8.0 Hz, J=8.0 Hz), 7.16 (1H, d, J=7.8 Hz), 6.98 (1H, s), 6.93–6.96 (1H, m), 6.87–6.90 (2H, m), 6.75–6.79 (1H, m), 3.81 (3H, s), 3.72 (1H, q, J=6.6 Hz), 2.81 (2H, t, J=7.3 Hz), 2.38–2.51 (2H, m), 2.34 (3H, s), 2.28 (3H, s), 1.56–1.64 (2H, m), 1.24–1.50 (6H, m), 1.34 (2H, d, J=6.6 Hz), m/z=371.

Example 169

Synthesis of S-22

S-22 was synthesized by almost the same method as the one employed for the synthesis of S-1 but replacing the 2,5-dimethylthiophenol and 1-bromo-2-chloroethane respectively by 2,4-dimethylthiophenol and 1,7-dibromoheptane.

400 MHz-$^1$H-NMR 7.23 (1H, dd, J=8.0 Hz, J=8.0 Hz), 7.16 (1H, d, J=7.8 Hz), 6.99 (1H, s), 6.93–6.96 (1H, m), 6.87–6.90 (2H, m), 6.73–6.79 (1H, m), 3.81 (3H, s), 3.72 (1H, q, J=6.6 Hz), 2.81 (2H, t, J=7.4 Hz), 2.37–2.51 (2H, m), 2.34 (3H, s), 2.28 (3H, s), 1.56–1.64 (2H, m), 1.24–1.46 (8H, m), 1.34 (3H, d, J=6.6 Hz), m/z=385.

Example 170

Synthesis of S-23

S-23 was synthesized by almost the same method as the one employed for the synthesis of S-1 but replacing the 2,5-dimethylthiophenol and 1-bromo-2-chloroethane respectively by 2,4-dimethylthiophenol and 1,8-dibromooctane.

400 MHz-$^1$H-NMR 7.23 (1H, dd, J=8.3 Hz, J=8.3 Hz), 7.17 (1H, d, J=8.0 Hz), 6.99 (1H, s), 6.95 (1H, d, J=8.0 Hz), 6.87–6.89 (1 H, m), 6.75–6.79 (1H, m), 3.81 (3H, s),3.72

(1H, q, J=6.6 Hz), 2.82 (2H, t, J=7.4 Hz), 2.38–2.52 (2H, m), 2.34 (3H, s), 2.28 (3H, s), 1.55–1.64 (2H, m), 1.20–1.50 (10H, m), 1.34 (3H, d, J=6.6 Hz), m/z=399.

Example 171

Synthesis of S-24

S-24 was synthesized by almost the same method as the one employed for the synthesis of S-1 but replacing the 2,5-dimethylthiophenol and (R)-(+)-3-methoxy-α-benzylmethylamine respectively by 2,4-dimethylthiophenol and (R)-(+)-1-(1-naphthyl)ethylamine.

400 MHz-$^1$H-NMR 8.15 (1H, d, J=8.16 Hz), 7.83–7.90 (1H, m), 7.72 (1H, d, J=8.0 Hz), 7.63 (1H, d, J=7.3 Hz), 7.42–7.52 (3H, m), 7.14 (1H, d, J=7.8 Hz), 6.98 (1H, s), 6.87–6.90 (1H, m), 4.61 (1H, q, J=6.5 Hz), 3.02 (2H, t, J=8.7 Hz), 2.73–2.81 (2H, m), 2.34 (3H, s), 2.27 (3H, s), 1.48 (3H, d, J=6.5 Hz), m/z=335.

Example 172

Synthesis of S-25

S-25 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4-dimethylthiophenol, 1,3-dibromopropane and (R)-(+)-1-(1-naphthyl)ethylamine. m/z=349.

Example 173

Synthesis of S-26

S-26 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4-dimethylthiophenol, 1,6-dibromohexane and (R)-(+)-1-(1-naphthyl)ethylamine.

400 MHz-$^1$H-NMR 8.15 (1H, d, J=8.31 Hz), 7.85–7.87 (1H, m), 7.23 (1H, d, J=8.3 Hz), 7.64 (1H, d, J=7.1 Hz), 7.15 (1H, d, J=7.8 Hz), 6.98 (1H, s), 6.93–6.95 (1H, m), 4.62 (1H, q, J=6.6 Hz), 2.80 (2H, t, J=7.3 Hz), 2.48–2.62 (2H, m), 2.35 (3H, s), 2.27 (3H, s), 1.57–1.63 (2H, m), 1.43–1.53 (2H, m), 1.25–1.44 (4H, m), 1.49 (3H, d, J=6.6 Hz), m/z=391.

Example 174

Synthesis of S-27

S-27 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4-dimethylthiophenol, 1,7-dibromoheptane and (R)-(+)-1-(1-naphthyl)ethylamine.

400 MHz-$^1$H-NMR 8.15 (1H, d, J=8.3 Hz), 7.87 (1H, d, J=6.0 Hz), 7.68–7.78 (2H, m), 7.45–7.55 (3H, m), 7.15 (1H, d, J=7.8 Hz), 6.98 (1H, s), 6.94 (1H, d, J=7.8 Hz), 4.69 (1H, q, J=6.6 Hz), 2.79 (2H, t, J=7.3 Hz), 2.50–2.63 (2H, m), 2.33 (3H, s), 2.27 (3H, s), 1.14–1.62 (13H, m), m/z=405.

Example 175

Synthesis of S-28

S-28 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4-dimethylthiophenol, 1,8-dibromooctane and (R)-(+)-1-(1-naphthyl) ethylamine.

400 MHz-$^1$H-NMR 8.15 (1H, d, J=8.0 Hz), 7.86–7.90 (1H, m), 7.70–7.80 (2H, m), 7.45–7.55 (3H, m), 7.16 (1H, d, J=7.8 Hz), 6.98 (1H, s), 6.94 (1H, d, J=7.8 Hz), 4.72 (1H, q, J=6.4 Hz), 2.80 (2H, t, J=7.4 Hz), 2.50–2.65 (2H, m), 2.33 (3H, s), 2.27 (3H, s), 1.17–1.63 (15H, m), m/z=419.

Example 176

Synthesis of S-29

S-29 was synthesized by almost the same method as the one employed for the synthesis of S-1 but replacing the 2,5-dimethylthiophenol by 2,6-dimethylthiophenol.

400 MHz-$^1$H-NMR 7.21 (1H, dd, J=8.1 Hz, J=8.1 Hz), 7.05–7.12 (3H, m), 6.83–6.86 (2H, m), 6.73–6.78 (1H, m), 3.80 (3H, s), 3.69 (1H, q, J=6.6 Hz), 2.72–2.82 (2H, m), 2.57–2.64 (2H, m), 2.51 (6H, s), 1.32 (3H, d, J=6.6 Hz), m/z=315.

Example 177

Synthesis of S-30

S-30 was synthesized by almost the same method as the one employed for the synthesis of S-1 but replacing the 2,5-dimethylthiophenol and 1-bromo-2-chloroethane respectively by 2,6-dimethylthiophenol and 1,3-dibromopropane.

400 MHz-$^1$H-NMR 7.22 (1H, dd, J=8.1 Hz, J=8.1 Hz), 7.05–7.09 (3H, m), 6.84–6.86 (2H, m), 6.74–6.78 (1H, m), 3.80 (3H, s), 3.69 (1H, q, J=6.6 Hz), 2.62–2.70 (2H, m), 2.51–2.60 (2H, m), 2.50 (6H, s), 1.61–1.70 (2H, m), 1.32 (3H, d, J=6.6 Hz), m/z=329.

Example 178

Synthesis of S-31

S-31 was synthesized by almost the same method as the one employed for the synthesis of S-1 but replacing the 2,5-dimethylthiophenol and 1-bromo-2-chloroethane respectively by 2,6-dimethylthiophenol and 1,4-dibromobutane.

400 MHz-$^1$H-NMR 7.22 (1H, dd, J=8.0 Hz, J=8.0 Hz), 7.04–7.09 (3H, m), 6.85–6.88 (2H, m), 6.77 (1H, ddd, J=8.0 Hz, J=2.4 Hz, J=1.0 Hz), 3.80 (3H, s), 3.70 (1H, q, J=6.6 Hz), 2.61 (2H, t, J=6.7 Hz), 2.51 (6H, s), 2.39–2.48 (2H, m), 1.48–1.58 (4H, m), 1.32 (3H, d, J=6.6 Hz), m/z=343.

Example 179

Synthesis of S-32

S-32 was synthesized by almost the same method as the one employed for the synthesis of S-1 but replacing the 2,5-dimethylthiophenol and 1-bromo-2-chloroethane respectively by 2,6-dimethylthiophenol and 1,5-dibromopentane.

400 MHz-$^1$H-NMR 7.23 (1H, dd, J=8.0 Hz, J=8.0 Hz), 7.06–7.11 (1H, m), 6.86–6.88 (2H, m), 6.75–6.79 (1H, m), 3.81 (3H, s), 3.71 (1H, q, J=6.6 Hz), 2.61 (2H, t, J=7.3 Hz), 2.52 (6H, s), 2.38–2.49 (2H, m), 1.34–1.54 (6H, m), 1.33 (3H, d, J=6.6 Hz), m/z=357.

Example 180

Synthesis of S-33

S-33 was synthesized by almost the same method as the one employed for the synthesis of S-1 but replacing the 2,5-dimethylthiophenol and 1-bromo-2-chloroethane respectively by 2,6-dimethylthiophenol and 1,6-dibromohexane.

400 MHz-$^1$H-NMR 7.23 (1H, dd, J=8.0 Hz, J=8.0 Hz), 7.07–7.11 (3H, m), 6.86–6.88 (2H, m), 6.75–6.79 (1H, m), 3.81 (3H, s), 3.71 (1H, q, J=6.6 Hz), 2.61 (2H, t, J=7.3 Hz), 2.52 (6H, s), 2.36–2.50 (2H, m), 1.21–1.54 (8H, m), 1.33 (3H, d, J=6.6 Hz), m/z=371.

Example 181

Synthesis of S-34

S-34 was synthesized by almost the same method as the one employed for the synthesis of S-1 but replacing the 2,5-dimethylthiophenol and 1-bromo-2-chloroethane respectively by 2,6-dimethylthiophenol and 1,7-dibromoheptane.

400 MHz-$^1$H-NMR 7.20–7.25 (1H, m), 7.07–7.09 (3H, m), 6.86–6.90 (2H, m), 6.75–6.78 (1H, m), 3.81 (3H, s), 3.72 (1 H, q, J=6.6 Hz), 2.61 (2H, t, J=7.32 Hz), 2.53 (6H, s), 2.36–2.50 (2H, m), 1.20–1.54 (10H, m), 1.34 (3H, d, J=6.6 Hz), m/z=385.

Example 182

Synthesis of S-35

S-35 was synthesized by almost the same method as the one employed for the synthesis of S-1 but replacing the 2,5-dimethylthiophenol and 1-bromo-2-chloroethane respectively by 2,6-dimethylthiophenol and 1,8-dibromooctane.

400 MHz-$^1$H-NMR 7.20–7.25 (1H, m), 7.05–7.10 (3H, m), 6.88–6.89 (2H, m), 6.76–6.79 (1H, m), 3.81 (3H, s), 3.73 (1H, q, J=6.5 Hz), 2.61 (2H, t, J=7.3 Hz), 2.53 (6H, s), 2.37–2.49 (2H, m), 1.20–1.55 (12H, m), 1.35 (3H, d, J=6.5 Hz), m/z=399.

Example 183

Synthesis of S-36

S-36 was synthesized by almost the same method as the one employed for the synthesis of S-1 but replacing the 2,5-dimethylthiophenol and (R)-(+)-3-methoxy-α-benzylmethylamine respectively by 2,6-dimethylthiophenol and (R)-(+)-1-(1-naphthyl)ethylamine.

400 MHz-$^1$H-NMR 8.15 (1H, d, J=8.0 Hz), 7.83–7.90 (1H, m), 7.73 (1H, d, J=8.3 Hz), 7.63 (1H, d, J=7.1 Hz), 7.43–7.52 (3H, m), 7.04–7.12 (3H, m), 4.59 (1H, q, J=6.6 Hz), 2.77–2.86 (2H, m), 2.70 (2H, t, J=6.6 Hz), 2.50 (6H, s), 1.47 (3H, d, J=6.6 Hz), m/z=335.

Example 184

Synthesis of S-37

S-37 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,6-dimethylthiophenol, 1,3-dibromopropane and (R)-(+)-1-(1-naphthyl)ethylamine.

400 MHz-$^1$H-NMR 8.15 (1H, d, J=8.0 Hz), 7.84–7.87 (1H, m), 7.73 (1H, d, J=8.3 Hz), 7.62 (1H, d, J=7.1 Hz), 7.44–7.51 (3H, m), 7.04–7.11 (3H, m), 4.58 (1H, q, J=6.5 Hz), 2.58–2.73 (4H, m), 2.50 (6H, s), 1.68–1.75 (2H, m), 1.47 (3H, d, J=6.5 Hz), m/z=349.

Example 185

Synthesis of S-38

S-38 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,6-dimethylthiophenol, 1,4-dibromobutane and (R)-(+)-1-(1-naphthyl)ethylamine.

400 MHz-$^1$H-NMR 8.16 (1H, d, J=8.3 Hz), 7.85–7.88 (1H, m), 7.73 (1H, d, J=8.3 Hz), 7.63 (1H, d, J=7.1 Hz), 7.44–7.52 (3H, m), 7.05–7.11 (3H, m), 4.61 (1H, q, J=6.5 Hz), 2.61 (2H, t, J=7.3 Hz), 2.50–2.59 (2H, m), 2.50 (6H, s), 1.50–1.64 (4H, m), 1.48 (3H, d, J=6.5 Hz), m/z=363.

Example 186

Synthesis of S-39

S-39 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,6-dimethylthiophenol, 1,5-dibromopentane and (R)-(+)-1-(1-naphthyl)ethylamine.

400 MHz-$^1$H-NMR 8.17 (1H, d, J=8.0 Hz), 7.85–7.88 (1H, m), 7.74 (1H, d, J=8.3 Hz), 7.63 (1H, d, J=7.1 Hz), 7.44–7.52 (3H, m), 7.06–7.08 (3H, m), 4.61 (1H, q, J=6.6 Hz), 2.61 (2H, t, J=7.1 Hz), 2.50–2.58 (2H, m), 2.51 (6H, s), 1.35–1.55 (6H, m), 1.48 (3H, d, J=6.6 Hz), m/z=377.

Example 187

Synthesis of S-40

S-40 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,6-dimethylthiophenol, 1,6-dibromohexane and (R)-(+)-1-(1-naphthyl)ethylamine.

400 MHz-$^1$H-NMR 8.17 (1H, d, J=8.0 Hz), 7.85–7.87 (1H, m), 7.74 (1H, d, J=8.0 Hz), 7.64 (1H, d, J=5.9 Hz), 7.44–7.52 (3H, m), 7.05–7.09 (3H, m), 4.62 (1H, q, J=6.5 Hz), 2.50–2.62 (4H, m), 2.52 (6H, s), 1.23–1.53 (8H, m), 1.49 (3H, d, J=6.5 Hz), m/z=391

Example 188

Synthesis of S-41

S-41 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,6-dimethylthiophenol, 1,7-dibromoheptane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.3 Hz), 7.64 (1H, d, J=7.1 Hz), 7.44–7.53 (3H, m), 7.07–7.09 (3H, m), 4.62 (1H, q, J=6.6 Hz), 2.50–2.62 (4H, m), 2.52 (6H, s), 1.20–1.53 (10H, m), 1.49 (3H, d, J=6.6 Hz), m/z=405.

Example 189

Synthesis of S-42

S-42 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,6-dimethylthiophenol, 1,8-dibromooctane and (R)-(+)-1-(1-naphthyl)ethylamine.

400 MHz-$^1$H-NMR 8.15 (1H, d, J=8.6 Hz), 7.86–7.89 (1H, m), 7.74–7.78 (2H, m) 7.46–7.54 (3H, m), 6.99–7.10 (3H, m) 4.70–4.78 (1H, m), 2.51–2.62 (4H, m), 2.52 (6H, s), 1.07–1.84 (12H, m), 1.59 (3H, d, J=6.1 Hz), m/z=419.

Example 190

Synthesis of S-43

S-43 was synthesized by almost the same method as the one employed for the synthesis of S-1 but replacing the 2,5-dimethylthiophenol by 3,4-dimethylthiophenol.

400 MHz-$^1$H-NMR 7.21 (1H, dd, J=8.0 Hz, J=8.0 Hz), 7.11 (1H, s), 7.00–7.07 (2H, m), 6.80–6.87 (2H, m), 6.75–6.87 (2H, m), 6.75–6.78 (1H, m), 3.79 (3H, s), 3.72 (1H, q, J=6.5 Hz), 2.95–2.99 (2H, m), 2.63–2.70 (2H, m), 2.21 (3H, s), 2.20 (3H, s),1.33 (3H, d, J=6.5 Hz), m/z=315.

Example 191

Synthesis of S-44

S-44 was synthesized by almost the sarne method as the one employed for the synthesis of S-1 but replacing the 2,5-dimethylthiophenol and 1-bromo-2-chloroethane respectively by 3,4-dimethylthiophenol and 1,3-dibromopropane.

400 MHz-$^1$H-NMR 7.20–7.25 (1H, m), 7.12 (1H, s), 7.01–7.08 (2H, m), 6.84–6.88 (2H, m), 6.75–6.78 (1H, m), 3.80 (3H, s), 3.70 (1H, q, J=7.0 Hz), 2.83–2.95 (2H, m), 2.50–2.63 (2H, m), 2.22 (3H, s), 2.21 (3H, s), 1.72–1.77 (2H, m), 1.32 (3H, d, J=7.0 Hz), m/z=329.

Example 192

Synthesis of S-45

S-45 was synthesized by almost the same method as the one employed for the synthesis of S-1 but replacing the 2,5-dimethylthiophenol and 1-bromo-2-chloroethane respectively by 3,4-dimethylthiophenol and 1,4-dibromobutane.

400 MHz-$^1$H-NMR 7.22 (1H, dd, J=8.0 Hz, J=8.0 Hz), 7.11 (1H, s), 7.01–7.07 (2H, m), 6.85–6.87 (2H, m), 6.75–6.78 (1 H, m), 3.80 (3H, s), 3.70 (1H, q, J=7.0 Hz), 2.84 (2H, t, J=7.5 Hz), 2.40–2.52 (2H, m), 2.22 (3H, s), 2.21 (3H, s), 1.54–1.65 (4H, m), 1.32 (3H, d, J=7.0 Hz), m/z=343.

Example 193

Synthesis of S-46

S-46 was synthesized by almost the same method as the one employed for the synthesis of S-1 but replacing the 2,5-dimethylthiophenol and 1-bromo-2-chloroethane respectively by 3,4-dimethylthiophenol and 1,5-dibromopentane. m/z=357.

Example 194

Synthesis of S-47

S-47 was synthesized by almost the same method as the one employed for the synthesis of S-1 but replacing the 2,5-dimethylthiophenol and 1-bromo-2-chloroethane respectively by 3,4-dimethylthiophenol and 1,6-dibromohexane.

400 MHz-$^1$H-NMR 7.23 (1H, dd, J=8.0 Hz, J=8.0 Hz), 7.12 (1H, s),7.02–7.08 (2H, m), 6.86–6.89 (2H, m), 6.75–6.78 (1H, m), 3.81 (3H, s), 3.71 (1H, q, J=7.0 Hz), 2.84 (2H, t, J=7.3 Hz), 2.38–2.50 (2H, m), 2.23 (3H, s), 2.22 (3H, s),1.56–1.62 (2H, m), 1.24–1.48 (6H, m), 1.33 (3H, d, J=7.0 Hz), m/z=377.

Example 195

Synthesis of S-48

S-48 was synthesized by almost the same method as the one employed for the synthesis of S-1 but replacing the 2,5-dimethylthiophenol and 1-bromo-2-chloroethane respectively by 3,4-dimethylthiophenol and 1,7-dibromoheptane.

400 MHz-$^1$H-NMR 7.22 (1H, dd, J=8.0 Hz, J=8.0 Hz), 7.11 (1H, s), 7.01–7.08 (2H, m), 6.86–6.88 (2H, m), 6.75–6.78 (1H, m), 3.80 (3H, s), 3.71 (1H, q, J=6.5 Hz), 2.80 (2H, t, J=7.5 Hz), 2.38–2.50 (2H, m), 2.22 (3H, s), 2.21 (3H, s), 1.56–1.62 (2H, m), 1.33–1.45 (4H, m), 1.33 (3H, d, J=6.5Hz), 1.24–1.28 (4H, m), m/z=385.

Example 196

Synthesis of S-49

S-49 was synthesized by almost the same method as the one employed for the synthesis of S-1 but replacing the 2,5-dimethylthiophenol and 1-bromo-2-chloroethane respectively by 3,4-dimethylthiophenol and 1,8-dibromooctane.

400 MHz-$^1$H-NMR 7.21–7.25 (1H, m), 7.12 (1 H, s), 7.02–7.08 (2H, m), 6.87–6.89 (1H, d, J=8.0 Hz), 6.87 (1H, s), 6.76–6.78 (1 H, m), 3.80 (3H, s), 3.70–3.74 (1H, m), 2.85 (2H, t, J=7.8 Hz), 2.38–2.50 (2H, m), 2.22 (3H, s), 2.21 (3H, s), 1.56–1.62 (2H, m), 1.33–1.46 (4H, m), 1.34 (3H, d, J=7.0 Hz), 1.25 (6H, bs), m/z=399.

Example 197

Synthesis of S-50

S-50 was synthesized by almost the same method as the one employed for the synthesis of S-1 but replacing the 2,5-dimethylthiophenol and (R)-(+)-3-methoxy-α-benzylmethylamine respectively by 3,4-dimethylthiophenol and (R)-(+)-1-(1-naphthyl)ethylamine.

Example 198

Synthesis of S-51

S-51 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,4-dimethylthiophenol, 1,3-dibromopropane and (R)-(+)-1-(1-naphthyl)ethylamine.

400 MHz-$^1$H-NMR 8.16 (1H, d, J=8.5 Hz), 8.85 (1H, d, J=9.0 Hz), 7.72 (1H, d, J=8.0 Hz), 7.61 (1H, d, J=7.5 Hz), 7.43–7.49 (3H, m), 7.11 (1H, s), 6.97–7.07 (2H, m), 4.58 (1H, q, J=6.5 Hz), 2.85–2.97 (2H, m), 2.61–2.73 (2H, m), 2.22 (6H, s), 1.76–1.82 (2H, m), 1.46 (3H, d, J=6.5 Hz), m/z=349.

Example 199

Synthesis of S-52

S-52 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,4-dimethylthiophenol, 1,4-dibromobutane and (R)-(+)-1-(1-naphthyl)ethylamine.

400 MHz-$^1$H-NMR 8.86 (1H, d, J=9.0 Hz), 8.18 (1H, d, J=8.5 Hz), 7.73 (1H, d, J=8.0 Hz), 7.62 (1H, d, J=7.0 Hz), 7.44–7.51 (3H, m), 7.11 (1H, s), 7.01–7.07 (2H, m), 4.60 (1H, q, J=6.5 Hz), 2.84 (2H, t, J=6.8 Hz), 2.50–2.62 (2H, m), 1.60–1.68 (4H, m), 1.47 (3H, d, J=6.5 Hz), m/z=363.

Example 200

Synthesis of S-53

S-53 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,4-dimethylthiophenol, 1,5-dibromopentane and (R)-(+)-1-(1-naphthyl)ethylamine.

400 MHz-$^1$H-NMR 8.17 (1H, d, J=8.5 Hz), 7.86 (1H, dd, J=8.0 Hz, J=1.5 Hz), 7.73 (1H, d, J=8.0 Hz), 7.62 (1H, d, J=7.0 Hz), 7.44–7.51 (3H, m), 7.11 (1 H s), 7.01–7.09 (2H, m), 4.60 (1H, q, J=6.5 Hz), 2.84 (2H, t, J=7.3 Hz), 2.50–2.61 (2H, m), 2.22 (3H, s), 2.24 (3H, s), 1.57–1.63 (2H, m), 1.41–1.53 (4H, m), 1.48 (3H, d, J=6.5 Hz), m/z=377.

Example 201

Synthesis of S-54

S-54 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,4-dimethylthiophenol, 1,6-dibromohexane and (R)-(+)-1-(1-naphthyl)ethylamine. m/z=391.

Example 202

Synthesis of S-55

S-55 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,4-dimethylthiophenol, 1,7-dibromoheptane and (R)-(+)-1-(1-naphthyl)ethylamine.

400 MHz-$^1$H-NMR 8.18 (1H, d, J=8.0 Hz), 7.86 (1H, d, J=8.0 Hz), 7.73 (1H, d, J=8.0 Hz), 7.63 (1H, d, J=7.5 Hz), 7.39–7.51 (3H, m), 7.11 (1H, s), 7.01–7.07 (2H, m), 4.60 (1H, q, J=6.5 Hz), 2.83 (2H, t, J=7.3 Hz), 2.49–2.59 (2H, m), 2.22 (3H, s), 2.20 (3H, s), 1.28–1.62 (10H, m), 1.48 (3H, d, J=6.5 Hz), m/z=405.

Example 203

Synthesis of S-56

S-56 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,4-dimethylthiophenol, 1,8-dibromooctane and (R)-(+)-1-(1-naphthyl)ethylamine.

400 MHz-$^1$H-NMR 8.18 (1H, d, J=8.0 Hz), 7.87 (1H, d, J=8.0 Hz), 7.74 (1H, d, J=8.0 Hz), 7.65 (1H, d, J=7.5 Hz), 7.45–7.52 (3H, m), 7.12 (1H, s), 7.02–7.08 (2H, m), 4.63 (1H, q, J=7.0 Hz), 2.84 (2H, t, J=7.3 Hz), 2.51–2.62 (2H, m), 2.22 (3H, s), 2.21 (3H, s), 1.56–1.62 (2H, m), 1.50 (3H, d, J=7.0 Hz), 1.45–1.55 (2H, m), 1.33–1.42 (2H, m),1.25–1.28 (6H, m), m/z=419.

Example 204

Synthesis of S-57

S-57 was synthesized by almost the same method as the one employed for the synthesis of S-1 but replacing the 2,5-dimethylthiophenol by 3,5-dimethylthiophenol.

400 MHz-$^1$H-NMR 7.24 (1H, dd, J=8.0 Hz, J=8.0 Hz), 6.96 (2H, s), 6.88–6.91 (2H, m), 6.82 (1H, s), 6.78–6.80 (1H, m), 3.82 (3H, s), 3.76 (1H, q, J=6.5 Hz), 3.01–3.06 (2H, m), 2.69–2.78 (2H, m), 2.28 (6H, s), 1.36 (3H, d, J=6.5 Hz), m/z=315

Example 205

Synthesis of S-58

S-58 was synthesized by almost the same method as the one employed for the synthesis of S-1 but replacing the 2,5-dimethylthiophenol and 1-bromo-2-chloroethane respectively by 3,5-dimethylthiophenol and 1,3-dibromopropane.

400 MHz-$^1$H-NMR 7.22 (1H, dd, J=8.0 Hz, J=8.0 Hz), 6.93 (2H, s), 6.86–6.88 (2H, m), 6.76–6.78 (2H, m), 3.80 (3H, s), 3.71 (1H, q, J=6.5 Hz), 2.86–2.98 (2H, m), 2.51–2.65 (2H, m), 2.27 (6H, s), 1.74–1.81 (2H, m), 1.32 (3H, d, J=6.5 Hz), m/z=329.

Example 206

Synthesis of S-59

S-59 was synthesized by almost the same method as the one employed for the synthesis of S-1 but replacing the 2,5-dimethylthiophenol and 1-bromo-2-chloroethane respectively by 3,5-dimethylthiophenol and 1,4-dibromobutane.

400 MHz-$^1$H-NMR 7.22 (1H, dd, J=7.5 Hz, J=7.5 Hz), 6.92 (2H, s), 6.86–6.88 (2H, m), 6.75–6.78 (2H, m), 3.80 (3H, s), 3.71 (1H, q, J=7.0 Hz), 2.86 (2H, t, J=7.0 Hz), 2.39–2.54 (2H, m), 2.27 (6H, s), 1.55–1.68 (4H, m), 1.33 (3H, d, J=7.0 Hz), m/z=343.

Example 207

Synthesis of S-60

S-60 was synthesized by almost the same method as the one employed for the synthesis of S-1 but replacing the 2,5-dimethylthiophenol and 1-bromo-2-chloroethane respectively by 3,5-dimethylthiophenol and 1,5-dibromopentane.

400 MHz-$^1$H-NMR 7.22 (1H, dd, J=8.0 Hz, J=8.0 Hz), 6.92 (2H, s), 6.86–6.88 (2H, m), 6.75–6.78 (2H, m), 3.81 (3H, m), 3.71 (1H, q, J=7.0 Hz), 2.87 (2H, t, J=7.3 Hz), 2.39–2.51 (2H, m), 2.27 (6H, s), 1.58–1.65 (2H, m), 1.40–1.49 (4H, m), 1.33 (3H, d, J=7.0 Hz), m/z=357.

Example 208

Synthesis of S-61

S-61 was synthesized by almost the same method as the one employed for the synthesis of S-1 but replacing the 2,5-dimethylthiophenol and 1-bromo-2-chloroethane respectively by 3,5-dimethylthiophenol and 1,6-dibromohexane.

400 MHz-$^1$H-NMR 7.23 (1H, dd, J=8.0 Hz, J=8.0 Hz), 6.93 (2H, s), 6.86–6.89 (2H, m), 6.76–6.78 (2H, m), 3.81 (3H, s), 3.71 (1H, q, J=6.5 Hz), 2.87 (2H, t, J=7.3 Hz), 2.39–2.88 (2H, m), 2.27 (6H, s),1.58–1.65 (2H, m), 1.36–1.49 (4H, m), 1.33 (3H, d, J=6.5 Hz), 1.25–1.31 (2H, m), m/z=371.

Example 209

Synthesis of S-62

S-62 was synthesized by almost the same method as the one employed for the synthesis of S-1 but replacing the 2,5-dimethylthiophenol and 1-bromo-2-chloroethane respectively by 3,5-dimethylthiophenol and 1,7-dibromoheptane.

400 MHz-$^1$H-NMR 7.23 (1H, dd, J=8.0 Hz, J=8.0 Hz), 6.93 (2H, s), 6.86–6.89 (2H, m), 6.75–6.78 (2H, m), 3.81 (3H, s), 3.72 (1 H, q, =7.0 Hz), 2.87 (2H, t, J=7.5 Hz), 2.38–2.51 (2H, m), 2.72 (6H, s), 1.58–1.64 (2H, m), 1.35–1.47 (4H, m), 1.33 (3H, d, J=7.0 Hz), 1.25–1.30 (4H, m), m/z=385.

Example 210

Synthesis of S-63

S-63 was synthesized by almost the same method as the one employed for the synthesis of S-1 but replacing the 2,5-dimethylthiophenol and 1-bromo-2-chloroethane respectively by 3,5-dimethylthiophenol and 1,8-dibromooctane.

400 MHz-$^1$H-NMR 7.21 (1H, dd, J=8.0 Hz, J=8.0 Hz), 6.91 (2H, s), 6.85–6.88 (2H, m), 6.77 (1H, s), 6.74–6.75 (1H, m), 3.79 (3H, s), 3.71 (1H, q, J=6.5 Hz), 2.86 (2H, t, J=7.5 Hz), 2.37–2.49 (2H, m), 2.26 (6H, s), 1.57–1.63 (2H, m), 1.34–1.43 (4H, m), 1.32 (3H, d, J=6.5 Hz), 1.20–1.30 (6H, m), m/z=399.

Example 211

Synthesis of S-64

S-64 was synthesized by almost the same method as the one employed for the synthesis of S-1 but replacing the 2,5-dimethylthiophenol and (R)-(+)-3-methoxy-α-benzylmethylamine respectively by 3,5-dimethylthiophenol and (R)-(+)-1-(1-naphthyl)ethylamine.

400 MHz-$^1$H-NMR 8.15 (1H, d, J=8.0 Hz), 7.85–7.87 (1H, m), 7.72 (1H, d, J=8.0 Hz), 7.63 (1H, d, J=6.5 Hz), 7.42–7.52 (3H, m), 6.93 (2H, s), 6.79 (1H,s), 4.62 (1H, q, J=6.5 Hz), 3.05 (2H, t, J=6.5 Hz), 2.76–2.84 (2H, m), 2.24 (6H, s,), 1.48 (3H, d, J=6.5 Hz), m/z=335.

Example 212

Synthesis of S-65

S-65 was synthesized by almost the same method as the one employed for the synthesis of S-1 but replacing the 2,5-dimethylthiophenol, 1-bromo-2-chloroethane and (R)-(+) -3-methoxy-α-benzylmethylamine respectively by 3,5-dimethylthiophenol, 1,3-dibromopropane and (R)-(+)-1-(1-naphthyl)ethylamine.

400 MHz-$^1$H-NMR 8.18 (1H, d, J=8.5 Hz), 7.86 (1H, d, J=7.0 Hz), 7.24 (1H, d, J=8.5 Hz), 7.63 (1H, d, J=6.5 Hz), 7.45–7.51 (3H, m), 6.93 (2H, s), 6.78 (1H, s), 4.60 (1H, q, J=6.5 Hz), 2.89–3.01 (2H, m), 2.63–2.75 (2H, m), 2.26 (6H, s), 1.79–1.85 (2H, m), 1.48 (3H, d, J=6.5 Hz), m/z=349.

Example 213

Synthesis of S-66

S-66 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,5-dimethylthiophenol, 1,4-dibromobutane and (R)-(+)-1-(1-naphthyl)ethylamine.

400 MHz-$^1$H-NMR 8.86 (1H, d, J=8.5 Hz), 8.18 (1H, d, J=8.0 Hz), 7.63 (1H, d, J=7.5 Hz), 7.23 (1H, d, J=8.0 Hz), 7.44–7.51 (3H, m), 6.92 (2H, s), 6.78 (1H, s), 4.61 (1H, q, J=7.0 Hz), 2.86–2.88 (2H, m), 2.53–2.64 (2H, m), 2.26 (6H, s), 1.60–1.70 (4H, m), 1.48 (3H, d, J=7.0 Hz), m/z=363.

Example 214

Synthesis of S-67

S-67 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,5-dimethylthiophenol, 1,5-dibromopentane and (R)-(+)-1-(1-naphthyl)ethylamine.

400 MHz-$^1$H-NMR 8.85 (1H, d, J=7.5 Hz), 8.16 (1H, d, J=8.5 Hz), 7.72 (1H, d, J=8.0 Hz), 7.61 (1H, d, J=7.5 Hz), 7.43–7.50 (3H, m), 6.91 (2H, s), 6.77 (1H, s), 4.60 (1H, q, J=6.5 Hz), 2.85 (2H, t, J=7.5 Hz), 2.49–2.60 (2H, m), 2.25 (6H, s), 1.58–1.64 (2H, m), 1.41–1.53 (4H, m), 1.47 (3H, d, J=6.5 Hz), m/z=377.

Example 215

Synthesis of S-68

S-68 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,5-dimethylthiophenol, 1,6-dibromohexane and (R)-(+)-1-(1-naphthyl)ethylamine.

400 MHz-$^1$H-NMR 8.18 (1H, d, J=8.5 Hz), 7.86 (1H, d, J=7.5 Hz), 7.73 (1H, d, J=8.0 Hz), 7.63 (1H, d, J=7.5 Hz), 7.46–7.50 (3H, m), 6.92 (2H, s), 6.77 (1H, s), 4.61 (1H, q, J=6.5 Hz), 2.86 (2H, t, J=7.3 Hz), 2.52–2.61 (2H, m), 2.26 (6H, s), 1.57–1.64 (2H, m), 1.45–1.57 (2H, m), 1.48 (3H, d, J=6.5 Hz), 1.35–1.44 (2H, m), 1.29–1.36 (2H, m), m/z=391.

Example 216

Synthesis of S-69

S-69 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,5-dimethylthiophenol, 1,7-dibromoheptane and (R)-(+)-1-(1-naphthyl)ethylamine.

400 MHz-$^1$H-NMR 8.18 (1H, d, J=8.0 Hz), 7.86 (1H, d, J=8.0 Hz), 7.73 (1H, d, J=8.0 Hz), 7.64 (1H, d, J=7.5 Hz), 7.45–7.52 (3H, m), 6.92 (2H, s), 6.78 (1H, s), 4.62 (1H, q, J=7.0 Hz), 2.86 (2H, t, J=7.3 Hz), 2.51–2.60 (2H, m), 2.27 (6H, s), 1.79–1.85 (2H, m), 1.57–1.63 (2H, m), 1.49 (3H, d, J=7.0 Hz), 1.39 (2H, bs), 1.29 (4H, bs), m/z=405.

Example 217

Synthesis of S-70

S-70 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3,5-dimethylthiophenol, 1,8-dibromooctane and (R)-(+)-1-(1-naphthyl)ethylamine.

400 MHz-$^1$H-NMR 8.18 (1H, d, J=8.5 Hz), 7.86 (1H, d, J=8.0 Hz), 7.73 (1H, d, J=8.0 Hz), 7.64 (1H, d, J=7.5 Hz), 7.44–7.52 (3H, m), 6.93 (2H, s), 6.78 (1H, s), 4.62 (1H, q, J=6.5 Hz), 2.87 (2H, t, J=7.5 Hz), 2.50–2.61 (2H, m), 2.27 (6H, s), 1.58–1.64 (2H, m), 1.47–1.52 (2H, m), 1.49 (3H, d, J=6.5 Hz), 1.35–1.42 (2H, m), 1.24–1.30 (6H, m), m/z=419.

Example 218

Synthesis of S-71

S-71 was synthesized by almost the same method as the one employed for the synthesis of S-1 but replacing the 2,5-dimethylthiophenol by 4-bromothiophenol.

400 MHz-$^1$H-NMR 7.33–7.37 (2H, m), 7.22 (1H, dd, J=8.0 Hz, J=8.0 Hz), 7.13–7.16 (2H, m), 6.83–6.87 (2H, m), 6.76–6.79 (1 H, m), 3.80 (3H, s), 3.72 (1H, q, J=6.5 Hz), 2.99 (2H, t, J=6.5 Hz), 2.59–2.75 (2H, m), 1.34 (3H, d, J=6.5 Hz), m/z=365, 367.

Example 219

Synthesis of S-72

S-72 was synthesized by almost the same method as the one employed for the synthesis of S-1 but replacing the 2,5-dimethylthiophenol and 1-bromo-2-chloroethane respectively by 4-bromothiophenol and 1,3-dibromopropane.

400 MHz-$^1$H-NMR 7.37 (2H, d, J=8.8 Hz), 7.23 (1 H, dd, J=8.1 Hz, J=8.1 Hz), 7.15 (2H, d, J=8.8 Hz), 6.85–6.88 (2H, m), 6.78 (1H, ddd, J=8.1 Hz, J=2.4 Hz, J=1.0 Hz), 3.80 (3H, s), 3.71 (1 H, q, J=8.2 Hz), 2.85–2.98 (2H, m), 2.50–2.65 (2H, m), 1.71–1.81 (2H, m), 1.33 (3H, d, J=6.6 Hz), m/z=379, 381.

Example 220

Synthesis of S-73

S-73 was synthesized by almost the same method as the one employed for the synthesis of S-1 but replacing the 2,5-dimethylthiophenol and 1-bromo-2-chloroethane respectively by 4-bromothiophenol and 1,4-dibromobutane.

400 MHz-$^1$H-NMR 7.37 (2H, d, J=8.5 Hz), 7.23 (1H, dd, J=8.1 Hz, J=8.1 Hz), 7.15 (2H, d, J=8.5 Hz), 6.85–6.88 (2H, m), 6.75–6.79 (1H, m), 3.80 (3H, s), 3.71 (1H, q, J=6.6 Hz), 2.85 (2H, t, J=7.1 Hz), 2.39–2.54 (2H, m), 1.51–1.69 (4H, m), 1.33 (3H, d, J=6.6 Hz), m/z=393, 395.

Example 221

Synthesis of S-74

S-74 was synthesized by almost the same method as the one employed for the synthesis of S-1 but replacing the 2,5-dimethylthiophenol and 1-bromo-2-chloroethane respectively by 4-bromothiophenol and 1,5-dibromopentane.

400 MHz-$^1$H-NMR 7.37 (2H, d, J=8.8 Hz), 7.23 (1H, dd, J=8.2 Hz, J=8.2 Hz), 7.15 (2H, d, J=8.8 Hz), 6.86–6.88 (2H, m), 6.76–6.79 (1H, m), 3.81 (3H, s), 3.72 (1H, q, J=6.6 Hz), 2.86 (2H, t, J=7.3 Hz), 2.38–2.52 (2H, m), 1.60 (2H, tt, J=7.3 Hz, J=7.3 Hz), 1.36–1.51 (4H, m), 1.34 (3H, d, J=6.6 Hz), m/z=407, 409.

Example 222

Synthesis of S-75

S-75 was synthesized by almost the same method as the one employed for the synthesis of S-1 but replacing the 2,5-dimethylthiophenol and 1-bromo-2-chloroethane respectively by 4-bromothiophenol and 1,6-dibromohexane.

400 MHz-$^1$H-NMR 7.37 (2H, d, J=8.6 Hz), 7.23 (1H, dd, J=8.1 Hz, J=8.1 Hz), 7.15 (2H, d, J=8.6 Hz), 6.87–6.89 (2H, m), 6.76–6.79 (1H, m), 3.81 (3H, s), 3.72 (1H, q, J=6.6 Hz), 2.86 (2H, t, J=7.3 Hz), 2.38–2.52 (2H, m), 1.60 (2H, tt, J=7.3 Hz, J=7.3 Hz), 1.23–1.50 (6H, m), 1.35 (3H, d, J=6.6 Hz), m/z=421, 423.

Example 223

Synthesis of S-76

S-76 was synthesized by almost the same method as the one employed for the synthesis of S-1 but replacing the 2,5-dimethylthiophenol and 1-bromo-2-chloroethane respectively by 4-bromothiophenol and 1,7-dibromoheptane.

400 MHz-$^1$H-NMR 7.38 (2H, d, J=8.5 Hz), 7.23 (1H, dd, J=8.1 Hz, J=8.1 Hz), 6.87–6.89 (2H, m), 6.78 (1H, ddd, J=8.3 Hz, J=2.4 Hz, J=1.0 Hz), 3.81 (3H, s), 3.73 (1H, q, J=6.6 Hz), 2.86 (2H, t, J=7.3 Hz), 2.38–2.52 (2H, m), 1.60 (2H, tt, J=7.3 Hz, J=7.3 Hz), 1.08–1.50 (8H, m), 1.36 (3H, d, J=6.6 Hz), m/z=435, 437.

Example 224

Synthesis of S-77

S-77 was synthesized by almost the same method as the one employed for the synthesis of S-1 but replacing the 2,5-dimethylthiophenol and 1-bromo-2-chlorcethane respectively by 4-bromothiophenol and 1,8-dibromooctane.

400 MHz-$^1$H-NMR 7.35–7.40 (2H, m), 7.23 (1H, d, J=8.0 Hz), 7.14–7.18 (2H, m), 6.88–6.92 (2H, m), 6.74–6.80 (1 H, m), 3.81 (3H, s), 3.75 (1H, q, J=6.7 Hz), 2.86 (2H, t, J=7.6 Hz), 2.39–2.53 (2H, m), 1.54–1.64 (2H, m), 1.20–1.50 (10H, m), 1.38 (3H, d, J=6.7 Hz), m/z=449, 451.

Example 225

Synthesis of S-78

S-78 was synthesized by almost the same method as the one employed for the synthesis of S-1 but replacing the 2,5-dimethylthiophenol and (R)-(+)-3-methoxy-α-benzylmethylamine respectively by 4-bromothiophenol and (R)-(+)-1-(1-naphthyl)ethylamine.

Example 226

Synthesis of S-79

S-79 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-bromothiophenol, 1,3-dibromopropane and (R)-(+)-1-(1-naphthyl)ethylamine.

400 MHz-$^1$H-NMR 8.16 (1H, d, J=7.8 Hz), 7.85–7.88 (1H, m), 7.74 (1H, d, J=8.3 Hz), 7.62 (1H, d, J=6.8 Hz), 7.44–7.52 (3H, m), 7.32–7.42 (2H, m), 7.10–7.15 (2H, m), 4.60 (1H, q, J=6.6 Hz), 2.83–3.05 (2H, m), 2.60–2.77 (2H, m), 1.76–1.87 (2H, m), 1.49 (3H, d, J=6.6 Hz), m/z=399, 401.

Example 227

Synthesis of S-80

S-80 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-bromothiophenol, 1,4-dibromobutane and (R)-(+)-1-(1-naphthyl)ethylamine.

400 MHz-$^1$H-NMR 8.17 (1H, d, J=7.8 Hz), 7.84–7.88 (1H, m), 7.74 (1H, d, J=8.28 Hz), 7.62 (1H, d, J=6.6 Hz), 7.43–7.52 (3H, m), 7.33–7.37 (2H, m), 7.11–7.16 (2H, m), 4.61 (1H, q, J=6.5 Hz), 2.85 (2H, d, J=7.0 Hz), 2.50–2.64 (2H, m), 1.58–1.68 (4H, m), 1.48 (3H, d, J=6.5 Hz), m/z=413, 415.

Example 228

Synthesis of S-81

S-81 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-bromothiophenol, 1,5-dibromopentane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.2 Hz), 7.64 (1H, d, J=7.3 Hz), 7.45–7.53 (3H, m), 7.34–7.37 (2H, m), 7.11–7.16 (2H, m), 4.62 (1H, q, J=6.6 Hz), 2.85 (2H, t, J=7.3 Hz), 2.49–2.62 (2H, m), 1.40–1.65 (6H, m), 1.49 (3H, d, J=6.6 Hz), m/z=427, 429.

Example 229

Synthesis of S-82

S-82 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-bromothiophenol, 1,6-dibromohexane and (R)-(+)-1-(1-naphthyl)ethylamine.

Example 230

Synthesis of S-83

S-83 was synthesized by almost the same method as the one employed. for the synthesis of S-1 but replacing the 2,5-dimethylthiophenol, 1-bromo-2-chloroethane and (R)-(+)-3-methoxy-α-benzylmethylamine respectively by 4-bromothiophenol, 1,7-dibromoheptane and (R)-(+)-1-(1-naphthyl)ethylamine.

400 MHz-$^1$H-NMR 8.30 (1H, bs), 8.10 (1H, d, J=8.0 Hz), 7.90 (1H, d, J=8.1 Hz), 7.82 (1H, d, J=8.1 Hz), 7.49–7.59 (3H, m), 7.33–7.38 (2H, m), 7.11–7.15 (2H, m), 4.96 (1H, bs), 2.80 (2H, t, J=7.3 Hz), 2.54–2.74 (2H, m), 0.95–1.88 (13H, m), m/z=455, 457.

Example 231

Synthesis of S-84

S-84 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-bromothiophenol, 1,8-dibromooctane and (R)-(+)-1-(1-naphthyl)ethylamine.

400 MHz-$^1$H-NMR 8.35 (1H, bs), 8.13 (1H, d, J=8.0 Hz), 7.88 (1H, d, J=8.2 Hz), 7.79 (1H, d, J=8.3 Hz), 7.45–7.56 (3H, m), 7.33–7.39 (2H, m), 7.12–7.18 (2H, m), 4.82 (1H, bs), 2.84 (2H, t, J=7.3 Hz), 2.58–2.64 (2H, m), 1.00–1.74 (15H, m), m/z=469, 471.

Example 232

Synthesis of S-85

S-85 was synthesized by almost the same method as the one employed for the synthesis of S-1 but replacing the 2,5-dimethylthiophenol and 1-bromo-2-chloroethane respectively by 4-iodophenol and 1,3-dibromopropane.

400 MHz-$^1$H-NMR 7.50–7.54 (2H, m), 7.21 (1H, dd, J=8.0 Hz, J=8.0 Hz), 6.86–6.88 (2H, m), 6.76 (1H, dd, J=8.0 Hz, J=2.5 Hz), 6.61–6.65 (2H, m), 3.93–4.00 (1H, m), 3.78 (3H, s), 3.72–3.76 (1H, m), 2.58–2.70 (2H, m), 1.86–1.94 (2H, m), 1.34 (3H, d, J=7.0 Hz), m/z=411.

Example 233

Synthesis of S-86

S-86 was synthesized by almost the same method as the one employed for the synthesis of S-1 but replacing the 2,5-dimethylthiophenol and 1-bromo-2-chloroethane respectively by 4-iodophenol and 1,4-dibromobutane.

400 MHz-$^1$H-NMR 7.50–7.53 (2H, m), 7.22 (1H, dd, J=3.0 Hz, J=3.0 Hz), 6.87–6.89 (2H, m), 6.76–6.78 (1H, m), 6.61–6.64 (2H, m), 3.88 (1H, t, J=6.8 Hz), 3.80 (3H, s), 3.73 (1H, q, J=6.8 Hz), 2.46–2.58 (2H, m), 1.72–1.82 (2H, m), 1.55–1.67 (2H, m), 1.34 (3H, d, J=6.8 Hz), m/z=425.

Example 234

Synthesis of S-87

S-87 was synthesized by almost the same method as the one employed for the synthesis of S-1 but replacing the 2,5-dimethylthiophenol and 1-bromo-2-chloroethane respectively by 4-iodophenol and 1,5-dibromopentane.

400 MHz-$^1$H-NMR 7.52 (2H, d, J=8.5 Hz), 7.20–7.25 (1H, m), 6.87 (2H, s), 6.74–6.80 (1H, m), 6.64 (2H, d, J=8.0 Hz), 3.88 (2H, t, J=6.5 Hz), 3.80 (3H, s), 3.72 (1H, q, J=6.3 Hz), 2.40–2.55 (2H, m), 1.71–1.77 (2H, m), 1.40–1.45 (4H, m), 1.34 (3H, d, J=6.3 Hz), m/z=439.

Example 235

Synthesis of S-88

S-88 was synthesized by almost the same method as the one employed for the synthesis of S-1 but replacing the 2,5-dimethylthiophenol and 1-bromo-2-chloroethane respectively by 4-iodophenol and 1,6-dibromohexane.

400 MHz-$^1$H-NMR 7.52 (2H, d, J=9.0 Hz), 7.23 (1H, dd, J=8.0 Hz, J=8.0 Hz), 6.87–6.89 (2H, m), 6.77 (1H, dd, J=8.0 Hz, J=2.0 Hz), 6.64 (2H, d, J=9.0 Hz), 3.88 (3H, t, J=6.5 Hz), 3.81 (3H, s), 3.72 (1H, q, J=7.0 Hz), 2.41–2.53 (2H, m), 1.71–1.76 (2H, m), 1.46–4.50 (2H, m), 1.39–1.45 (2H, m), 1.31–1.38 (2H, m), 1.34 (3H, d, J=6.5 Hz), m/z=453.

Example 236

Synthesis of S-89

S-89 was synthesized by almost the same method as the one employed for the synthesis of S-1 but replacing the 2,5-dimethylthiophenol and 1-bromo-2-chloroethane respectively by 4-iodophenol and 1,7-dibromoheptane.

400 MHz-$^1$H-NMR 7.52 (2H, d, J=9.0 Hz), 7.22 (1H, dd, J=8.0 Hz, J=8.0 Hz), 6.87–6.89 (2H, m), 6.76–6.78 (1H, m), 6.65 (2H, d, J=8.5 Hz), 3.88 (2H, t, J=6.5 Hz), 3.81 (3H, s), 3.72 (1H, q, J=6.5 Hz), 2.39–2.51 (2H, m), 1.70–1.76 (2H, m), 1.37–1.49 (4H, m), 1.34 (3H, d, J=6.5 Hz), 1.25–1.35 (6H, m), m/z=467.

Example 237

Synthesis of S-90

S-90 was synthesized by almost the same method as the one employed for the synthesis of S-1 but replacing the 2,5-dimethylthiophenol and 1-bromo-2-chloroethane respectively by 4-iodophenol and 1,8-dibromooctane.

400 MHz-$^1$ H-NMR 7.53 (2H, d, J=8.5 Hz), 7.23 (1H, dd, J=8.0 Hz, J=8.0 Hz), 6.87–6.89 (2H, m), 6.75–6.78 (1H, m), 6.65 (2H, d, J=8.5 Hz), 3.89 (2H, t, J=6.8 Hz), 3.81 (3H, s), 3.72 (1H, q, J=6.5 Hz), 2.39–2.51 (2H, m), 1.71–1.76 (2H, m), 1.38–1.47 (4H, m), 1.34 (3H, d, J=6.5 Hz), 1.25–1.35 (6H, m), m/z=481.

Example 238

Synthesis of S-91

S-91 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-iodophenol, 1,3-dibromopropane and (R)-(+)-1-(1-naphthyl)ethylamine.

400 MHz-$^1$H-NMR 8.17–8.19 (1H, m), 7.84–7.87 (1H, m), 7.73 (1H, d, J=8.0 Hz) 7.61 (1H, d, J=7.0 Hz), 7.50–7.53 (2H, m), 7.34–7.49 (3H, m), 6.61 (2H, d, J=9.0 Hz), 4.63 (1H, q, J=6.5 Hz), 3.95–4.01 (2H, m), 2.69–2.80 (2H, m), 1.91–1.97 (2H, m), 1.49 (3H, d, J=6.5 Hz), m/z=431.

Example 239

Synthesis of S-92

S-92 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-iodophenol, 1,4-dibromobutane and (R)-(+)-1-(1-naphthyl)ethylamine.

400 MHz-$^1$H-NMR 8.19 (1H, d, J=7.5 Hz), 7.86 (1H, d, J=8.0 Hz), 7.73 (1H, d, J=8.0 Hz), 7.64 (1H, d, J=8.0 Hz), 7.45–7.52 (5H, m), 6.61 (2H, d, J=7.5 Hz), 4.63 (1H, q, J=6.5 Hz), 3.88 (2H, t, J=6.5 Hz), 2.56–2.69 (2H, m), 1.74–1.84 (2H, m), 1.62–1.68 (2H, m), 1.49 (3H, d, J=6.5 Hz), m/z=445.

Example 240

Synthesis of S-93

S-93 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-iodophenol, 1,5-dibromopentane and (R)-(+)-1-(1-naphthyl)ethylamine.

400 MHz-$^1$H-NMR 8.18 (1H, d, J=8.0 Hz), 7.86 (1H, d, J=8.5 Hz), 7.73 (1H, d, J=8.0 Hz), 7.64 (1H, d, J=7.0 Hz), 7.45–7.53 (5H, m), 6.63 (2H, d, J=8.5 Hz), 4.58–4.64 (1H, m), 3.85–3.88 (2H, m), 2.50–2.65 (2H, m), 1.70–1.76 (2H, m), 1.40–1.55 (4H, m), 1.49 (3H, d, J=6.5 Hz), m/z=459.

Example 241

Synthesis of S-94

S-94 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-iodophenol, 1,6-dibromohexane and (R)-(+)-1-(1-naphthyl)ethylamine.

400 MHz-$^1$H-NMR 8.18 (1H, d, J=8.5 Hz), 7.83 (1H, d, J=7.0 Hz), 7.72 (1H, d, J=7.5 Hz), 7.64 (1H, d, J=7.5 Hz), 7.40–7.53 (5H, m), 6.63 (2H, d, J=9.5 Hz), 4.62 (1H, q, J=6.5 Hz), 3.87 (2H, t, J=6.5 Hz), 2.50–2.62 (2H, m), 1.70–1.75 (2H, m), 1.35–1.60 (6H, m), 1.49 (3H, d, J=6.5 Hz), m/z=473.

Example 242

Synthesis of S-95

S-95 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-iodophenol, 1,7-dibromoheptane and (R)-(+)-1-(1-naphthyl)ethylamine.

400 MHz-$^1$H-NMR 8.17 (1H, d, J=8.5 Hz), 7.87 (1H, d, J=8.0 Hz), 7.74 (1H, d, J=7.5 Hz), 7.67 (1H, d, J=7.0 Hz), 7.45–7.53 (5H, m), 6.64 (2H, d, J=8.5 Hz), 4.65 (1H, q, J=7.0 Hz), 3.87 (2H, t, J=6.8 Hz), 2.51–2.63 (2H, m), 1.78–1.84 (2H, m), 1.69–1.75 (2H, m), 1.52 (3H, d, J=7.0 Hz), 1.25–1.45 (6H, m), m/z=487.

Example 243

Synthesis of S-96

S-96 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-iodophenol, 1,8-dibromooctane and (R)-(+)-1-(1-naphthyl)ethylamine.

400 MHz-$^1$H-NMR 8.86 (1H, d, J=7.5 Hz), 8.18 (1H, d, J=8.5 Hz), 7.74 (1H, d, J=8.0 Hz), 7.66 (1H, d, J=7.5 Hz), 7.45–7.54 (5H, m), 6.65 (2H, d, J=8.5 Hz), 4.64 (1H, q, J=6.5 Hz), 3.88 (2H, t, J=6.8 Hz), 2.51–2.63 (2H, m), 1.79–1.85 (2H, m), 1.70–1.75 (2H, m), 1.51 (3H, d, J=6.5 Hz), 1.24–1.43 (8H, m), m/z=501.

Example 244

Synthesis of S-97

S-97 was synthesized by almost the same method as the one employed for the synthesis of S-1 but replacing the 2,5-dimethylthiophenol by 2-napthalenethiol. m/z=337.

Example 245

Synthesis of S-98

S-98 was synthesized by almost the same method as the one employed for the synthesis of S-1 but replacing the 2,5-dimethylthiophenol and 1-bromo-2-chloroethane respectively by 2-naphthalenethiol and 1,3-dibromopropane.

400 MHz-$^1$H-NMR 7.75–7.77 (1H, m), 7.69–7.73 (3H, m), 7.37–7.48 (3H, m), 7.21 (1H, dd, J=8.2 Hz, J=8.2 Hz), 6.85–6.88 (2H, m), 6.75–6.79 (1H, m), 3.79 (3H, s), 3.71 (1H, q, J=6.6 Hz), 2.98–3.11 (2H, m), 2.54–2.68 (2H, m), 1.78–1.87 (2H, m), 1.32 (3H, d, J=6.6 Hz), m/z=351.

Example 246

Synthesis of S-99

S-99 was synthesized by almost the same method as the one employed for the synthesis of S-1 but replacing the 2,5-dimethylthiophenol and 1-bromo-2-chloroethane respectively by 2-naphthalenethiol and 1,4-dibromobutane.

400 MHz-$^1$H-NMR 7.69–7.78 (4H, m), 7.38–7.51 (3H, m), 7.21 (1H, dd, J=8.0 Hz, J=8.0 Hz), 6.85–6.88 (2H, m), 6.76 (1 H, ddd, J=8.3 Hz, J=2.4 Hz, J=1.0 Hz), 3.79 (3H, s), 3.71 (1H, q, J=6.6 Hz), 2.99 (2H, t, J=7.1 Hz), 2.41–2.55 (2H, m), 1.56–1.74 (4H, m), 1.33 (3H, d, J=6.6 Hz), m/z=365.

Example 247

Synthesis of S-100

S-100 was synthesized by almost the same method as the one employed for the synthesis of S-1 but replacing the 2,5-dimethylthiophenol and 1-bromo-2-chloroethane respectively by 2-naphthalenethiol and 1,5-dibromopentane.

400 MHz-$^1$H-NMR 7.69–778 (4H, m), 7.37–7.51 (3H, m), 7.22 (1H, dd, J=8.0 Hz, J=8.0 Hz), 6.86–6.88 (2H, m), 6.77 (1H, ddd, J=8.0 Hz, J=2.4 Hz, J=1.0 Hz), 3.80 (3H, s), 3.71 (1H, q, J=6.6 Hz), 2.99 (2H, t, J=7.3 Hz), 2.39–2.52 (2H, m), 1.67 (2H, tt, J=7.3 Hz, J=7.3 Hz), 1.41–1.53 (4H, m), 1.33 (3H, d, J=6.6 Hz), m/z=379.

Example 248

Synthesis of S-101

S-101 was synthesized by almost the same method as the one employed for the synthesis of S-1 but replacing the 2,5-dimethylthiophenol and 1-bromo-2-chloroethane respectively by 2-naphthalenethiol and 1,6-dibromohexane.

400 MHz-$^1$H-NMR 7.70–7.78 (4H, m), 7.38–7.47 (3H, m), 7.23 (1H, dd, J=8.3 Hz, J=8.3 Hz), 6.86–6.88 (2H, m), 6.77 (1 H, ddd, J=8.3 Hz, J=2.4 Hz, J=1.0 Hz), 3.80 (3H, s), 3.71 (1H, q, J=6.6 Hz), 2.99 (2H, t, J=7.3 Hz), 2.37–2.51 (2H, m), 1.67 (2H, tt, J=7.3 Hz, J=7.3 Hz), 1.39–1.50 (4H, m), 1.25–1.35 (2H, m), 1.33 (3H, d, J=6.6 Hz), m/z=393.

Example 249

Synthesis of S-102

S-102 was synthesized by almost the same method as the one employed for the synthesis of S-1 but replacing the 2,5-dimethylthiophenol and 1-bromo-2-chloroethane respectively by 2-naphthalenethiol and 1,7-dibromoheptane.

400 MHz-$^1$H-NMR 7.70–7.78 (4H, m), 7.38–7.47 (3H, m), 7.24 (1H, dd, J=8.1 Hz, J=8.1 Hz), 6.90–6.95 (2H, m), 6.78–6.81 (1 H, m), 3.81 (3H, s), 3.79–3.82 (1H, m), 2.99 (2H, t, J=7.4 Hz), 2.41–2.54 (2H, m), 1.66 (2H, tt, J=7.4 Hz, J=7.4 Hz), 1.15–1.55 (8H, m), 1.43 (3H, d, J=6.6 Hz), m/z=407.

Example 250

Synthesis of S-103

S-103 was synthesized by almost the same method as the one employed for the synthesis of S-1 but replacing the 2,5-dimethylthiophenol and 1-bromo-2-chloroethane respectively by 2-naphthalenethiol and 1,8-dibromooctane.

400 MHz-$^1$H-NMR 7.70–7.78 (4H, m), 7.38–7.47 (3H, m), 7.23 (1H, d, J=7.8 Hz), 6.88–6.92 (2H, m), 6.78 (1H, ddd, J=8.3 Hz, J=2.7 Hz, J=1.0 Hz), 3.81 (3H, s), 3.76 (1H, q, J=6.4 Hz), 2.99 (2H, t, J=7.3 Hz), 2.39–2.52 (2H, m), 1.66 (2H, tt, J=7.3 Hz, J=7.3 Hz), 1.15–1.55 (10H, m), m/z=421.

Example 251

Synthesis of S-104

S-104 was synthesized by almost the same method as the one employed for the synthesis of S-1 but replacing the 2,5-dimethylthiophenol and (R)-(+)-3-methoxy-α-benzylrnethylamine respectively by 2-naphthalenethiophenol and (R)-(+)-1-(1-naphthyl)ethylamine. m/z 357.

Example 252

Synthesis of S-105

S-105 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-naphthalenethiol, 1,3-dibromopropane and (R)-(+)-1-(1-naphthyl)ethylamine.

400 MHz-$^1$H-NMR 8.14–8.16 (1H, m), 7.84–7.88 (1H, m), 7.75–7.77 (2H, m), 7.68–7.76 (3H, m), 7.64 (1H, d, J=6.6 Hz), 7.36–7.48 (6H, m), 4.61 (1H, q, J=6.6 Hz), 3.00–3.14 (2H, m), 2.66–279 (2H, m), 1.88 (2H, m), 1.49 (3 J=6.6 Hz), m/z=371.

Example 253

Synthesis of S-106

S-106 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-naphthalenethiol, 1,4-dibromobutane and (R)-(+)-1-(1-naphthyl)ethylamine.

400 MHz-$^1$H-NMR 8.16 (1H, d, J=8.1 Hz), 7.84–7.87 (1H, m), 7.74–7.77 (2H, m), 7.68–7.72 (3H, m), 7.63 (1H, d, J=7.1 Hz), 7.36–7.51 (6H, m), 4.62 (1H, q, J=6.6 Hz), 2.98 (2H, t, J=7.0 Hz), 2.52–2.65 (2H, m), 1.63–1.76 (4H, m), 1.48 (3H, d, J=6.6 Hz), m/z=385.

Example 254

Synthesis of S-107

S-107 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-naphthalenethiol, 1,5-dibromopentane and (R)-(+)-1-(1-naphthyl)ethylamine.

Example 255

Synthesis of S-108

S-108 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-naphthalenethiol, 1,6-dibromohexane and (R)-(+)-1-(1-naphthyl)ethylamine.

400 MHz-¹H-NMR 8.16 (1H, d, J=8.3 Hz), 7.85–7.88 (1H, m), 7.74–7.77 (2H, m), 7.69–7.73 (3H, m), 7.64 (1H, d, J=7.1 Hz), 7.38–7.52 (6H, m), 4.62 (1H, q, J=6.5 Hz), 2.98 (2H, t, J=7.4 Hz), 2.49–2.62 (2H, m), 1.66 (2H, tt, J=7.4 Hz, J=7.4 Hz), 1.27–1.54 (6H, m), 1.49 (3H, d, J=6.5 Hz), m/z=413.

Example 256

Synthesis of S-109

S-109 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-naphthalenethiol, 1,7-dibromoheptane and (R)-(+)-1-(1-naphthyl)ethylamine.

400 MHz-¹H-NMR 8.16 (1H, m), 7.84–7.87 (1H, m), 7.69–7.77 (5H, m), 7.64 (1H, d, J=6.8 Hz), 7.37–7.53 (6H, m), 4.62 (1H, q, J=6.6 Hz), 2.98 (2H, t, J=7.4 Hz), 2.48–2.62 (2H, m), 1.65 (2H, tt, J=7.4 Hz, J=7.4 Hz), 1.25–1.52 (8H, m), 1.49 (3H, d, J=6.6 Hz), m/z=427.

Example 257

Synthesis of S-110

S-110 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-naphthalenethiol, 1,8-dibromooctane and (R)-(+)-1-(1-naphthyl)ethylamine.

400 MHz-¹H-NMR 8.14 (1H, d, J=8.3 Hz), 7.85–7.88 (1H, m), 7.67–7.79 (6H, m), 7.37–7.53 (6H, m), 4.70 (1H, q, J=6.6 Hz), 2.98 (2H, t, J=7.3 Hz), 2.50–2.65 (2H, m), 1.65 (2H, tt, J=7.3 Hz, J=7.3 Hz), 1.05–1.60 (10H, m), 1.57 (3H, d, J=6.6 Hz), m/z=441.

Example 258

Synthesis of S-111

S-111 was synthesized by almost the same method as the one employed for the synthesis of S-1 but replacing the 2,5-dimethylthiophenol by 2-methoxythiophenol.

400 MHz-¹H-NMR 7.14–7.22 (3H, m), 6.81–6.89 (4H, m), 6.73–6.76 (1H, m), 3.85 (3H, s), 3.78 (3H, s), 3.71 (1H, q, J=6.6 Hz), 2.98 (2H, t, J=6.5 Hz), 2.61–2.73 (2H, m), 1.32 (3H, d, J=6.6 Hz), m/z=317.

Example 259

Synthesis of S-112

S-112 was synthesized by almost the same method as the one employed for the synthesis of S-1 but replacing the 2,5-dimethylthiophenol and 1-bromo-2-chloroethane respectively by 2-methoxythiophenol and 1,3-dibromopropane.

400 MHz-¹H-NMR 7.21–7.25 (2H, m), 7.14–7.19 (1H, m), 6.82–6.92 (4H, m), 6.77 (1H, ddd, J=8.3 Hz, J=2.4 Hz, J=1.0 Hz), 3.87 (3H, s), 3.80 (3H, s), 3.73 (1H, q, J=6.6 Hz), 2.85–2.98 (2H, m), 2.52–2.67 (2H, m), 1.73–1.86 (2H, m), 1.33 (3H, d, J=6.6 Hz), m/z=331.

Example 260

Synthesis of S-113

S-113 was synthesized by almost the same method as the one employed for the synthesis of S-1 but replacing the 2,5-dimethylthiophenol and 1-bromo-2-chloroethane respectively by 2-methoxythiophenol and 1,4-dibromobutane.

400 MHz-¹H-NMR 7.21–7.25 (2H, m), 7.14–7.19 (1H, m), 6.82–6.93 (4H, m), 6.75–6.79 (1H, ddd, J=8.0 Hz, J=2.4 Hz, J=1.0 Hz), 3.88 (3H, s), 3.80 (3H, s), 3.72 (1H, q, J=6.6 Hz), 2.86 (2H, t, J=7.0 Hz), 2.41–2.55 (2H, m), 1.58–1.71 (4H, m), 1.34 (3H, d, J=6.6 Hz), m/z=345.

Example 261

Synthesis of S-114

S-114 was synthesized by almost the same method as the one employed for the synthesis of S-1 but replacing the 2,5-dimethylthiophenol and 1-bromo-2-chloroethane respectively by 2-methoxythiophenol and 1,5-dibromopentane.

400 MHz-¹H-NMR 7.21–7.26 (2H, m), 7.13–7.18 (1H, m), 6.82–6.93 (4H, m), 6.76–6.79 (1H, m), 3.88 (3H, s), 3.81 (3H, s), 3.72 (1H, q, J=6.6 Hz), 2.86 (2H, t, J=7.4 Hz), 2.38–2.52 (2H, m), 1.56–1.67 (2H, m), 1.38–1.53 (4H, m), 1.34 (3H, d, J=6.6 Hz), m/z=359.

Example 262

Synthesis of S-115

S-115 was synthesized by almost the same method as the one employed for the synthesis of S-1 but replacing the 2,5-dimethylthiophenol and 1-bromo-2-chloroethane respectively by 2-methoxythiophenol and 1,6-dibromohexane.

400 MHz-¹H-NMR 7.19–7.24 (2H, m), 7.12–7.16 (1H, m), 6.81–6.91 (4H, m), 6.74–6.77 (1H, m), 3.86 (3H, s), 3.79 (3H, s), 3.70 (1H, q, J=6.6 Hz), 2.84 (2H, t, J=7.5 Hz), 2.36–2.50 (2H, m), 1.57–1.65 (2H, m), 1.23–1.48 (6H, m), 1.32 (3H, d, J=6.6 Hz), m/z=373.

Example 263

Synthesis of S-116

S-116 was synthesized by almost the same method as the one employed for the synthesis of S-1 but replacing the 2,5-dimethylthiophenol and 1-bromo-2-chloroethane respectively by 2-methoxythiophenol and 1,7-dibromoheptane.

400 MHz-¹H-NMR 7.21–7.27 (2H, m), 7.13–7.18 (1H, m), 6.89–6.97 (4H, m), 6.80–6.85 (1H, m), 3.88 (3H, s), 3.83 (3H, s), 3.80–3.83 (2H, t, J=7.3 Hz), 2.85 (1H, m), 2.43–2.56 (2H, m), 1.36–1.66 (6H, m), 1.47 (3H, d, J=6.2 Hz), 1.18–1.30 (4H, m), m/z=387.

Example 264

Synthesis of S-117

S-117 was synthesized by almost the same method as the one employed for the synthesis of S-1 but replacing the 2,5-dimethylthiophenol and 1-bromo-2-chloroethane respectively by 2-methoxythiophenol and 1,8-dibromooctane.

400 MHz-¹H-NMR 7.21–7.25 (2H, m), 7.13–7.18 (1H, m), 6.82–6.94 (4H, m), 6.76–6.79 (1H, m), 3.88 (3H, s), 3.81 (3H, s), 3.73 (2H, t, J=7.3 Hz), 2.86 (1H, q, J=6.5 Hz), 2.38–2.52 (2H, m), 1.60–1.70 (2H, m), 1.20–1.60 (10H, m), 1.35 (3H, d, J=6.5 Hz), m/z=401.

Example 265

Synthesis of S-118

S-118 was synthesized by almost the same method as the one employed for the synthesis of S-1 but replacing the 2,5-dimethylthiophenol and (R)-(+)-3-methoxy-α-benzylmethylamine respectively by 2-methoxythiophenol and (R)-(+)-1-(1-naphthyl)ethylamine.

400 MHz-¹H-NMR 8.15 (1H, d, J=7.6 Hz), 7.84–7.87 (1H, m), 7.73 (1H, d, J=8.0 Hz), 7.64 (1H, d, J=6.4 Hz), 7.40–7.51 (3H, m), 7.24 (1H, dd, J=7.6 Hz, J=1.7 Hz), 7.18 (1H, ddd, J=7.8 Hz, J=7.8 Hz, J=1.7 Hz), 6.81–6.88 (2H, m), 4.62 (1H, q, J=6.6 Hz), 3.84 (3H, s), 3.05 (2H, t, J=6.4 Hz), 2.73–2.82 (2H, m), 1.48 (3H, d, J=6.6 Hz), m/z=337.

Example 266

Synthesis of S-119

S-119 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-methoxythiophenol, 1,3-dibromopropane and (R)-(+)-1-(1-naphthyl)ethylamine.

400 MHz-¹H-NMR 8.15 (1H, d, J=7.6 Hz), 7.82–7.86 (1H, m), 7.72 (1H, d, J=8.3 Hz), 7.63 (1H, d, J=6.8 Hz), 7.43–7.50 (3H, m), 7.21 (1H, dd, J=7.6 Hz, J=1.5 Hz), 7.14 (1H, ddd, J=8.0 HZ, J=8.0 Hz, J=1.5 Hz), 6.87 (1H, dd, J=7.6 Hz, J=1.2 Hz), 6.81 (1H, dd, J=8.0 Hz, J=1.1 Hz), 4.61 (1H, q, J=6.6 Hz), 3.84 (3H, s), 2.85–2.99 (2H, m), 2.61–2.77 (2H, m), 1.78–1.86 (2H, m), 1.47 (3H, d, J=6.6 Hz), m/z=351.

Example 267

Synthesis of S-120

S-120 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-methoxythiophenol, 1,4-dibromobutane and (R)-(+)-1-(1-naphthyl)ethylamine.

400 MHz-¹H-NMR 8.17 (1H, d, J=8.0 Hz), 7.85–7.88 (1H, m), 7.73 (1H, d, J=8.3 Hz), 7.64 (1H, d, J=7.1 Hz), 7.44–7.52 (3H, m), 7.21 (1H, dd, J=7.8 Hz, J=1.6 Hz), 7.13–7.18 (1H, m), 6.89 (ddd, J=7.6 Hz, J=7.6 Hz, J=1.2 Hz), 6.82 (1H, dd, J=8.3 Hz, J=1.2 Hz), 4.62 (1H, q, J=6.5 Hz), 3.86 (3H, s), 2.83–2.88 (2H, m), 2.52–2.65 (2H, m), 1.64–1.70 (4H, m), 1.49 (3H, d, J=6.5 Hz), m/z=365.

Example 268

Synthesis of S-121

S-121 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-methoxythiophenol, 1,5-dibromopentane and (R)-(+)-1-(1-naphthyl)ethylamine.

400 MHz-¹H-NMR 8.17 (1H, d, J=8.0 Hz), 7.83–7.88 (1H, m), 7.71–7.75 (1H, m), 7.63 (1H, d, J=7.0 Hz), 7.41–7.52 (3H, m), 7.21 (1H, dd, J=7.6 Hz, J=1.7 Hz), 7.15 (1H, ddd, J=7.6 Hz, J=7.6 Hz, J=1.7 Hz), 6.90 (1H, ddd, J=7.6 Hz, J=7.6 Hz, J=1.2 Hz), 6.82 (1H, dd, J=8.2 Hz, J=1.1 Hz), 4.61 (1H, q, J=6.6 Hz), 3.87 (3H, s), 2.85 (2H, t, J=7.3 Hz), 2.50–2.62 (2H, m), 1.40–1.48 (6H, m), 1.49 (3H, d, J=6.6 Hz), m/z=379.

Example 269

Synthesis of S-122

S-122 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-methoxythiophenol, 1,6-dibromohexane and (R)-(+)-1-(1-naphthyl)ethylamine. m/z=393.

Example 270

Synthesis of S-123

S-123 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-methoxythiophenol, 1,7-dibromoheptane and (R)-(+)-1-(1-naphthyl)ethylamine.

400 MHz-¹H-NMR 8.15 (1H, d, J=8.3 Hz), 7.87 (1H, d, J=7.1 Hz), 7.70–7.78 (2H, m), 7.41–7.51 (3H, m), 7.21 (1H, dd, J=7.6 Hz, J=1.5 Hz), 7.12–7.17 (1H, m), 6.90 (1H, ddd, J=7.6 Hz, J=7.6 Hz, J=1.2 Hz), 6.80–6.83 (1H, m), 4.67–4.75 (1H, m), 3.87 (3H, s), 2.84 (2H, t, J=7.3 Hz), 2.51–2.64 (2H, m), 1.05–1.64 (13H, m), m/z=407.

Example 271

Synthesis of S-124

S-124 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-methoxythiophenol, 1,8-dibromooctane and (R)-(+)-1-(1-naphthyl)ethylamine.

400 MHz-¹H-NMR 8.16 (1H, d, J=8.3 Hz), 7.86–7.89 (1H, m), 7.70–7.78 (2H, m), 7.46–7.55 (3H, m), 7.22 (1H, dd, J=7.6 Hz, J=1.7 Hz), 7.13–7.17 (1H, m), 6.87–6.92 (1H, m), 4.70 (1H, bs), 3.88 (3H, s), 2.85 (2H, t, J=7.4 Hz), 2.52–2.64 (2H, m), 1.05–1.65 (15H, m), m/z=421.

Example 272

Synthesis of S-125

S-125 was synthesized by almost the same method as the one employed for the synthesis of S-1 but replacing the 2,5-dimethylthiol by 3-methoxythiophenol.

400 MHz-¹H-NMR 7.22 (1H, d, J=8.0 Hz), 7.16 (1H, dd, J=8.0 Hz, J=8.0 Hz), 6.83–6.89 (4H, m), 6.77 (1H, ddd, J=8.0 Hz, J=2.6 Hz, J=1.0 Hz), 6.71 (1H, ddd, J=7.5 Hz, J=2.6 Hz, J=1.0 Hz), 3.80 (3H, s), 3.78 (3H, s), 3.74 (1H, q, J=6.5 Hz), 3.02–3.06 (2H, m), 2.67–2.78 (2H, m), 1.35 (3H, d, J=6.5 Hz), m/z=317.

Example 273

Synthesis of S-126

S-126 was synthesized by almost the same method as the one employed for the synthesis of S-1 but replacing the 2,5-dimethylthiophenol and 1-bromo-2-chloroethane respectively by 3-methoxythiophenol and 1,3-dibromopropane.

400 MHz-¹H-NMR 7.23 (1H, dd, J=8.0 Hz, J=8.0 Hz), 7.18 (1H, dd, J=8.0 Hz, J=8.0 Hz), 6.86–6.89 (3H, m), 6.85 (1H, dd, J=2.1 Hz, J=2.1 Hz), 6.78 (1H, ddd, J=8.0 Hz, J=2.4 Hz, J=1.2 Hz), 6.70 (1H, ddd, J=8.4 Hz, J=2.7 Hz, J=1.0 Hz), 3.81 (3H, s), 3.78 (3H, s), 3.72 (1H, q, J=6.6 Hz), 2.88–3.02 (2H, m), 2.51–2.66 (2H, m), 1.74–1.87 (2H, m), 1.33 (3H, d, J=6.6 Hz), m/z=331.

Example 274

Synthesis of S-127

S-127 was synthesized by almost the same method as the one employed for the synthesis of S-1 but replacing the 2,5-dimethylthiophenol and 1-bromo-2-chloroethane respectively by 3-methoxythiophenol and 1,4-dibromobutane.

400 MHz-$^1$H-NMR 7.23 (1H, dd, J=8.0 Hz, J=8.0 Hz), 7.18 (1H, dd, J=8.0 Hz, J=8.0 Hz), 6.86–6.89 (3H, m), 6.83–6.84 (1H, m), 6.76–6.79 (1H, m), 6.69 (1H, ddd, J=8.0 Hz, J=2.4 Hz, J=1.0 Hz), 3.81 (3H, s), 3.79 (3H, s), 3.72 (1H, q, J=6.6 Hz), 2.89 (2H, t, J=7.1 Hz), 2.40–2.55 (2H, m), 1.53–1.72 (4H, m), 1.34 (4H, m), m/z=345.

Example 275

Synthesis of S-128

S-128 was synthesized by almost the same method as the one employed for the synthesis of S-1 but replacing the 2,5-dimethylthiophenol and 1-bromo-2-chloroethane respectively by 3-methoxythiophenol and 1,5-dibromopentane.

400 MHz-$^1$H-NMR 7.23 (1H, dd, J=8.0 Hz, J=8.0 Hz), 7.18 (1H, dd, J=8.0 Hz, J=8.0 Hz), 6.86–6.89 (3H, m), 6.84 (1H, dd, J=4.1 Hz, J=4.1 Hz), 6.76–6.79 (1H, m), 6.70 (1H, ddd, J=8.0 Hz, J=2.4 Hz, J=1.0 Hz), 3.81 (3H, s), 3.79 (3H, s), 3.72 (1H, q, J=6.5 Hz), 2.89 (2H, t, J=7.3 Hz), 2.38–2.52 (2H, m), 1.59–1.67 (2H, m), 1.37–1.52 (4H, m), 1.34 (3H, d, J=6.5 Hz), m/z=359.

Example 276

Synthesis of S-129

S-129 was synthesized by almost the same method as the one employed for the synthesis of S-1 but replacing the 2,5-dimethylthiophenol and 1-bromo-2-chloroethane respectively by 3-methoxythiophenol and 1,6-dibromohexane.

400 MHz-$^1$H-NMR 7.24 (1H, dd, J=8.0 Hz, J=8.0 Hz), 7.18 (1H, dd, J=8.0 Hz, J=8.0 Hz), 6.86–6.90 (3H, m), 6.83–6.85 (1H, m), 6.76–6.79 (1H, m), 6.69 (1H, ddd, J=8.3 Hz, J=2.6 Hz, J=1.0 Hz), 3.81 (3H, s), 3.79 (3H, s), 3.72 (1H, q, J=6.6 Hz), 2.89 (2H, t, J=7.3 Hz), 2.37–2.51 (2H, m), 1.59–1.67 (2H, m), 1.24–1.52 (6H, m), 1.35 (3H, d, J=6.6 Hz), m/z=373.

Example 277

Synthesis of S-130

S-130 was synthesized by almost the same method as the one employed for the synthesis of S-1 but replacing the 2,5-dimethylthiophenol and 1-bromo-2-chloroethane respectively by 3-methoxythiophenol and 1,7-dibromoheptane.

400 MHz-$^1$H-NMR 7.24 (1H, dd, J=8.0 Hz, J=8.0 Hz), 7.18 (1H, dd, J=8.0 Hz, J=8.0 Hz), 6.86–6.90 (3H, m), 6.76–6.80 (1H, m), 6.69 (1H, ddd, J=8.0 Hz, J=2.4 Hz, J=1.0 Hz), 3.81 (3H, s), 3.79 (3H, s), 3.74 (1H, q, J=6.6 Hz), 2.89 (2H, t, J=7.3 Hz), 2.38–2.52 (2H, m), 1.58–1.66 (2H, m), 1.19–1.49 (8H, m), 1.37 (3H, d, J=6.6 Hz), m/z=387.

Example 278

Synthesis of S-131

S-131 was synthesized by almost the same method as the one employed for the synthesis of S-1 but replacing the 2,5-dimethylthiophenol and 1-bromo-2-chloroethane respectively by 3-methoxythiophenol and 1,8-dibromooctane.

400 MHz-$^1$H-NMR 7.23 (1H, dd, J=8.0 Hz, =8.0 Hz), 7.18 (1H, dd, J=8.0 Hz, J=8.0 Hz), 6.87–6.91 (3H, m), 6.84–6.85 (1H, m), 6.78 (1H, ddd, J=8.0 Hz, J=2.4 Hz, J=0.8 Hz), 6.69 (1H, ddd, J=8.0 Hz, J=2.4 Hz, J=0.8 Hz), 3.81 (3H, s), 3.79 (3H, s), 3.73 (1H, q, J=6.5 Hz), 2.89 (2H, t, J=7.4 Hz), 2.38–2.52 (2H, m), 1.59–1.70 (2H, m), 1.20–1.50 (10H, m), 1.35 (3H, d, J=6.5 Hz), m/z=401.

Example 279

Synthesis of S-132

S-132 was synthesized by almost the same method as the one employed for the synthesis of S-1 but replacing the 2,5-dimethylthiophenol and (R)-(+)-3-methoxy-α-benzylmethylamine respectively by 3-methoxythiophenol and (R)-(+)-1-(1-naphthyl)ethylamine.

400 MHz-$^1$H-NMR 8.15 (1H, d, J=7.8 Hz), 7.85–7.87 (1H, m), 7.73 (1H, d, J=8.3 Hz), 7.63 (1H, d, J=6.6 Hz), 7.42–7.55 (3H, m), 7.12–7.16 (1H, m), 6.85–6.89 (2H, m), 6.69–6.72 (1H, m), 4.63 (1H, q, J=6.5 Hz), 3.76 (1H, s), 3.08 (2H, t, J=6.4 Hz), 2.76–2.87 (2H, m), 1.49 (3H, d, J=6.5 Hz), m/z=337.

Example 280

Synthesis of S-133

S-133 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3-methoxythiophenol, 1,3-dibromopropane and (R)-(+)-1-(1-naphthyl)ethylamine.

400 MHz-$^1$H-NMR 8.18 (1H, d, J=9.4 Hz), 7.85–7.88 (1H, m), 7.74 (1H, d, J=8.0 Hz), 7.63 (1H, d, J=6.6 Hz), 7.44–7.52 (3H, m), 7.16 (1H, dd, J=7.8 Hz, J=7.8 Hz), 6.84–6.89 (2H, m), 6.68–6.71 (1H, m), 4.61 (1H, q, J=6.6 Hz), 3.77 (3H, s), 2.91–3.04 (2H, m), 2.62–2.76 (2H, m), 1.80–1.90 (2H, m), 1.48 (3H, d, J=6.6 Hz), m/z=351.

Example 281

Synthesis of S-134

S-134 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3-methoxythiophenol, 1,4-dibromobutane and (R)-(+)-1-(1-naphthyl)ethylamine.

400 MHz-$^1$H-NMR 8.17 (1H, d, J=8.0 Hz), 7.85–7.88 (1H, m), 7.73 (1H, d, J=8.0 Hz), 7.63 (1H, d, J=6.84 Hz), 7.44–7.52 (3H, m), 7.16 (1H, dd, J=7.8 Hz, J=7.8 Hz), 6.83–6.88 (2H, m), 6.67–6.70 (1H, m), 4.62 (1H, q, J=6.6 Hz), 3.77 (3H, s), 2.89 (2H, t, J=7.1 Hz), 2.51–2.65 (2H, m), 1.59–1.73 (4H, m), 1.49 (3H, d, J=6.6 Hz), m/z=365.

Example 282

Synthesis of S-135

S-135 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3-methoxythiophenol, 1,5-dibromopentane and (R)-(+)-1-(1-naphthyl)ethylamine.

400 MHz-$^1$H-NMR 8.17 (1H, d, J=8.0 Hz), 7.85–7.88 (1H, m), 7.74 (1H, d, J=8.1 Hz), 7.63 (1H, d, J=6.6 Hz), 7.43–7.52 (3H, m), 7.17 (1H, dd, J=8.0 Hz, J=8.0 Hz), 6.85–6.88 (1H, m), 6.84 (1H, dd, J=2.1 Hz, J=2.1 Hz), 6.69 (1H, ddd, J=6.7 Hz, J=2.4 Hz, J=0.7 Hz), 4.62 (1H, q, J=6.6 Hz), 3.78 (3H, s), 2.88 (2H, t, J=7.3 Hz), 2.50–2.63 (2H, m), 1.59–1.67 (2H, m), 1.40–1.55 (4H, m), 1.49 (3H, d, J=6.6 Hz), m/z=379.

Example 283

Synthesis of S-136

S-136 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3-methoxythiophenol, 1,6-dibromohexane and (R)-(+)-1-(1-naphthyl)ethylamine.

400 MHz-$^1$H-NMR 8.16 (1H, d, J=8.3 Hz), 7.80–7.88 (2H, m), 7.73–7.76 (1H, m), 7.41–7.53 (3H, m), 6.85–6.88 (1H, m), 6.83 (1H, dd, J=2.1 Hz, J=2.1 Hz), 6.68 (1H, ddd, J=8.4 Hz, J=2.4 Hz, J=0.9 Hz), 4.67 (1H, q, J=6.6 Hz), 2.87 (2H, t, J=7.3 Hz), 2.51–2.63 (2H, m), 1.25–1.66 (11H, m), m/z=393.

Example 284

Synthesis of S-137

S-137 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3-methoxythiophenol, 1,7-dibromoheptane and (R)-(+)-1-(1-naphthyl)ethylamine.

400 MHz-$^1$H-NMR 8.15 (1H, d, J=8.3 Hz), 7.86–7.89 (1H, m), 7.75–7.80 (2H, m), 7.45–7.55 (3H, m), 7.16 (1H, dd, J=8.1 Hz, J=8.1 Hz), 6.82–6.88 (2H, m), 6.68 (1H, ddd, J=8.3 Hz, J=2.4 Hz, J=0.7 Hz), 4.70–4.78 (1H, m), 3.78 (3H, s), 2.86 (2H, t, J=7.3 Hz), 2.52–2.65 (2H, m), 1.05–1.65 (13H, m), m/z=407.

Example 285

Synthesis of S-138

S-138 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 3-methoxythiophenol, 1,8-dibromooctane and (R)-(+)-1-(1-naphthyl)ethylamine.

400 MHz-$^1$H-NMR 8.14 (1H, d, J=8.0 Hz), 7.87–7.89 (1H, m), 7.77 (1H, d, J=8.0 Hz), 7.47–7.55 (3H, m), 7.17 (1H, dd, J=8.1 Hz, J=8.1 Hz), 6.83–6.89 (2H, m), 6.68 (1H, ddd, J=8.3 Hz, J=2.4 Hz, J=1.0 Hz), 4.75 (1H, bs), 3.78 (3H, s), 2.88 (2H, t, J=7.3 Hz), 2.53–2.66 (2H, m), 1.00–1.75 (15H, m), m/z=421.

Example 286

Synthesis of S-139

S-139 was synthesized by almost the same method as the one employed for the synthesis of S-1 but replacing the 2,5-dimethylthiol by 4-methoxythiophenol.

400 MHz-$^1$H-NMR 7.28 (2H, d, J=8.0 Hz), 7.21 (1H, dd, J=8.0 Hz, J=8.0 Hz), 6.75–6.88 (5H, m), 3.80 (3H, s), 3.78 (3H, s), 3.70 (1H, q, J=6.6 Hz), 2.88–2.93 (2H, m), 2.57–2.70 (2H, m), 1.34 (3H, d, J=6.6 Hz), m/z=317.

Example 287

Synthesis of S-140

S-140 was synthesized by almost the same method as the one employed for the synthesis of S-1 but replacing the 2,5-dimethylthiophenol and 1-bromo-2-chloroethane respectively by 4-methoxythiophenol and 1,3-dibromopropane.

400 MHz-$^1$H-NMR 7.31 (2H, d, J=8.8 Hz), 7.23 (1H, dd, J=8.1 Hz, J=8.1 Hz), 6.85–6.88 (2H, m), 6.82 (2H, d, J=8.8 Hz), 6.77 (1H, ddd, J=8.2 Hz, J=2.7 Hz, J=1.0 Hz), 3.80 (3H, s), 3.79 (3H, s), 3.70 (1H, q, J=6.6 Hz), 2.77–2.89 (2H, m), 2.49–2.64 (2H, m), 1.64–1.80 (2H, m), 1.32 (3H, d, J=6.6 Hz), m/z=331.

Example 288

Synthesis of S-141

S-141 was synthesized by almost the same method as the one employed for the synthesis of S-1 but replacing the 2,5-dimethylthiophenol and 1-bromo-2-chloroethane respectively by 4-methoxythiophenol and 1,4-dibromobutane.

400 MHz-$^1$H-NMR 7.31 (2H, d, J=8.8 Hz), 7.23 (1H, dd, J=8.0 Hz, J=8.0 Hz), 6.85–6.89 (2H, m), 6.82 (2H, d, J=8.8 Hz), 6.76–6.79 (1H, m), 3.81 (3H, s), 3.79 (3H, s), 3.71 (1H, q, J=6.6 Hz), 2.75–2.80 (2H, m), 2.33–2.53 (2H, m), 1.53–1.62 (4H, m), 1.33 (3H, d, J=6.6 Hz), m/z=345.

Example 289

Synthesis of S-142

S-142 was synthesized by almost the same method as the one employed for the synthesis of S-1 but replacing the 2,5-dimethylthiophenol and 1-bromo-2-chloroethane respectively by 4-methoxythiophenol and 1,5-dibromopentane.

400 MHz-$^1$H-NMR 7.31 (2H, d, J=8.8 Hz), 7.23 (1H, dd, J=8.0 Hz, J=8.0 Hz), 6.86–6.89 (2H, m), 6.83 (2H, d, J=8.8 Hz), 6.76–6.80 (1H, m), 3.81 (3H, s), 3.79 (3H, s), 3.71 (1H, q, J=6.6 Hz), 2.78 (2H, t, J=7.3 Hz), 2.38–2.52 (2H, m), 1.50–1.60 (2H, m), 1.36–1.50 (4H, m), 1.34 (3H, d, J=6.6 Hz), m/z=359.

Example 290

Synthesis of S-143

S-143 was synthesized by almost the same method as the one employed for the synthesis of S-1 but replacing the 2,5-dimethylthiophenol and 1-bromo-2-chloroethane respectively by 4-methoxythiophenol and 1,6-dibromohexane.

400 MHz-$^1$H-NMR 7.31 (2H, d, J=8.8 Hz), 7.23 (1H, dd, J=8.0 Hz, J=8.0 Hz), 6.87–6.90 (2H, m), 6.81–6.85 (2H, m), 6.76–6.80 (1H, m), 3.81 (3H, s), 3.79 (3H, s), 3.73 (1H, q, J=6.6 Hz), 2.78 (2H, t, J=7.3 Hz), 2.38–2.51 (2H, m), 1.21–1.59 (8H, m), 1.35 (3H, d, J=6.6 Hz), m/z=373.

Example 291

Synthesis of S-144

S-144 was synthesized by almost the same method as the one employed for the synthesis of S-1 but replacing the 2,5-dimethylthiophenol and 1-bromo-2-chloroethane respectively by 4-methoxythiophenol and 1,7-dibromoheptane.

400 MHz-$^1$H-NMR 7.32 (2H, d, J=8.8 Hz), 7.24 (1H, dd, J=8.0 Hz, J=8.0 Hz), 6.88–6.91 (2H, m), 6.83 (2H, d, J=8.8 Hz), 6.76–6.80 (1H, m), 3.81 (3H, s), 3.79 (3H, s), 3.75 (1H, q, J=6.6 Hz), 2.78 (2H, t, J=7.4 Hz), 2.38–2.52 (2H, m), 1.40–1.60 (4H, m), 1.20–1.30 (4H, m), 1.32–1.40 (2H, m), 1.37 (3H, d, J=6.6 Hz), m/z=387.

Example 292

Synthesis of S-145

S-145 was synthesized by almost the same method as the one employed for the synthesis of S-1 but replacing the 2,5-dimethylthiophenol and 1-bromo-2-chloroethane respectively by 4-methoxythiophenol and 1,8-dibromooctane.

400 MHz-$^1$H-NMR 7.29–7.33 (2H, m), 7.25 (1H, dd, J=8.0 Hz, J=8.0 Hz), 6.92–6.99 (2H, m), 6.79–6.85 (2H, m), 3.83 (3H, s), 3.79 (3H, s), 3.81–3.84 (1H, m), 2.78 (2H, t, J=7.4 Hz), 2.43–2.56 (2H, m), 1.43–1.60 (4H, m), 1.19–1.40 (8H, m), 1.48 (3H, d, J=5.9 Hz), m/z=401.

Example 293

Synthesis of S-146

S-146 was synthesized by almost the same method as the one employed for the synthesis of S-1 but replacing the 2,5-dimethylthiophenol and (R)-(+)-3-methoxy-α-benzylmethylamine respectively by 4-methoxythiophenol and (R)-(+)-1-(1-naphthyl)ethylamine.

400 MHz-$^1$H-NMR 8.15 (1H, d, J=7.6 Hz), 7.85–7.89 (1H, m), 7.73 (1H, d, J=8.2 Hz), 7.62 (1H, d, J=6.6 Hz), 7.42–7.52 (3H, m), 7.27–7.30 (2H, m), 6.75–6.80 (2H, m), 4.61 (1H, q, J=6.5 Hz), 3.78 (3H, s), 2.97 (2H, t, J=6.2 Hz), 2.68–2.78 (2H, m), 1.48 (3H, d, J=6.5 Hz), m/z=337.

Example 294

Synthesis of S-147

S-147 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-methoxythiophenol, 1,3-dibromopropane and (R)-(+)-1-(1-naphthyl)ethylamine.

400 MHz-$^1$H-NMR 8.15 (1H, d, J=7.8 Hz), 7.85–7.88 (1H, m), 7.74 (1H, d, J=8.3 Hz), 7.64 (1H, d, J=7.1 Hz), 7.46–7.52 (3H, m), 7.27–7.31 (2H, m), 6.77–6.82 (2H, m), 4.61 (1H, q, J=6.5 Hz), 3.78 (3H, s), 2.79–2.92 (2H, m), 2.61–2.75 (2H, m), 1.73–1.81 (2H, m), 1.49 (3H, d, J=6.5 Hz), m/z=351.

Example 295

Synthesis of S-148

S-148 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-methoxythiophenol, 1,4-dibromobutane and (R)-(+)-1-(1-naphthyl)ethylamine.

400 MHz-$^1$H-NMR 8.16 (1H, d, J=8.0 Hz), 7.85–7.88 (1H, m), 7.74 (1H, d, J=8.3 Hz), 7.64 (1H, d, J=6.4 Hz), 7.45–7.53 (3H, m), 7.28–7.31 (2H, m), 6.78–6.82 (2H, m), 4.62 (1H, q, J=6.4 Hz), 3.78 (3H, s), 2.78 (2H, t, J=6.7 Hz), 2.49–2.63 (2H, m), 1.46–1.68 (4H, m), 1.49 (3H, d, J=6.4 Hz), m/z=365.

Example 296

Synthesis of S-149

S-149 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-methoxythiophenol, 1,5-dibromopentane and (R)-(+)-1-(1-naphthyl)ethylamine.

400 MHz-$^1$H-NMR 8.17 (1H, d, J=8.3 Hz), 7.83–7.88 (1H, m), 7.74 (1H, d, J=8.0 Hz), 7.63 (1H, d, J=7.1 Hz), 7.46–7.53 (3H, m), 7.28–7.32 (2H, m), 6.79–6.83 (2H, m), 4.62 (1H, q, J=6.6 Hz), 3.78 (3H, s), 2.78 (2H, t, J=7.3 Hz), 2.48–2.61 (2H, m), 1.46–1.60 (4H, m), 1.49 (3H, d, J=6.6 Hz), 1.36–1.44 (2H, m), m/z=379.

Example 297

Synthesis of S-150

S-150 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-methoxythiophenol, 1,6-dibromohexane and (R)-(+)-1-(1-naphthyl)ethylamine.

400 MHz-$^1$H-NMR 8.17 (1H, d, J=8.0 Hz), 7.82–7.88 (1H, m), 7.74 (1H, d, J=8.3 Hz), 7.65 (1H, d, J=7.1 Hz), 7.41–7.54 (3H, m), 7.28–7.33 (2H, m), 6.80–6.84 (2H, m), 4.63 (1H, q, J=6.4 Hz), 3.78 (3H, s), 2.75–2.79 (2H, m), 2.49–2.61 (2H, m), 1.24–1.58 (8H, m), m/z=393.

Example 298

Synthesis of S-151

S-151 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-methoxythiophenol, 1,7-dibromoheptane and (R)-(+)-1-(1-naphthyl)ethylamine.

400 MHz-$^1$H-NMR 8.15 (1H, d, J=8.0 Hz), 7.86–7.88 (1H, m), 7.71–7.77 (2H, m), 7.46–7.54 (3H, m), 7.29–7.32 (2H, m), 6.80–6.84 (2H, m), 4.69 (1H, bs), 3.80 (3H, s), 2.77 (2H, t, J=7.5 Hz), 2.51–2.64 (2H, m), 1.00–1.64 (13H, m), m/z=407.

Example 299

Synthesis of S-152

S-152 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-methoxythiophenol, 1,8-dibromooctane and (R)-(+)-1-(1-naphthyl)ethylamine.

400 MHz-$^1$H-NMR 8.15 (1H, d, J=8.0 Hz), 7.86–7.89 (1H, m), 7.71–7.77 (2H, m), 7.45–7.54 (3H, m), 7.29–7.33 (2H, m), 6.80–6.85 (2H, m), 4.66–4.76 (1H, m), 3.78 (3H, s), 2.78 (2H, t, J=7.3 Hz), 2.51–2.64 (2H, m), 1.05–1.56 (15H, m), m/z=421.

Example 300

Synthesis of S-153

S-153 was synthesized by almost the same method as the one employed for the synthesis of S-1 but replacing the 2,5-dimethylthiol by 2,3,5,6-tetrafluorothiophenol.

400 MHz-$^1$H-NMR 7.21 (1H, dd, J=8.0 Hz, J=8.0 Hz), 6.96–7.06 (1H, m), 6.82–6.86 (2H, m), 6.74–6.77 (1H, m), 3.80 (3H, s), 3.70 (1H, q, J=6.6 Hz), 3.03 (2H, t, J=6.0 Hz), 2.55–2.67 (2H, m), 1.34 (3H, d, J=6.6 Hz), m/z=359.

Example 301

Synthesis of S-154

S-154 was synthesized by almost the same method as the one employed for the synthesis of S-1 but replacing the 2,5-dimethylthiophenol and 1-bromo-2-chloroethane respectively by 2,3,5,6-tetrafluorothiophenol and 1,3-dibromopropane.

400 MHz-$^1$H-NMR 7.23 (1H, dd, J=8.3 Hz, J=8.3 Hz), 6.97–7.06 (1H, m), 6.84–6.87 (2H, m), 6.74–6.79 (1H, m), 3.81 (3H, s), 3.70 (1H, q, J=6.6 Hz), 2.90–3.03 (2H, m), 2.49–2.65 (2H, m), 1.66–1.75 (2H, m), 1.33 (3H, d, J=6.6 Hz), m/z=373.

Example 302

Synthesis of S-155

S-155 was synthesized by almost the same method as the one employed for the synthesis of S-1 but replacing the 2,5-dimethylthiophenol and 1-bromo-2-chloroethane respectively by 2,3,5,6-tetrafluorothiophenol and 1,4-dibromobutane.

400 MHz-$^1$H-NMR 7.23 (1H, dd, J=8.1 Hz.J=8.1 Hz), 6.97–7.06 (1H, m), 6.84–6.88 (2H, m), 6.76–6.78 (1H, m), 3.81 (3H, s), 3.70 (1H, q, J=6.6 Hz), 2.91 (2H, t, J=6.6 Hz), 2.37–2.53 (2H, m), 1.53–1.63 (4H, m), 1.32 (3H, d, J=6.6 Hz), m/z=387.

Example 303

Synthesis of S-156

S-156 was synthesized by almost the same method as the one employed for the synthesis of S-1 but replacing the 2,5-dimethylthiophenol and 1-bromo-2-chloroethane respectively by 2,3,5,6-tetrafluorothiophenol and 1,5-dibromopentane.

400 MHz-$^1$H-NMR 7.23 (1H, dd, J=8.0 Hz, J=8.0 Hz), 6.96–7.05 (1H, m), 6.85–6.89 (2H, m), 6.75–6.79 (1H, m), 3.81 (3H, s), 3.71 (1H, q, J=6.5 Hz), 2.91 (2H, t, J=7.3 Hz), 2.37–2.51 (2H, m), 1.50–1.59 (2H, m), 1.36–1.46 (4H, m), 1.33 (3H, d, J=6.6 Hz), m/z=401.

Example 304

Synthesis of S-157

S-157 was synthesized by almost the same method as the one employed for the synthesis of S-1 but replacing the 2,5-dimethylthiophenol and 1-bromo-2-chloroethane respectively by 2,3,5,6-tetrafluorothiophenol and 1,6-dibromohexane.

400 MHz-$^1$H-NMR 7.23 (1H, dd, J=8.1 Hz, J=8.1 Hz), 6.97–7.06 (1H, m), 6.86–6.89 (2H, m), 6.78–6.79 (1H, m), 3.81 (3H, s), 3.72 (1H, q, J=6.6 Hz), 2.91 (2H, t, J=7.3 Hz), 2.37–2.51 (2H, m), 1.51–1.58 (2H, m), 1.23–1.49 (6H, m), 1.34 (3H, d, J=6.6 Hz), m/z=415.

Example 305

Synthesis of S-158

S-158 was synthesized by almost the same method as the one employed for the synthesis of S-1 but replacing the 2,5-dimethylthiophenol and 1-bromo-2-chloroethane respectively by 2,3,5,6-tetrafluorothiophenol and 1,7-dibromoheptane.

400mHz-$^1$H-NMR 7.24 (1H, dd, J=8.0 Hz, J=8.0 Hz), 6.97–7.05 (1H, m), 6.88–6.90 (2H, m), 6.78 (1H, m), 3.81 (3H, s), 3.74 (1H, q, J=6.7 Hz), 2.91 (2H, t, J=7.3 Hz), 2.38–2.51 (2H, m), 1.20–1.58 (8H, m), 1.36 (3H, d, J=6.7 Hz), m/z=429.

Example 306

Synthesis of S-159

S-159 was synthesized by almost the same method as the one employed for the synthesis of S-1 but replacing the 2,5-dimethylthiophenol and 1-bromo-2-chloroethane respectively by 2,3,5,6-tetrafluorothiophenol and 1,8-dibromooctane.

400 MHz-$^1$H-NMR 7.22–7.26 (1H, m), 6.97–7.05 (1H, m), 6.89–6.92 (2H, m), 6.78–6.81 (1H, m), 3.81 (3H, s), 3.77 (1H, q, J=6.6 Hz), 2.91 (2H, t, J=7.4 Hz), 2.40–2.54 (2H, m), 1.17–1.57 (12H, m), 1.40 (3H, d, J=6.6 Hz), m/z=443.

Example 307

Synthesis of S-160

S-160 was synthesized by almost the same method as the one employed for the synthesis of S-1 but replacing the 2,5-dimethylthiophenol and (R)-(+)-3-methoxy-α-benzylmethylamine respectively by 2,3,5,6-tetrafluorothiophenol and (R)-(+)-1-(1-naphthyl)ethylamine.

400 MHz-$^1$H-NMR 8.15 (1H, d, J=8.3 Hz), 7.84–7.89 (1H, m), 7.72 (1H, d, J=8.3 Hz), 7.61 (1H, d, J=7.1 Hz), 7.48 (1H, d, J=7.1 Hz), 7.43–7.52 (3H, m), 6.95–7.03 (1H, m), 4.61 (1H, q, J=6.6 Hz), 3.06 (2H, t, J=6.1 Hz), 2.65–2.75 (2H, m), 1.48 (3H, d, J=6.6 Hz), m/z=379.

Example 308

Synthesis of S-161

S-161 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluorothiophenol, 1,3-dibromopropane and (R)-(+)-1-(1-naphthyl)ethylamine.

400 MHz-$^1$H-NMR 8.16 (1H, d, J=8.0 Hz), 7.85–7.88 (1H, m), 7.74 (1H, d, J=8.3 Hz), 7.61 (1H, d, J=6.6 Hz), 7.44–7.52 (3H, m), 6.95–7.04 (1H, m), 4.60 (1H, q, J=6.5 Hz), 2.93–3.05 (2H, m), 2.61–2.75 (2H, m), 1.68–1.78 (2H, m), 1.48 (3H, d, J=6.5 Hz), m/z=393.

Example 309

Synthesis of S-162

S-162 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5, 6-tetrafluorothiophenol, 1,4-dibromobutane and (R)-(+)-1-(1-naphthyl)ethylamine.

400 MHz-$^1$H-NMR 8.17 (1H, d, J=8.3 Hz), 7.85–7.87 (1H, m), 7.73 (1H, d, J=8.3 Hz), 7.62 (1H, d, J=7.1 Hz), 7.44–7.52 (3H, m), 6.95–7.04 (1H, m), 4.61 (1H, q, J=6.6 Hz), 2.90 (2H, t, J=6.7 Hz), 2.48–2.62 (2H, m), 1.57–1.63 (4H, m), 1.48 (3H, d, J=6.6 Hz), m/z=407.

Example 310

Synthesis of S-163

S-163 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluorothiophenol, 1,5-dibromopentane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.3 Hz), 7.63 (1H, d, J=6.8 Hz), 7.44–7.52 (3H, m), 6.95–7.04 (1H, m), 4.61 (1H, q, J=6.6 Hz), 2.90 (2H, t, J=7.2 Hz), 2.48–2.62 (2H, m), 1.38–1.58 (6H, m), 1.49 (3H, d, J=6.6 Hz), m/z=421.

Example 311

Synthesis of S-164

S-164 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluorothiophenol, 1,6-dibromohexane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.1 Hz), 7.65 (1H, d, J=7.1 Hz), 7.45–7.53 (3H, m), 6.98–7.02 (1H, m), 4.63 (1H, q, J=6.6 Hz), 2.89 (2H, t, J=7.3 Hz), 2.47–2.62 (2H, m), 1.23–1.57 (8H, m), 1.50 (3H, d, J=6.6 Hz), m/z=435.

Example 312

Synthesis of S-165

S-165 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluorothiophenol, 1,7-dibromoheptane and (R)-(+)-1-(1-naphthyl)ethylamine.

400 MHz-$^1$H-NMR 8.13 (1H, d, J=8.3 Hz), 7.87–7.89 (1H, m), 7.78 (1H, d, J=8.0 Hz), 7.47–7.56 (3H, m), 6.95–7.04 (1H, m), 4.79 (1H, q, J=6.4 Hz), 2.87 (2H, t, J=7.3 Hz), 2.52–2.68 (2H, m), 1.02–1.70 (10H, m), 1.65 (3H, d, J=6.4 Hz), m/z=449.

Example 313

Synthesis of S-166

S-166 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluorothiophenol, 1,8-dibromooctane and (R)-(+)-1-(1-naphthyl)ethylamine.

400 MHz-$^1$H-NMR 8.11 (1H, d, J=8.5 Hz), 7.88–7.91 (1H, m), 7.80 (1H, d, J=8.3 Hz), 7.44–7.57 (3H, m), 6.95–7.03 (1H, m), 4.89 (1H, bs), 2.88 (2H, t, J=7.3 Hz), 2.54–2.72 (2H, m), 1.00–1.80 (15H, m), m/z=463.

Example 314

Synthesis of S-167

S-167 was synthesized by almost the same method as the one employed for the synthesis of S-1 but replacing the 2,5-dimethylthiol by 5-chloro-2-mercaptobenzothiazole.

400 MHz-$^1$H-NMR 7.80 (1H, d, J=1.7 Hz), 7.63 (1H, dd, J=8.6 Hz, J=1.2 Hz), 7.18–7.28 (2H, m), 6.86–6.90 (2H, m), 6.74–6.78 (1H, m), 3.80 (3H, s), 3.77–3.82 (1H, m), 3.43–3.47 (2H, m), 2.85–3.00 (2H, m), 1.35 (3H, d, J=6.6 Hz), m/z=378.

Example 315

Synthesis of S-168

S-168 was synthesized by almost the same method as the one employed for the synthesis of S-1 but replacing the 2,5-dimethylthiophenol and 1-bromo-2-chloroethane respectively by 5-chloro-2-mercaptobenzothiazole and 1,3-dibromopropane.

400 MHz-$^1$H-NMR 7.79 (1H, d, J=2.0 Hz), 7.63 (1H, d, J=8.2 Hz), 7.19–7.27 (2H, m), 6.87–6.89 (2H, m), 6.77–6.79 (1H, m), 3.80 (3H, s), 3.74 (1H, q, J=6.6 Hz), 3.33–3.47 (2H, m), 2.55–2.72 (2H, m), 1.93–2.00 (2H, m), 1.35 (3H, d, J=6.6 Hz), m/z=392.

Example 316

Synthesis of S-169

S-169 was synthesized by almost the same method as the one employed for the synthesis of S-1 but replacing the 2,5-dimethylthiophenol and 1-bromo-2-chloroethane respectively by 5-chloro-2-mercaptobenzothiazole and 1,4-dibromobutane.

400 MHz-$^1$H-NMR 7.82 (1H, d, J=2.0 Hz), 7.63 (1H, d, J=8.5 Hz), 7.21–7.27 (2H, m), 6.87–6.90 (2H, m), 6.76–6.79 (1H, m), 3.80 (3H, s), 3.73 (1H, q, J=6.6 Hz), 3.32 (2H, t, J=7.3 Hz), 2.45–2.60 (2H, m), 1.78–1.90 (2H, m), 1.59–1.65 (2H, m), 1.34 (3H, d, J=6.6 Hz), m/z=406.

Example 317

Synthesis of S-170

S-170 was synthesized by almost the same method as the one employed for the synthesis of S-1 but replacing the 2,5-dimethylthiophenol and 1-bromo-2-chloroethane respectively by 5-chloro-2-mercaptobenzothiazole and 1,5-dibromopentane.

400 MHz-$^1$H-NMR 7.83 (1H, d, J=2.0 Hz), 7.63 (1H, d, J=7.6 Hz), 7.20–7.27 (2H, m), 6.86–6.87 (2H, m), 6.75–6.78 (1H, m), 3.81 (3H, s), 3.72 (3H, s), 3.72 (1H, q, J=6.6 Hz), 3.31 (2H, t, J=7.3 Hz), 2.41–2.55 (2H, m), 1.80 (2H, tt, J=7.3 Hz, J=7.3 Hz), 1.43–1.57 (4H, m), 1.34 (3H, d, J=6.6 Hz), m/z=420.

Example 318

Synthesis of S-171

S-171 was synthesized by almost the same method as the one employed for the synthesis of S-1 but replacing the 2,5-dimethylthiophenol and 1-bromo-2-chloroethane respectively by 5-chloro-2-mercaptobenzothiazole and 1,6-dibromohexane.

400 MHz-$^1$H-NMR 7.82–7.83 (1H, m), 7.63 (1H, dd, J=8.6 Hz, J=1.7 Hz), 7.19–7.26 (2H, m), 6.88–6.93 (2H, m), 6.75–6.81 (1H, m), 3.82 (3H, s), 3.75–3.83 (1H, m), 3.30 (2H, t, J=7.3 Hz), 2.42–2.56 (2H, m), 1.79 (2H, tt, J=7.3 Hz, J=7.3 Hz), 1.30–1.56 (6H, m), 1.40 (3H, d, J=6.4 Hz), m/z=434.

Example 319

Synthesis of S-172

S-172 was synthesized by almost the same method as the one employed for the synthesis of S-1 but replacing the 2,5-dimethylthiophenol and 1-bromo-2-chloroethane respectively by 5-chloro-2-mercaptobenzothiazole and 1,7-dibromoheptane.

400 MHz-¹H-NMR 7.83 (1H, d, J=2.2 Hz), 7.63 (1H, d, J=8.3 Hz), 7.24–7.27 (2H, m), 6.89–6.92 (2H, m), 6.77–6.80 (1H, m), 3.81 (3H, s), 3.77 (1H, q, J=6.6 Hz), 3.31 (2H, t, J=7.3 Hz), 2.41–2.45 (2H, m), 1.79 (2H, tt, J=7.3 Hz, =7.3 Hz), 1.21–1.55 (8H, m), 1.40 (3H, d, J=6.6 Hz), m/z=448.

Example 320

Synthesis of S-173

S-173 was synthesized by almost the same method as the one employed for the synthesis of S-1 but replacing the 2,5-dimethylthiophenol and 1-bromo-2-chloroethane respectively by 5-chloro-2-mercaptobenzothiazole and 1,8-dibromooctane.

400 MHz-¹H-NMR 8.83 (1H, d, J=1.6 Hz), 7.63 (1H, d, J=8.5 Hz), 7.22–7.27 (2H, m), 6.91–6.94 (2H, m), 6.80 (1H, dd, J=8.3 Hz, J=2.7 Hz), 3.82 (3H, s), 3.78–3.85 (1H, m), 3.31 (2H, t, J=8.8 Hz), 2.42–2.53 (2H, m), 1.79 (2H, tt, J=8.8 Hz, J=8.8 Hz), 1.20–1.57 (10H, m), 1.43 (3H, d, J=6.3 Hz), m/z=462.

Example 321

Synthesis of S-174

S-174 was synthesized by almost the same method as the one employed for the synthesis of S-1 but replacing the 2,5-dimethylthiophenol and (R)-(+)-3-methoxy-α-benzylmethylamine respectively by 5-chloro-2-mercaptobenzothiazole and (R)-(+)-1-(1-naphthyl)ethylamine. m/z=398.

Example 322

Synthesis of S-175

S-175 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 5-chloro-2-mercaptobenzothiazole, 1,3-dibromopropane and (R)-(+)-1-(1-naphthyl)ethylamine.

400 MHz-¹H-NMR 8.18 (1H, d, J=7.3 Hz), 7.84–7.88 (1H, m), 7.73–7.76 (2H, m), 7.64 (1H, d, J=7.8 Hz), 7.62 (1H, d, J=8.3 Hz), 7.43–7.48 (3H, m), 7.23–7.26 (1H, m), 4.63 (1H, q, J=6.6 Hz), 3.35–3.50 (2H, m), 2.67–2.82 (2H, m), 2.01 (2H, tt, J=6.9 Hz, J=6.9 Hz), 1.50 (3H, d, J=6.6 Hz), m/z=412.

Example 323

Synthesis of S-176

S-176 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 5-chloro-2-mercaptobenzothiazole, 1,4-dibromobutane and (R)-(+)-1-(1-naphthyl)ethylamine.

400 MHz-¹H-NMR 8.18 (1H, d, J=8.1 Hz), 7.84–7.87 (1H, m), 8.80 (1H, d, J=1.9 Hz), 7.73 (1H, d, J=8.3 Hz), 7.65 (1H, d, J=6.8 Hz), 7.62 (1H, d, J=8.3 Hz), 7.43–7.52 (3H, m), 7.23–7.26 (1H, m), 4.63 (1H, q, J=6.6 Hz), 3.31 (2H, t, J=7.2 Hz), 2.56–2.70 (2H, m), 1.82–1.90 (2H, m), 1.68 (2H, tt, J=7.2 Hz, J=7.2 Hz), 1.49 (3H, d, J=6.6 Hz), m/z=426.

Example 324

Synthesis of S-177

S-177 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 5-chloro-2-mercaptobenzothiazole, 1,5-dibromopentane and (R)-(+)-1-(1-naphthyl)ethylamine.

400 MHz-¹H-NMR 8.17 (1H, d, J=8.3 Hz), 7.82–7.87 (2H, m), 7.71–7.42 (1H, m), 7.58–7.64 (2H, m), 7.41–7.52 (3H, m), 7.23–7.26 (1H, m), 4.62 (1H, q, J=6.6 Hz), 3.30 (2H, t, J=7.3 Hz), 2.51–2.65 (2H, m), 1.79 (2H, tt, J=7.3 Hz, J=7.3 Hz), 1.58–1.60 (4H, m), 1.49 (3H, d, J=6.6 Hz), m/z=440.

Example 325

Synthesis of S-178

S-178 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 5-chloro-2-mercaptobenzothiazole, 1,6-dibromohexane and (R)-(+)-1-(1-naphthyl)ethylamine.

400 MHz-¹H-NMR 8.17 (1H, d, J=8.5 Hz), 7.82–7.88 (2H, m), 7.71–7.75 (1H, m), 7.65 (1H, d, J=7.1 Hz), 7.62 (1H, d, J=8.5 Hz), 7.42–7.52 (3H, m), 7.23–7.26 (1H, m), 4.63 (1H, q, J=6.6 Hz), 3.29 (2H, t, J=7.3 Hz), 2.51–2.64 (2H, m), 1.78 (2H, tt, J=7.3 Hz, J=7.3 Hz), 1.32–1.56 (6H, m), 1.50 (3H, d, J=6.6 Hz), m/z=454.

Example 326

Synthesis of S-179

S-179 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 5-chloro-2-mercaptobenzothiazole, 1,7-dibromoheptane and (R)-(+)-1-(1-naphthyl)ethylamine.

400 MHz-¹H-NMR 8.15 (1H, d, J=8.3 Hz), 7.86–7.88 (1H, m), 7.82–7.83 (1H, m), 7.72–7.78 (2H, m), 7.62 (1H, dd, J=8.6 Hz, J=0.5 Hz), 7.45–7.55 (3H, m), 7.23–7.26 (1H, m), 4.71 (1H, q, J=6.6 Hz), 3.29 (1H, t, J=7.3 Hz), 2.50–2.66 (2H, m), 1.71–1.80 (2H, m), 1.58 (3H, d, J=6.6 Hz), 1.06–1.64 (8H, m), m/z=468.

Example 327

Synthesis of S-180

S-180 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 5-chloro-2-mercaptobenzothiazole, 1,8-dibromooctane and (R)-(+)-1-(1-naphthyl)ethylamine.

400 MHz-¹H-NMR 8.15 (1H, d, J=8.3 Hz), 7.85–7.88 (1H, m), 7.83 (1H, d, J=2.4 Hz), 7.45 (1H, d, J=8.0 Hz), 7.71 (1H, d, J=6.8 Hz), 7.62 (1H, d, J=8.6 Hz), 7.45–7.54 (1H, m), 7.23–7.24 (1H, m), 4.70 (1H, q, J=6.6 Hz), 3.30 (2H, t, J=7.3 Hz), 2.52–2.65 (2H, m), 1.68–1.84 (2H, m), 1.56 (3H, d, J=6.6 Hz), 1.06–1.59 (10H, m), m/z=482.

Example 328

Synthesis of S-181

S-181 was synthesized by almost the same method as the one employed for the synthesis of S-1 but replacing the 2,5-dimethylthiol by 2,3,5,6-tetrachloro-4-mercaptopyridine.

400 MHz-$^1$H-NMR 7.23 (1H, d, J=8.0 Hz), 6.84–6.87 (2H, m), 6.76–6.79 (1H, m), 3.81 (3H s), 3.69 (1H, q, J=6.6 Hz), 3.06–3.19 (2H, m), 2.50–2.66 (2H, m), 1.69 (2H, tt, J=7.0 Hz, J=7.0 Hz), 1.33 (3H, d, J=6.6 Hz), m/z=424, 426.

Example 329

Synthesis of S-182

S-182 was synthesized by almost the same method as the one employed for the synthesis of S-1 but replacing the 2,5-dimethylthiophenol and 1-bromo-2-chloroethane respectively by 2,3,5,6-tetrachloro-4-mercaptopyridine and 1,3-dibromopropane. m/z=438, 440.

Example 330

Synthesis of S-183

S-183 was synthesized by almost the same method as the one employed for the synthesis of S-1 but replacing the 2,5-dimethylthiophenol and 1-bromo-2-chloroethane respectively by 2,3,5,6-tetrachloro-4-mercaptopyridine and 1,4-dibromobutane. m/z=452, 454.

Example 331

Synthesis of S-184

S-184 was synthesized by almost the same method as the one employed for the synthesis of S-1 but replacing the 2,5-dimethylthiophenol and 1-bromo-2-chloroethane respectively by 2,3,5,6-tetrachloro-4-mercaptopyridine and 1,5-dibromopentane.

400 MHz-$^1$H-NMR 7.24 (1H, dd, J=8.0 Hz, J=8.0 Hz), 6.86–6.88 (2H, m), 6.76–6.79 (1H, m), 3.05 (2H, t, J=7.3 Hz), 3.81 (3H, s), 3.71 (1H, q, J=6.5 Hz), 2.38–2.52 (2H, m), 1.55 (2H, tt, J=7.1 Hz, J=7.1 Hz), 1.36–1.50 (4H, m), 1.34 (3H, d, J=6.5 Hz), m/z=466, 468.

Example 332

Synthesis of S-185

S-185 was synthesized by almost the same method as the one employed for the synthesis of S-1 but replacing the 2,5-dimethylthiophenol and 1-bromo-2-chloroethane respectively by 2,3,5,6-tetrachloro-4-mercaptopyridine and 1,6-dibromohexane.

400 MHz-$^1$H-NMR 7.23 (1H, dd, J=8.0 Hz, J=8.0 Hz), 6.86–6.89 (2H, m), 6.76–6.81 (1H, m), 3.81 (3H, s), 3.72 (1H, q, J=6.6 Hz), 3.05 (2H, t, J=7.3 Hz), 2.37–2.52 (2H, m), 1.55 (2H, tt, J=7.2 Hz, J=7.2 Hz), 1.23–1.49 (6H, m), 1.34 (3H, d, J=6.6 Hz), m/z=480, 482.

Example 333

Synthesis of S-186

S-186 was synthesized by almost the same method as the one employed for the synthesis of S-1 but replacing the 2,5-dimethylthiophenol and 1-bromo-2-chloroethane respectively by 2,3,5,6-tetrachloro-4-mercaptopyridine and 1,7-dibromoheptane.

400 MHz-$^1$H-NMR 7.24 (1H, dd, J=8.2 Hz, J=8.2 Hz), 6.87–6.90 (2H, m), 6.76–6.81 (1H, m), 3.81 (3H, s), 3.72 (1H, q, J=6.6 Hz), 3.05 (2H, t, J=7.3 Hz), 2.38–2.51 (2H, m), 1.55 (2H, tt, J=7.3 Hz, J=7.3 Hz), 1.20–1.49 (8H, m), 1.35 (3H, d, J=6.6 Hz), m/z=494, 496.

Example 334

Synthesis of S-187

S-187 was synthesized by almost the same method as the one employed for the synthesis of S-1 but replacing the 2,5-dimethylthiophenol and 1-bromo-2-chloroethane respectively by 2,3,5,6-tetrachloro-4-mercaptopyridine and 1,8-dibromooctane.

400 MHz-$^1$H-NMR 7.24 (1H, dd, J=8.0 Hz, J=8.0 Hz), 6.88–6.90 (2H, m), 6.76–6.79 (1H, m), 3.81 (3H, s), 3.73 (1H, q, J=6.6 Hz), 3.06 (2H, t, J=7.3 Hz), 2.39–2.53 (2H, m), 1.55 (2H, tt, J=7.3 Hz, J=7.3 Hz), 1.20–1.50 (10H, m), 1.35 (3H, d, J=6.6 Hz), m/z=508, 510.

Example 335

Synthesis of S-188

S-188 was synthesized by almost the same method as the one employed for the synthesis of S-1 but replacing the 2,5-dimethylthiophenol and (R)-(+)-3-methoxy-α-benzylmethylamine respectively by 2,3,5,6-tetrachloro-4-mercaptopyridine and (R)-(+)-1-(1-naphthyl)ethylamine. m/z=444, 446.

Example 336

Synthesis of S-189

S-189 was synthesized by almost the same method as the one employed for the synthesis of S-1 but replacing the 2,5-dimethylthiophenol, 1-bromo-2-chloroethane and (R)-(+)-3-methoxy-α-benzylmethyiamine respectively by 2,3,5,6-tetrachloro-4-mercaptopyridine, 1,3-dibromopropane and (R)-(+)-1-(1-naphthyl)ethylamine.

400 MHz-$^1$H-NMR 8.17 (1H, d, J=7.8 Hz), 7.85–7.88 (1H, m), 7.74 (1H, d, J=8.0 Hz), 7.60 (1H, d, J=6.8 Hz), 7.44–7.52 (3H, m), 4.60 (1H, q, J=6.5 Hz), 3.08–3.21 (2H, m), 2.61–2.75 (2H, m), 1.69–1.76 (2H, m), 1.49 (3H, d, J=6.5 Hz), m/z=458, 460.

Example 337

Synthesis of S-190

S-190 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrachloro-4-mercaptopyridine, 1,4-dibromobutane and (R)-(+)-1-(1-naphthyl)ethylamine.

400 MHz-$^1$H-NMR 8.40 (1H, d, J=8.0 Hz), 7.82–7.88 (1H, m), 7.69–7.75 (2H, m), 7.43–7.51 (3H, m), 4.04 (1H, q, J=6.6 Hz), 2.47–2.70 (4H, m), 1.78–1.82 (4H, m), 1.53 (3H, d, J=6.6 Hz), m/z=472, 474.

Example 338

Synthesis of S-191

S-191 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5, 6-tetrachloro-4-mercaptopyridine, 1,5-dibromopentane and (R)-(+)-1-(1-naphthyl)ethylamine.

400 MHz-$^1$H-NMR 8.17 (1H, d, J=8.3 Hz), 7.85–7.88 (1H, m), 7.75 (1H, d, J=8.0 Hz), 7.66 (1H, d, J=6.8 Hz), 7.45–7.53 (3H, m), 4.64 (1H, q, J=6.6 Hz), 3.03 (2H, t, J=7.2 Hz), 2.49–2.63 (2H, m), 1.35–1.60 (9H, m), m/z=486, 488.

Example 339

Synthesis of S-192

S-192 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrachloro-4-mercaptopyridine, 1,6-dibromohexane and (R)-(+)-1-(1-naphthyl)ethylamine.

400 MHz-$^1$H-NMR 8.16 (1H, d, J=8.0 Hz), 7.86–7.89 (1H, m), 7.76 (1H, d, J=8.3 Hz), 7.70 (1H, bs), 7.46–7.54 (3H, m), 4.69 (1H, bs), 3.02 (2H, t, J=7.2 Hz), 2.51–2.64 (2H, m), 1.25–1.60 (11H, m), m/z=500, 502.

Example 340

Synthesis of S-193

S-193 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrachloro-4-mercaptopyridine, 1,7-dibromoheptane and (R)-(+)-1-(1-naphthyl)ethylamine.

400 MHz-$^1$H-NMR 8.15 (1H, d, J=8.3 Hz), 7.86–7.89 (1H, m), 7.70–7.78 (1H, m), 7.46–7.55 (3H, m), 4.74 (1H, bs), 3.03 (2H, t, J=7.2 Hz), 2.50–2.66 (2H, m), 1.05–1.65 (13H, m), m/z=514, 516.

Example 341

Synthesis of S-194

S-194 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrachloro-4-mercaptopyridine, 1,8-dibromooctane and (R)-(+)-1-(1-naphthyl)ethylamine.

400 MHz-$^1$H-NMR 8.15 (1H, d, J=8.3 Hz), 7.86–7.89 (1H, m), 7.72–7.78 (2H, m), 7.46–7.54 (3H, m), 4.72 (1H, q, J=7.2 Hz), 3.04 (2H, t, J=7.2 Hz), 2.52–2.57 (2H, m), 1.00–1.56 (12H, m), 1.58(3H, d, J=6.2 Hz), m/z=528, 530.

Example 342

Synthesis of S-195

S-195 was synthesized by almost the same method as the one employed for the synthesis of S-1 but replacing the 2,5-dimethylthiophenol and (R)-(+)-3-methoxy-α-benzylmethylamine respectively by 2,3,5,6-tetrafluoro-4-trifluoromethylthiophenol and (R)-(+)-1-(1-naphthyl)ethylamine. m/z=447.

Example 343

Synthesis of S-196

S-196 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluoro-4-trifluoromethylthiophenol, 1,3-dibromopropane and (R)-(+)-1-(1-naphthyl)ethylamine.

400 MHz-$^1$H-NMR 8.16 (1H, d, J=8.0 Hz), 7.84–7.86 (1H, m), 7.73 (1H, d, J=8.0 Hz), 7.60 (1H, d, J=6.8 Hz), 7.43–7.51 (3H, m), 4.59 (1H, q, J=6.2 Hz), 3.02–3.15 (2H, m), 2.60–2.74 (2H, m), 1.67–1.77 (2H, m), 1.48 (3H, d, J=6.2 Hz), m/z=461.

Example 344

Synthesis of S-197

S-197 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluoro-4-trifluoromethylthiophenol, 1,6-dibromohexane and (R)-(+)-1-(1-naphthyl)ethylamine.

400 MHz-$^1$H-NMR 8.17 (1H, d, J=8.2 Hz), 7.85–7.88 (1H, m), 7.75 (1H, d, J=8.3 Hz), 7.66 (1H, d, J=6.8 Hz), 7.45–7.53 (3H, m), 4.64 (1H, q, J=6.4 Hz), 2.99 (2H, t, J=7.3 Hz), 2.50–2.63 (2H, m), 1.48–1.60 (4H, m), 1.52 (3H, d, J=6.4 Hz), 1.26–1.42 (4H, m), m/z=503.

Example 345

Synthesis of S-198

S-198 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluoro-4-trifluoromethylthiophenol, 1,7-dibromoheptane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.3 Hz), 7.66 (1H, d, J=6.8 Hz), 7.45–7.52 (3H, m), 4.65 (1H, q, J=6.4 Hz), 3.00 (2H, t, J=7.4 Hz), 2.50–2.63 (2H, m), 1.47–1.60 (4H, m), 1.52 (3H, d, J=6.4 Hz), 1.23–1.41 (6H, m), m/z=517.

Example 346

Synthesis of S-199

S-199 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluoro-4-trifluoromethylthiophenol, 1,8-dibromooctane and (R)-(+)-1-(1-naphthyl)ethylamine.

400 MHz-$^1$H-NMR 8.16 (1H, d, J=8.3 Hz), 7.86–7.88 (1H, m), 7.75 (1H, d, J=8.3 Hz), 7.69 (1H, d, J=6.1 Hz), 7.45–7.53 (3H, m), 4.67 (1H, q, J=6.4 Hz), 3.01 (2H, t, J=7.3 Hz), 2.51–2.64 (2H, m), 1.20–1.70 (15H, m), m/z=531.

Example 347

Synthesis of S-200

S-200 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,3,5,6-tetrafluoro-4-trifluoromethylthiophenol, 1,10-dibromodecane and (R)-(+)-1-(1-naphthyl)ethylamine.

400 MHz-$^1$H-NMR 8.17 (1H, d, J=8.3 Hz), 7.51–7.88 (1H, m), 7.74 (1H, d, J=8.3 Hz), 7.64 (1H, d, J=7.1 Hz), 7.44–7.52 (3H, m), 4.62 (1H, q, J=6.6 Hz), 3.02 (2H, t, J=7.4 Hz), 2.50–2.62 (2H, m), 1.54–1.62 (2H, m), 1.49 (3H, d, J=6.6 Hz), 1.00–1.54 (14H, m), m/z=559.

Example 348

Synthesis of S-201

S-201 was synthesized by almost the same method as the one employed for the synthesis of S-1 but replacing the 2,5-dimethylthiophenol, 1-bromo-2-chloroethane and (R)-

(+)-3-methoxy-α-benzylmethylamine respectively by 2,3,5,6-tetrafluoro-4-trifluoromethylthiophenol, 1,12-dibromododecane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.0 Hz), 7.66 (1H, d, J=7.1 Hz), 7.45–7.53 (3H, m), 4.64 (1H, q, J=6.6 Hz), 3.03 (2H, t, J=7.4 Hz), 2.50–2.63 (2H, m), 1.20–1.63 (18H, m), 1.51 (3H, d, J=6.6 Hz), m/z=587.

Example 349

Synthesis of S-202

S-202 was synthesized by almost the same method as the one employed for the synthesis of S-1 but replacing the 2,5-dimethylthiophenol and (R)-(+)-3-methoxy-α-benzylmethylamine respectively by 2-isopropylthiophenol and (R)-(+)-1-(1-naphthyl)ethylamine.

400 MHz-$^1$H-NMR 8.16 (1H, d, J=7.8 Hz), 7.84–7.87 (1H, m), 7.72 (1H, d, J=8.0 Hz), 7.63 (1H, d, J=7.1 Hz), 7.41–7.54 (3H, m), 7.23–7.27 (2H, m), 7.13–7.16 (1H, m), 7.03–7.07 (1H, m), 4.63 (1H, q, J=6.5 Hz), 3.45–3.54 (1H, m), 3.04 (2H, t, J=6.2 Hz), 2.81 (2H, t, J=6.8 Hz), 1.48 (2H, d, J=6.5 Hz), 1.19–1.22 (6H, m), m/z=349.

Example 350

Synthesis of S-203

S-203 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-isopropylthiophenol, 1,3-dibromopropane and (R)-(+)-1-(1-naphthyl)ethylamine.

400 MHz-$^1$H-NMR 8.17 (1H, d, J=7.8 Hz), 7.86 (1H, d, J=7.8 Hz), 7.73 (1H, J=8.0 Hz), 7.63 (1H, d, J=7.3 Hz), 7.43–7.51 (3H, m), 7.22–7.29 (2H, m), 7.08–7.17 (2H, m), 4.60 (1H, q, J=6.4 Hz), 3.42–3.50 (1H, m), 2.87–3.00 (2H, m), 2.62–2.76 (2H, m), 1.79–1.86 (2H, m), 1.48 (3H, d, J=6.4 Hz), 1.18–1.22 (6H, m), m/z=363.

Example 351

Synthesis of S-204

S-204 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-isopropylthiophenol, 1,4-dibromobutane and (R)-(+)-1-(1-naphthyl)ethylamine.

400 MHz-$^1$H-NMR 8.17 (1H, d, J=8.0 Hz), 7.85–7.87 (1H, m), 7.73 (1H, d, J=8.3 Hz), 7.63 (1H, d, J=6.8 Hz), 7.44–7.51 (3H, m), 7.22–7.27 (2H, m), 7.07–7.18 (2H, m), 4.61 (1H, q, J=6.5 Hz), 3.44–3.53 (1H, m), 2.85 (2H, t, J=6.8 Hz), 2.51–2.65 (2H, m), 1.63–1.70 (4H, m), 1.48 (3H, d, J=6.5 Hz), 1.21 (6H, d, J=6.8 Hz), m/z=377.

Example 352

Synthesis of S-205

S-205 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-isopropylthiophenol, 1,5-dibromopentane and (R)-(+)-1-(1-naphthyl)ethylamine.

400 MHz-$^1$H-NMR 8.17 (1H, d, J=8.0 Hz), 7.85–7.88 (1H, m), 7.73 (1H, d, J=8.3 Hz), 7.63 (1H, d, J=7.1 Hz), 7.44–7.52 (3H, m), 7.22–7.28 (2H, m), 7.08–7.18 (2H, m), 4.61 (1H, q, J=6.5 Hz), 3.42–3.53 (1H, m), 2.85 (2H, t, J=7.3 Hz), 2.49–2.62 (2H, m), 1.59–1.67 (2H, m), 1.40–1.56 (4H, m), 1.48 (3H, d, J=6.5 Hz), 1.21 (6H, d, J=6.8 Hz), m/z=391.

Example 353

Synthesis of S-206

S-206 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-isopropylthiophenol, 1,6-dibromohexane and (R)-(+)-1-(1-naphthyl)ethylamine.

400 MHz-$^1$H-NMR 8.17 (1H, d, J=8.0 Hz), 7.85–7.88 (1H, m), 7.73 (1H, d, J=8.3 Hz), 7.64 (1H, d, J=6.8 Hz), 7.41–7.52 (3H, m), 7.21–7.29 (2H, m), 7.09–7.17 (2H, m), 4.62 (1H, q, J=6.5 Hz), 3.43–3.53 (1H, m), 2.84 (2H, t, J=7.3 Hz), 2.49–2.62 (2H, m), 1.58–1.66 (2H, m), 1.45–1.55 (2H, m), 1.25–1.45 (4H, m), 1.49 (3H, m), 1.21–1.23 (6H, m), m/z=405.

Example 354

Synthesis of S-207

S-207 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-isopropylthiophenol, 1,7-dibromoheptane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.0 Hz), 7.65 (1H, d, J=7.1 Hz), 7.44–7.52 (3H, m), 7.22–7.29 (2H, m), 7.09–7.17 (2H, m), 4.63 (1H, q, J=6.6 Hz), 3.43–3.54 (1H, m), 2.85 (2H, t, J=7.4 Hz), 2.49–2.62 (2H, m), 1.57–1.65 (2H, m), 1.36–1.55 (4H, m), 1.49 (3H, d, J=6.6 Hz), 1.25–1.30 (4H, m), 1.20–1.25 (6H, m), m/z=419.

Example 355

Synthesis of S-208

S-208 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-isopropylthiophenol, 1,8-dibromooctane and (R)-(+)-1-(1-naphthyl)ethylamine.

400 MHz-$^1$H-NMR 8.18 (1H, d, J=8.5 Hz), 7.85–7.88 (1H, m), 7.74 (1H, d, J=8.0 Hz), 7.65 (1H, d, J=7.1 Hz), 7.44–7.53 (3H, m), 7.23–7.29 (2H, m), 7.09–7.17 (2H, m), 4.63 (1H, q, J=6.6 Hz), 3.43–3.54 (1H, m), 2.85 (2H, t, J=7.4 Hz), 2.50–2.62 (2H, m), 1.58–1.67 (2H, m), 1.24–1.52 (10H, m), 1.50 (3H, d, J=6.6 Hz), 1.22 (6H, d, J=6.8 Hz), m/z=433.

Example 356

Synthesis of S-209

S-209 was synthesized by almost the same method as the one employed for the synthesis of S-1 but replacing the 2,5-dimethylthiol by 2,4,5-trichlorothiophenol.

400 MHz-$^1$H-NMR 7.44 (1H, s), 7.29 (1H, s), 7.23 (1H, dd, J=8.3 Hz, J=8.3 Hz), 6.87–6.89 (2H, m), 6.76–6.79 (1H, m), 3.80 (3H, s), 3.76 (1H, q, J=6.6 Hz), 3.03 (2H, t, J=6.5 Hz), 2.70–2.85 (2H, m), 1.36 (3H, d, J=6.6 Hz), m/z=389, 391.

Example 357

Synthesis of S-210

S-210 was synthesized by almost the same method as the one employed for the synthesis of S-1 but replacing the 2,5-dimethylthiophenol and 1-bromo-2-chloroethane respectively by 2,4,5-trichlorothiophenol and 1,3-dibromopropane.

400 MHz-$^1$H-NMR 7.44 (1H, s), 7.30 (1H, s), 7.22–7.25 (1H, m), 6.87–6.90 (2H, m), 6.77–6.80 (1H, m), 3.81 (3H, s), 3.74 (1H, q, J=6.5 Hz), 2.89–3.03 (2H, m), 2.54–2.70 (2H, m), 1.77–1.85 (2H, m), 1.36 (3H, d, J=6.5 Hz), m/z=403, 405.

Example 358

Synthesis of S-211

S-211 was synthesized by almost the same method as the one employed for the synthesis of S-1 but replacing the 2,5-dimethylthiophenol and 1-bromo-2-chloroethane respectively by 2,4,5-trichlorothiophenol and 1,4-dibromobutane.

400 MHz-$^1$H-NMR 7.44 (1H, s), 7.21–7.27 (2H, m), 6.86–6.90 (2H, m), 6.76–6.79 (1H, m), 3.81 (3H, s), 3.72 (1H, q, J=6.6 Hz), 2.86–2.91 (2H, m), 2.43–2.58 (2H, m), 1.58–1.76 (4H, m), 1.34 (3H, d, J=6.6 Hz), m/z=419, 421.

Example 359

Synthesis of S-212

S-212 was synthesized by almost the same method as the one employed for the synthesis of S-1 but replacing the 2,5-dimethylthiophenol and 1-bromo-2-chloroethane respectively by 2,4,5-trichlorothiophenol and 1,5-dibromopentane.

400 MHz-$^1$H-NMR 7.44 (1H, s), 7.21–7.26 (2H, m), 6.87–6.90 (2H, m), 6.76–6.79 (1H, m), 3.81 (3H, s), 3.72 (1H, q, J=6.6 Hz), 2.89 (2H, t, J=7.3 Hz), 2.41–2.55 (2H, m), 1.64–1.71 (2H, m), 1.43–1.56 (4H, m), 1.35 (3H, d, J=6.6 Hz), m/z=431, 433.

Example 360

Synthesis of S-213

S-213 was synthesized by almost the same method as the one employed for the synthesis of S-1 but replacing the 2,5-dimethylthiophenol and 1-bromo-2-chloroethane respectively by 2,4,5-trichlorothiophenol and 1,6-dibromohexane.

400 MHz-$^1$H-NMR 7.44 (1H, s), 7.21–7.26 (2H, m), 6.87–6.90 (2H, m), 6.76–6.79 (1H, m), 3.81 (3H, s), 3.72 (1H, q, J=6.6 Hz), 2.88 (2H, t, J=7.3 Hz), 2.39–2.53 (2H, m), 1.63–1.71 (2H, m), 1.28–1.52 (6H, m), 1.34 (3H, d, J=6.6 Hz), m/z=445, 447.

Example 361

Synthesis of S-214

S-214 was synthesized by almost the same method as the one employed for the synthesis of S-1 but replacing the 2,5-dimethylthiophenol and 1-bromo-2-chloroethane respectively by 2,4,5-trichlorothiophenol and 1,7-dibromoheptane.

400 MHz-$^1$H-NMR 7.44 (1H, s), 7.21–7.26 (2H, m), 6.87–6.91 (2H, m), 6.76–6.80 (2H, m), 3.81 (3H, s), 3.73 (1H, q, J=6.6 Hz), 2.89 (2H, t, J=7.3 Hz), 2.39–2.53 (2H, m), 1.64–1.71 (2H, m), 1.39–1.48 (4H, m), 1.25–1.37 (6H, m), 1.35 (3H, d, J=6.6 Hz), m/z=459, 461.

Example 362

Synthesis of S-215

S-215 was synthesized by almost the same method as the one employed for the synthesis of S-1 but replacing the 2,5-dimethyithiophenol and 1-bromo-2-chloroethane respectively by 2,4,5-trichlorothiophenol and 1,8-dibromooctane.

400 MHz-$^1$H-NMR 7.44 (1H, s), 7.25 (1H, s), 7.24 (1H, dd, J=8.0 Hz, J=8.0 Hz), 6.87–6.90 (2H, m), 6.76–6.79 (1H, m), 3.81 (3H, s), 3.73 (1H, q, J=6.6 Hz), 2.89 (1H, t, J=7.3 Hz), 2.38–2.52 (2H, m), 1.64–1.71 (2H, m), 1.40–1.50 (4H, m), 1.35 (3H, d, J=6.6 Hz), 1.25–1.35 (6H, m), m/z=473, 735.

Example 363

Synthesis of S-216

S-216 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4,5-trichlorothiophenol, 1,3-dibromopropane and (R)-(+)-1-(1-naphthyl)ethylamine.

400 MHz-$^1$H-NMR 8.20 (1H, d, J=8.0 Hz), 7.85–7.88 (1H, m), 7.75 (1H, d, J=8.0 Hz), 7.64 (1H, d, J=7.1 Hz), 7.45–7.52 (3H, m), 7.43 (1H, s), 7.29 (1H, s), 4.63 (1H, q, J=6.5 Hz), 2.90–3.05 (2H, m), 2.64–2.80 (2H, m), 1.81–1.89 (2H, m), 1.52 (3H, d, J=6.5 Hz), m/z=423, 425.

Example 364

Synthesis of S-217

S-217 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4,5-trichlorothiophenol, 1,6-dibromohexane and (R)-(+)-1-(1-naphthyl)ethylamine.

400 MHz-$^1$H-NMR 8.17 (1H, d, J=8.3 Hz), 7.86–7.88 (1H, m), 7.75 (1H, d, J=8.3 Hz), 7.66 (1H, d, J=6.8 Hz), 7.45–7.53 (3H, m), 7.44 (1H, s), 7.23 (1H, s), 4.65 (1H, q, J=6.6 Hz), 2.86 (2H, t, J=7.3 Hz), 2.51–2.66 (2H, m), 1.30–1.73 (8H, m), 1.52 (3H, d, J=6.6 Hz), m/z=465, 467.

Example 365

Synthesis of S-218

S-218 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4,5-trichlorothiophenol, 1,7-dibromoheptane and (R)-(+)-1-(1-naphthyl)ethylamine.

400 MHz-$^1$H-NMR 8.17 (1H, d, J=8.3 Hz), 7.86–7.88 (1H, m), 7.75 (1H, d, J=8.3 Hz), 7.68 (1H, d, J=6.6 Hz), 7.45–7.53 (3H, m), 7.43 (1H, s), 7.24 (1H, s), 4.66 (1H, q,

J=6.4 Hz), 2.87 (2H, t, J=7.3 Hz), 2.51–2.64 (2H, m), 1.25–1.70 (10H, m), 1.53 (3H, d, J=6.4 Hz), m/z=423, 425.

Example 366

Synthesis of S-219

S-219 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4,5-trichlorothiophenol, 1,8-dibromooctane and (R)-(+)-1-(1-naphthyl)ethylamine.

400 MHz-$^1$H-NMR 8.17 (1H, d, J=8.3 Hz), 7.86–7.89 (1H, m), 7.75 (1H, d, J=8.3 Hz), 7.68 (1H, bs), 7.45–7.53 (3H, m), 7.44 (1H, s), 7.24 (1H, s), 4.67 (1H, bs), 2.88 (2H, t, J=7.3 Hz), 2.51–2.64 (2H, m), 1.23–1.71 (15H, m), m/z=493, 495.

Example 367

Synthesis of S-220

S-220 was synthesized by almost the same method as the one employed for the synthesis of S-1 but replacing the 2,5-dimethylthiophenol and 1-bromo-2-chloroethane respectively by 6-ethoxy-2-mercaptobenzothiazole and 1,3-dibromopropane. m/z=402.

Example 368

Synthesis of S-221

S-221 was synthesized by almost the same method as the one employed for the synthesis of S-1 but replacing the 2,5-dimethylthiophenol and 1-bromo-2-chloroethane respectively by 6-ethoxy-2-mercaptobenzothiazole and 1,4-dibromobutane.

400 MHz-$^1$H-NMR 7.71 (1H, d, J=8.8 Hz), 7.20–7.24 (2H, m), 6.98 (1H, dd, J=9.0 Hz, J=2.4 Hz), 6.87–6.89 (2H, m), 6.77 (1H, ddd, J=8.0 Hz, J=2.4 Hz, J=1.0 Hz), 4.06 (2H, q, J=6.9 Hz), 3.80 (3H, s), 3.28 (2H, t, J=7.5 Hz), 2.45–2.61 (2H, m), 1.75–1.88 (2H, m), 1.58–1.70 (2H, m), 1.44 (3H, t, J=7.5 Hz), 1.35 (3H, d, J=6.9 Hz), m/z=416.

Example 369

Synthesis of S-222

S-222 was synthesized by almost the same method as the one employed for the synthesis of S-1 but replacing the 2,5-dimethylthiophenol and 1-bromo-2-chloroethane respectively by 6-ethoxy-2-mercaptobenzothiazole and 1,5-dibromopentane.

400 MHz-$^1$H-NMR 7.23 (1H, d, J=8.8 Hz), 7.20–7.25 (2H, m), 6.99 (1H, dd, J=8.8 Hz, J=2.4 Hz), 6.87–6.90 (2H, m), 6.76–6.77 (1H, m), 4.03–4.11 (2H, m), 3.81 (3H, s), 3.72 (1H, q, J=6.6 Hz), 3.27 (2H, t, J=7.6 Hz), 2.41–2.54 (2H, m), 1.74–1.82 (2H, m), 1.41–1.56 (4H, m), 1.44 (3H, t, J=6.8 Hz), 1.34 (3H, d, J=6.6 Hz), m/z=430.

Example 370

Synthesis of S-223

S-223 was synthesized by almost the same method as the one employed for the synthesis of S-1 but replacing the 2,5-dimethylthiophenol and 1-bromo-2-chloroethane respectively by 6-ethoxy-2-mercaptobenzothiazole and 1,6-dibromohexane.

400 MHz-$^1$H-NMR 7.73 (1H, d, J=9.0 Hz), 7.20–7.25 (2H, m), 6.99 (1H, dd, J=8.8 Hz, J=2.4 Hz), 6.88–6.90 (2H, m), 6.77 (1H, ddd, J=8.3 Hz, J=2.4 Hz, J=1.0 Hz), 4.06 (2H, q, J=7.0 Hz), 3.81 (3H, s), 3.73 (1H, q, J=6.0 Hz), 3.27 (2H, t, J=7.3 Hz), 2.40–2.53 (2H, m), 1.74–1.81 (2H, m), 1.25–1.53 (6H, m), 1.44 (3H, t, J=7.0 Hz), 1.35 (3H, d, J=6.0 Hz), m/z=444.

Example 371

Synthesis of S-224

S-224 was synthesized by almost the same method as the one employed for the synthesis of S-1 but replacing the 2,5-dimethylthiophenol and 1-bromo-2-chloroethane respectively by 6-ethoxy-2-mercaptobenzothiazole and 1,7-dibromoheptane.

400 MHz-$^1$H-NMR 7.72 (1H, d, J=9.0 Hz), 7.25 (1H, dd, J=6.9 Hz, J=6.9 Hz), 7.21 (1H, d, J=2.4 Hz), 6.98 (1H, dd, J=9.0 Hz, J=2.4 Hz), 6.78–6.82 (1H, m), 4.06 (3H, q, J=7.0 Hz), 3.82 (3H, s), 3.79–3.85 (1H, m), 3.27 (2H, t, J=7.3 Hz), 2.43–2.56 (2H, m), 1.73–1.80 (2H, m), 1.18–1.57 (11H, m), 1.44 (3H, t, J=7.0 Hz), m/z=458.

Example 372

Synthesis of S-225

S-225 was synthesized by almost the same method as the one employed for the synthesis of S-1 but replacing the 2,5-dimethylthiophenol and 1-bromo-2-chloroethane respectively by 6-ethoxy-2-mercaptobenzothiazole and 1,8-dibromooctane.

400 MHz-$^1$H-NMR 7.23 (1H, d, J=8.8 Hz), 7.21–7.24 (2H, m), 6.99 (1H, dd, J=8.8 Hz, J=2.7 Hz), 6.87–6.91 (2H, m), 6.76–6.80 (1H, m), 4.06 (2H, q, J=7.0 Hz), 3.81 (3H, s), 3.75 (1H, q, J=6.6 Hz), 3.28 (2H, t, J=7.3 Hz), 1.99–2.53 (2H, m), 1.74–1.81 (2H, m), 1.24–1.48 (10H, m), 1.44 (3H, t, J=7.0 Hz), 1.37 (3H, d, J=6.6 Hz), m/z=472.

Example 373

Synthesis of S-226

S-226 was synthesized by almost the same method as the one employed for the synthesis of S-1 but replacing the 2,5-dimethylthiophenol and (R)-(+)-3-methoxy-α-benzylmethylamine respectively by 6-ethoxy-2-mercaptobenzothiazole and (R)-(+)-1-(1-naphthyl)ethylamine. m/z=408.

Example 374

Synthesis of S-227

S-227 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 6-ethoxy-2-mercaptobenzothiazole, 1,3-dibromopropane and (R)-(+)-1-(1-naphthyl)ethylamine. m/z=422.

Example 375

Synthesis of S-228

S-228 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 6-ethoxy-2-mercaptobenzothiazole, 1,4-dibromobutane and (R)-(+)-1-(1-naphthyl)ethylamine.

400 MHz-$^1$H-NMR 8.18 (1H, d, J=8.3 Hz), 7.84–7.88 (1H, m), 7.73 (1H, d, J=8.3 Hz), 7.70 (1H, d, J=9.0 Hz), 7.65 (1H, d, J=7.1 Hz), 7.44–7.52 (3H, m), 7.20 (1H, d, J=2.4 Hz), 6.97 (1H, dd, J=9.0 Hz, J=2.4 Hz), 4.63 (1H, q, J=6.6 Hz), 4.05 (2H, q, J=7.0 Hz), 3.28 (2H, dt, J=9.2 Hz, J=1.2 Hz), 2.55–2.69 (2H, m), 1.81–1.90 (2H, m), 1.63–1.72 (2H, m), 1.50 (3H, d, J=6.6 Hz), 1.43 (3H, t, J=7.0 Hz), m/z=436.

Example 376

Synthesis of S-229

S-229 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 6-ethoxy-2-mercaptobenzothiazole, 1,5-dibromopentane and (R)-(+)-1-(1-naphthyl)ethylamine.

400 MHz-$^1$H-NMR 8.17 (1H, d, J=8.3 Hz), 7.83–7.88 (1H, m), 7.73 (1H, d, J=8.0 Hz), 7.72 (1H, d, J=8.8 Hz), 7.64 (1H, d, J=7.3 Hz), 7.44–7.52 (3H, m), 7.20 (1H, d, J=2.4 Hz), 6.98 (1H, dd, J=9.0 Hz, J=2.7 Hz), 4.62 (1H, q, J=6.5 Hz), 4.06 (2H, q, J=7.0 Hz), 3.27 (2H, t, J=7.3 Hz), 2.52–2.65 (2H, m), 1.70–1.82 (2H, m), 1.49 (3H, d, J=6.5 Hz), 1.44 (3H, t, J=7.0 Hz), 1.41–1.60 (4H, m), m/z=450.

Example 377

Synthesis of S-230

S-230 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 6-ethoxy-2-mercaptobenzothiazole, 1,6-dibromohexane and (R)-(+)-1-(1-naphthyl)ethylamine.

400 MHz-$^1$H-NMR 8.17 (1H, d, J=8.5 Hz), 7.82–7.88 (1H, m), 7.71–7.75 (2H, m), 7.66 (1H, d, J=7.0 Hz), 7.41–7.53 (3H, m), 7.20 (1H, d, J=2.7 Hz), 6.98 (1H, dd, J=8.8 Hz, J=2.7 Hz), 4.64 (1H, q, J=6.4 Hz), 4.05 (2H, q, J=7.0 Hz), 3.26 (2H, t, J=7.3 Hz), 2.50–2.64 (2H, m), 1.73–1.81 (2H, m), 1.30–1.55 (6H, m), 1.51 (3H, d, J=6.4 Hz), 1.43 (3H, t, J=7.0 Hz), m/z=464.

Example 378

Synthesis of S-231

S-231 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 6-ethoxy-2-mercaptobenzothiazole, 1,7-dibromoheptane and (R)-(+)-1-(1-naphthyl)ethylamine.

400 MHz-$^1$H-NMR 8.15 (1H, d, J=8.3 Hz), 7.86–7.88 (1H, m), 7.72–7.73 (2H, m), 7.72 (1H, d, J=9.1 Hz), 7.45–7.55 (3H, m), 6.98 (1H, dd, J=8.8 Hz, J=2.4 Hz), 4.72 (1H, q, J=6.4 Hz), 4.05 (2H, q, J=7.0 Hz), 3.25 (2H, t, J=7.3 Hz), 2.52–2.66 (2H, m), 1.64–1.82 (2H, m), 1.59 (3H, d, J=6.4 Hz), 1.43 (3H, t, J=7.0 Hz), 1.03–1.68 (8H, m), m/z=478.

Example 379

Synthesis of S-232

S-232 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 6-ethoxy-2-mercaptobenzothiazole, 1,8-dibromooctane and (R)-(+)-1-(1-naphthyl)ethylamine.

400 MHz-$^1$H-NMR 8.16 (1H, d, J=8.5 Hz), 7.86–7.88 (1H, m), 7.68–7.76 (3H, m), 7.45–7.53 (3H, m), 7.21 (1H, d, J=2.4 Hz), 6.98 (1H, dd, J=8.8 Hz, J=2.4 Hz), 4.67 (1H, q, J=6.4 Hz), 4.06 (2H, q, J=7.0 Hz), 3.27 (2H, t, J=7.4 Hz), 2.51–2.64 (2H, m), 1.69–1.80 (2H, m), 1.54 (3H, d, J=6.4 Hz), 1.43 (3H, t, J=7.0 Hz), 1.20–1.60 (10H, m), m/z=492.

Example 380

Synthesis of S-233

S-233 was synthesized by almost the same method as the one employed for the synthesis of S-1 but replacing the 2,5-dimethylthiophenol and (R)-(+)-3-methoxy-α-benzylmethylamine respectively by 2,4-dichlorothiophenol and (R)-(+)-1-(1-naphthyl)ethylamine. m/z=375.

Example 381

Synthesis of S-234

S-234 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4-dichlorothiophenol, 1,3-dibromopropane and (R)-(+)-1-(1-naphthyl)ethylamine.

400 MHz-$^1$H-NMR 8.18 (1H, d, J=7.6 Hz), 7.84–7.89 (1H, m), 7.74 (1H, d, J=8.3 Hz), 7.63 (1H, d, J=7.1 Hz), 7.45–7.56 (3H, m), 7.34–7.56 (1H, m), 7.33–7.34 (2H, m), 4.62 (1H, q, J=6.6 Hz), 2.88–3.04 (2H, m), 2.63–2.78 (2H, m), 1.79–1.87 (2H, m), 1.50 (3H, d, J=6.6 Hz), m/z=389.

Example 382

Synthesis of S-235

S-235 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4-dichlorothiophenol, 1,4-dibromobutane and (R)-(+)-1-(1-naphthyl)ethylamine.

400 MHz-$^1$H-NMR 8.18 (1H, d, J=8.0 Hz), 7.86–7.88 (1H, m), 7.75 (1H, bs), 7.67 (1H, bs), 7.45–7.53 (3H, m), 7.35–7.36 (1H, m), 7.13–7.14 (2H, m), 4.61–4.69 (1H, m), 2.84–2.89 (2H, m), 2.52–2.68 (2H, m), 1.48–1.73 (7H, m), m/z=403.

Example 383

Synthesis of S-236

S-236 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,4-dichlorothiophenol, 1,5-dibromopentane and (R)-(+)-1-(1-naphthyl)ethylamine.

400 MHz-$^1$H-NMR 8.18 (1H, d, J=8.0 Hz), 7.86–7.88 (1H, m), 7.75 (1H, d, J=8.3 Hz), 7.65 (1H, d, J=7.1 Hz), 7.45–7.53 (3H, m), 7.35–7.37 (1H, m), 7.14–7.16 (2H, m), 4.64 (1H, q, J=6.4 Hz), 2.87 (2H, t, J=7.3 Hz), 2.51–2.64 (2H, m), 1.60–1.68 (2H, m), 1.42–1.58 (4H, m), 1.51 (3H, d, J=6.4 Hz), m/z=417.

Example 384

Synthesis of S-237

S-237 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,5-dichlorothiophenol, 1,3-dibromopropane and (R)-(+)-1-(1-naphthyl)ethylamine.

400 MHz-$^1$H-NMR 8.20 (1H, d, J=8.0 Hz), 7.84–7.87 (1H, m), 7.74 (1H, d, J=8.0 Hz), 7.66 (1H, d, J=7.1 Hz), 7.44–7.52 (3H, m), 7.19–7.25 (2H, m), 7.03 (1H, dd, J=3.5 Hz, J=2.4 Hz), 4.62 (1H, q, J=6.6 Hz), 2.90–3.06 (2H, m), 2.62–2.80 (2H, m), 1.86 (2H, tt, J=7.0 Hz, J=7.0 Hz), 1.50 (3H, d, J=6.6 Hz), m/z=3.89.

Example 385

Synthesis of S-238

S-238 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,5-dichlorothiophenol, 1,6-dibromohexane and (R)-(+)-1-(1-naphthyl)ethylamine.

400 MHz-$^1$H-NMR 8.18 (1H, d, J=8.3 Hz), 7.85–7.88 (1H, m), 7.73 (1H, d, J=8.0 Hz), 7.64 (1H, d, J=6.8 Hz), 7.44–7.53 (3H, m), 7.23–7.26 (1H, m), 7.14 (1H, d, J=2.4 Hz), 7.03 (1H, dd, J=8.6 Hz, J=2.4 Hz), 4.63 (1H, q, J=6.5 Hz), 2.87 (2H, t, J=7.3 Hz), 2.51–2.64 (2H, m), 1.68 (1H, tt, J=7.3 Hz, J=7.3 Hz), 1.30–1.56 (6H, m), 1.50 (3H, d, J=6.5 Hz), m/z=431.

Example 386

Synthesis of S-239

S-239 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,5-dichlorothiophenol, 1,7-dibromoheptane and (R)-(+)-1-(1-naphthyl)ethylamine.

400 MHz-$^1$H-NMR 8.16 (1H, d, J=8.3 Hz), 7.86–7.88 (1H, m), 7.75 (1H, d, J=8.0 Hz), 7.70 (1H, d, J=7.1 Hz), 7.45–7.53 (3H, m), 7.23 (1H, s), 7.14 (1H, d, J=2.4 Hz), 7.03 (1H, d, J=2.4 Hz, J=6.3 Hz), 4.68 (1H, q, J=6.4 Hz), 2.87 (2H, t, J=7.3 Hz), 2.50–2.65 (2H, m), 1.66 (2H, tt, J=7.3 Hz, 7.3 Hz), 1.55 (3H, d, J=6.4 Hz), 1.05–1.60 (8H, m), m/z=445.

Example 387

Synthesis of S-240

S-240 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2,5-dichlorothiophenol, 1,8-dibromooctane and (R)-(+)-1-(1-naphthyl)ethylamine.

400 MHz-$^1$H-NMR 8.16 (1H, d, J=8.3 Hz), 8.85–8.88 (2H, m), 7.75 (1H, d, J=8.3 Hz), 7.70 (1H, d, J=7.1 Hz), 7.45–7.54 (3H, m), 7.24 (1H, s), 7.14 (1H, d, J=2.4 Hz), 7.02 (1H, dd, j=8.5 Hz, J=2.4 Hz), 4.69 (1H, q, J=6.5 Hz), 2.86 (2H, t, J=6.8 Hz), 2.51–2.65 (2H, m), 1.66 (2H, tt, J=6.8 Hz, J=6.8 Hz), 1.55 (3H, d, J=6.5 Hz), 1.03–1.55 (10H, m), m/z=459.

Example 388

Synthesis of S-241

S-241 was synthesized by almost the same method as the one employed for the synthesis of S-1 but replacing the 2,5-dimethylthiophenol and (R)-(+)-3-methoxy-α-benzylmethylamine respectively by 4-trifluoromethoxythiophenol and (R)-(+)-1-(1-naphthyl)ethylamine. m/z=391.

Example 389

Synthesis of S-242

S-242 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-trifluoromethoxythiophenol, 1,3-dibromopropane and (R)-(+)-1-(1-naphthyl)ethylamine.

400 MHz-$^1$H-NMR 8.16–8.20 (1H, m), 7.82–7.89 (1H, m), 7.74 (1H, d, J=8.0 Hz), 7.62 (1H, d, J=6.6 Hz), 7.44–7.52 (3H, m), 7.27–2.30 (2H, m), 7.08–7.11 (2H, m), 4.61 (1H, q, J=6.6 Hz), 2.88–3.05 (2H, m), 2.61–2.76 (2H, m), 1.77–1.85 (2H, m), 1.49 (3H, d, J=6.6 Hz), m/z=405.

Example 390

Synthesis of S-243

S-243 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-trifluoromethoxythiophenol, 1,7-dibromoheptane and (R)-(+)-1-(1-naphthyl)ethylamine.

400 MHz-$^1$H-NMR 8.10 (1H, d, J=8.3 Hz), 7.78–7.81 (1H, m), 7.66 (1H, d, J=8.3 Hz), 7.57 (1H, d, J=6.8 Hz), 7.37–7.45 (3H, m), 7.21–7.24 (2H, m), 7.03–7.05 (2H, m), 4.55 (1H, q, J=6.6 Hz), 2.80 (2H, t, J=7.3 Hz), 2.41–2.55 (2H, m), 1.49–1.57 (2H, m), 1.18–1.45 (8H, m), 1.42 (3H, d, J=6.6 Hz), m/z=461.

Example 391

Synthesis of S-244

S-244 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-trifluoromethoxythiophenol, 1,8-dibromooctane and (R)-(+)-1-(1-naphthyl)ethylamine.

400 MHz-$^1$H-NMR 8.17 (1H, d, J=8.3 Hz), 7.85–7.88 (1H, m), 7.74 (1H, d, J=8.0 Hz), 7.65 (1H, d, J=7.1 Hz), 7.44–7.53 (3H, m), 7.28–7.33 (2H, m), 7.10–7.13 (2H, m), 4.64 (1H, q, J=6.6 Hz), 2.87 (2H, t, J=7.4 Hz), 2.49–2.62 (2H, m), 1.56–1.65 (2H, m), 1.46–1.55 (2H, m), 1.50 (3H, d, J=6.6 Hz), 1.33–1.42 (2H, m), 1.23–1.30 (6H, m), m/z=475.

Example 392

Synthesis of S-245

S-245 was synthesized by almost the same method as the one employed for the synthesis of S-1 but replacing the 2,5-dimethylthiophenol by 2-chlorobenzylmercaptan.

400 MHz-$^1$H-NMR 7.33–7.38 (1H, m), 7.28–7.31 (1H, m), 7.47–7.26 (3H, m), 6.87–6.88 (2H, m), 6.78 (1H, ddd, J=8.1 Hz, J=2.4 Hz, J=1.0 Hz), 3.81 (3H, s), 3.77 (2H, s), 3.70 (1H, q, J=6.5 Hz), 2.57–2.73 (4H, m), 1.33 (3H, d, J=6.5 Hz), m/z=335.

Example 393

Synthesis of S-246

S-246 was synthesized by almost the same method as the one employed for the synthesis of S-1 but replacing the 2,5-dimethylthiophenol and 1-bromo-2-chloroethane respectively by 2-chlorobenzylmercaptan and 1,3-dibromopropane.

400 MHz-$^1$H-NMR 7.32–7.37 (2H, m), 7.14–7.25 (3H, m), 6.86–6.88 (2H, m), 6.77 (1H, ddd, J=8.3 Hz, J=2.7 Hz, J=1.0 Hz), 3.80 (5H, s), 3.71 (1H, q, J=6.6 Hz), 2.44–2.61 (4H, m), 1.70–1.78 (2H, m), 1.32 (3H, d, J=6.6 Hz), m/z=349.

Example 394

Synthesis of S-247

S-247 was synthesized by almost the same method as the one employed for the synthesis of S-1 but replacing the 2,5-dimethylthiophenol and 1-bromo-2-chloroethane respectively by 2-chlorobenzylmercaptan and 1,5-dibromopentane.

400 MHz-$^1$H-NMR 7.32–7.36 (2H, m), 7.14–7.27 (3H, m), 6.88–6.89 (2H, m), 6.76–6.79 (1H, m), 3.81 (3H, s), 3.80 (2H, s), 3.73 (1H, q, J=6.6 Hz), 2.38–2.51 (4H, m), 1.30–1.60 (6H, m), 1.35 (3H, d, J=6.6 Hz), m/z=377.

Example 395

Synthesis of S-248

S-248 was synthesized by almost the same method as the one employed for the synthesis of S-1 but replacing the 2,5-dimethylthiophenol and 1-bromo-2-chloroethane respectively by 2-chlorobenzylmercaptan and 1,6-dibromohexane.

400 MHz-$^1$H-NMR 7.33–7.36 (2H, m), 7.14–7.27 (3H, m), 6.87–6.90 (2H, m), 6.74–6.79 (1H, m), 3.81 (5H, s), 3.72 (1H, q, J=6.6 Hz), 2.37–2.51 (4H, m), 1.56 (2H, tt, J=7.3 Hz, J=7.3 Hz), 1.40–1.49 (2H, m), 1.20–1.38 (4H, m), 1.34 (3H, d, J=6.6 Hz), m/z=391.

Example 396

Synthesis of S-249

S-249 was synthesized by almost the same method as the one employed for the synthesis of S-1 but replacing the 2,5-dimethylthiophenol and (R)-(+)-3-methoxy-α-benzylmethylamine respectively by 2-chlorobenzylmercaptan and (R)-(+)-1-(1-naphthyl)ethylamine.

400 MHz-$^1$H-NMR 8.16 (1H, d, J=8.0 Hz), 7.85–7.87 (1H, m), 7.74 (1H, d, J=8.3 Hz), 7.65 (1H, d, J=6.8 Hz), 7.44–7.53 (3H, m), 7.24–7.34 (2H, m), 7.13–7.18 (2H, m), 4.60 (1H, q, J=6.6 Hz), 3.77 (2H, s), 2.63–2.78 (4H, m), 1.48 (3H, d, J=6.6 Hz), m/z=355.

Example 397

Synthesis of S-250

S-250 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-chlorobenzylmercaptan, 1,3-dibromopropane and (R)-(+)-1-(1-naphthyl) ethylamine.

400 MHz-$^1$H-NMR 8.16 (1H, d, J=8.3 Hz), 7.84–7.88 (1H, m), 7.74 (1H, d, J=8.3 Hz), 7.63 (1H, d, J=6.8 Hz), 7.44–7.52 (3H, m), 7.28–7.34 (2H, m), 7.12–7.18 (2H, m), 4.62 (1H, q, J=6.6 Hz), 3.79 (2H, s), 2.45–2.72 (4H, m), 1.75–1.81 (2H, m), 1.49 (3H, d, J=6.6 Hz), m/z=369.

Example 398

Synthesis of S-251

S-251 was synthesized by almost the same method as the one employed for the synthesis of S-1 but replacing the 2,5-dimethylthiophenol by 4-chlorobenzylmercaptan.

400 MHz-$^1$H-NMR 7.21–7.26 (3H, m), 7.15–7.19 (2H, m), 6.85–6.87 (2H, m), 6.76–6.80 (1H, m), 3.81 (3H, s), 3.68 (1H, q, J=6.6 Hz), 3.58 (2H, d, J=2.0 Hz), 2.49–2.67 (4H, m), 1.33 (3H, d, J=6.6 Hz), m/z=335.

Example 399

Synthesis of S-252

S-252 was synthesized by almost the same method as the one employed for the synthesis of S-1 but replacing the 2,5-dimethylthiophenol and 1-bromo-2-chloroethane respectively by 4-chlorobenzylmercaptan and 1,3-dibromopropane.

400 MHz-$^1$H-NMR 7.19–7.27 (5H, m), 6.85–6.87 (2H, m), 6.76–6.79 (1H, m), 3.80 (3H, s), 3.69 (1H, q, J=6.6 Hz), 3.63 (2H, s), 2.35–2.59 (4H, m), 1.63–1.73 (2H, m), 1.32 (3H, d, J=6.6 Hz), m/z=349.

Example 400

Synthesis of S-253

S-253 was synthesized by almost the same method as the one employed for the synthesis of S-1 but replacing the 2,5-dimethylthiophenol and (R)-(+)-3-methoxy-α-benzylmethylamine respectively by 4-chlorobenzylmercaptan and (R)-(+)-1-(1-naphthyl)ethylamine. m/z=355.

Example 401

Synthesis of S-254

S-254 was synthesized by almost the same method as the one employed for the synthesis of S-1 but replacing the 2,5-dimethylthiophenol, 1-bromo-2-chlorcethane and (R)-(+)-3-methoxy-α-benzylmethylamine respectively by 4-chlorobenzylmercaptan, 1,3-dibromopropane and (R)-(+)-1-(1-naphthyl)ethylamine.

400 MHz-$^1$H-NMR 8.17 (1H, d, J=2.1 Hz), 7.85–7.88 (1H, m), 7.73–7.75 (1H, d, J=8.1 Hz), 7.62 (1H, d, J=7.4 Hz), 7.45–7.53 (3H, m), 7.17–7.25 (4H, m), 4.60 (1H, q, J=6.6 Hz), 3.61 (2H, s), 2.55–2.71 (2H, m), 2.37–2.48 (2H, m), 1.70–1.78 (2H, m), 1.48 (3H, d, J=6.6 Hz), m/z=369.

Example 402

Synthesis of S-255

S-255 was synthesized by almost the same method as the one employed for the synthesis of S-1 but replacing the 2,5-dimethylthiophenol and 1-bromo-2-chloroethane respectively by 2-quinolinethiol and 1,4-dibromobutane.

400 MHz-¹H-NMR 7.83–7.88 (2H, m), 7.69 (1H, d, J=8.0 Hz), 7.59–7.63 (1H, m), 7.37–7.41 (1H, m), 7.15–7.24 (2H, m), 6.86–6.90 (2H, m), 6.73–6.78 (1H, m), 3.78 (3H, s), 3.73 (1H, q, J=6.8 Hz), 3.30 (2H, t, J=6.8 Hz), 2.47–2.61 (2H, m), 1.58–1.84 (4H, m), 1.33 (3H, d, J=6.8 Hz), m/z=366.

Example 403

Synthesis of S-256

S-256 was synthesized by almost the same method as the one employed for the synthesis of S-1 but replacing the 2,5-dimethylthiophenol and 1-bromo-2-chloroethane respectively by 2-quinolinethiol and 1,5-dibromopentane.

400 MHz-¹H-NMR 7.90 (1H, d, J=8.4 Hz), 7.85 (1H, d, J=8.4 Hz), 7.67–6.70 (1H, m), 7.60–7.64 (1H, m), 7.38–7.42 (1H, m), 7.22 (1H, dd, J=6.2 Hz, J=6.2 Hz), 7.18 (1H, d, J=8.4 Hz), 6.86–6.90 (2H, m), 6.75–6.78 (1H, m), 3.80 (3H, s), 3.74 (1H, q, J=6.4 Hz), 3.32 (2H, t, J=7.4 Hz), 2.40–2.55 (2H, m), 1.76 (2H, tt, J=7.4 Hz, J=7.4 Hz), 1.44–1.59 (4H, m), 1.34 (3H, d, J=6.4 Hz), m/z=380.

Example 404

Synthesis of S-257

S-257 was synthesized by almost the same method as the one employed for the synthesis of S-1 but replacing the 2,5-dimethylthiophenol and 1-bromo-2-chloroethane respectively by 2-quinolinethiol and 1,6-dibromohexane.

400 MHz-¹H-NMR 7.91 (1H, d, J=8.2 Hz), 7.85 (1H, d, J=8.8 Hz), 7.70 (1H, dd, J=8.0 Hz, J=1.2 Hz), 7.61–7.64 (1H, m), 7.38–7.43 (1H, m), 7.23 (1H, dd, J=8.0 Hz, J=8.0 Hz), 7.18 (1H, d, J=8.4 Hz), 6.88–6.90 (2H, m), 6.76–6.79 (1H, m), 3.80 (3H, s), 3.74 (1H, q, J=6.4 Hz), 3.34 (2H, t, J=7.2 Hz), 2.41–2.54 (2H, m), 1.78 (2H, tt, J=7.2 Hz, J=7.2 Hz), 1.41–1.54 (4H, m), 1.35 (3H, d, J=6.4 Hz), m/z=394.

Example 405

Synthesis of S-258

S-258 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-quinolinethiol, 1,4-dibromobutane and (R)-(+)-1-(1-naphthyl)ethylamine.

400 MHz-¹H-NMR 8.18 (1H, d, J=8.0 Hz), 7.83–7.87 (3H, m), 7.73 (1H, d, J=8.0 Hz), 7.65–7.70 (2H, m), 7.56–7.60 (1H, m), 7.43–7.52 (3H, m), 7.37–7.42 (1H, m), 7.17 (1H, d, J=8.8 Hz), 4.65 (1H, q, J=6.4 Hz), 3.32 (2H, t, J=7.2 Hz), 2.59–2.75 (2H, m), 1.67–1.87 (4H, m), 1.49 (3H, d, J=6.4 Hz), m/z=386.

Example 406

Synthesis of S-259

S-259 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-quinolinethiol, 1,5-dibromopentane and (R)-(+)-1-(1-naphthyl)ethylamine.

400 MHz-¹H-NMR 8.16 (1H, d, J=8.0 Hz), 7.83–7.92 (3H, m), 7.58–7.74 (4H, m), 7.37–7.52 (4H, m), 7.18 (1H, d, J=8.4 Hz), 4.63 (1H, q, J=6.4 Hz), 3.32 (2H, t, J=7.4 Hz), 2.54–2.66 (2H, m), 1.40–1.82 (6H, m), 1.49 (3H, d, J=6.4 Hz), m/z=400.

Example 407

Synthesis of S-260

S-260 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 2-quinolinethiol, 1,6-dibromohexane and (R)-(+)-1-(1-naphthyl)ethylamine.

400 MHz-¹H-NMR 8.17 (1H, d, J=8.4 Hz), 7.37–7.82 (11H, m), 7.18 (1H, d, J=8.8 Hz), 4.60–4.70 (1H, m), 3.30 (2H, t, J=7.4 Hz), 2.46–2.83 (4H, m), 1.20–1.77 (9H, m), m/z=414.

Example 408

Synthesis of S-261

S-261 was synthesized by almost the same method as the one employed for the synthesis of S-1 but replacing the 2,5-dimethylthiophenol and (R)-(+)-3-methoxy-α-benzylmethylamine respectively by 4-methylthiophenol and (R)-(+)-1-(1-naphthyl)ethylamine.

400 MHz-¹H-NMR 8.13–8.16 (1H, m), 7.83–7.89 (1H, m), 7.72 (1H, d, J=8.4 Hz), 7.62 (1H, d, J=6.8 Hz), 7.41–7.52 (3H, m), 7.21 (2H, d, J=8.0 Hz), 7.02–7.05 (2H, m), 4.61 (1H, q, J=6.8 Hz), 3.02 (2H, t, J=6.2 Hz), 2.71–2.82 (2H, m), 2.29 (3H, s), 1.48 (3H, d, J=6.8 Hz), m/z=321.

Example 409

Synthesis of S-262

S-262 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-methylthiopheol, 1,3-dibromopropane and (R)-(+)-1-(1-naphthyl)ethylamine.

400 MHz-¹H-NMR 8.16 (1H, d, J=7.6 Hz), 7.83–7.88 (1H, m), 7.73 (1H, d, J=8.4 Hz), 7.63 (1H, d, J=7.2 Hz), 7.44–7.51 (3H, m), 7.21 (2H, d, J=8.0 Hz), 7.04–7.07 (2H, m), 4.59 (1H, q, J=6.8 Hz), 2.85–2.96 (2H, m), 2.61–2.74 (2H, m), 2.30 (3H, s), 1.79 (2H, tt, J=7.1 Hz, J=7.1 Hz), 1.47 (3H, d, J=6.8 Hz), m/z=335.

Example 410

Synthesis of S-263

S-263 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 5-fluoro-2-mercaptobenzothiazole, 1,5-dibromopentane and (R)-(+)-1-(1-naphthyl)ethylamine. m/z=424.

Example 411

Synthesis of S-264

S-264 was synthesized by almost the same method as the one employed for the synthesis of S-1 but replacing the 2,5-dimethylthiophenol, 1-bromo-2-chloroethane and (R)-(+)-3-methoxy-α-benzyimethylamine respectively by 5-fluoro-2-mercaptobenzothiazole, 1,6-dibromohexane and (R)-(+)-1-(1-naphthyl)ethylamine. m/z=438.

Example 412

Synthesis of S-265

K-2117 (hydrochloride) (110 mg, 0.267 mmol) was dissolved in 2.2 ml of toluene (reagent grade). Next, m-chloroperbenzoic acid (56.0 mg, 0.325 mmol) was added thereto at room temperature and the obtained mixture was stirred at the same temperature for 1 hour.

After confirming the completion of the reaction by TLC, a saturated aqueous solution of sodium hydrogencarbonate and a saturated aqueous solution of sodium thiosulfate were added thereto at room temperature and the reaction mixture was subjected to separatory extraction with chloroform and a saturated aqueous solution of sodium chloride and washed. The organic layer thus obtained was dried over anhydrous sodium sulfate. The obtained organic layer was further concentrated under reduced pressure and the residue was purified by column chromatography [silica gel, 5 g, chloroform/methanol=150/1] to thereby give a pale yellow, syrupy compound S-265 (82 mg, 0.214 mmol, yield: 78.3%). m/z=391.

Example 413

Synthesis of S-266

K-2117 (hydrochloride) (500 mg, 0.121 mmol) was dissolved in 20 ml of toluene (reagent grade). Next, m-chloroperbenzoic acid (58.0 mg, 0.336 mmol) was added thereto at room temperature and the obtained mixture was stirred at the same temperature for 8 hours. After confirming the completion of the reaction by TLC, a saturated aqueous solution of sodium hydrogencarbonate and a saturated aqueous solution of sodium thiosulfate were added thereto at room temperature and the reaction mixture was subjected to separatory extraction with chloroform and a saturated aqueous solution of sodium chloride and washed. The organic layer thus obtained was dried over anhydrous sodium sulfate. The obtained organic layer was further concentrated under reduced pressure and the residue was purified by column chromatography [silica gel, 5 g, chloroform/methanol=150/1] to thereby give a pale yellow, syrupy compound S-266 (28 mg, 0.0686 mmol, yield: 56.7). m/z=408.

Example 414

Synthesis of F-8

2,5-Dichlorothiophenol (5 g) was dissolved in acetonitrile (100 ml). Then N-(2-bromoethylphthalimide) (7.8 g) was added thereto while stirring at 0° C. Further, potassium carbonate (4.04 g) was added thereto. After 1 hour, water was added and the resulting mixture was extracted with ethyl acetate. The organic layer was washed with a saturated aqueous solution of sodium chloride, dried over sodium sulfate, filtered and concentrated. The crystals thus obtained were washed with chloroform to thereby give N-(2-(2',5'-dichlorophenylthio)ethyl)phthalimide (F-8) (8.28 g). MS m/z: 351 (M$^+$).

Example 415

Synthesis of F-37

N-(2-(2',5'-Dichlorophenylthio)ethyl)phthalimide (F-8) (7.06 g) was added to ethanol (120 ml). After further adding hydrazine monohydrate (6.9 ml), the obtained mixture was heated under reflux for 1.5 hours. Then it was brought to room temperature and water was added thereto followed by extraction with chloroform. The organic layer was washed with a saturated aqueous solution of sodium chloride, dried over sodium sulfate, filtered and concentrated. The crude product thus obtained was purified by column chromatography (silica gel, chloroform/methanol=20:1) to thereby give 2-(2',5'-dichlorophenylthio)ethylamine (F-37) (4.29 g). MS m/z: 221 (M$^+$).

Example 416

Synthesis of F-12

2-(2',5'-Dichlorophenylthio)ethylamine (F-37) (250 mg) was mixed with 3'-methoxyacetophenone (0.15 ml). After adding titanium tetraisopropoxide (0.4 ml), the mixture was stirred for 3 hours. After adding ethanol (3 ml), sodium boron hydride (43 mg) was further added to the reaction mixture under ice-cooling. Then the mixture was brought to room temperature and stirred for 15 hours. The reaction mixture was concentrated and ethyl acetate and water were added thereto. The insoluble matters were filtered off and the organic layer was washed with a saturated aqueous solution of sodium chloride, dried over sodium sulfate, filtered and concentrated. The crude product thus obtained was purified by column chromatography (silica gel, chloroform/methanol=50:1) to thereby give (±)-N-(1-(3-methoxyphenyl)ethyl)-2-(2',5'-dichlorophenylthio)ethylamine (F-12) (146 mg). MS m/z: 355 (M$^+$).

Example 417

Synthesis of F-13

The procedure employed for the synthesis of F-12 was repeated but replacing the 3'-methoxyacetophenone by 3',4'-dimehtoxyacetophenone to thereby give (±)-N-(1-(3,4-dimethoxyphenyl)ethyl)-2-(2',5'-dichlorophenylthio)ethylamine (F-13). MS m/z: 385 (M$^+$).

Example 418

Synthesis of F-14

The procedure employed for the synthesis of F-12 was repeated but replacing the 3'-methoxyacetophenone by 3'-methylacetophenone to thereby give (±)-N-(1-(3-methylphenyl)ethyl)-2-(2',5'-dichlorophenylthio)ethylamine (F-14). MS m/z: 339 (M$^+$).

Example 419

Synthesis of F-15

The procedure employed for the synthesis of F-12 was repeated but replacing the 3'-methoxyacetophenone by 4'-methylacetophenone to thereby give (±)-N-(1-(4-methylphenyl)ethyl)-2-(2',5'-dichlorophenylthio)ethylamine (F-13). MS m/z: 339 (M$^+$).

Example 420

Synthesis of F-16

The procedure employed for the synthesis of F-12 was repeated but replacing the 3'-methoxyacetophenone by 3',4',5'-trimethoxyacetophenone to thereby give (±)-N-(1-(3,4,5-trimethoxyphenyl)ethyl)-2-(2',5'-dichlorophenylthio)ethylamine (F-16). MS m/z: 415 (M$^+$).

Example 421

Synthesis of F-17

The procedure employed for the synthesis of F-12 was repeated but replacing the 3'-methoxyacetophenone by 4'-hydroxyacetophenone to thereby give (±)-N-(1-(4-hydroxyphenyl)ethyl)-2-(2',5'-dichlorophenylthio) ethylamine (F-17). MS m/z: 341 (M$^+$).

Example 422

Synthesis of F-18

The procedure employed for the synthesis of F-12 was repeated but replacing the 3'-methoxyacetophenone by 3'-(trifluoromethyl)acetophenone to thereby give (±)-N-(1-(3-trifluoromethylphenyl)ethyl)-2-(2',5'-dichlorophenylthio) ethylamine (F-18). MS m/z: 393 (M$^+$).

Example 423

Synthesis of F-21

The procedure employed for the synthesis of F-12 was repeated but replacing the 3'-methoxyacetophenone by 4'-hydroxy-3'-methoxyacetophenone to thereby give (±)-N-(1-(4-hydroxy-3-methoxyphenyl)ethyl)-2-(2',5'-dichlorophenylthio)ethylamine (F-21). MS m/z: 371 (M$^+$).

Example 424

Synthesis of F-22

The procedure employed for the synthesis of F-12 was repeated but replacing the 3'-methoxyacetophenone by 4'-bromoacetophenone to thereby give (±)-N-(1-(4-bromophenyl)ethyl)-2-(2',5'-dichlorophenylthio)ethylamine (F-22). MS m/z: 405 (M$^+$).

Example 425

Synthesis of F-23

The procedure employed for the synthesis of F-12 was repeated but replacing the 3'-methoxyacetophenone by 3'-bromoacetophenone to thereby give (±)-N-(1-(3-bromophenyl)ethyl)-2-(2',5'-dichlorophenylthio)ethylamine (F-23). MS m/z: 405 (M$^+$).

Example 426

Synthesis of F-24

The procedure employed for the synthesis of F-12 was repeated but replacing the 3'-methoxyacetophenone by 2'-bromoacetophenone to thereby give (±)-N-(1-(2-bromophenyl)ethyl)-2-(2',5'-dichlorophenylthio)ethylamine (F-24). MS m/z: 405 (M$^+$).

Example 427

Synthesis of F-29

The procedure employed for the synthesis of F-12 was repeated but replacing the 3'-methoxyacetophenone by 3',4'-dihydroxyacetophenone to thereby give (±)-N-(1-(3,4-dihydroxyphenyl)ethyl)-2-(2',5'-dichlorophenylthio)ethylamine (F-29). MS m/z: 357 (M$^+$).

Example 428

Synthesis of F-30

The procedure employed for the synthesis of F-12 was repeated but replacing the 3'-methoxyacetophenone by 2',5'-dichloroacetophenone to thereby give (±)-N-(1-(2,5-chlorophenyl)ethyl)-2-(2,5'-dichlorophenylthio)ethylamine (F-30). MS m/z: 395 (M$^+$).

Example 429

Synthesis of F-31

The procedure employed for the synthesis of F-12 was repeated but replacing the 3'-methoxyacetophenone by 3'-fluoro-4'-methoxyacetophenone to thereby give (±)-N-(1-(3-fluoro-4-methoxyphenyl)ethyl)-2-(2',5'-dichlorophenylthio)ethylamine (F-31). MS m/z: 373 (M$^+$).

Example 430

Synthesis of F-35

The procedure employed for the synthesis of F-12 was repeated but replacing the 3'-methoxyacetophenone by 3'-(trifluoromethoxy)acetophenone to thereby give (±)-N-(1-(3-trifluoromethoxyphenyl)ethyl)-2-(2',5'-dichlorophenylthio)ethylamine (F-35). MS m/z: 409 (M$^+$).

Example 431

Synthesis of F-48

The procedure employed for the synthesis of F-12 was repeated but replacing the 3'-methoxyacetophenone by 3',4'-dimethylacetophenone to thereby give (±)-N-(1-(3,4-dimethylphenyl)ethyl)-2-(2',5'-dichlorophenylthio) ethylamine (F-48). MS m/z: 353 (M$^+$).

Example 432

Synthesis of F-49

The procedure employed for the synthesis of F-12 was repeated but replacing the 3'-methoxyacetophenone by 2'-chloroacetophenone to thereby give (±)-N-(1-(2-chlorophenyl)ethyl)-2-(2',5'-dichlorophenylthio)ethylamine (F-49). MS m/z: 359 (M$^+$).

Example 433

Synthesis of F-50

The procedure employed for the synthesis of F-12 was repeated but replacing the 3'-methoxyacetophenone by 3'-chloroacetophenone to thereby give (±)-N-(1-(3-chlorophenyl)ethyl)-2-(2',5'-dichlorophenylthio)ethylamine (F-50). MS m/z: 359 (M$^+$).

Example 434

Synthesis of F-51

The procedure employed for the synthesis of F-12 was repeated but replacing the 3'-methoxyacetophenone by 4'-chloroacetophenone to thereby give (±)-N-(1-(4-chlorophenyl)ethyl)-2-(2',5'-dichlorophenylthio)ethylamine (F-51). MS m/z: 359 (M$^+$).

Example 435

Synthesis of F-52

The procedure employed for the synthesis of F-12 was repeated but replacing the 3'-methoxyacetophenone by 3'-fluoroacetophenone to thereby give (±)-N-(1-(3-fluorophenyl)ethyl)-2-(2',5'-dichlorophenylthio)ethylamine (F-52). MS m/z: 343 (M$^+$).

Example 436

Synthesis of F-53

The procedure employed for the synthesis of F-12 was repeated but replacing the 3'-methoxyacetophenone by 4'-fluoroacetophenone to thereby give (±)-N-(1-(4-fluorophenyl)ethyl)-2-(2',5'-dichlorophenylthio)ethylamine (F-53). MS m/z: 343 (M+).

Example 437

Synthesis of F-54

The procedure employed for the synthesis of F-12 was repeated but replacing the 3'-methoxyacetophenone by 2',5'-dimethylacetophenone to thereby give (±)-N-(1-(2,5-dimethylphenyl)ethyl)-2-(2',5'-dichlorophenylthio)ethylamine (F-54). MS m/z: 353 (M+).

Example 438

Synthesis of F-55

The procedure employed for the synthesis of F-12 was repeated but replacing the 3'-methoxyacetophenohe by 2',4'-dimethylacetophenone to thereby give (±)-N-(1-(2,4-dimethylphenyl)ethyl)-2-(2',5'-dichloraphenylthio)ethylamine (F-55). MS m/z: 353 (M+).

Example 439

Synthesis of F-57

The procedure employed for the synthesis of F-12 was repeated but replacing the 3'-methoxyacetophenone by 2',4'-dichloroacetophenone to thereby give (±)-N-(1-(2,4-dichlorophenyl)ethyl)-2-(2',5'-dichlorophenylthio)ethylamine (F-57). MS m/z: 395 (M+).

Example 440

Synthesis of F-58

The procedure employed for the synthesis of F-12 was repeated but replacing the 3'-methoxyacetophenone by 3',4'-dichlcroacetophenone to thereby give (±)-N-(1-(3,4-dichlorophenyl)ethyl)-2-(2',5'-dichlorophenylthio)ethylamine (F-58). MS m/z: 395 (M+).

Example 441

Synthesis of F-63

3'-Hydroxyacetophenone (200 mg) was dissolved in acetonitrile (4 ml). After adding ethyl iodide (0.2 ml) and potassium carbonate (347 mg), the mixture was stirred at 70° C. for 9 hours. After 9 hours, water and ethyl acetate were added to the reaction mixture followed by separation. The organic layer was washed with a saturated aqueous solution of sodium chloride, dried over sodium sulfate, filtered and concentrated. The crude product thus obtained was purified by silica gel chromatography (n-hexane:ethyl acetate=8:1) to thereby give 204 mg of 3'-ethoxyacetophenone. The procedure employed for the synthesis of F-12 was repeated, but replacing the 3'-methoxyacetophenone by 3'-ethoxyacetophenone to thereby give (±)-N-(1-(3-ethoxyphenyl)ethyl)-2-(2',5'-dichlorophenylthio)ethylamine (F-63). MS m/z: 369 (M+).

Example 442

Synthesis of F-64

The procedure employed for the synthesis of 3'-ethoxyacetophenone was repeated but replacing the ethyl iodide by n-propyl iodide to thereby give 3'-n-propoxyacetophenone. The procedure employed for the synthesis of F-12 was repeated but replacing the 3'-methoxyacetophenone by 3'-n-propoxyacetophenone to thereby give (±)-N-(1-(3-n-propoxyphenyl)ethyl)-2-(2',5'-dichlorophenylthio)ethylamine (F-64). MS m/z: 383 (M+).

Example 443

Synthesis of F-65

The procedure employed for the synthesis of 3'-ethoxyacetophenone was repeated but replacing the ethyl iodide by n-butyl iodide to thereby give 3'-n-butoxyacetophenone. The procedure employed for the synthesis of F-12 was repeated but replacing the 3'-methoxyacetophenone by 3'-n-butoxyacetophenone to thereby give (±)-N-(1-(3-n-butoxyphenyl)ethyl)-2-(2',5'-dichlorophenylthio)ethylamine (F-65). MS m/z: 397 (M+).

Example 444

Synthesis of K-2255

The procedure employed for the synthesis of 3'-ethoxyacetophenone was repeated but replacing the ethyl iodide by n-hexyl bromide to thereby give 3'-n-hexyloxyacetophenone. The procedure employed for the synthesis of F-12 was repeated but replacing the 3'-methoxyacetophenone by 3'-n-hexyloxyacetophenone to thereby give (±)-N-(1-(3-n-hexyloxyphenyl)ethyl)-2-(2',5'-dichlorophenylthio)ethylamine (K-2255). MS m/z: 425 (M+).

Example 445

Synthesis of F-67

The procedure employed for the synthesis of 3'-ethoxyacetophenone was repeated but replacing the ethyl iodide by isopropyl iodide to thereby give 3'-isopropoxyacetophenone. The procedure employed for the synthesis of F-12 was repeated but replacing the 3'-methoxyacetophenone by 3'-isopropoxyacetophenone to thereby give (±)-N-(1-(3-isopropoxyphenyl)ethyl)-2-(2',5'-dichlorophenylthio)ethylamine (F-67). MS m/z: 383 (M+).

Example 446

Synthesis of F-68

The procedure employed for the synthesis of 3'-ethoxyacetophenone was repeated but replacing the ethyl iodide by dodecane iodide to thereby give 3'-dodecyloxyacetophenone. The procedure employed for the synthesis of F-12 was repeated but replacing the 3'-methoxyacetophenone by 3'-n-dodecyloxyacetophenone to thereby give (±)-N-(1-(3-n-dodecyloxyphenyl)ethyl)-2-(2',5'-dichlorophenylthio)ethylamine (F-68). MS m/z: 509 (M+).

Example 447

Synthesis of F-69

The procedure employed for the synthesis of 3'-ethoxyacetophenone was repeated but replacing the ethyl iodide by isobutyl iodide to thereby give 3'-isobutoxyacetophenone. The procedure employed for the synthesis of F-12 was repeated but replacing the 3'-methoxyacetophenone by 3'-isobutoxyacetophenone to thereby give (±)-N-(1-(3-isobutoxyphenyl)ethyl)-2-(2',5'-dichlorophenylthio)ethylamine (F-69). MS m/z: 397 (M$^+$).

Example 448

Synthesis of K-2258

The procedure employed for the synthesis of 3'-ethoxyacetophenone was repeated but replacing the ethyl iodide by 4-chrolobenzyl bromide to thereby give 3'-(4-chlorobenzyloxy)acetophenone. The procedure employed for the synthesis of F-12 was repeated but replacing the 3'-methoxyacetophenne by 3'-(4-chlorobenzyloxy)acetophenone to thereby give (±)-N-(1-(3-(4-chlorobenzyloxy)phenyl)ethyl)-2-(2',5'-dichlorophenylthio)ethylamine (K-2258). MS m/z: 465 (M$^+$).

Example 449

Synthesis of F-71

The procedure employed for the synthesis of 3'-ethoxyacetophenone was repeated but replacing the ethyl iodide by 2-chlorobenzyl bromide to thereby give 3'-(2-chlorobenzyloxy)acetophenone. The procedure employed for the synthesis of F-12 was repeated but replacing the 3'-methoxyacetophenone by 3'-(2-chlorobenzyloxy)acetophenone to thereby give (±)-N-(1-(3-(2-chlorobenzyloxy)phenyl)ethyl)-2-(2',5'-dichlorophenylthio)ethylamine (F-71). MS m/z: 465 (M$^+$).

Example 450

Synthesis of F-72

The procedure employed for the synthesis of 3'-ethoxyacetophenone was repeated but replacing the ethyl iodide by benzyl bromide to thereby give 3'-benzyloxyacetophenone. The procedure employed for the synthesis of F-12 was repeated but replacing the 3'-methoxyacetophenone by 3'-benzyloxyacetophenone to thereby give (±)-N-(1-(3-benzyloxyphenyl)ethyl)-2-(2',5'-dichlorophenylthio)ethylamine (F-72). MS m/z: 431 (M$^+$).

Example 451

Synthesis of F-73

The procedure employed for the synthesis of 3'-ethoxyacetophenone was repeated but replacing the ethyl iodide by 2,6-dichlorobenzyl bromide to thereby give 3'-(2,6-dichlorobenzyloxy)acetophenone. The procedure employed for the synthesis of F-12 was repeated but replacing the 3'-methoxyacetophenone by 3'-(2,6-dichlorobenzyloxy)acetophenone to thereby give (±)-N-(1-(3-(2,6-dichlorobenzyloxy)phenyl)ethyl)-2-(2',5'-dichlorophenylthio)ethylamine (F-73). MS m/z: 501 (M$^+$).

Example 452

Synthesis of K-2260

The procedure employed for the synthesis of 3'-ethoxyacetophenone was repeated but replacing the ethyl iodide by 1-bromo-6-chlorohexane to thereby give 3'-(6-chlorohexyloxy)acetophenone. The procedure employed for the synthesis of F-12 was repeated but replacing the 3'-methoxyacetophenone by 3'-(6-chlorohexyloxy)acetophenone to thereby give (±)-N-(1-(3-(6-chlorohexyloxy)phenyl)ethyl)-2-(2',5'-dichlorophenylthio)ethylamine (K-2260). MS m/z: 459 (M$^+$).

Example 453

Synthesis of F-75

The procedure employed for the synthesis of 3'-ethoxyacetophenone was repeated but replacing the ethyl iodide by 1-bromo-6-chlorohexane to thereby give 3'-(2-chloroethoxy)acetophenone. The procedure employed for the synthesis of F-12 was repeated but replacing the 3'-methoxyacetophenone by 3'-(2-chloroethoxy)acetophenone to thereby give (±)-N-(1-(3-(2-chloroethoxy)phenyl)ethyl)-2-(2',5'-dichlorophenylthio)ethylamine (F-75). MS m/z: 403 (M$^+$).

Example 454

Synthesis of F-76

The procedure employed for the synthesis of 3'-ethoxyacetophenone was repeated but replacing the ethyl iodide by 2-methylbenzyl bromide to thereby give 3'-(2-methylbenzyl)acetophenone. The procedure employed for the synthesis of F-12 was repeated but replacing the 3'-methoxyacetophenone by 3'-(2-methylbenzyl)acetophenone to thereby give (±)-N-(1-(3-(2-methylbenzyl)phenyl)ethyl)-2-(2',5'-dichlorophenylthio)ethylamine (F-76). MS m/z: 445 (M$^+$).

Example 455

Synthesis of K-2268

The procedure employed for the synthesis of 3'-ethoxyacetophenone was repeated but replacing the ethyl iodide by 4-methylbenzyl bromide to thereby give 3'-(4-methylbenzyloxy)acetophenone. The procedure employed for the synthesis of F-12 was repeated but replacing the 3'-methoxyacetophenone by 3'-(4-methylbenzyloxy)acetophenone to thereby give (±)-N-(1-(3-(4-methylbenzyloxy)phenyl)ethyl)-2-(2',5'-dichlorophenylthio)ethylamine (K-2268). MS m/z: 445 (M$^+$).

Example 456

Synthesis of F-78

The procedure employed for the synthesis of F-12 was repeated but replacing the 3'-methoxyacetophenone by 2-acetyl-5-methylfuran to thereby give (±)-N-(1-(2-(5-methyl)furanyl)ethyl)-2-(2',5'-dichlorophenylthio)ethylamine (F-78). MS m/z: 329 (M$^+$).

Example 457

Synthesis of F-79

The procedure employed for the synthesis of F-12 was repeated but replacing the 3'-methoxyacetophenone by 2-acetylfuran to thereby give (±)-N-(1-(2-furanyl)ethyl)-2-(2',5'-dichlorophenylthio)ethylamine (F-79). MS m/z: 315 (M$^+$).

Example 458

Synthesis of F-80

The procedure employed for the synthesis of F-12 was repeated but replacing the 3'-methoxyacetophenone by 2-acetyl-1-methylpyrrole to thereby give (±)-N-(1-(2-(1-methyl)pyrrolyl)ethyl)-2-(2',5'-dichlorophenylthio)ethylamine (F-80). MS m/z: 328 (M$^+$).

Example 459

Synthesis of F-81

The procedure employed for the synthesis of F-12 was repeated but replacing the 3'-methoxyacetophenone by 2-acetylthiophene to thereby give (±)-N-(1-(2-thienyl)ethyl)-2-(2',5'-dichlorophenylthio)ethylamine (F-81). MS m/z: 331 (M$^+$).

Example 460

Synthesis of F-82

The procedure employed for the synthesis of F-12 was repeated but replacing the 3'-methoxyacetophenone by 3-acetyl-2,5-dimethylfuran to thereby give (±)-N-(1-(3-(2,5-dimethyl)furanyl)ethyl)-2-(2',5'-dichlorophenylthio)ethylamine (F-82). MS m/z: 343 (M$^+$).

Example 461

Synthesis of F-83

The procedure employed for the synthesis of F-12 was repeated but replacing the 3'-methoxyacetophenone by 3-acetylthiophene to thereby give (±)-N-(1-(3-thienyl)ethyl)-2-(2',5'-dichlorophenylthio)ethylamine (F-83). MS m/z: 331 (M$^+$).

Example 462

Synthesis of F-84

The procedure employed for the synthesis of F-12 was repeated but replacing the 3'-methoxyacetophenone by 2-acetyl-5-methylthiophene to thereby give (±)-N-(1-(2-(5-methyl)thienyl)ethyl)-2-(2',5'-dichlorophenylthio)ethylamine (F-84). MS m/z: 345 (M$^+$).

Example 463

Synthesis of F-85

The procedure employed for the synthesis of F-12 was repeated but replacing the 3'-methoxyacetophenone by 3-acetyl-1-methylpyrrole to thereby give (±)-N-(1-(3-(1-methyl)pyrrolyl)ethyl)-2-(2',5'-dichlorophenylthio)ethylamine (F-85). MS m/z: 329 (M$^+$).

Example 464

Synthesis of F-86

The procedure employed for the synthesis of F-12 was repeated but replacing the 3'-methoxyacetophenone by 5-acetyl-2,4-dimethylthiazle to thereby give (±)-N-(1-(5-(2,4-dimethyl)thiazolyl)ethyl)-2-(2',5'-dichlorophenylthio)ethylamine (F-86). MS m/z: 360 (M$^+$).

Example 465

Synthesis of F-90

The procedure employed for the synthesis of 3'-ethoxyacetophenone was repeated but replacing the ethyl iodide by cyclohexylmethyl bromide to thereby give 3'-(cyclohexylmethoxybenzyloxy)acetophenone. The procedure employed for the synthesis of F-12 was repeated but replacing the 3'-methoxyacetophenone by 3'-(cyclohexylmethoxybenzyloxy)-acetophenone to thereby give (±)-N-(1-(3-(cyclohexylmethoxybenzyloxy)phenyl)ethyl)-2-(2',5'-dichlorophenylthio)ethylamine (F-90). MS m/z: 437 (M$^+$).

Example 466

Synthesis of F-91

The procedure employed for the synthesis of F-12 was repeated but replacing the 3'-methoxyacetophenone by 2-acetylpyridine to thereby give (±)-N-(1-(2-pyridyl)ethyl)-2-(2',5'-dichlorophenylthio)ethylamine (F-91). MS m/z: 327 (M$^+$).

Example 467

Synthesis of F-92

The procedure employed for the synthesis of F-12 was repeated but replacing the 3'-methoxyacetophenone by 3-acetylpyridine to thereby give (±)-N-(1-(3-pyridyl)ethyl)-2-(2',5'-dichlorophenylthio)ethylamine (F-92). MS m/z: 326 (M$^+$).

Example 468

Synthesis of F-93

The procedure employed for the synthesis of F-12 was repeated but replacing the 3'-methoxyacetophenone by 4-acetylpyridine to thereby give (±)-N-(1-(4-pyridyl)ethyl)-2-(2',5'-dichlorophenylthio)ethylamine (F-93). MS m/z: 326 (M$^+$).

Example 469

Synthesis of F-94

The procedure employed for the synthesis of F-12 was repeated but replacing the 3'-methoxyacetophenone by 2-acetylpyrazine to thereby give (±)-N-(1-(2-pyrazyl)ethyl)-2-(2',5'-dichlorophenylthio)ethylamine (F-94). MS m/z: 327 (M$^+$).

Example 470

Synthesis of F-95

The procedure employed for the synthesis of F-12 was repeated but replacing the 3'-methoxyacetophenone by 3-acetyl-2-(methylaminesulfonyl)thiophene to thereby give (±)-N-(1-(3-(2-methylaminosulfonyl)thienyl)ethyl)-2-(2',5'-dichlorophenylthio)ethylamine (F-95). MS m/z: 425 (M$^+$).

Example 471

Synthesis of F-96

The procedure employed for the synthesis of F-12 was repeated but replacing the 3'-methoxyacetophenone by 3-acetylindole to thereby give (±)-N-(1-(3-indolyl)ethyl)-2-(2',5'-dichlorophenylthio)ethylamine (F-96). MS m/z: 364 (M$^+$).

Example 472

Synthesis of F-97

Di(4-trifluoromethyl)benzylamine (450 mg) was dissolved in methylene chloride (10 ml) and bromoacetic acid (186 mg) was added thereto. After further adding WSC. HCl (390 mg), the reaction mixture was heated under reflux for 30 minutes. Then it was brought back to room temperature and separated into aqueous and ethyl acetate layers. The organic layer was washed with a saturated aqueous solution of sodium chloride, dried over sodium sulfate, filtered and concentrated. The crude product thus obtained was purified by silica gel chromatography (n-hexane:ethyl acetate=3:1) to thereby give 510 mg of a bromo compound. This bromo compound (500 mg) was dissolved in acetonitrile (10 ml) and potassium carbonate (763 mg) and (R)-(+)-1-(1-naphthyl)ethylamine (0.18 ml) was added thereto. After further adding tetrabutylammonium iodide (41 mg), the mixture was heated under reflux. After 2 hours, it was brought back to room temperature and separated into aqueous and chloroform layers. The organic layer washed with a saturated aqueous solution of sodium chloride, dried over sodium sulfate, filtered and concentrated. The crude product thus obtained was purified by silica gel chromatography (n-hexane:ethyl acetate=2:1) to thereby give 280 mg of a F-97. MS m/z: 544 (M+1$^+$).

Example 473

Synthesis of F-98

The procedure employed for the synthesis of F-97 was repeated but replacing the di(4-trifluoromethyl)benzylamine by (4-trifluoromethoxy)benzylamine to thereby give F-98. MS m/z: 576 (M+1$^+$).

Example 474

Synthesis of F-99

The procedure employed for the synthesis of F-97 was repeated but replacing the bromoacetic acid by 5-bromopentanoic acid to thereby give F-99. MS m/z: 586 (M$^+$).

Example 475

Synthesis of F-100

The procedure employed for the synthesis of F-97 was repeated but replacing the di(4-trifluoromethyl)benzylamine by (4-chloro)benzylamine to thereby give F-100. MS m/z: 476 (M$^+$).

Example 476

Synthesis of F-101

The procedure employed for the synthesis of F-99 was repeated but replacing the di(4-trifluoromethyl)benzylamine by di(4-trifluoromethoxy)benzylamine to thereby give F-101. MS m/z: 618 (M$^+$).

Example 477

Synthesis of F-102

The procedure employed for the synthesis of F-98 was repeated but replacing the bromoacetic acid by 4-bromobutyric acid to thereby give F-102. MS m/z: 604 (M$^+$).

Example 478

Synthesis of F-103

The procedure employed for the synthesis of F-98 was repeated but replacing the bromoacetic acid by 6-bromohexanoic acid to thereby give F-103. MS m/z: 632 (M$^+$).

Example 479

Synthesis of F-104

The procedure employed for the synthesis of F-103 was repeated but replacing the di(4-trifluoromethoxy)benzylamine by di(4-trifluoromethyl)benzylamine to thereby give F-104. MS m/z: 600 (M$^+$).

Example 480

Synthesis of F-105

The procedure employed for the synthesis of F-101 was repeated but replacing the di(4-trifluoromethyl)benzylamine by di(4-chloro)benzylamine to thereby give F-105. MS m/z: 533 (M+1$^+$).

Example 481

Synthesis of F-106

The procedure employed for the synthesis of F-102 was repeated but replacing the di(4-trifluoromethoxy)benzylamine by di(4-chloro)benzylamine to thereby give F-106. MS m/z: 505 (M+1$^+$).

Example 482

Synthesis of F-107

The procedure employed for the synthesis of F-99 was repeated but replacing the di(4-trifluoromethyl)benzylamine by di(4-chloro)benzylamine to thereby give F-107. MS m/z: 519 (M+1$^+$).

Example 483

Synthesis of F-108

The procedure employed for the synthesis of F-98 was repeated but replacing the bromoacetic acid by 8-bromooctanoic acid to thereby give F-108. MS m/z: 660 (M$^+$).

Example 484

Synthesis of F-109

The procedure employed for the synthesis of F-108 was repeated but replacing the di(4-trifluoromethoxy)benzylamine by di(4-trifluoromethyl)benzylamine to thereby give F-109. MS m/z: 628 (M$^+$).

Example 485

Synthesis of F-110

The procedure employed for the synthesis of F-108 was repeated but replacing the di(4-trifluoromethyl)benzylamine by di(4-chloro)benzylamine to thereby give F-110. MS m/z: 561 (M+1$^+$).

Example 486

Synthesis of F-111

The procedure employed for the synthesis of F-99 was repeated but replacing the di(4-trifluoromethyl)benzylamine by N-(4-trifluoromethylbenzyl)-N-(3,4-dichlorobenzyl)amine to thereby give F-111. MS m/z: 587 (M+1$^+$).

Example 487

Synthesis of F-112

The procedure employed for the synthesis of F-103 was repeated but replacing the di(4-trifluoromethoxy)

Example 488

Synthesis of F-113

The procedure employed for the synthesis of F-97 was repeated but replacing the di(4-trifluoromethyl)benzylamine by N-(4-trifluoromethylbenzyl)-N-(3,4-dichlorobenzyl)amine to thereby give F-113. MS m/z: 544 (M$^+$).

Example 489

Synthesis of F-114

The procedure employed for the synthesis of F-108 was repeated but replacing the di(4-trifluoromethoxy)benzylamine by N-(4-trifluorbmethylbenzyl)-N-(3,4-dichlorobenzyl)amine to thereby give F-114. MS m/z: 628 (M$^+$).

Example 490

Synthesis of F-115

The procedure employed for the synthesis of F-102 was repeated but replacing the di(4-trifluoromethoxy)benzylamine by N-(4-trifluoromethylbenzyl)-N-(3,4-dichlorobenzyl)amine to thereby give F-115. MS m/z: 572 (M$^+$).

Example 491

Synthesis of F-116

The procedure employed for the synthesis of F-115 was repeated but replacing the 4-bromobutyric acid by 12-bromododecanoic acid to thereby give F-116. MS m/z: 684 (M$^+$).

Example 492

Synthesis of F-117

The procedure employed for the synthesis of F-102 was repeated but replacing the di(4-trifluoromethoxy)benzylamine by dibenzylamine to thereby give F-117. MS m/z: 450 (M$^+$).

Example 493

Synthesis of F-118

The procedure employed for the synthesis of F-103 was repeated but replacing the di(4-trifluoromethoxy)benzylamine by dibenzylamine to thereby give F-118. MS m/z: 464 (M$^+$).

Example 494

Synthesis of F-119

The procedure employed for the synthesis of F-108 was repeated but replacing the di(4-trifluoromethoxy)benzylamine by dibenzylamine to thereby give F-119. MS m/z: 492 (M$^+$).

Example 495

Synthesis of F-120

The procedure employed for the synthesis of F-97 was repeated but replacing the di(4-trifluoromethoxy)benzylamine by dibenzylamine to thereby give F-120. MS m/z: 408 (M$^+$).

Example 496

Synthesis of S-267

S-267 was synthesized by almost the same method as the one employed for the synthesis of S-1 but replacing the 2,5-dimethylthiophenol and (R)-(+)-3-methoxy-α-benzylmethylamine respectively by 4-tert-butylthiophenol and (R)-(+)-1-(1-naphthyl)ethylamine. m/z=363.

Example 497

Synthesis of S-268

S-268 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-tert-butylthiophenol, 1,3-dibromopropane and (R)-(+)-1-(1-naphthyl)ethylamine. m/z=377.

Example 498

Synthesis of S-269

S-269 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-tert-butylthiophenol, 1,4-dibromobutane and (R)-(+)-1-(1-naphthyl)ethylamine. m/z=391.

Example 499

Synthesis of S-270

S-270 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-tert-butylthiophenol, 1,5-dibromopentane and (R)-(+)-1-(1-naphthyl)ethylamine. m/z=405.

Example 500

Synthesis of S-271

S-271 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-tert-butylthiophenol, 1,6-dibromohexane and (R)-(+)-1-(1-naphthyl)ethylamine. m/z=419.

Example 501

Synthesis of S-272

S-272 was synthesized by almost the same method as the one employed for the synthesis of S-1 but replacing the 2,5-dimethylthiophenol, 1-bromo-2-chloroethane and (R)-(+)-3-methoxy-α-benzylmethylamine respectively by 4-tert-butylthiophenol, 1,7-dibromoheptane and (R)-(+)-1-(1-naphthyl)ethylamine. m/z=433.

Example 502

Synthesis of S-273

S-273 was synthesized by almost the same method as the one employed for the synthesis of S-1 but replacing the benzylamine by N-(4-trifluoromethylbenzyl)-N-(3,4-dichlorobenzyl)amine to thereby give F-112. MS m/z: 601 (M+1$^+$).

2,5-dimethylthiophenol, 1-bromo-2-chloroethane and (R)-(+)-3-methoxy-α-benzylmethylamine respectively by 4-tert-butylthiophenol, 1,8-dibromooctane and (R)-(+)-1-(1-naphthyl)ethylamine. m/z=447.

Example 503

Synthesis of S-274

S-274 was synthesized by almost the same method as the one employed for the synthesis of S-265 but replacing the K-2117 by K-2027. m/z=399.

Example 504

Synthesis of S-275

S-275 was synthesized by almost the same method as the one employed for the synthesis of S-265 but replacing the K-2117 by K-2076. m/z=433.

Example 505

Synthesis of S-276

S-276 was synthesized by almost the same method as the one employed for the synthesis of K-2310 but replacing the 4-(trifluoromethoxy)benzaldehyde by 4-dimethylaminobenzaldehyde.

Example 506

Synthesis of S-277

S-277 can be synthesized by almost the same method as the one employed for the synthesis of K-2310 but replacing the 4-methylbenzylamine and 4-(trifluoromethoxy)benzaldehyde respectively by 4-tert-butylbenzylamine and 3,4-dichlorobenzaldehyde.

Example 507

Synthesis of S-278

S-278 can be synthesized by almost the same method as the one employed for the synthesis of K-2310 but replacing the 4-methylbenzylamine and 4-(trifluoromethoxy)benzaldehyde respectively by 4-nitrobenzylamine and 3,4-dichlorobenzaldehyde.

Example 508

Synthesis of S-279

S-279 can be synthesized by almost the same method as the one employed for the synthesis of K-2310 but replacing the 4-methylbenzylamine and 4-(trifluoromethoxy)benzaldehyde respectively by 3,4-dichlorobenzylamine and 4-dimethylaminobenzaldehyde.

Example 509

Synthesis of S-280

S-280 was synthesized by almost the same method as the one employed for the synthesis of K-2310 but replacing the 4-(trifluoromethoxy)benzaldehyde by 3,4-dimethoxybenzaldehyde.

Example 510

Synthesis of S-281

S-281 was synthesized by almost the same method as the one employed for the synthesis of K-2310 but replacing the 4-methylbenzylamine and 4-(trifluoromethoxy)benzaldehyde respectively by 4-(trifluoromethyl)benzylamine and 3,4-dimethoxybenzaldehyde.

Example 511

Synthesis of S-282

S-282 was synthesized by almost the same method as the one employed for the synthesis of K-2310 but replacing the 4-(trifluoromethoxy)benzaldehyde by 3,4-dimethylbenzaldehyde.

Example 512

Synthesis of S-283

S-283 was synthesized by almost the same method as the one employed for the synthesis of K-2310 but replacing the 4-methylbenzylamine and 4-(trifluoromethoxy)benzaldehyde respectively by 4-(trifluoromethyl)benzylamine and 3,4-dimethylbenzaldehyde.

Example 513

Synthesis of S-284

S-284 was synthesized by almost the same method as the one employed for the synthesis of K-2310 but replacing the 4-(trifluoromethoxy)benzaldehyde by 3,4-methylenedioxybenzaldehyde.

Example 514

Synthesis of S-285

S-285 was synthesized by almost the same method as the one employed for the synthesis of K-2310 but replacing the 4-methylbenzylamine and 4-(trifluoromethoxy)benzaldehyde respectively by 4-tert-butylbenzylamine and 4-tert-butylbenzaldehyde.

Example 515

Synthesis of S-286

S-286 was synthesized by almost the same method as the one employed for the synthesis of K-2310 but replacing the 4-(trifluoromethoxy)benzaldehyde by 4-chlorobenzaldehyde.

Example 516

Synthesis of S-287

S-287 was synthesized by almost the same method as the one employed for the synthesis of K-2310 but replacing the 4-methylbenzylamine and 4-(trifluoromethoxy)benzaldehyde respectively by 4-chlorobenzylamine and 4-pyridinecarboxyaldehyde.

Example 517

Synthesis of S-288

S-288 was synthesized by almost the same method as the one employed for the synthesis of K-2310 but replacing the 4-methylbenzylamine and 4-(trifluoromethoxy)benzaldehyde respectively by 4-(trifluoromethyl)benzylamine and 4-pyridinecarboxyaldehyde.

Example 518

Synthesis of S-289

S-289 can be synthesized by almost the same method as the one employed for the synthesis of K-2310 but replacing the 4-methylbenzylamine and 4-(trifluoromethoxy) benzaldehyde respectively by 3,4-dichlorobenzylamine and 4-phenylbenzaldehyde.

Example 519

Synthesis of S-290

S-290 can be synthesized by almost the same method as the one employed for the synthesis of K-2310 but replacing the 4-methylbenzylamine and 4-(trifluoromethoxy) benzaldehyde respectively by 3,4-dimethylbenzylamine and 4-phenylbenzaldehyde.

Example 520

Synthesis of S-291

S-291 can be synthesized by almost the same method as the one employed for the synthesis of K-2310 but replacing the 4-methylbenzylamine and 4-(trifluoromethoxy) benzaldehyde respectively by 3,4-dimethoxybenzylamine and 4-phenylbenzaldehyde.

Example 521

Synthesis of S-292

S-292 can be synthesized by almost the same method as the one employed for the synthesis of K-2310 but replacing the 4-methylbenzylamine and 4-(trifluoromethoxy) benzaldehyde respectively by 3,4-dichlorobenzylamine and 4-methylthiobenzaldehyde.

Example 522

Synthesis of S-293

S-293 can be synthesized by almost the same method as the one employed for the synthesis of K-2310 but replacing the 4-methylbenzylamine and 4-(trifluoromethoxy) benzaldehyde respectively by 3,4-dimethylbenzylamine and 4-methylthiobenzaldehyde.

Example 523

Synthesis of S-294

S-294 can be synthesized by almost the same method as the one employed for the synthesis of K-2310 but replacing the 4-methylbenzylamine and 4-(trifluoromethoxy) benzaldehyde respectively by 3,4-dimethoxybenzylamine and 4-methylthiobenzaldehyde.

Example 524

Synthesis of S-295

S-295 can be synthesized by almost the same method as the one employed for the synthesis of K-2310 but replacing the 4-methylbenzylamine and 4-(trifluoromethoxy) benzaldehyde respectively by 4-(trifluoromethyl) benzylamine and 3-chloro-4-fluorobenzaldehyde.

Example 525

Synthesis of S-296

S-296 can be synthesized by almost the same method as the one employed for the synthesis of K-2310 but replacing the 4-(trifluoromethoxy)benzaldehyde by 3-chloro-4-fluorobenzaldehyde.

Example 526

Synthesis of S-297

S-297 can be synthesized by almost the same method as the one employed for the synthesis of K-2310 but replacing the 4-methylbenzylamine and 4-(trifluoromethoxy) benzaldehyde respectively by 4-(trifluoromethyl) benzylamine and 4-chloro-3-nitrobenzaldehyde.

Example 527

Synthesis of S-298

S-298 can be synthesized by almost the same method as the one employed for the synthesis of K-2310 but replacing the 4-(trifluoromethoxy)benzaldehyde by 4-chloro-3-nitrobenzaldehyde.

Example 528

Synthesis of S-299

S-299 was synthesized by almost the same method as the one employed for the synthesis of K-2310 but replacing the 4-methylbenzylamine and 4-(trifluoromethoxy) benzaldehyde respectively by 4-chlorobenzylamine and 5-methyl-2-thiophenecarboxyaldehyde.

Example 529

Synthesis of S-300

S-300 was synthesized by almost the same method as the one employed for the synthesis of K-2310 but replacing the 4-methylbenzylamine and 4-(trifluoromethoxy) benzaldehyde respectively by 4-(trifluoromethyl) benzylamine and 5-methyl-2-thiophenecarboxyaldehyde.

Example 530

The activities of the compounds of the present invention on calcium receptors were measured. The measurement was performed in accordance with the method described in Example 4 of Nemeth et al., PCT/US95/13704 (International Publication No. WO96/12697). In brief, HEK293 cells were transfected with a plasmid pHuPCaR4.0 containing a human calcium receptor gene and loaded with fluo-3. The loading was carried out by incubating the cells at 37° C. for 1 hour in Dulbecco's modified Eagle's medium which contained about 5 μM of fluo-3/AM and had been buffered with 20 mM HEPES. Next, the cells were rinsed with Hank's balanced salt solution which contained 1 mM $CaCl_2$ and 1 mM $MgCl_2$ and had been buffered with 20 mM HEPES. Then each test compound was added to the cells and the fluorescence was measured with the use of an excitation wavelength of 485 nm and an emission wavelength of 540 nm. The results are shown in Table 1.

TABLE 1

| Compound | $EC_{50}$ (μM) |
| --- | --- |
| 2 | 13 |
| 6 | 7.6 |
| 8 | 1.9 |
| 10 | 1.0 |
| 12 | 1.2 |
| 14 | 2.9 |
| 16 | 0.55 |
| 18 | 0.75 |

TABLE 1-continued

| Compound | EC$_{50}$ ($\mu$M) |
| --- | --- |
| 20 | 3.2 |
| 22 | 0.31 |
| 24 | 0.44 |
| 26 | 1.8 |
| 28 | 1.6 |
| 30 | 0.071 |
| 32 | 0.051 |
| 34 | 0.71 |
| 36 | 0.21 |
| 38 | 0.98 |
| 40 | 5.1 |
| 42 | 0.14 |
| 44 | 0.15 |
| 46 | 0.93 |
| 52 | 0.48 |
| 53 | 1.6 |
| 56 | 0.28 |
| 59 | 1.02 |
| 62 | 0.509 |
| 65 | 0.524 |
| 68 | 0.65 |
| 71 | 0.27 |
| 74 | 7.2 |
| 77 | 1.0 |
| 80 | 0.464 |
| 83 | 1.0 |
| 88 | 3.2 |
| 93 | 0.11 |
| 103 | 0.3 |
| 106 | 0.064 |
| 109 | 0.27 |
| 112 | 0.078 |
| 117 | 0.2 |
| 123 | 0.1 |
| K-2003 | 0.29 |
| K-2004 | 0.42 |
| K-2005 | 0.43 |
| K-2006 | 0.77 |
| K-2007 | 0.47 |
| K-2008 | 0.86 |
| K-2010 | 0.14 |
| K-2011 | 0.21 |
| K-2012 | 0.87 |
| K-2015 | 0.49 |
| K-2016 | 0.36 |
| K-2017 | 0.36 |
| K-2018 | 0.33 |
| K-2027 | 0.39 |
| K-2030 | 0.049 |
| K-2033 | 0.35 |
| K-2034 | 0.061 |
| K-2035 | 0.22 |
| K-2040 | 0.08 |
| K-2041 | 0.1 |
| K-2045 | 0.87 |
| K-2046 | 0.14 |
| K-2047 | 0.13 |
| K-2048 | 0.73 |
| K-2049 | 0.83 |
| K-2050 | 0.55 |
| K-2051 | 0.34 |
| K-2052 | 5.7 |
| K-2055 | 0.057 |
| K-2056 | 0.039 |
| K-2057 | 0.41 |
| K-2058 | 0.39 |
| K-2059 | 0.27 |
| K-2061 | 0.15 |
| K-2066 | 0.26 |
| K-2075 | 0.14 |
| K-2076 | 6.2 |
| K-2078 | 0.17 |
| K-2079 | 0.2 |
| K-2080 | 0.77 |
| K-2082 | 2.81 |
| K-2084 | 0.12 |
| K-2085 | 0.13 |

TABLE 1-continued

| Compound | EC$_{50}$ ($\mu$M) |
| --- | --- |
| K-2087 | 0.087 |
| K-2117 | 0.043 |
| K-2177 | 0.075 |
| K-2240 | 0.36 |
| K-2243 | 0.092 |
| K-2246 | 0.12 |
| K-2247 | 0.13 |
| K-2248 | 0.078 |
| K-2249 | 0.082 |
| K-2250 | 0.076 |
| K-2251 | 0.051 |
| K-2252 | 0.018 |
| K-2253 | 0.19 |
| K-2254 | 0.088 |
| K-2255 | 9.6 |
| K-2256 | 0.18 |
| K-2257 | 0.039 |
| K-2258 | 0.38 |
| K-2259 | 0.0024 |
| K-2260 | 0.096 |
| K-2261 | 0.026 |
| K-2262 | 0.084 |
| K-2263 | 0.11 |
| K-2264 | 0.016 |
| K-2265 | 0.061 |
| K-2266 | 0.036 |
| K-2267 | 0.014 |
| K-2268 | 0.089 |
| K-2269 | 0.071 |
| K-2270 | 0.14 |
| K-2271 | 0.14 |
| K-2272 | 0.052 |
| K-2273 | 0.16 |
| K-2274 | 1.2 |
| K-2275 | 0.27 |
| K-2276 | 0.064 |
| K-2277 | 0.93 |
| K-2278 | 2.50 |
| K-2279 | 0.63 |
| K-2280 | 0.27 |
| K-2281 | 0.43 |
| K-2282 | 0.34 |
| K-2283 | 0.093 |
| K-2284 | 0.36 |
| K-2285 | 0.32 |
| K-2286 | 0.62 |
| K-2287 | 0.062 |
| K-2288 | 0.14 |
| K-2289 | 0.074 |
| K-2290 | 0.1 |
| K-2291 | 0.081 |
| K-2292 | 0.074 |
| K-2293 | 0.28 |
| K-2294 | 0.062 |
| K-2295 | 1.36 |
| K-2296 | 0.22 |
| K-2297 | 0.23 |
| K-2298 | 0.34 |
| K-2299 | 0.15 |
| K-2300 | 0.14 |
| K-2301 | 0.8 |
| K-2302 | 0.5 |
| K-2303 | 0.35 |
| K-2304 | 0.098 |
| K-2305 | 0.11 |
| K-2306 | 1.85 |
| K-2309 | 0.066 |
| K-2310 | 0.059 |
| K-2311 | 0.053 |
| K-2312 | 0.08 |
| K-2314 | 0.29 |
| S-16 | 0.11 |
| S-52 | 0.16 |
| S-64 | 0.098 |
| S-69 | 0.31 |
| S-80 | 0.1 |
| S-165 | 0.15 |

TABLE 1-continued

| Compound | EC$_{50}$ ($\mu$M) |
|---|---|
| S-193 | 0.066 |
| S-201 | 0.18 |
| S-202 | 0.15 |
| S-265 | 0.91 |

Example 531

The compound of the present invention was administered to rats so as to examine the effects of the compound on the plasma calcium ion level and serum PTH level. The test was performed by orally administering single dose of the compound of the invention or a control compound to normal male SD rats with six animals in each group.

To the group 1 was administered as a control a 10% cyclodextrin aqueous solution in a dose of 2.5 ml/kg. To the group 2 was administered as a reference (R)-N-(3-(2-chlorophenyl)propyl)-1-(3-methoxyphenyl)ethylamine (KRN568) dissolved in a 10% cyclodextrin aqueous solution in a dose of 30 $\mu$mol/kg. To the group 3 was administered the compound of the present invention dissolved in a 10% cyclodextrin aqueous solution in a dose of 30 $\mu$mol/kg, provided that 1% sodium-CMC aqueous solution was used in place of 10% cyclodextrin aqueous solution for the compounds marked with ** in Table 2.

Blood of each rat was collected from the tail tip before the administration and 30 minutes and 1, 2, 4, 8 and 24 hours thereafter (or at the time indicated in Table 2), and the plasma Ca$^{2+}$ level and serum PTH level were measured. The data of the serum PTH level were statistically processed by the multiple comparison analysis in accordance with Steel's calibration by using the group 1 as the control. The results are shown in Table 2 and FIGS. 46–96.

TABLE 2

| Compound | | Plasma Ca$^{2+}$(mmol/l) | | | | | | |
|---|---|---|---|---|---|---|---|---|
| | | 0 hr | 1 hr | 2 hr | 4 hr | 8 hr | 24 hr | 48 hr |
| K-2027 | mean | 1.427 | 1.197 | 1.102 | 0.995 | 1.048 | 1.363 | |
| | S.E. | 0.010 | 0.053 | 0.027 | 0.027 | 0.024 | 0.013 | |
| K-2052 | mean | 1.425 | 1.283 | 1.187 | 1.087 | 1.185 | | |
| | S.E. | 0.015 | 0.012 | 0.007 | 0.016 | 0.006 | | |
| K-2087 | mean | 1.470 | 1.325 | 1.243 | 1.197 | 1.255 | | |
| | S.E. | 0.008 | 0.015 | 0.009 | 0.012 | 0.008 | | |
| K-2240 | mean | 1.415 | 1.302 | 1.272 | 1.175 | 1.230 | | |
| | S.E. | 0.009 | 0.038 | 0.022 | 0.027 | 0.003 | | |
| K-2247 | mean | 1.400 | 1.378 | 1.298 | 1.175 | 1.217 | | |
| | S.E. | 0.016 | 0.014 | 0.018 | 0.018 | 0.016 | | |
| K-2250 | mean | 1.457 | 1.327 | 1.225 | 1.122 | 1.203 | | |
| | S.E. | 0.014 | 0.030 | 0.022 | 0.010 | 0.019 | | |
| K-2255 | mean | 1.413 | 1.328 | 1.212 | 1.177 | 1.232 | | |
| | S.E. | 0.020 | 0.013 | 0.019 | 0.009 | 0.012 | | |
| K-2258 | mean | 1.452 | 1.317 | 1.227 | 1.133 | 1.207 | | |
| | S.E. | 0.009 | 0.015 | 0.026 | 0.031 | 0.014 | | |
| K-2262 | mean | 1.413 | 1.390 | 1.260 | 1.138 | 1.142 | | |
| | S.E. | 0.020 | 0.009 | 0.021 | 0.017 | 0.020 | | |
| K-2263 | mean | 1.423 | 1.273 | 1.237 | 1.212 | 1.308 | | |
| | S.E. | 0.011 | 0.028 | 0.024 | 0.016 | 0.011 | | |
| K-2264** | mean | 1.403 | 1.335 | 1.203 | 1.013 | 0.998 | 1.182 | 1.240*[a] |
| | S.E. | 0.015 | 0.019 | 0.019 | 0.019 | 0.021 | 0.027 | 0.017 |
| K-2265 | mean | 1.425 | 1.430 | 1.363 | 1.260 | 1.218 | | |
| | S.E. | 0.019 | 0.012 | 0.010 | 0.023 | 0.008 | | |
| K-2266 | mean | 1.417 | 1.368 | 1.222 | 1.065 | 1.045 | 1.370 | |
| | S.E. | 0.020 | 0.021 | 0.036 | 0.023 | 0.017 | 0.009 | |
| K-2267 | mean | 1.417 | 1.347 | 1.212 | 1.027 | 1.022 | 1.312 | |
| | S.E. | 0.015 | 0.018 | 0.019 | 0.016 | 0.018 | 0.023 | |
| K-2269 | mean | 1.450 | 1.152 | 1.140 | 1.097 | 1.173 | | |
| | S.E. | 0.016 | 0.057 | 0.029 | 0.017 | 0.017 | | |
| K-2270** | mean | 1.430 | 1.355 | 1.238 | 1.088 | 1.175 | | |
| | S.E. | 0.012 | 0.014 | 0.019 | 0.016 | 0.020 | | |
| K-2271 | mean | 1.428 | 1.278 | 1.227 | 1.128 | 1.197 | | |
| | S.E. | 0.012 | 0.017 | 0.017 | 0.023 | 0.022 | | |
| K-2272** | mean | 1.442 | 1.382 | 1.237 | 1.075 | 1.022 | 1.240 | |
| | S.E. | 0.015 | 0.014 | 0.011 | 0.011 | 0.015 | 0.012 | |
| K-2279 | mean | 1.443 | 1.200 | 1.155 | 1.130 | 1.210 | 1.445 | |
| | S.E. | 0.014 | 0.064 | 0.034 | 0.022 | 0.010 | 0.015 | |
| K-2280 | mean | 1.443 | 1.233 | 1.167 | 1.077 | 1.142 | 1.405 | |
| | S.E. | 0.010 | 0.017 | 0.013 | 0.011 | 0.017 | 0.008 | |
| K-2281 | mean | 1.437 | 1.380 | 1.245 | 1.103 | 0.993 | 1.230*[b] | |
| | S.E. | 0.015 | 0.017 | 0.031 | 0.011 | 0.011 | 0.014 | |
| K-2282** | mean | 1.435 | 1.425 | 1.298 | 1.168 | 1.078 | 1.230*[b] | |
| | S.E. | 0.016 | 0.019 | 0.015 | 0.017 | 0.010 | 0.014 | |
| K-2283** | mean | 1.433 | 1.395 | 1.305 | 1.210 | 1.253 | | |
| | S.E. | 0.016 | 0.015 | 0.014 | 0.013 | 0.014 | | |
| K-2284 | mean | 1.428 | 1.377 | 1.267 | 1.152 | 1.102 | | |
| | S.E. | 0.018 | 0.011 | 0.025 | 0.025 | 0.020 | | |
| K-2286 | mean | 1.405 | 1.318 | 1.218 | 1.088 | 1.098 | 1.390 | 1.412 |
| | S.E. | 0.017 | 0.015 | 0.018 | 0.021 | 0.018 | 0.008 | 0.014 |

TABLE 2-continued

| Compound | | 0 hr | 1 hr | 2 hr | 4 hr | 8 hr | 24 hr | 48 hr |
|---|---|---|---|---|---|---|---|---|
| K-2287 | mean | 1.403 | 1.180 | 1.042 | 0.955 | 0.950 | 1.200 | 1.392 |
| | S.E. | 0.0.13 | 0.019 | 0.017 | 0.019 | 0.006 | 0.041 | 0.012 |
| K-2288 | mean | 1.405 | 1.190 | 1.057 | 0.955 | 0.905 | 1.162 | 1.387 |
| | S.E. | 0.012 | 0.018 | 0.020 | 0.018 | 0.009 | 0.020 | 0.015 |
| K-2289** | mean | 1.407 | 1.270 | 1.173 | 1.003 | 1.093 | | |
| | S.E. | 0.013 | 0.018 | 0.022 | 0.017 | 0.025 | | |
| K-2290** | mean | 1.380 | 1.428 | 1.248 | 1.063 | 1.055 | | |
| | S.E. | 0.007 | 0.014 | 0.028 | 0.019 | 0.033 | | |
| K-2291** | mean | 1.410 | 1.298 | 1.247 | 1.130 | 1.132 | | |
| | S.E. | 0.017 | 0.041 | 0.022 | 0.021 | 0.019 | | |
| K-2292 | mean | 1.412 | 1.375 | 1.252 | 1.152 | 1.108 | | |
| | S.E. | 0.014 | 0.007 | 0.012 | 0.015 | 0.015 | | |
| K-2293 | mean | 1.408 | 1.245 | 1.152 | 1.068 | 1.088 | | |
| | S.E. | 0.012 | 0.039 | 0.022 | 0.020 | 0.014 | | |
| K-2294** | mean | 1.410 | 1.357 | 1.255 | 1.117 | 1.022 | | |
| | S.E. | 0.018 | 0.014 | 0.022 | 0.026 | 0.015 | | |
| K-2296** | mean | 1.410 | 1.340 | 1.195 | 1.1.13 | 1.083 | | |
| | S.E. | 0.013 | 0.009 | 0.013 | 0.014 | 0.016 | | |
| K-2297 | mean | 1.405 | 1.393 | 1.305 | 1.172 | 1.082 | | |
| | S.E. | 0.016 | 0.010 | 0.022 | 0.016 | 0.022 | | |
| K-2298 | mean | 1.405 | 1.348 | 1.265 | 1.187 | 1.100 | | |
| | S.E. | 0.015 | 0.015 | 0.030 | 0.024 | 0.017 | | |
| K-2299 | mean | 1.395 | 1.287 | 1.192 | 0.998 | 0.983 | 1.382*c | |
| | S.E. | 0.015 | 0.013 | 0.021 | 0.019 | 0.014 | 0.013 | |
| K-2300** | mean | 1.395 | 1.293 | 1.158 | 0.958 | 1.022 | 1.397*c | |
| | S.E. | 0.014 | 0.015 | 0.019 | 0.022 | 0.014 | 0.020 | |
| K-2301 | mean | 1.397 | 1.237 | 1.165 | 1.077 | 1.075 | 1.350*c | |
| | S.E. | 0.009 | 0.030 | 0.017 | 0.024 | 0.019 | 0.010 | |
| K-2302** | mean | 1.412 | 1.238 | 1.130 | 0.978 | 1.010 | | |
| | S.E. | 0.014 | 0.019 | 0.013 | 0.016 | 0.016 | | |
| K-2303 | mean | 1.415 | 1.255 | 1.165 | 1.020 | 1.032 | | |
| | S.E. | 0.018 | 0.021 | 0.018 | 0.010 | 0.023 | | |
| K-2304 | mean | 1.382 | 1.262 | 1.157 | 1.053 | 1.065 | | |
| | S.E. | 0.014 | 0.029 | 0.023 | 0.006 | 0.012 | | |
| K-2305 | mean | 1.415 | 1.242 | 1.170 | 1.098 | 1.202 | | |
| | S.E. | 0.015 | 0.018 | 0.013 | 0.025 | 0.022 | | |
| K-2309 | mean | 1.428 | 1.320 | 1.207 | 1.018 | 0.963 | 1.332*d | |
| | S.E. | 0.016 | 0.012 | 0.024 | 0.029 | 0.008 | 0.003 | |
| K-2310 | mean | 1.428 | 1.342 | 1.188 | 1.008 | 0.943 | 1.330*d | |
| | S.E. | 0.014 | 0.014 | 0.025 | 0.026 | 0.013 | 0.014 | |
| K-2311** | mean | 1.447 | 1.375 | 1.232 | 1.075 | 1.110 | | |
| | S.E. | 0.014 | 0.011 | 0.012 | 0.016 | 0.034 | | |
| KRN568 | mean | 1.378 | 1.305 | 1.237 | 1.290 | 1.340 | | |
| | S.E. | 0.018 | 0.014 | 0.008 | 0.012 | 0.015 | | |

NOTE
*a 31 hr,
*b 27 hr,
*c 23 hr,
*d 28 hr

As these tables and figures clearly show, the compound of the present invention was able to lower the plasma $Ca^{2+}$ level and serum PTH level in vivo.

What is claimed is:

1. A compound having the formula:

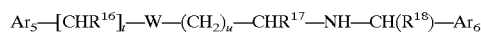

$$Ar_5-[CHR^{16}]_t-W-(CH_2)_u-CHR^{17}-NH-CH(R^{18})-Ar_6$$

wherein:

$Ar_5$ is naphthyl, phenyl, indole, carbazole, dibenzofuran, or fluorene, optionally substituted with one or more groups independently selected from the group consisting of unsubstituted lower alkyl, halogen, unsubstituted lower alkoxy, lower alkyl substituted with one or more halogens, lower alkoxy substituted with one or more halogens, nitro, dimethylamino, and unsubstituted phenyl;

$Ar_6$ is 3-methoxy phenyl or alpha-naphthyl;

t is 1;

u is an integer of from 1 to 11, inclusive;

W is selected from the group consisting of oxygen, sulfur, sulfinyl, sulfonyl, and amino;

$R^{16}$ and $R^{17}$ are H or unsubstituted lower alkyl;

$R^{18}$ is unsubstituted lower alkyl;

or a pharmaceutically acceptable salt or hydrate of said compound;

provided that:

when $Ar_6$ is 3-methoxy-phenyl, then $Ar_5$ is not 2-chloro-phenyl; and when t=1, $R^{16}$ is unsubstituted lower alkyl, W is amino, u=2, each of $R^{17}$ end $R^{18}$ is H, and $Ar_6$ is 3-methoxy-phenyl, then $Ar_5$ is not 3-methoxyphenyl.

2. The compound, salt or hydrate of claim 1 wherein:

$Ar_5$ is phenyl, napthyl, or carbazole, optionally substituted with one or more groups independently selected from the group consisting of halogen, lower alkyl, unsubstituted lower alkoxy, and lower alkyl substituted with one or more halogens;

Ar₆ is alpha-napthyl;

$R^{16}$ is lower alkyl;

$R^{17}$ is hydrogen;

W is amino.

3. A compound according to claim 2 selected from the group consisting of:

93

117 or a pharmaceutically acceptable salt or hydrate thereof.

4. A pharmaceutical composition comprising a compound claim 1.

5. The compound, salt or hydrate of claim 1 wherein:

Ar₅ is phenyl, napthyl, or carbazole, optionally substituted with one or more groups independently selected from the group consisting of halogen, lower alkyl, unsubstituted lower alkoxy, and lower alkyl substituted with one or more halogens;

Ar₆ is alpha-napthyl;

t is 1;

$R^{16}$ is lower alkyl;

$R^{17}$ is hydrogen;

$R^{18}$ is lower alkyl; and

W is amino.

6. A pharmaceutical composition comprising a compound having the formula:

Ar₅—[CHR¹⁶]ₜ—W—(CH₂)ᵤ—CHR¹⁷—NH—CH(R¹⁸)—Ar₆ wherein:

Ar₅ is phenyl, indole, carbazole, dibenzofuran, or fluorene, optionally substituted with one or more groups independently selected from the group consisting of unsubstituted lower alkyl, halogen, unsubstituted lower alkoxy, lower alkyl substituted with one or more halogens, lower alkoxy substituted with one or more halogens, nitro, dimethylamino, and unsubstituted phenyl;

Ar₆ is 3-methoxy phenyl or alpha-naphthyl;

t is 1;

u is an integer of from 1 to 11, inclusive;

W is selected from the group consisting of oxygen, sulfur, sulfinyl, sulfonyl, and amino;

$R^{16}$ and $R^{17}$ are H or unsubstituted lower alkyl;

$R^{18}$ is unsubstituted lower alkyl;

or a pharmaceutically acceptable salt or hydrate of said compound;

in a form suitable for administration to a mammal;

provided that:

when Ar₅ is 3-methoxy-phenyl, then Ar₅ is not 2-chloro-phenyl.

7. The compound, salt or hydrate of claim 1 wherein:

Ar₅ is phenyl, napthyl, or carbazole, optionally substituted with one or more groups independently selected from the group consisting of halogen, lower alkyl, unsubstituted lower alkoxy, and lower alkyl substituted with one or more halogens;

Ar₆ is 3-methoxyphenyl;

t is 1;

$R^{16}$ is lower alkyl;

$R^{17}$ is hydxogen;

$R^{18}$ is lower alkyl; and

W is amino.

8. The compound, salt or hydrate of claim 7, wherein Ar₅ is phenyl optionally substituted with one or more groups independently selected from the group consisting of halogen, lower alkyl, unsubstituted lower alkoxy, and lower alkyl substituted with one or more halogens.

9. The compound, salt or hydrate of claim 8, wherein Ar₅ is phenyl optionally substituted with one or more unsubstituted lower alkoxy groups.

10. The compound of claim 7, having the structure:

88

11. The compound of claim 10, in a form suitable for administration to a mammal.

12. A composition comprising a therapeutically effective amount of a compound of claim 1 in a pharmaceutically acceptable carrier.

13. A composition comprising a therapeutically effective amount of a compound of claim 2 in a pharmaceutically acceptable carrier.

14. A composition comprising a therapeutically effective amount of a compound of claim 7 in a pharmaceutically acceptable carrier.

15. A composition comprising a therapeutically effective amount of a compound of claim 3 in a pharmaceutically acceptable carrier.

16. A composition comprising a therapeutically effective amount of the compound of claim 10 in a pharmaceutically acceptable carrier.

17. A compound of claim 3, in a form suitable for administration to a mammal.

18. A method of treating a patient with hyperparathyroidism, said method comprising administering to said patient an effective amount of a compound of claim 1.

19. The method of claim 18, wherein said hyperparathyroidism is primary hyperparathyroidism.

20. The method of claim 18, wherein said hyperparathyroidism is secondary hyperparathyroidism.

* * * * *